United States Patent
Albrecht et al.

(10) Patent No.: US 9,085,583 B2
(45) Date of Patent: Jul. 21, 2015

(54) MODULATORS OF METHYL MODIFYING ENZYMES, COMPOSITIONS AND USES THEREOF

(71) Applicant: Constellation_Pharmaceuticals, Inc., Cambridge, MA (US)

(72) Inventors: Brian K. Albrecht, Cambridge, MA (US); James Edmund Audia, Cambridge, MA (US); Andrew S. Cook, Stow, MA (US); Les A. Dakin, Natick, MA (US); Martin Duplessis, Somerville, MA (US); Victor S. Gehling, Somerville, MA (US); Jean-Christophe Harmange, Andover, MA (US); Christopher G. Nasveschuk, Stoneham, MA (US); Rishi G. Vaswani, Newton, MA (US)

(73) Assignee: Constellation_Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/377,214

(22) PCT Filed: Feb. 11, 2013

(86) PCT No.: PCT/US2013/025639
§ 371 (c)(1),
(2) Date: Aug. 7, 2014

(87) PCT Pub. No.: WO2013/120104
PCT Pub. Date: Aug. 15, 2013

(65) Prior Publication Data
US 2015/0011546 A1  Jan. 8, 2015

Related U.S. Application Data

(60) Provisional application No. 61/597,695, filed on Feb. 10, 2012, provisional application No. 61/667,821, filed on Jul. 3, 2012.

(51) Int. Cl.
| | | |
|---|---|---|
| *A61K 31/535* | (2006.01) | |
| *C07D 401/00* | (2006.01) | |
| *C07D 487/04* | (2006.01) | |
| *C07D 401/14* | (2006.01) | |
| *C07D 401/12* | (2006.01) | |
| *C07D 417/04* | (2006.01) | |
| *C07D 417/14* | (2006.01) | |

(52) U.S. Cl.
CPC .......... *C07D 487/04* (2013.01); *C07D 401/12* (2013.01); *C07D 401/14* (2013.01); *C07D 417/04* (2013.01); *C07D 417/14* (2013.01)

(58) Field of Classification Search
None
See application file for complete search history.

(56) References Cited

U.S. PATENT DOCUMENTS

| | | |
|---|---|---|
| 4,738,971 A | 4/1988 | Eriksoo et al. |
| 5,308,854 A | 5/1994 | Hoffman, Jr. et al. |
| 7,838,520 B2 | 11/2010 | Delorme et al. |
| 8,410,088 B2 | 4/2013 | Kuntz et al. |
| 2003/0207875 A1 | 11/2003 | Gymer et al. |
| 2003/0229081 A1 | 12/2003 | Maduskuie |
| 2005/0266473 A1 | 12/2005 | Zhang et al. |
| 2006/0035938 A1 | 2/2006 | Bladh et al. |
| 2007/0155744 A1 | 7/2007 | Jones et al. |
| 2008/0027050 A1 | 1/2008 | Terauchi et al. |
| 2008/0227826 A1 | 9/2008 | Frechette et al. |
| 2008/0280917 A1 | 11/2008 | Albrecht et al. |
| 2009/0029991 A1 | 1/2009 | Stokes et al. |
| 2009/0075833 A1 | 3/2009 | Chinnaiyan et al. |
| 2010/0069630 A1 | 3/2010 | Lee et al. |
| 2010/0222420 A1 | 9/2010 | Chinnaiyan et al. |
| 2010/0261743 A1 | 10/2010 | Londregan et al. |
| 2010/0298270 A1 | 11/2010 | Keana et al. |
| 2011/0105509 A1 | 5/2011 | Kaila et al. |
| 2011/0212946 A1 | 9/2011 | Barrow et al. |
| 2012/0071418 A1 | 3/2012 | Copeland et al. |
| 2013/0040906 A1 | 2/2013 | Kuntz et al. |
| 2013/0230511 A1 | 9/2013 | Heymach et al. |
| 2014/0107122 A1 | 4/2014 | Kuntz et al. |

FOREIGN PATENT DOCUMENTS

| | | |
|---|---|---|
| WO | 03/020722 A1 | 3/2003 |
| WO | 03/079986 A2 | 10/2003 |
| WO | 2007/014838 A1 | 2/2007 |
| WO | 2007/067968 A2 | 6/2007 |
| WO | 2009/006577 A2 | 1/2009 |
| WO | 2009/087285 A1 | 7/2009 |
| WO | 2009/153721 A1 | 12/2009 |
| WO | 2011/127219 A1 | 10/2011 |
| WO | 2011/131741 A1 | 10/2011 |
| WO | 2011/140324 A1 | 11/2011 |

(Continued)

OTHER PUBLICATIONS

Woo, et al., "Biological Evaluation of Tanshindiols as EZH2 Histone Methyltransferase Inhibitors," Bioorganic & Medicinal Chemistry Letters, 24(11), 2014, 2486-2492.

Knutson et al., "Selective Inhibition of EZH2 by EPZ-6438 Leads to Potent Antitumor Activity in EZH2-Mutant Non-Hodgkin Lymphoma," Molecular Cancer Therapeutics, 13(4), 2014, 842-854.

Amatangelo et al., "Three-Dimensional Culture Sensitizes Epithelial Ovarian Cancer Cells to EZH2 Methyltransferase Inhibition," Cell Cycle, 12(13), 2013, 2113-2119.

Van Aller, et al., "Long Residence Time Inhibition of EZH2 in Activated Polycomb Repressive Complex 2," ACS Chem. Biol., 9(3), 2014, 622-629.

(Continued)

*Primary Examiner* — Heidi Reese
(74) *Attorney, Agent, or Firm* — McCarter & English, LLP; Steven G. Davis; Michael J. DeGrazia

(57) ABSTRACT

Agents for modulating methyl modifying enzymes, compositions and uses thereof are provided herein.

14 Claims, 118 Drawing Sheets

(56) References Cited

FOREIGN PATENT DOCUMENTS

| | | | |
|---|---|---|---|
| WO | 2011/140325 | A1 | 11/2011 |
| WO | 2012/005805 | A1 | 1/2012 |
| WO | 2012/024543 | A1 | 2/2012 |
| WO | 2012/051492 | A2 | 4/2012 |
| WO | 2012/068589 | A2 | 5/2012 |
| WO | 2012/075080 | A1 | 6/2012 |
| WO | 2012/115885 | A1 | 8/2012 |
| WO | 2012/118812 | A2 | 9/2012 |
| WO | 2013/039988 | A1 | 3/2013 |
| WO | 2013/049770 | A2 | 4/2013 |
| WO | 2013/067296 | A1 | 5/2013 |
| WO | 2013/067300 | A1 | 5/2013 |
| WO | 2013/067302 | A1 | 5/2013 |
| WO | 2013/075083 | A1 | 5/2013 |
| WO | 2013/075084 | A1 | 5/2013 |
| WO | 2013/078320 | A1 | 5/2013 |
| WO | 2013/120104 | A2 | 8/2013 |
| WO | 2013/138361 | A1 | 9/2013 |
| WO | 2013/155317 | A1 | 10/2013 |
| WO | 2013/155464 | A1 | 10/2013 |
| WO | 2013/173441 | A2 | 11/2013 |
| WO | 2014/049488 | A1 | 4/2014 |
| WO | 2014/062720 | A2 | 4/2014 |
| WO | 2014/071109 | A1 | 5/2014 |
| WO | 2014/077784 | A1 | 5/2014 |
| WO | 2014/085666 | A1 | 6/2014 |
| WO | 2014/092905 | A1 | 6/2014 |
| WO | 2014/097041 | A1 | 6/2014 |
| WO | 2014/100080 | A1 | 6/2014 |

OTHER PUBLICATIONS

Knutson, et al., "Durable Tumor Regression in Genetically Altered Malignant Rhabdoid Tumors by Inhibition of Methyltransferase EZH2," Proceedings of the National Academy of Sciences of the United States of America, 110(19), 2013, 7922-7927.

Konze, et al., "An Orally Bioavailable Chemical Probe of the Lysine Methyltransferases EZH2 and EZH1," ACS Chemical Biology, 8(6), 2013, 1324-1334.

Qi, et al., "Selective Inhibition of Ezh2 by a Small Molecule Inhibitor Blocks Tumor Cells Proliferation," Proceedings of the National Academy of Sciences of the United States of America, 109(52), 2012, 21360-21365.

Verma, et al., "Identification of Potent, Selective, Cell-Active Inhibitors of the Histone Lysine Methyltransferase EZH2," ACS Medicinal Chemistry Letters, 3(12), 2012, 1091-1096.

McCabe, et al., "EZH2 Inhibition as a Therapeutic Strategy for Lymphoma with EZH2-Activating Mutations," Nature, 492(7427), 2012, 108-112.

Knutson, et al., "A Selective Inhibitor of EZH2 Blocks H3K27 Methylation and Kills Mutant Lymphoma Cells," Nature Chemical Biology, 8(11), 2012, 890-896.

Yap, et al., "Somatic mutations at EZH2 Y641 act dominantly through a mechanism of selectively altered PRC2 catalytic activity, to increase H3K27 trimethylation," Blood, vol. 117, No. 8, Feb. 24, 2011, pp. 2451-2459.

Alexei Vazquez, "Optimization of Personalized Therapies for Anticancer Treatment," BMC Systems Biology, 2013, 7:31, 11 pages, http://www.biomedcentral.com/1752-0509/7/31.

Fiskus, et al., "Combined Epigenetic Therapy with the Histone Methyltransferase EZH2 Inhibitor 3-Deazaneplanocin A and the Histone Deacetylase Inhibitor Panobinostat Against Human AML Cells," Blood, Sep. 24, 2009, 114:13, pp. 2733-2743.

Fiskus, et al., "Histone Deacetylase Inhibitors Deplete Enhancer of Zeste 2 and Associated Polycomb Repressive Complex 2 Proteins in Human Acute Leukemia Cells," Molecular Cancer Therapeutics, 2006;5:3096-3104.

PubChem Compound Summary for CID 6918837, Jul. 28, 2006, 2 pages.

PubChem Compound Summary for CID 73087, Aug. 1, 2005, 2 pages.

PubChem Compound Summary for CID 50961558, Mar. 29, 2011, 2 pages.

PubChem Compound Summary for CID 40170690, May 30, 2009, 2 pages.

100

101

102

103

104

105

106

107

108

109

110

111

112

113

114

115

116

117

118

119

120

121

122

123

124

125

126

127

128

129

130

131

132

133

134

135

136

137

138

139

140

141

142

143

144

145

146

147

148

149

150

151

152

153

154

155

156

157

158

159

160

161

162

163

164

165

166

167

168

169

170

171

172

173

174

175

176

177

178

179

180

181

182

183

184

185

186

187

188

189

191

192

193

194

195

196

197

198

199

200

201

202

203

204

205

206

207

208

209

210

211

212

213

214

215

216

217

218

219

220

221

222

223

224

225

226

227

228

229

230

231

232

233

234

235

236

237

238

239

240

241

242

243

244

245

246

247

248

249

250

251

252

253

254

255

256

257

258

259

260

261

262

263

264

265

266

267

268

269

270

271

272

273

275

276

277

278

279

280

283

284

285

286

287

288

290

291

292

293

294

295

296

297

298

299

300

301

302

303

304

305

306

307

308

309

310

311

312

313

314

315

316

317

318

319

320

321

322

323

324

326

327

329

330

331

332

333

334

335

336

337

338

339

340

341

342

343

344

345

346

347

348

349

350

351

352

353

354

355

356

357

358

359

360

361

362

363

364

365

366

367

368

369

370

371

372

373

374

375

376

377

378

379

380

381

382

383

384

385

386

387

388

389

390

391

392

393

394

395

398

399

400

401

402

403

404

405

406

407

408

409

410

411

412

413

414

415

416

417

418

419

420

421

422

423

424

425

426

427

428

429

430

431

432

433

434

435

436

437

438

439

440

442

443

444

445

446

447

MODULATORS OF METHYL MODIFYING ENZYMES, COMPOSITIONS AND USES THEREOF

CROSS-REFERENCE TO RELATED APPLICATIONS

This application is a 35 U.S.C. §371 national stage filing of International Application No. PCT/US2013/025639, filed Feb. 11, 2013, which claims the benefit of U.S. Provisional Application Ser. Nos. 61/597,695, filed Feb. 10, 2012, and 61/667,821, filed Jul. 03, 2012. The entire contents of each of the aforementioned applications are incorporated herein by reference.

BACKGROUND OF THE INVENTION

Eukaryotic chromatin is composed of macromolecular complexes called nucleosomes. A nucleosome has 147 base pairs of DNA wrapped around a protein octamer having two subunits of each of histone protein H2A, H2B, H3, and H4. Histone proteins are subject to post-translational modifications which in turn affect chromatin structure and gene expression. One type of post-translational modification found on histones is methylation of lysine and arginine residues. Histone methylation plays a critical role in the regulation of gene expression in eukaryotes. Methylation affects chromatin structure and has been linked to both activation and repression of transcription (Zhang and Reinberg, Genes Dev. 15:2343-2360, 2001). Enzymes that catalyze attachment and removal of methyl groups from histones are implicated in gene silencing, embryonic development, cell proliferation, and other processes.

SUMMARY OF THE INVENTION

The present disclosure encompasses the recognition that methyl modifying enzymes are an attractive target for modulation, given their role in the regulation of diverse biological processes. It has now been found that compounds of this invention, and pharmaceutically acceptable compositions thereof, are effective as agents that stimulate activity of histone methyl modifying enzymes, including histone methylases and histone demethylases. Such compounds have the general formula I:

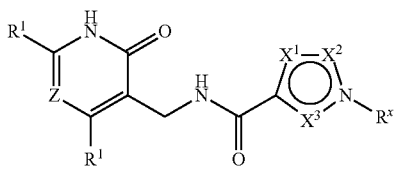

or a pharmaceutically acceptable salt thereof, wherein each variable is as defined herein.

Compounds of the present invention, and pharmaceutically acceptable compositions thereof, are useful for treating a variety of diseases, disorders or conditions, associated with a methyl modifying enzyme. Such diseases, disorders, or conditions include those described herein.

Compounds provided by this invention are also useful for the study of methyl modifying enzymes in biological and pathological phenomena; the study of intracellular signal transduction pathways mediated by methyl modifying enzymes and the comparative evaluation of new methyl modifying enzyme modulators.

DETAILED DESCRIPTION OF CERTAIN EMBODIMENTS

Figure 1:
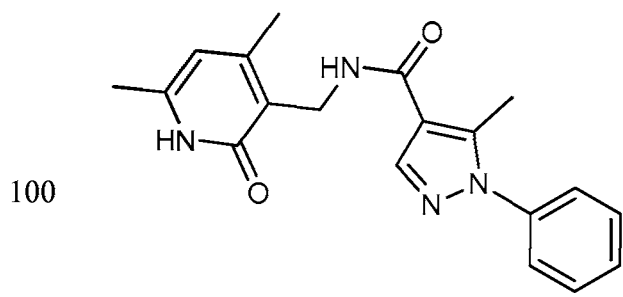
FIG. 1. Exemplary compounds of formulae I and II.
Figure 1:
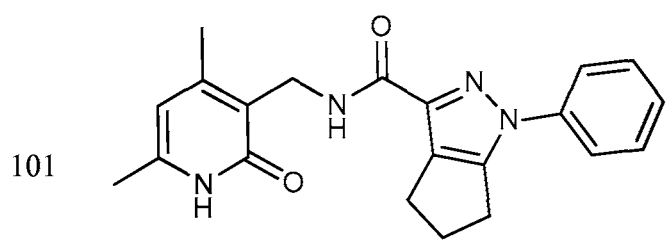
Figure 1:
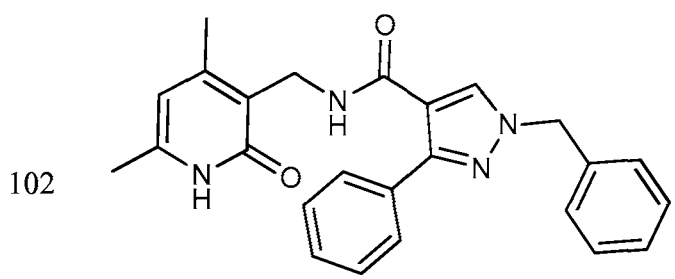
Figure 1:
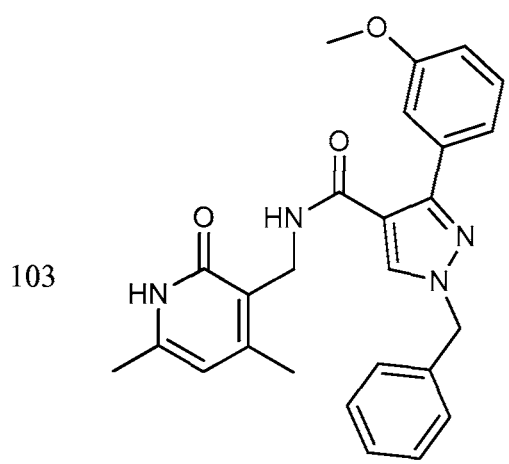
Figure 1:
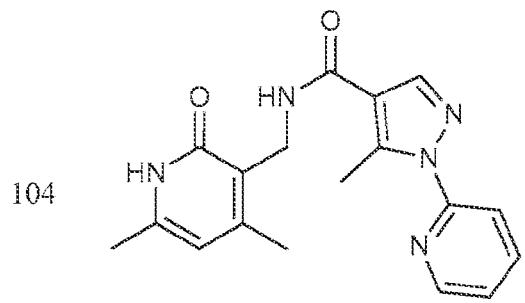
Figure 1:
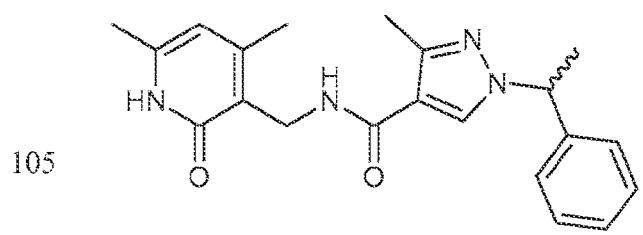
Figure 1:
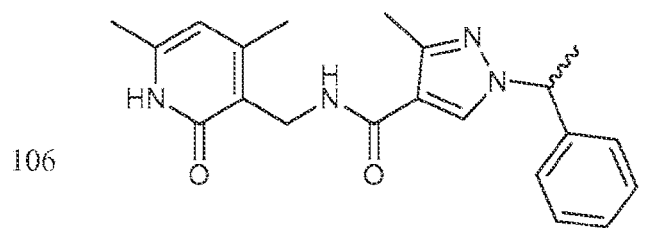
Figure 1:
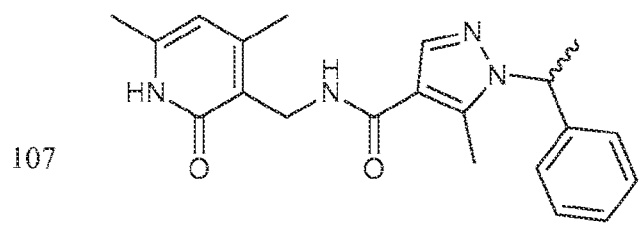
Figure 1:
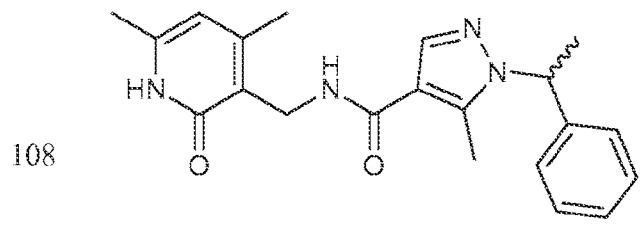
Figure 1:
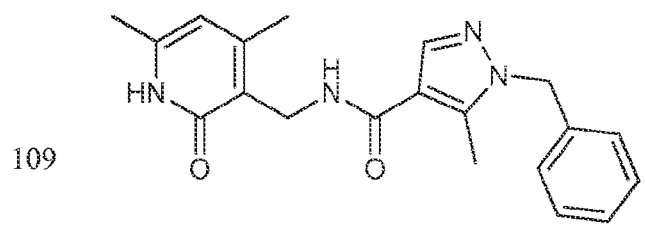
Figure 1:
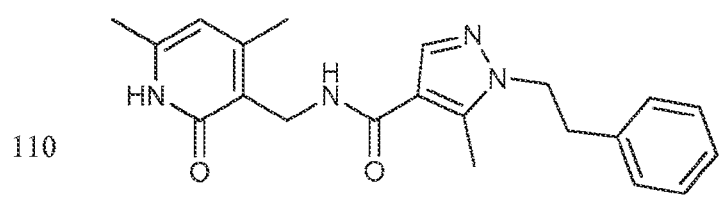
Figure 1:
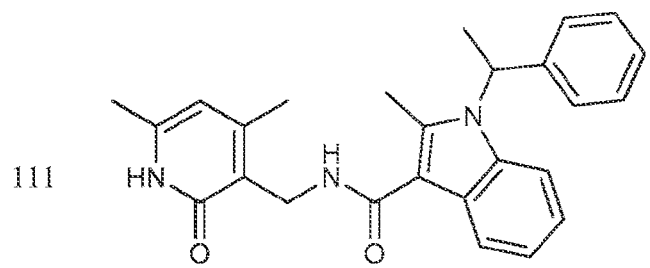
Figure 1:
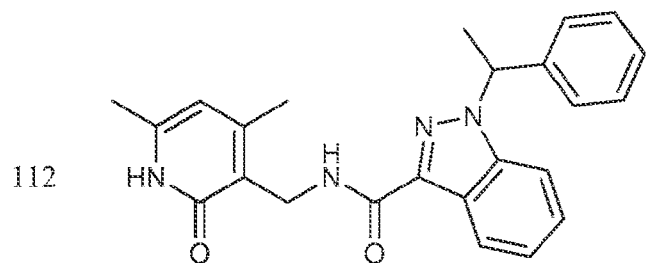
Figure 1:
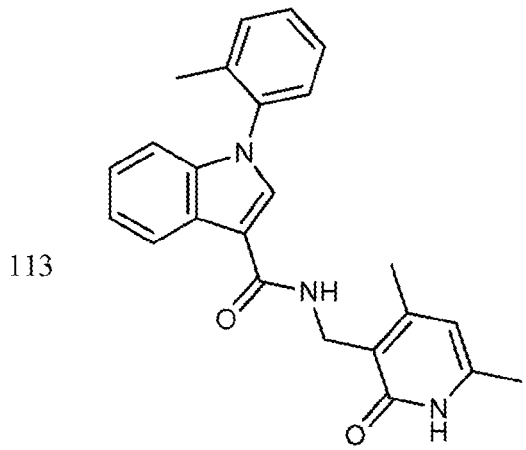
Figure 1:
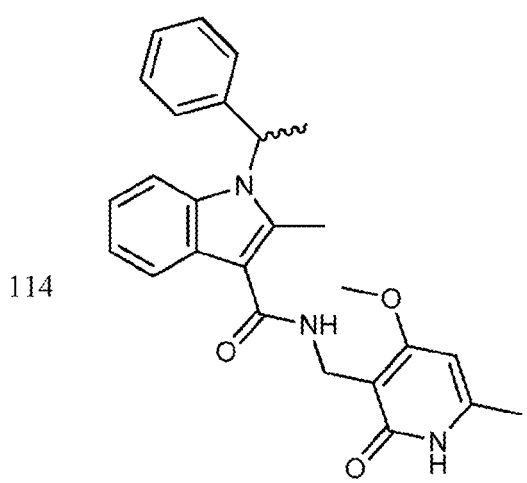
Figure 1:
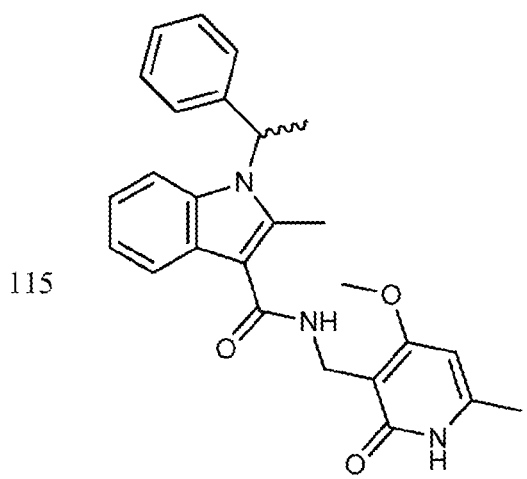
Figure 1:
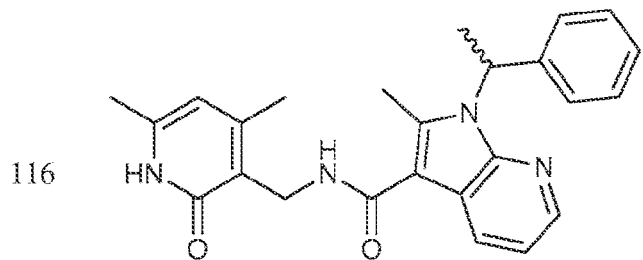
Figure 1:
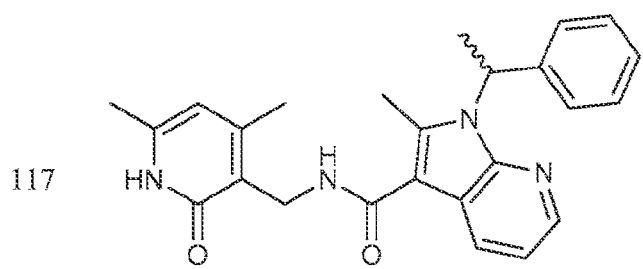
Figure 1:
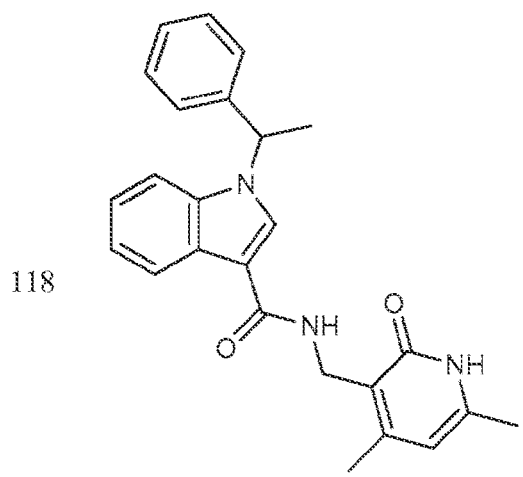
Figure 1:
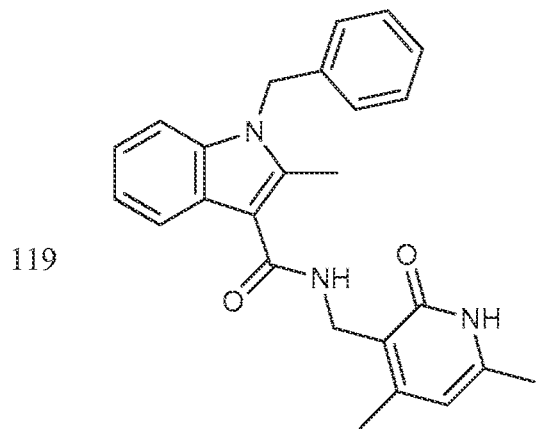
Figure 1:

Figure 1:

Figure 1:
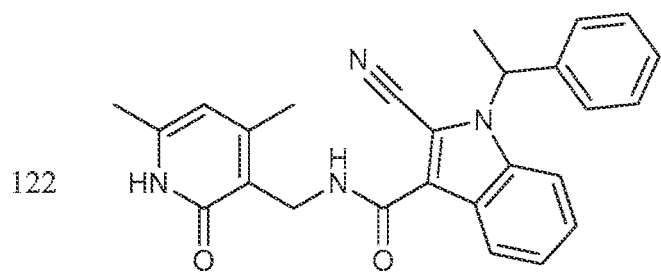
Figure 1:
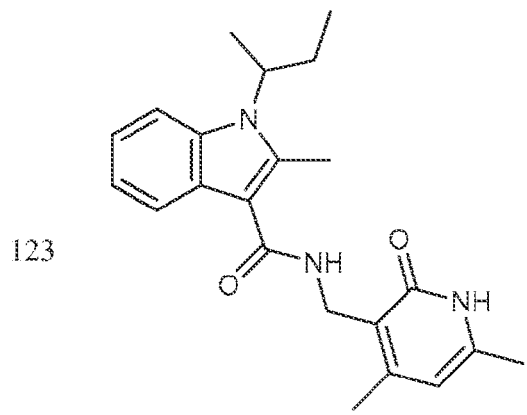
Figure 1:
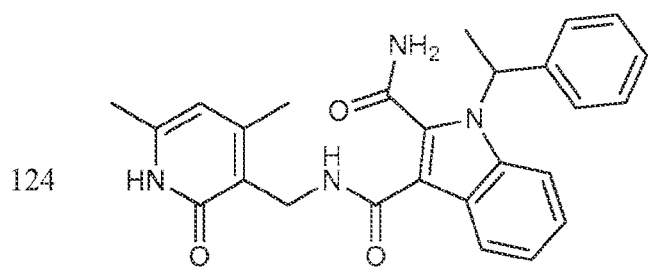
Figure 1:
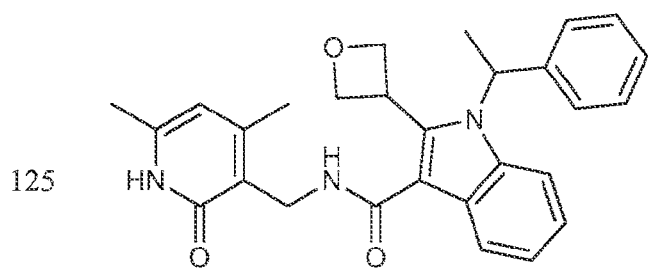
Figure 1:
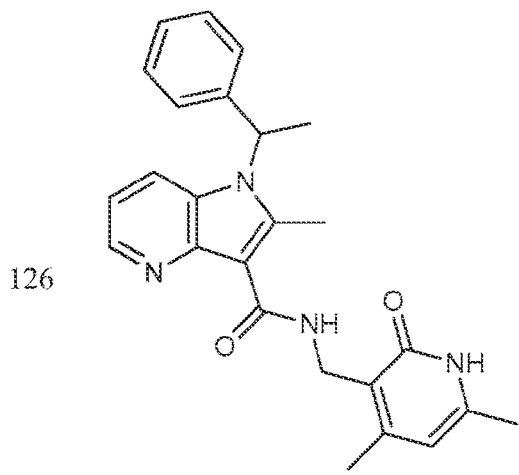
Figure 1:
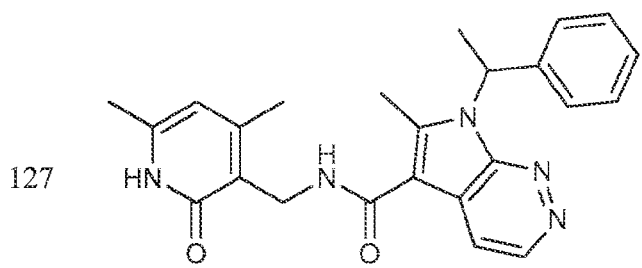
Figure 1:
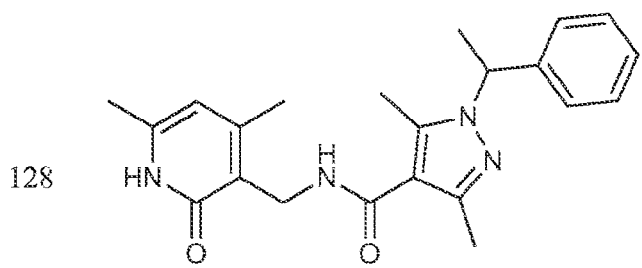
Figure 1:
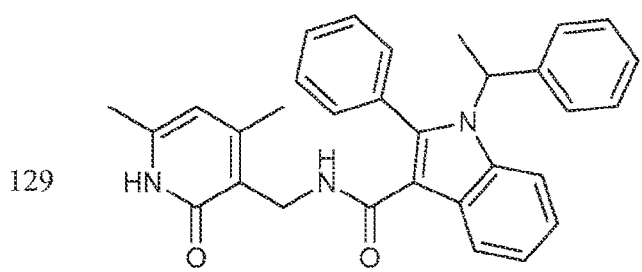
Figure 1:
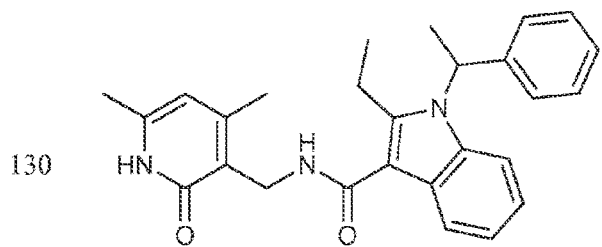
Figure 1:
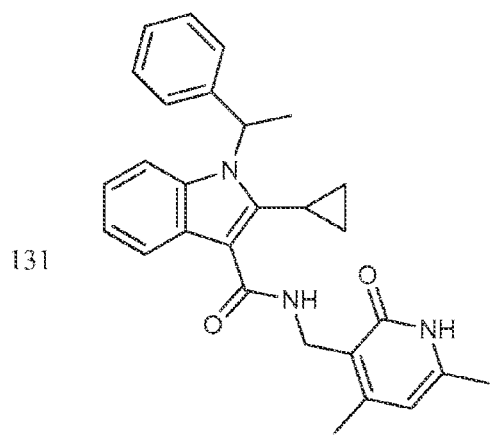
Figure 1:
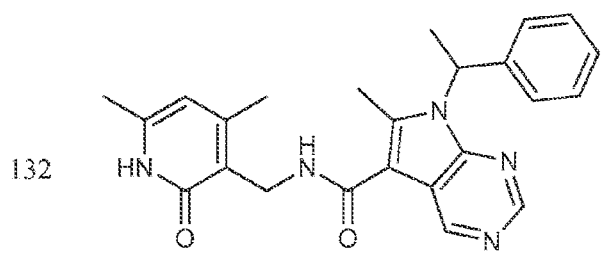
Figure 1:
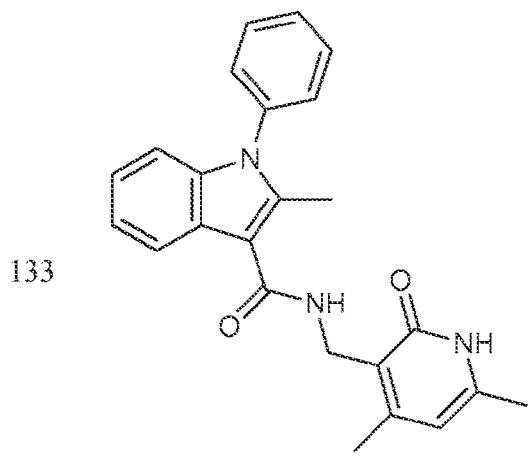
Figure 1:
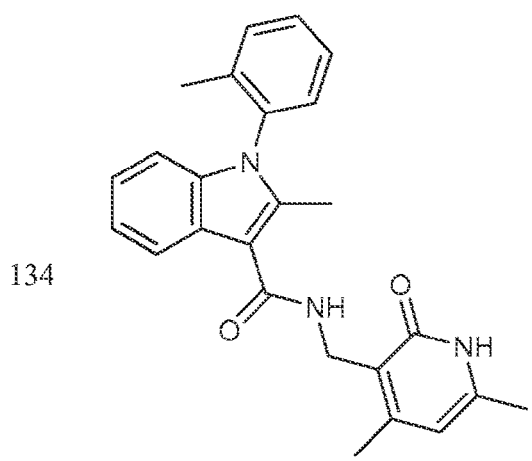
Figure 1:
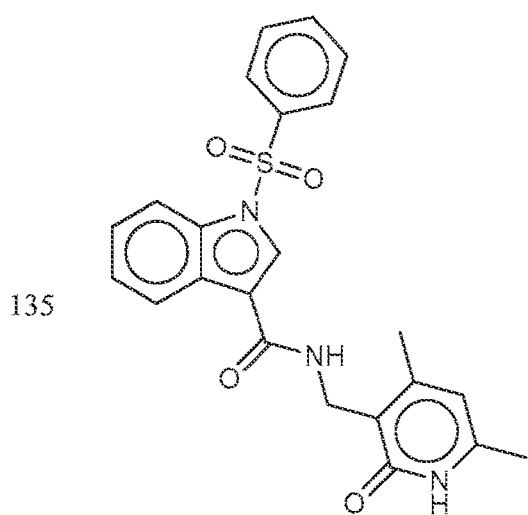
Figure 1:
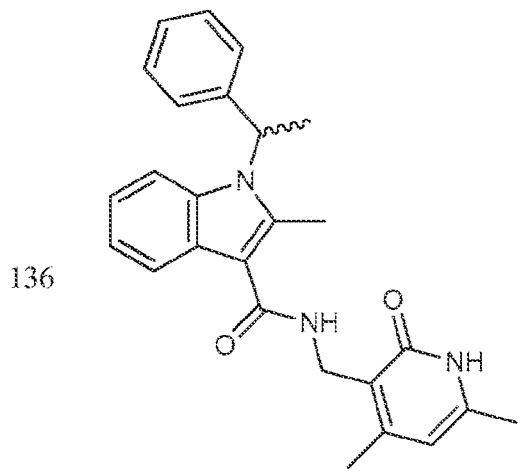
Figure 1:
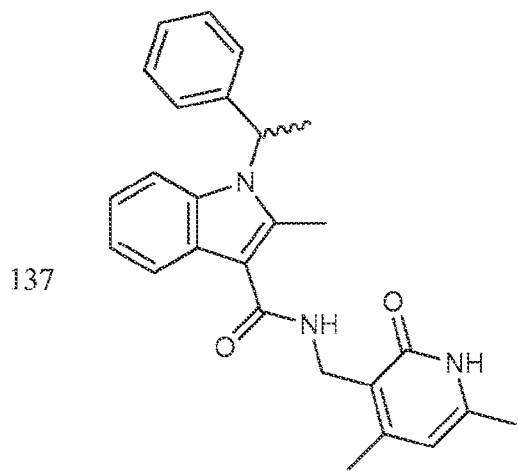
Figure 1:
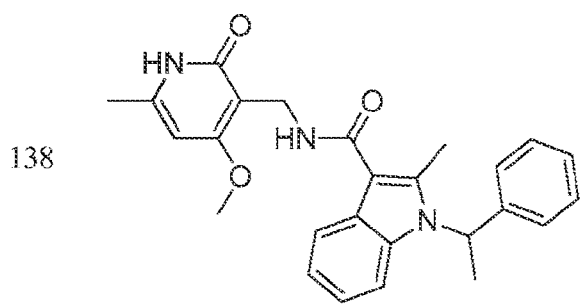
Figure 1:
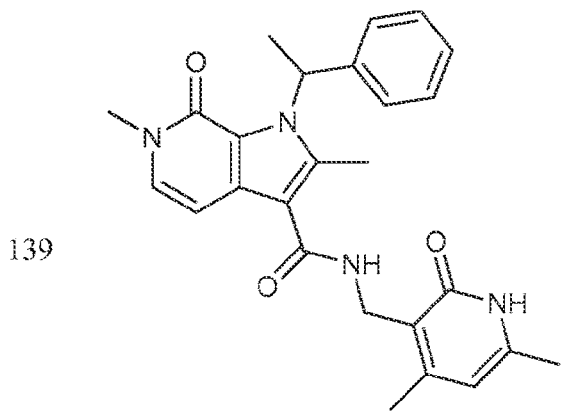
Figure 1:
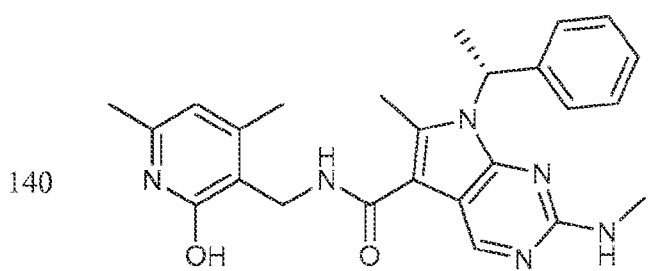
Figure 1:
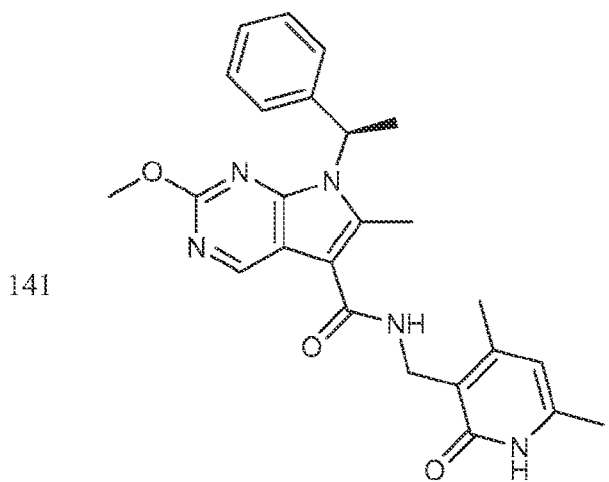
Figure 1:
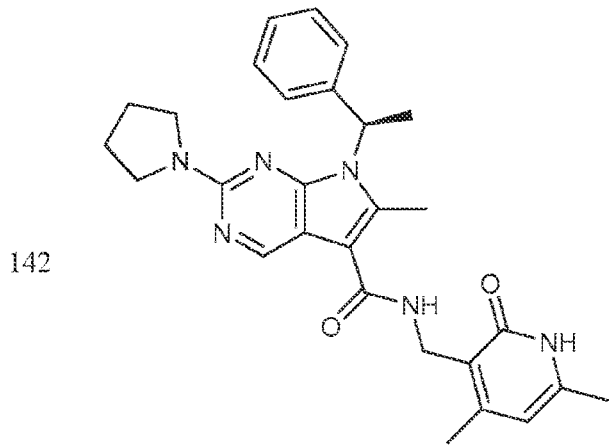
Figure 1:
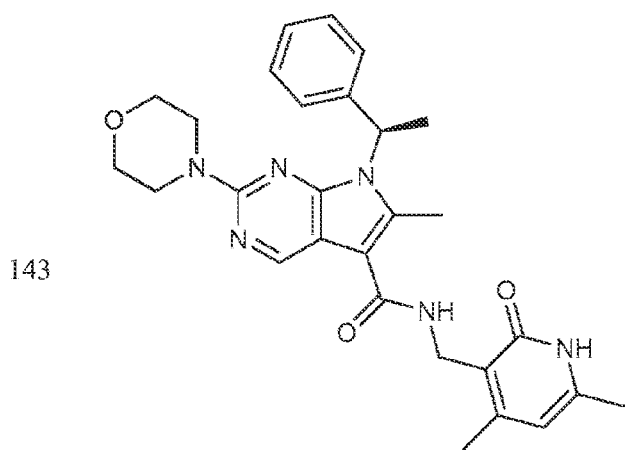
Figure 1:
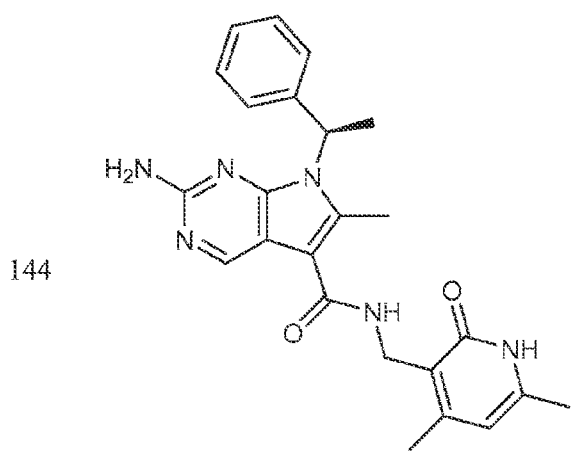
Figure 1:
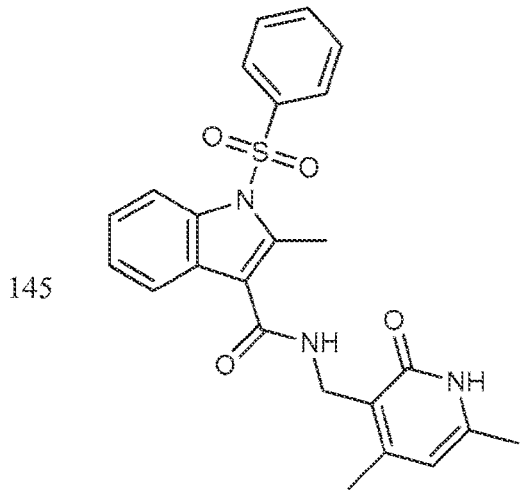
Figure 1:
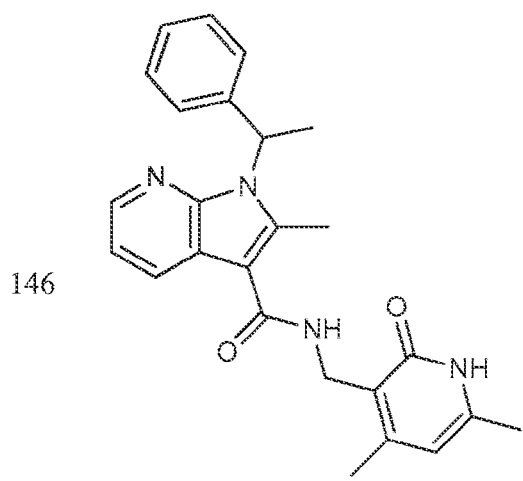
Figure 1:
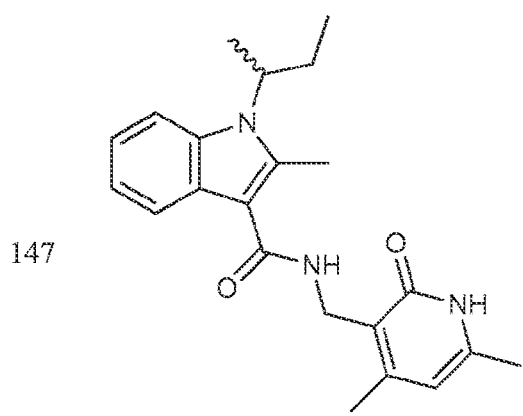
Figure 1:
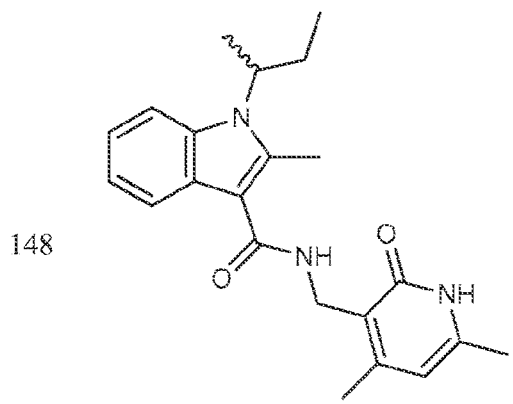
Figure 1:
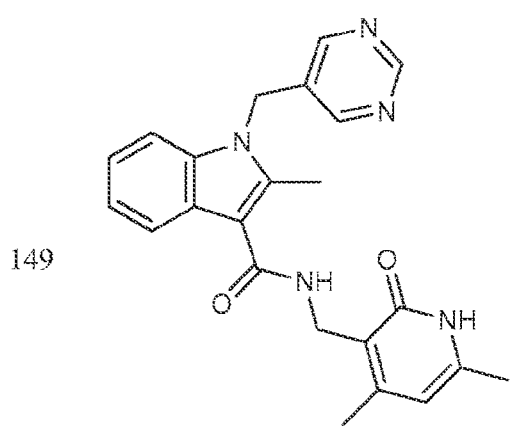
Figure 1:
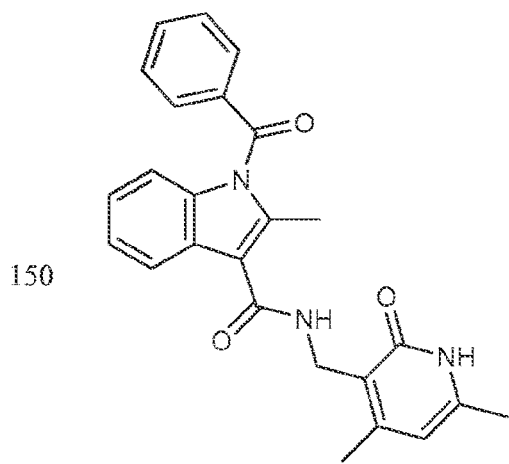
Figure 1:
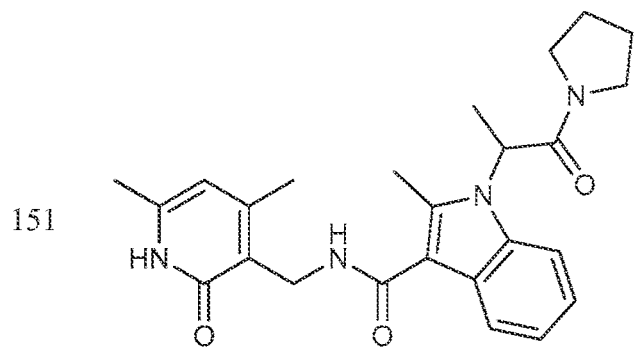
Figure 1:

Figure 1:

Figure 1:
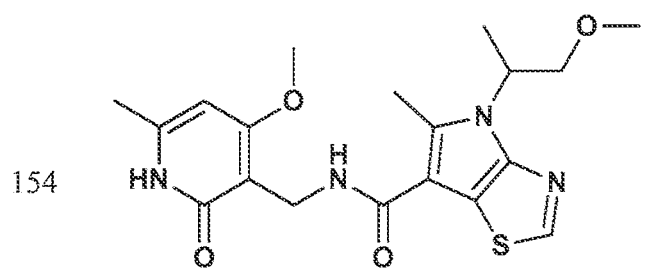
Figure 1:
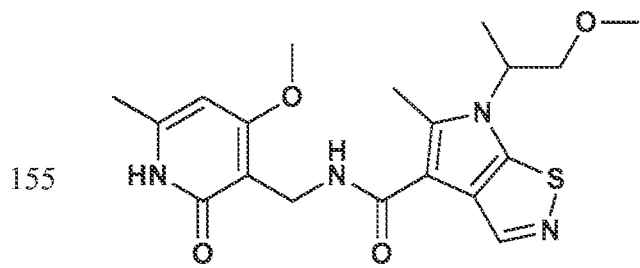
Figure 1:
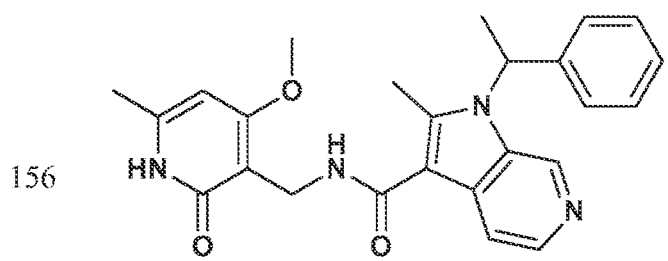
Figure 1:
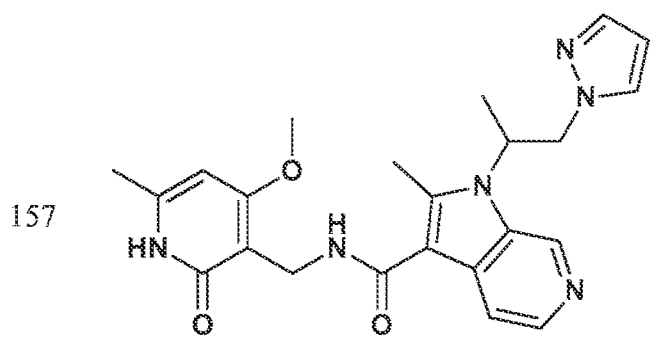
Figure 1:
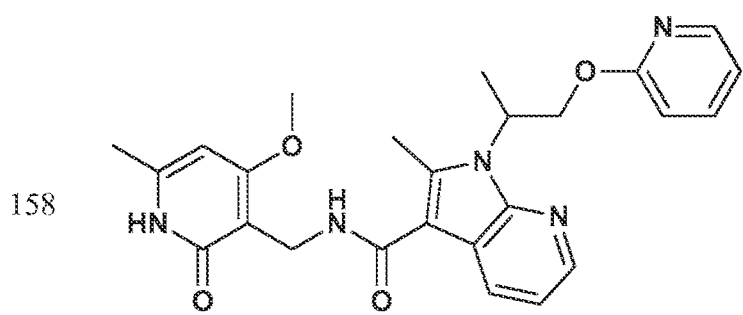
Figure 1:
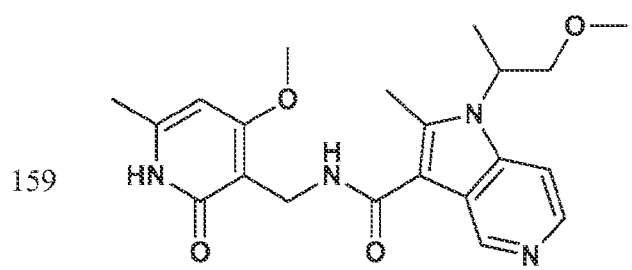
Figure 1:
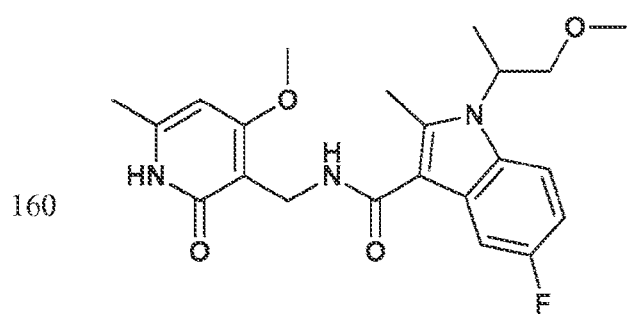
Figure 1:
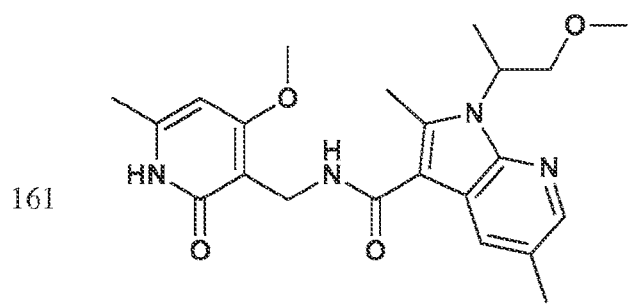
Figure 1:
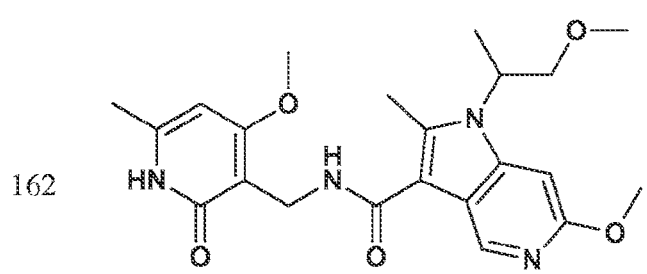
Figure 1:
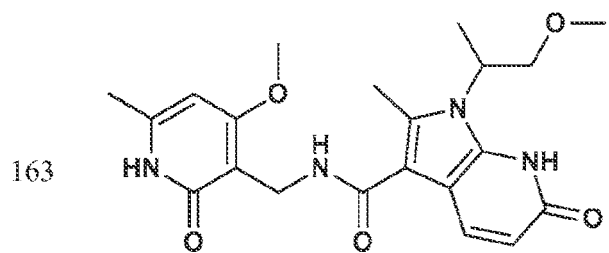
Figure 1:
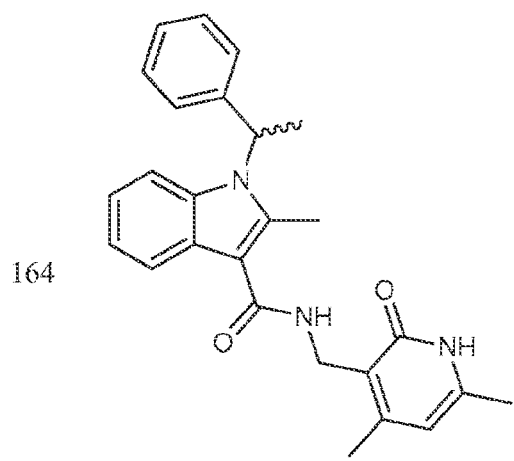
Figure 1:
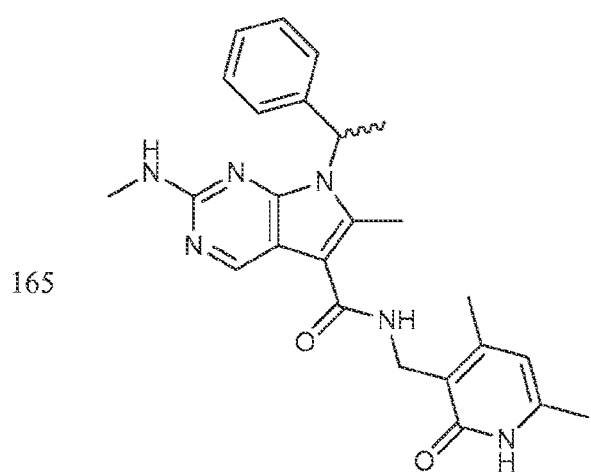
Figure 1:
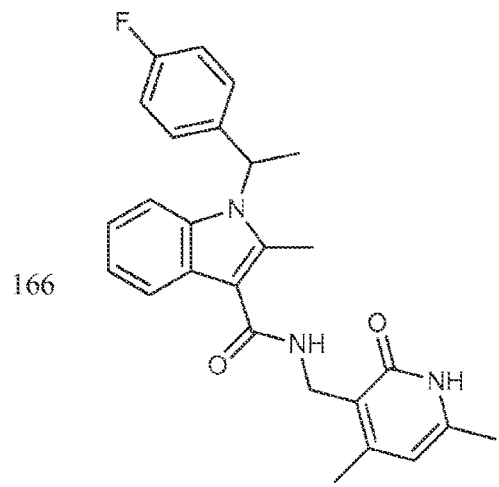
Figure 1:
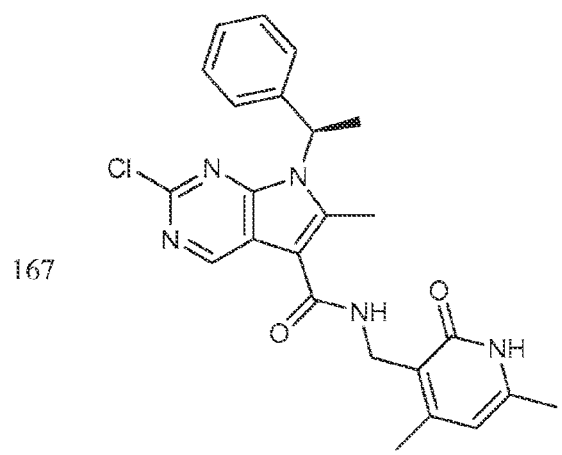
Figure 1:
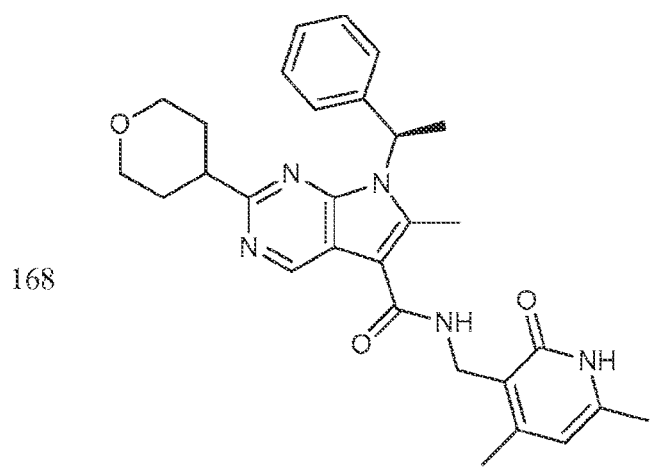
Figure 1:
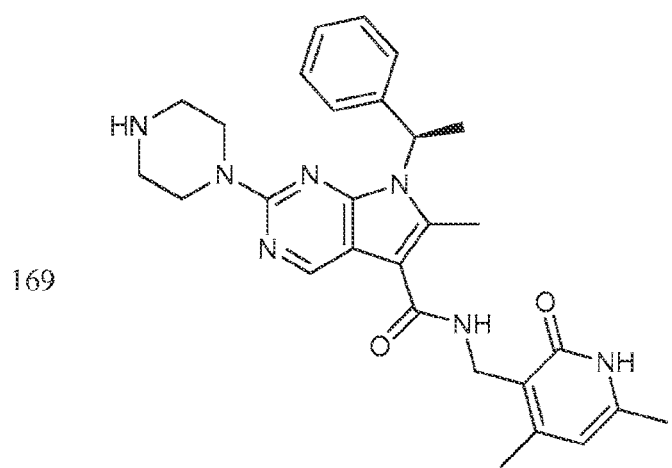
Figure 1:
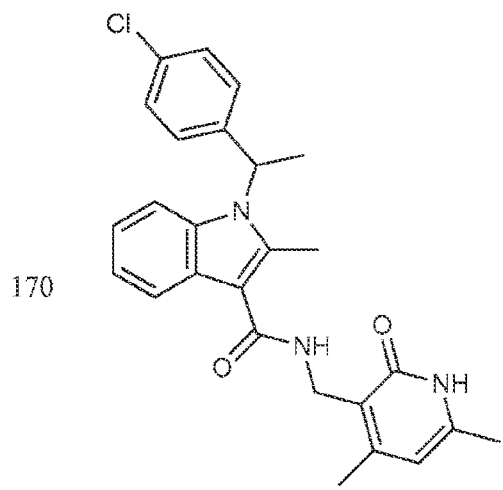
Figure 1:
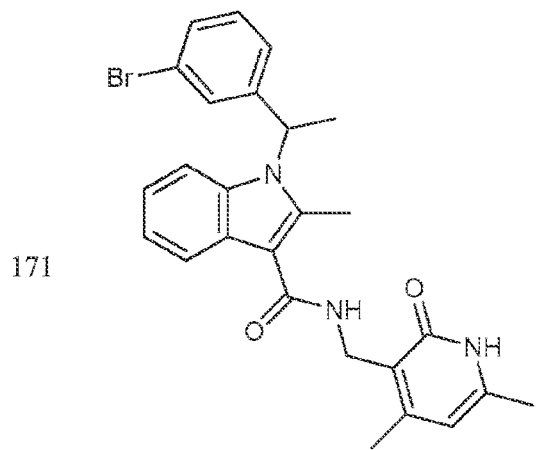
Figure 1:
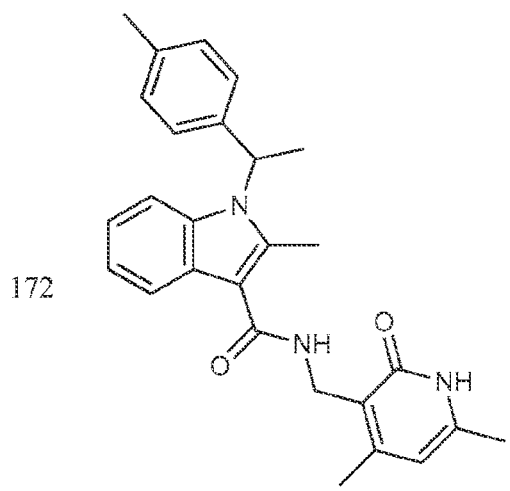
Figure 1:
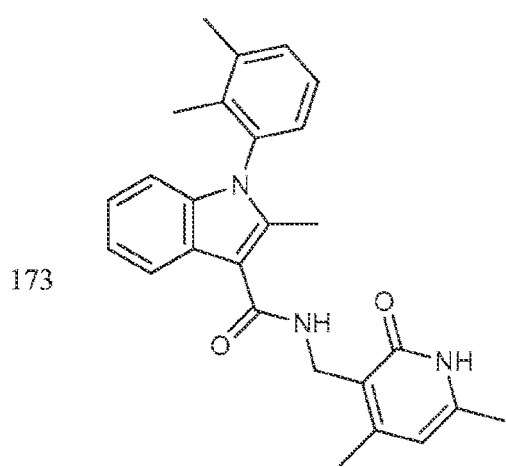
Figure 1:
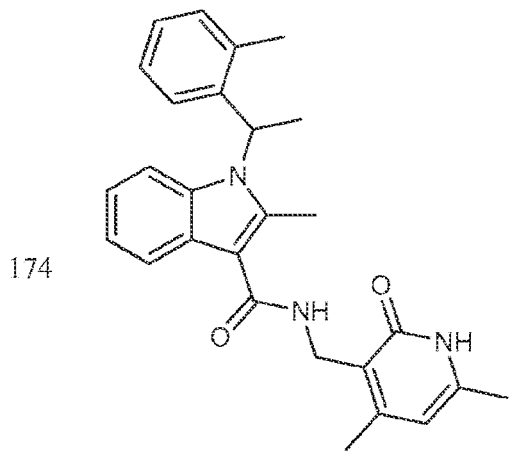
Figure 1:
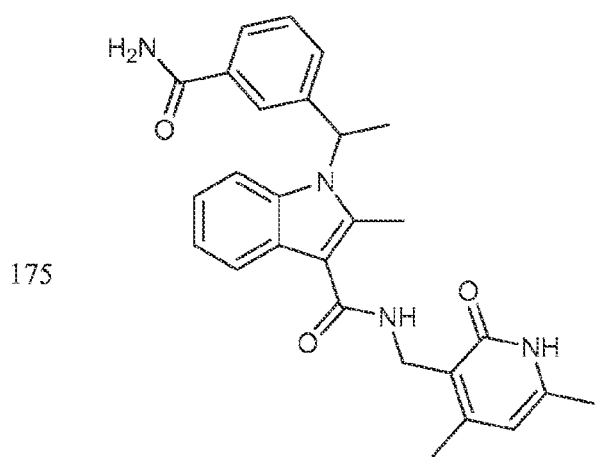
Figure 1:
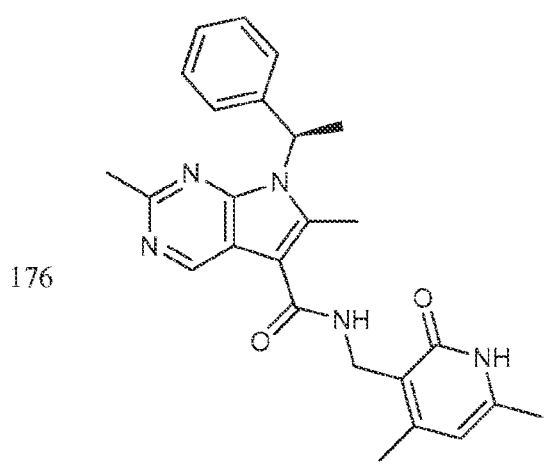
Figure 1:
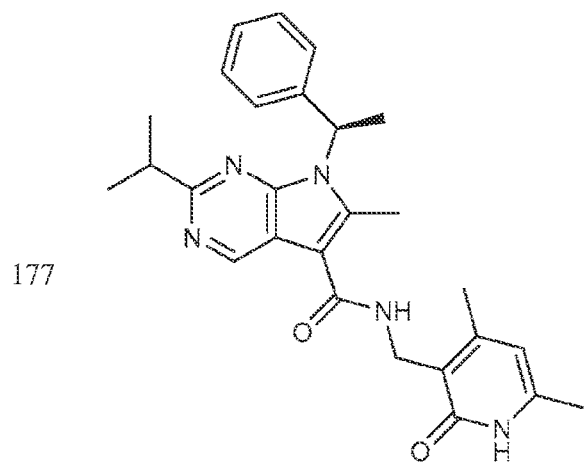
Figure 1:
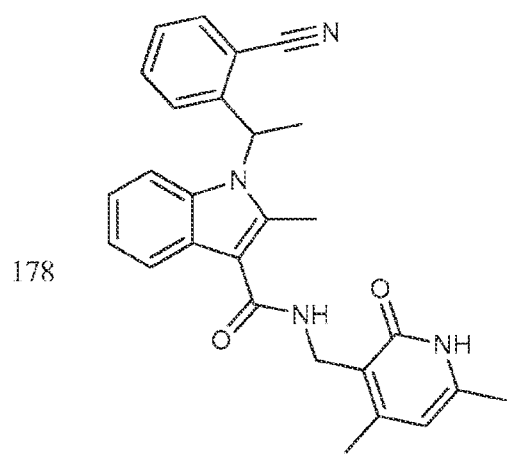
Figure 1:
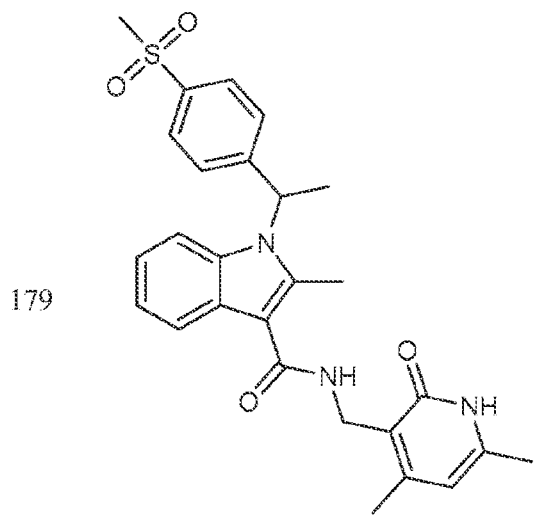
Figure 1:
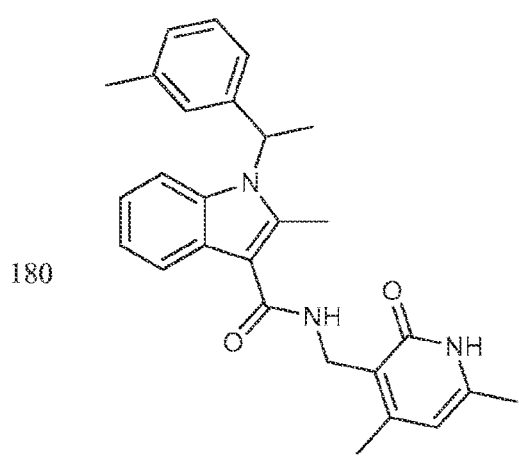
Figure 1:
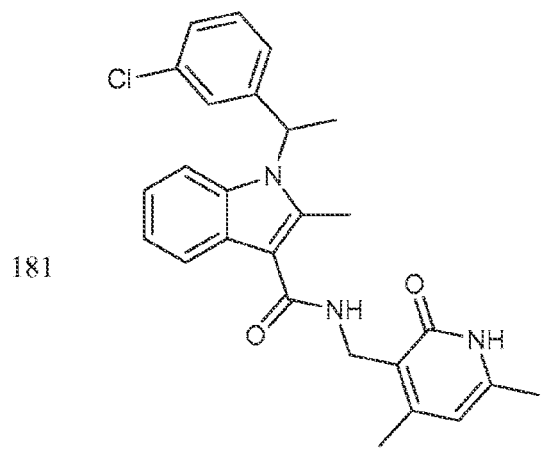
Figure 1:
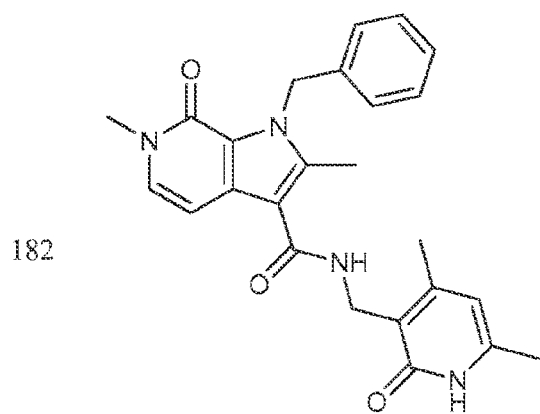
Figure 1:
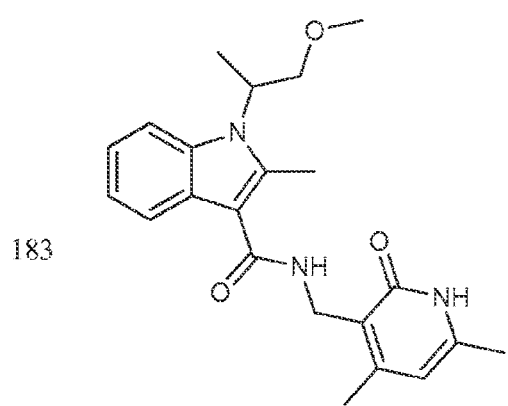
Figure 1:
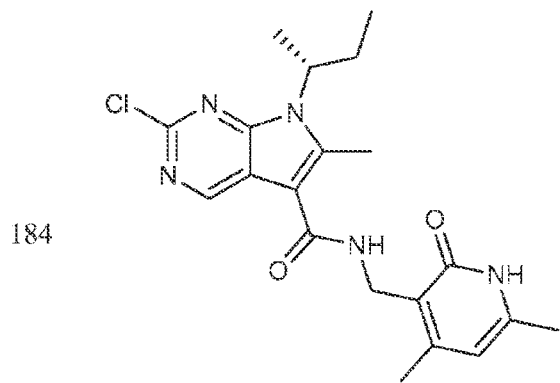
Figure 1:
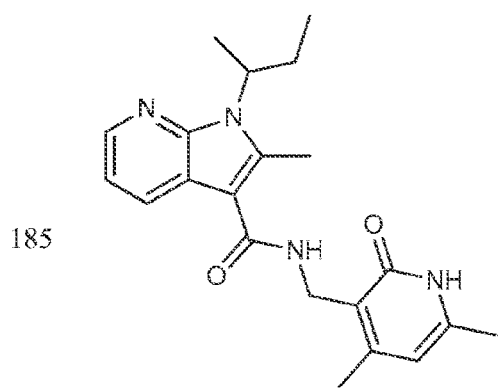
Figure 1:
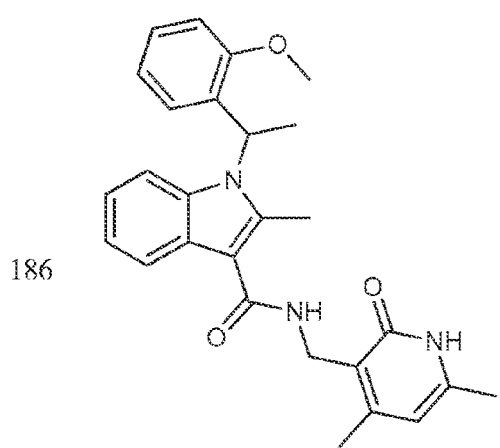
Figure 1:
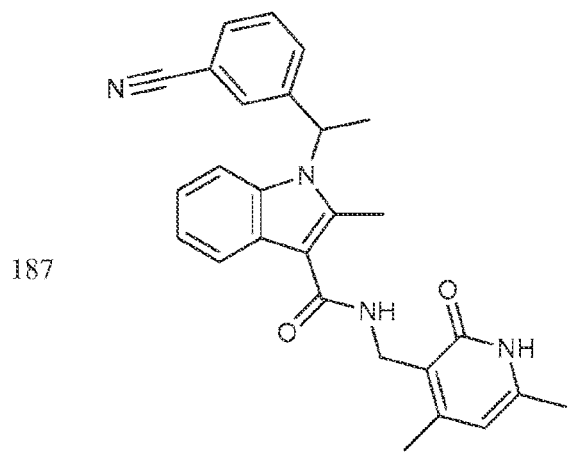
Figure 1:
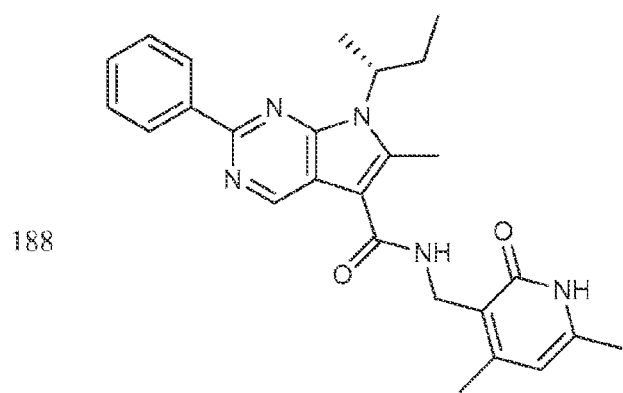
Figure 1:
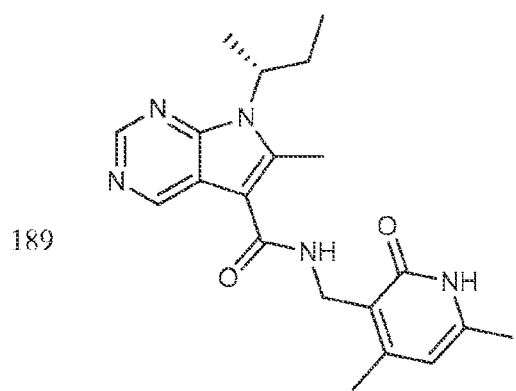
Figure 1:
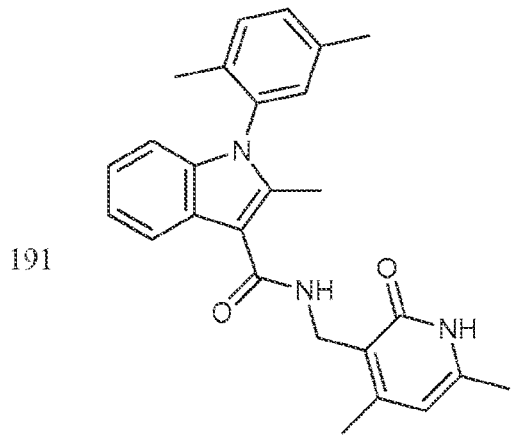
Figure 1:
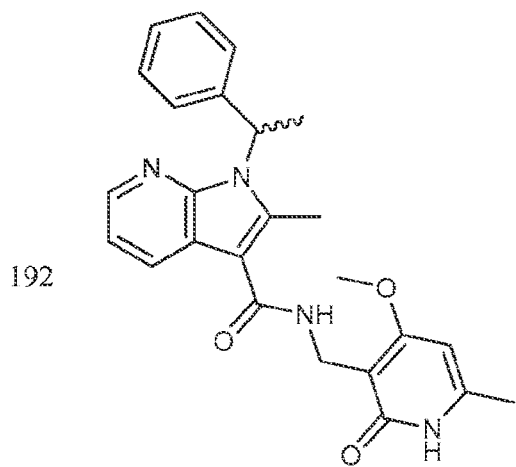
Figure 1:
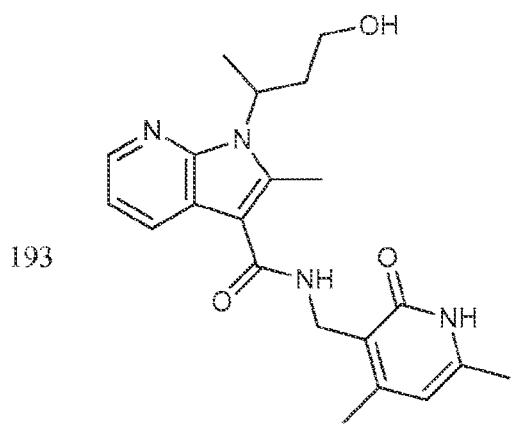
Figure 1:
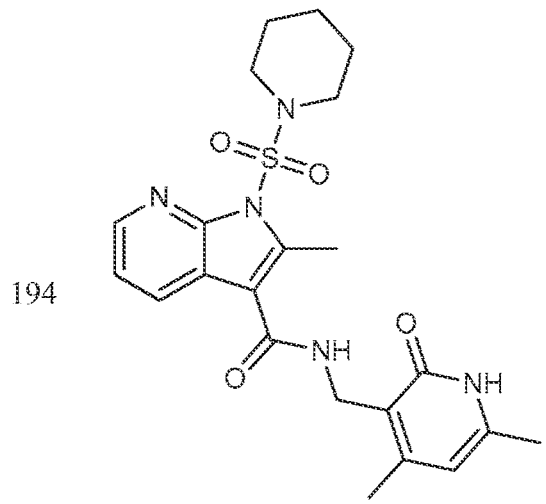
Figure 1:
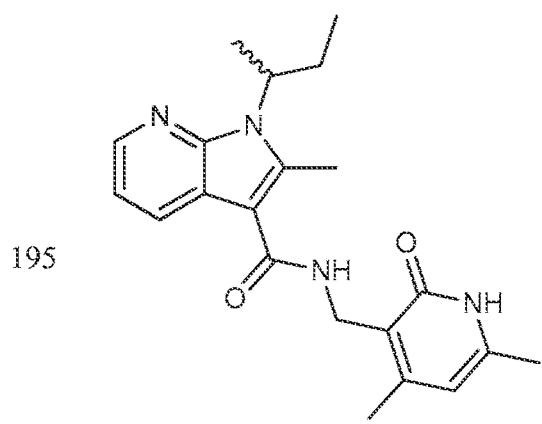
Figure 1:
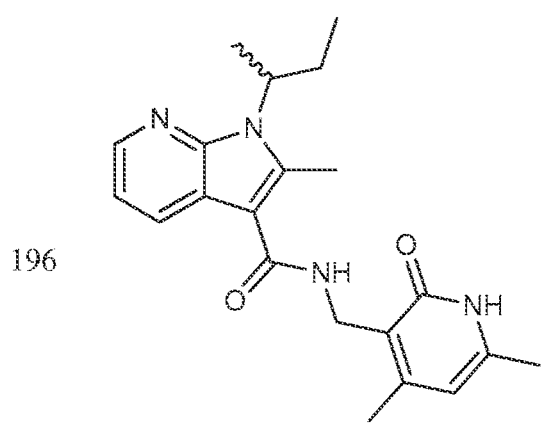
Figure 1:
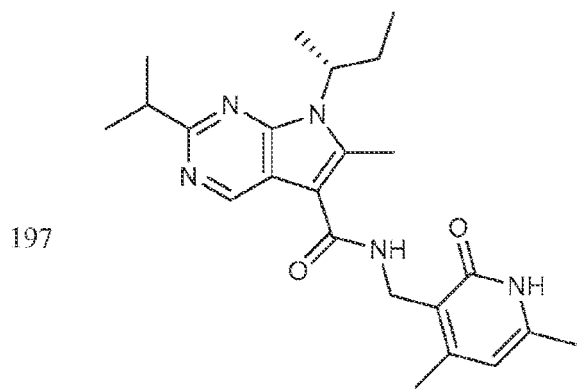
Figure 1:
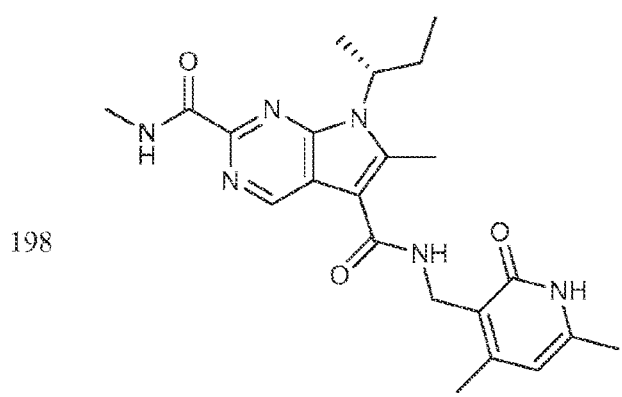
Figure 1:
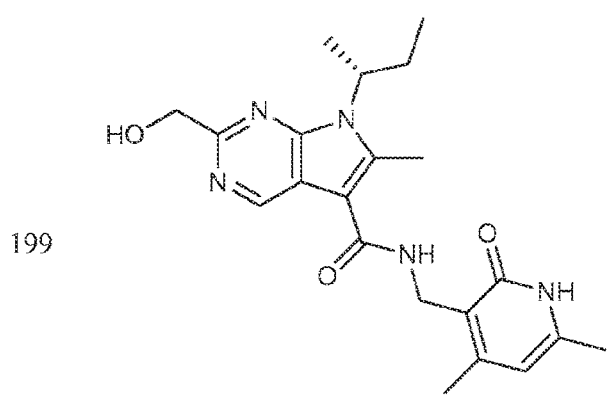
Figure 1:
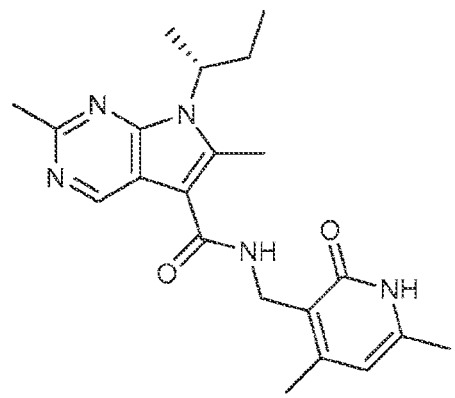
Figure 1:
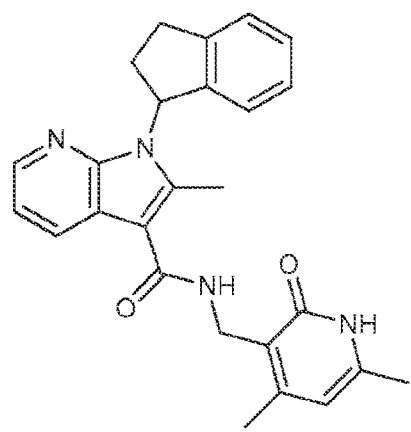
Figure 1:
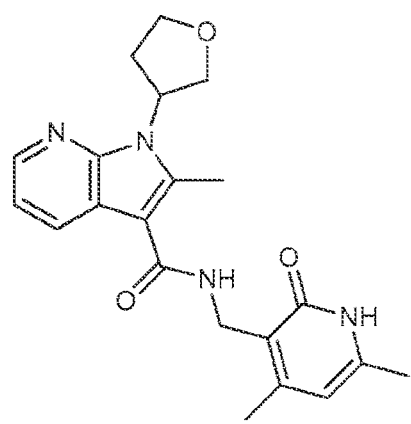
Figure 1:
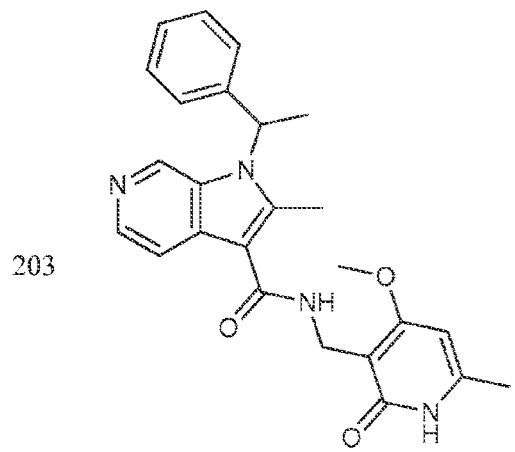
Figure 1:
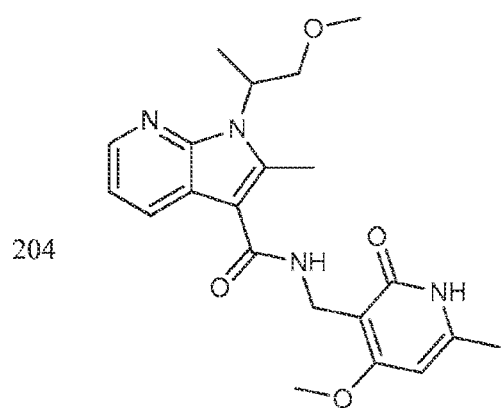
Figure 1:
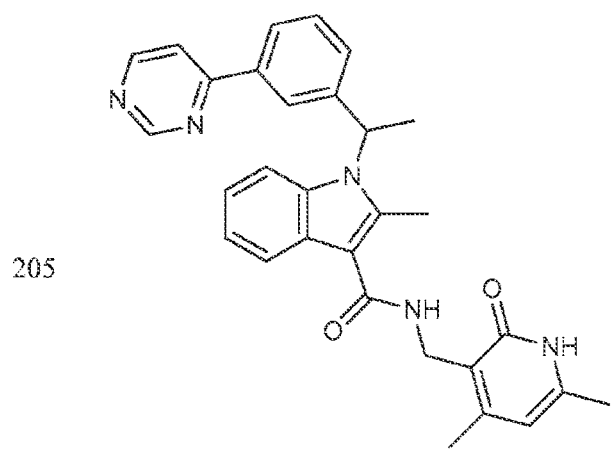
Figure 1:
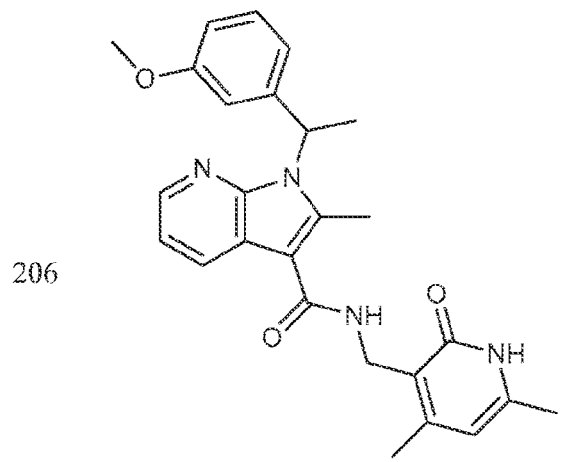
Figure 1:
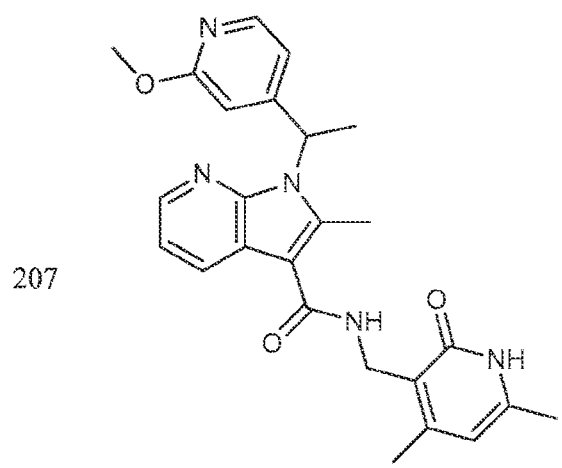
Figure 1:
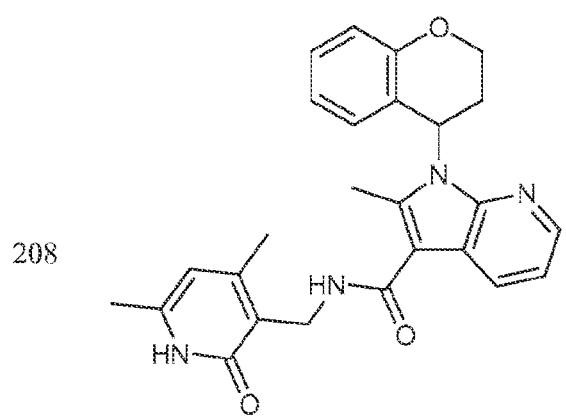
Figure 1:
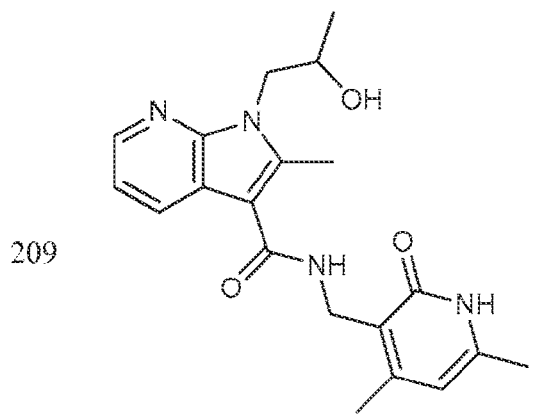
Figure 1:
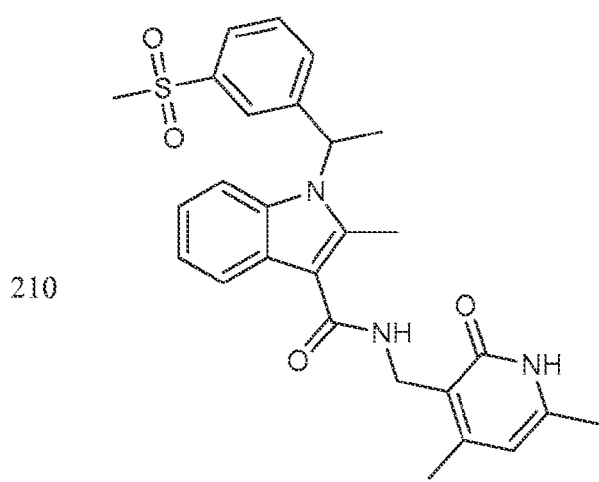
Figure 1:
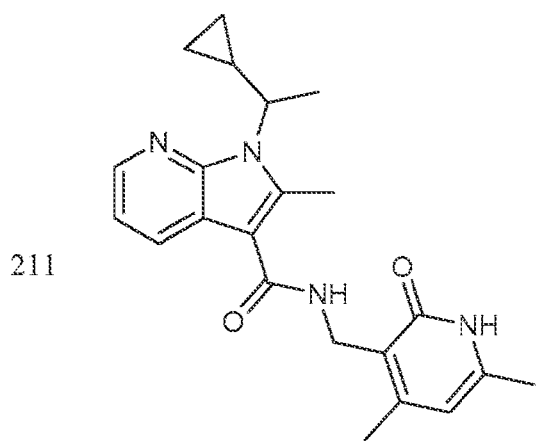
Figure 1:
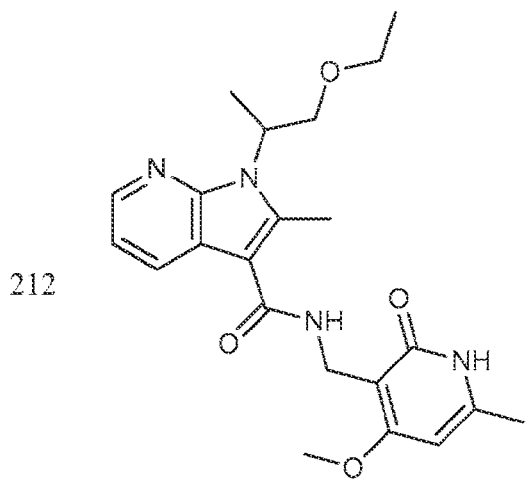
Figure 1:
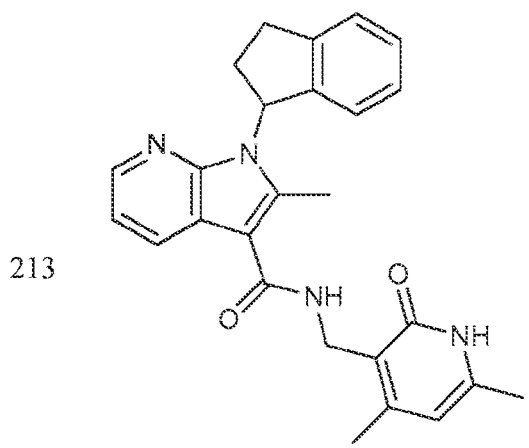
Figure 1:
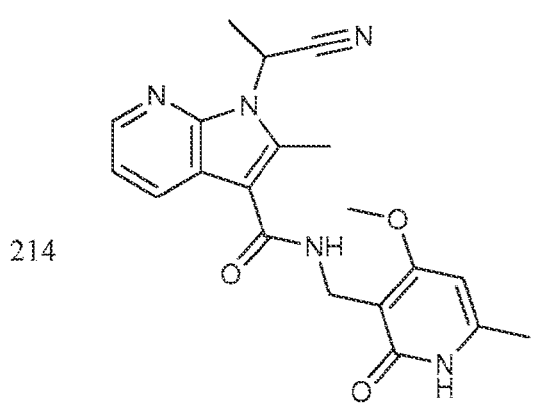
Figure 1:
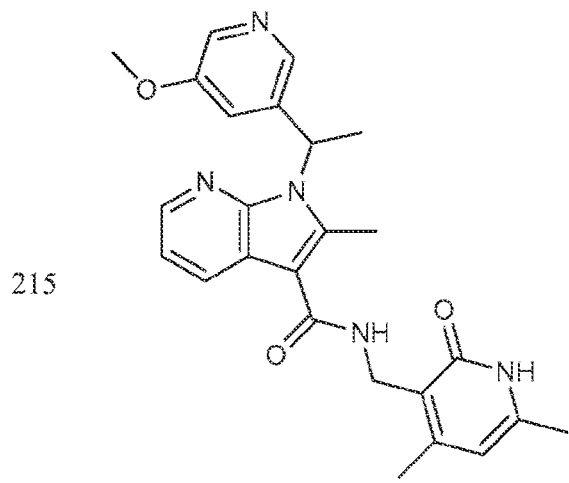
Figure 1:
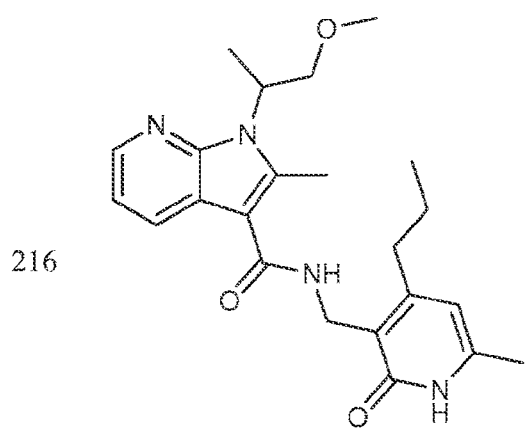
Figure 1:
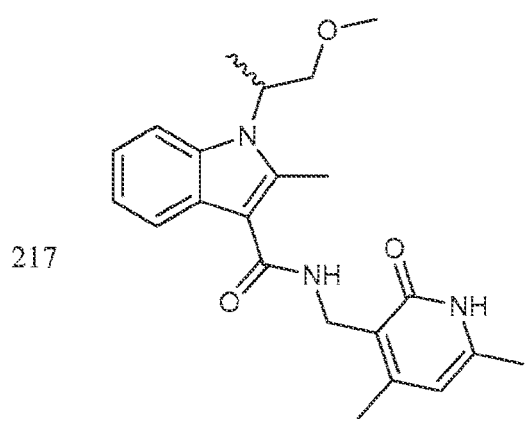
Figure 1:
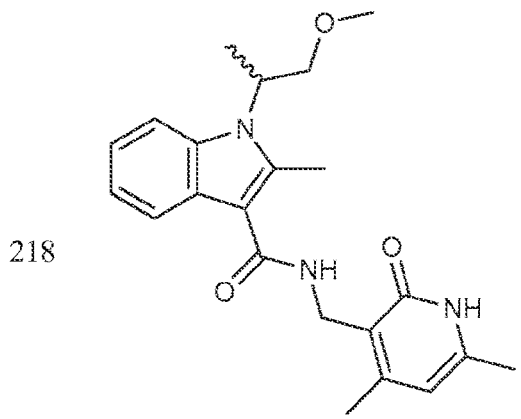
Figure 1:
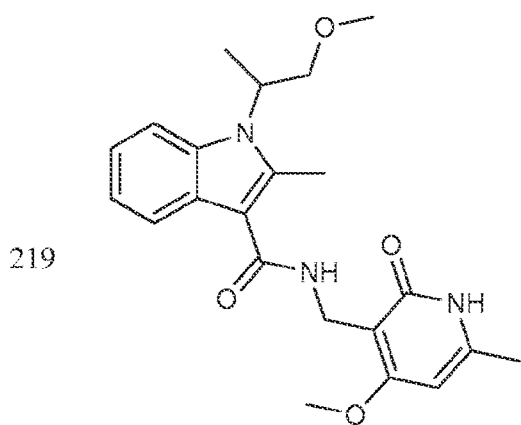
Figure 1:
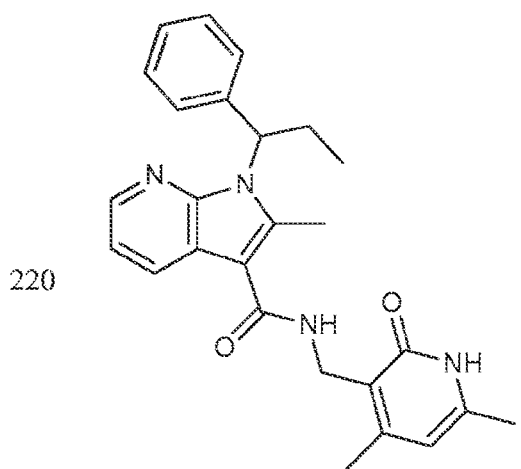
Figure 1:
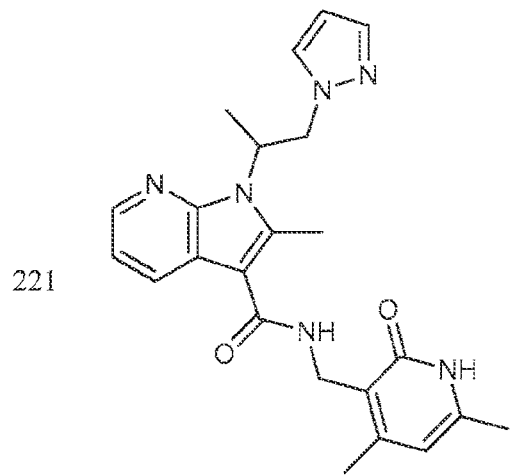
Figure 1:
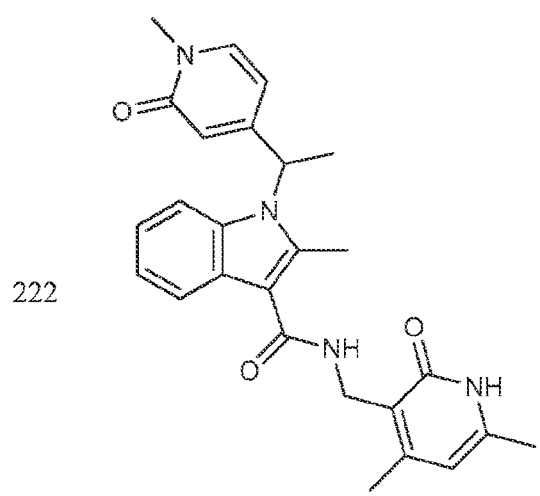
Figure 1:
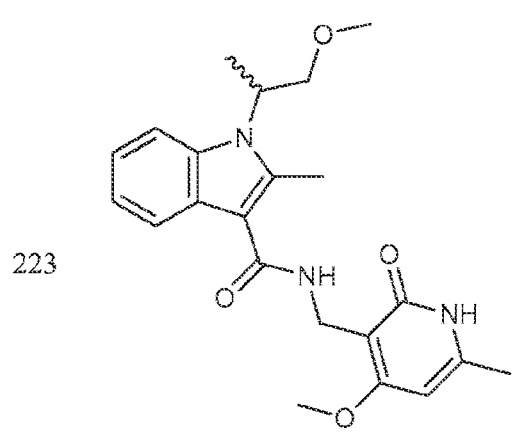
Figure 1:
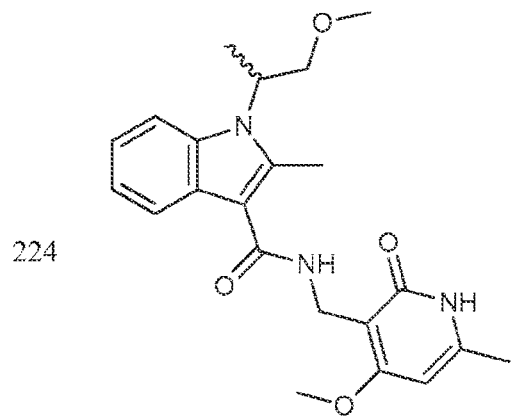
Figure 1:
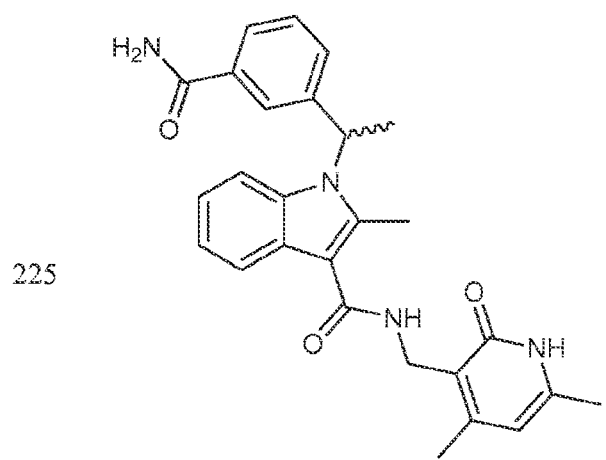
Figure 1:
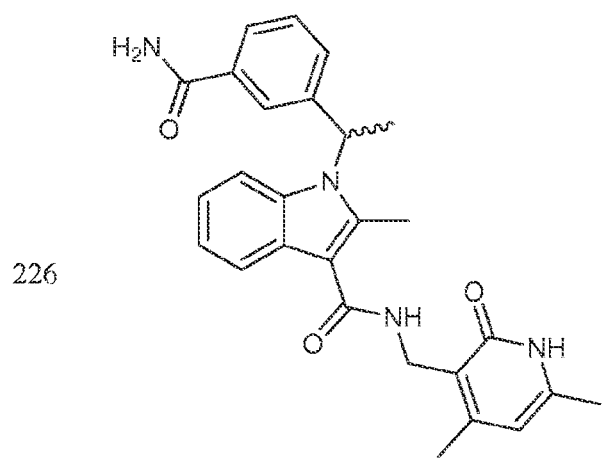
Figure 1:
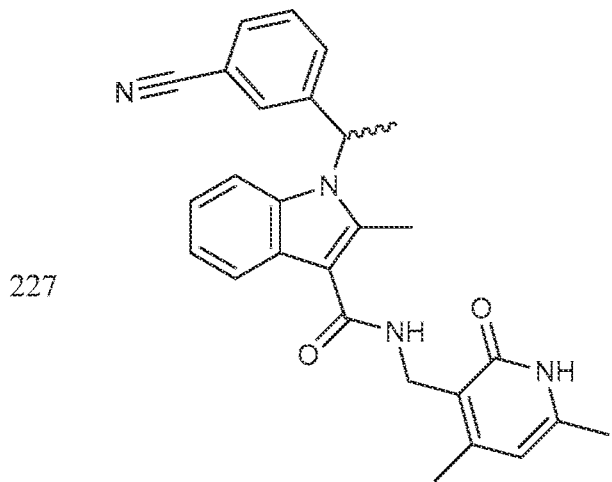
Figure 1:
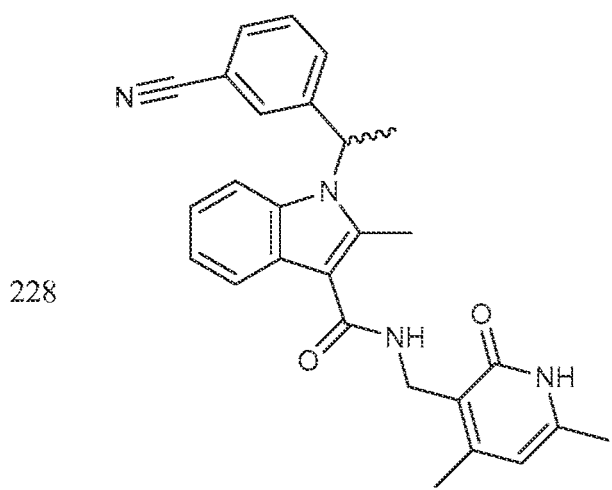
Figure 1:
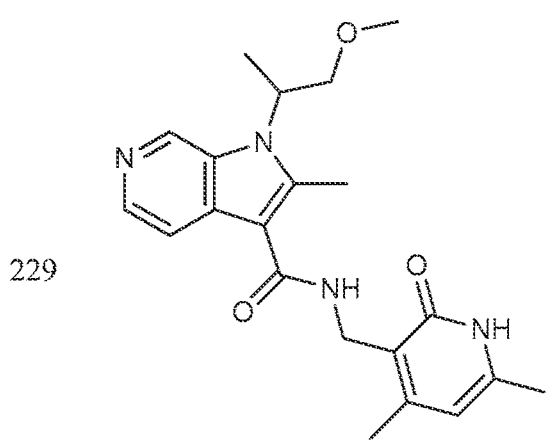
Figure 1:
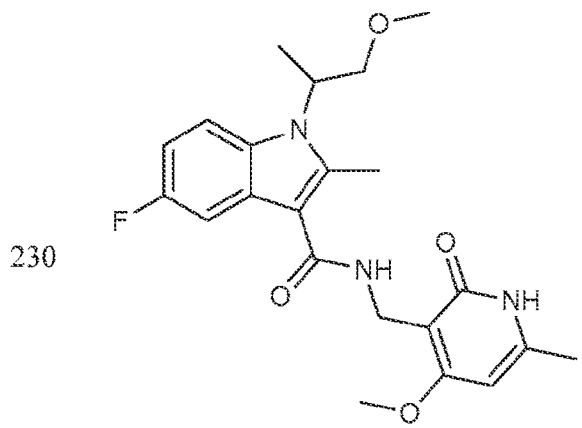
Figure 1:
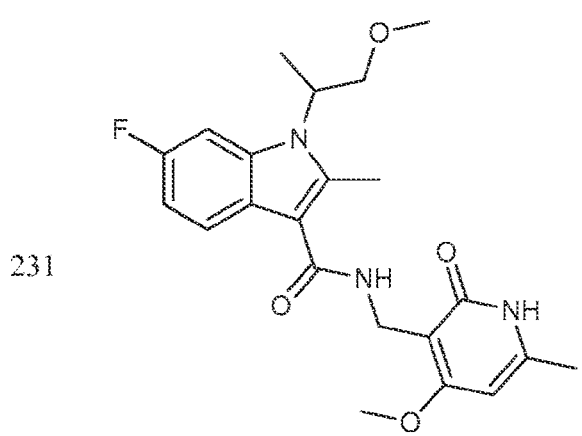
Figure 1:
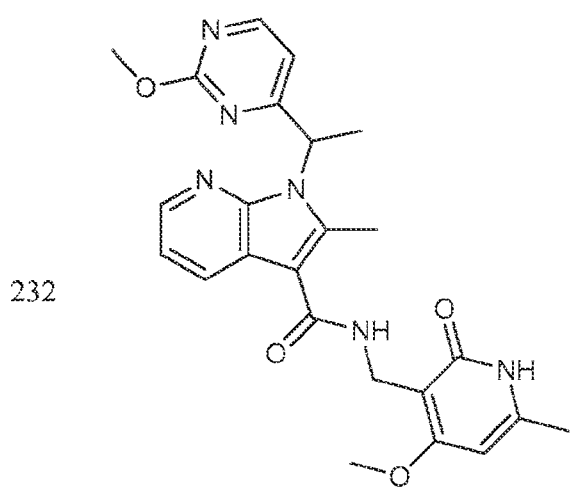
Figure 1:
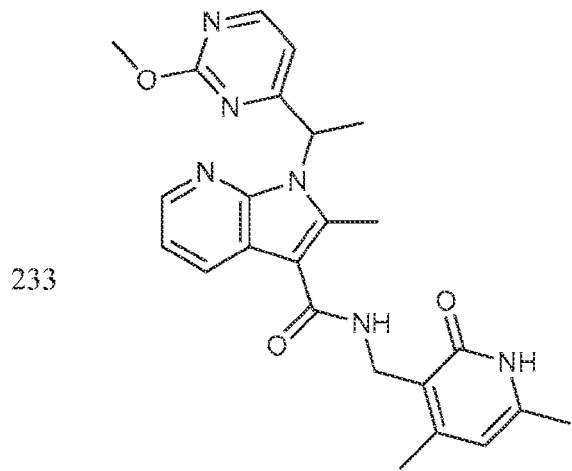
Figure 1:
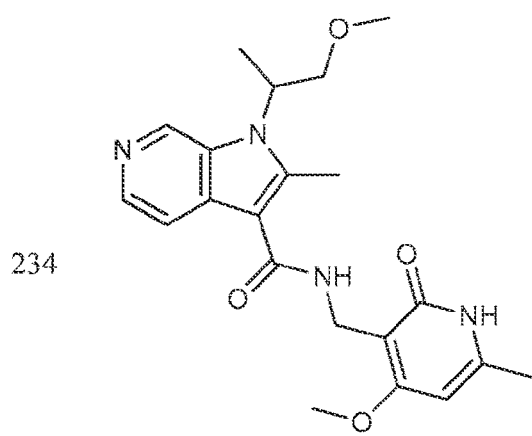
Figure 1:
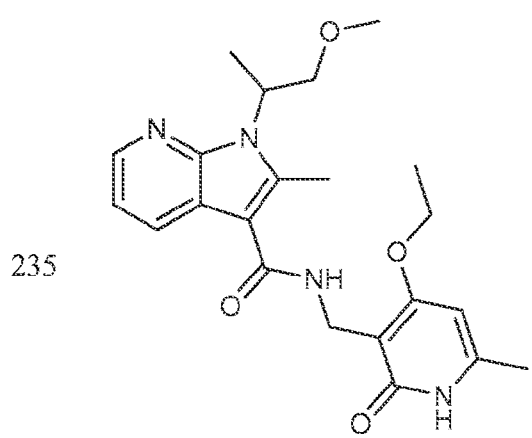
Figure 1:
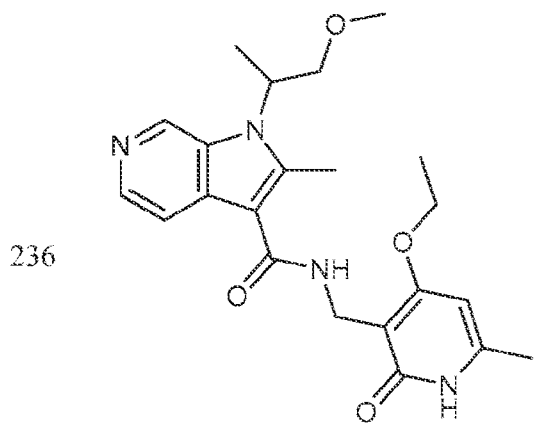
Figure 1:
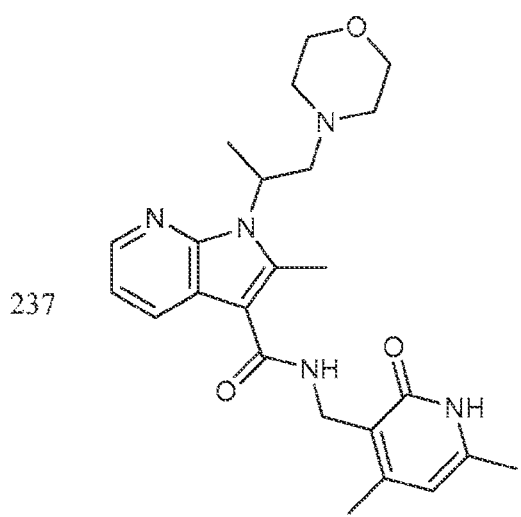
Figure 1:
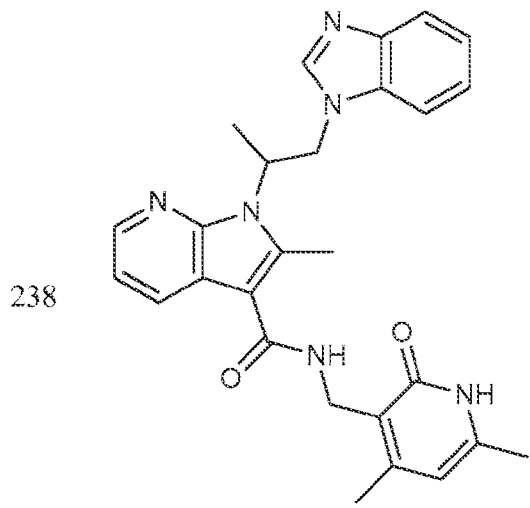
Figure 1:
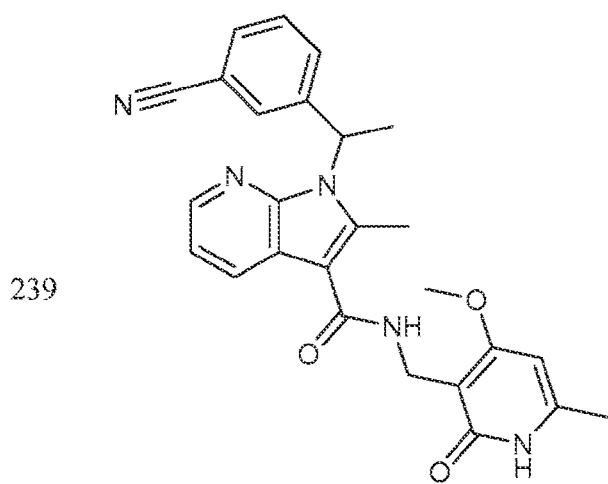
Figure 1:
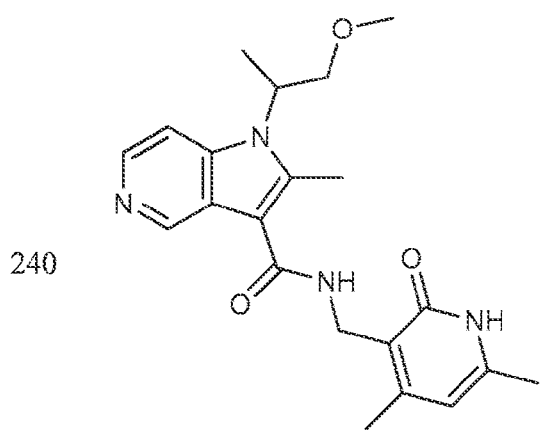
Figure 1:
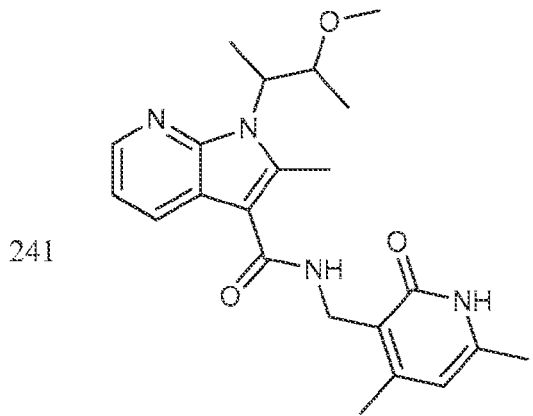
Figure 1:
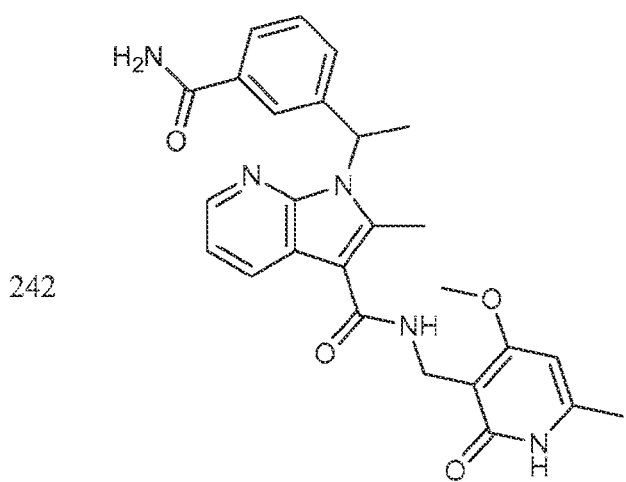
Figure 1:
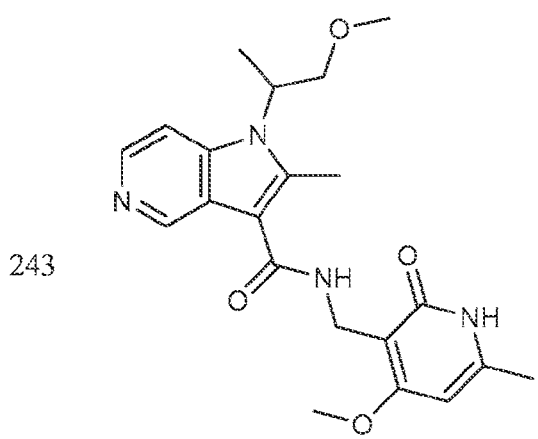
Figure 1:
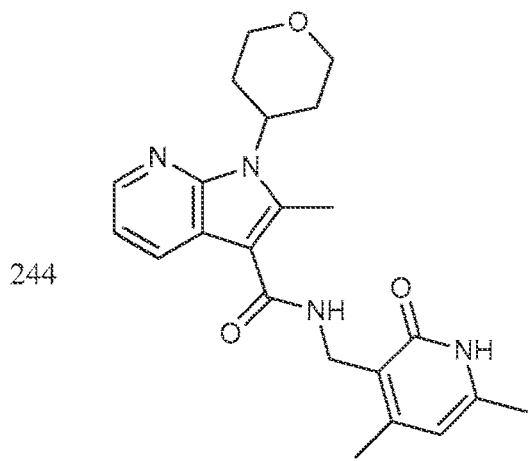
Figure 1:
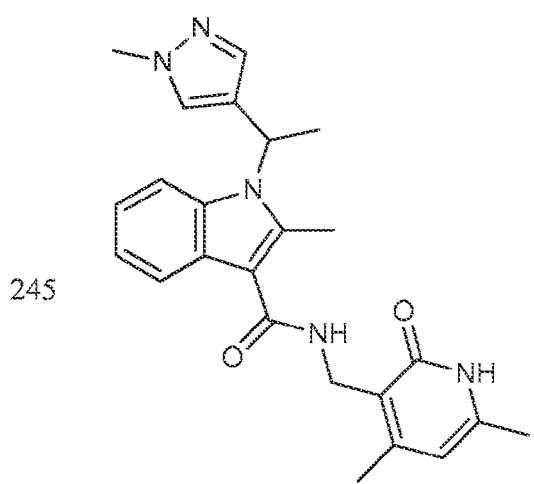
Figure 1:
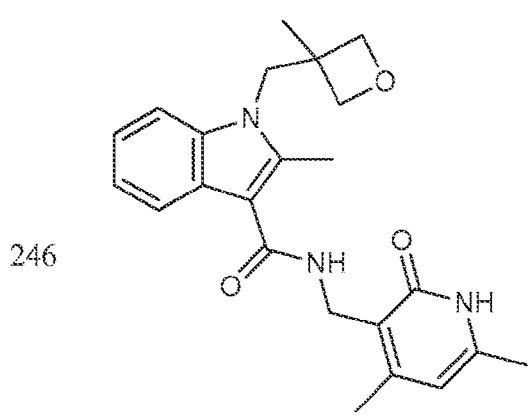
Figure 1:
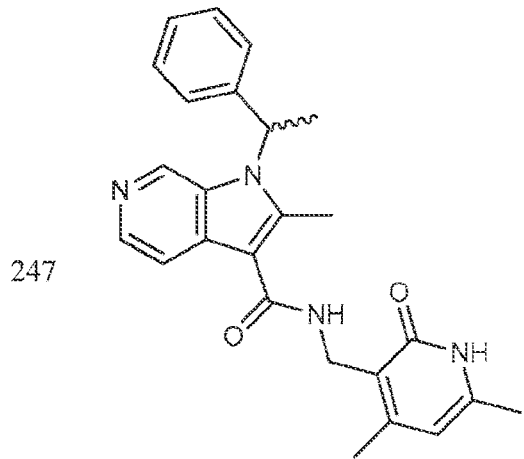
Figure 1:
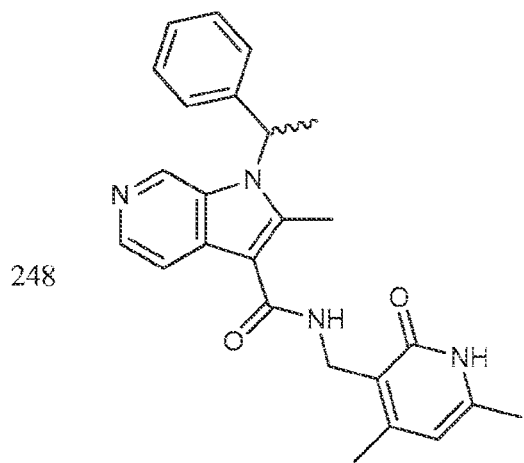
Figure 1:
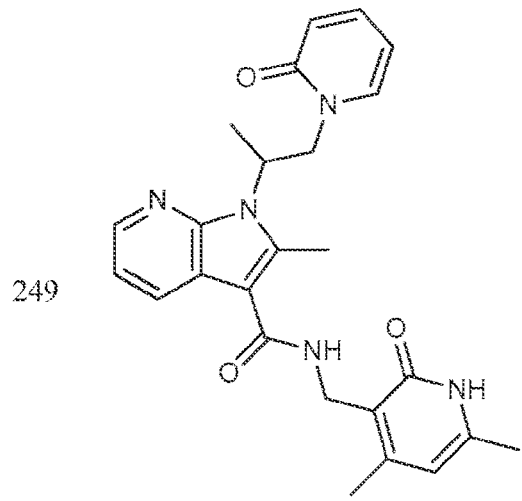
Figure 1:
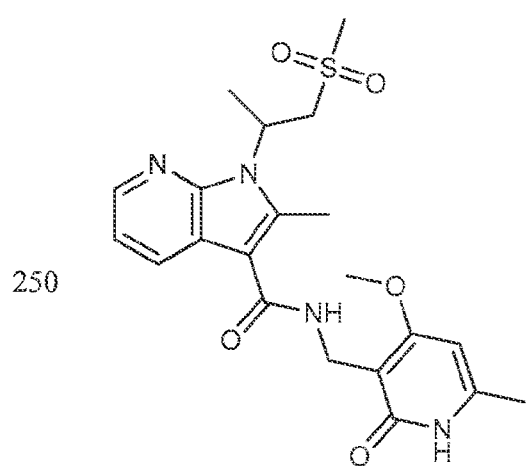
Figure 1:
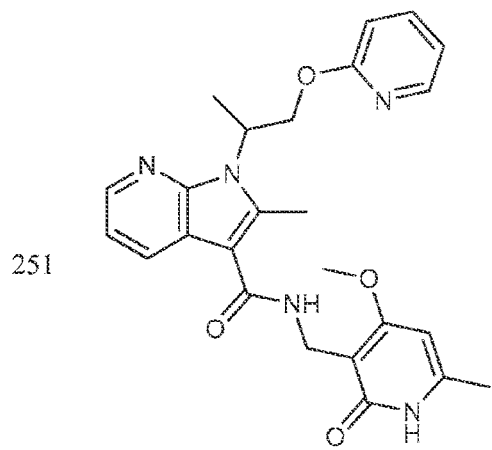
Figure 1:
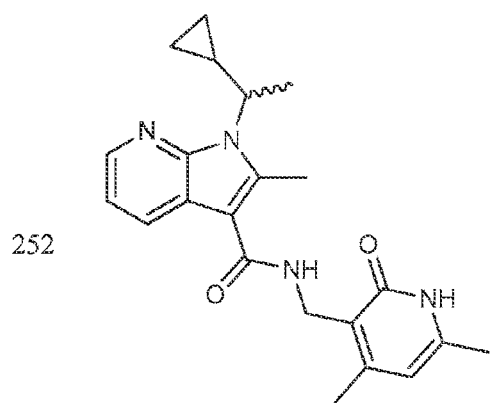
Figure 1:
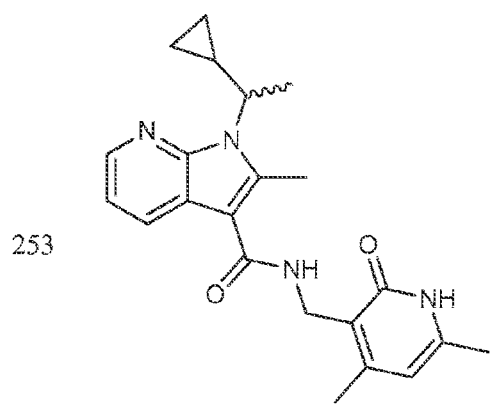
Figure 1:
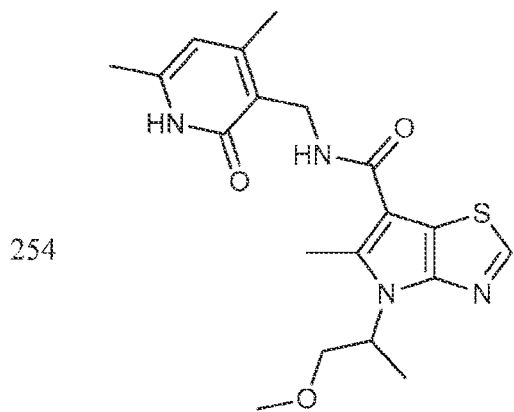
Figure 1:
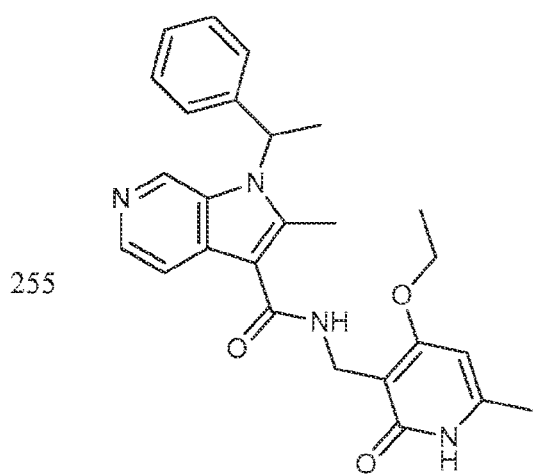
Figure 1:
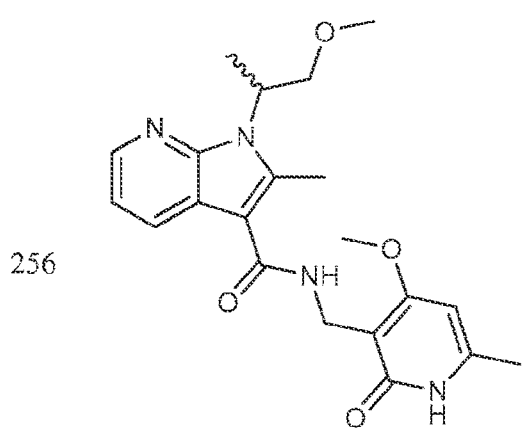
Figure 1:
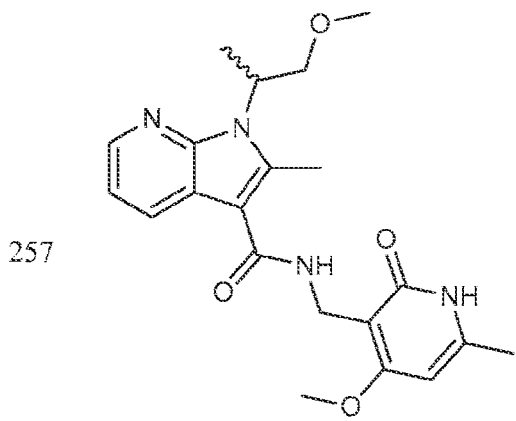
Figure 1:
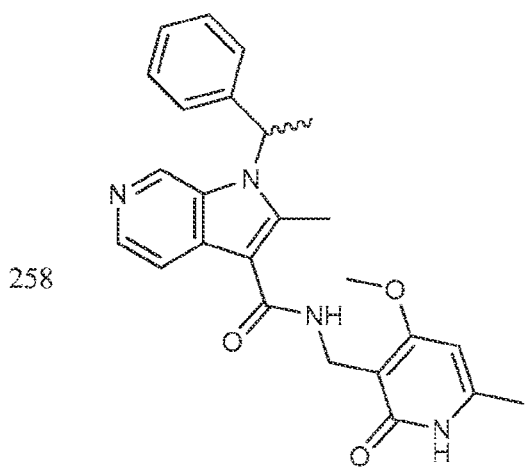
Figure 1:

Figure 1:
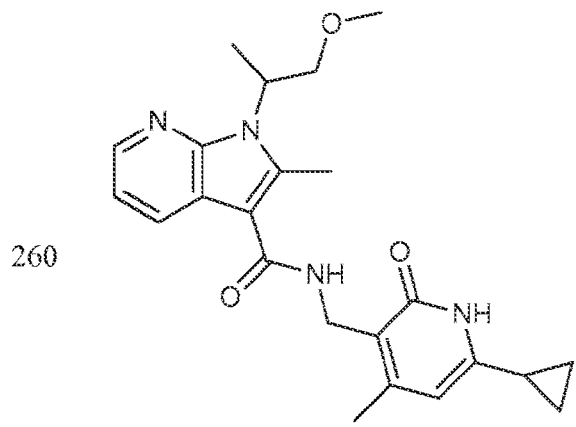
Figure 1:
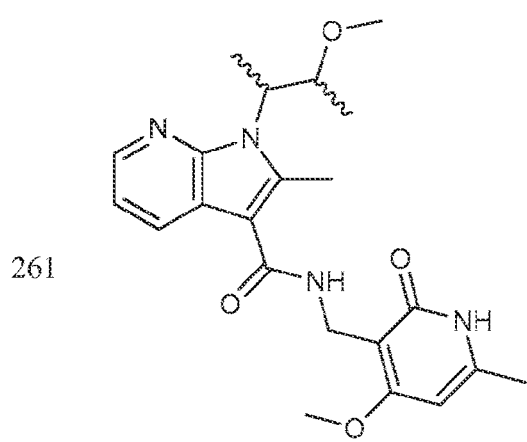
Figure 1:
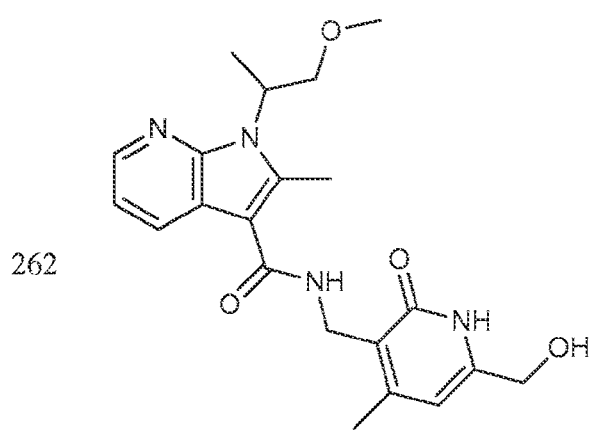
Figure 1:
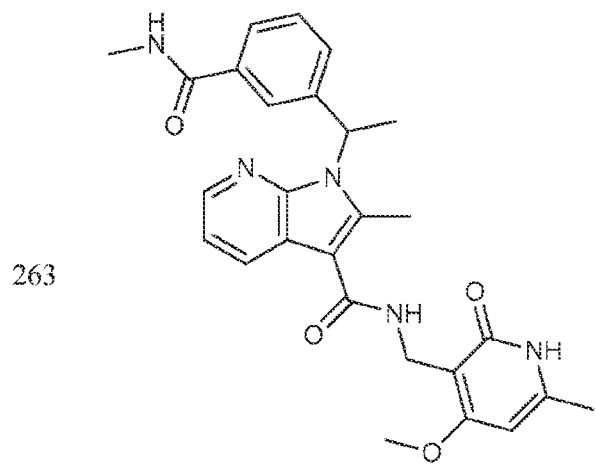
Figure 1:
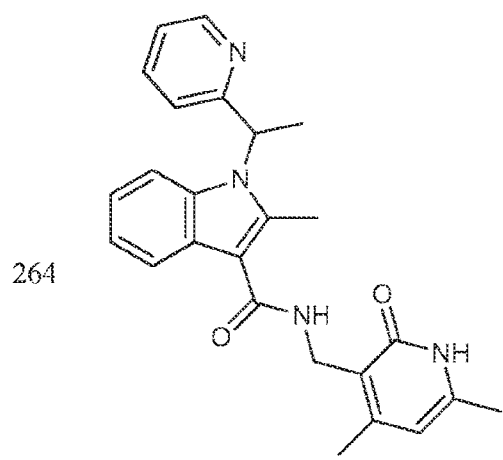
Figure 1:
Figure 1:
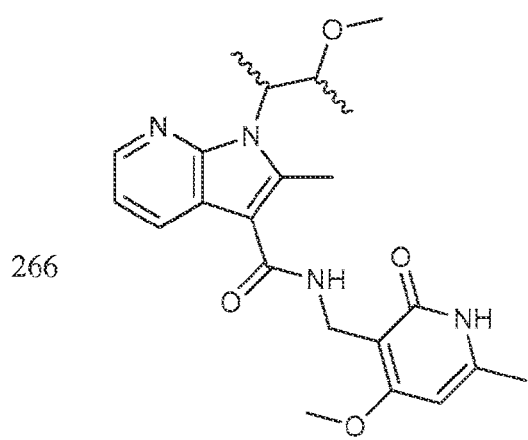
Figure 1:
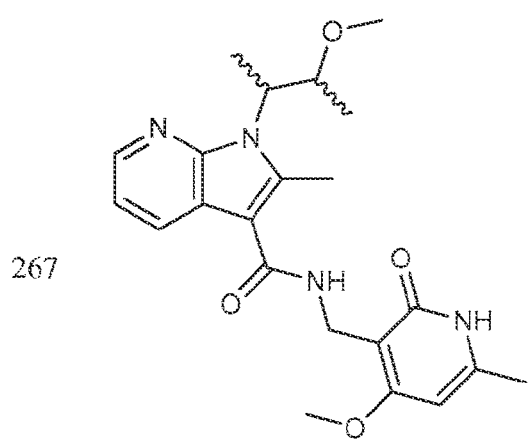
Figure 1:
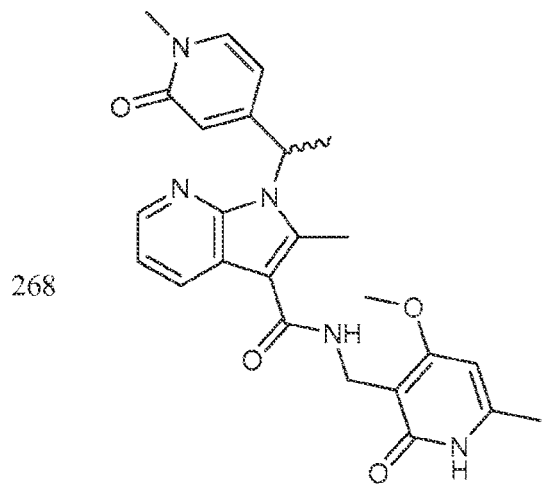
Figure 1:
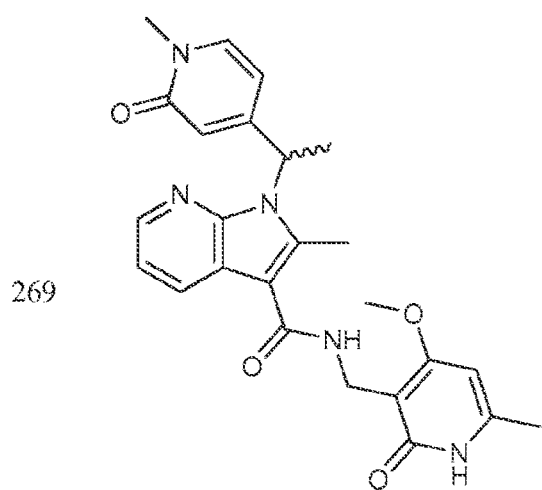
Figure 1:
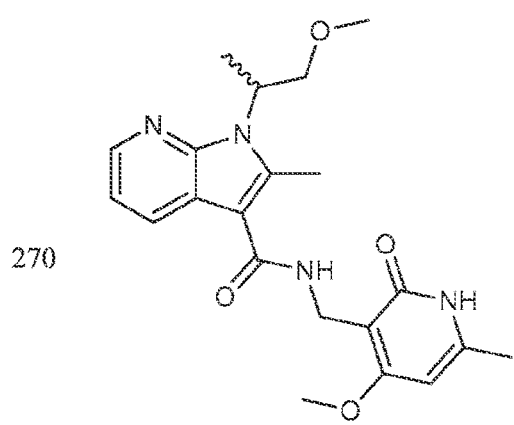
Figure 1:
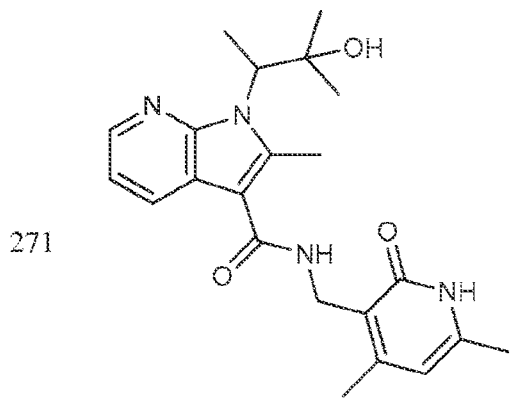
Figure 1:
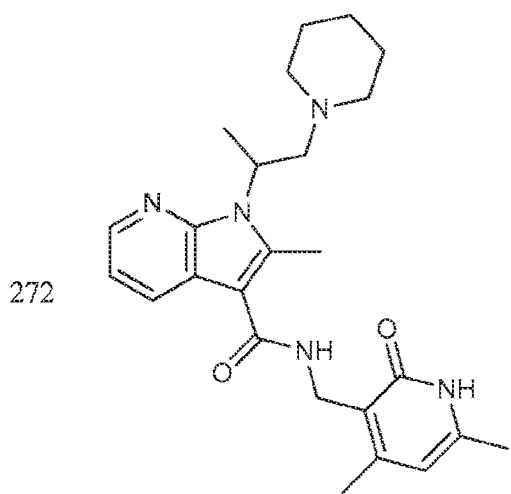
Figure 1:
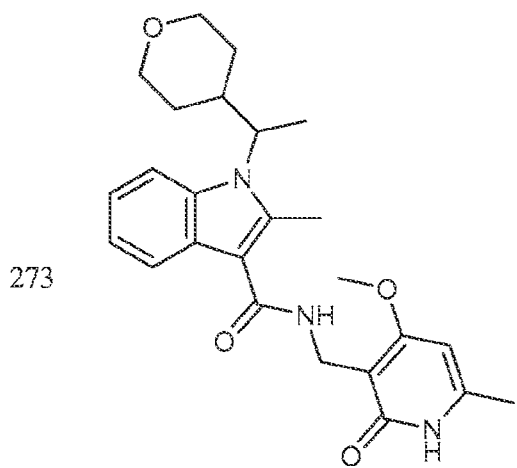
Figure 1:
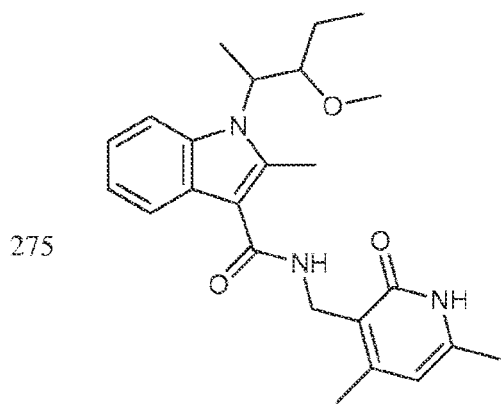
Figure 1:
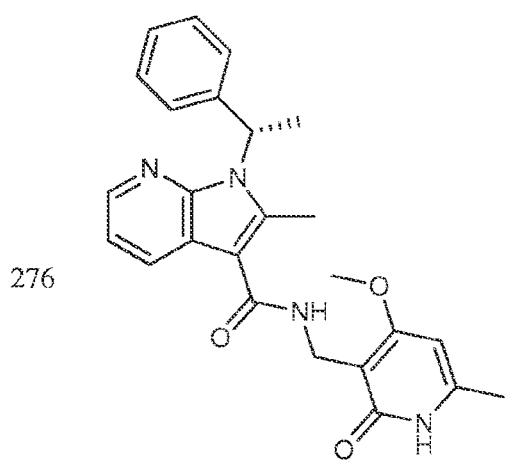
Figure 1:
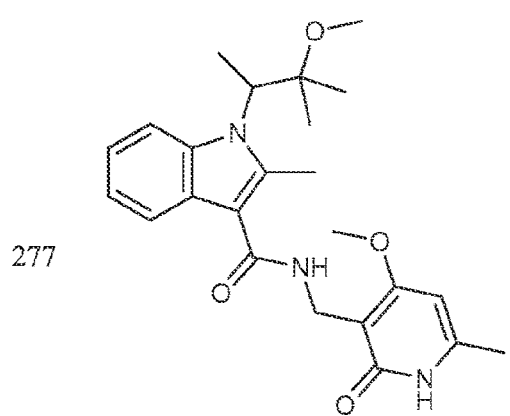
Figure 1:
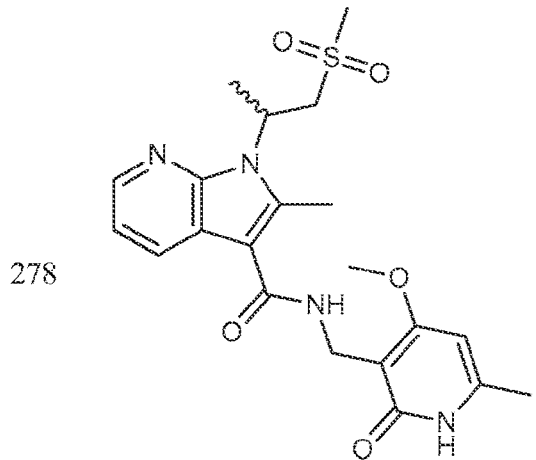
Figure 1:
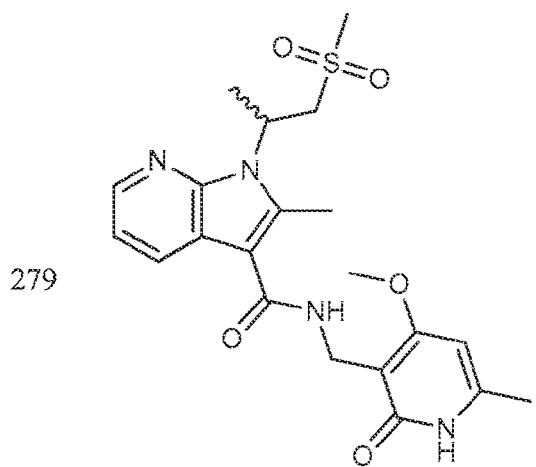
Figure 1:
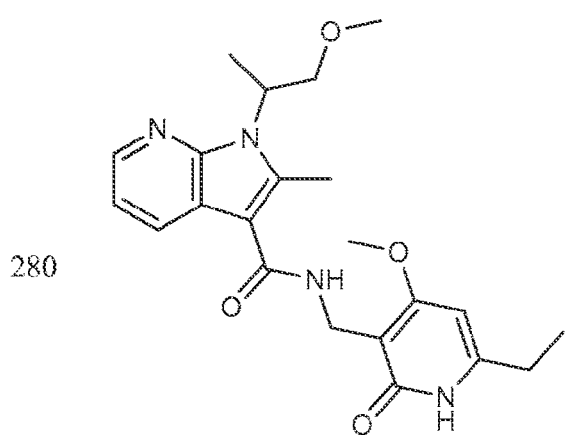
Figure 1:
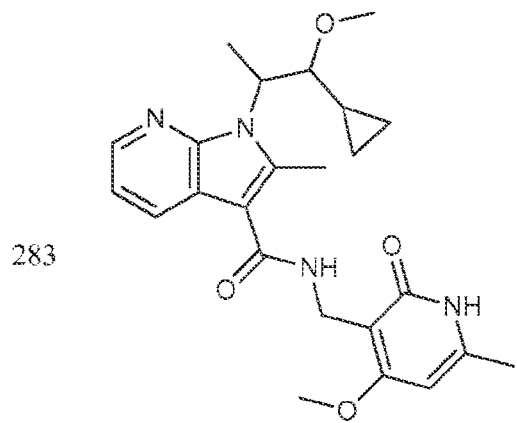
Figure 1:
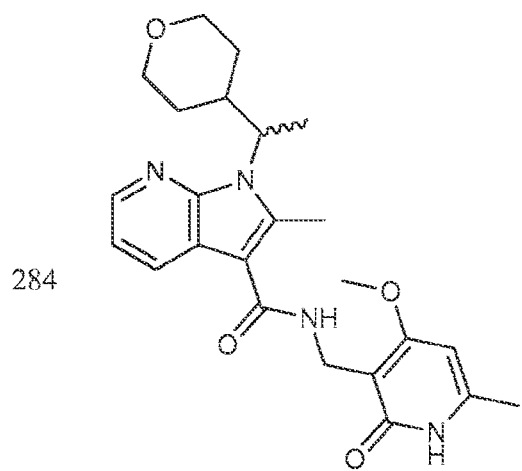
Figure 1:
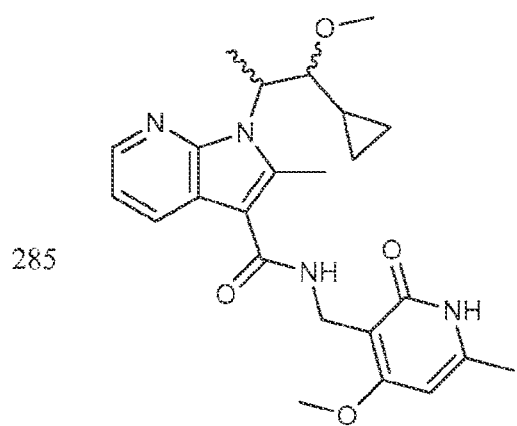
Figure 1:
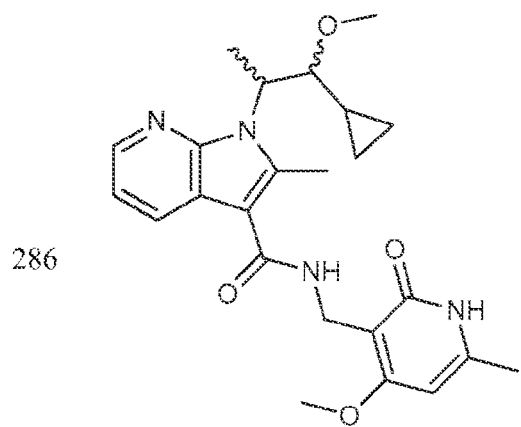
Figure 1:
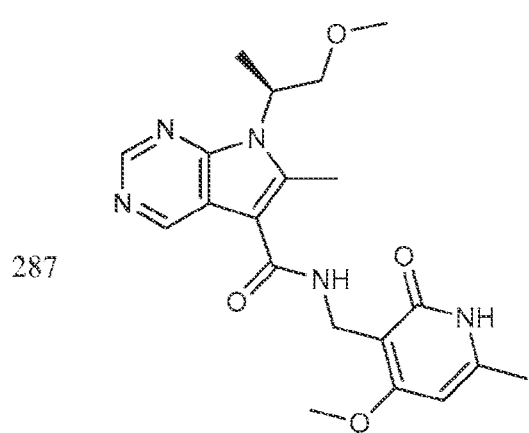
Figure 1:
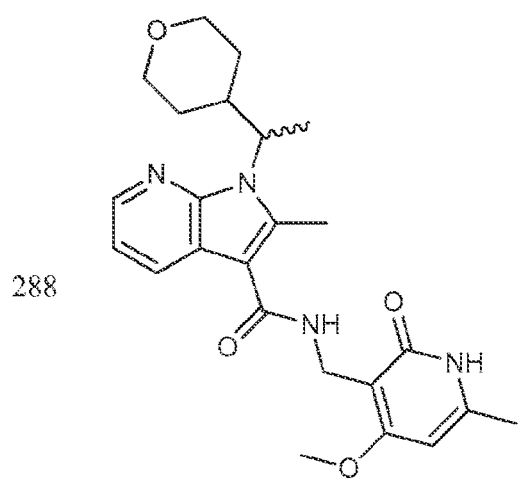
Figure 1:
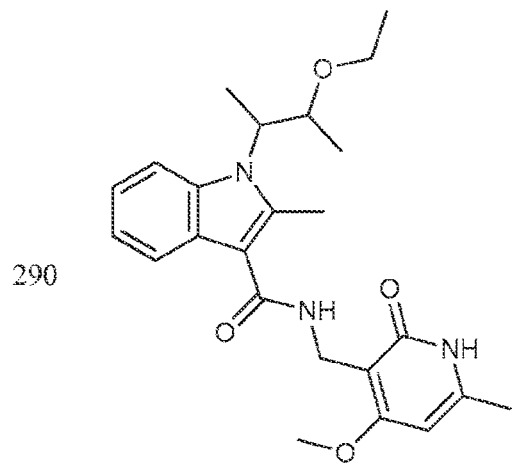
Figure 1:
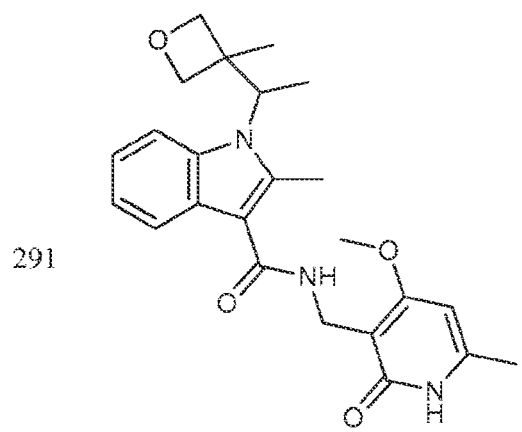
Figure 1:
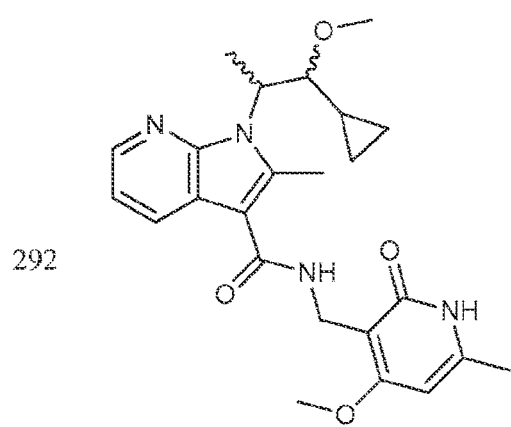
Figure 1:
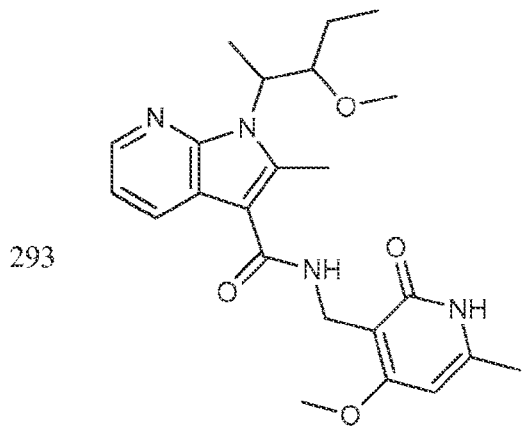
Figure 1:
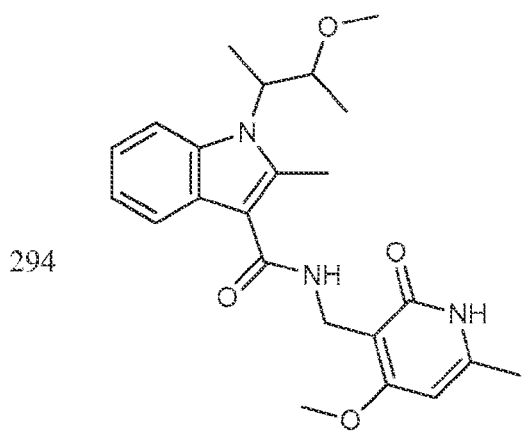
Figure 1:
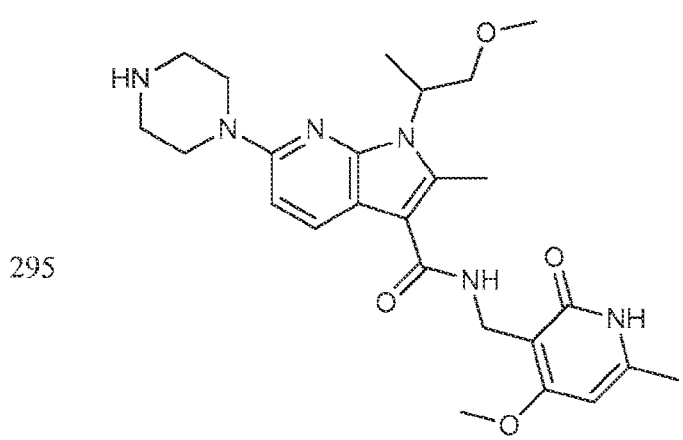
Figure 1:
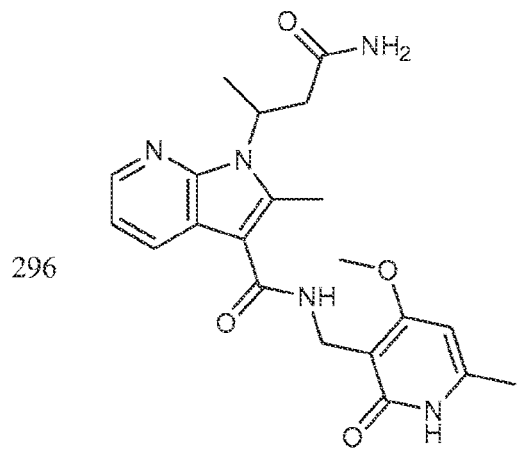
Figure 1:
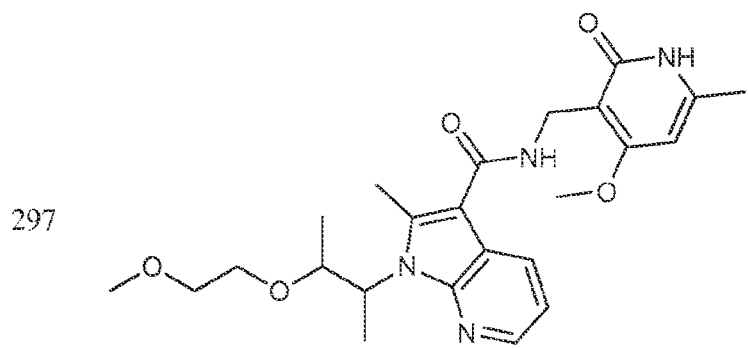
Figure 1:
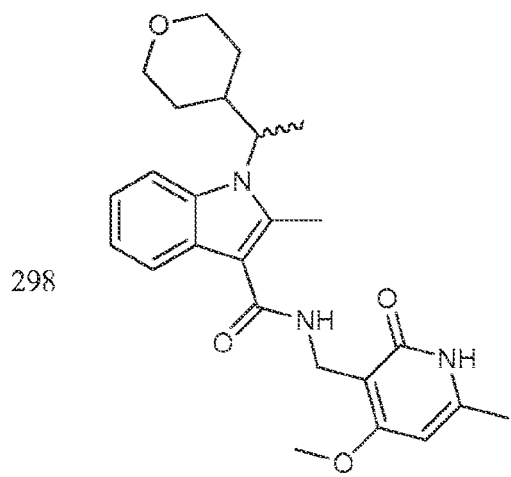
Figure 1:
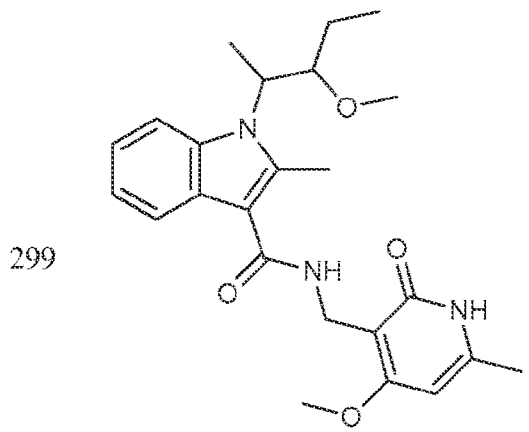
Figure 1:
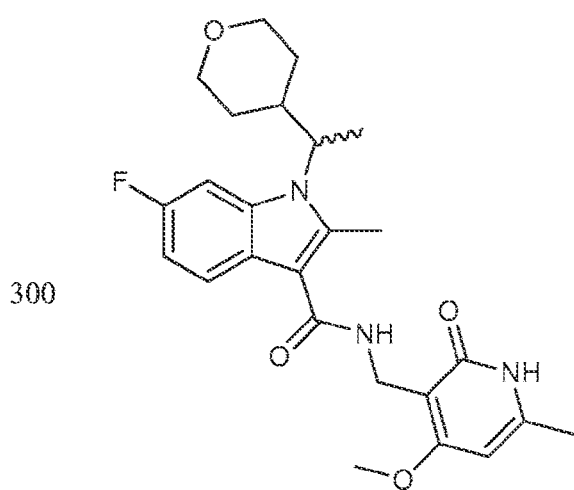
Figure 1:
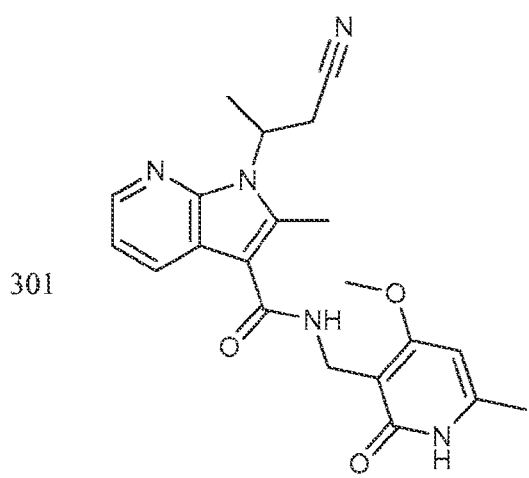
Figure 1:
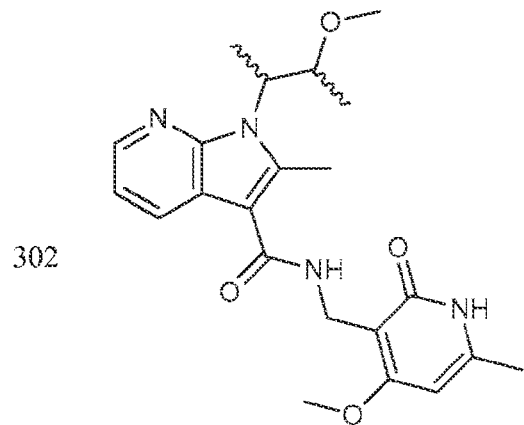
Figure 1:
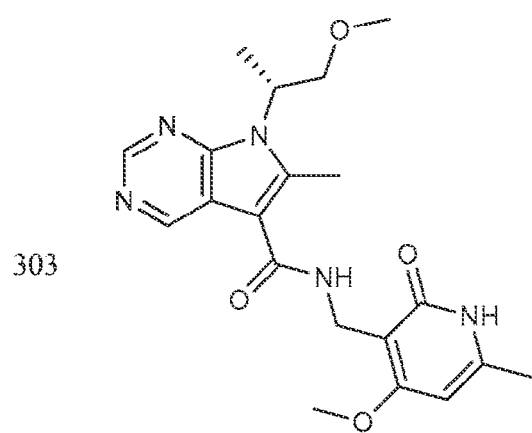
Figure 1:
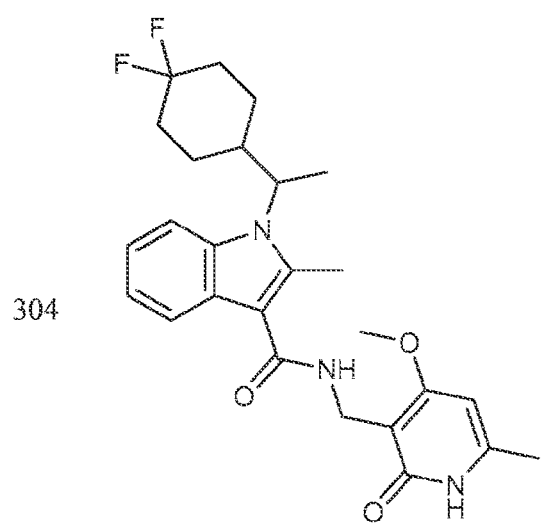
Figure 1:
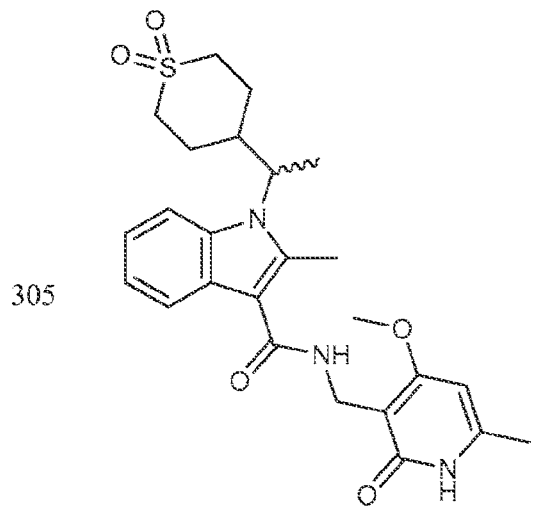
Figure 1:
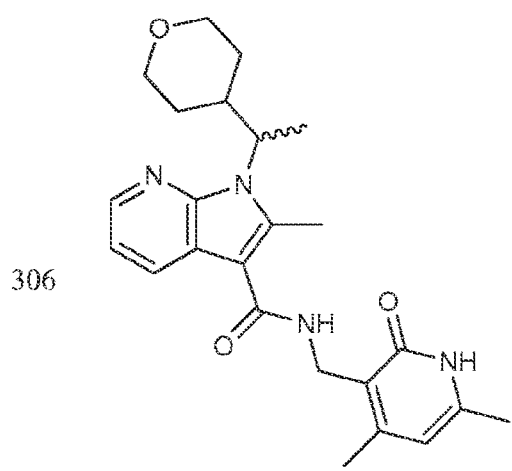
Figure 1:
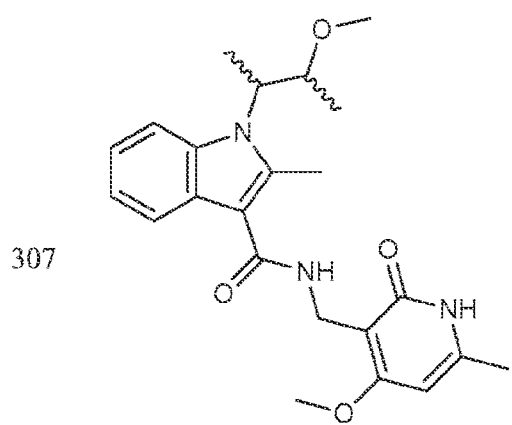
Figure 1:
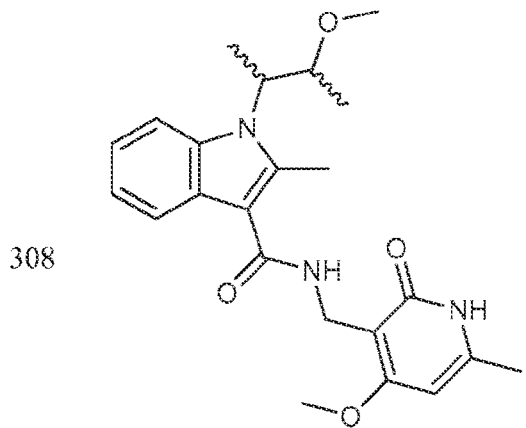
Figure 1:
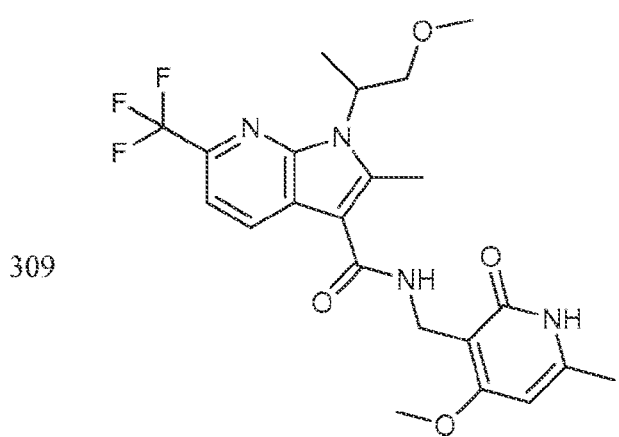
Figure 1:
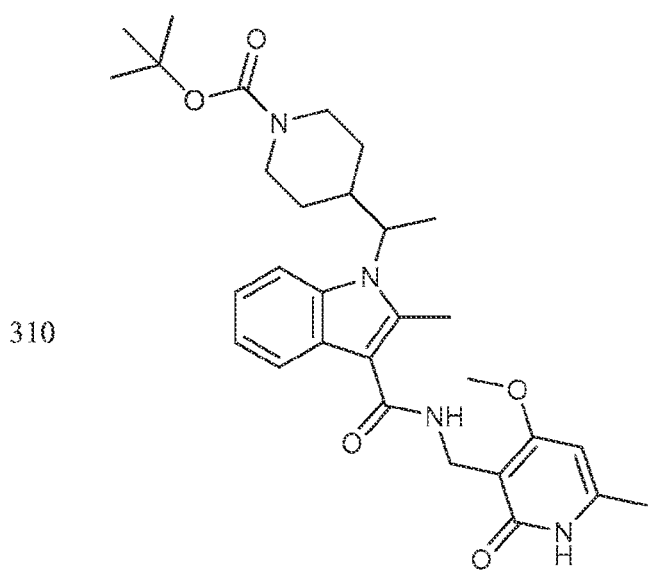
Figure 1:
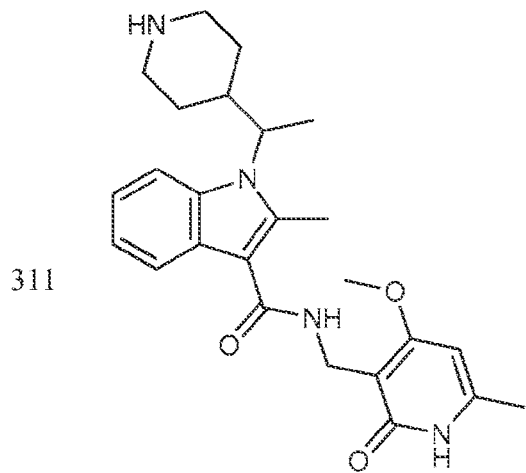
Figure 1:
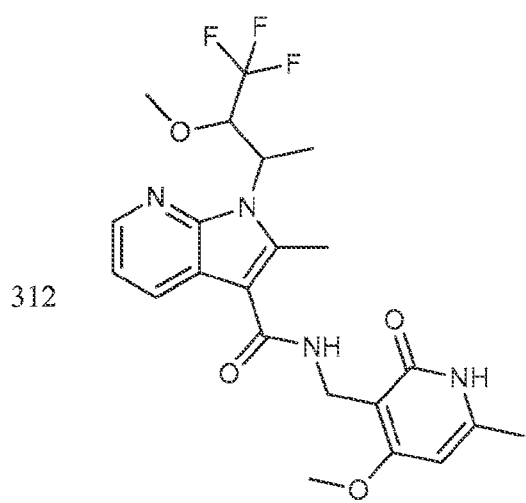
Figure 1:
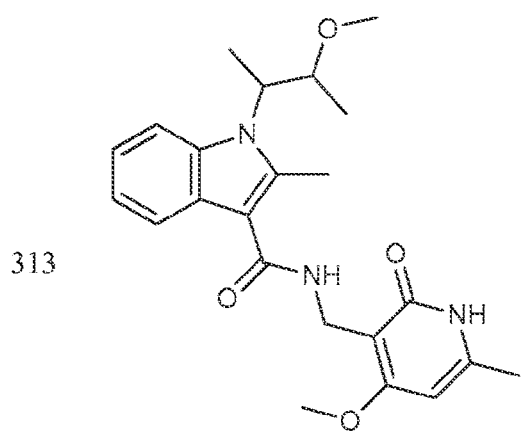
Figure 1:
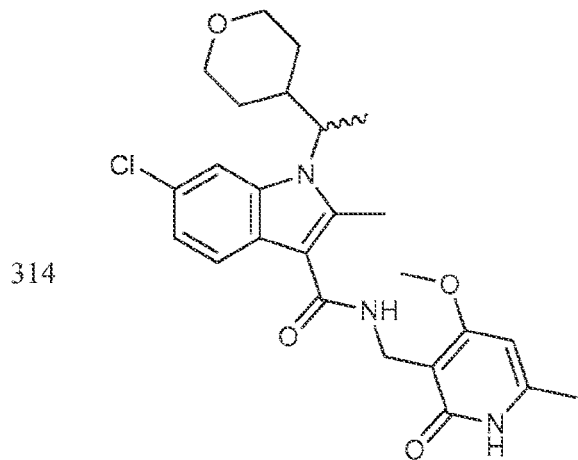
Figure 1:
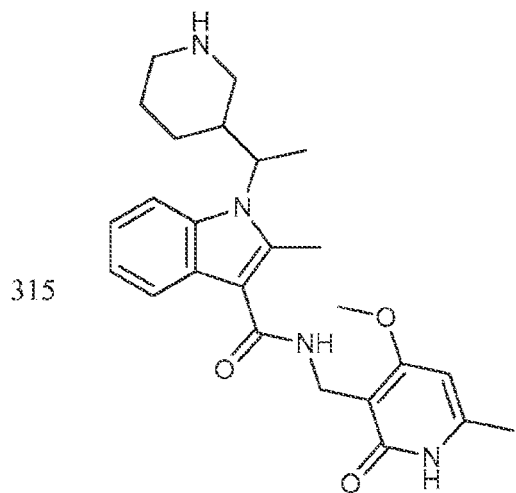
Figure 1:
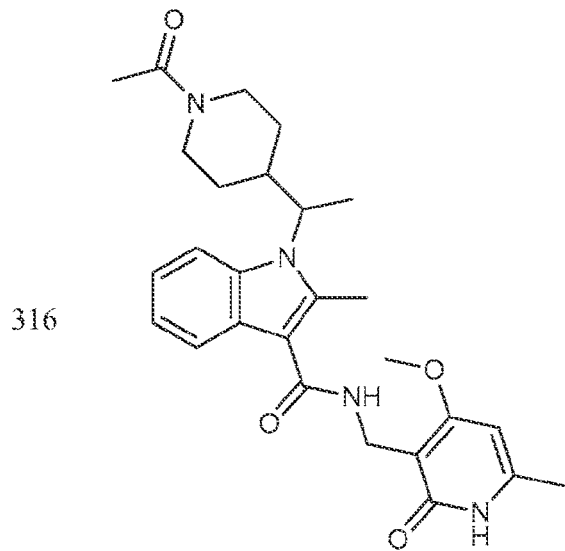
Figure 1:
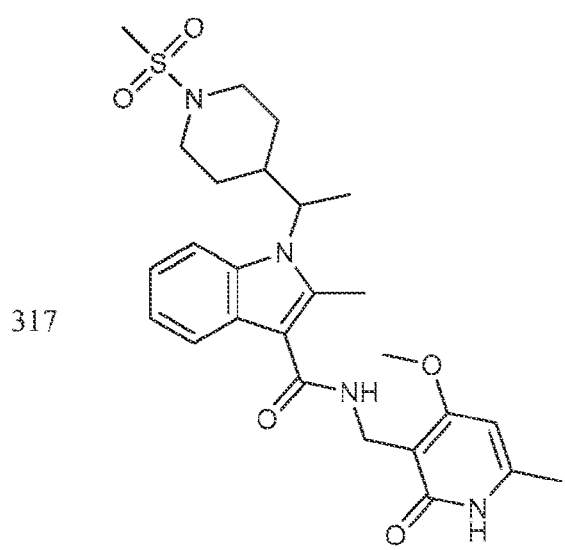
Figure 1:
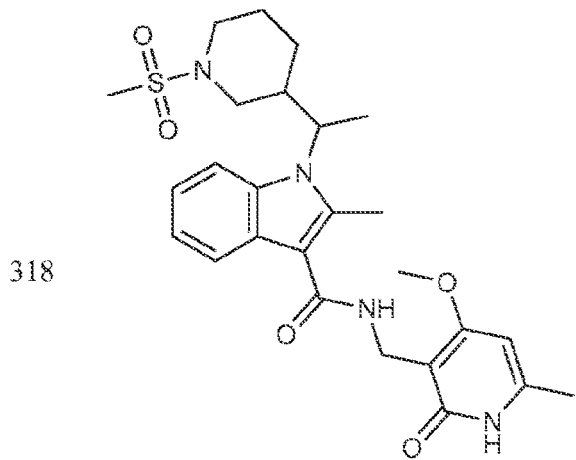
Figure 1:
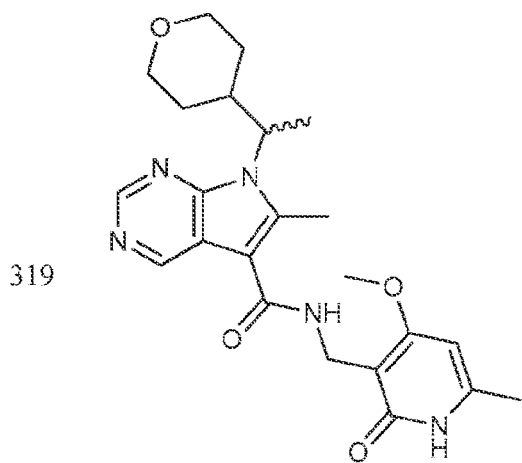
Figure 1:
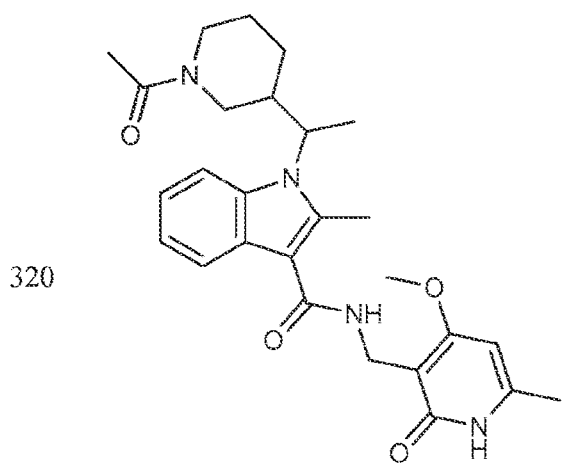
Figure 1:
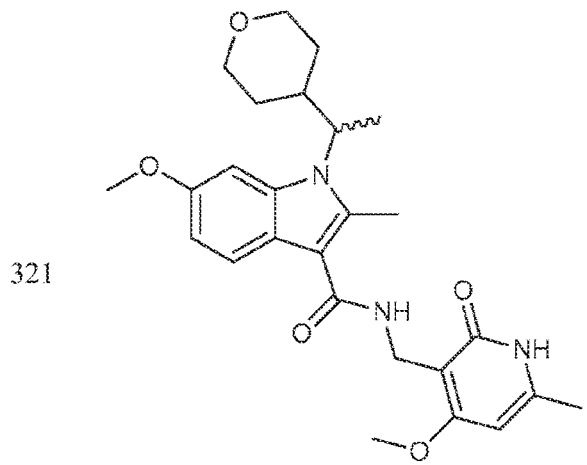
Figure 1:
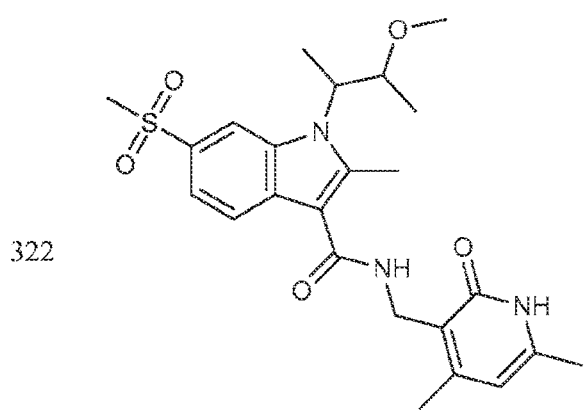
Figure 1:
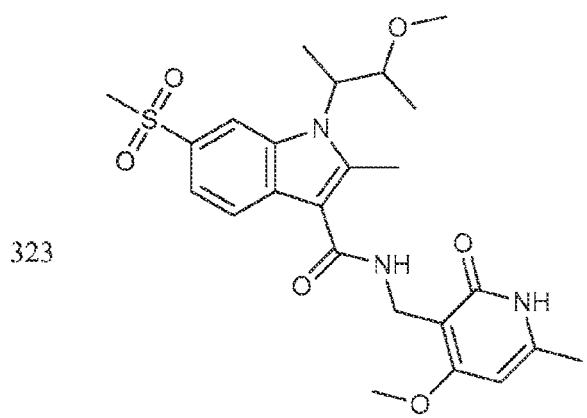
Figure 1:
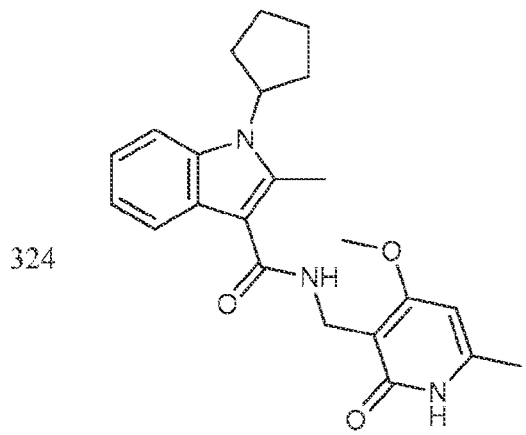
Figure 1:
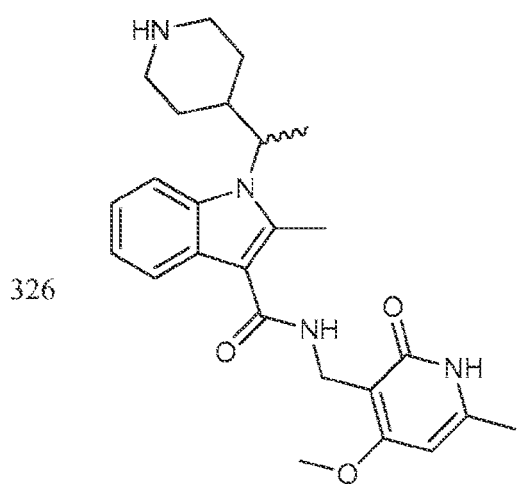
Figure 1:
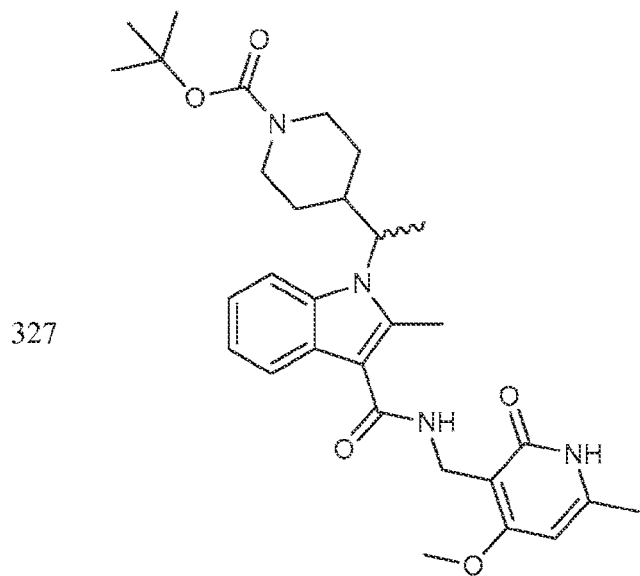
Figure 1:
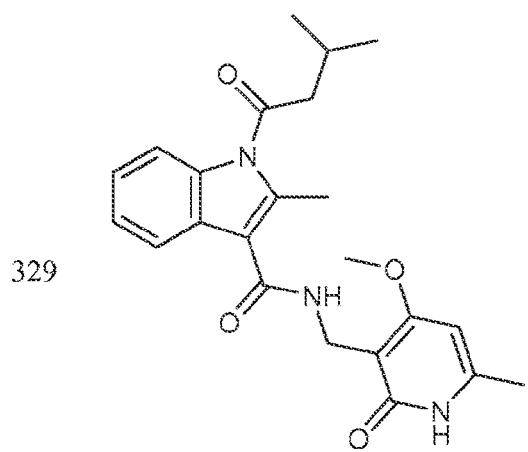
Figure 1:
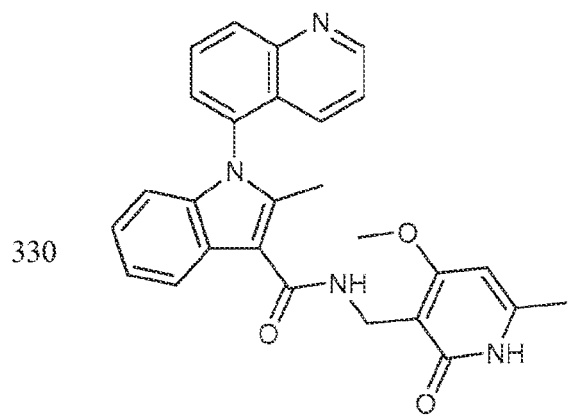
Figure 1:
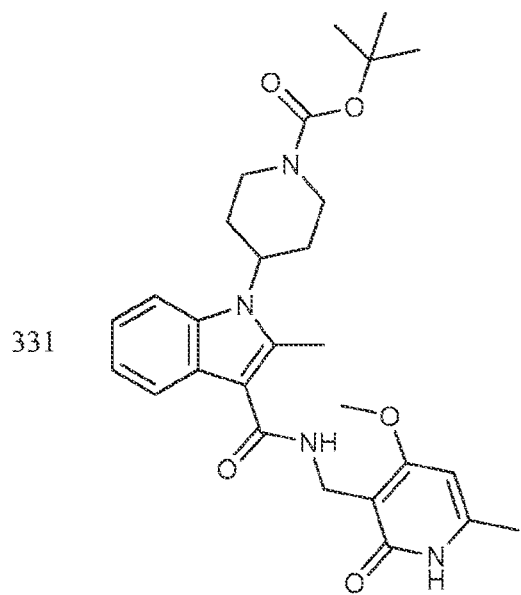
Figure 1:
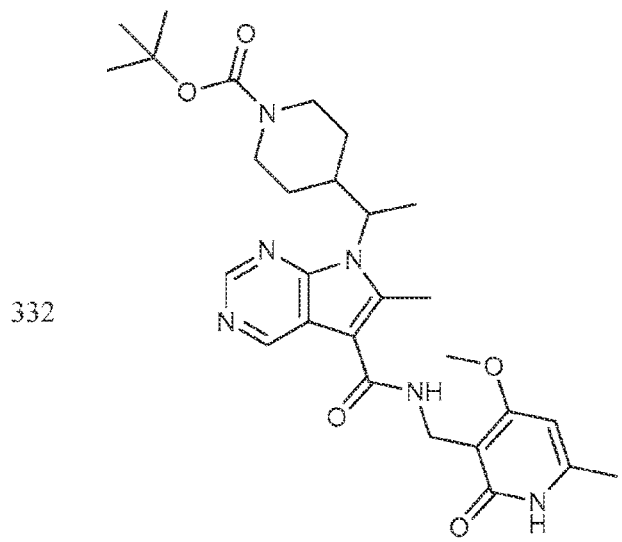
Figure 1:
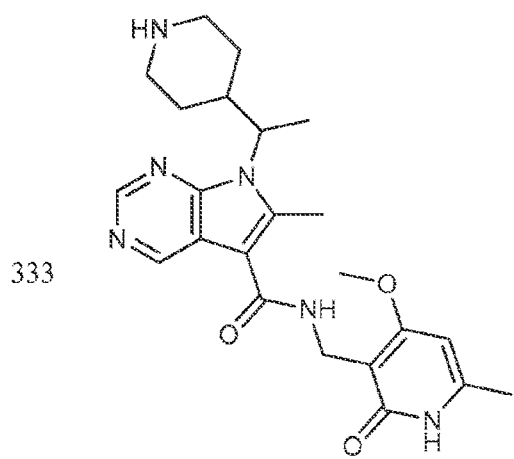
Figure 1:
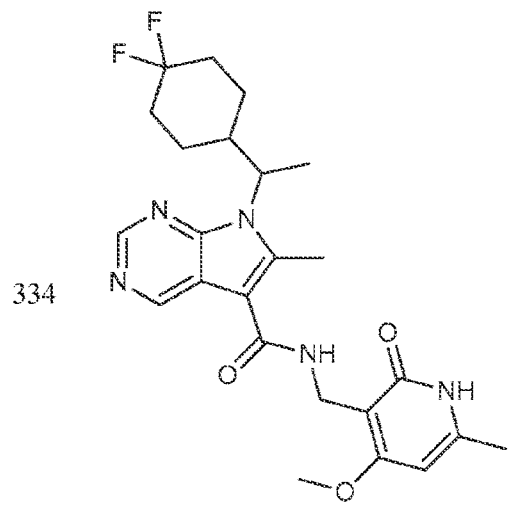
Figure 1:
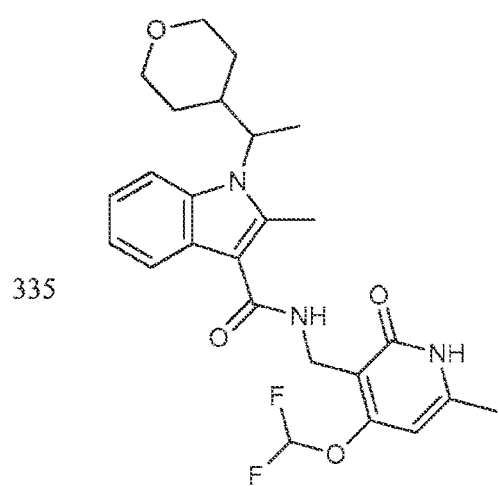
Figure 1:
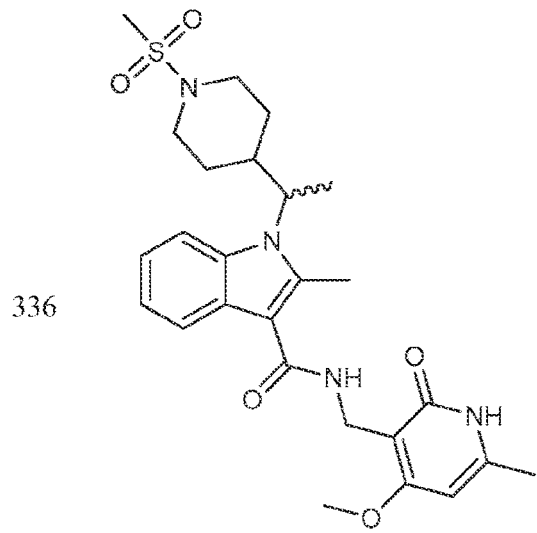
Figure 1:
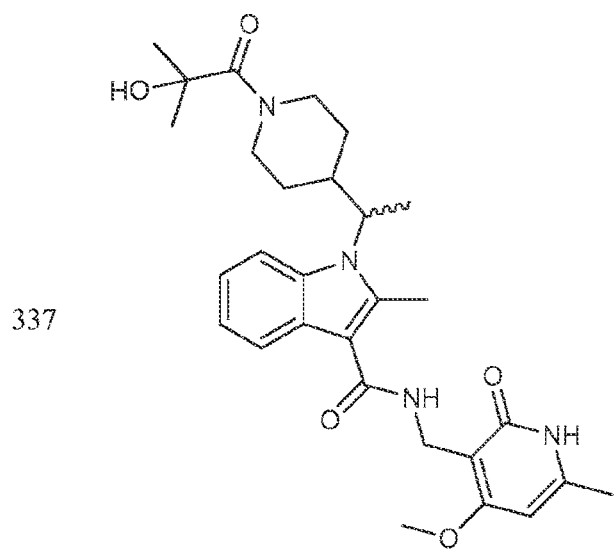
Figure 1:
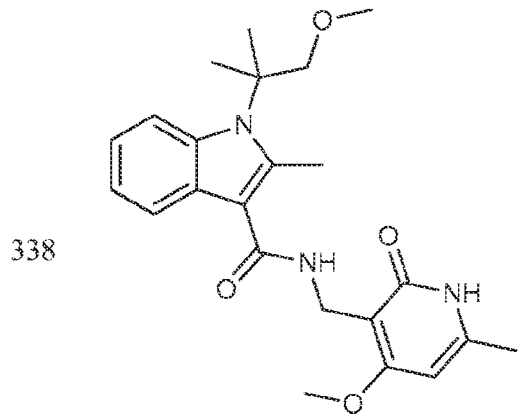
Figure 1:
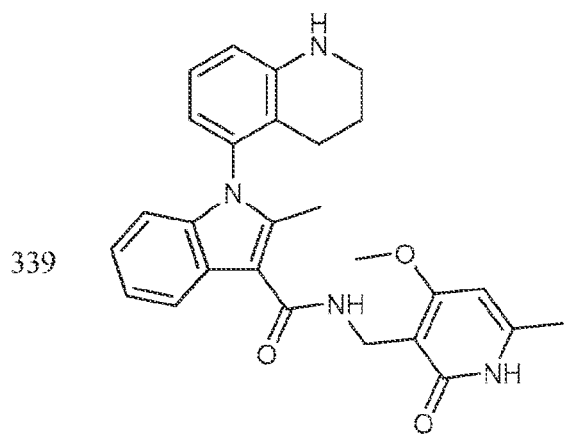
Figure 1:
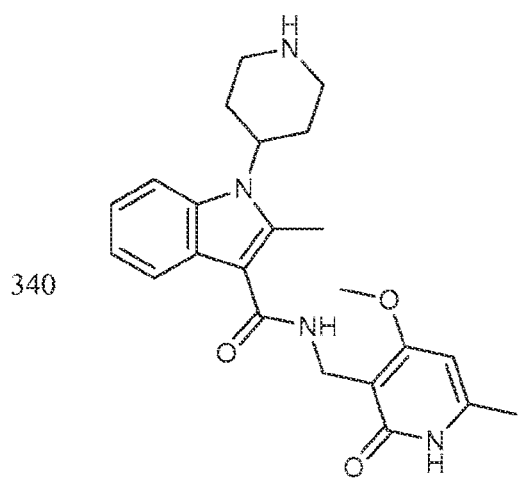
Figure 1:
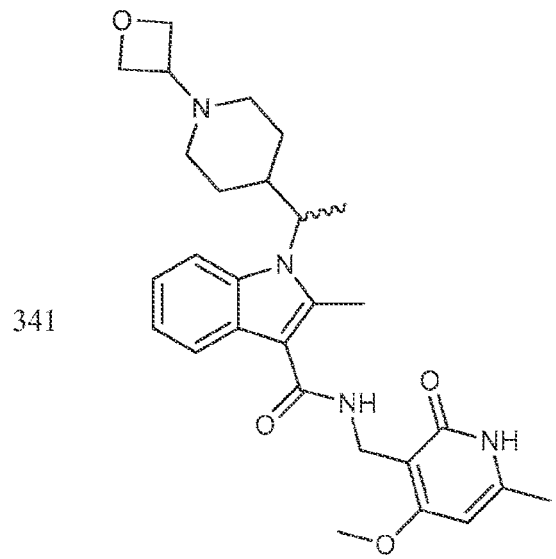
Figure 1:
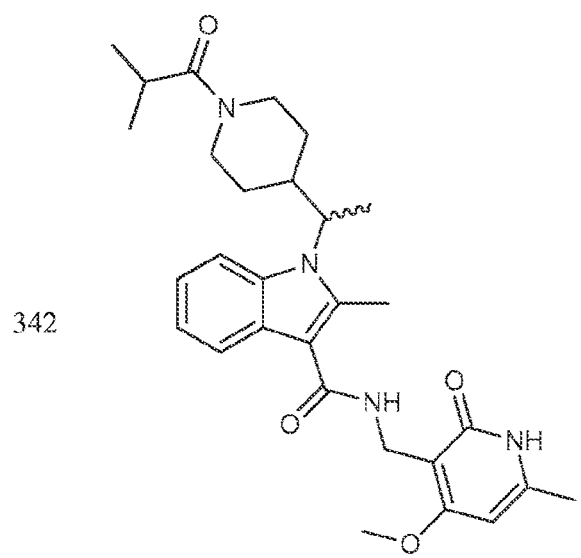
Figure 1:
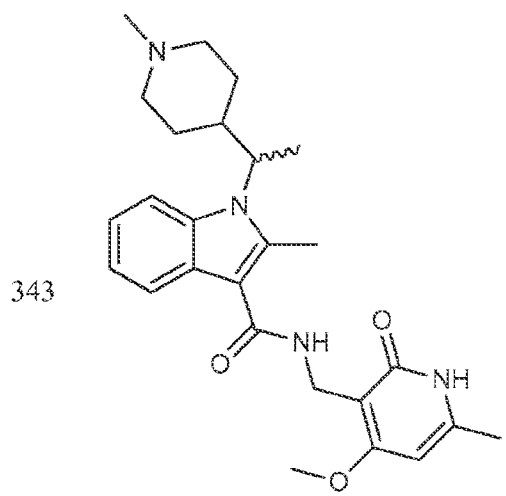
Figure 1:
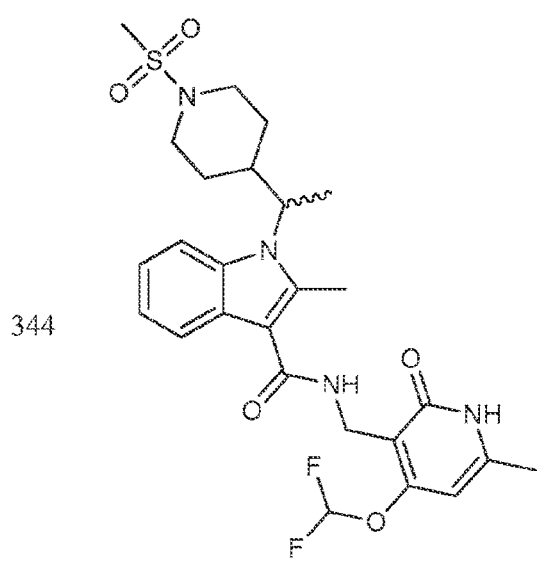
Figure 1:
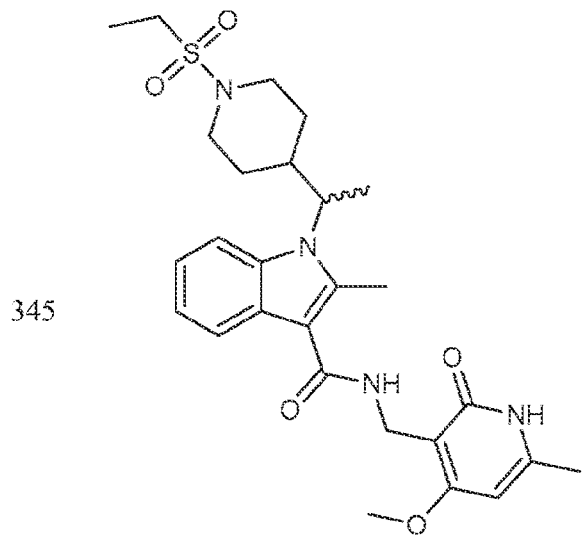
Figure 1:
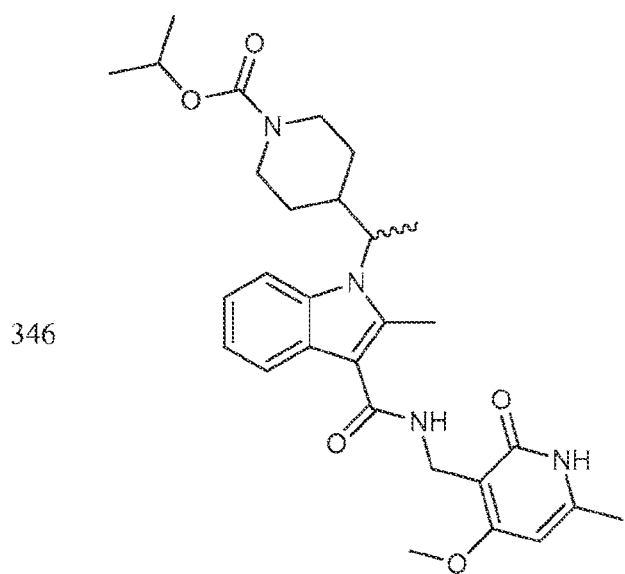
Figure 1:
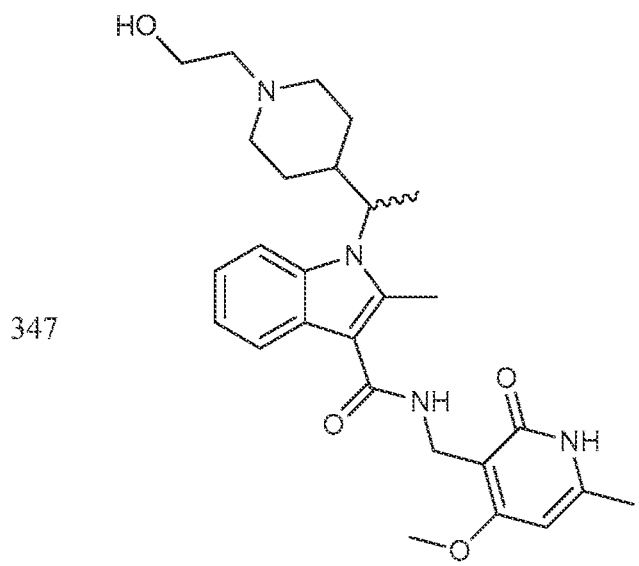
Figure 1:
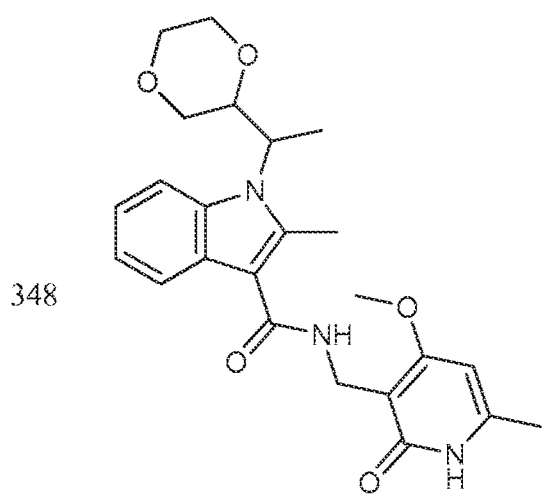
Figure 1:
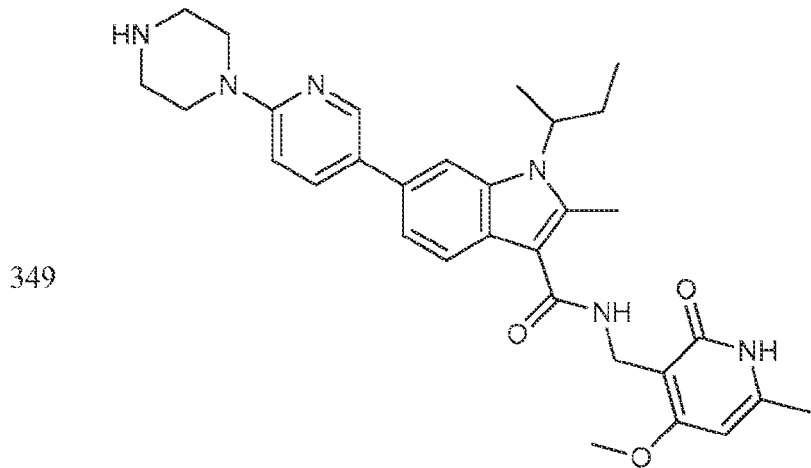
Figure 1:
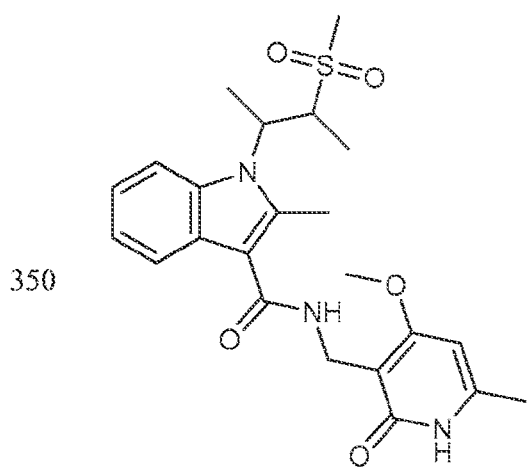
Figure 1:
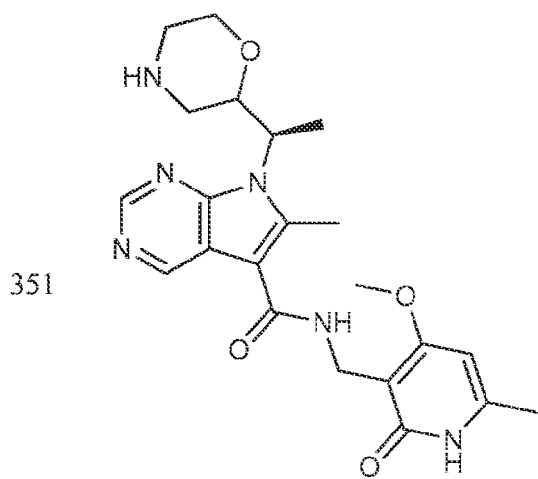
Figure 1:
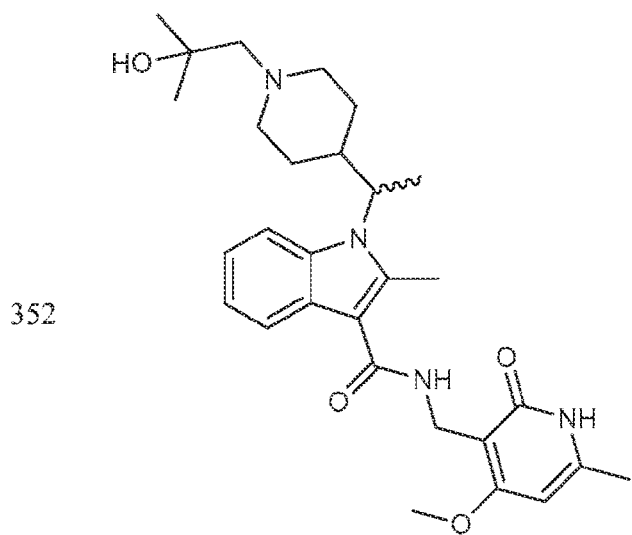
Figure 1:
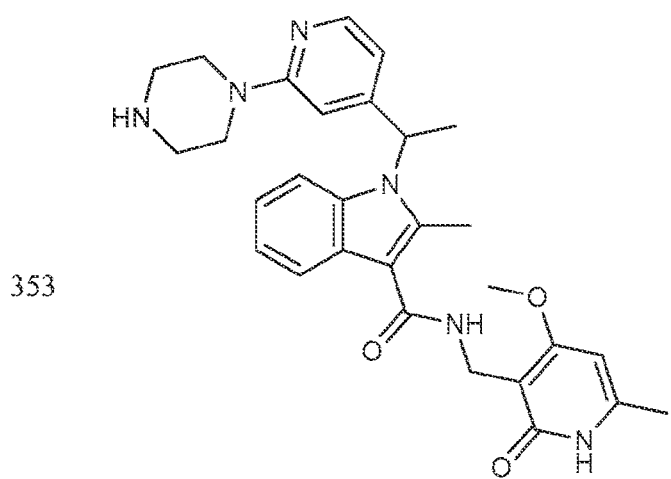
Figure 1:
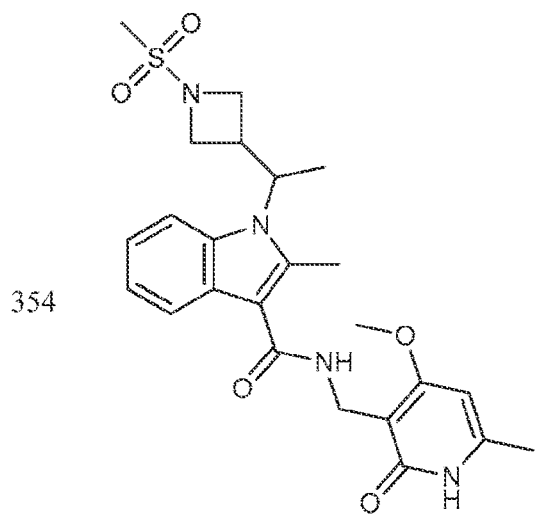
Figure 1:
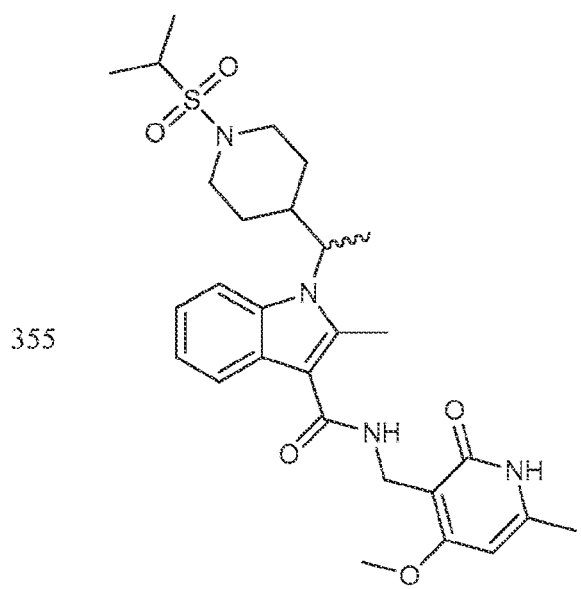
Figure 1:
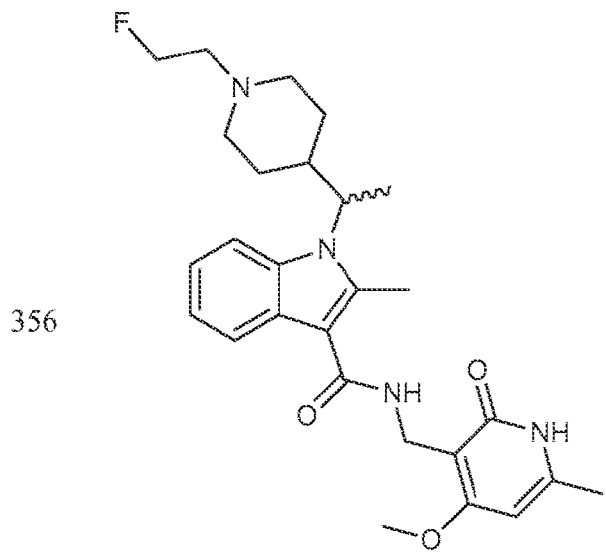
Figure 1:
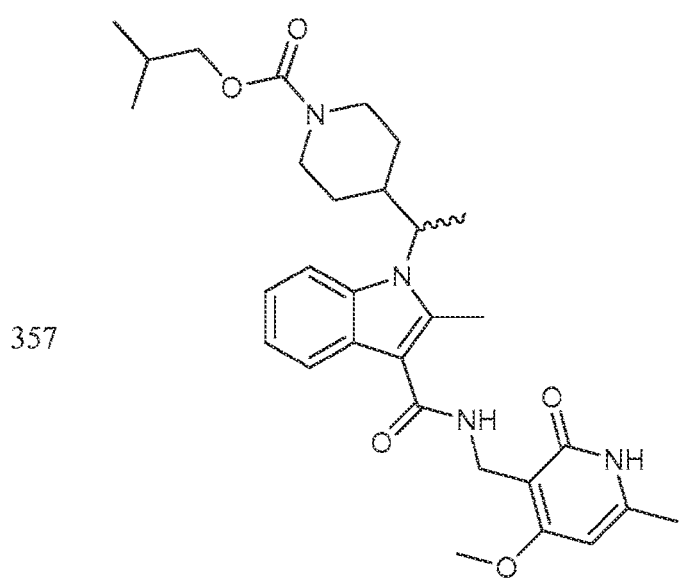
Figure 1:
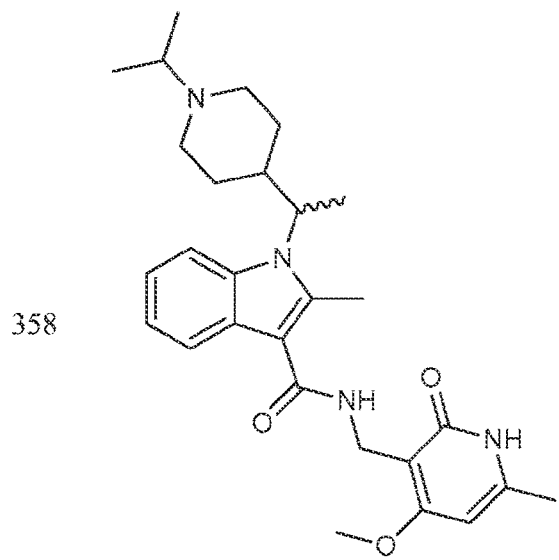
Figure 1:
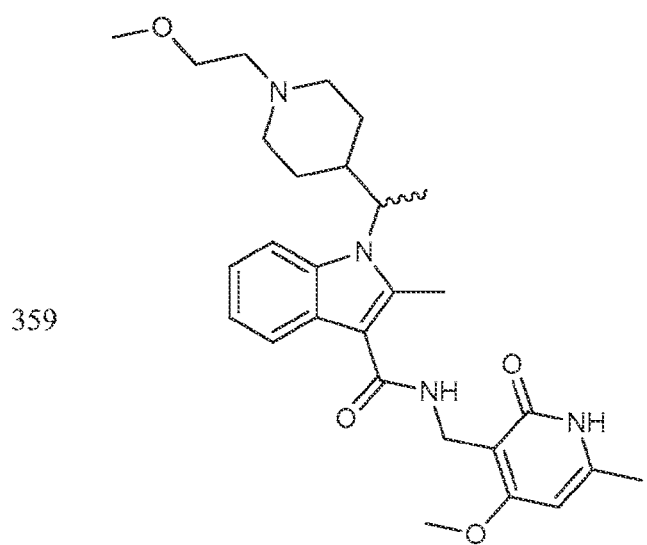
Figure 1:
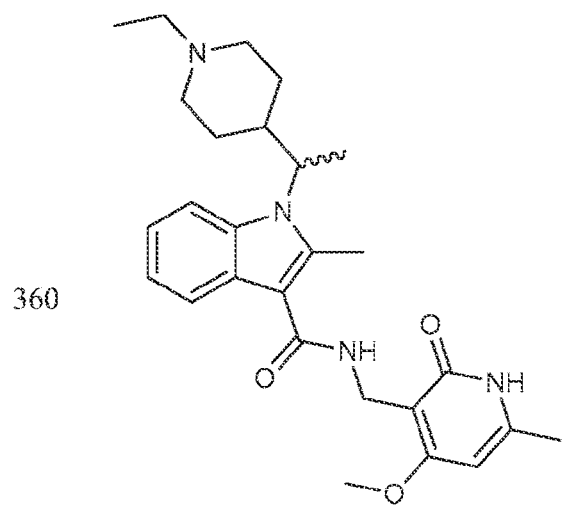
Figure 1:
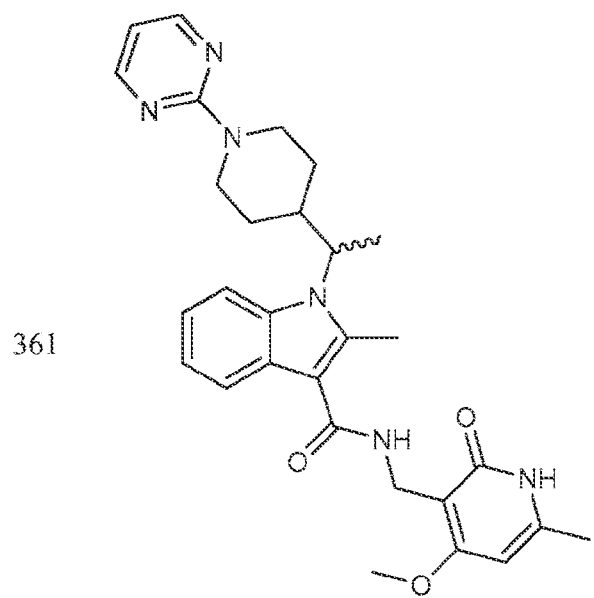
Figure 1:
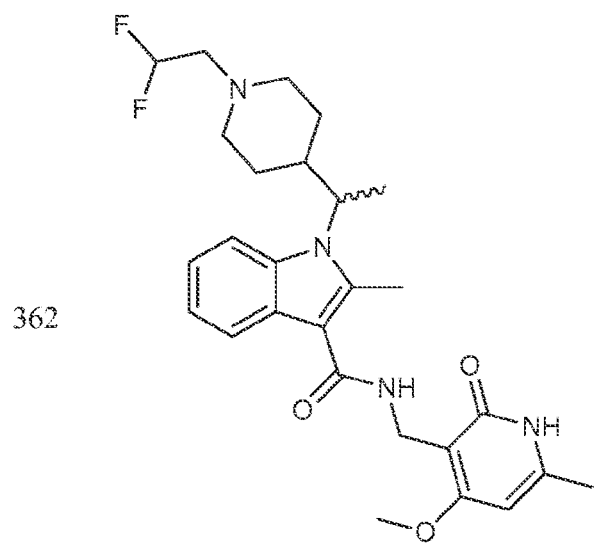
Figure 1:
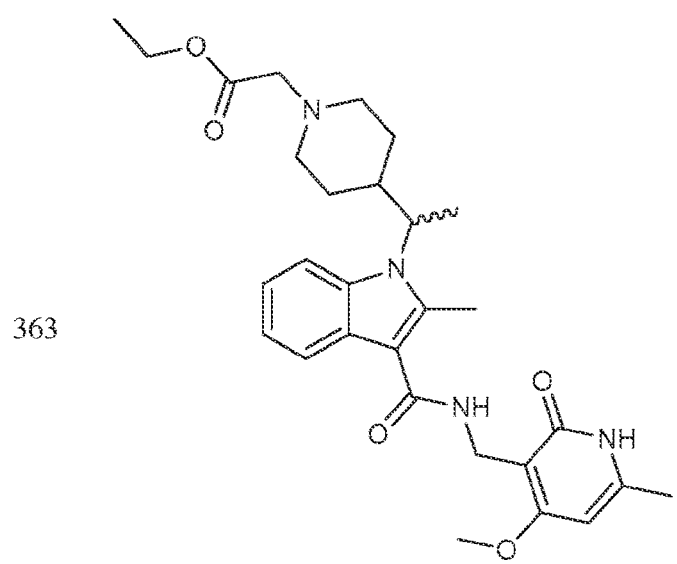
Figure 1:
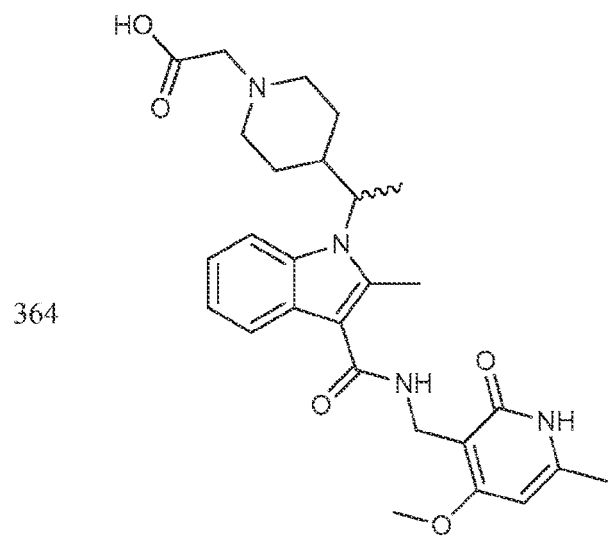
Figure 1:
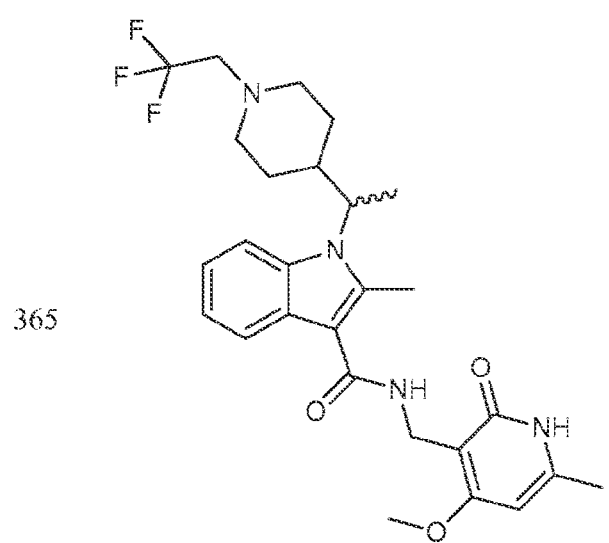
Figure 1:
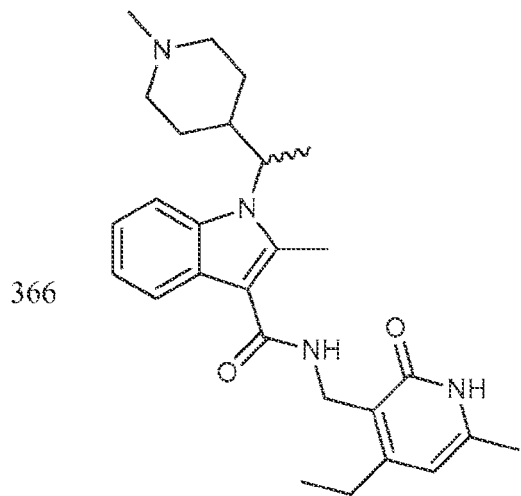
Figure 1:
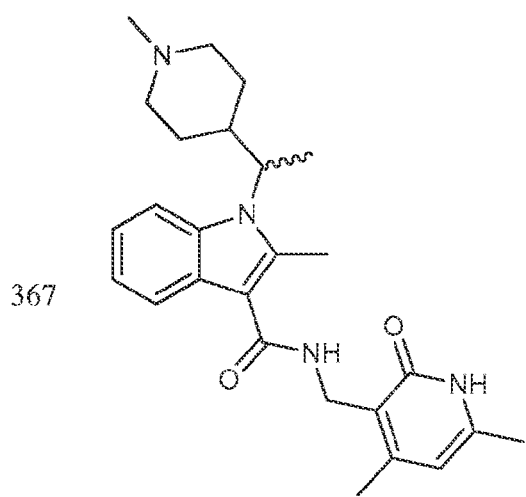
Figure 1:
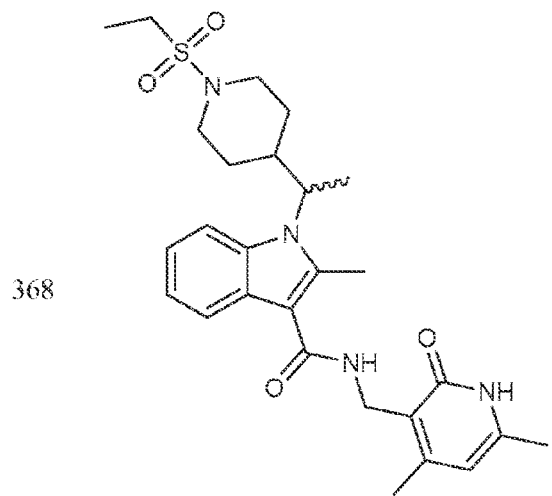
Figure 1:
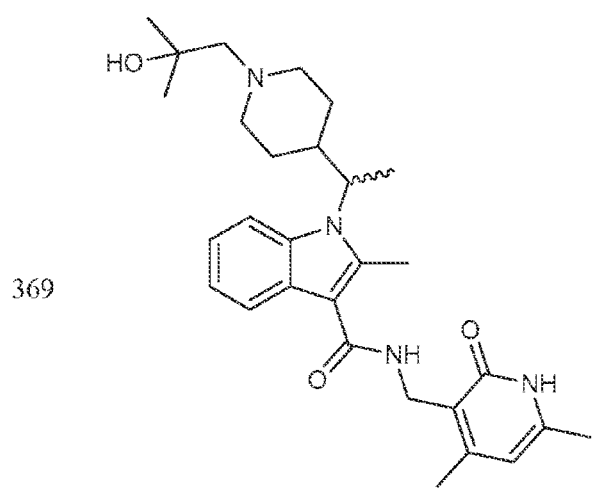
Figure 1:
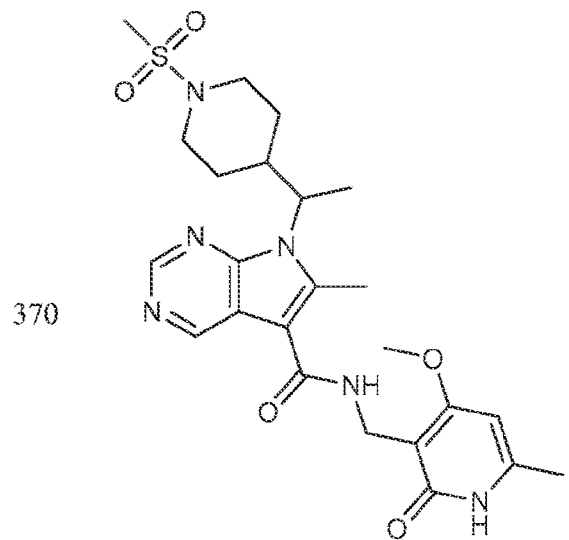
Figure 1:
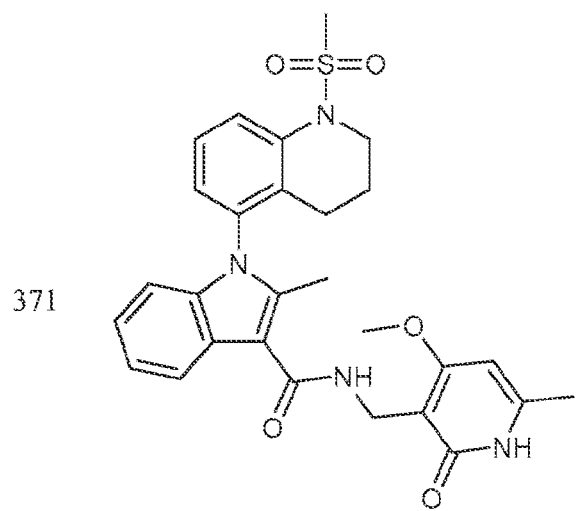
Figure 1:
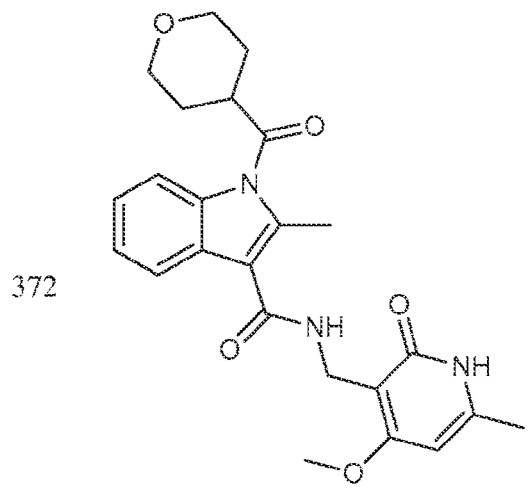
Figure 1:
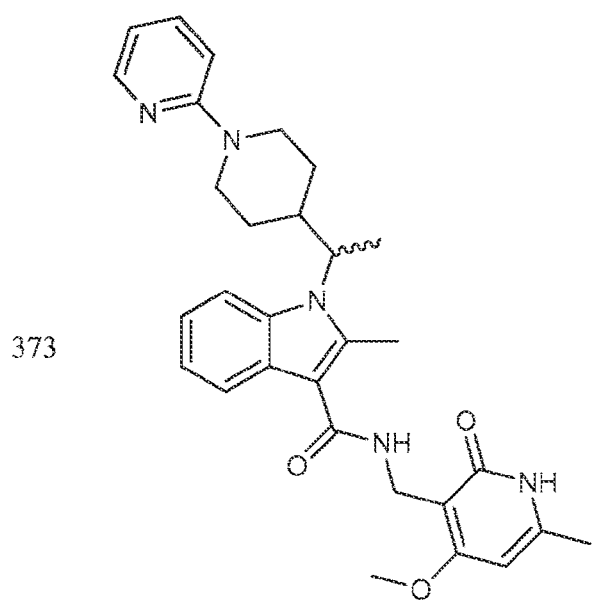
Figure 1:
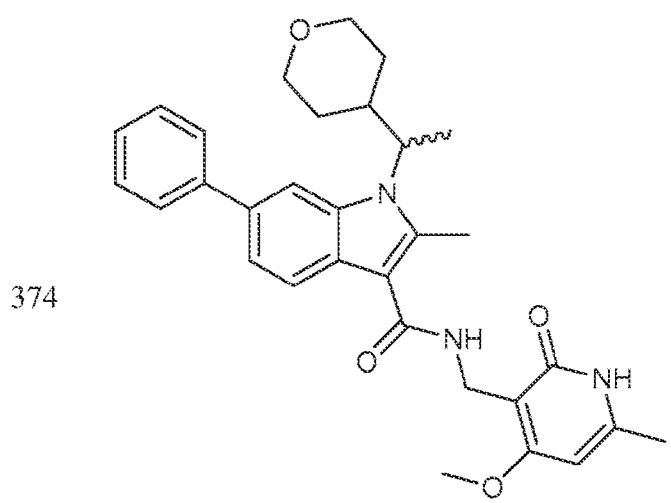
Figure 1:
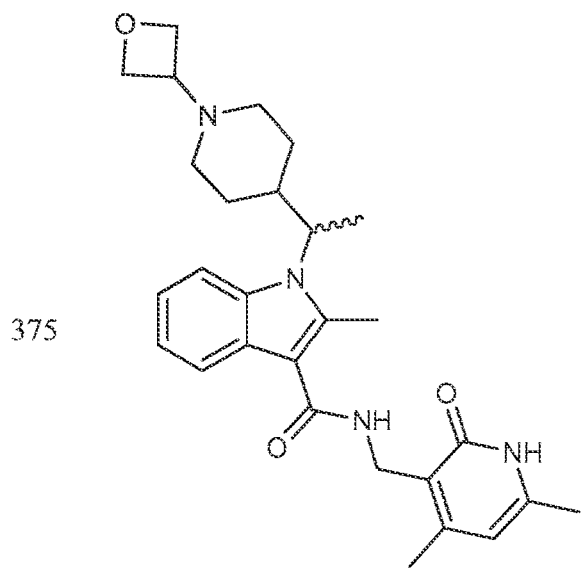
Figure 1:
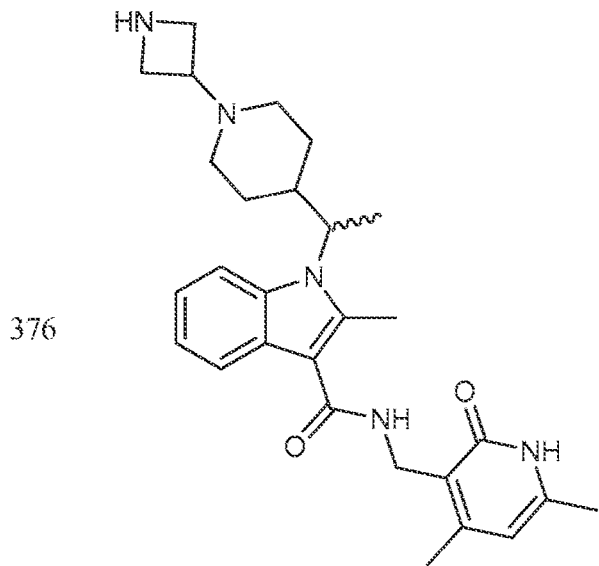
Figure 1:
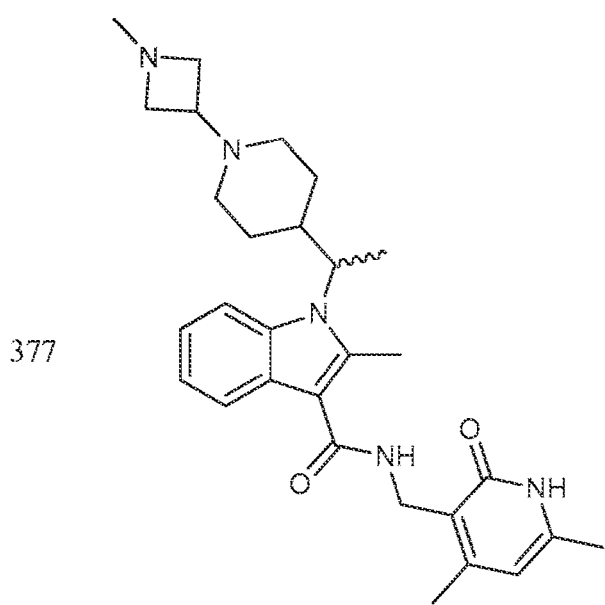
Figure 1:
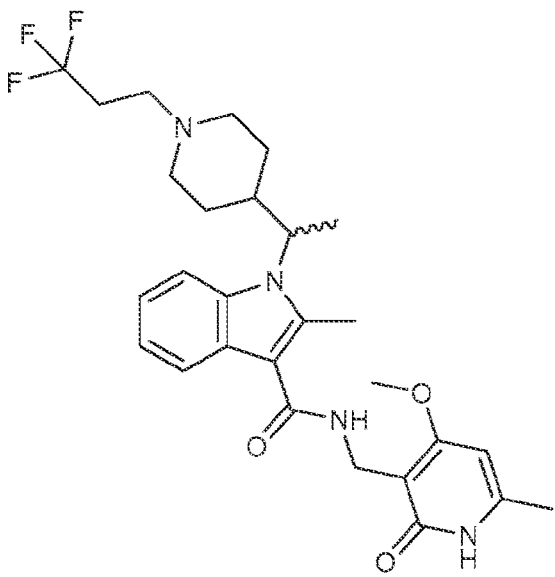
Figure 1:
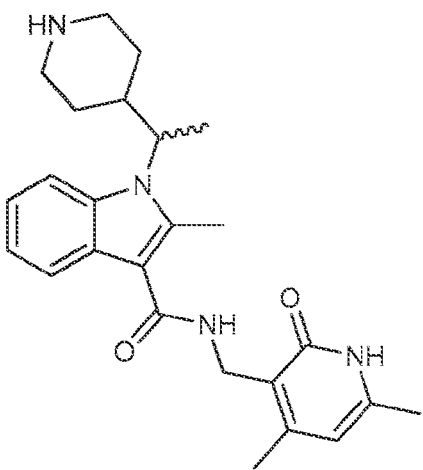
Figure 1:
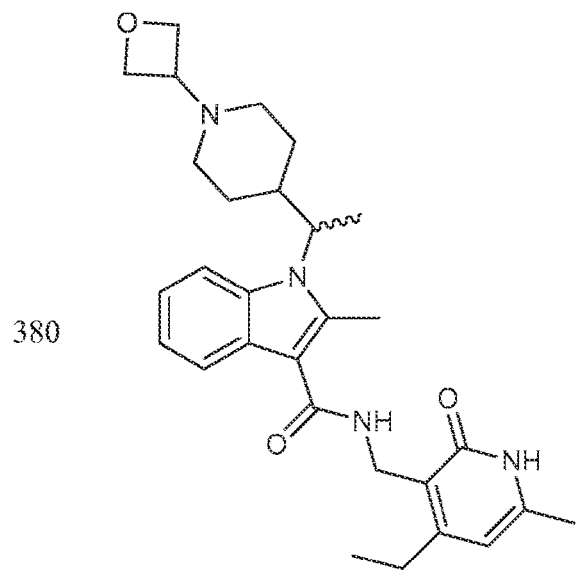
Figure 1:
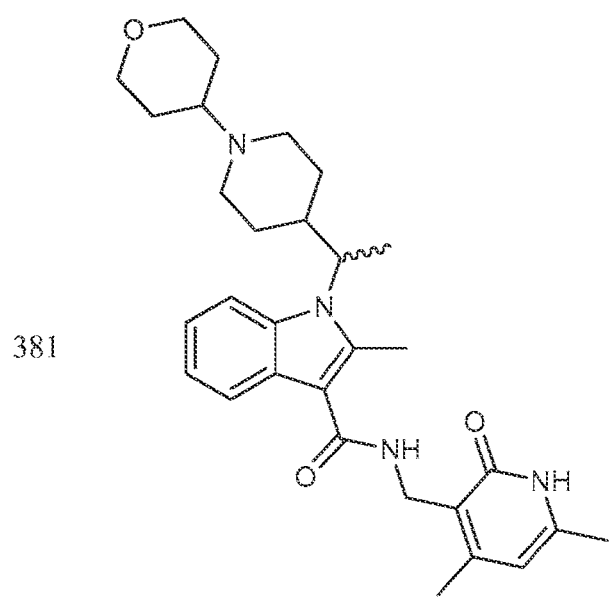
Figure 1:
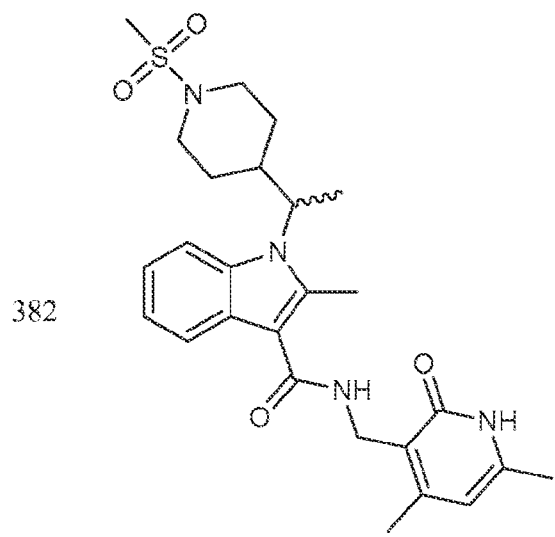
Figure 1:
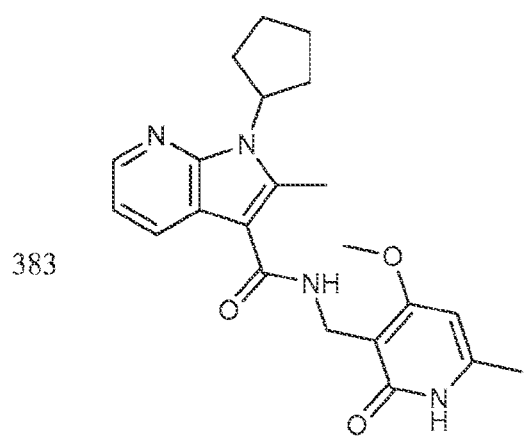
Figure 1:
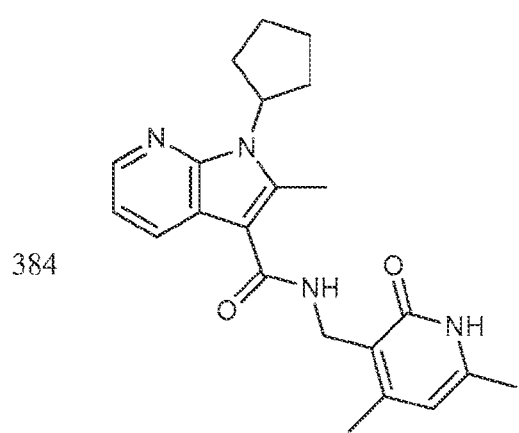
Figure 1:
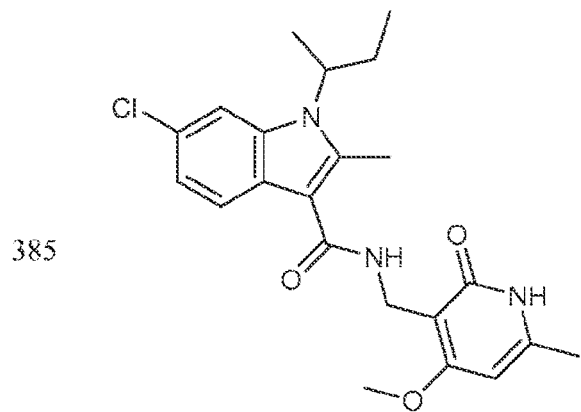
Figure 1:
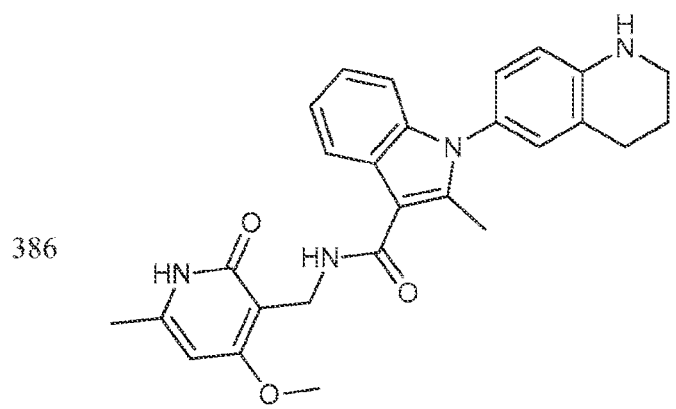
Figure 1:
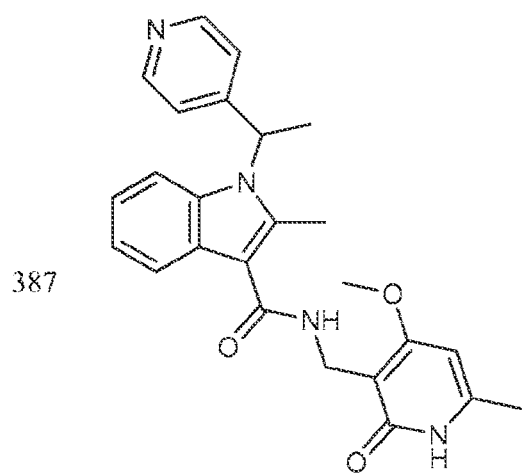
Figure 1:
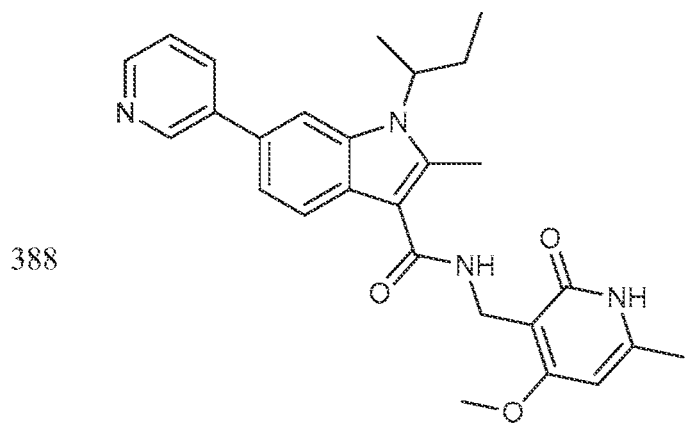
Figure 1:
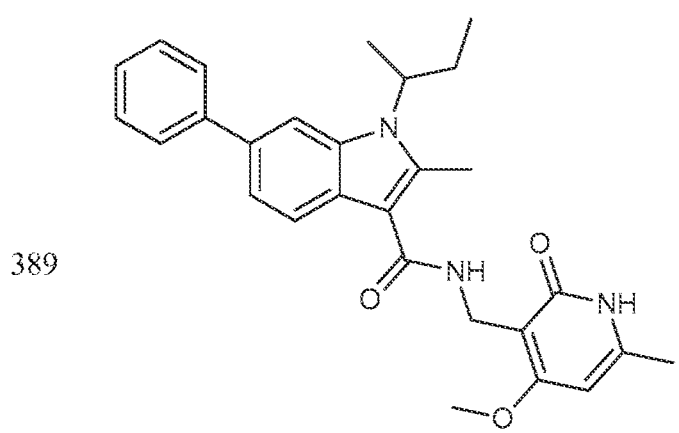
Figure 1:
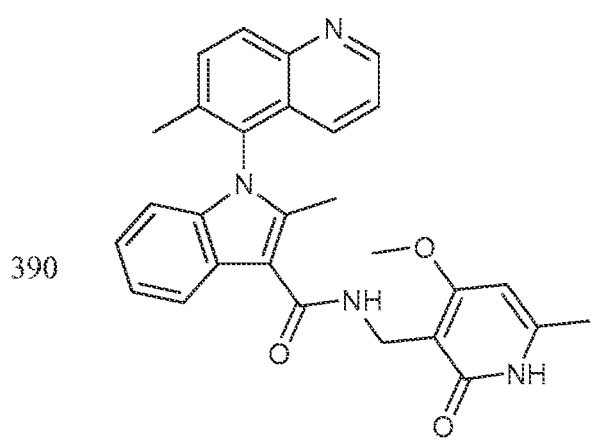
Figure 1:
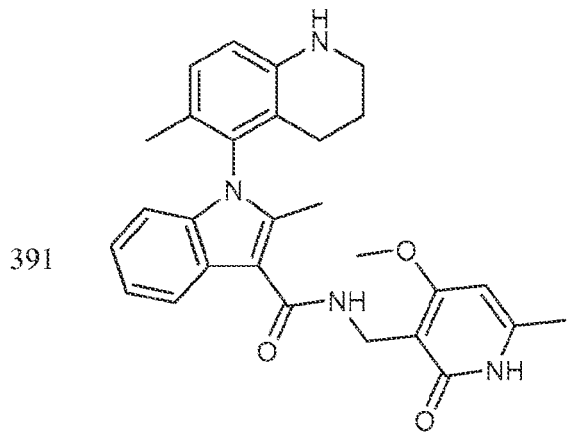
Figure 1:
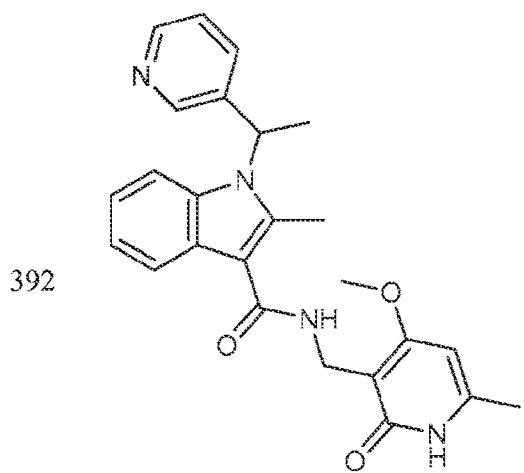
Figure 1:
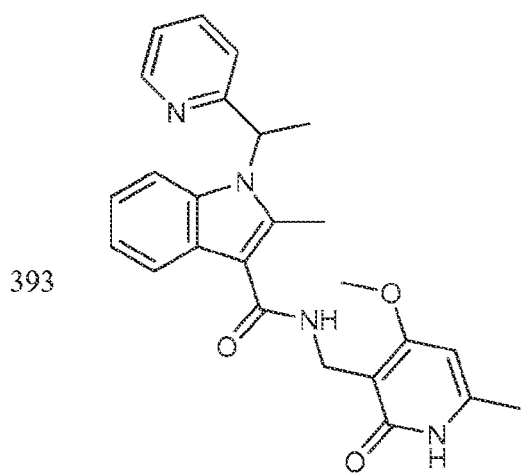
Figure 1:
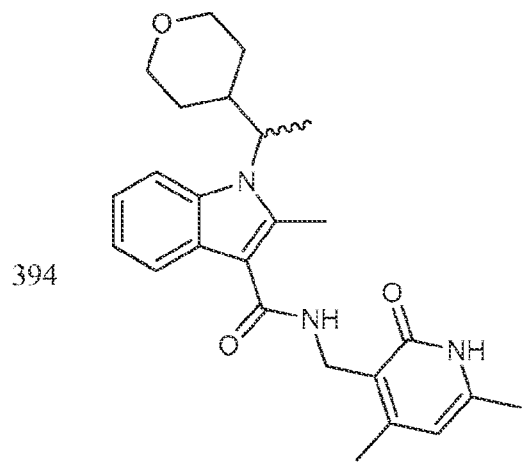
Figure 1:
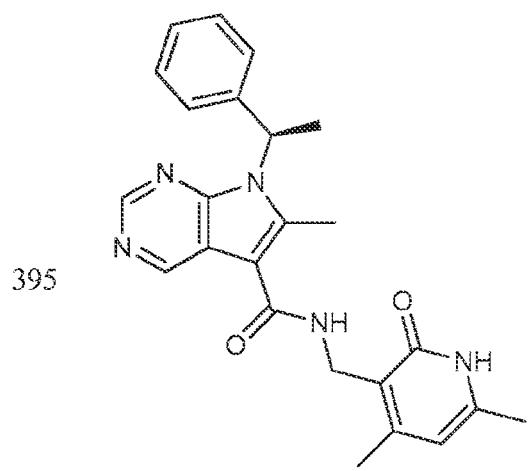
Figure 1:
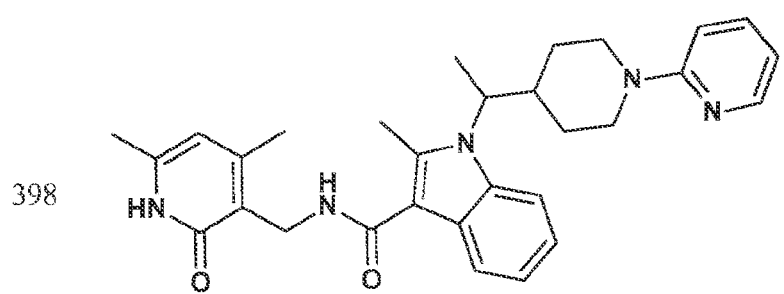
Figure 1:
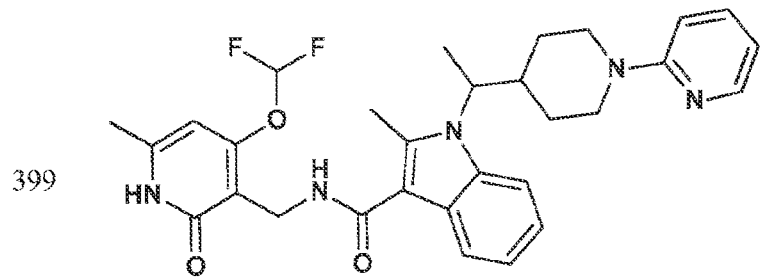
Figure 1:
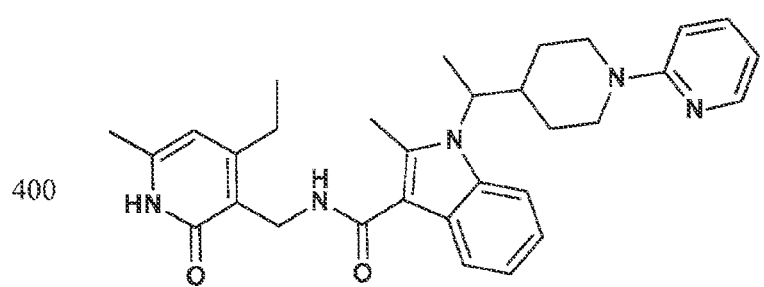
Figure 1:
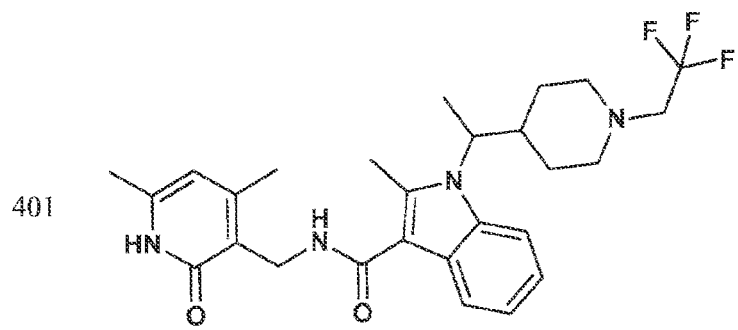
Figure 1:
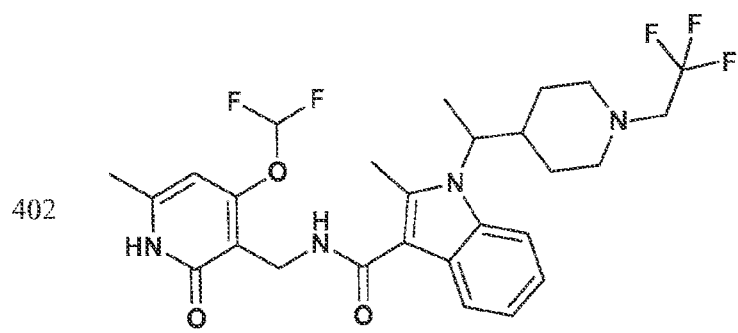
Figure 1:
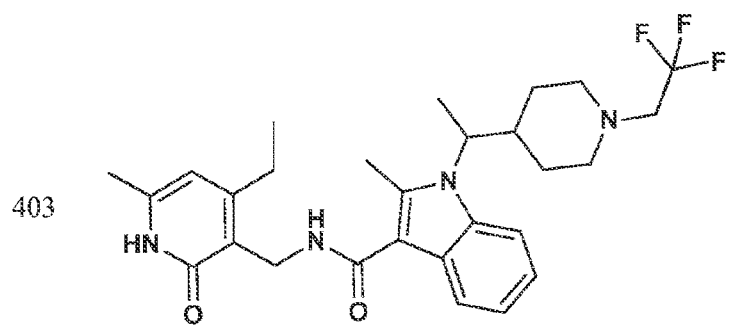
Figure 1:
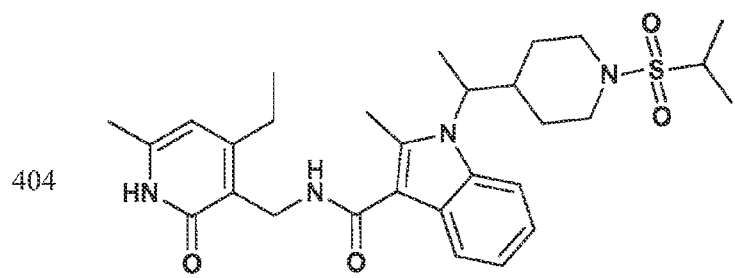
Figure 1:
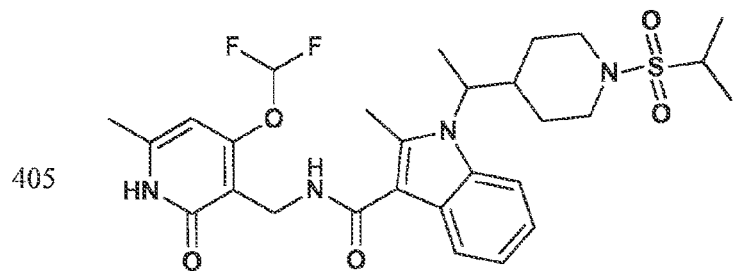
Figure 1:
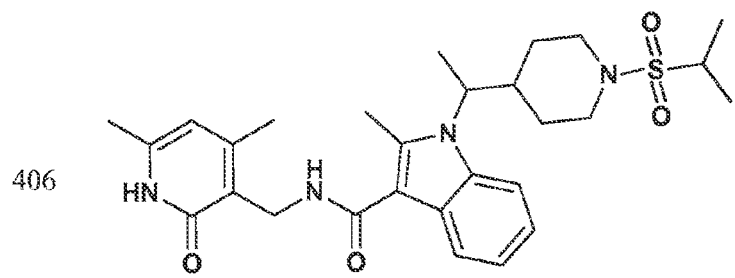
Figure 1:
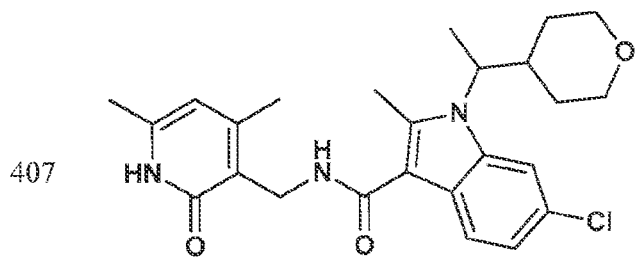
Figure 1:
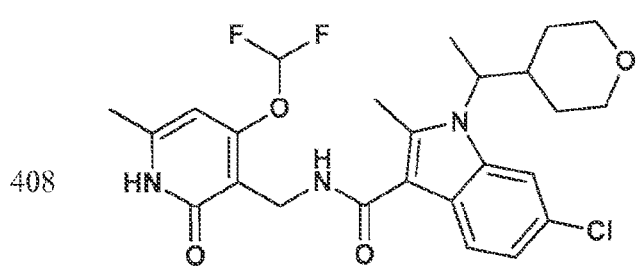
Figure 1:
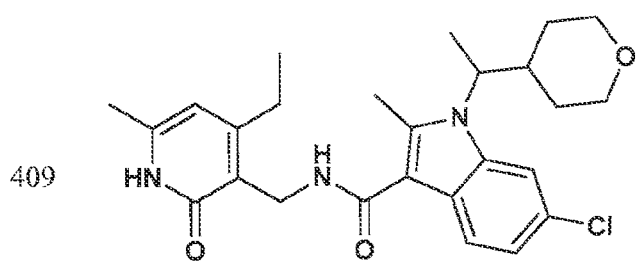
Figure 1:
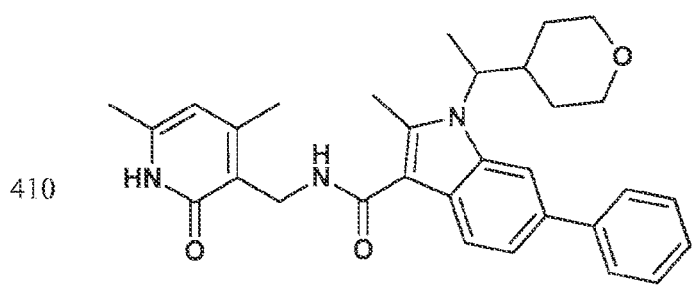
Figure 1:
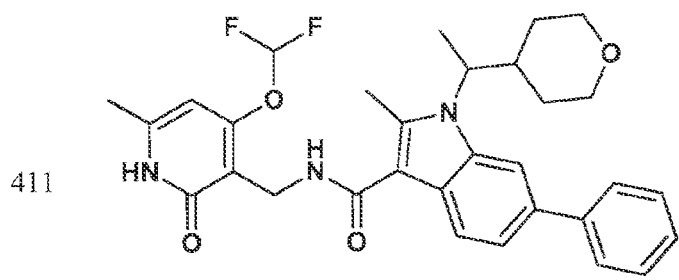
Figure 1:
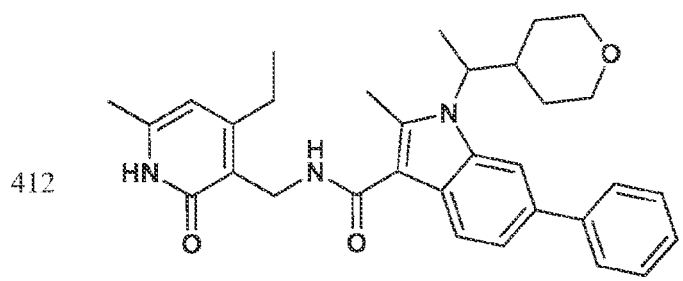
Figure 1:
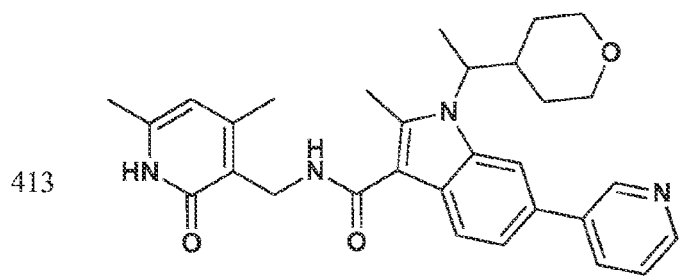
Figure 1:
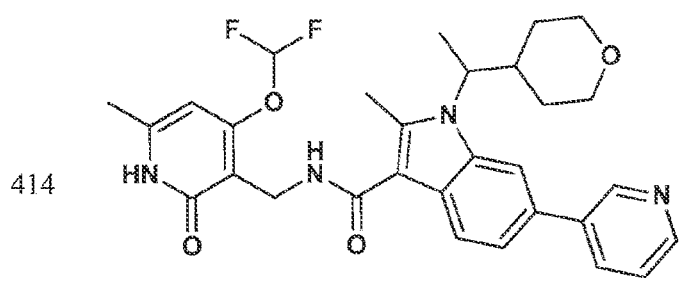
Figure 1:
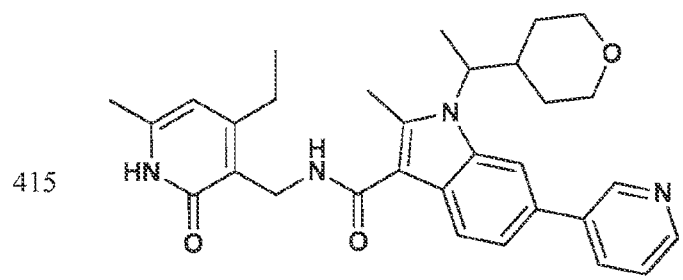
Figure 1:
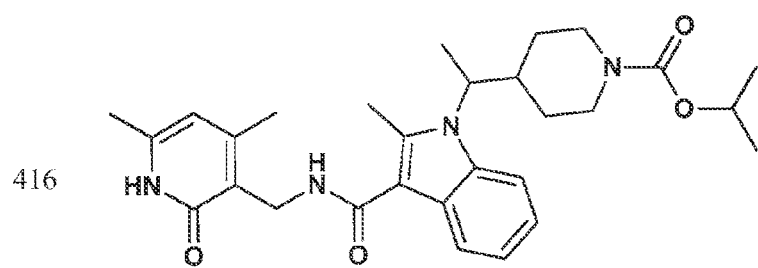
Figure 1:
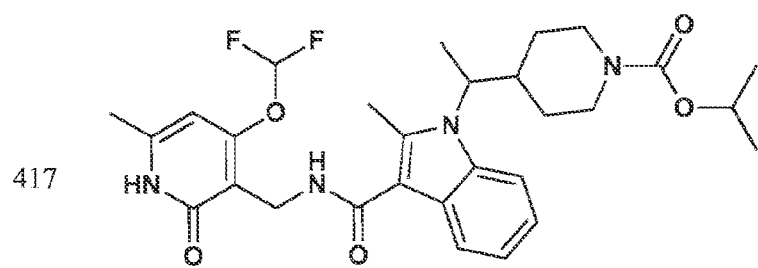
Figure 1:
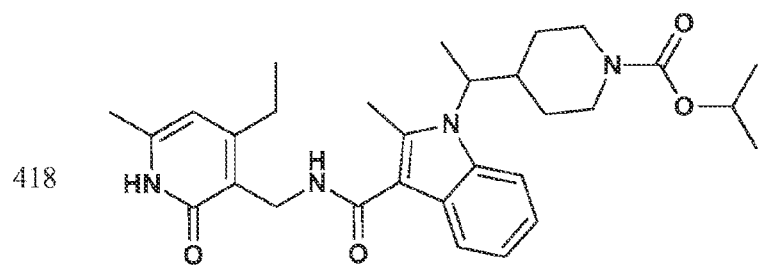
Figure 1:
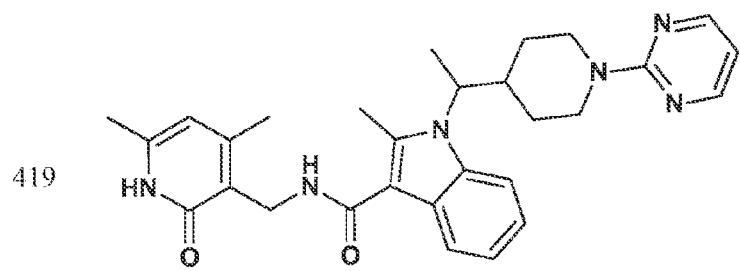
Figure 1:
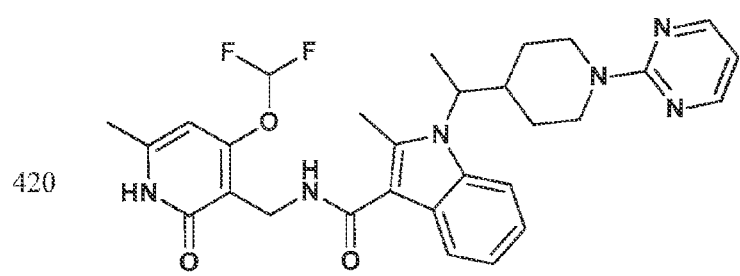
Figure 1:
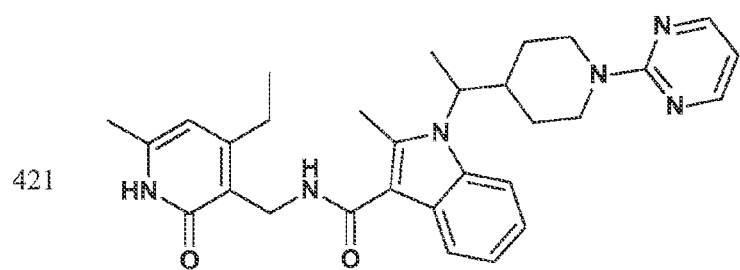
Figure 1:
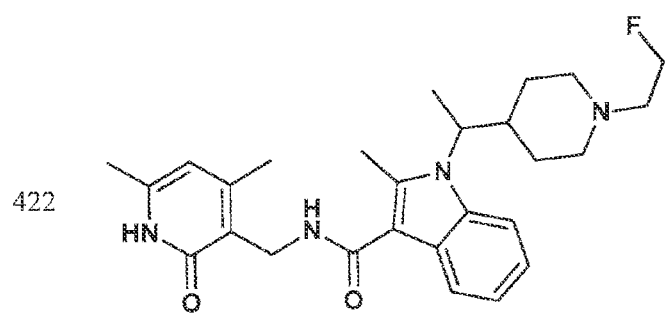
Figure 1:
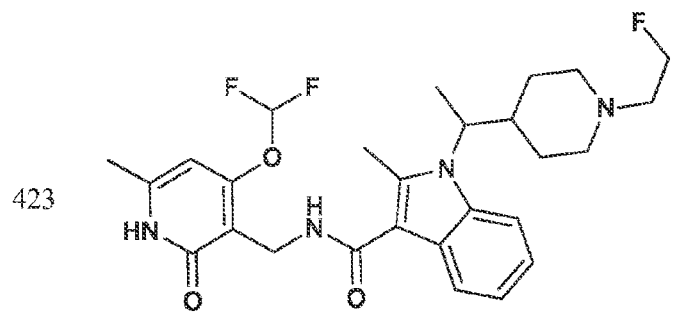
Figure 1:
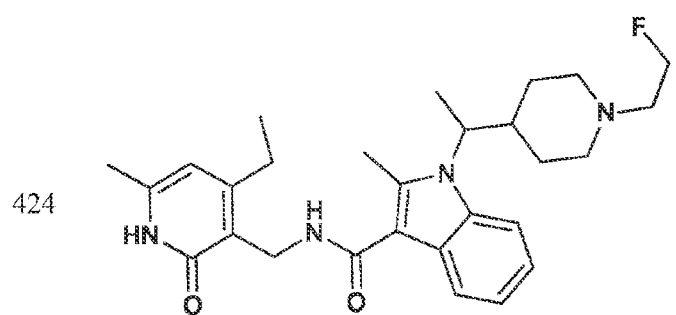
Figure 1:
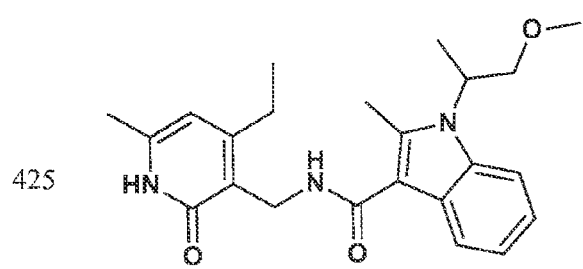
Figure 1:
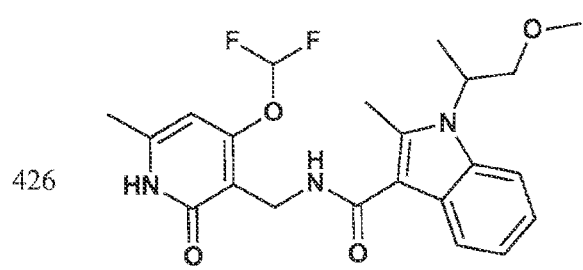
Figure 1:
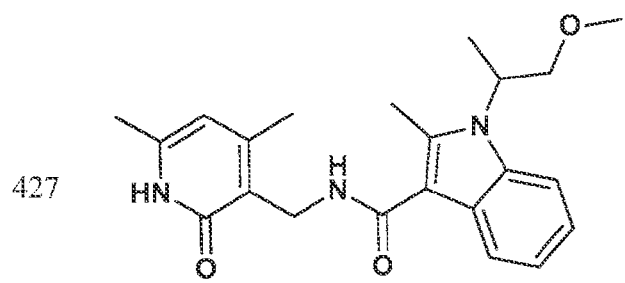
Figure 1:
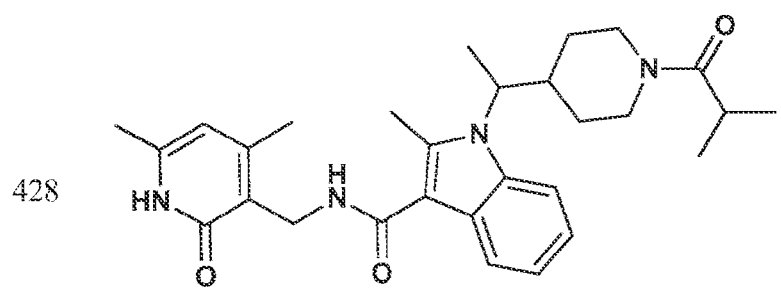
Figure 1:
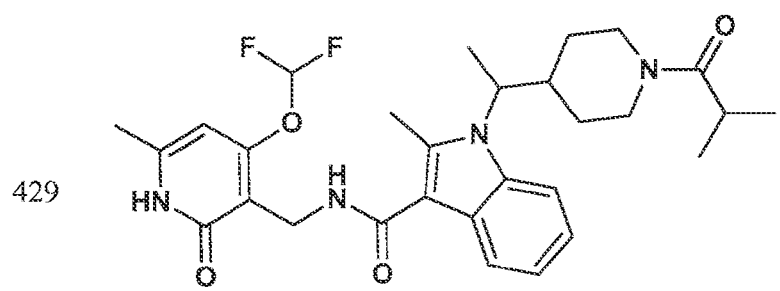
Figure 1:
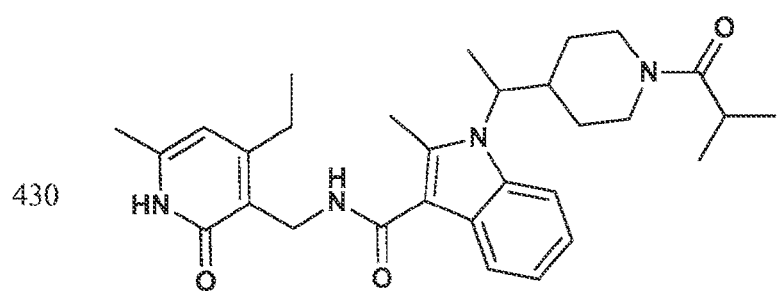
Figure 1:
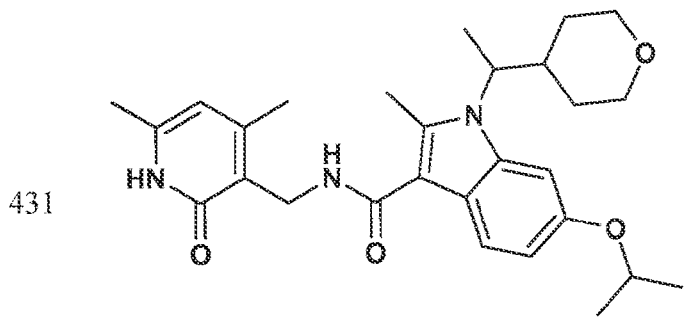
Figure 1:
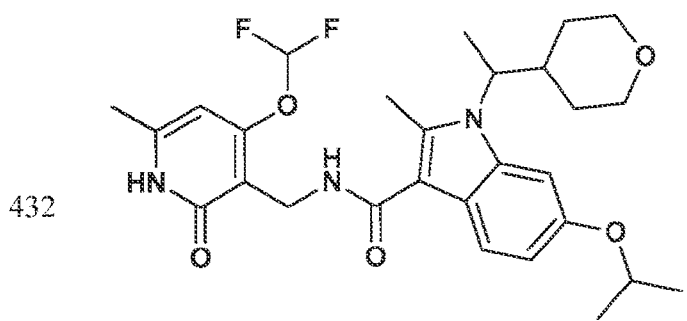
Figure 1:
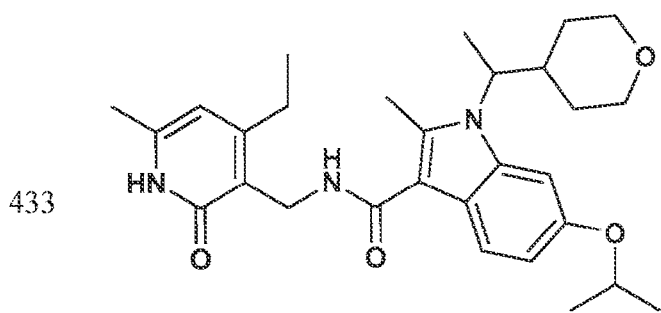
Figure 1:
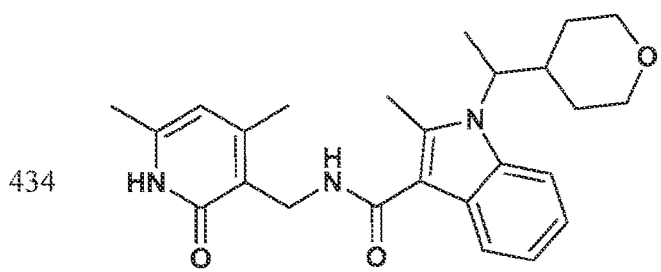
Figure 1:
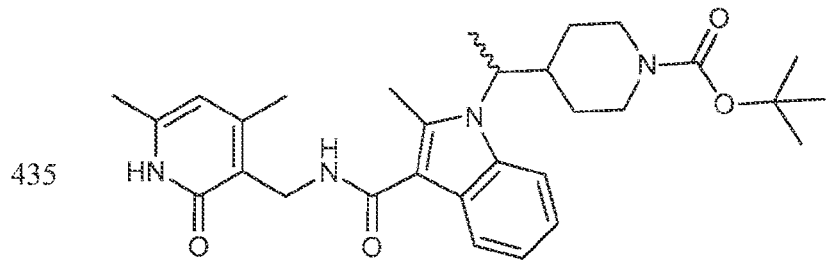
Figure 1:
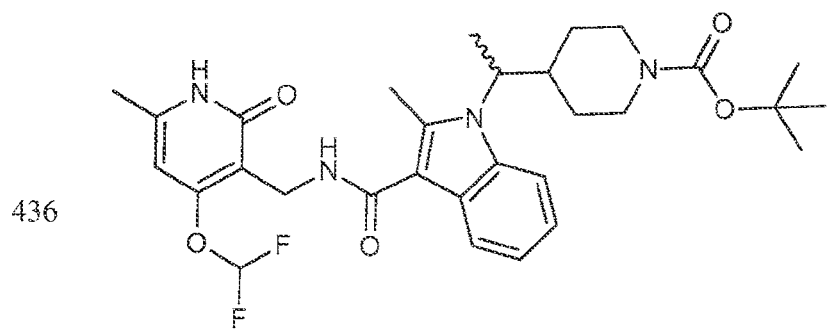
Figure 1:
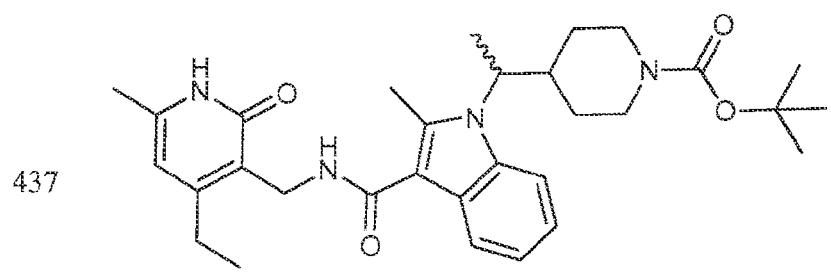
Figure 1:
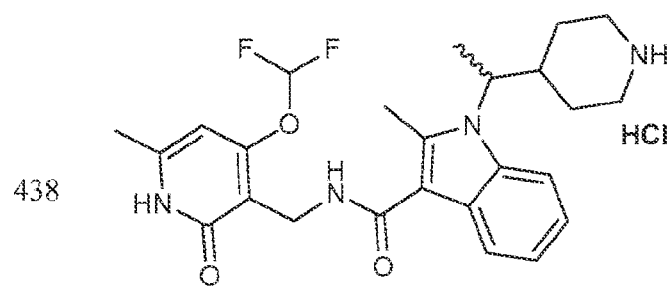
Figure 1:
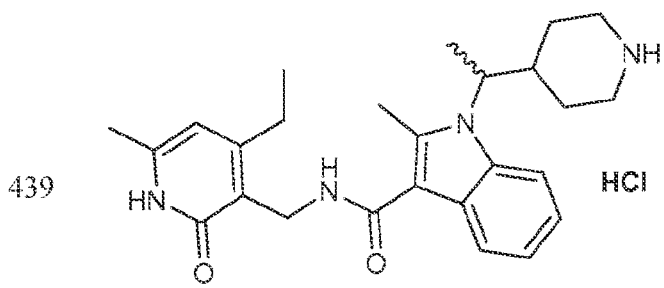
Figure 1:
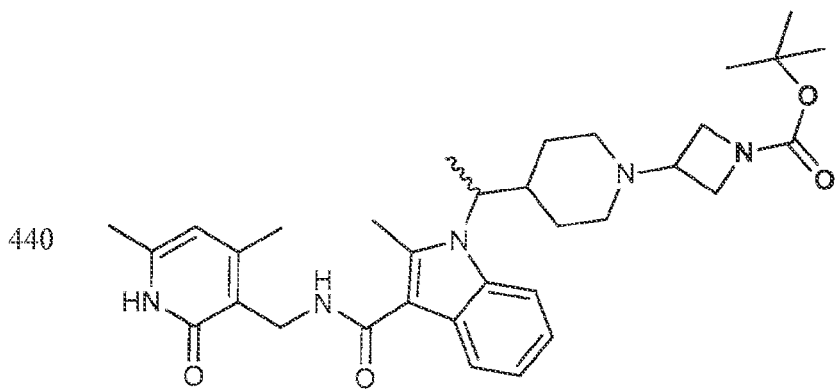
Figure 1:
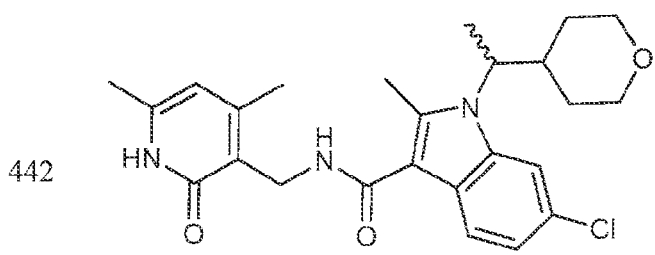
Figure 1:
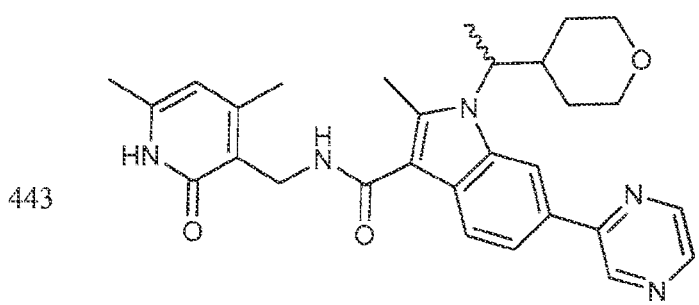
Figure 1:
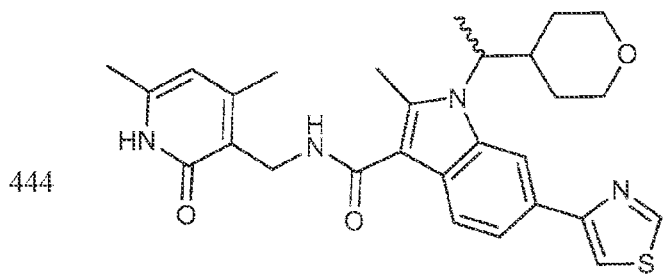
Figure 1:
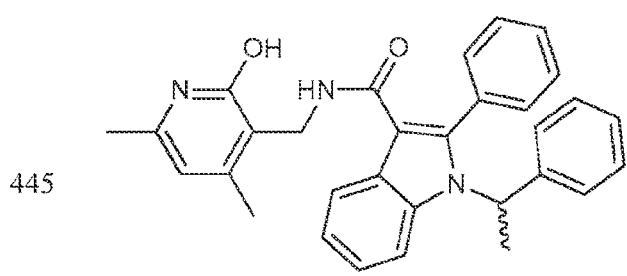
Figure 1:
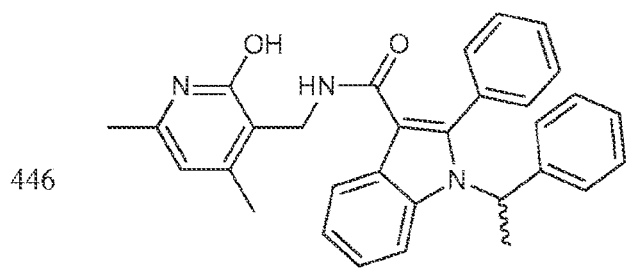
Figure 1:
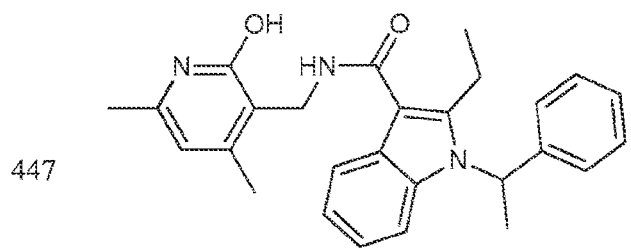

1. General Description of Compounds of the Invention

In certain embodiments, the present invention provides a compound of formula I:

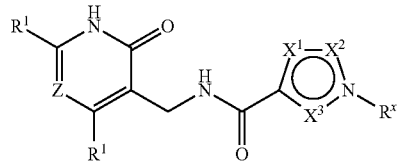

or a pharmaceutically acceptable salt thereof, wherein
Z is =C($R^2$)— or =N—;
each of $X^1$ and $X^2$ is independently selected from =N—, and =C($R^3$)—;
$X^3$ is selected from =N—, and =C($R^6$)—;
no more than one of $X^1$, $X^2$, and $X^3$ is =N—;
each $R^1$ and $R^2$ is independently selected from hydrogen, halo, —OH, —CN, $C_1$-$C_4$ alkyl, —O—($C_1$-$C_4$ alkyl), —N($R^7$)$_2$, —($C_0$-$C_4$ alkylene)-aryl, —($C_0$-$C_4$ alkylene)-heteroaryl, —($C_0$-$C_4$ alkylene)-heterocyclyl, and —($C_0$-$C_4$ alkylene)-carbocyclyl; or
one $R^1$ and $R^2$ are taken together with atoms to which they are bound to form an aryl, heteroaryl, heterocyclyl, or carbocyclyl ring;
each $R^3$ and $R^6$ is independently selected from hydrogen, halo, —CN, —($C_0$-$C_4$ alkylene)-$R^8$, —($C_2$-$C_6$ alkenyl or alkynyl)-$R^9$, —($C_1$-$C_4$ alkylene)-O—$R^9$, —($C_1$-$C_4$ alkylene)-O—($C_1$-$C_4$ alkylene)-$R^8$, —O—($C_0$-$C_4$ alkylene)-$R^9$, —O—($C_2$-$C_4$ alkylene)-O—$R^8$, —O—($C_1$-$C_4$ alkylene)-$R^9$, —($C_0$-$C_4$ alkylene)-N($R^7$)$_2$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^7$)$_2$, —($C_0$-$C_4$ alkylene)-N($R^9$)—C(O)—$R^9$, —O—($C_1$-$C_4$ alkylene)-C(O)—N($R^7$)$_2$, —O—($C_2$-$C_4$ alkylene)-N($R^9$)—C(O)—($R^7$), —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—N($R^7$)$_2$; or
two $R^3$ are taken together with the carbon atoms to which they are bound to form an aryl, heteroaryl, heterocyclyl, or carbocyclyl fused to the ring comprising $X^1$, $X^2$ and $X^3$;
$R^x$ is Q, —S(O)$_2$-Q, —C(O)-Q, or —CH($R^4$)($R^5$);
Q is selected from aryl, heteroaryl, heterocyclyl, or carbocyclyl;
$R^4$ is selected from $C_2$-$C_6$ alkyl, —CH$_2$—O—($C_1$-$C_4$ alkyl) and —($C_0$-$C_6$ alkylene)-Q, wherein one or two methylene units in the alkyl or alkylene portion of $R^4$ are optionally and independently replaced by —O—, —S—, —S(=O)—, —S(=O)$_2$—, or —N($R^{10}$)—; or
one methylene unit of $R^4$ is taken together with $X^2$ or $X^3$, when the $X^2$ or $X^3$ is =C($R^3$)—, and the intervening atoms to form a heteroaryl or heterocyclyl fused to the ring comprising $X^1$, $X^2$, and $X^3$;

$R^5$ is selected from hydrogen, —($C_0$-$C_6$ alkylene)-Q, and $C_1$-$C_6$ alkyl, wherein one or two methylene units in $R^5$ are optionally and independently replaced by —O—, —S—, —S(=O)—, —S(=O)$_2$—, or —NR$^{10}$—;

each $R^7$ is independently selected from —($C_0$-$C_4$ alkylene)-$R^9$, —($C_0$-$C_4$ alkylene)-O—$R^9$, —S(O)$_2$—$R^8$, —C(=O)—$R^8$, —C(=O)—N($R^9$)$_2$, —($C_1$-$C_4$ alkylene)-O—C(=O)—$R^8$ and —($C_0$-$C_4$ alkylene)-C(=O)—O—$R^9$; or two $R^7$ are taken together with the nitrogen atom to which they are commonly bound to form an optionally substituted heterocyclyl or heteroaryl;

$R^8$ is selected from $C_1$-$C_4$ alkyl, aryl, heteroaryl, carbocyclyl and heterocyclyl;

$R^9$ is selected from hydrogen or $R^8$;

$R^{10}$ is selected from hydrogen, $C_1$-$C_4$ alkyl, —S(=O)$_2$—$R^9$, —C(=O)—$R^8$, —C(=O)—N($R^9$)($R^{12}$), and —C(=O)—O—$R^{11}$;

$R^{11}$ is selected from unsubstituted $C_1$-$C_4$ alkyl and $C_1$-$C_4$ haloalkyl;

$R^{12}$ is selected from hydrogen, unsubstituted $C_1$-$C_4$ alkyl and $C_1$-$C_4$ haloalkyl; and wherein unless otherwise designated any alkyl, alkylene, alkenyl, alkynyl, aryl, heteroaryl, heterocyclyl or carbocyclyl portion of the compound is optionally substituted.

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5th Edition, John Wiley & Sons, Inc., New York, 2001; Larock, *Comprehensive Organic Transfrmations*, VCH Publishers, Inc., New York, 1989; Carruthers, *Some Modern MAethodc of Organic Synthesis,* 3rd Edition. Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

A wavy bond ( ∼ ) at a chiral center in a chemical structure is used to denote compounds of the invention that are optically pure, but whose optical rotation has not been determined. A straight bond at a chiral center indicates a racemic mixture although, as stated above, the invention also includes all possible isomeric forms of the racemate.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group.

The term "methylene unit" refers to a divalent —$CH_2$— group present in an alkyl, alkenyl, alkynyl, alkylene, alkenylene, or alkynylene moiety.

The term "$C_0$ alkylene" as used herein means a bond. Thus, a moiety defined herein as "—($C_0$-$C_6$, alkylene)-aryl" includes both -aryl (i.e., $C_0$ alkylene-aryl) and —($C_1$-$C_6$ alkylene)-aryl.

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms.

Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "carbocyclyl" (also referred to herein as "carbocycle" "cycloaliphatic" or "cycloalkyl"), as used herein, means a monocyclic hydrocarbon or bicyclic hydrocarbon that is completely saturated or that contains one or more units of unsaturation, but where there is no ring is aromatic.

The term "aryl" used alone or as part of a larger moiety as in "aralkyl", "aralkoxy", or "aryloxyalkyl", refers to monocyclic and bicyclic carbon ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more carbocyclyl rings regardless of whether the aromatic carbon ring or the carbocyclic ring is the pendant ring, or a group in which an aromatic carbon ring is fused to one or more heteroaryl or heterocyclyl, rings, such as indanyl, phthalimidyl, naphthimidyl, phenantriidinyl, or tetrahydronaphthyl, and the like, wherein the pendant ring of the fused ring system is the aromatic carbon ring.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, wherein the pendant ring of the fused ring system is heteroaromatic. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, 5,6,7,8-tetrahydroquinolinyl, 5,6,7,8-tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. The term "heteroarylene" refers to a bivalent mono- or bicyclic heteroaryl ring.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. In certain embodiments, a "heterocycle", group is a 1,1'-heterocyclylene group (i.e., a spiro-fused ring). When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, 1,2,3,4-tetrahydroquinolinyl, 1,2,3,4-tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, wherein the pendant ring of the fused ring system is heterocyclyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

As used herein, the terms "carbocyclylene" or "cycloalylene" are used interchangeably and refer to a bivalent carbocyclyl or cycloalkyl group. In certain embodiments, a carbocyclylene or cycloalkylene group is a 1,1-cycloalkylene group (i.e., a spiro-fused ring). Exemplary 1,1-cycloalkylene groups include

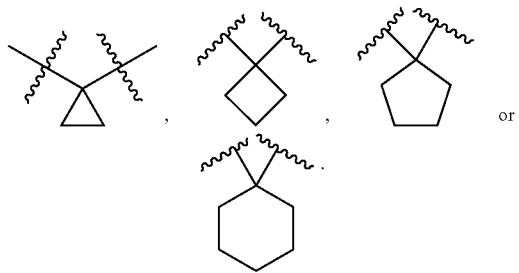

In other embodiments, a cycloalkylene group is a 1,2-cycloalkylene group or a 1,3-cycloalkylene group. Exemplary 1,2-cycloalkylene groups include

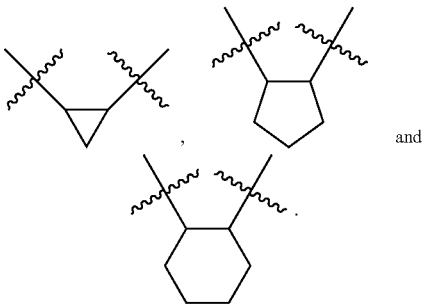

Exemplary 1,3-cycloalkylene groups include

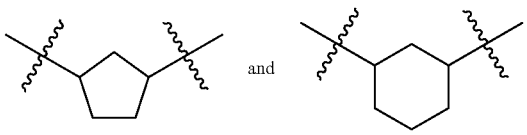

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$; $-SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)O_2CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$; $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R*_2))_{23}O-$, or $-S(C(R*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "inhibitor" is defined as a compound that binds to and/or inhibits a target S-adenosylmethionine (SAM) utilizing enzyme with measurable affinity. In certain embodiments, an inhibitor has an IC$_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in activity of at least one SAM utilizing enzyme between a sample comprising a provided compound, or composition thereof, and at least one SAM dependent enzyme, and an equivalent sample comprising at least one SAM dependent enzyme, in the absence of said compound, or composition thereof.

3. Description of Exemplary Compounds

In certain embodiments, the present invention provides a compound of formula I:

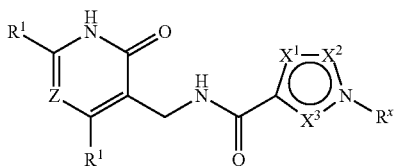

I or a pharmaceutically acceptable salt thereof, wherein each variable is as defined above and described herein. This same structure may also be represented as:

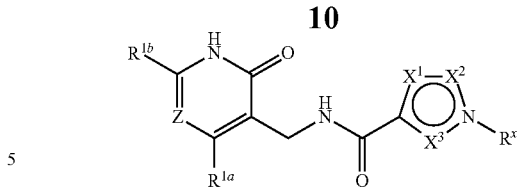

to distinguish between the two R$^1$ moieties attached to the left-hand ring.

As defined generally above and herein, Z is =C(R$^2$)— or =N—, wherein R$^2$ is as defined above and described herein. In some embodiments, Z is =C(R$^2$)— wherein R$^2$ is as defined above and described herein. In some embodiments, Z is =CH—. In some embodiments, Z is =N—.

As defined generally above and herein, each of X$^1$ and X$^2$ is independently selected from =N— and =C(R$^3$)—, wherein R$^3$ is as defined above and described herein. In some embodiments, each of X$^1$ and X$^2$ is independently =C(R$^3$)—, wherein R$^3$ is as defined above and described herein. In some embodiments, X$^1$ is =C(R$^3$)— and X$^2$ is =N—, wherein R$^3$ is as defined above and described herein. In some embodiments, X$^1$ is selected from =CH—, =C(C$_1$-C$_4$alkyl)- and =C(aryl)-, and X$^2$ is =N—. In some embodiments, X$^1$ is selected from =CH—, =C(CH$_3$)— and =C(phenyl)- and X$^2$ is =N—, wherein the phenyl is optionally substituted. In some embodiments, X$^1$ is =C(H)— and X$^2$ is =N—. In some embodiments, X$^1$ is =C(CH$_3$)— and X$^2$ is =N. In some embodiments, X$^2$ is =C(R$^3$)— and X$^1$ is =N—, wherein R$^3$ is as defined above and described herein. In some embodiments, X$^2$ is =C(H)— and X$^1$ is =N—. In some embodiments, X$^2$ is =C(CH$_3$)— and X$^1$ is =N—. In some embodiments, X$^1$ is selected from =CH—, =C(C$_1$-C$_4$alkyl)- and =C(aryl)-. In some embodiments, X$^2$ is =N—.

In some embodiments, each of X$^1$ and X$^2$ is independently =C(R$^3$)—, wherein two R$^3$ are taken together with the carbon atoms to which they are bound to form an aryl, heteroaryl, heterocyclyl, or carbocyclyl fused to the ring comprising X$^1$, X$^2$ and X$^3$, wherein each of X$^1$, X$^2$ and X$^3$ is as defined above and described herein. In some embodiments, each of X$^1$ and X$^2$ is independently =C(R$^3$)—, wherein two R$^3$ are taken together with the carbon atoms to which they are bound to form an aryl, heteroaryl, or carbocyclyl fused to the ring comprising X$^1$, X$^2$ and X$^3$, wherein each of X$^1$, X$^2$ and X$^3$ is as defined above and described herein.

As defined generally above and herein, X$^3$ is independently selected from =N— and =C(R$^6$)—, wherein R$^6$ is as defined above and described herein.

In some embodiments, X$^1$ is =N—.

In some embodiments, X$^3$ is =C(R$^6$)—, wherein R$^6$ is as defined above and described herein. In some embodiments, X$^3$ is selected from =C(C$_1$-C$_4$ alkyl)-, =CH—, =C(OH)—, =C(CN)—, =C(O—C$_1$-C$_4$ alkyl), =C(C(O)—N(R$^7$)$_2$)—, =C(aryl)-, =C(carbocyclyl)-, and =C(heterocyclyl)-, wherein each R$^7$ is independently as defined above and described herein. In some embodiments, X$^3$ is selected from =CH—, =C(CH$_3$)—, =C(CH$_2$CH$_3$)—, =C(OH)—, =C(CN)—, =C(OCH$_3$)—, =C(C(O)NH$_2$)—, =C(cyclopropyl)-, =C(phenyl)-, and =C(oxetanyl)-, wherein the cyclopropyl, phenyl or oxetanyl is optionally substituted. In some embodiments, X$^3$ is selected from =CH—, =C(CH$_3$)—, =C(CH$_2$CH$_3$)—, =C(OH)—, =C(CN)—, =C(O—CH$_3$), =C(C(O)—NH$_2$)—, =C(cyclopropyl)-, =C(phenyl)-, and =C(oxetanyl)-, wherein the cyclopropyl, phenyl or oxetanyl is substituted. In some embodiments, X$^3$ is selected from =CH—, =C(CH$_3$)—, =C(CH$_2$CH$_3$)—, =C(OH)—, =C(CN)—, =C(O—CH$_3$), =C(C(O)—NH$_2$)—, =C(cyclopropyl)-, =C(phenyl)-, and =C(oxetanyl)-, wherein the cyclopropyl, phenyl or oxetanyl is unsubstituted. In some embodiments, X$^3$ is selected from =CH—, =C(CH$_3$)—, or =C(phenyl)-, wherein the phenyl is optionally substituted.

As defined generally above and herein, each $R^1$ and $R^2$ is independently selected from hydrogen, halo, —OH, —CN, $C_1$-$C_4$ alkyl, —O—($C_1$-$C_4$ alkyl), —N($R^7$)$_2$, —($C_0$-$C_4$ alkylene)-aryl, —($C_0$-$C_4$ alkylene)-heteroaryl, —($C_0$-$C_4$ alkylene)-heterocyclyl, and —($C_0$-$C_4$ alkylene)-carbocyclyl; or
one $R^1$ and $R^2$ are taken together with atoms to which they are bound to form an aryl, heteroaryl, heterocyclyl, or carbocyclyl ring;
wherein each $R^7$ is independently as defined above and described herein.

In some embodiments, each $R^1$ and $R^2$ is hydrogen. In one embodiment, each $R^1$ and $R^2$ is independently selected from halo, —OH, —CN, $C_1$-$C_4$ alkyl, —O—($C_1$-$C_4$ alkyl), —N($R^7$)$_2$, —($C_0$-$C_4$ alkylene)-aryl, —($C_0$-$C_4$ alkylene)-heteroaryl, —($C_0$-$C_4$ alkylene)-heterocyclyl, and —($C_0$-$C_4$ alkylene)-carbocyclyl; or
one $R^1$ and $R^2$ are taken together with atoms to which they are bound to form an aryl, heteroaryl, heterocyclyl, or carbocyclyl ring;
wherein each $R^7$ is independently as defined above and described herein.

In some embodiments, each $R^1$ and $R^2$ is independently selected from halo, —OH, —CN, $C_1$-$C_4$ alkyl, —O—($C_1$-$C_4$ alkyl), —N($R^7$)$_2$, —($C_0$-$C_4$ alkylene)-aryl, —($C_0$-$C_4$ alkylene)-heteroaryl, —($C_0$-$C_4$ alkylene)-heterocyclyl, and —($C_0$-$C_4$ alkylene)-carbocyclyl, wherein each $R^7$ is independently as defined above and described herein. In some embodiments, one $R^1$ and $R^2$ are taken together with atoms to which they are bound to form an aryl, heteroaryl, heterocyclyl, or carbocyclyl ring.

In some embodiments, each $R^1$ is independently selected from hydrogen and —$CH_3$. In some embodiments, each $R^1$ is hydrogen. In some embodiments, each $R^1$ is —$CH_3$. In some embodiments, one $R^1$ is hydrogen. In some embodiments, one $R^1$ is —$CH_3$. In some embodiments, one $R^1$ is —$CH_3$ and the other $R^1$ is selected from —O—$CH$, and —NH—$CH_3$ In some embodiments, each of $R^1$ and $R^2$ is hydrogen. In some embodiments, each $R^1$ is —$CH_3$; and Z is =C(H)—. In some embodiments, one $R^1$ is —$CH_3$; the other $R^1$ is —O—$CH_3$ or —NH—$CH_3$; and Z is =C(H)—.

In some embodiments, $R^2$ is hydrogen.

In some embodiments, one $R^1$ is —$CH_3$ and the other $R^1$ is selected from —$C_1$-$C_2$ alkyl and —O—($C_1$-$C_2$ alkyl), wherein $R^1$ is optionally substituted with one or more fluoro. In one aspect of this embodiment $R^{1b}$ is —$CH_3$. In another aspect of this embodiment $R^{1a}$ is selected from —$OCH_3$, —$CH_3$, —$OCHF_2$, and —$CH_2CH_3$. In a more specific aspect of this embodiment $R^{1b}$ is —$CH_3$ and Z is =CH—. In an even more specific aspect of this embodiment $R^{1a}$ is selected from —$OCH_3$, —$CH_3$, —$OCHF_2$, and —$CH_2CH_3$; $R^{1b}$ is —$CH_3$; and Z is =CH—.

As defined generally above and herein, each $R^3$ and $R^6$ is independently selected from hydrogen, halo, —CN, —($C_0$-$C_4$ alkylene)-$R^8$, —($C_2$-$C_6$ alkenyl or alkynyl)-$R^9$, —($C_1$-$C_4$ alkylene)-O—$R^9$, —($C_1$-$C_4$ alkylene)-O—($C_1$-$C_4$ alkylene)-$R^8$, —O—($C_0$-$C_4$ alkylene)-$R^9$, —O—($C_2$-$C_4$ alkylene)-O—$R^8$, —O—($C_1$-$C_4$ alkylene)-$R^9$, —($C_0$-$C_4$ alkylene)-N($R^7$)$_2$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^7$)$_2$, —($C_0$-$C_4$ alkylene)-N($R^9$)—C(O)—$R^9$, —O—($C_1$-$C_4$ alkylene)-C(O)—N($R^7$)$_2$, —O—($C_2$-$C_4$ alkylene)-N($R^9$)—C(O)—($R^7$), —($C_0$-$C_4$ alkylene)-S(O)—$R^8$, —($C_0$-$C_4$ alkylene)-S(O)$_2$—$R^8$ and —($C_1$-$C_4$ alkylene)-S(O)$_2$—N($R^7$)$_2$; or
two $R^3$ are taken together with the carbon atoms to which they are bound to form an aryl, heteroaryl, heterocyclyl, or carbocyclyl fused to the ring comprising $X^1$, $X^2$ and $X^3$;
wherein each of $X^1$, $X^2$, $X^3$, $R^7$, $R^8$ and $R^9$ is independently as defined above and described herein.

In some embodiments, each $R^3$ and $R^6$ is independently selected from hydrogen, halo, —CN, —($C_0$-$C_4$ alkylene)-$R^8$, —($C_2$-$C_6$ alkenyl or alkynyl)-$R^9$, —($C_1$-$C_4$ alkylene)-O—$R^8$, —($C_1$-$C_4$ alkylene)-O—($C_1$-$C_4$ alkylene)-$R^8$, —O—($C_0$-$C_4$ alkylene)-$R^9$, —O—($C_2$-$C_4$ alkylene)-O—$R^8$, —O—($C_1$-$C_4$ alkylene)-$R^9$, —($C_0$-$C_4$ alkylene)-N($R^7$)$_2$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^7$)$_2$, —($C_0$-$C_4$ alkylene)-N($R^9$)—C(O)—$R^9$, —O—($C_1$-$C_4$ alkylene)-C(O)—N($R^7$)$_2$, —O—($C_2$-$C_4$ alkylene)-N($R^9$)—C(O)—($R^9$), —($C_0$-$C_4$ alkylene)-S(O)—$R^8$ and —($C_0$-$C_4$ alkylene)-S(O)$_2$—N($R^7$)$_2$; or
two $R^3$ are taken together with the carbon atoms to which they are bound to form an aryl, heteroaryl, heterocyclyl, or carbocyclyl fused to the ring comprising $X^1$, $X^2$ and $X^3$;
wherein each of $X^1$, $X^2$, $X^3$, $R^7$, $R^8$ and $R^9$ is independently as defined above and described herein.

In some embodiments, each $R^3$ and $R^6$ is independently selected from hydrogen, halo, —CN, —($C_0$-$C_4$ alkylene)-$R^8$, —($C_2$-$C_6$ alkenyl or alkynyl)-$R^9$, —($C_1$-$C_4$ alkylene)-O—$R^9$, —($C_1$-$C_4$ alkylene)-O—($C_1$-$C_4$ alkylene)-$R^8$, —O—($C_0$-$C_4$ alkylene)-$R^9$, —O—($C_2$-$C_4$ alkylene)-O—$R^8$, —O—($C_1$-$C_4$ alkylene)-$R^9$, —($C_0$-$C_4$ alkylene)-N($R^7$)$_2$, —($C_0$-$C_4$ alkylene)-C(O)—O—$R^9$, —($C_0$-$C_4$ alkylene)-C(O)—N($R^7$)$_2$, —($C_0$-$C_4$ alkylene)-N($R^9$)—C(O)—$R^9$, —O—($C_1$-$C_4$ alkylene)-C(O)—N($R^7$)$_2$, —($C_0$-$C_4$ alkylene)-N($R^9$)—C(O)—$R^9$, —O—($C_1$-$C_4$ alkylene)-C(O)—N($R^7$)$_2$, —O—($C_2$-$C_4$ alkylene)-N($R^9$)—C(O)—($R^7$), —($C_0$-$C_4$ alkylene)-S(O)—R, —($C_0$-$C_4$ alkylene)-S(O)$_2$—R and —($C_0$-$C_4$ alkylene)-S(O)$_2$—N($R^7$)$_2$, wherein each of $R^7$, $R^8$ and $R^9$ is independently as defined above and described herein.

In some embodiments, one $R^3$ is —($C_0$-$C_4$ alkylene)-$R^8$, wherein $R^8$ is as defined above and described herein. In some embodiments, one $R^3$ is $R^8$, wherein $R^8$ is as defined above and described herein. In some embodiments, one $R^3$ is aryl. In some embodiments, one $R^3$ is optionally substituted phenyl. In some embodiments, one $R^3$ is unsubstituted phenyl. In some embodiments, one $R^3$ is substituted phenyl. In some embodiments, one $R^3$ is $C_1$-$C_4$ alkyl. In some embodiments, one $R^3$ is methyl. In some embodiments, $R^3$ is 3-methoxy.

In some embodiments, two $R^3$ are taken together with the carbon atoms to which they are bound to form an aryl, heteroaryl, heterocyclyl, or carbocyclyl fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an aryl, heteroaryl, or carbocyclyl fused to the ring comprising $X^1$, $X^2$ and $X^3$, wherein each of $X^1$, $X^2$ and $X^3$ is independently as defined above and described herein.

In some embodiments, two $R^3$ are taken together with the carbon atoms to which they are bound to form an aryl fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an optionally substituted phenyl fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an unsubstituted phenyl fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form a substituted phenyl fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an aryl fused to the ring comprising $X^1$, $X^2$ and $X^3$; wherein $X^3$ is selected from =CH—, =C(CH$_3$)—, or =C(phenyl)-, wherein the phenyl is optionally substituted; and wherein each of $X^1$, and $X^2$ is independently as defined above and described herein. In some embodiments, two $R^3$ are taken together with the carbon atoms to which they are bound to form an aryl fused to the ring comprising $X^1$, $X^2$ and $X^3$, wherein the fused ring has the structure:

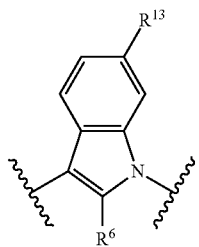

wherein $R^6$ is as defined herein; and $R^{13}$ is selected from hydrogen, halo, phenyl, pyridinyl, and —O—($C_1$-$C_4$ alkyl).

In some embodiments, two $R^3$ are taken together with the carbon atoms to which they are bound to form a heteroaryl fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an optionally substituted pyrazinyl, pyrimidinyl or pyridyl ring fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an unsubstituted pyrazinyl, pyrimidinyl or pyridyl ring fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form a substituted pyrazinyl, pyrimidinyl or pyridyl ring fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an optionally substituted pyridyl ring fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an optionally substituted pyridazinyl ring fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an optionally substituted pyrimidinyl ring fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form an optionally substituted pyrazinyl ring fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form a pyridyl fused to the ring comprising $X^1$, $X^2$ and $X^3$, wherein the fused ring has the structure:

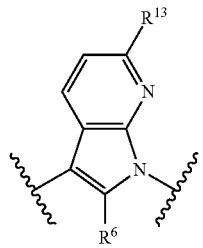

wherein $R^6$ is as defined herein; and $R^{13}$ is selected from hydrogen, halo, phenyl, pyridinyl, and —O—($C_1$-$C_4$ alkyl).

In some embodiments, two $R^3$ are taken together with the carbon atoms to which they are bound to form a heterocyclyl fused to the ring comprising $X^1$, $X^2$ and $X^3$, wherein each of $X^1$, $X^2$ and $X^3$ is independently as defined above and described herein.

In some embodiments, two $R^3$ are taken together with the carbon atoms to which they are bound to form a carbocyclyl fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form a cyclobutyl, cyclopentyl, cyclohexyl, or cycloheptyl ring fused to the ring comprising $X^1$, $X^2$ and $X^3$, wherein each of $X^1$, $X^2$ and $X^3$ is independently as defined above and described herein. In some embodiments, two $R^3$ are taken together with the carbon atoms to which they are bound to form a cyclopentyl ring fused to the ring comprising $X^1$, $X^2$ and $X^3$, wherein each of $X^1$, $X^2$ and $X^3$ is independently as defined above and described herein.

In some embodiments, $R^6$ is selected from hydrogen, halo, —CN, —($C_0$-$C_4$ alkylene)-$R^8$, —($C_2$-$C_6$ alkenyl or alkynyl)-$R^9$, —($C_1$-$C_4$ alkylene)-O—$R^9$, —($C_1$-$C_4$ alkylene)-O—($C_1$-$C_4$ alkylene)-$R^8$, —O—($C_0$-$C_4$ alkylene)-$R^9$, —O—($C_2$-$C_4$ alkylene)-O—$R^8$, —O—($C_1$-$C_4$ alkylene)-$R^9$, —($C_0$-$C_4$ alkylene)-N($R^7$)$_2$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^7$)$_2$, —($C_0$-$C_4$ alkylene)-N($R^9$)—C(O)—$R^9$, —O—($C_1$-$C_4$ alkylene)-C(O)—N($R^7$)$_2$, —O—($C_2$-$C_4$ alkylene)-N($R^9$)—C(O)—($R^7$), —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—N($R^7$)$_2$, wherein each of $R^7$, $R^8$ and $R^9$ is independently as defined above and described herein.

In some embodiments. R⁶ is hydrogen. In some embodiments, R⁶ is selected from halo, —CN, —(C₀-C₄ alkylene)-R⁸, —(C₂-C₆ alkenyl or alkynyl)-R⁹, —(C₁-C₄ alkylene)-O—R⁹, —(C₁-C₄ alkylene)-O—(C₁-C₄ alkylene)-R⁸, —O—(C₀-C₄ alkylene)-R⁹, —O—(C₂-C₄ alkylene)-O—R⁸, —O—(C₁-C₄ alkylene)-R⁹, —(C₀-C₄ alkylene)-N(R⁷)₂, —(C₀-C₄ alkylene)-C(O)—O—R⁹, —(C₀-C₄ alkylene)-O—C(O)—R⁹, —(C₀-C₄ alkylene)-C(O)—N(R⁷)₂, —(C₀-C₄ alkylene)-N(R⁹)—C(O)—R⁹, —O—(C₁-C₄ alkylene)-C(O)—N(R⁷)₂, —O—(C₂-C₄ alkylene)-N(R⁹)—C(O)—(R⁷), —(C₀-C₄ alkylene)-S(O)—R⁸, —(C₀-C₄ alkylene)-S(O)₂—R⁸ and —(C₀-C₄ alkylene)-S(O)₂—N(R⁷)₂, wherein each of R⁷, R⁸ and R⁹ is independently as defined above and described herein.

In some embodiments, R⁶ is —O—(C₂-C₄ alkylene)-N(R⁹)—C(O)—(R⁷), wherein each of R⁷ and R⁹ is independently as defined above and described herein. In some embodiments, R⁶ is —O—(C₂-C₄ alkylene)-N(R⁹)—C(O)—(C₀-C₄ alkylene)-R⁹, wherein each R⁹ is independently as defined above and described herein.

In some embodiments, R⁶ is selected from hydrogen and —(C₀-C₄ alkylene)-R⁸, wherein R⁸ is as defined above and described herein. In some embodiments, R⁶ is selected from hydrogen and R⁸, wherein R⁸ is as defined above and described herein. In some embodiments, R⁶ is selected from hydrogen, methyl and optionally substituted phenyl.

In some embodiments, R⁶ is —(C₀-C₄ alkylene)-R⁸, wherein R⁸ is as defined above and described herein. In some embodiments, R⁶ is R⁸, wherein R⁸ is as defined above and described herein.

In some embodiments. R⁶ is C₁-C₄ alkyl. In some embodiments, R⁶ is methyl. In some embodiments, R⁶ is ethyl.

In some embodiments, R⁶ is aryl. In some embodiments, R⁶ is optionally substituted phenyl. In some embodiments. R⁶ is substituted phenyl. In some embodiments, R⁶ is unsubstituted phenyl.

In some embodiments, R⁶ is heteroaryl.

In some embodiments. R⁶ is heterocyclyl. In some embodiments, R⁶ is tetrahydro-2H-pyranyl, tetrahydrofuranyl, or oxetanyl. In some embodiments, R⁶ is oxetanyl. In some embodiments, R⁶ is 3-oxetanyl. In some embodiments, R⁶ is piperidinyl pyrrolidinyl, azetidinyl, or aziridinyl.

In some embodiments, R⁶ is carbocyclyl. In some embodiments, R⁶ is cyclopropyl. In some embodiments, R⁶ is cyclobutyl. In some embodiments, R⁶ is cyclopentyl. In some embodiments, R⁶ is cyclohexyl.

In some embodiments, R⁶ is halo. In some embodiments, R⁶ is —CN. In some embodiments, R⁶ is —(C₀-C₄ alkylene)-C(O)—N(R⁷)₂, wherein each R⁷ is independently as defined above and described herein. In some embodiments, R⁶ is —CONH₂.

In some embodiments, R⁶ is —O—(C₀-C₄ alkylene)-R⁹, wherein R⁹ is as defined above and described herein. In some embodiments, R⁶ is —OH. In some embodiments, R⁶ is —OCH₃.

In some embodiments, R⁶ is selected from C₁-C₄ alkyl, hydrogen, —OH, —CN, —O—(C₁-C₄ alkyl), —C(O)N(R⁷)₂, aryl, carbocyclyl and heterocyclyl, wherein each R⁷ is independently as defined above and described herein. In some embodiments, R⁶ is hydrogen, —CH₃, —CH₂CH₃, —OH, —CN, —OCH₃, —C(O)NH₂, cyclopropyl, phenyl or oxetanyl, wherein the cyclopropyl, phenyl or oxetanyl is optionally substituted. In some embodiments, R⁶ is hydrogen, —CH₃, —CH₂CH₃, —OH, —CN, —OCH₃, —C(O)NH₂, cyclopropyl, phenyl or oxetanyl, wherein the cyclopropyl, phenyl or oxetanyl is substituted. In some embodiments, R⁶ is hydrogen, —CH₃, —CH₂CH₃, —OH, —CN, —OCH₃, —C(O)NH₂, cyclopropyl, phenyl or oxetanyl, wherein the cyclopropyl, phenyl or oxetanyl is unsubstituted.

Exemplary

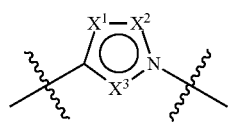

are depicted below.

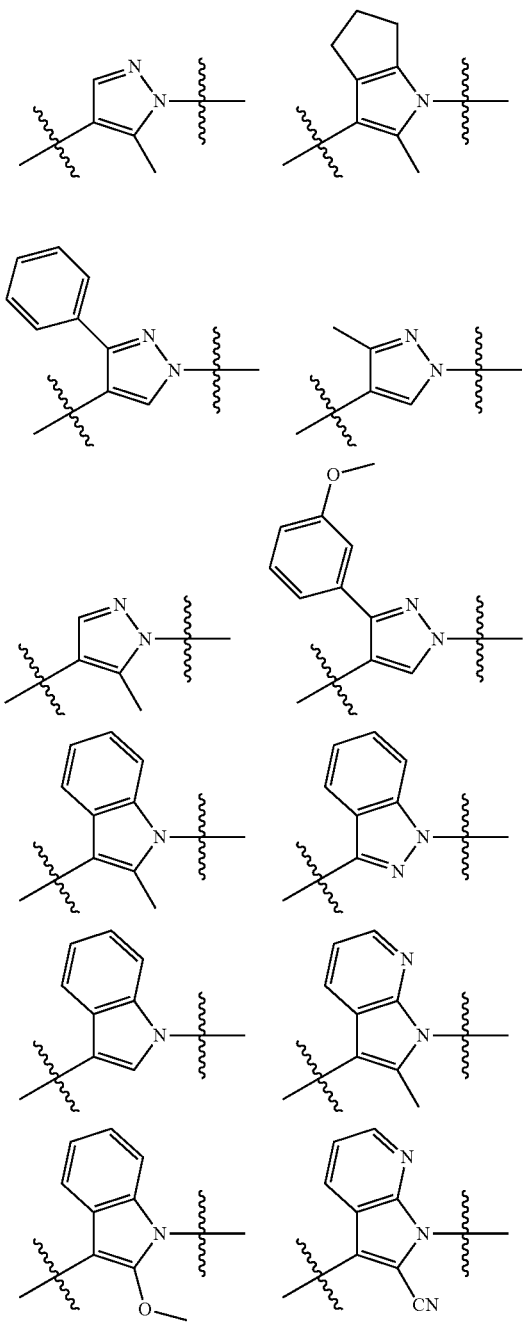

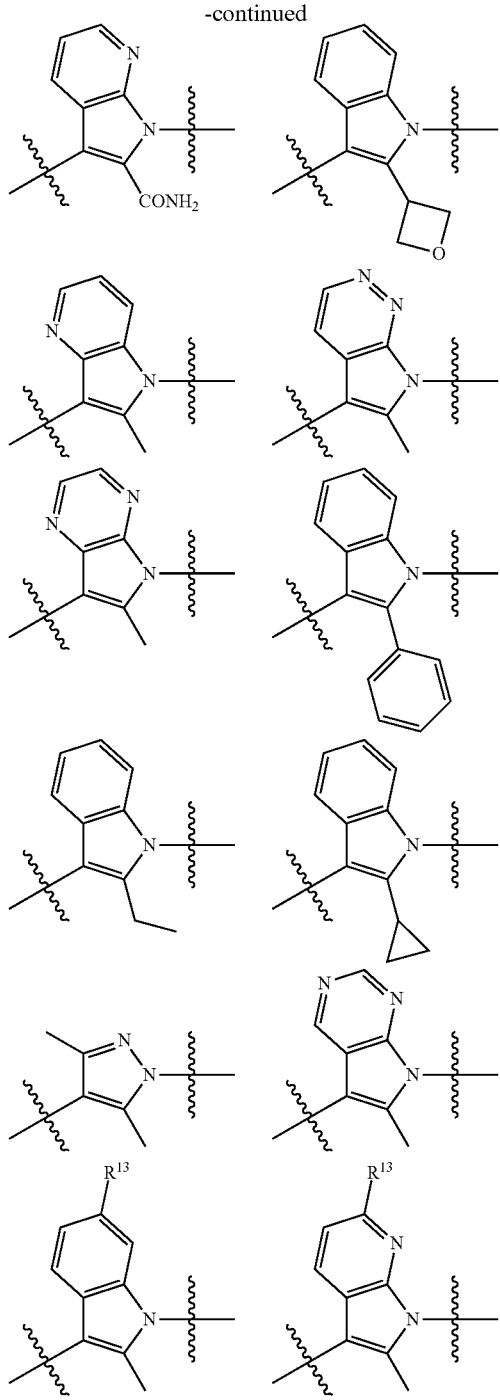

wherein $R^{13}$ is selected from hydrogen, halo, phenyl, pyridinyl, and —O—($C_1$-$C_4$ alkyl).

As defined generally above and herein, $R^x$ is Q, —S(O)$_2$-Q, —C(O)-Q, or —CH($R^4$)($R^5$), wherein each of Q, $R^4$ and $R^5$ is independently as defined above and described herein.

In some embodiments, $R^x$ is Q or —CH($R^4$)($R^5$).

In some embodiments, $R^x$ is Q wherein Q is as defined above and described herein. In some embodiments, $R^x$ is aryl. In some embodiments, $R^x$ is optionally substituted phenyl. In some embodiments, $R^x$ is unsubstituted phenyl. In some embodiments, $R^x$ is substituted phenyl. In some embodiments, $R^x$ is phenyl substituted with branched or straight chain $C_1$-$C_6$ alkyl. In some embodiments, $R^x$ is phenyl substituted with methyl. In some embodiments, $R^x$ is 2-methylphenyl. In some embodiments, $R^x$ is heteroaryl. In some embodiments, $R^x$ is pyridyl. In some embodiments, $R^x$ is 2-pyridinyl. In some embodiments, $R^x$ is 3-pyridinyl. In some embodiments, $R^x$ is 4-pyridinyl. In some embodiments, $R^x$ is carbocyclyl. In some embodiments, $R^x$ is heterocyclyl. In some embodiments, $R^x$ is optionally substituted tetrahydropyranyl. In some embodiments, $R^x$ is substituted tetrahydropyranyl. In some embodiments, $R^x$ is unsubstituted tetrahydropyranyl. In some embodiments, $R^x$ is aryl, heterocyclyl or heteroaryl.

In some embodiments, $R^x$ is —CH($R^4$)($R^5$), wherein each of $R^4$ and $R^5$ is independently as defined above and described herein.

In some embodiments, $R^x$ is —S(O)$_2$-Q, wherein Q is defined above and described herein. In some embodiments, $R^x$ is —S(O)$_2$-phenyl.

In some embodiments, $R^x$ is —C(O)-Q, wherein Q is defined above and described herein. In some embodiments, $R^x$ is —C(O)-phenyl.

As defined generally above and herein, Q is selected from aryl, heteroaryl, heterocyclyl and carbocyclyl. In some embodiments, Q is aryl. In some embodiments, Q is heteroaryl. In some embodiments, Q is heterocyclyl. In some embodiments, Q is carbocyclyl.

As defined generally above and herein, $R^4$ is selected from $C_2$-$C_6$ alkyl, —CH$_2$—O—($C_1$-$C_4$ alkyl) and —($C_0$-$C_6$ alkylene)-Q, wherein one or two methylene units in the alkyl or alkylene portion of $R^4$ are optionally and independently replaced by —O—, —S—, —S(=O)—, —S(=O)$_2$—, or —N($R^3$)—; or
one methylene unit of $R^4$ is taken together with $X^2$ or $X^3$, when the $X^2$ or $X^3$ is =C($R^3$)—, and the intervening atoms to form a heteroaryl or heterocyclyl fused to the ring comprising $X^1$, $X^2$, and $X^3$;
wherein each of Q, $X^1$, $X^2$, $X^3$, $R^3$ and $R^{10}$ is independently as defined above and described herein.

In some embodiments, $R^4$ is selected from $C_2$-$C_6$ alkyl, —CH$_2$—O—($C_1$-$C_4$ alkyl) and —($C_0$-$C_6$ alkylene)-Q, wherein one or two methylene units in the alkyl or alkylene portion of $R^4$ are optionally and independently replaced by —O—, —S—, —S(=O)—, —S(=O)$_2$—, or —N($R^{10}$)—; and wherein each of Q and $R^{10}$ is independently as defined above and described herein. In some embodiments, $R^4$ is $C_2$-$C_6$ alkyl. In some embodiments, $R^4$ is ethyl. In some embodiments, $R^4$ is —($C_0$-$C_6$ alkylene)-Q, wherein Q is as defined above and described herein. In some embodiments, $R^4$ is Q, wherein Q is as defined above and described herein. In some embodiments, $R^4$ is aryl. In some embodiments, $R^4$ is optionally substituted phenyl. In some embodiments, $R^4$ is unsubstituted phenyl. In some embodiments, $R^4$ is substituted phenyl. In some embodiments, $R^4$ is —($C_0$-$C_6$ alkylene)-Q wherein Q is as defined above and described herein. In some embodiments, $R^4$ is benzyl. In some embodiments, $R^4$ is —($C_0$-$C_2$ alkylene)-Q wherein Q is as defined above and described herein. In some embodiments, $R^4$ is —CH$_2$-phenyl, wherein the phenyl is optionally substituted. In some embodiments, $R^4$ is —CH$_2$-phenyl, wherein the phenyl is substituted. In some embodiments. $R^4$ is —CH$_2$-phenyl, wherein the phenyl is unsubstituted. In some embodiments. $R^4$ is —($C_0$-$C_2$ alkylene)-aryl. In some embodiments, $R^4$ is —($C_0$-$C_2$ alkylene)-heterocyclyl. In some embodiments, $R^4$ is —($C_0$-$C_2$ alkylene)-heteroaryl. In some embodiments, $R^4$ is —($C_0$-$C_2$ alkylene)-carbocyclyl.

In some embodiments, $R^4$ is selected from $C_2$-$C_6$ alkyl and —($C_0$-$C_6$ alkylene)-Q, wherein Q is as defined above and described herein. In some embodiments, $R^4$ is selected from $C_2$-$C_6$ alkyl, —($C_0$-$C_2$ alkylene)-aryl, —($C_0$-$C_2$ alkylene)-heterocyclyl, and —($C_0$-$C_2$ alkylene)-heteroaryl.

In some embodiments, one methylene unit of $R^4$ is taken together with $X^2$ or $X^3$, when the $X^2$ or $X^3$ is =C($R^3$)—, and the intervening atoms to form a heteroaryl or heterocyclyl fused to the ring comprising $X^1$, $X^2$, and $X^3$; wherein each of Q, $X^1$, $X^2$, $X^3$, $R^3$ and $R^{10}$ is independently as defined above and described herein.

In some embodiments, one methylene unit in the alkyl or alkylene portion of $R^4$ is optionally replaced by —N($R^{10}$)—, wherein $R^{10}$ is as defined above and described herein.

In some embodiments, the alkyl or alkylene portion of $R^4$ is optionally substituted with =O. In some embodiments, one methylene unit in the alkyl or alkylene portion of $R^4$ is replaced by —N($R^{10}$)— and the methylene unit next to the —N($R^{10}$)— is substituted with =O to form —C(O)N($R^{10}$)—, wherein $R^{10}$ is as defined above and described herein.

In some embodiments $R^4$ is selected from —($C_1$-$C_3$ alkylene)-O—($C_1$-$C_2$ alkyl), 1-substituted-pipieridin-4-yl, $C_3$-$C_6$ cycloalkyl optionally substituted with one or more fluoro, and tetrahydropyranyl. In one aspect of this embodiment, $R^4$ is selected from —CH$_2$OCH$_3$, —CH(CH$_3$)OCH$_3$, 4,4-difluorocyclohexyl, cyclopropyl, tetrayhyrdopyran-4-yl, 1-(t-butoxycarbonyl)-piperidin-4-yl, 1-(isobutoxycarbonyl)-piperidin-4-yl, 1-(isopropoxycarbonyl)-piperidin-4-yl, 1-(2-fluoroethyl)-piperidin-4-yl, 1-(2,2-difluoroethyl)-piperidin-4-yl, 1-(2,2,2-trifluoroethyl)-piperidin-4-yl, 1-(2-hydroxyisobutyl)-piperidin-4-yl, 1-(hydroxyisopropylcarbonyl)-piperidin-4-yl, 1-(ethoxycarbonylmethyl)-piperidin-4-yl, 1-(isopropylcarbonyl)-piperidin-4-yl, 1-methylpiperidin-4-yl, 1-(methylsulfonyl)-piperidin-4-yl, 1-(ethylsulfonyl)-piperidin-4-yl, 1-(isopropylsulfonyl)-piperidin-4-yl, 1-(phenyl)-piperidin-4-yl, 1-(oxetan-3-yl)piperidin-4-yl, 1-(pyridin-2-yl)-piperidin-4-yl, and 1-(pyrimidin-2-yl)-piperidin-4-yl.

As defined generally above and herein, $R^5$ is selected from hydrogen, —($C_0$-$C_6$ alkylene)-Q, and $C_1$-$C_6$ alkyl, wherein one or two methylene units in $R^5$ are optionally and independently replaced by —O—, —S—, —S(=O)—, —S(=O)$_2$—, or —NR$^{10}$—, wherein each of Q and $R^{10}$ is independently as defined above and described herein.

In some embodiments, $R^5$ is hydrogen. In some embodiments, $R^5$ is selected from —($C_0$-$C_6$ alkylene)-Q and $C_1$-$C_6$ alkyl, wherein one or two methylene units in $R^5$ are optionally and independently replaced by —O—, —S—, —S(=O)—, —S(=O)$_2$—, or —NR$^{10}$—, wherein each of Q and $R^{10}$ is independently as defined above and described herein. In some embodiments, $R^5$ is $C_1$-$C_6$ alkyl. In some embodiments, $R^5$ is methyl. In some embodiments, $R^5$ is ethyl. In some embodiments, $R^5$ is aryl. In some embodiments, $R^5$ is optionally substituted phenyl. In some embodiments, $R^5$ is unsubstituted phenyl. In some embodiments, $R^5$ is substituted phenyl. In some embodiments, $R^5$ is —($C_0$-$C_6$ alkylene)-Q wherein Q is as defined above and described herein. In some embodiments, $R^5$ is benzyl.

In some embodiments, one methylene unit in the alkyl or alkylene portion of $R^5$ is optionally replaced by —N($R^{10}$)—, wherein $R^{10}$ is as defined above and described herein.

In some embodiments, the alkyl or alkylene portion of $R^5$ is optionally substituted with =O. In some embodiments, one methylene unit in the alkyl or alkylene portion of $R^5$ is replaced by —N($R^{10}$)— and the methylene unit next to the —N($R^{10}$)— is substituted with =O to form —C(O)N($R^{10}$)—, wherein $R^{10}$ is as defined above and described herein.

In some embodiments, $R^x$ is aryl, heterocyclyl or heteroaryl. In some embodiments, $R^x$ is —CH($R^4$)($R^5$), wherein $R^4$ is selected from $C_2$-$C_6$ alkyl, —($C_0$-$C_2$ alkylene)-aryl, —($C_0$-$C_2$ alkylene)-heterocyclyl and —($C_0$-$C_2$ alkylene)-heteroaryl; and wherein $R^5$ is selected from hydrogen and methyl.

In some embodiments, $R^x$ is optionally substituted phenyl, or tetrahydropyranyl. In some embodiments, $R^x$ is —CH($R^4$)($R^5$), wherein $R^4$ is selected from —CH$_2$CH$_3$, -phenyl, and —CH$_2$-phenyl; and wherein $R^5$ is selected from hydrogen and methyl.

Exemplary $R^x$ are depicted below.

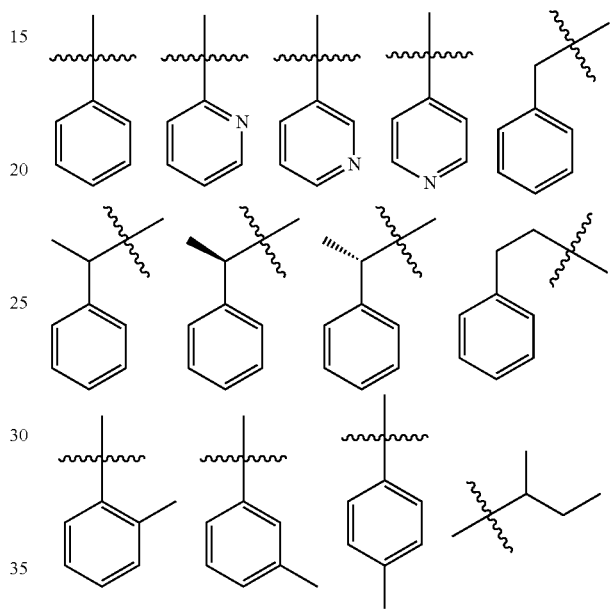

As defined generally above and herein, each $R^7$ is independently selected from —($C_0$-$C_4$ alkylene)-$R^9$, —($C_0$-$C_4$ alkylene)-O—$R^9$, —S(O)$_2$—$R^8$, —C(=O)—$R^8$, —C(=O)—N($R^9$)$_2$, —($C_1$-$C_4$ alkylene)-O—C(=O)—$R^8$ and —($C_0$-$C_4$ alkylene)-C(=O)—O—$R^9$; or two $R^7$ are taken together with the nitrogen atom to which they are commonly bound to form an optionally substituted heterocyclyl or heteroaryl ring;

wherein each of $R^8$ and $R^9$ is independently as defined above and described herein.

In some embodiments, each $R^7$ is independently selected from —($C_0$-$C_4$ alkylene)-$R^9$, —($C_0$-$C_4$ alkylene)-O—$R^9$, —S(O)$_2$—$R^8$, —C(=O)—$R^8$, —C(=O)—N($R^9$)$_2$, —($C_1$-$C_4$ alkylene)-O—C(=O)—$R^8$ and —($C_0$-$C_4$ alkylene)-C(=O)—O—$R^9$, wherein each of $R^8$ and $R^9$ is independently as defined above and described herein. In some embodiments, two $R^7$ are taken together with the nitrogen atom to which they are commonly bound to form an optionally substituted heterocyclyl or heteroaryl. In some embodiments, each $R^7$ is independently —($C_0$-$C_4$ alkylene)-$R^9$, wherein $R^9$ is as defined above and described herein. In some embodiments, each $R^7$ is independently $R^9$, wherein $R^9$ is as defined above and described herein.

As defined generally above and herein, $R^8$ is selected from $C_1$-$C_4$ alkyl, aryl, heteroaryl, carbocyclyl and heterocyclyl. In some embodiments, $R^8$ is $C_1$-$C_4$ alkyl. In some embodiments, $R^8$ is methyl. In some embodiments. $R^8$ is aryl. In some embodiments, $R^8$ is optionally substituted phenyl. In some embodiments, $R^8$ is unsubstituted phenyl. In some embodiments, $R^8$ is substituted phenyl. In some embodiments, $R^8$ is heteroaryl. In some embodiments, $R^8$ is carbocyclyl. In some embodiments, $R^8$ is heterocyclyl.

As defined generally above and herein, $R^9$ is selected from hydrogen and $R^8$, wherein $R^8$ is as defined above and described herein. In some embodiments, $R^9$ is hydrogen. In some embodiments, $R^9$ is $R^8$, wherein $R^8$ is as defined above and described herein. In some embodiments, $R^9$ is $C_1$-$C_4$ alkyl. In some embodiments, $R^9$ is aryl. In some embodiments, $R^9$ is heteroaryl. In some embodiments, $R^9$ is carbocyclyl. In some embodiments, $R^9$ is heterocyclyl.

As defined generally above and herein, $R^{10}$ is selected from hydrogen, $C_1$-$C_4$alkyl, —S(=O)$_2$—$R^9$, —C(=O)—$R^8$, —C(=O)—N($R^9$)($R^2$), and —C(=O)—O—$R^9$, wherein each of $R^8$, $R^9$, $R^{11}$ and $R^{12}$ is independently as defined above and described herein. In some embodiments, $R^{10}$ is selected from hydrogen. In some embodiments, $R^{10}$ is $C_1$-$C_4$ alkyl. In some embodiments, $R^{10}$ is —S(=O)$_2$—$R^9$, wherein $R^9$ is as defined above and described herein. In some embodiments, $R^{10}$ is —C(=O)—$R^8$ wherein $R^8$ is as defined above and described herein. In some embodiments, $R^{10}$ is —C(=O)—N($R^9$)($R^{12}$) wherein each of $R^9$ and $R^{12}$ is independently as defined above and described herein. In some embodiments, $R^{10}$ is —C(=O)—O—$R^{11}$ wherein $R^{11}$ is as defined above and described herein.

As defined generally above and herein, $R^{11}$ is selected from unsubstituted $C_1$-$C_4$ alkyl and $C_1$-$C_4$ haloalkyl. In some embodiments, $R^{11}$ is unsubstituted $C_1$-$C_4$ alkyl. In some embodiments, $R^{11}$ is $C_1$-$C_4$ haloalkyl.

As defined generally above and herein, $R^{12}$ is selected from hydrogen, unsubstituted $C_1$-$C_4$ alkyl and $C_1$-$C_4$ haloalkyl. In some embodiments, $R^{12}$ is hydrogen. In some embodiments, $R^{12}$ is unsubstituted $C_1$-$C_4$ alkyl. In some embodiments, $R^{12}$ is $C_1$-$C_4$ haloalkyl.

Unless otherwise designated, any alkyl, alkylene, alkenyl, alkenylene, alkynyl, alkynylene, aryl, heteroaryl, heterocyclyl or carbocyclyl portion of the compound is optionally substituted.

It will be understood by those of skill in the art that the compounds of the invention are limited to compounds that are stable. $R^4$ and/or $R^5$ moieties formed by replacing two methylene units with certain combinations of —O—, —S—, —S(=O)—, —S(=O)$_2$—, or —NR$^{10}$— are not within the scope of the present invention if the structures formed are not stable. For example, compounds wherein the $R^4$ and/or $R^5$ moiety comprises an —O—, —S—, —S(O)—, —S(O)$_2$, or —N($R^{10}$)—, adjacent to an —O—, —S—, —S(O)—, —S(O)$_2$, or —N($R^{10}$)— are not within the scope of the present invention, except for an —S(O)$_2$— adjacent to a —N($R^{10}$)—. In addition, neither $R^4$, nor $R^5$ should comprise —O—C($R^a$)$_2$—O—, —N—C($R^a$)$_2$—O—, or —O—C($R^a$)$_2$—N— if the structures formed are not stable.

Unless otherwise stated, all tautomeric forms of the compounds of the invention are within the scope of the invention.

In some embodiments,

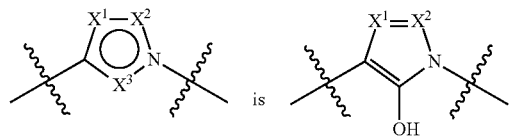

In some embodiments,

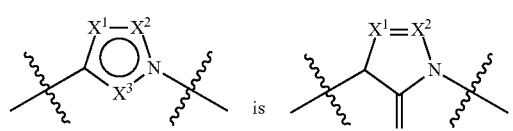

In some embodiments,

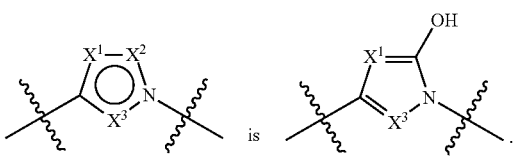

In some embodiments,

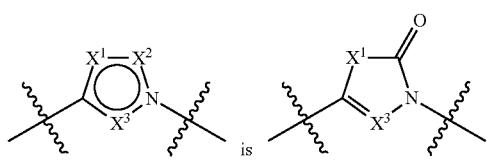

In some embodiments,

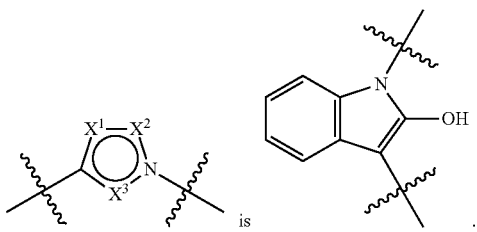

In some embodiments,

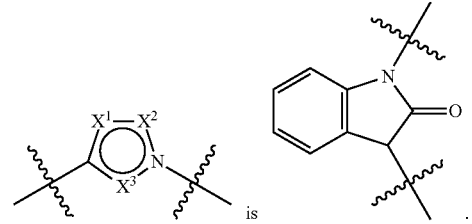

In certain embodiments, a compound of formula I is not

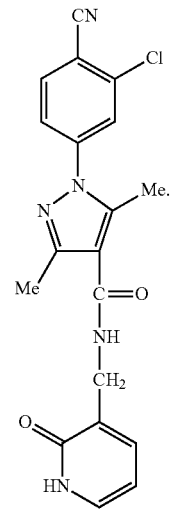

In certain embodiments of a compound of formula I:

when $X^3$ is =N—, $X^2$ is =C(CH$_3$)—, $X^1$ is =C(H)—, and $R^x$ is 2-fluorophenyl; then $R^1$ and $R^2$ are not taken together with atoms to which they are bound to form

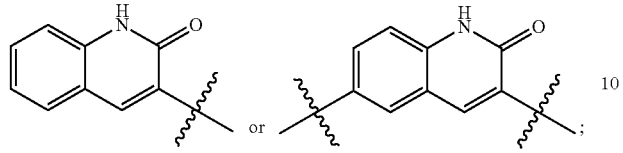

when each $R^1$ is methyl, Z is =C(H)—, each of $X^2$ and $X^3$ is =C(CH$_3$)—, and $X^1$ is =C(H)—; then $R^x$ is other than unsubstituted cyclohexyl, benzyl, pyridin-3-yl, or pyridin-2-yl;

when each $R^1$ is methyl, Z is =C(H)—, $X^3$ is =N—, and $R^x$ is phenyl or 4-fluorophenyl; then the $R^3$ of $X^1$ and the $R^3$ of $X^2$ are not taken together to form unsubstituted $C_5$-$C_7$ cycloalkyl fused to the ring comprising $X^1$, $X^2$ and $X^3$;

when $X^1$ is =N—, $R^5$ is hydrogen, and $R^4$ is taken together with $X^3$ to form

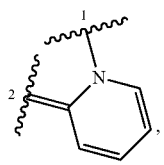

wherein "1" represents the portion of the ring bound to $X^2$, and "2" represents the portion of the ring bound to the ring carbon adjacent to $X^3$; then $X^2$ is other than =C(cyclopropyl)-, =C(C(CH$_3$)$_3$)—, or =C(CH$_2$CH(CH$_3$)$_2$)—, wherein the cyclopropyl is unsubstituted;

when $X^2$ is =N—, $X^3$ is =C(H)—, each $R^1$ is methyl, Z is =C(H)—, and $R^x$ is 4-methylphenyl, unsubstituted phenyl, or unsubstituted benzyl; then $X^1$ is other than =C($_3$-methylphenyl)-, =C($_3$-methoxyphenyl)-, =C(phenyl)-, =C(4-chlorophenyl). =C(thien-2-yl)-, or =C(pyridin-3-yl); and when $X^2$ is =N—, $X^1$ is =C(H)—, each $R^1$ is methyl, Z is =C(H)—, and $R^x$ is pyridin-2-yl, 2,4-dichlorophenyl or 3-methylphenyl; then $X^1$ is other than =C(CH$_3$)—, =C(CH$_2$CH$_3$)—, or =C(cyclopropyl)- when $X^2$ is =N—, $X^1$ is =C(CH$_3$)—, and $X^3$ is =C(CH$_3$)—, the $R^x$ is other than 2,4-difluorophenyl or 3-chloro-4-cyanophenyl; and the compound is other than:

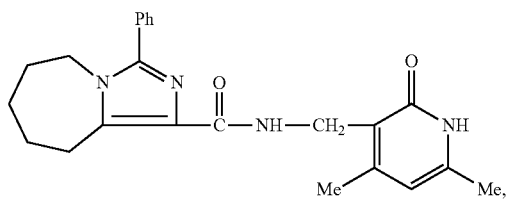

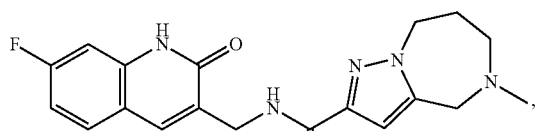

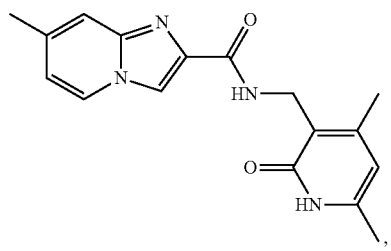

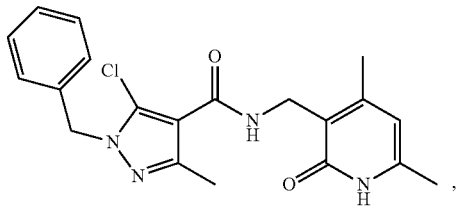

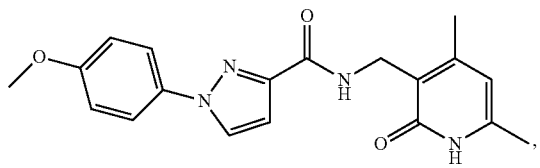

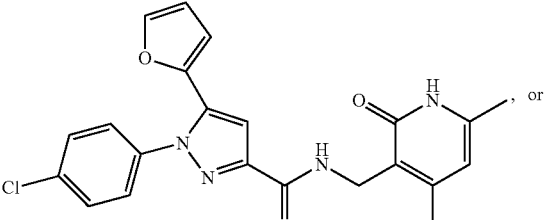

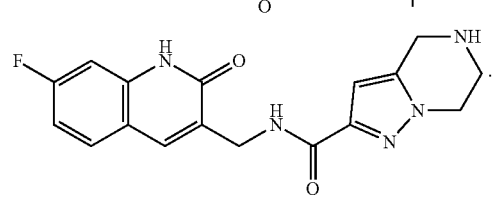

In certain embodiments, the invention provides a compound of Formula II:

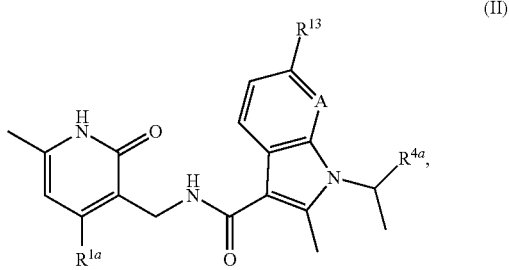

(II)

or a pharmaceutically acceptable salt thereof, wherein:

A is CH or N;

$R^{1a}$ is selected from $—C_1-C_2$ alkyl and $—O—(C_1-C_2$ alkyl), wherein $R^{1a}$ is optionally substituted with one or more fluoro;

$R^{4a}$ is selected from $—(C_1-C_4$ alkylene)$-O—(C_1-C_3$ alkyl), 1-substituted-pipieridin-4-yl, $C_3-C_6$ cycloalkyl optionally substituted with one or more fluoro, and tetrahydropyranyl; and $R^{13}$ is selected from hydrogen, halo, phenyl, pyridinyl, and $—O—(C_1-C_4$ alkyl).

In some embodiments of Formula II, $R^{1a}$ is selected from $—OCH_3$, $—CH_3$, $—OCHF_2$, and $—CH_2CH_3$.

In some embodiments of Formula II, $R^{4a}$ is selected from $—CH_2OCH_3$, $—CH(CH_3)OCH_3$, 4,4-difluorocyclohexyl, cyclopropyl, tetrayhrdopyran-4-yl, 1-(t-butoxycarbonyl)-piperidin-4-yl, 1-(isobutoxycarbonyl)-piperidin-4-yl, 1-(isopropoxycarbonyl)-piperidin-4-yl, 1-(2-fluoroethyl)-piperidin-4-yl, 1-(2,2-difluoroethyl)-piperidin-4-yl, 1-(2,2,2-trifluoroethyl)-piperidin-4-yl, 1-(2-hydroxyisobutyl)-piperidin-4-yl, 1-(hydroxyisopropylcarbonyl)-piperidin-4-yl, 1-(ethoxycarbonylmethyl)-piperidin-4-yl, 1-(isopropylcarbonyl)-piperidin-4-yl, 1-methylpiperidin-4-yl, 1-(methylsulfonyl)-piperidin-4-yl, 1-(ethylsulfonyl)-piperidin-4-yl, 1-(isopropylsulfonyl)-piperidin-4-yl, 1-(phenyl)-piperidin-4-yl, 1-(oxetan-3-yl)piperidin-4-yl, 1-(pyridin-2-yl)-piperidin-4-yl, and 1-(pyrimidin-2-yl)-piperidin-4-yl.

In some embodiments of Formula II, $R^{13}$ is selected from hydrogen, chloro, fluoro, $—OCH(CH_3)_2$, phenyl, and pyridin-2-yl.

Exemplary compounds of formula I and II are set forth in FIG. 1. In some cases two (or more) of the compounds in FIG. 1 having one (or more) wavy bonds will have the exact same structure. Because the wavy bond represents a chiral center of undetermined optical rotation, such compounds will be understood to be separate and distinct optical isomers of one another. FIG. 1 is annotated to indicate those sets of two or more compounds that have the same depicted structure, but are of different stereochemistry.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate a histone methyl modifying enzyme, or a mutant thereof, in a biological sample or in a patient. In certain embodiments, the amount of compound in compositions of this invention is such that is effective to measurably modulate a histone methyl modifying enzyme, or a mutant thereof, in a biological sample or in a patient.

In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens. Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulating of activity of one or more enzymes involved in epigenetic regulation.

Epigenetics is the study of heritable changes in gene expression caused by mechanisms other than changes in the underlying DNA sequence. Molecular mechanisms that play a role in epigenetic regulation include DNA methylation and chromatin/histone modifications. Histone methylation, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) *Curr. Opin. Genet. Dev.* 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) *Nature* 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation, sumoylation, ubiquitination, citrullination, deimination, and biotinylation. The core of histones H2A and H3 can also be modified. Histone modifications are integral to diverse biological processes such as gene regulation, DNA repair, and chromosome condensation.

The present disclosure provides compounds and compositions for modulating activity of histone methyl modifying enzymes. Histone methyl modifying enzymes are key regulators of cellular and developmental processes. Histone methyl modifying enzymes may be characterized as either histone methyl transferases or histone demethylases. Histone demethylase enzymes have modules that mediate binding to methylated residues. For example, multiple demethylases contain a Tudor domain (e.g., JMJD2C/GASC1) or a PHD domain (e.g., JARID1C/SMCX, PHF8).

The lysine specificities of many histone methyltransferases have been characterized. For example SET7/9, SMYD3, and MLL1-5 are specific for H3K4. SUV39H1, DIM-5, and G9a are specific for H3K9. SET8 is specific for H4K20.

DOT1 is an example of a non-SET domain containing histone methylase. DOT1 methylates H3 on lysine 79.

Just as histone methylases have been shown to regulate transcriptional activity, chromatin structure, and gene silencing, demethylases have also been discovered which impact gene expression. LSD1 was the first histone lysine demethylase to be characterized. This enzyme displays homology to FAD-dependent amine oxidases and acts as a transcriptional corepressor of neuronal genes (Shi et al., Cell 119:941-953, 2004). Additional demethylases defining separate demethylase families have been discovered, including JHDM1 (or KDM2), JHDM2 (or KDM3), JMJD2 (or KDM4), JARID (or KDM5), JMJD3 (or KDM6), and JMJD6 families (Lan et al., Curr. Opin. Cell Biol. 20(3):316-325, 2008).

Demethylases act on specific lysine residues within substrate sequences and discriminate between the degree of methylation present on a given residue. For example, LSD1 removes mono- or dimethyl-groups from H3K4. Members of the JARID1A-D family remove trimethyl groups from H3K4. UTX and JMJD3 demethylate H3K27, counteracting effects of EZH2 methylase activity. Substrate specificities of other demethylases have been characterized (see Shi, Nat. Rev. 8:829-833, 2007).

One class of histone methylases is characterized by the presence of a SET domain, named after proteins that share the domain, Su(var)3-9, enhancer of zeste [E(Z)], and trithorax. A SET domain includes about 130 amino acids. SET domain-containing methylase families include SUV39H1, SET1, SET2, EZH2, RIZ1, SMYD3, SUV4-20H1, SET7/9, and PR-SET7/SET8 families (reviewed in Dillon et al., Genome Biol. 6:227, 2005). Members of a family typically include similar sequence motifs in the vicinity of and within the SET domain. The human genome encodes over 50 SET domain-containing histone protein methylases, any of which can be used in an assay described herein.

EZH2 is an example of a human SET-domain containing methylase. EZH2 associates with EED (Embryonic Ectoderm Development) and SUZ12 (suppressor of zeste 12 homolog) to form a complex known as PRC2 (Polycomb Group Repressive Complex 2) having the ability to tri-methylate histone H3 at lysine 27 (Cao and Zhang, Mol. Cell 15:57-67, 2004). PRC2 complexes can also include RBAP46 and RBAP48 subunits.

The oncogenic activities of EZH2 have been shown by a number of studies. In cell line experiments, over-expression of EZH2 induces cell invasion, growth in soft agar, and motility while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor supressors, including E-cadherin, DAB2IP and RUNX3 among others. In xenograft models, EZH2 knockdown inhibits tumor growth and metastasis. Recently, it has been shown that down modulation of EZH2 in murine models blocks prostate cancer metastasis (Min et al., "An oncogene-tumor suppressor cascade drives metastatic prostate cancer by coordinately activating Ras and nuclear factor-kappaB," Nat Med. 2010 March; 16(3):286-94). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18; 17(5):443-454).

In some embodiments, compounds of the present invention modulate the activity of one or more enzymes involved in epigenetic regulation. In some embodiments, compounds of the present invention modulate the activity of a histone methyl modifying enzyme, or a mutant thereof. In some embodiments, compounds of the present invention modulate EZH2 activity. In some embodiments, compounds of the present invention down-regulate or suppress the activity of EZH2. In some embodiments, compounds of the present invention are antagonists of EZH2 activity.

In some embodiments, compounds and compositions of the present invention are useful in treating diseases and/or disorders associated with a histone methyl modifying enzyme. Accordingly, in some embodiments, the present invention provides a method of modulating a disease and/or disorder associated with a histone methyl modifying enzyme. In some embodiments, the present invention provides a method of treating a subject suffering from a disease and/or disorder associated with a histone methyl modifying enzyme comprising the step of administering a compound or composition of formula I.

In some embodiments, compounds and compositions of the present invention are useful in treating diseases and/or disorders associated with overexpression of EZH2. In some embodiments, the present invention provides a method of treating a subject suffering from a disease and/or disorder associated with overexpression of EZH2 comprising the step of administering a compound or composition of formula I. In some embodiments, the above method additionally comprises the preliminary step of determining if the subject is overexpressing EZH2.

In some embodiments, compounds and compositions of the present invention are useful in treating diseases and/or disorders associated with cellular proliferation. In some embodiments, compounds and compositions of the present invention are useful in treating diseases and/or disorders associated with misregulation of cell cycle or DNA repair. In some embodiments, compounds and compositions of the present invention are useful in treating cancer. Exemplary types of cancer include breast cancer, prostate cancer, colon cancer, renal cell carcinoma, glioblastoma multiforme cancer, bladder cancer, melanoma, bronchial cancer, lymphoma and liver cancer.

The study of EZH2 deletions, missense and frameshift mutations suggest that EZH2 functions as a tumor suppressor in blood disorders such as myelodysplastic syndromes (MDS) and myeloid malignancies (Ernst et al., Nat Genet. 2010 August; 42(8):722-6; Nikoloski et al., Nat Genet. 2010 August; 42(8):665-7). Accordingly, in some embodiments, compounds and compositions of the present invention are useful in treating diseases and/or disorders associated with the presence of a mutant form of EZH2. In some embodiments, compounds and compositions of the present invention are useful in treating diseases and/or disorders associated with the presence of Y641N EZH2. In some embodiment, the disease or disorder associated with the presence of a mutant form of EZH2 is a human B cell lymphoma. In some embodiments, the disease and/or disorder associated with the presence of Y641N EZH2 is follicular lymphoma or diffuse large-B-cell lymphoma. In some embodiments, compounds or compositions of the present invention are useful in treating blood disorders, such as myelodysplastic syndromes, leukemia, anemia and cytopenia. Sneeringer et al., "Coordinated activities of wild-type plus mutant EZH2 drive tumor-associated hypertrimethylation of lysine 27 on histone H3 (H3K27) in human B-cell lymphomas." Proceedings of the National Academy of Sciences, PNAS Early Edition published ahead of print on Nov. 15, 2010.

In some embodiments, the present invention provides a method of reducing the activity of EZH2 in a subject comprising the step of administering a compound or composition of formula I. In some embodiments, the present invention provides a method of reducing the activity of wide-type EZH2 in a subject comprising the step of administering a compound or composition of formula I. In some embodiments, the present invention provides a method of reducing the activity of a mutant form of EZH2 in a subject comprising the step of administering a compound or composition of formula I. In some embodiments, the present invention provides a method of reducing the activity of a mutant form of EZH2 in a subject comprising the step of administering a compound or composition of formula I, wherein the mutant form of EZH2 is Y641N EZH2. In some embodiments, the present invention provides a method of treating a subject suffering from a disease and/or disorder associated with EZH2 comprising the step of administering a compound or composition of formula I. In some embodiments, the present invention provides a method of treating a subject suffering from a disease and/or disorder associated with wide-type EZH2 comprising the step of administering a compound or composition of formula I. In some embodiments, the present invention provides a method of treating a subject suffering from a disease and/or disorder associated with a mutant form of EZH2 comprising the step of administering a compound or composition of formula I. In some embodiments, the present invention provides a method of treating a subject suffering from a disease and/or disorder associated with a mutant form of EZH2 comprising the step of administering a compound or composition of formula I, wherein the mutant form of EZH2 is Y641N EZH2. In some embodiments, the above method additionally comprises the preliminary step of determining if the subject is expressing a mutant form of EZH2, such as Y641N EZH2. In some embodiments, the present invention provides a method of reducing the activity of a mutant form of EZH2, such as Y641N EZH2, in a subject in need thereof comprising the step of administering a compound or composition of formula I. In some embodiments, the present invention provides a method of treating a subject suffering from a disease and/or disorder associated with a mutant form of EZH2 comprising the step of administering a compound or composition of formula I. In some embodiments, the above method additionally comprises the preliminary step of determining if the subject is expressing a mutant form of EZH2, such as Y641N EZH2. In some embodiments, that determination is made by determining if the subject has increased levels of histone H3 Lys-27-specific trimethylation (H3K27me3), as compared to a subject known not to express a mutant form of EZH2.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

It will be appreciated that for compound preparations described herein, when reverse phase HPLC is used to purify a compound, a compound may exist as an acid addition salt. In some embodiments, a compound may exist as a formic acid or mono-, di-, or tri-trifluoroacetic acid salt.

It will further be appreciated that the present invention contemplates individual compounds described herein. Where individual compounds exemplified are isolated and/or characterized as a salt, for example, as a trifluoroacetic acid salt, the present invention contemplates a free base of the salt, as well as other pharmaceutically acceptable salts of the free base.

The following examples contain important additional information, exemplification and guidance that can be adapted to the practice of this invention in its various embodiments and the equivalents thereof

EXAMPLES

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

Unless otherwise noted, all solvents, chemicals, and reagents were obtained commercially and used without purification. The $^1$H NMR spectra were obtained in CDCl$_3$, d$_6$-DMSO, CD$_3$OD, or d$_6$-acetone at 25° C. at 300 MHz on an OXFORD (Varian) with chemical shift ($\delta$, ppm) reported relative to TMS as an internal standard. HPLC-MS chromatograms and spectra were obtained with Shimadzu LC-MS-2020 system. Chiral analysis and purification were obtained with Yilite P270.

Example 1

Synthesis of N-((4,6-dimethyl-2-oxo-1,2-dihydropyridin-3-yl)methyl)-5-methyl-1-phenyl-1H-pyrazole-4-carboxamide (Compound 100)

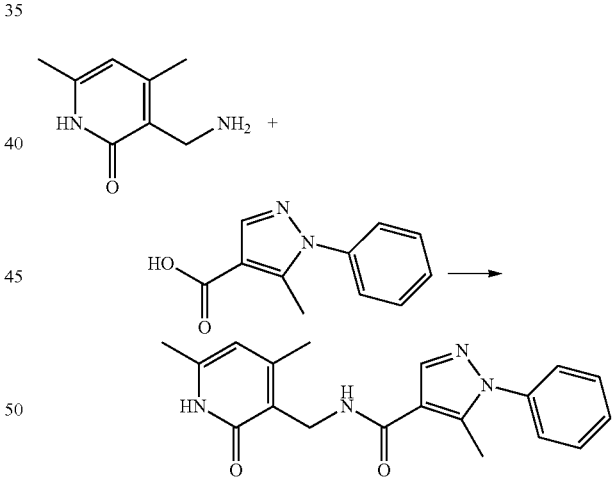

A mixture of 3-(aminomethyl)-4,6-dimethylpyridin-2 (1H)-one (70 mg, 0.46 mmol), 5-methyl-1-phenyl-1H-pyrazole-4-carboxylic acid (93 mg, 0.46 mmol), O-(7-azabenzotriazole-1-yl)-N,N,N',N'-tetramethyluronium hexafluorophosphate (210 mg, 0.55 mmol) and triethylamine (70 mg, 0.69 mmol) in anhydrous dichloromethane (5 mL) was stirred at room temperature for 15 hours. Then the mixture was filtered and the solid was washed with water (10 mL), methanol (10 mL) and dichloromethane (10 mL) in turns to give N-((4,6-dimethyl-2-oxo-1,2-dihydropyridin-3-yl)methyl)-5-methyl-1-phenyl-1H-pyrazole-4-carboxamide as a white solid (40 mg, 26%). LRMS (M+H$^+$) m/z: calcd 336.16. found 336.

Example 2

Synthesis of N-((4,6-dimethyl-2-oxo-1,2-dihydropyridin-3-yl)methyl)-1-(phenylsulfonyl)-1H-indole-3-carboxamide (Compound 135)

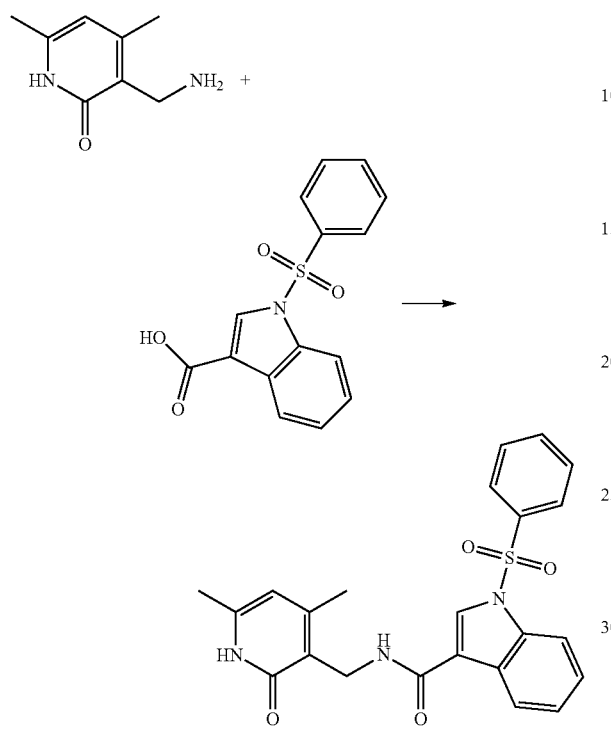

A mixture of 3-(aminomethyl)-4,6-dimethylpyridin-2(1H)-one (100 mg, 0.65 mmol), 1-(phenylsulfonyl)-1H-indole-3-carboxylic acid (196 mg, 0.65 mmol), O-(7-azabenzotriazole-1-yl)-N,N,N',N'-tetramethyluronium hexafluorophosphate (319 mg, 0.84 mmol) and triethylamine (98 mg, 0.97 mmol) in anhydrous dichloromethane (10 mL) was stirred at room temperature for 15 hours. Then the mixture was filtered and the solid was washed with water (10 mL), methanol (10 mL) and dichloromethane (10 mL) in turns to give N-((4,6-dimethyl-2-oxo-1,2-dihydropyridin-3-yl)methyl)-1-(phenylsulfonyl)-1H-indole-3-carboxamide as a white solid (78 mg, 28%). LRMS (M+H+) m/z: calcd 435.13. found 435.

Example 3

Synthesis of (R or S)-N-((2-hydroxy-4,6-dimethylpyridin-3-yl)methyl)-3-methyl-1-(1-phenylethyl-1H-pyrazole-4-carboxamide (Compound 106) and (R or S)-N-((2-hydroxy-4,6-dimethyl-pyridin-3-yl)methyl)-3-methyl-1-(1-phenylethyl)-1H-pyrazole-4-carboxamide (Compound 105)

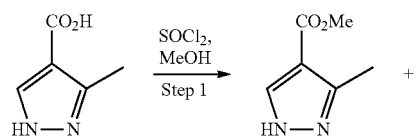

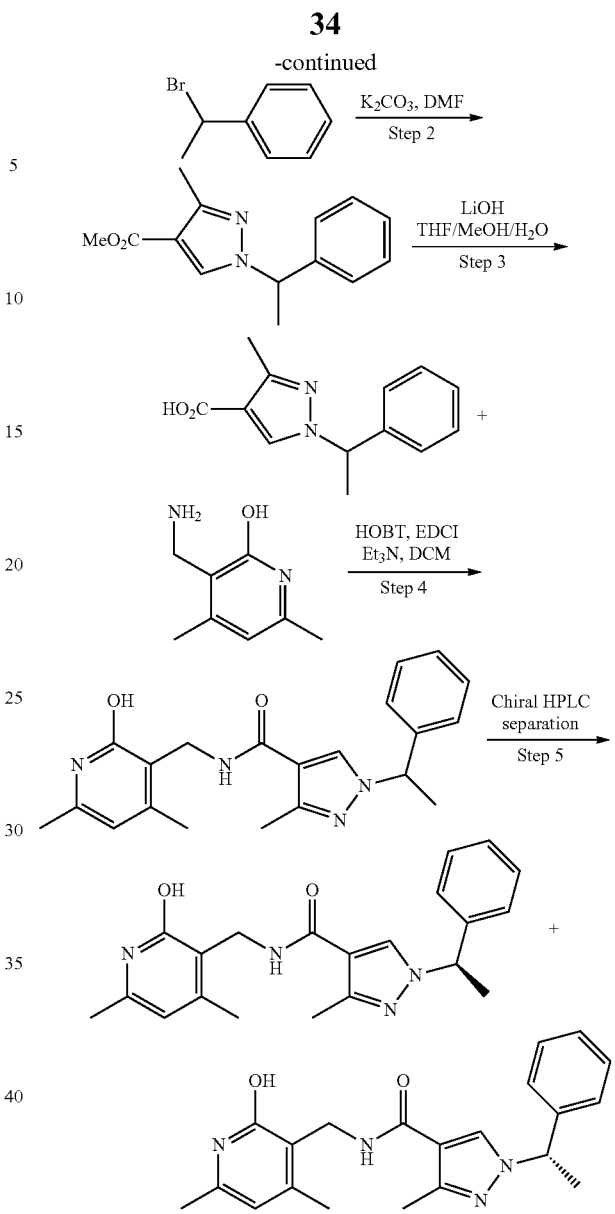

Synthesis of methyl 3-methyl-1H-pyrazole-4-carboxylate

To a solution of 3-methyl-1H-pyrazole-4-carboxylic acid (1.26 g, 10 mmol) in methanol (100 mL) was added thionyl chloride (5.73 g, 48 mmol) at 0° C. The mixture was stirred for 12 hours. The solvent was evaporated in vacuo. To the residue, saturated sodium bicarbonate aqueous solution was added and the mixture was extracted with ethyl acetate (100 mL×3). The organic phases were combined, dried over sodium sulfate, filtered and concentrated in vacuo to give methyl 3-methyl-1H-pyrazole-4-carboxylate (0.8 g, 57%). ¹H NMR (300 MHz, CDCl₃): δ 7.87 (s, 1H), 3.84 (s, 3H), 2.53 (s, 3H).

Synthesis of methyl 3-methyl-1-(1-phenylethyl)-1H-pyrazole-4-carboxylate and methyl 5-methyl-1-(1-phenylethyl)-1H-pyrazole-4-carboxylate

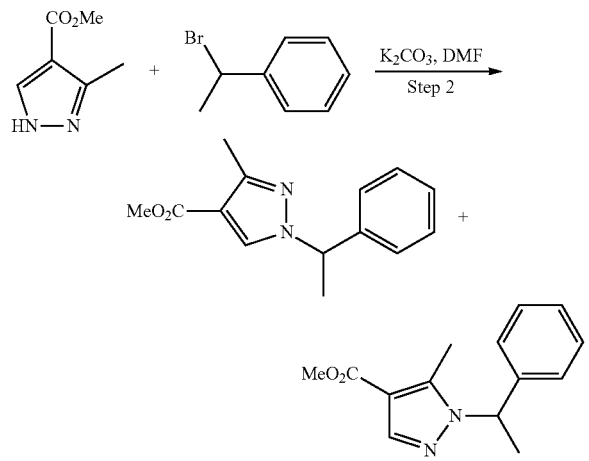

To a solution of methyl 3-methyl-1H-pyrazole-4-carboxylate (280 mg, 2 mmol) in N,N-dimethylformamide (30 mL) was added (1-bromoethyl)benzene (0.37 g, 2 mmol) and potassium carbonate (0.55 g, 4 mmol). The mixture was stirred at 20° C. and stirred for 12 hours. The solvent was evaporated in vacuo and the residue was purified by CXTH (Column: Dsisol, 10 μM, C18, 250 mm*50 mm; Mobile: acetonitrile (0.1% formic acid)-water (0.1% formic acid), acetonitrile from 30% to 70% in 80 minutes; oven: 20° C.; flow rate: 50 ml/minute, wavelength: 214 nm) to give methyl 3-methyl-1-(1-phenylethyl)-1H-pyrazole-4-carboxylate (90 mg, 19%) and methyl 5-methyl-1-(1-phenylethyl)-1H-pyrazole-4-carboxylate (80 mg, 16%). The product was used directly in the following reaction. LRMS (M+H⁺) m/z: calcd 244.12. found 244.

Synthesis of 3-methyl-1-(1-phenylethyl)-1H-pyrazole-4-carboxylic acid

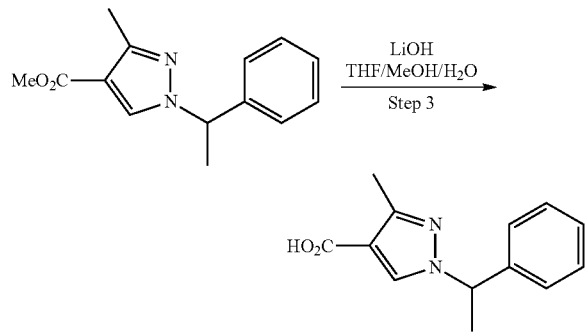

A mixture of methyl 3-methyl-1-(1-phenylethyl)-1H-pyrazole-4-carboxylate (90 mg, 0.37 mmol), lithium hydroxide monohydrate (57.1 mg, 1.36 mmol), tetrahydrofuran (5 mL), methanol (1 mL) and water (1 mL) was stirred at 20° C. for 4 hours. The mixture was acidified to pH=1 with concentrated hydrochloric acid and then extracted with ethyl acetate (15 mL×3). The combined organic phase was dried by sodium sulfate, and then filtered. The filtrate was concentrated in vacuo to give 3-methyl-1-(1-phenylethyl)-1H-pyrazole-4-carboxylic acid as a white solid (60 mg, 70%). ¹H NMR (300 MHz, d⁶-DMSO): δ 12.24 (s, 1H), 7.82 (s, 1H), 7.36-7.17 (m, 5H), 5.67 (q, J=7.2 Hz, 1H), 2.43 (s, 3H), 1.79 (d, J=6.9 Hz, 3H).

Synthesis of N-((2-hydroxy-4,6-dimethylpyridin-3-yl)methyl)-3-methyl-1-(1-phenylethyl)-1H-pyrazole-4-carboxamide

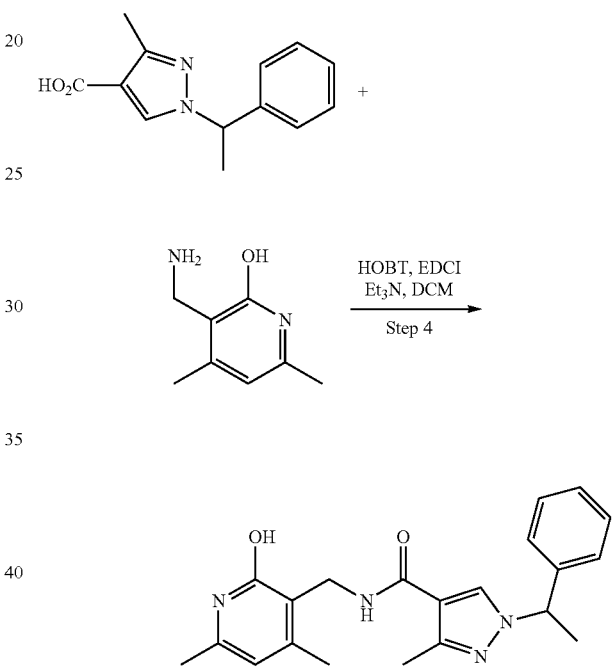

A mixture of 3-methyl-1-(1-phenylethyl)-1H-pyrazole-4-carboxylic acid (60 mg, 0.26 mmol), 1-ethyl-3-(3-dimethylaminopropyl)carbodiimide hydrochloride (95 mg, 0.5 mmol), N-hydroxybenzotrizole (67 mg, 0.5 mmol), triethylamine (0.1 mL) and dichloromethane (5 mL) was stirred at 25° C. for 0.5 hours. And then 3-(aminomethyl)-4,6-dimethylpyridin-2-ol (50 mg, 0.33 mmol) was added. The mixture was stirred at 25° C. for 12 hours. To the mixture, water (10 ml) was added and the mixture was extracted with dichloromethane (10 mL×3). The combined organic phase was dried by sodium sulfate and then filtered. The filtrate was concentrated in vacuo. The residue was purified by column chromatography (silica gel, dichloromethane/methanol=20:1) to give N-((2-hydroxy-4,6-dimethylpyridin-3-yl)methyl)-3-methyl-1-(1-phenylethyl)-1H-pyrazole-4-carboxamide as a white solid (56 mg, 58%). LRMS (M+H⁺) m/z: calcd 364.19. found 364. ¹H NMR (300 MHz, d⁶-DMSO): δ 11.46 (s, 1H), 7.96 (s, 1H), 7.82 (t, J=4.5 Hz, 1H), 7.33-7.13 (m, 5H), 5.84 (s, 1H), 5.62 (q, J=7.2 Hz, 1H), 4.20 (d, J=5.1 Hz, 2H), 2.40 (s, 3H), 2.14 (s, 3H), 1.99 (s, 3H), 1.76 (d, J=7.2 Hz, 3H).

Synthesis of (R or S)-N-((2-hydroxy-4,6-dimethylpyridin-3-yl)methyl)-3-methyl-1-(1-phenylethyl)-1H-pyrazole-4-carboxamide (Compound 106) and (R or S)-N-((2-hydroxy-4,6-dimethylpyridin-3-yl)methyl)-3methyl-1-(1-phenylethyl)-1H-pyrazole-4-carboxamide (Compound 105)

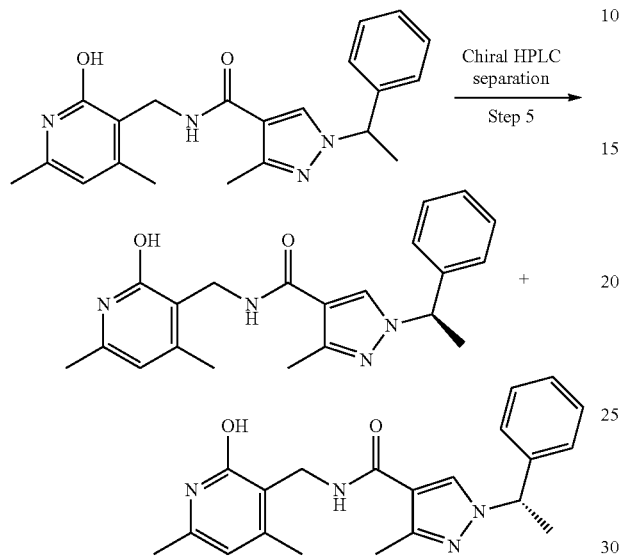

N-((2-hydroxy-4,6-dimethylpyridin-3-yl)methyl)-3-methyl-1-(1-phenylethyl)-1H-pyrazole-4-carboxamide was separated by chiral HPLC (condition: column AD-H (20 mm*250 mm*5 μm), hexane:ethanol (0.2% DEA)=50:50, flow rate: 13 ml/min). The two isomers of N-((2-hydroxy-4,6-dimethylpyridin-3-yl)methyl)-3-methyl-1-(1-phenylethyl)-1H-pyrazole-4-carboxamide were obtained, but absolute stereochemistry was not determined. The retention times were 9.552 minutes ("Peak 1"; Compound 105) and 15.505 minutes ("Peak 2"; Compound 106) in chiral HPLC chromatography. LRMS (M+H$^+$) m/z: calcd. 364.19. found 364. $^1$H NMR (300 MHz, d$^6$-DMSO): δ 11.46 (s, 1H), 7.96 (s, 1H), 7.82 (t, J=4.5 Hz, 1H), 7.33-7.13 (m, 5H), 5.84 (s, 1H), 5.62 (q, J=7.2 Hz, 1H), 4.20 (d, J=5.1 Hz, 2H), 2.40 (s, 3H), 2.14 (s, 3H), 1.99 (s, 3H), 1.76 (d, J=7.2 Hz, 3H).

Example 4

Synthesis of (R or S)-N-((2-hydroxy-4,6-dimethylpyridin-3-yl)methyl)-5-methyl-1-(1-phenylethyl)-1H-pyrazole-4-carboxamide (Compound 107) and (R or S)-N-((2-hydroxy-4,6-dimethyl-pyridin-3-yl)methyl-5-methyl-1-(1-phenylethyl)-1H-pyrazole-4-carboxamide (Compound 108)

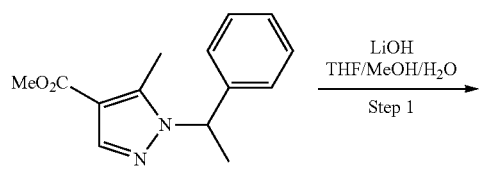

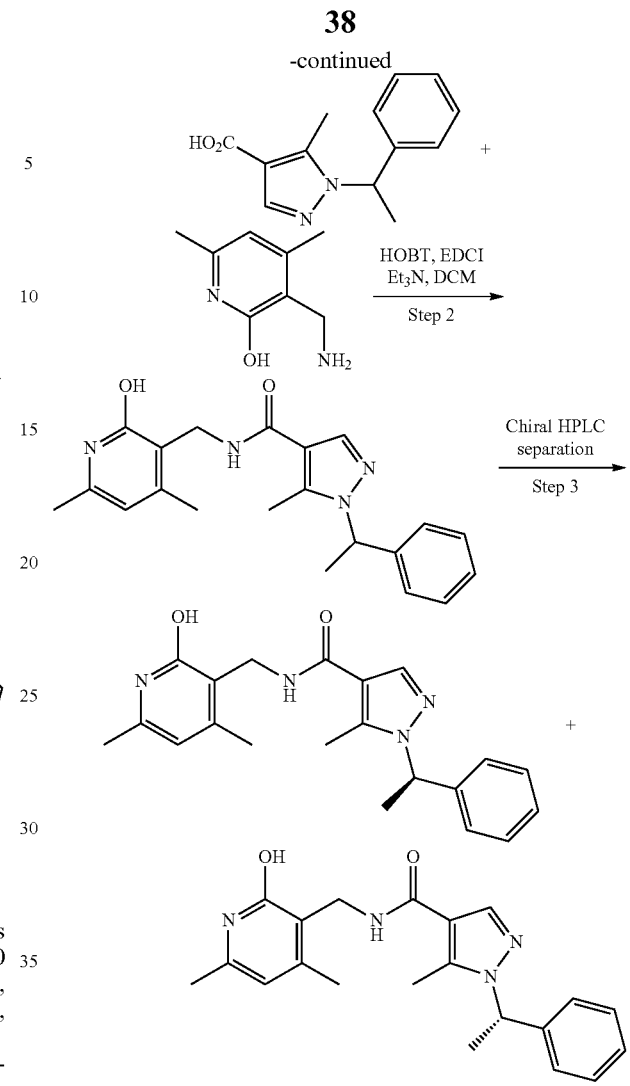

Synthesis of 5-methyl-1-(1-phenylethyl)-1H-pyrazole-4-carboxylic acid

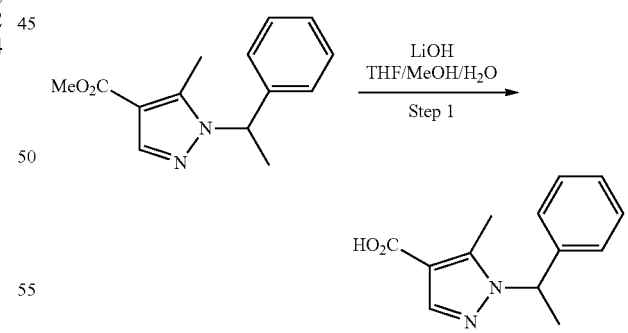

A mixture of methyl 5-methyl-1-(1-phenylethyl)-1H-pyrazole-4-carboxylate (80 mg, 0.32 mmol), lithium hydroxide monohydrate (57.1 mg, 1.36 mmol), tetrahydrofuran (5 mL), methanol (1 mL) and water (1 mL) was stirred at 20° C. for 4 hours. The mixture was acidified to pH=1 with concentrated hydrochloric acid and then extracted with ethyl acetate (15 mL×3). The combined organic phase was dried by sodium sulfate, and then filtered. The filtrate was concentrated in vacuo to give 5-methyl-1-(1-phenylethyl)-1H-pyrazole-4-carboxylic acid as a white solid (49 mg, 62%). $^1$H NMR (300

MHz, d⁶-DMSO): δ 12.16 (s, 1H), 8.26 (s, 1H), 7.37-7.25 (m, 5H), 5.55 (q, J=7.2 Hz, 1H), 2.30 (s, 3H), 1.78 (d, J=6.9 Hz, 3H).

Synthesis of N-((2-hydroxy-4,6-dimethylpyridin-3-yl)methyl)-5-methyl-1-(1-phenylethyl)-1H-pyrazole-4-carboxamide

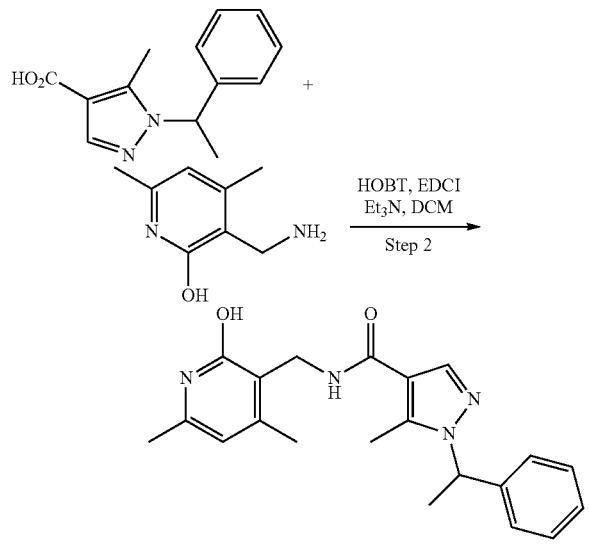

A mixture of 5-methyl-1-(1-phenylethyl)-1H-pyrazole-4-carboxylic acid (49 mg, 0.21 mmol), 1-ethyl-3-(3-dimethylaminopropyl)carbodiimide hydrochloride (95 mg, 0.5 mmol), N-hydroxybenzotrizole (67 mg, 0.5 mmol), triethylamine (0.1 mL) and dichloromethane (5 mL) was stirred at 25° C. for 0.5 hours. Then 3-(aminomethyl)-4,6-dimethylpyridin-2-ol (50 mg, 0.33 mmol) was added. The mixture was stirred at 25° C. for 12 hours. To the mixture, water (10 ml) was added and the mixture was extracted with dichloromethane (10 mL×3). The combined organic phase was dried by sodium sulfate and then filtered. The filtrate was concentrated in vacuo. The residue was purified by column chromatography (silica gel, dichloromethane/methanol=20:1) to give N-((2-hydroxy-4,6-dimethylpyridin-3-yl)methyl)-5-methyl-1-(1-phenylethyl)-1H-pyrazole-4-carboxamide as a white solid (43 mg, 56%). LRMS (M+H⁺) m/z: calcd 364.19. found 364. ¹H NMR (300 MHz, d⁶-DMSO): δ 11.46 (s, 1H), 8.34 (s, 1H), 7.70 (t, J=5.1 Hz, 1H), 7.35-7.18 (m, 5H), 5.84 (s, 1H), 5.49 (q, J=7.2 Hz, 1H), 4.20 (d, J=4.8 Hz, 2H), 2.29 (s, 3H), 2.15 (s, 3H), 2.10 (s, 3H), 1.73 (d, J=6.9 Hz, 3H).

Synthesis of (R or S)-N-((2-hydroxy-4,6-dimethylpyridin-3-yl)methyl)-5-methyl-1-(1-phenylethyl)-1H-pyrazole-4-carboxamide (Compound 107) and (R or S)-N-((2-hydroxy-4,6-dimethylpyridin-3-yl)methyl)-5-methyl-1-(1-phenylethyl)-1H-pyrazole-4-carboxamide (Compound 108)

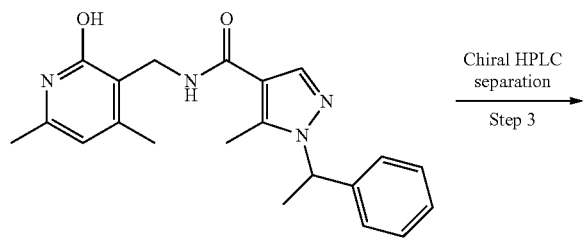

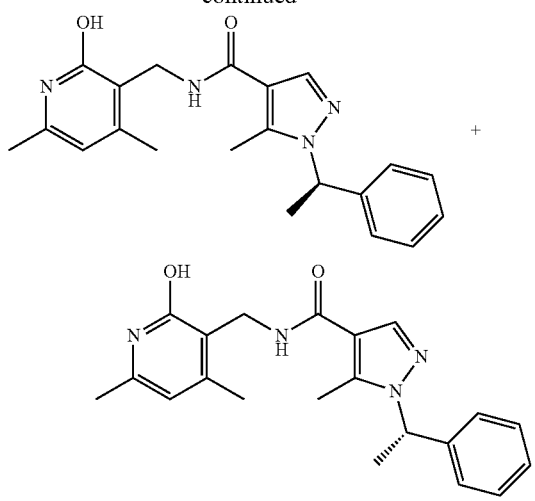

N-((2-hydroxy-4,6-dimethylpyridin-3-yl)methyl)-5-methyl-1-(1-phenylethyl)-1H-pyrazole-4-carboxamide was separated by chiral HPLC (condition: column AD-H (20 mm*250 mm*5 μm), hexane:ethanol (0.2% DEA)=50:50, flow rate: 13 ml/min). The two isomers of N-((2-hydroxy-4,6-dimethylpyridin-3-yl)methyl)-5-methyl-1-(1-phenylethyl)-1H-pyrazole-4-carboxamide were obtained, but absolute stereochemistry was not determined. The retention times were 6.574 minutes ("Peak 1"; Compound 107) and 7.974 minutes by Chiral HPLC chromatography ("Peak 2"; Compound 108). LRMS (M+H⁺) m/z: calcd 364.19. found 364. ¹H NMR (300 MHz, d⁶-DMSO): δ 11.46 (s, 1H), 8.34 (s, 1H), 7.70 (t, J=5.1 Hz, 1H), 7.35-7.18 (m, 5H), 5.84 (s, 1H), 5.49 (q, J=7.2 Hz, 1H), 4.20 (d, J=4.8 Hz, 2H), 2.29 (s, 3H), 2.15 (s, 3H), 2.10 (s, 3H), 1.73 (d, J=6.9 Hz, 3H).

Example 5

Synthesis of N-((2-hydroxy-4,6-dimethylpyridin-3-yl)methyl)-5-methyl-1-(1-benzyl)-1H-pyrazole-4-carboxamide (Compound 109)

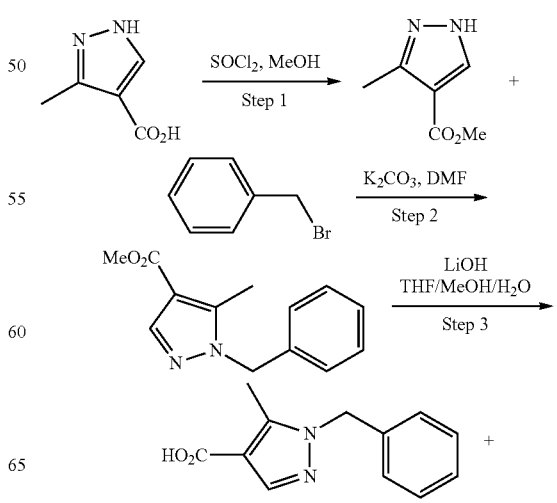

-continued

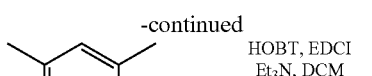

flow rate: 50 mL/minute, wavelength: 214 nm) to give crude methyl 1-benzyl-5-methyl-1H-pyrazole-4-carboxylate (200 mg, 42%). LRMS (M+H⁺) m/z: calcd. 230.11. found 230.

Synthesis of 1-benzyl-5-methyl-1H-pyrazole-4-carboxylic acid

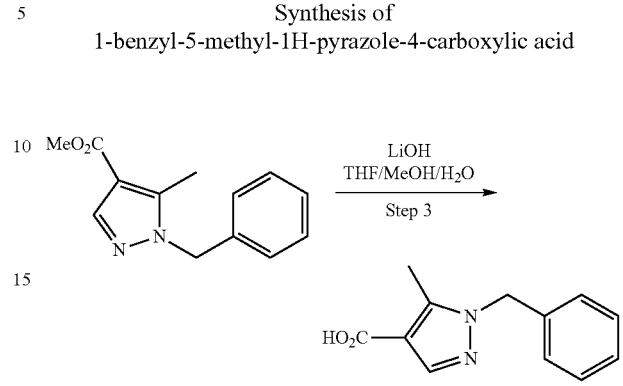

Synthesis of methyl 3-methyl-1H-pyrazole-4-carboxylate

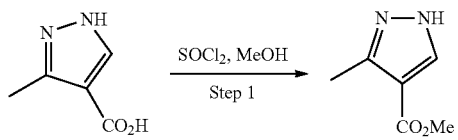

To a solution of 3-methyl-1H-pyrazole-4-carboxylic acid (1.26 g, 10 mmol) in methanol (100 mL) was added thionyl chloride (5.73 g, 45 mmol) at 0° C. The mixture was stirred for 12 hours. The solvent was evaporated in vacuo. To the residue, saturated sodium bicarbonate aqueous solution was added and the mixture was extracted with ethyl acetate (100 mL×3), the organic phase was dried by sodium sulfate. The mixture was filtered and the filtrate was concentrated in vacuo to give methyl 3-methyl-1H-pyrazole-4-carboxylate (0.8 g, 57%). $^1$H NMR (300 MHz, CDCl$_3$): δ 7.87 (s, 1H), 3.84 (s, 3H), 2.53 (s, 3H).

Synthesis of methyl 1-benzyl-5-methyl-1H-pyrazole-4-carboxylate

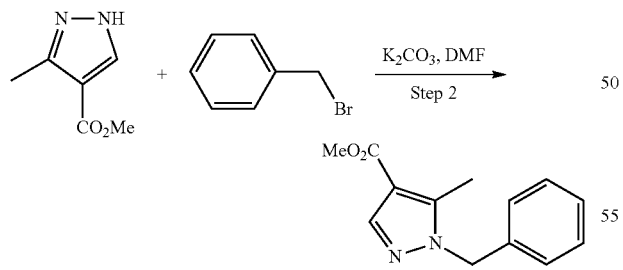

To a solution of methyl 3-methyl-1H-pyrazole-4-carboxylate (280 mg, 2 mmol) in N, N-dimethylformamide (30 mL) was added (bromomethyl)benzene (0.34 g, 2 mmol) and potassium carbonate (0.55 g, 4 mmol). The mixture was stirred at 20° C. and stirred for 12 hours. The solvent was evaporated in vacuo and the residue was purified by CXTH (Column: Dsisol, 10 µM, C18, 250 mm*50 mm; Mobile: acetonitrile (0.1% formic acid)-water (0.1% formic acid), acetonitrile from 30% to 70% in 80 minutes; oven: 20° C.;

A mixture of methyl 1-benzyl-5-methyl-1H-pyrazole-4-carboxylate (200 mg, 0.86 mmol), lithium hydroxide monohydrate (111 mg, 2.62 mmol), tetrahydrofuran (10 mL), methanol (2 mL) and water (2 mL) was stirred at 20° C. for 4 hours. The mixture was acidified to pH=1 with concentrated hydrochloric acid and then extracted with ethyl acetate (15 mL×3). The combined organic phase was dried by sodium sulfate, and then filtered. The filtrate was concentrated in vacuo and separated by chiral HPLC (condition: column AD-H (20 mm*250 mm*5 µm), hexane:ethanol (0.2% DEA)=50:50, flow rate: 13 mL/min) to give 1-benzyl-5-methyl-1H-pyrazole-4-carboxylic acid (75 mg, 40%). LRMS (M+H⁺) m/z: calcd. 216.09. found 216.

Synthesis of 1-benzyl-N-((2-hydroxy-4,6-dimethylpyridin-3-yl)methyl)-5-methyl-1H-pyrazole-4-carboxamide (Compound 109)

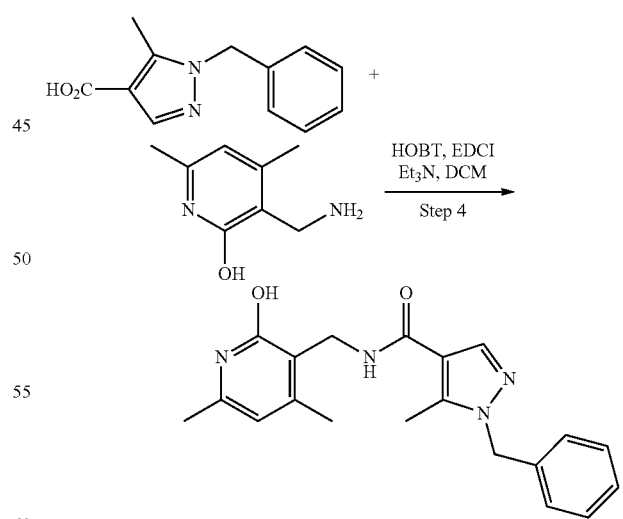

A mixture of 1-benzyl-5-methyl-1H-pyrazole-4-carboxylic acid (75 mg, 0.34 mmol), 1-ethyl-3-(3-dimethylaminopropyl)carbodiimide hydrochloride (95 mg, 0.5 mmol), N-hydroxybenzotrizole (67 mg, 0.5 mmol), triethylamine (0.1 mL) and dichloromethane (5 mL) were stirred at 25° C. for 0.5 hours. Then 3-(aminomethyl)-4,6-dimethylpyridin-2-ol (50 mg, 0.33 mmol) was added. The mixture was stirred at 25° C. for 12 hours. To the mixture, water (10 ml) was added and the mixture was extracted with dichloromethane (10 mL×3). The combined organic phase was dried by sodium sulfate and then filtered. The filtrate was concentrated in vacuo. The residue was purified by column chromatography (silica gel, dichloromethane/methanol=20:1) to give 1-benzyl-N-((2-hydroxy-4,6-dimethylpyridin-3-yl)methyl)-5-methyl-1H-pyrazole-4-carboxamide as a white solid (35 mg, 29%). LRMS (M+H$^+$) m/z: calcd 350.17; found 350. $^1$H NMR (300 MHz, d$^6$-DMSO): δ 11.46 (s, 1H), 8.21 (s, 1H), 7.68 (t, J=5.1 Hz, 1H), 7.38-7.21 (m, 5H), 5.85 (s, 1H), 5.20 (s, 2H), 4.19 (d, J=5.4 Hz, 2H), 2.29 (s, 3H), 2.15 (s, 3H), 2.10 (s, 3H).

Example 6

Synthesis of N-((2-hydroxy-4,6-dimethylpyridin-3-yl)methyl)-5-methyl-1-phenethyl-1H-pyrazole-4-carboxamide (Compound 110)

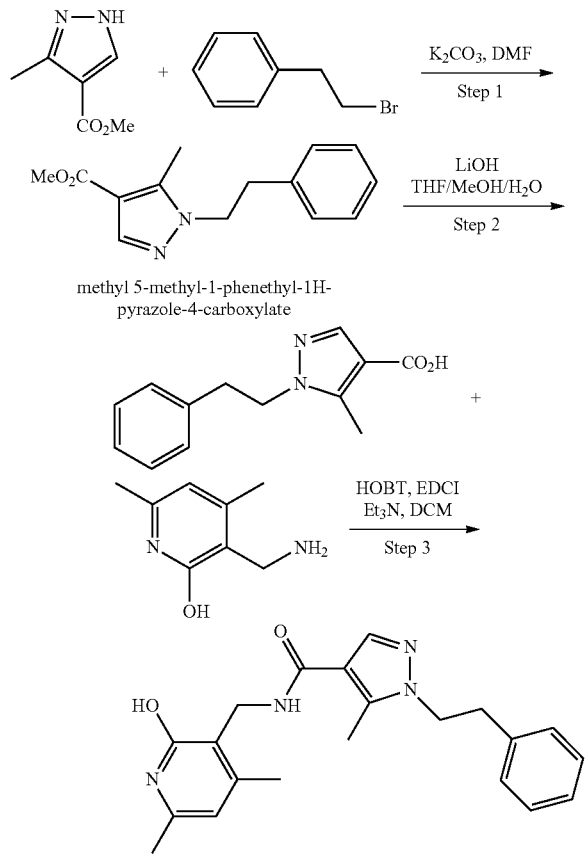

Synthesis of methyl 5-methyl-1-phenethyl-1H-pyrazole-4-carboxylate

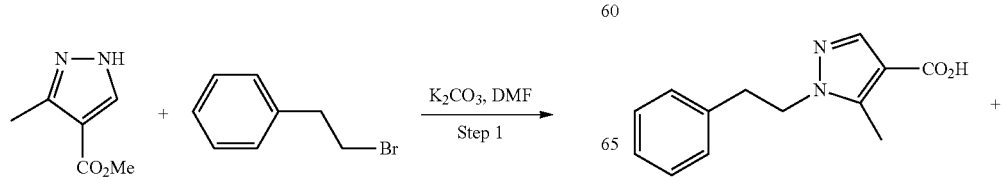

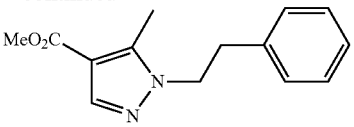

To a solution of methyl 3-methyl-1H-pyrazole-4-carboxylate (280 mg, 2 mmol) in N,N-dimethylformamide (30 mL) was added (bromoethyl)benzene (0.37 g, 2 mmol) and potassium carbonate (0.55 g, 4 mmol). The mixture was stirred at 20° C. for 12 hours. The solvent was evaporated in vacuo and the residue was purified by CXTH (Column: Dsisol, 10 μM, C18, 250 mm*50 mm; Mobile: acetonitrile (0.1% formic acid)—water (0.1% formic acid), acetonitrile from 30% to 70% in 80 minutes; oven: 20° C.; flow rate: 50 mL/minute, wavelength: 214 nm) to give crude methyl 5-methyl-1-phenethyl-1H-pyrazole-4-carboxylate (177 mg, 36%). The product was used for the next step directly. LRMS (M+H$^+$) m/z: calcd. 244.12. found 244.

Synthesis of 5-methyl-1-phenethyl-1H-pyrazole-4-carboxylic acid

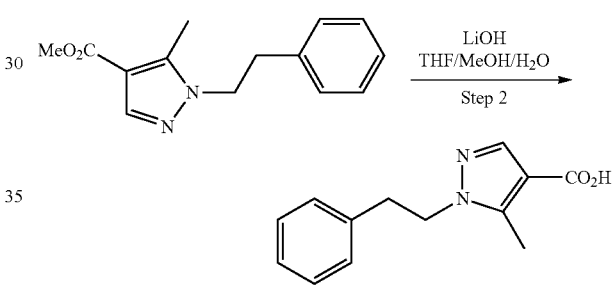

A mixture of methyl 5-methyl-1-phenethyl-1H-pyrazole-4-carboxylate (177 mg, 0.72 mmol), lithium hydroxide monohydrate (111 mg, 2.62 mmol), tetrahydrofuran (5 mL), methanol (1 mL) and water (1 mL) was stirred at 20° C. for 4 hours. The mixture was acidified to pH=1 with concentrated hydrochloric acid and then extracted with ethyl acetate (15 mL×3). The combined organic phase was dried by sodium sulfate, and then filtered. The filtrate was concentrated in vacuum and separated by HPLC (condition: column AD-H (20 mm*250 mm*5 μm), hexane:ethanol (0.2% DEA)=50:50, flow rate: 13 mL/min) to give 5-methyl-1-phenethyl-1H-pyrazole-4-carboxylic acid (60 mg, 36%). LRMS (M+H$^+$) m/z: calcd. 230.11; found 230.

Synthesis of N-((2-hydroxy-4,6-dimethylpyridin-3-yl)methyl)-5-methyl-1-phenethyl-1H-pyrazole-4-carboxamide (Compound 110)

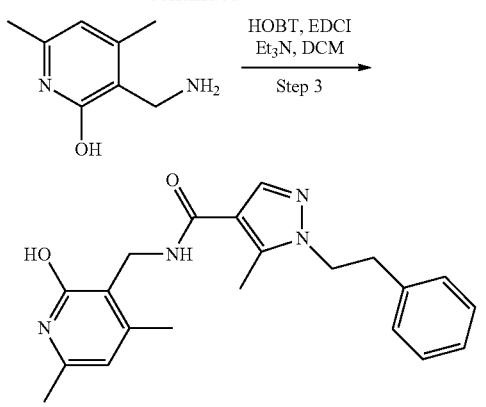

A mixture of 5-methyl-1-phenethyl-1H-pyrazole-4-carboxylic acid (60 mg, 0.27 mmol), 1-ethyl-3-(3-dimethylaminopropyl)carbodiimide hydrochloride (95 mg, 0.5 mmol), N-hydroxybenzotrizole (67 mg, 0.5 mmol), triethylamine (0.1 mL) and dichloromethane (5 mL) were stirred at 25° C. for 0.5 hours. Then 3-(aminomethyl)-4,6-dimethylpyridin-2-ol (50 mg, 0.33 mmol) was added. The mixture was stirred at 25° C. for 12 hours. To the mixture, water (10 ml) was added and the mixture was extracted with dichloromethane (10 mL×3). The combined organic phase was dried by sodium sulfate and then filtered. The filtrate was concentrated in vacuo. The residue was purified by column chromatography (silica gel, dichloromethane/methanol=20:1) to give N-((2-hydroxy-4,6-dimethylpyridin-3-yl)methyl)-5-methyl-1-phenethyl-1H-pyrazole-4-carboxamide as a white solid (30 mg, 31%). LRMS (M+H+) m/z: calcd 364.19. found 364. $^1$H NMR (300 MHz, d$^6$-DMSO): δ 11.47 (s, 1H), 8.08 (s, 1H), 7.57 (t, J=5.1 Hz, 1H), 7.30-7.15 (m, 5H), 5.85 (s, 1H), 4.23-4.18 (m, 4H), 3.06 (t, J=7.2 Hz, 2H), 2.31 (s, 3H), 2.15 (s, 3H), 2.11 (s, 3H).

Example 7

Synthesis of N-((2-hydroxy-4,6-dimethylpyridin-3-yl)methyl)-2-methyl-1-(1-phenylethyl) 1H-indole-3-carboxamide (Compound 111), (R or S)-N-((2-hydroxy-4,6-dimethylpyridin-3-yl)methyl) 2-methyl-1-1-phenylethyl) 1H-indole-3-carboxamide (Compound 137) and (S or R)-N-((2-hydroxy-4,6-dimethylpyridin-3-yl)methyl) 2-methyl-1-1-phenylethyl) 1H-indole-3-carboxamide (Compound 136)

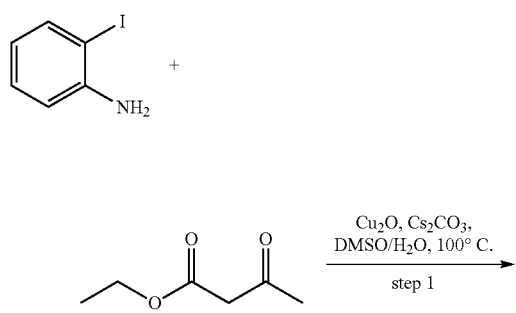

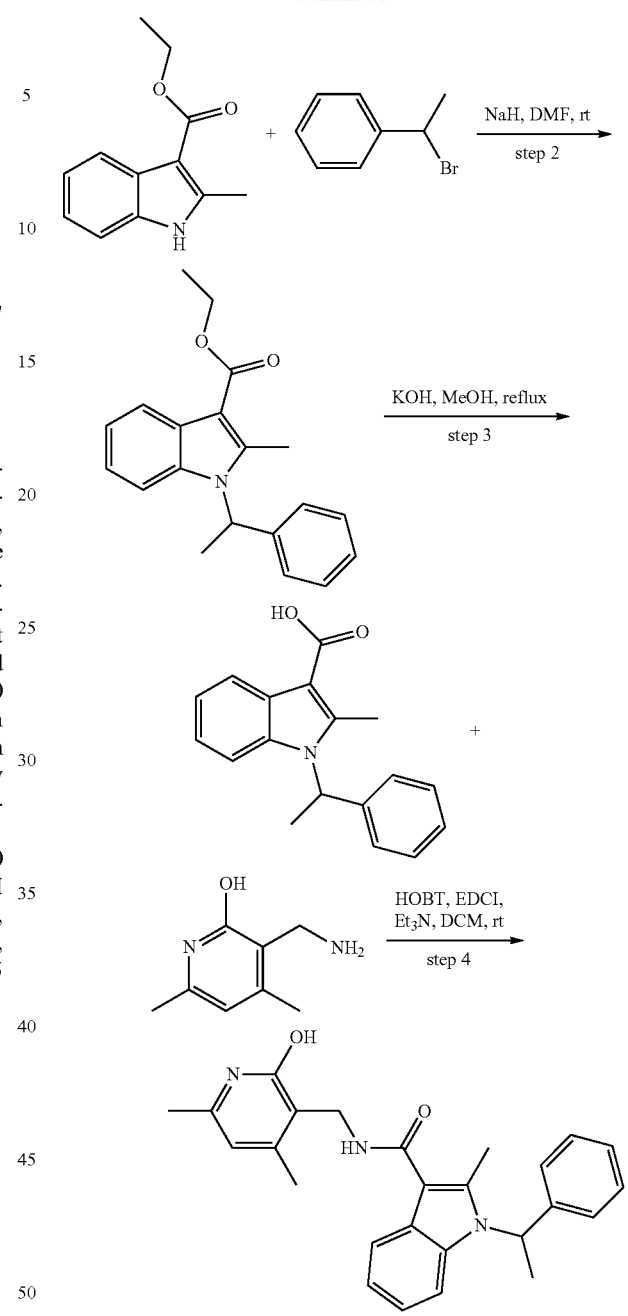

Synthesis of ethyl 2-methyl-1H-indole-3-carboxylate

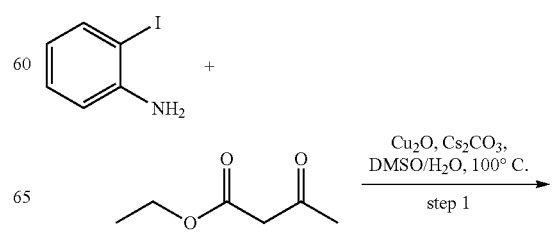

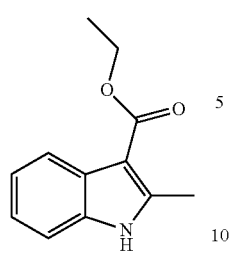

To a mixed solution of dimethyl sulfoxide and water (20 mL), 2-iodobenzenamine (3.0 g, 13.7 mmol), ethyl 3-oxobutanoate (2.0 g, 15.1 mmol), copper(I) oxide (0.2 g, 1.4 mmol) and cesium carbonate (4.5 g, 13.7 mmol) was added. The mixture was stirred at 100° C. for 9 hours under nitrogen gas atmosphere. The reaction mixture was filtered through a pad of celite. The filtrate was diluted with water and extracted with ethyl acetate. The organic phase was concentrated in vacuo, and then the residue was purified by column chromatography (silica gel, petroleum ether/ethyl acetate=5:1) to give ethyl 2-methyl-1H-indole-3-carboxylate as a light yellow solid (0.42 g, 15%). $^1$H NMR (300 MHz, CDCl$_3$): δ 8.12-8.09 (m, 1H), 7.31-7.16 (m, 3H), 4.40 (q, J=6.9 Hz, 2H), 2.77 (s, 3H), 1.45 (t, J=6.9 Hz, 3H).

Synthesis of ethyl 2-methyl-1-(1-phenylethyl)-1H-indole-3-carboxylate

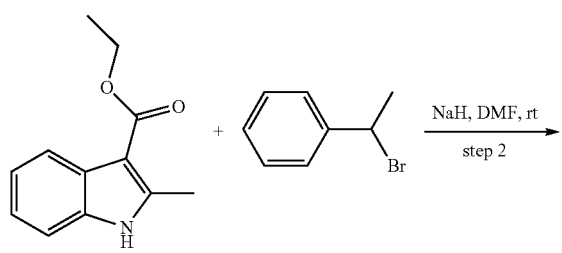

A mixture of ethyl 2-methyl-1H-indole-3-carboxylate (400 mg, 1.97 mmol) and sodium hydride (47 mg, 2.0 mmol) in N,N-dimethylformamide (5.0 mL) was stirred at room temperature for 0.5 hours, and then (1-bromoethyl)benzene (361 mg, 2.0 mmol) was added. The mixture was stirred at room temperature for 3 hours. The reaction mixture was poured into ice-cold water and extracted with ethyl acetate. Organic layers were combined and concentrated to give a residue. The residue was purified by chromatography (petroleum ether/ethyl acetate=5:1) to give ethyl 2-methyl-1-(1-phenylethyl)-1H-indole-3-carboxylate (340 mg, 56%). LRMS (M+H$^+$) m/z: calcd 307.16. found 307.

Synthesis of 2-methyl-1-(1-phenylethyl)-1H-indole-3-carboxylic acid

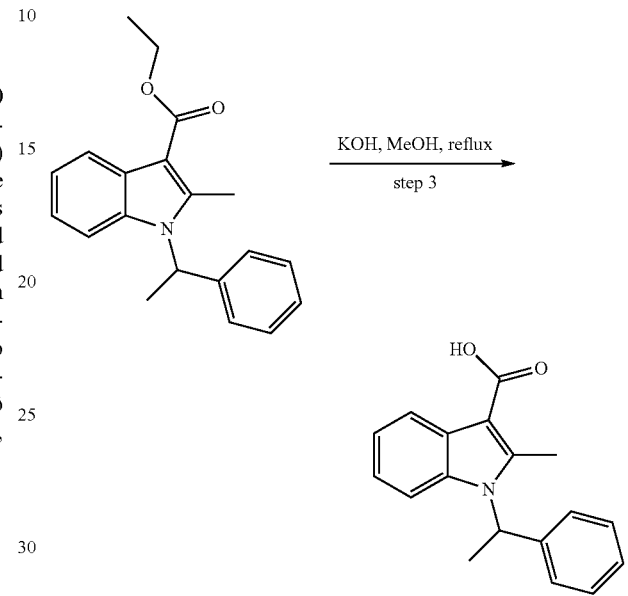

To a mixed solution of methanol and water (4 mL), ethyl 2-methyl-1-(1-phenylethyl)-1H-indole-3-carboxylate (300 mg, 0.98 mmol) and potassium hydroxide (546 mg, 9.76 mmol) was added. The mixture was refluxed with stirring for 4 hours. The reaction mixture was concentrated to give a residue. To the residue, water (10 mL) was added and the mixture was extracted with dichloromethane (20 mL×3). The organic phase was concentrated to give crude product 2-methyl-1-(1-phenylethyl)-1H-indole-3-carboxylic acid (150 mg). LRMS (M–H)$^-$ m/z: calcd 279.13. found 279.

Synthesis of N-((2-hydroxy-4,6-dimethylpyridin-3-yl)methyl)-2-methyl-1-(1-phenylethyl)-1H-indole-3-carboxamide (Compound 111)

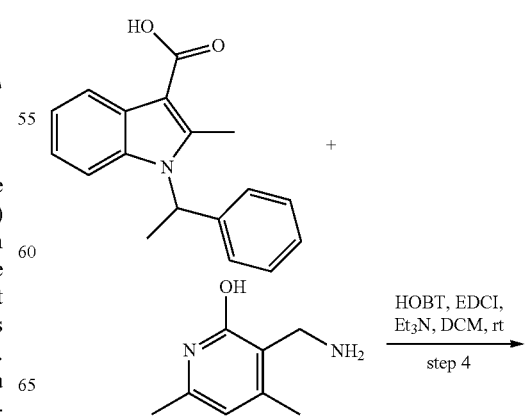

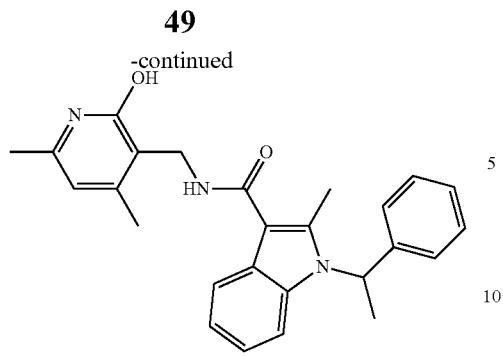

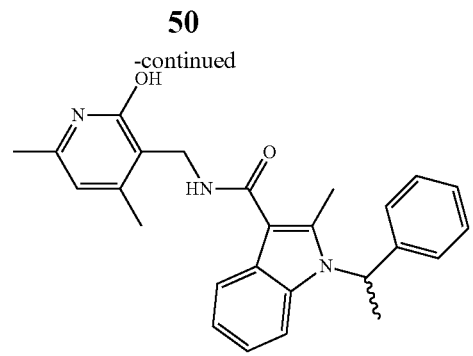

To a solution of 2-methyl-1-(1-phenylethyl)-1H-indole-3-carboxylic acid (150 mg, 0.54 mmol) in anhydrous dichloromethane (10 mL) was added N-hydroxybenzotriazole (87 mg, 0.64 mmol), 1-ethyl-3-[3-(dimethylamino)propyl]carbodiimide hydrochloride (124 mg, 0.64 mmol) and trimethylamine (163 mg, 1.61 mmol). The mixture was stirred at room temperature for 0.5 hours, then 3-(aminomethyl)-4,6-dimethylpyridin-2-ol (98 mg, 0.64 mmol) was added. The mixture was stirred at room temperature for 12 hours. To the reaction mixture was added water (20 mL), extracted with dichloromethane (20 mL×2). The organic layers were combined and concentrated to give a residue. The residue was purified by column chromatography (silica gel, dichloromethane/methanol=20:1) to give compound N-((2-hydroxy-4,6-dimethylpyridin-3-yl)methyl)-2-methyl-1-(1-phenylethyl)-1H-indole-3-carboxamide as an off-white solid (130 mg, 59%). LRMS (M+H⁺) m/z: calcd 413.21. found 413. ¹H NMR (300 MHz, d⁶-DMSO) δ: 11.59 (s, 1H), 7.73-7.66 (m, 2H), 7.34-7.29 (m, 3H), 7.23 (d, J=7.5 Hz, 1H), 7.16-6.89 (m, 4H), 5.94 (q, J=7.2 Hz, 1H), 5.88 (s, 1H), 4.32 (d, J=5.4 Hz, 2H), 2.60 (s, 3H), 2.27 (s, 3H), 2.11 (s, 3H), 1.88 (d, J=7.2 Hz, 3H).

Synthesis of (R or S)-N-((2-hydroxy-4,6-dimethylpyridin-3-yl)methyl) 2-methyl-1-1-phenylethyl) 1H-indole-3-carboxamide (Compound 137) and (R or S)-N-((2-hydroxy-4,6-dimethylpyridin-3-yl)methyl) 2-methyl-1-1-phenylethyl) 1H-indole-3-carboxamide (Compound 136)

N-((2-hydroxy-4,6-dimethylpyridin-3-yl)methyl)2-methyl-1-1-phenylethyl) 1H-indole-3-carboxamide (130 mg, 0.31 mmol) was separated by chiral prep-HPLC (Daicel AD-H (250 mm×20 mm×5 um), hexane:ethanol (0.2% DEA)=50:50, flow rate: 13 mL/min), then (R or S) N-((2-hydroxy-4,6-dimethylpyridin-3-yl)methyl) 2-methyl-1-1-phenylethyl) 1H-indole-3-carboxamide (30 mg, 23%) and (S or R)N-((2-hydroxy-4,6-dimethylpyridin-3-yl)methyl) 2-methyl-1-1-phenylethyl) 1H-indole-3-carboxamide (30 mg, 23%) was obtained. The retention times were 8.030 minutes ("Peak 1"; Compound 137) and 14.126 minutes ("Peak 2"; Compound 136) respectively in chiral HPLC chromatography. LRMS (M+H⁺) m/z: calcd 413.21. found 413. ¹H NMR (300 MHz, d⁶-DMSO) δ: 11.59 (s, 1H), 7.73-7.66 (m, 2H), 7.34-7.29 (m, 3H), 7.23 (d, J=7.5 Hz, 1H), 7.16-6.89 (m, 4H), 5.94 (q, J=7.2 Hz, 1H), 5.88 (s, 1H), 4.32 (d, J=5.4 Hz, 2H), 2.60 (s, 3H), 2.27 (s, 3H), 2.11 (s, 3H), 1.88 (d, J=7.2 Hz, 3H).

Example 8

Synthesis of N-((2-hydroxy-4,6-dimethylpyridin-3-yl)methyl)-1-(1-phenylethyl)-1H-indazole-3-carboxamide (Compound 112)

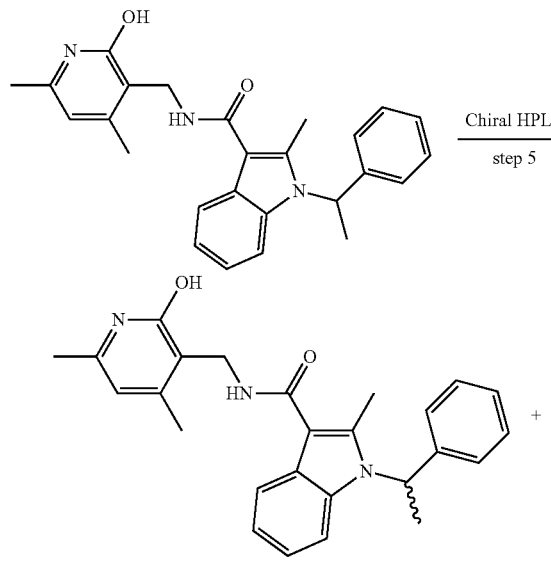

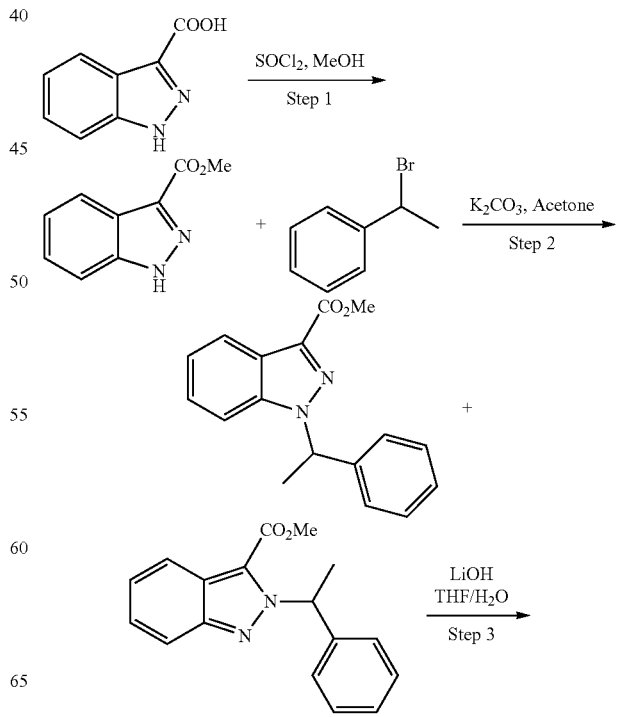

-continued

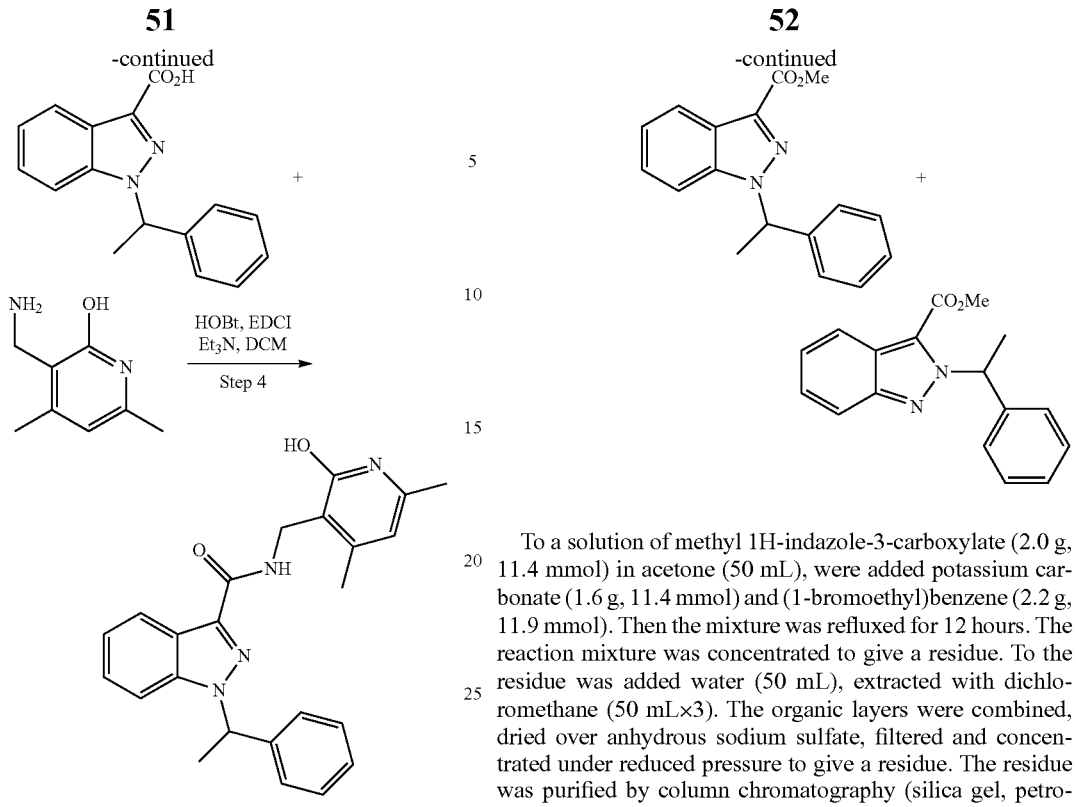

Synthesis of methyl 1H-indazole-3-carboxylate

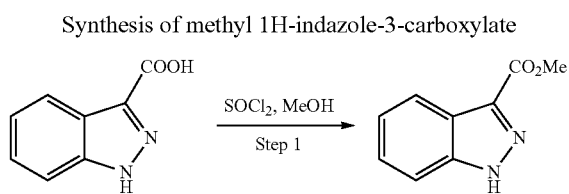

To a solution of 1H-indazole-3-carboxylic acid (5.0 g, 30.8 mmol) in methanol (50 mL), thionyl chloride (15 mL) was added dropwise at 0° C. After the addition, the mixture was heated to reflux and maintained at the temperature for 1.5 hours. Then the reaction mixture was concentrated to give a residue. To the residue was added saturated sodium bicarbonate (50 mL), and then extracted with ethyl acetate (50 mL×3). The organic phase was combined and dried over anhydrous sodium sulfate. The mixture was filtered and the filtrate was concentrated under reduced pressure to give methyl 1H-indazole-3-carboxylate as a white solid (5.1 g, 94%). $^1$H NMR (300 MHz, d$^6$-DMSO): δ 13.91 (s, 1H), 8.06 (d, J=8.2 Hz, 1H), 7.65 (d, J=8.4 Hz, 1H), 7.44 (ddd, J=8.3 Hz, J=6.9 Hz, J=1.1 Hz, 1H), 7.30 (ddd, J=7.9 Hz, J=6.9 Hz, J=0.9 Hz, 1H), 3.92 (s, 3H).

Synthesis of methyl 1-(1-phenylethyl)-1H-indazole-3-carboxylate

To a solution of methyl 1H-indazole-3-carboxylate (2.0 g, 11.4 mmol) in acetone (50 mL), were added potassium carbonate (1.6 g, 11.4 mmol) and (1-bromoethyl)benzene (2.2 g, 11.9 mmol). Then the mixture was refluxed for 12 hours. The reaction mixture was concentrated to give a residue. To the residue was added water (50 mL), extracted with dichloromethane (50 mL×3). The organic layers were combined, dried over anhydrous sodium sulfate, filtered and concentrated under reduced pressure to give a residue. The residue was purified by column chromatography (silica gel, petroleum ether/ethyl acetate=5:1) to afford two isomers.

Methyl 1-(1-phenylethyl)-1H-indazole-3-carboxylate (2.3 g, 73%) as a white solid. LRMS (M+H$^+$) m/z: calcd 280.32. found 280. $^1$H NMR (300 MHz, d$^6$-DMSO): δ 8.08 (d, J=8.1 Hz, 1H), 7.79 (d, J=8.5 Hz, 1H), 7.43 (ddd, J=8.4, 6.9, 1.1 Hz, 1H), 7.37-7.16 (m, 6H), 6.23 (q, J=6.9 Hz, 1H), 3.93 (s, 3H), 2.04-1.92 (m, 3H).

Methyl 2-(1-phenylethyl)-2H-indazole-3-carboxylate as a white solid (0.9 g). LRMS (M+H$^+$) m/z: calcd 280.32. found 280. $^1$H NMR (300 MHz, d$^6$-DMSO): δ 7.98 (d, J=8.1 Hz, 1H), 7.84 (d, J=8.5 Hz, 1H), 7.55-7.18 (m, 7H), 7.13-6.82 (m, 1H), 3.95 (s, 3H), 1.96 (d, J=6.9 Hz, 3H).

Synthesis of 1-(1-phenylethyl)-1H-indazole-3-carboxylic acid

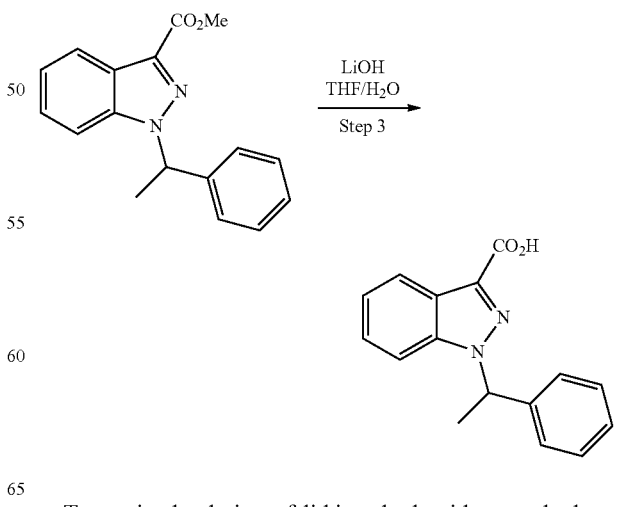

To a mixed solution of lithium hydroxide monohydrate (0.68 g, 16.8 mmol) in tetrahydrofuran (20 mL) and water (10 mL), methyl 1-(1-phenylethyl)-1H-indazole-3-carboxylate (2.3 g, 8.4 mmol) was added. The mixture was stirred at 45° C. for 12 hours. Then the organic solvent was removed under reduced pressure. To the residue, 1 N hydrochloride aqueous solution was added to adjust the pH to 3-4, and then the mixture was extracted with ethyl acetate (20 mL×3). The organic phase was combined, dried over anhydrous sodium sulfate, filtered and concentrated to afford 1-(1-phenylethyl)-1H-indazole-3-carboxylic acid (1.3 g, 60%) as a white solid, which was directly used in next step. LRMS (M+H$^+$) m/z: calcd 266.29. found 266.

Synthesis of N-((2-hydroxy-4,6-dimethylpyridin-3-yl)methyl)-1-(1-phenylethyl)-1H-indazole-3-carboxamide (Compound 112)

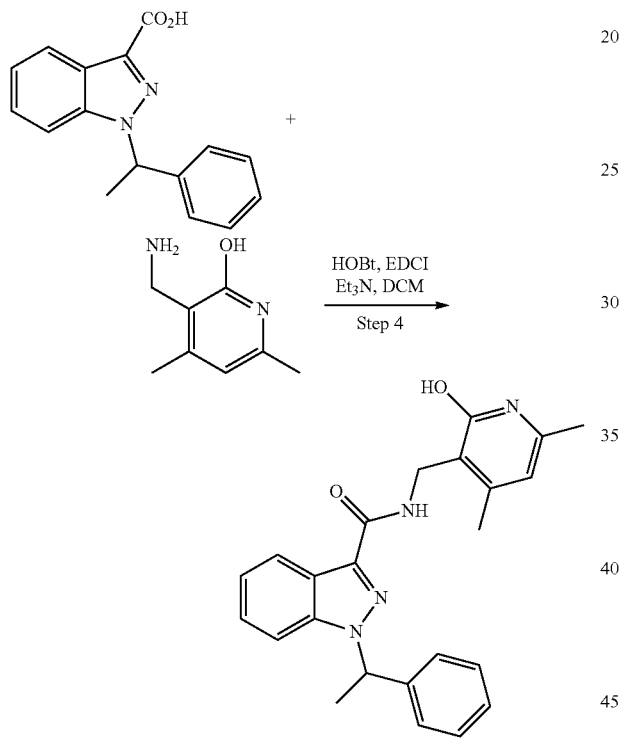

To a solution of 1-(1-phenylethyl)-1H-indazole-3-carboxylic acid (0.3 g, 1.12 mmol) in anhydrous dichloromethane (20 mL) was added 1H-benzo[d][1,2,3]triazol-1-ol (0.14 g, 1.0 mmol), 1-ethyl-3-(3-dimethyllaminopropyl)carbodiimide hydrochloride (0.26 g, 1.37 mmol) and triethylamine (0.184 g, 1.83 mmol). The mixture was stirred at room temperature for 0.5 hours, and 3-(aminomethyl)-4,6-dimethylpyridin-2-ol (0.15 g, 1.0 mmol) was added. The mixture was stirred at room temperature for 3 hours. To the reaction mixture was added water (50 mL), and the mixture was extracted with dichloromethane (20 mL×3). The organic phase was combined, dried over anhydrous sodium sulfate, filtered and concentrated to give a residue. The residue was purified by column chromatography (silica gel, dichloromethane/methanol=50:1) to give N-((2-hydroxy-4,6-dimethylpyridin-3-yl)methyl)-1-(1-phenylethyl)-1H-indazole-3-carboxamide (70 mg, 18%). LRMS (M+H$^+$) m/z: calcd. 400.47. found 400. $^1$H NMR (300 MHz, d$^6$-DMSO): δ 11.59 (s, 1H), 8.24 (s, 1H), 8.16 (d, J=8.1 Hz, 1H), 7.68 (d, J=8.6 Hz, 1H), 7.52-7.33 (m, 1H), 7.30-7.06 (m, 6H), 6.13 (d, J=7.0 Hz, 1H), 5.89 (s, 1H), 4.41-4.37 (m, 2H), 2.26 (s, 3H), 2.12 (s, 3H), 1.94 (d, J=7.0 Hz, 3H).

Example 9

Synthesis of N-((2-hydroxy-4,6-dimethylpyridin-3-yl)methyl)-(o-tolyl)-1H-indole-3-carboxamide (Compound 113)

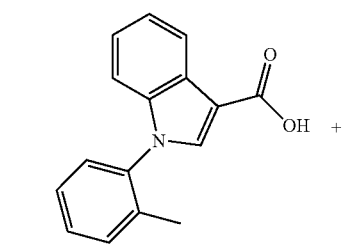

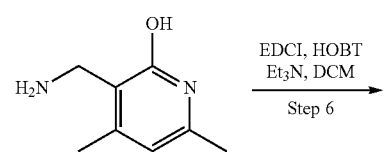

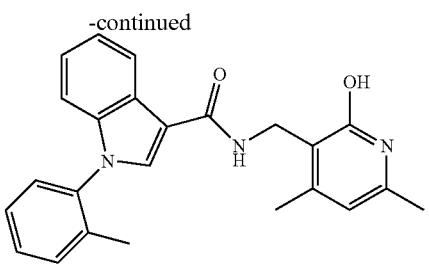

Synthesis of methyl 2-(2-bromophenyl)acetate

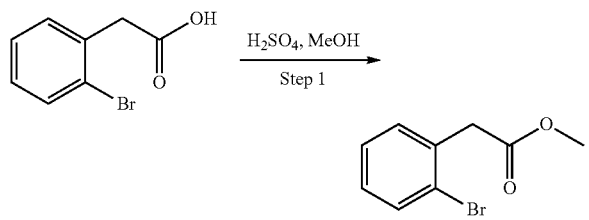

A solution of o-bromophenylacetic acid (5 g, 23.2 mmol) in dry methanol (40 mL) containing concentrated sulphuric acid (1 mL) was heated to reflux for 6 hours. The reaction mixture was cooled, then poured into ice water (100 mL) and extracted with ethyl acetate (30 mL×2). The organic layers were combined, washed successively with water (20 mL×2), saturated sodium bicarbonate solution (40 mL×2) and brine. And then the organic layers were combined, dried over sodium sulfate, filtered and concentrated in vacuo to give methyl 2-(2-bromophenyl) acetate as a pale yellow liquid (5.2 g, 98%). $^1$H NMR (300 MHz, CDCl$_3$): δ 7.57 (d, J=7.8 Hz, 1H), 7.34-7.22 (m, 2H), 7.17-7.11 (m, 1H), 3.80 (s, 2H), 3.72 (s, 3H).

Synthesis of ethyl 2-(2-bromophenyl)-3-hydroxyacrylate

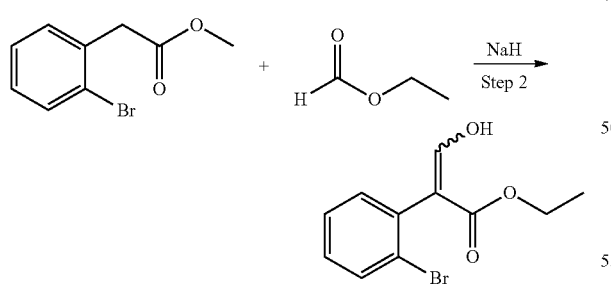

To a stirred solution of methyl 2-(2-bromophenyl)acetate (5.2 g, 22.7 mmol) in ethyl formate (40 mL) was added in portions the powder of sodium hydride (100%, 2.18 g, 90.8 mmol) over a period of 1 hour at 10-15° C. After the mixture was stirred for an additional hour, the reaction was quenched with ice water (100 mL) and the two layers were separated. The aqueous layer was acidified with 10% hydrochloric acid aqueous solution and then extracted with ethyl acetate (30 mL×3). The organic layers were combined and washed with water (2×20 mL), saturated sodium bicarbonate solution (2×40 mL) and brine in turns. Then organic layers were dried over sodium sulfate, filtered and concentrated in vacuo to give ethyl 2-(2-bromophenyl)-3-hydroxyacrylate as a pink oil (5.33 g, 87%). $^1$H NMR (300 MHz, CDCl$_3$): δ 11.99 (d, J=12.7 Hz, 1H), 7.59 (dd, J=7.8 Hz, 0.9 Hz, 1H), 7.46-6.98 (m, 4H), 4.25 (q, J=7.2 Hz, 2H), 1.24 (t, J=7.2 Hz, 3H).

Synthesis of ethyl 3-(o-toluidino)-2-(2-bromophenyl)acrylate

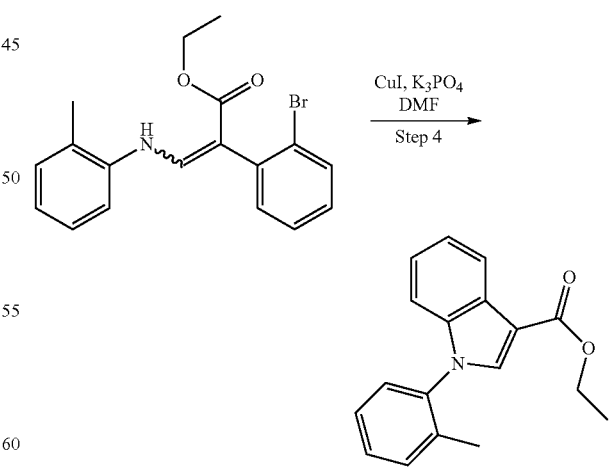

To a solution of ethyl 2-(2-bromophenyl)-3-hydroxyacrylate (1 g, 3.88 mmol) in methanol (10 mL) was added o-toluidine (0.416 g, 3.88 mmol) via syringe at room temperature. After being stirred for 18 hours at the same temperature, solvent was removed under reduced pressure to give the crude product of ethyl 3-(o-toluidino)-2-(2-bromophenyl)acrylate (1.326 g, 95%), which was used in the next step without further purification. LRMS (M+H$^+$) m/z: calcd 359.05. found 359.

Synthesis of ethyl 1-(o-tolyl)-1H-indole-3-carboxylate

A mixture of ethyl 3-(o-toluidino)-2-(2-bromophenyl) acrylate (1.326 g, 3.68 mmol), cuprous iodide (38 mg, 0.38 mmol), potassium phosphate (1.652 g, 7.8 mmol) and N,N-dimethylformamide (16 mL) was stirred at 75-80° C. under nitrogen gas atmosphere for 16 hours. The reaction mixture was allowed to cool to room temperature. Solvent was removed under reduced pressure. Water (16 mL) was added to the residue and the mixture was extracted with ethyl acetate (8 mL×3). The combined organic layers were washed with brine, dried over sodium sulfate, filtered and concentrated in vacuo to give a residue. The residue was purified by column chromatography (silica gel, petroleum ether:ethyl acetate=20:1) to give pure ethyl 1-(o-tolyl)-1H-indole-3-carboxylate as a pale yellow solid (0.789 g, 77%). LRMS (M+H$^+$) m/z: calcd 279.13. found 279. $^1$H NMR (300 MHz, CDCl$_3$): δ 8.26 (dd, J=7.9, 0.7 Hz, 1H), 7.89 (d, J=0.7 Hz, 1H), 7.53-7.11 (m, 6H), 7.02 (dd, J=8.1, 0.8 Hz, 1H), 4.43 (q, J=7.2 Hz, 2H), 2.07 (s, 3H), 1.45 (t, J=7.2 Hz, 3H).

Synthesis of 1-(o-tolyl)-1H-indole-3-carboxylic acid

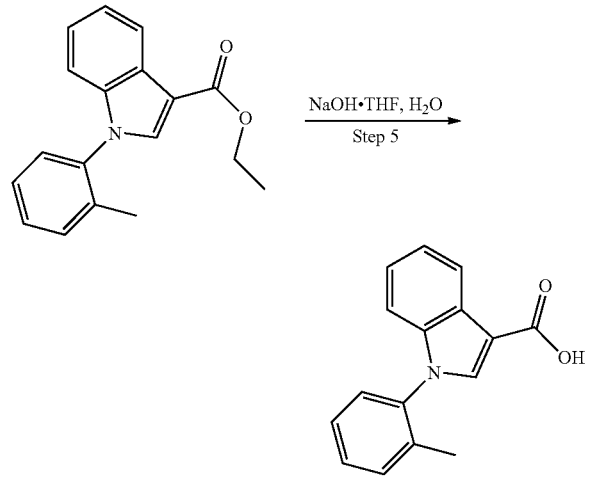

A mixture of ethyl 1-(o-tolyl)-1H-indole-3-carboxylate (0.789 g, 2.82 mmol), 4N sodium hydroxide aqueous (20 mL) and tetrahydrofuran (20 mL) was stirred at 60° C. for 18 hours. Most solvent was removed and the rest was acidified with 10% hydrochloric acid aqueous to adjust to pH=5. Pale yellow precipitate formed and was collected by filtration. The solid was washed with petroleum ether, dried in vacuo to give 1-(o-tolyl)-1H-indole-3-carboxylic acid as a pale yellow solid (0.675 g, 95%). LRMS (M+H$^+$) m/z: calcd 251.09. found 251.

Synthesis of N-((2-hydroxy-4,6-dimethylpyridin-3-yl)methyl)-1-(o-tolyl)-1H-indole-3-carboxamide (Compound 113)

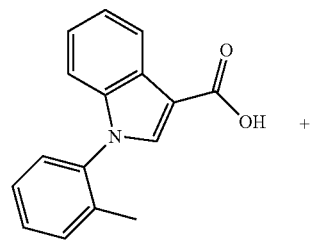

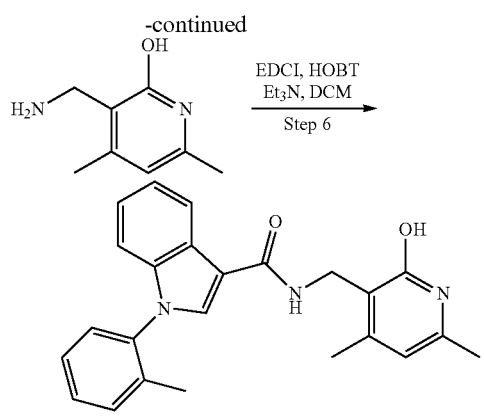

A mixture of 1-(o-tolyl)-1H-indole-3-carboxylic acid (100 mg, 0.398 mmol), 3-(aminomethyl)-4,6-dimethylpyridin-2-ol (60 mg, 0.398 mmol), 1-ethyl-3-(3-dimethylaminopropyl) carbodiimide hydrochloride (114 mg, 0.597 mmol), N-hydroxybenzotriazole (81 mg, 0.597 mmol), triethylamine (81 mg, 0.796 mmol) and dichloromethane (5 mL) was stirred at room temperature for 18 hours. The solvent was removed under reduced pressure and ethyl acetate (10 mL) was added. The resulting mixture was washed with water (10 mL) and brine in turns and then dried over sodium sulfate. The mixture was filtered and the filtrate was concentrated in vacuo. The residue was purified by preparative-TLC(silica gel, dichloromethane:methanol=15:1) to give pure desired product of N-((2-hydroxy-4,6-dimethylpyridin-3-yl)methyl)-1-((o-tolyl)-1H-indole-3-carboxamide as an off white solid (100 mg, 65%). LRMS (M+H$^+$) m/z: calcd 385.18. found 385. $^1$H NMR (300 MHz, CD_OD) δ 8.16 (dd, J=6.1, 2.5 Hz, 1H), 7.87 (s, 1H), 7.44 (d, J=4.9 Hz, 2H), 7.41-7.26 (m, 2H), 7.26-7.12 (m, 2H), 6.93 (dd, J=6.3, 2.4 Hz, 1H), 6.11 (s, 1H), 4.53 (s, 2H), 2.41 (s, 3H), 2.24 (s, 3H), 2.01 (s, 3H).

Example 10

Synthesis of compound (R or S) N-((4-methoxy-6-methyl-2-oxo-1,2-dihydropyridin-3-yl)methyl)-2-methyl-1-(1-phenylethyl)-1H-indole-3-carboxamide (Compounds 114 and 115)

Synthesis of 3-(aminomethyl)-4-methoxy-6-methylpyridin-2-ol

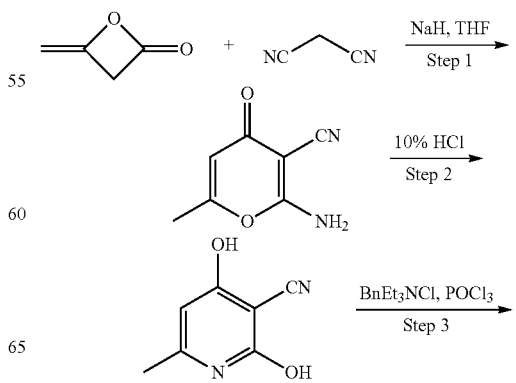

-continued

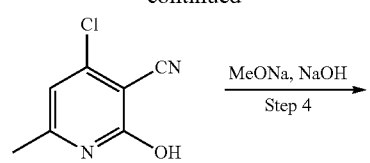

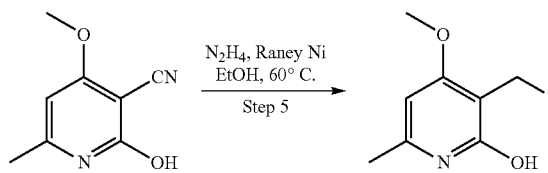

2-amino-6-methyl-4-oxo-4H-pyran-3-carbonitrile

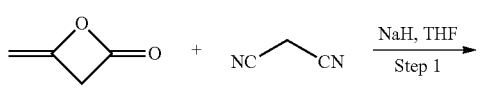

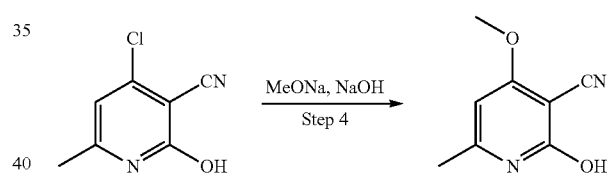

To a solution of malononitrile (3.3 g, 50 mmol) in anhydrous tetrahydrofuran (100 mL) was added sodium hydride (60% w/w, 2.2 g, 55 mmol) at −10° C. The resultant mixture was stirred for 2 hours. Then diketene (4.2 g, 50 mmol) was added dropwise to the solution. The mixture was allowed to warm to room temperature and continued stirring for 30 minutes. The mixture was neutralized with hydrochloric acid and then concentrated in vacuo to give crude 2-amino-6-methyl-4-oxo-4H-pyran-3-carbonitrile (6.0 g, 80%) as a red solid, which was used in the next step without further purification.

2,4-dihydroxy-6-methylnicotinonitrile

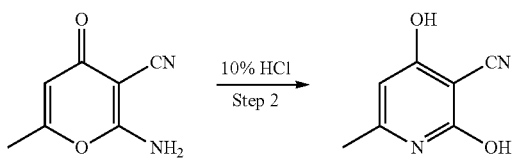

A suspension of 2-amino-6-methyl-4-oxo-4H-pyran-3-carbonitrile (6.0 g, 40 mmol) in 10% hydrochloride acid (60 mL) was heated under reflux for 4 hours. The precipitate was collected by filtration and washed with water, and then recrystallized from methanol to give 2,4-dihydroxy-6-methylnicotinonitrile (5.0 g, 83%) as a brown solid. $^1$H NMR (300 MHz, CD$_3$OD): δ 12.46-12.44 (m, 1H), 11.69 (s, 1H), 5.85 (s, 1H), 2.15 (s, 3H).

4-chloro-2-hydroxy-6-methylnicotinonitrile

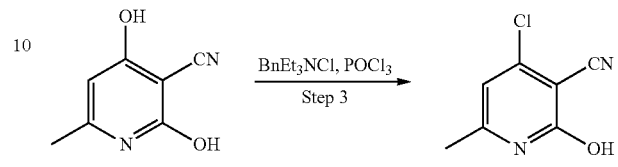

To a solution of 2,4-dihydroxy-6-methylnicotinonitrile (1.5 g, 10 mmol) in acetonitrile (50 mL) was added benzyltriethylammonium chloride (9.1 g, 40 mmol) and phosphorus oxychloride (6.13 g, 40 mmol). The resulting mixture was stirred for 4 hours at room temperature. The solvent was removed by rotary evaporation. To the residue was added dichloromethane (100 mL) and water (50 mL). The organic phase was separated, washed with brine (50 mL), dried over anhydrous magnesium sulfate, filtered and concentrated to give crude product which was purified by column chromatography (silica gel, petroleum ether/ethyl acetate=4:1) to afford 4-chloro-2-hydroxy-6-methylnicotinonitrile (800 mg, 48%) as a brown solid.

2-hydroxy-4-methoxy-6-methylnicotinonitrile

To a pressure vessel was added 4-chloro-2-hydroxy-6-methylnicotinonitrile (337 mg, 2.0 mmol), sodium methoxide (530 mg, 10.0 mmol), methanol (15 mL), and a magnetic stirrer. The pressure vessel was sealed, and was stirred at 100° C. for 16 hours before the solvent was removed by rotary evaporation. To the residue was added water (10 mL) and ethyl acetate (50 mL). The organic layer was separated and concentrated in vacuo to provide crude product which was purified by column chromatography (silica gel, dichloromethane/methanol=40:1) to afford 2-hydroxy-4-methoxy-6-methylnicotinonitrile (70 mg, 21%) as a brown solid.

3-(aminomethyl)-4-methoxy-6-methylpyridin-2-ol

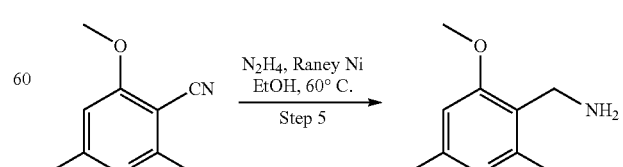

2-Hydroxy-4-methoxy-6-methylnicotinonitrile (70 mg, 0.43 mmol) was dissolved in ethanol (10 mL) and warmed to 60° C. before it was treated with raney nickel (0.5 mL slurry in water) followed by addition of hydrazine monohydrate (2 mL). The resultant mixture was allowed to stir at 60° C. for 2 hours. The cooled reaction mixture was filtered through celite and rinsed with methanol. The filtrate was concentrated in vacuo to provide crude product which was purified by column chromatography (silica gel, dichloromethane/methanol=10:1) to afford 3-(aminomethyl)-4-methoxy-6-methylpyridin-2-ol (40 mg, 56%) as a white solid. LRMS (M+H$^+$) m/z: calcd 168.09. found 168. HPLC purity (214 nm): 73%. $^1$H NMR (300 MHz, d$^6$-DMSO): δ 6.04 (s, 1H), 3.77 (s, 3H), 3.42 (s, 2H), 2.15 (s, 3H).

Synthesis of N-((4-methoxy-6-methyl-2-oxo-1,2-dihydropyridin-3-yl)methyl)-2-methyl-1-(1-phenylethyl)-1H-indole-3-carboxamide (Compound 138)

Synthesis of (R or S) N-((4-methoxy-6-methyl-2-oxo-1,2-dihydropyridin-3-yl)methyl)-2-methyl-1-(1-phenylethyl)-1H-indole-3-carboxamide (Compounds 114 and 115)

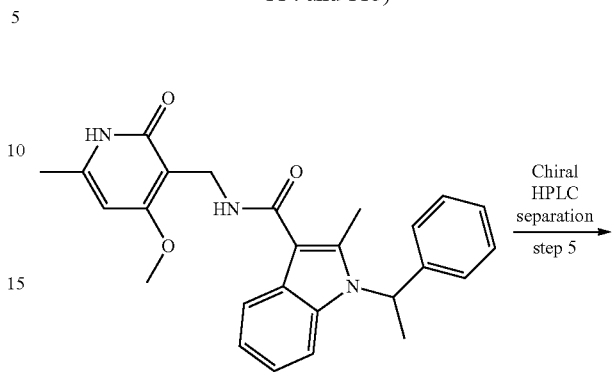

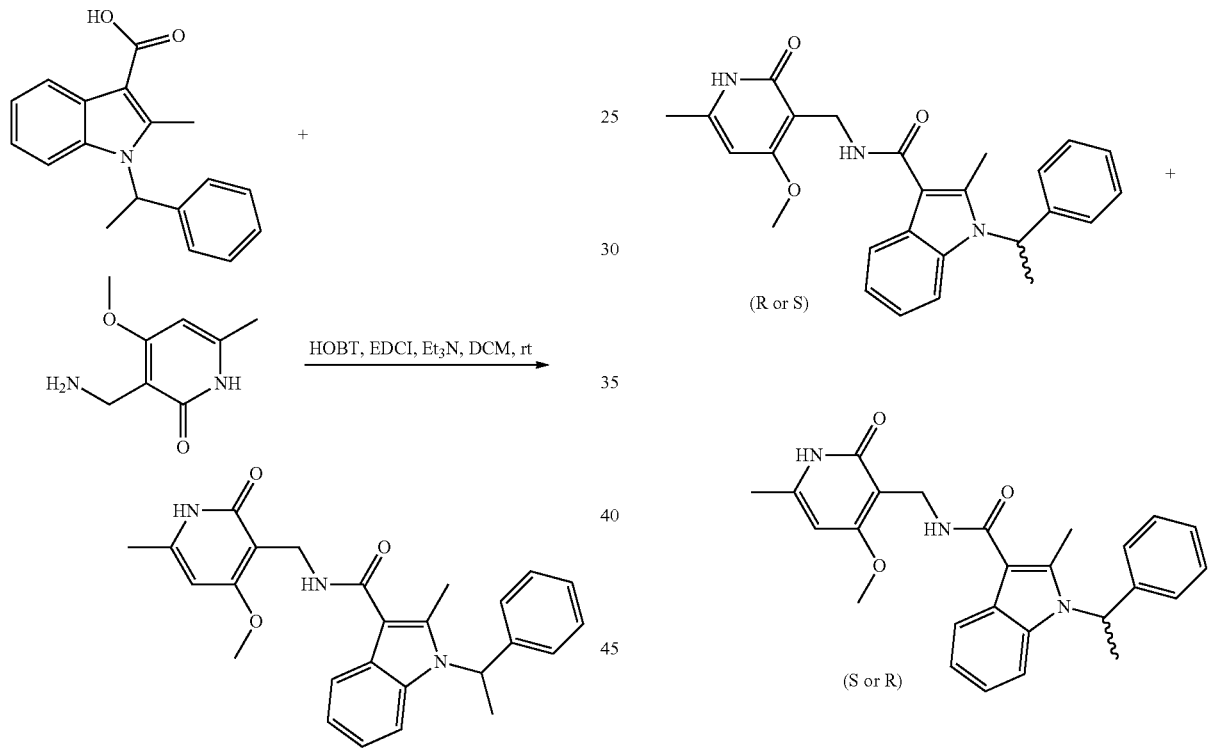

To a solution of 2-methyl-1-(1-phenylethyl)-1H-indole-3-carboxylic acid (66 mg, 0.24 mmol) in anhydrous dichloromethane (5 mL) was added N-hydroxybenzotriazole (38 mg, 0.29 mmol), 1-ethyl-3-[3-(dimethylamino)propyl]carbodiimide (55 mg, 0.29 mmol) and trimethylamine (36 mg, 0.36 mmol), and stirred at room temperature for 0.5 hour, 3-(aminomethyl)-4-methoxy-6-methylpyridin-2(1H)-one (40 mg, 0.24 mmol) was added and stirred at room temperature for 16 hours. To the reaction mixture was added water (10 mL), extracted with dichloromethane (10 mL) 2 times, combined and concentrated the organic layers, the residue was purified by column chromatography (silica gel, dichloromethane/methanol=20:1) to give N-((4-methoxy-6-methyl-2-oxo-1,2-dihydropyridin-3-yl)methyl)-2-methyl-1-(1-phenylethyl)-1H-indole-3-carboxamide as an off-white solid (0.08 g, 52%). LRMS (M+H$^+$) m/z: calcd 429.21. found 429.

N-((6-hydroxy-2-methoxy-4-methylpyridin-3-yl)methyl)-2-methyl-1-(1-phenylethyl)-1H-indole-3-carboxamide (80 mg, 0.19 mmol) was separated by chiral HPLC (LA (AD50)-TEA20 min, then (R or S) N-((4-methoxy-6-methyl-2-oxo-1,2-dihydropyridin-3-yl)methyl)-2-methyl-1-(1-phenylethyl)-1H-indole-3-carboxamide (25 mg, 31%) and (S or R)N-((4-methoxy-6-methyl-2-oxo-1,2-dihydropyridin-3-yl)methyl)-2-methyl-1-(1-phenylethyl)-1H-indole-3-carboxamide (15 mg, 19%) were obtained. The retention times were 8.222 minute ("Peak 1"; Compound 114) and 13.531 ("Peak 2"; Compound 115) minute respectively in chiral prep-HPLC chromatography. LRMS (M+H$^+$) m/z: calcd 429.21. found 429. HPLC Purity (214 nm): 100%. $^1$H NMR (300 MHz, d$^6$-DMSO): δ 11.59 (s, 1H), 7.75-7.72 (m, 2H), 7.35-7.25 (m, 3H), 7.15 (d, J=7.5 Hz, 2H), 7.10-7.07 (m, 1H), 7.02-6.93 (m, 2H), 6.15 (s, 1H), 5.96 (q, J=6.9 Hz, 1H), 4.33 (d, J=5.1 Hz, 2H), 3.85 (s, 3H), 2.62 (s, 3H), 2.20 (s, 3H), 1.89 (d, J=7.5 Hz, 3H).

Example 11

Synthesis of compound N-((4,6-dimethyl-2-oxo-1,2-dihydropyridin-3-yl)methyl)-2,6-dimethyl-7-oxo-1-(1-phenylethyl-6,7-dihydro-1H-pyrrolo[2,3-c]pyridine-3-carboxamide (Compound 139)

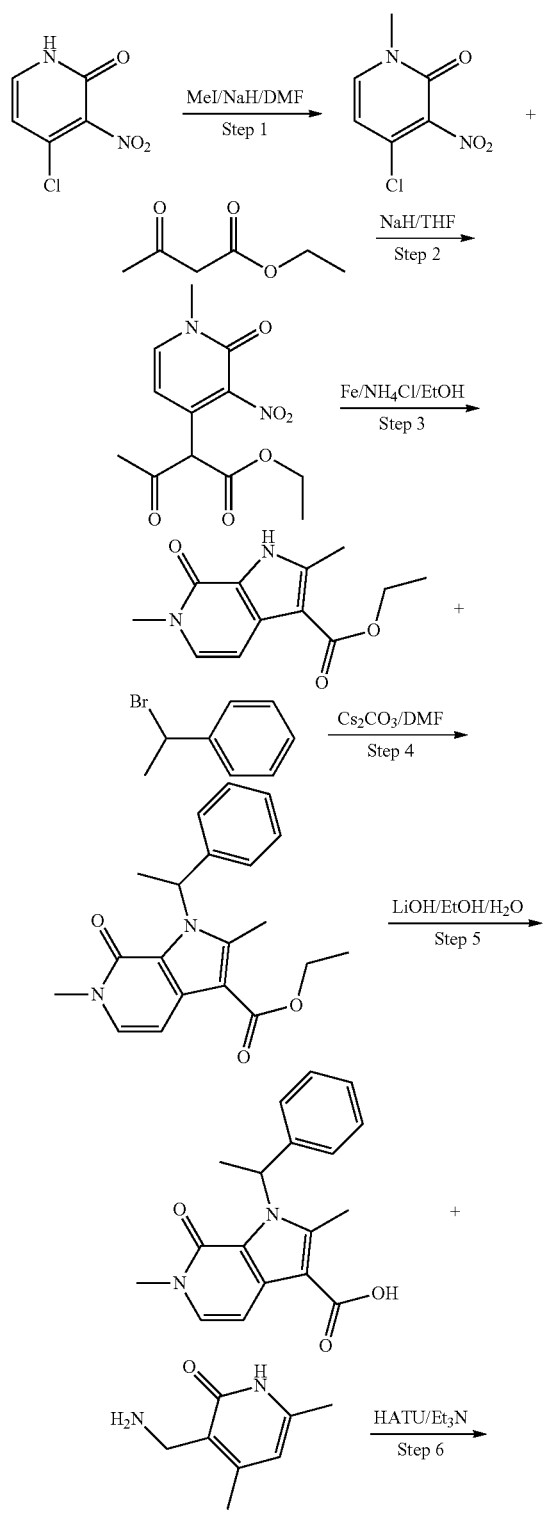

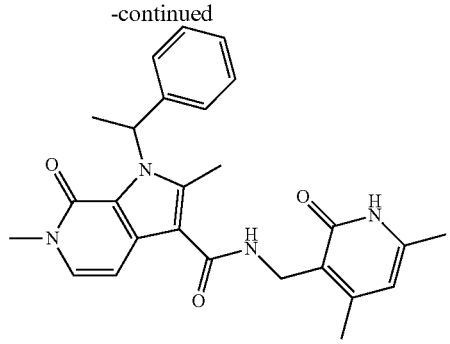

Synthesis of 4-chloro-1-methyl-3-nitropyridin-2(1H)-one

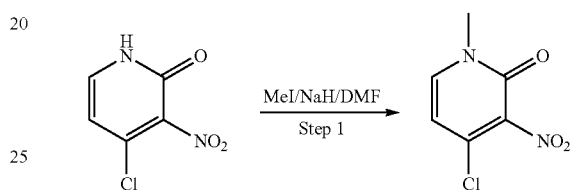

To a stirred solution of 4-chloro-3-nitropyridin-2(1H)-one (3.0 g, 17 mmol) in N,N-dimethylformamide (50 mL) was added sodium hydride (60% w/w, 1.0 g, 25.5 mmol) in batches at 0° C. The mixture was stirred at room temperature for 30 minutes. Then iodomethane (2.9 g, 20.4 mmol) was added dropwise to the above solution at room temperature. The resultant solution was stirred at room temperature for 12 hours. Once starting material was consumed, the reaction mixture was quenched with ice water (100 mL) at 0-10° C., and extracted with ethyl acetate (100 mL×3). The organic phase was washed with brine (100 mL×2), dried over anhydrous sodium sulfate, filtered and concentrated to give a residue. The residue was purified by column chromatography (silica gel, dichloromethane/methanol=10:1) to give 4-chloro-1-methyl-3-nitropyridin-2(1H)-one (3 g, 94%) as a yellow solid. LRMS (M+H$^+$) m/z: calcd 188.0. found 188.

Synthesis of ethyl 2-(1-methyl-3-nitro-2-oxo-1,2-dihydropyridin-4-yl)-3-oxobutanoate

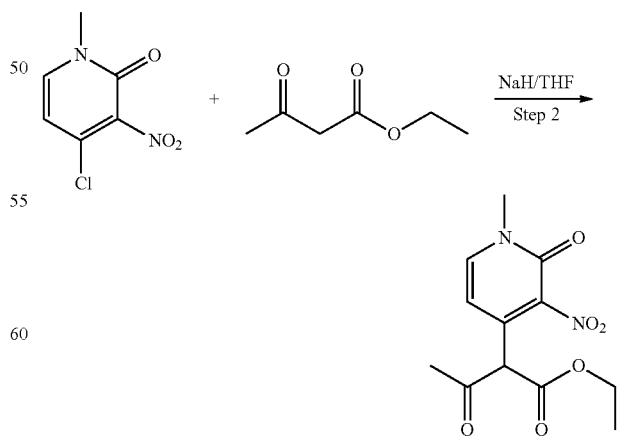

To a stirred solution of ethyl 3-oxobutanoate (2.5 g, 19 mmol) in tetrahydrofuran (50 mL) was added sodium hydride (60% w/w, 0.96 g, 23.9 mmol) in batches at 0° C. The mixture was stirred at room temperature for 30 minutes. Then the solution of 4-chloro-1-methyl-3-nitropyridin-2(1H)-one (3.0 g, 16 mmol) in tetrahydrofuran (50 mL) was added in one portion. The resultant solution was stirred and heated to 50° C. for 12 hours. Once the starting material had been consumed, the reaction solution was quenched with water (100 mL) at 0° C., and extracted with ethyl acetate (100 mL×3). The combined organic layers were washed with brine (100 mL×2), dried over anhydrous sodium sulfate, filtered and concentrated to give a residue. The residue was purified by column chromatography (silica gel, dichloromethane/methanol=10:1) to give ethyl 2-(1-methyl-3-nitro-2-oxo-1,2-dihydropyridin-4-yl)-3-oxobutanoate (2.5 g, 56%) as a yellow solid. LRMS (M+H⁺) m/z: calcd 282.09. found 282.

Synthesis of ethyl 2,6-dimethyl-7-oxo-6,7-dihydro-1H-pyrrolo[2,3-c]pyridine-3-carboxylate

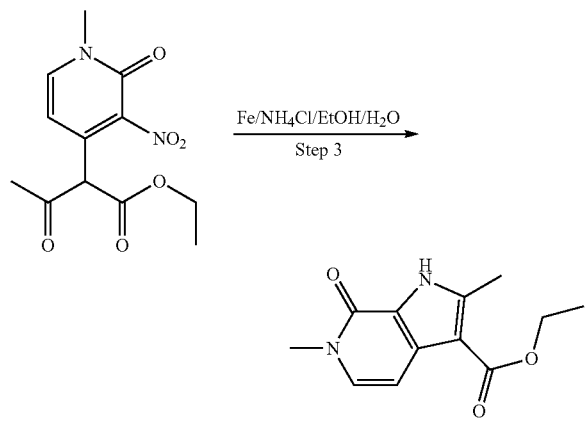

To a solution of ethyl 2-(1-methyl-3-nitro-2-oxo-1,2-dihydropyridin-4-yl)-3-oxobutanoate (2.5 g, 8.8 mmol) in ethanol (50 mL) was added ammonium chloride (0.5 g, 9 mmol) in water (5 mL) at room temperature. The mixture was stirred and heated to reflux. Then iron powder (0.5 g, 8.9 mmol) was added in one portion. The mixture was stirred at reflux for 2 hours. Once starting material was consumed, the resultant mixture was filtered when it was hot, and the filtrate was concentrated to give a residue. The residue was purified by column chromatography (silica gel, dichloromethane/methanol=10:1) to give ethyl 2,6-dimethyl-7-oxo-6,7-dihydro-1H-pyrrolo[2,3-c]pyridine-3-carboxylate (1.5 g, 75%) as a brown solid. LRMS (M+H⁺) m/z: calcd 234.1; found 234. ¹H NMR (400 MHz, d⁶-DMSO): δ 12.54 (s, 1H), 7.30 (d, J=5.1 Hz, 1H), 6.78 (d, J=5.1 Hz, 1H), 4.24 (q, J=5.1 Hz, 2H), 3.51 (s, 3H), 2.56 (s, 3H), 1.32 (t, J=5.1 Hz, 3H).

Synthesis of ethyl 2,6-dimethyl-7-oxo-1-(1-phenylethyl)-6,7-dihydro-1H-pyrrolo[2,3-c]pyridine-3-carboxylate

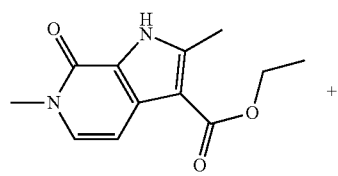 +

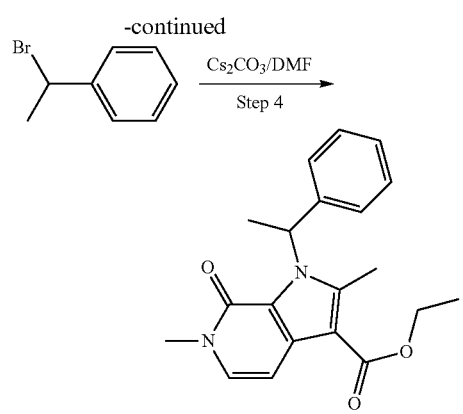

To a stirred solution of ethyl 2,6-dimethyl-7-oxo-6,7-dihydro-1H-pyrrolo[2,3-c]pyridine-3-carboxylate (1.5 g, 6.4 mmol) in N,N-dimethylformamide (50 mL) was added (1-bromoethyl)-benzene (1.5 g, 7.9 mmol) and cesium carbonate (3.14 g, 9.6 mmol). The resultant solution was stirred at 80° C. for 12 hours. Once starting material was consumed, the reaction mixture was quenched with water (50 mL), and extracted with ethyl acetate (100 mL×3). The combined organic layers were washed with brine (100 mL*2), dried over anhydrous sodium sulfate, filtered and concentrated to give a residue. The residue was purified by column chromatography (silica gel, petroleum ether/ethyl acetate=5:1) to give ethyl 2,6-dimethyl-7-oxo-1-(1-phenylethyl)-6,7-dihydro-1H-pyrrolo[2,3-c]pyridine-3-carboxylate (1.5 g, 69%) as a yellow solid. LRMS (M+H⁺) m/z: calcd 338.16. found 338.

Synthesis of 2,6-dimethyl-7-oxo-1-(1-phenylethyl)-6,7-dihydro-1H-pyrrolo[2,3-c]pyridine-3-carboxylic acid

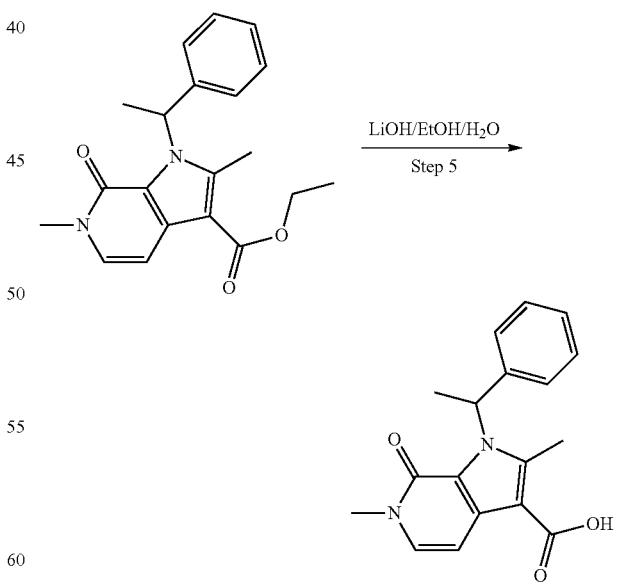

A mixture of ethyl 2,6-dimethyl-7-oxo-1-(1-phenylethyl)-6,7-dihydro-1H-pyrrolo[2,3-c]pyridine-3-carboxylate (500 mg, 1.5 mmol) and lithium hydroxide (50 mg, 2.1 mmol) in ethanol (20 mL) and water (5 mL) was stirred and heated at 80° C. for 12 hours. Once starting material was consumed, the mixture was concentrated and the residue was dissolved into water (50 mL). Then the solution was extracted with ethyl acetate (20 mL×2). The aqueous layer was collected, adjusted to pH 4, and extracted with ethyl acetate (20 mL×3). The combined organic layers were washed with brine (20 mL×2), dried over anhydrous sodium sulfate, filtered and concentrated to give 2,6-dimethyl-7-oxo-1-(1-phenylethyl)-6,7-dihydro-1H-pyrrolo[2,3-c]pyridine-3-carboxylic acid (200 mg, 44%) as a light yellow solid which was used directly in the next step without further purification. LRMS (M+H$^+$) m/z: calcd 310.13. found 310.

Synthesis of N-((4,6-dimethyl-2-oxo-1,2-dihydropyridin-3-yl)methyl)-2,6-dimethyl-7-oxo-1-(1-phenylethyl)-6,7-dihydro-1H-pyrrolo[2,3-c]pyridine-3-carboxamide (Compound 139)

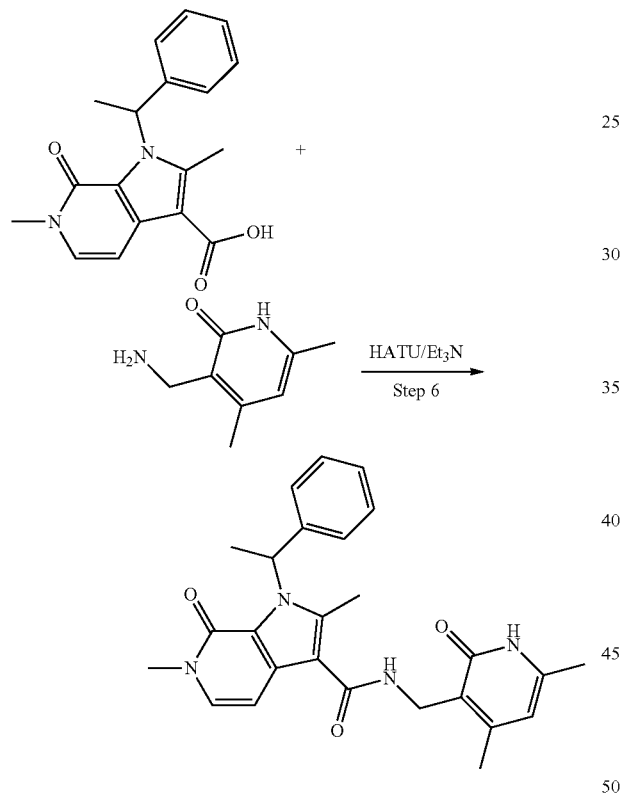

To a mixture of 2,6-dimethyl-7-oxo-1-(1-phenylethyl)-6,7-dihydro-1H-pyrrolo[2,3-c]pyridine-3-carboxylic acid (200 mg, 0.64 mmol) and 4-(aminomethyl)-3,6-dimethylpyridin-2(1H)-one (118 mg, 0.78 mmol) in N,N-dimethylformamide (20 mL) was added o-(7-azabenzotriazol-1-yl)-N,N,N',N'-tetramethyluronium hexafluorophosphate (365 mg, 0.96 mmol) and triethylamine (388 mg, 3.84 mmol) at room temperature. The resultant mixture was stirred at room temperature for 2 hours. Once starting material left was consumed, the reaction mixture was quenched with water (50 mL), and extracted with ethyl acetate (50 mL*3). The combined organic layers were washed with brine (100 mL*2), dried over anhydrous sodium sulfate, filtered and concentrated to give a residue. The residue was purified by column chromatography (silica gel, petroleum ether/ethyl acetate=1:2) to give N-((4,6-dimethyl-2-oxo-1,2-dihydropyridin-3-yl)methyl)-2.6-dimethyl-7-oxo-1-(1-phenylethyl)-6,7-dihydro-1H-pyrrolo[2,3-c]pyridine-3-carboxamide (150 mg, 53%) as a white solid. LRMS (M+H$^+$) m/z: calcd 444.22. found 444. HPLC purity (214 nm): 97%. $^1$H NMR (400 MHz, CD$_3$OD): δ 7.22-7.13 (m, 4H), 7.01 (d, J=7.2 Hz, 2H), 6.69 (d, J=7.2 Hz, 1H), 5.99 (s, 1H), 4.35 (s, 2H), 3.50-3.21 (m, 4H), 2.26 (s, 3H), 2.13 (s, 3H), 2.06 (s, 3H), 1.82 (d, J=7.2 Hz, 3H).

Example 12

Synthesis of compound (R)-N-((2-hydroxy-4,6-dimethylpyridin-3-yl)methyl)-6-methyl-2-(methylamino)-7-(1-phenylethyl)-7H-pyrrolo[2,3-d]pyrimidine-5-carboxamide (Compound 140)

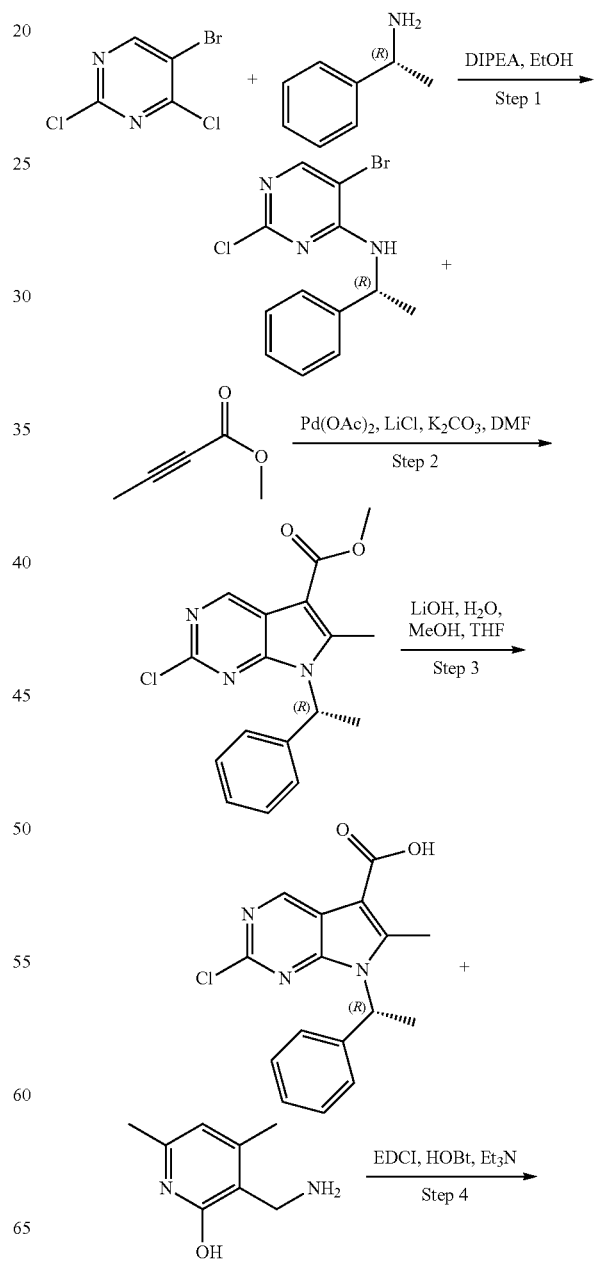

-continued

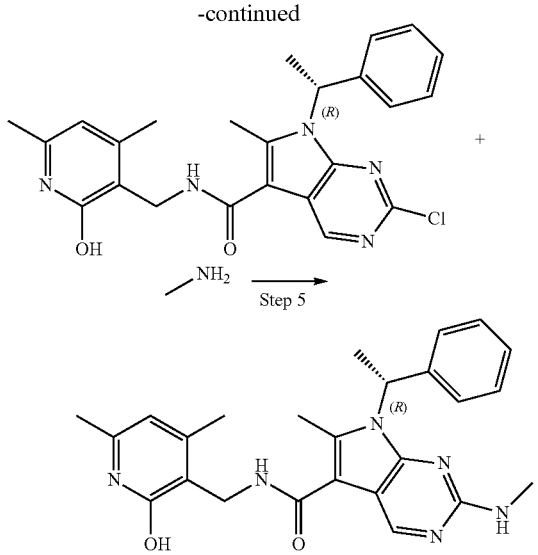

Step 5, NH2

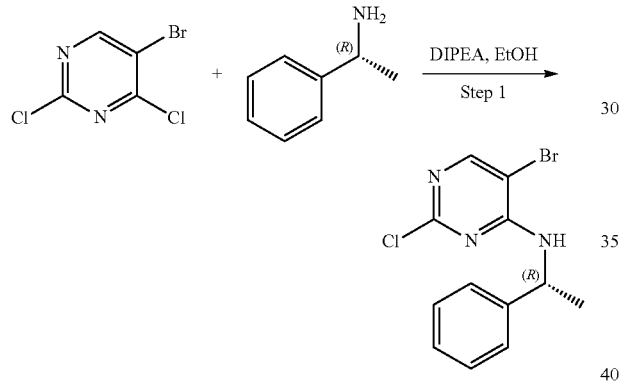

Synthesis of (R)-5-bromo-2-chloro-N-(1-phenylethyl)pyrimidin-4-amine

To a solution of 5-bromo-2,4-dichloropyrimidine (5 g, 22 mmol) and (R)-1-phenylethanamine (2.7 g, 22 mmol) in ethanol (50 mL) was added N,N-diisopropylethylamine (4.3 g, 33 mmol). The reaction solution was stirred at room temperature for 12 hours, the resultant mixture was concentrated in vacuo. The residue was purified by column chromatography (silica gel, petroleum ether/ethyl acetate=6:1) to give (R)-5-bromo-2-chloro-N-(1-phenylethyl)pyrimidin-4-amine as a white solid (5 g, 74%). LRMS (M+H$^+$) m/z: calcd 310.98. found 310. $^1$H NMR (300 MHz, CDCl$_3$): δ 8.10 (s, 1H), 7.41-7.25 (m, 5H), 5.73 (d, J=6.9 Hz, 1H), 5.39-5.34 (m, 1H), 1.61 (d, J=6.6 Hz, 3H).

Synthesis of (R)-methyl 2-chloro-6-methyl-7-(1-phenylethyl)-7H-pyrrolo[2,3-d]pyrimidine-5-carboxylate

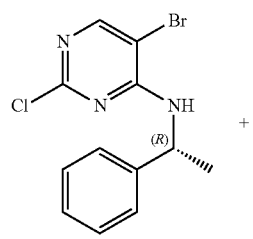

+

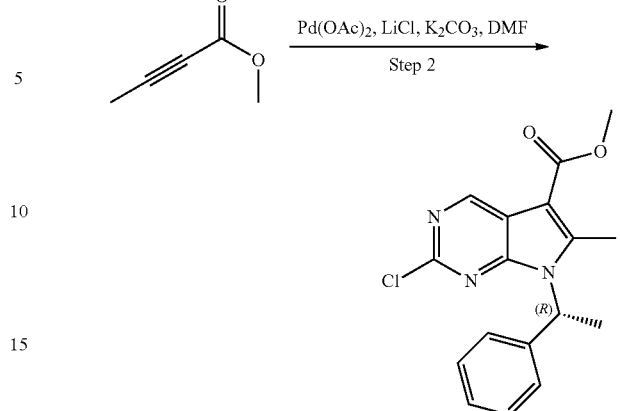

A solution of (R)-5-bromo-2-chloro-N-(1-phenylethyl)pyrimidin-4-amine (5 g, 16 mmol), methyl but-2-ynoate (3.1 g, 32 mmol), lithium chloride (690 mg, 16 mmol), potassium carbonate (5.5 g, 40 mmol) and palladium acetate (360 mg, 1.6 mmol) in N,N-dimethylformamide (50 mL) was degassed and back-filled with nitrogen for three times, then heated at 120° C. for 4 hours. The reaction mixture was filtered and the filtrate was concentrated in vacuo, extracted with ethyl acetate (50 mL), washed with water (50 mL), dried over anhydrous magnesium sulfate and purified by column chromatography (silica gel, petroleum ether/ethyl acetate=5:1) to give (R)-methyl 2-chloro-6-methyl-7-(1-phenylethyl)-7H-pyrrolo[2,3-d]pyrimidine-5-carboxylate as a yellow oil (800 mg, 15%). LRMS (M+H$^+$) m/z: calcd 329.09. found 329. $^1$H NMR (300 MHz, CDCl$_3$): δ 9.16 (s, 1H), 7.39-7.18 (m, 5H), 6.45-6.42 (m, 1H), 3.96 (s, 3H), 2.57 (s, 3H), 2.05 (d, J=7.2 Hz, 3H).

Synthesis of (R)-2-chloro-6-methyl-7-(1-phenylethyl)-7H-pyrrolo[2,3-d]pyrimidine-5-carboxylic acid

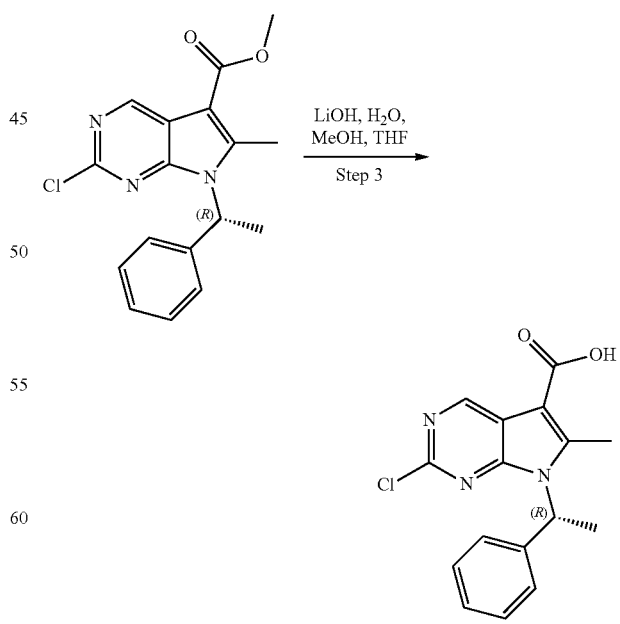

Lithium hydroxide anhydrate (882 mg, 21 mmol) in water (3 mL) was added to (R)-methyl 2-chloro-6-methyl-7-(1- phenylethyl)-7H-pyrrolo[2,3-d]pyrimidine-5-carboxylate (700 mg, 2.1 mmol) in tetrahydrofuran (5 mL) and methanol (10 mL) and the resultant mixture was stirred at room temperature for 12 hours. The mixture was evaporated, added with water (5 mL), acidified with aqueous hydrochloric acid (1M) to pH=2. The precipitate solid was filtered and dried to obtain (R)-2-chloro-6-methyl-7-(1-phenylethyl)-7H-pyrrolo[2,3-d]pyrimidine-5-carboxylic acid as a white solid (500 mg, 75%). LRMS (M+H$^+$) m/z: calcd 315.08. found 315.

Synthesis of (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide

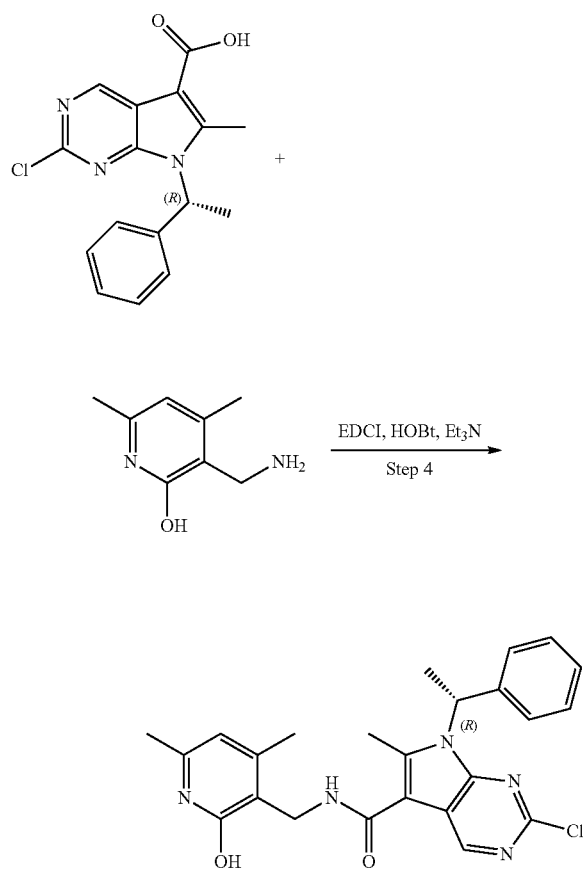

To a solution of (R)-2-chloro-6-methyl-7-(1-phenylethyl)-7H-pyrrolo[2,3-d]pyrimidine-5-carboxylic acid (100 mg, 0.32 mmol) in dichloromethane (10 mL) was added with 1-hydroxybenzotriazole (65 mg, 0.48 mmol), 1-Ethyl-3-(3-dimethylaminopropyl)ethyl-carbodiimide hydrochloride (92 mg, 0.48 mmol) and triethylamine (97 mg, 0.96 mmol). After stirred for 30 minutes, 3-(aminomethyl)-4,6-dimethylpyridin-2-ol (49 mg, 0.32 mmol) was added and the reaction mixture was stirred at room temperature for 12 hours. The solution was concentrated, diluted with water (20 mL), extracted with ethyl acetate (20 mL). The organic layers were separated, combined, dried over anhydrous sodium sulfate, filtered and concentrated to give a residue. The residue was purified by column chromatography (silica gel, dichloromethane/methanol=20:1) to afford (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide (100 mg, 70%). LRMS (M+H$^+$) m/z: calcd 449.16. found 449.

Synthesis of (R)-N-((2-hydroxy-4,6-dimethylpyridin-3-yl)methyl)-6-methyl-2-(methylamino)-7-(1-phenylethyl)-7H-pyrrolo[2,3-d]pyrimidine-5-carboxamide (Compound 140)

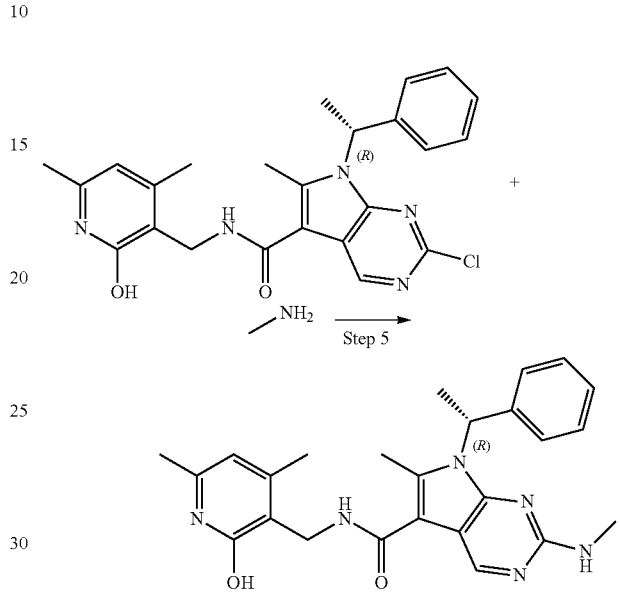

A solution of (R)-2-chloro-N-((2-hydroxy-4,6-dimethyl)-6-methyl-7-(1-phenyl ethyl)-7H-pyrrolo[2,3-d]pyrimidine-5-carboxamide (30 mg, 0.07 mmol) in methylamine (1 M in tetrahydrofuran, 3 mL) was stirred at 150° C. for 30 minutes under microwave (pressure: 17.2 bar, equipment power: 150 W). The mixture was concentrated in vacuo and purified by column chromatography (silica gel, dichloromethane/methanol=10:1) to afford (R)-N-((2-hydroxy-4,6-dimethylpyridin-3-yl)methyl)-6-methyl-2-(methylamino)-7-(1-phenylethyl)-7H-pyrrolo[2,3-d]pyrimidine-5-carboxamide (10 mg, 34%). LRMS (M+H$^+$) m/z: calcd 444.23; found 444. HPLC purity (214 nm): 92%. $^1$H NMR (300 MHz, CD$_3$OD): δ 8.55 (s, 1H), 7.30-7.23 (m, 5H), 6.15-6.10 (m, 2H), 4.47 (s, 2H), 2.90 (s, 3H), 2.40 (s, 3H), 2.38 (s, 3H), 2.24 (s, 3H), 2.03 (d, J=7.2 Hz, 3H).

Example 13

Synthesis of compound (R)-N-((2-hydroxy-4,6-dimethylpyridin-3-yl)methyl)-2-methoxy-6-methyl-7-(1-phenylethyl)-7H-pyrrolo[2,3-d]pyrimidine-5-carboxamide (Compound 141)

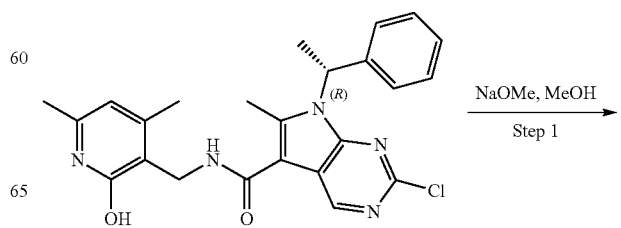

73
-continued

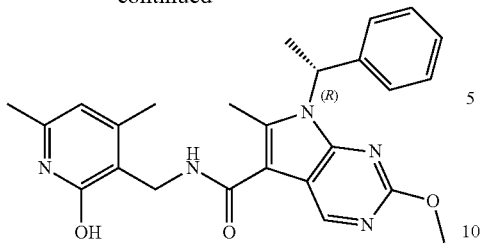

A solution of (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide (70 mg, 0.15 mmol) in MeOH (1 mL) solution of sodium methanolate (20 mg) was stirred at 100° C. for 60 minutes under microwave (pressure: 15.3 bar, equipment power: 150 W). The mixture was concentrated in vacuo and purified by column chromatography (silica gel, dichloromethane/methanol=10:1) to afford (R)-N-((2-hydroxy-4,6-dimethylpyridin-3-yl)methyl)-2-methoxy-6-methyl-7-(1-phenylethyl)-7H-pyrrolo[2,3-d]pyrimidine-5-carboxamide (37 mg, 51.9%). LRMS (M+H$^+$) m/z: calcd 445.21. found 445. HPLC purity (214 nm): 100%. 1H NMR (400 MHz, CD3OD) δ 8.75 (s, 1H), 7.29-7.22 (m, 5H), 6.11-6.07 (m, 2H), 4.46 (s, 2H), 3.90 (s, 3H), 2.48 (s, 3H), 2.36 (s, 3H), 2.21 (s, 3H), 2.05 (d, J=7.2 Hz, 3H).

Example 14

Synthesis of (R)-N-((2-hydroxy-4,6-dimethylpyridin-3-yl)methyl)-6-methyl-7-(1-phenylethyl)-2-(pyrrolidin-1-yl)-7H-pyrrolo[2,3-d]pyrimidine-5-carboxamide (Compound 142)

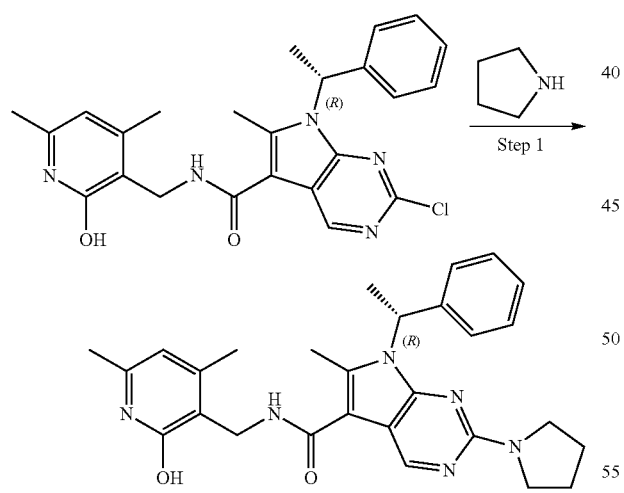

A solution of (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide (70 mg, 0.15 mmol) in pyrrolidine (1.0 mL) was stirred at 150° C. for 30 minutes under microwave (pressure: 12.2 bar, equipment power: 150 W). The mixture was concentrated in vacuo and purified by column chromatography (silica gel, dichloromethane/methanol=10:1) to afford (R)-N-((2-hydroxy-4,6-dimethylpyridin-3-yl)methyl)-6-methyl-7-(1-phenylethyl)-2-(pyrrolidin-1-yl)-7H-pyrrolo[2,3-d]pyrimidine-5-carboxamide (45 mg, 60.0%). LRMS (M+H$^+$) m/z: calcd 484.26. found 484. HPLC purity (214 nm): 97.8%. $^1$H NMR (400 MHz, CD$_3$OD) δ 8.56 (s, 1H), 7.27-7.20 (m, 5H), 6.06-6.02 (m, 2H), 4.45 (s, 2H), 3.52-3.45 (m, 4H), 2.40 (s, 3H), 2.35 (s, 3H), 2.21 (s, 3H), 2.01-1.94 (m, 7H).

Example 15

Synthesis of compound (R)-N-((2-hydroxy-4,6-dimethylpyridin-3-yl)methyl)-6-methyl-2-morpholino-7-(1-phenylethyl)-7H-pyrrolo[2,3-d]pyrimidine-5-carboxamide (Compound 143)

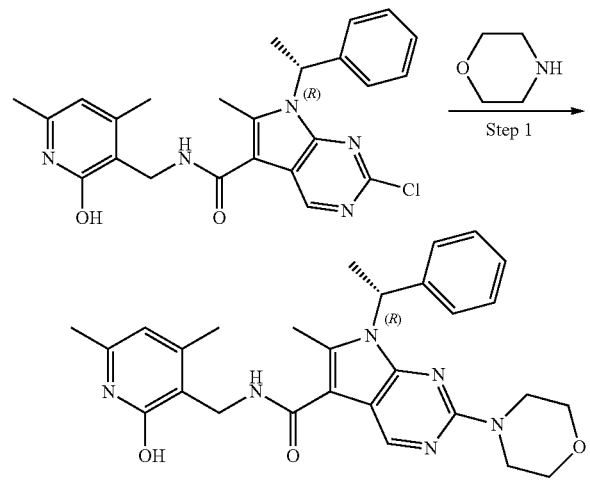

A solution of (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide (70 mg, 0.15 mmol) in morpholine (1.0 mL) was stirred at 150° C. for 30 minutes under microwave (pressure: 10.5 bar, equipment power: 150 W). The mixture was concentrated in vacuo and purified by column chromatography (silica gel, dichloromethane/methanol=10:1) to afford (R)-N-((2-hydroxy-4,6-dimethylpyridin-3-yl)methyl)-6-methyl-2-morpholino-7-(1-phenylethyl)-7H-pyrrolo[23-d]pyrimidine-5-carboxamide (55 mg, 70.5%). LRMS (M+H$^+$) m/z: calcd 500.25. found 500. HPLC purity (214 nm): 98.6%. $^1$H NMR (400 MHz, CD$_3$OD) δ 8.65 (s, 1H), 7.28 (dt, J=11.9, 7.7 Hz, 5H), 6.10 (dd, J=13.7, 6.5 Hz, 2H), 4.51 (s, 2H), 3.78-3.65 (m, 8H), 2.47 (s, 3H), 2.41 (s, 3H), 2.26 (s, 3H), 2.03 (d, J=7.2 Hz, 3H).

Example 16

Synthesis of compound (R)-2-amino-N-((2-hydroxy-4,6-dimethylpyridin-3-yl)methyl)-7-(1-phenylethyl)-7H-pyrrolo[2,3-d]pyrimidine-5-carboxamide (Compound 144)

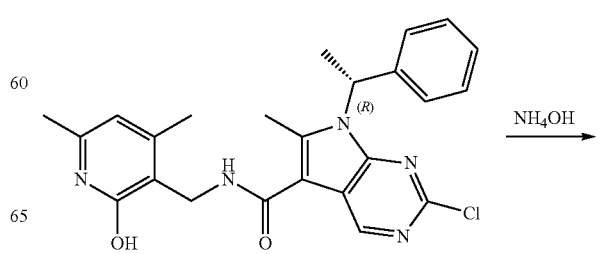

75
-continued

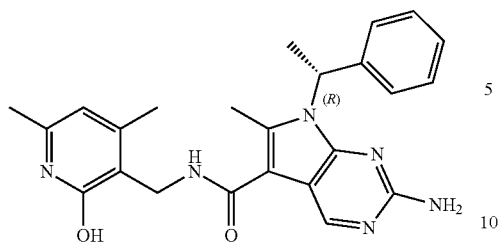

A solution of (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide (70 mg, 0.15 mmol) in ammonium hydroxide (5 mL) was stirred at 150° C. for 30 minutes under microwave (pressure: 17.2 bar, equipment power: 150 W). The mixture was concentrated in vacuo and purified by column chromatography (silica gel, dichloromethane/methanol=10:1) to afford (R)-2-amino-N-((2-hydroxy-4,6-dimethylpyridin-3-yl)methyl)-6-methyl-7-(1-phenylethyl)-7H-pyrrolo[2,3-d]pyrimidine-5-carboxamide (25 mg, 38%). LRMS (M+H$^+$) m/z: calcd 430.21. found 430. HPLC purity (214 nm): 93%. $^1$H NMR (300 MHz, CD$_3$OD): δ 8.57 (s, 1H), 7.34-7.19 (m, 5H), 6.19-6.17 (m, 1H), 6.10 (s, 1H), 4.47 (s, 2H), 2.33 (s, 3H), 2.30 (s, 3H), 2.23 (s, 3H), 1.99 (d, J=7.2 Hz, 3H).

Example 17

Synthesis of N-((4,6-dimethyl-2-oxo-1,2-dihydropyridin-3-yl)methyl)-2-methyl-1-(phenylsulfonyl)-1H-indole-3-carboxamide (Compound 145)

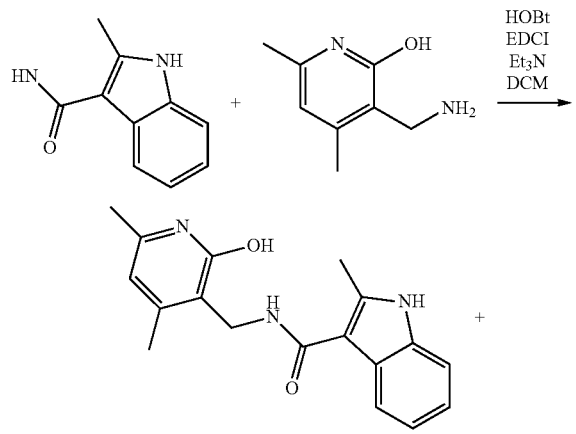

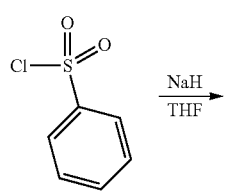

76
-continued

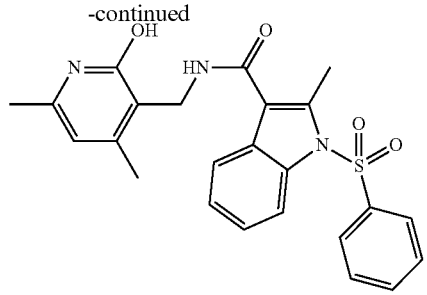

Synthesis of N-((2-hydroxy-4,6-dimethylpyridin-3-yl)methyl)-2-methyl-1H-indole-3-carboxamide

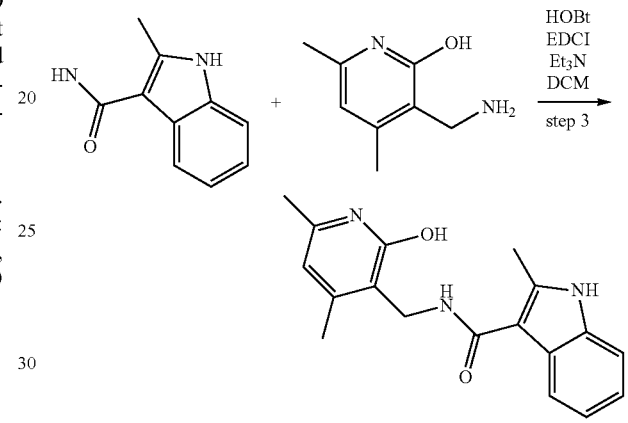

To a solution of 2-methyl-1H-indole-3-carboxylic acid (3.3 g, 18.85 mmol), 1-hydroxybenzotriozole (4.69 g, 37.7 mmol, 2 eq), 1-(3-dimethylaminopropyl)-3-ethylcarbodiimide hydrochloride (7.24 g, 37.7 mmol, 2 eq), triethylamine (20.0 mL) in dichloromethane (100 mL) was added 3-(aminomethyl)-4,6-dimethylpyridin-2-ol (5.77 g, 37.7 mmol, 2 eq). The reaction mixture was stirred at 20° C. for 13 hours. The mixture was washed with water (20 mL×2). The organic phase was dried over anhydrous sodium sulfate and filtered. The filtrate was concentrated to give the residue, which was purified by column chromatography (silica gel, dichloromethane/methanol=10:2) to give N-((2-hydroxy-4,6-dimethylpyridin-3-yl)methyl)-2-methyl-1H-indole-3-carboxamide as a white solid (3.00 g, 9.7 mmol, 51%). LRMS (M+H$^+$) m/z: calcd 309.36. found 310. HPLC Purity (214 nm): >95%. $^1$H NMR (300 MHz, d$^6$-DMSO): δ 11.61 (s, 1H), 11.43 (s, 1H) 7.74 (d, J=5.1 Hz, 1H), 7.58-7.54 (m, 1H), 7.31 (d, J=7.2 Hz, 1H), 7.04 (t, J=6 Hz, 3H), 5.89 (s, 1H), 4.32 (d, J=4.5 Hz, 2H), 2.57 (s, 3H), 2.26 (s, 3H), 2.12 (s, 3H).

Synthesis of N-((4,6-dimethyl-2-oxo-1,2-dihydropyridin-3-yl)methyl)-2-methyl-1-(phenylsulfonyl)-1H-indole-3-carboxamide (Compound 145)

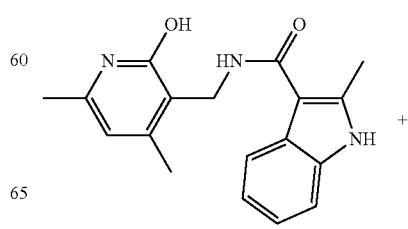

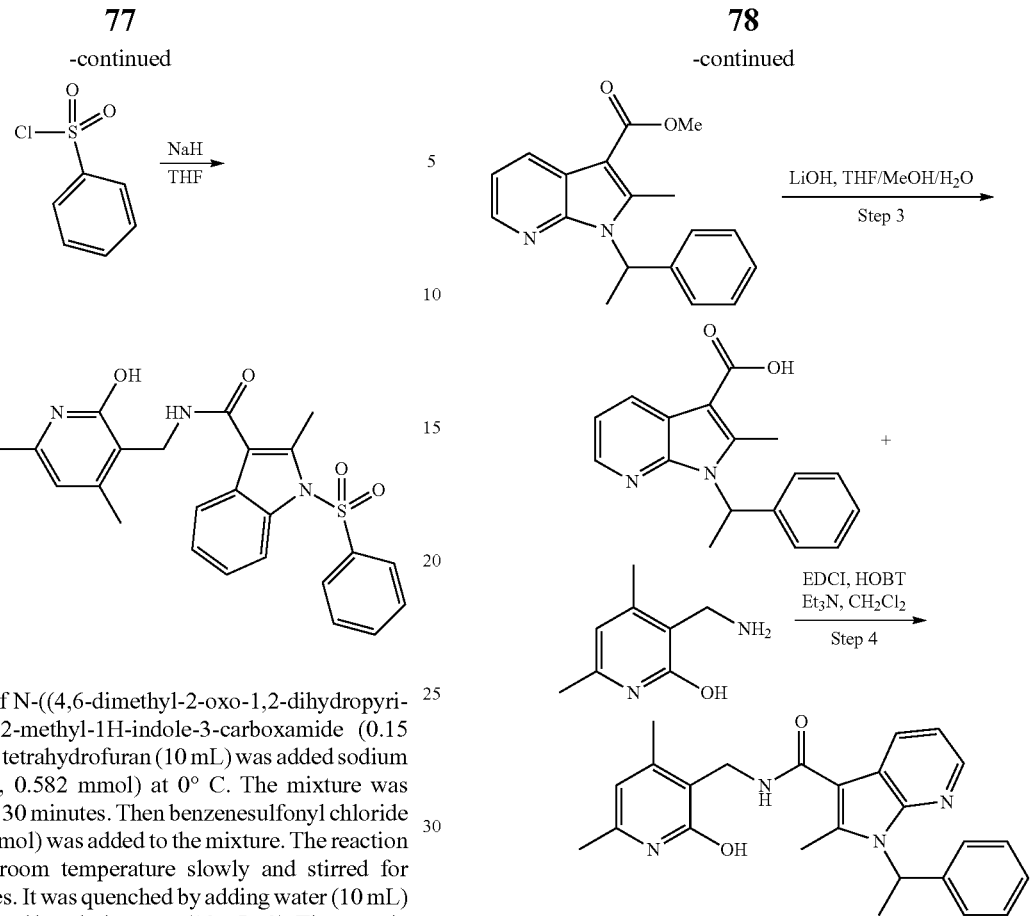

To a solution of N-((4,6-dimethyl-2-oxo-1,2-dihydropyridin-3-yl)methyl)-2-methyl-1H-indole-3-carboxamide (0.15 g, 0.485 mmol) in tetrahydrofuran (10 mL) was added sodium hydride (0.023 g, 0.582 mmol) at 0° C. The mixture was stirred at 0° C. for 30 minutes. Then benzenesulfonyl chloride (0.086 g, 0.485 mmol) was added to the mixture. The reaction was warmed to room temperature slowly and stirred for another 30 minutes. It was quenched by adding water (10 mL) slowly, and extracted by ethyl acetate (10 mL×3). The organic layer was dried and purified by Prep-HPLC to afford N-((4,6-dimethyl-2-oxo-1,2-dihydropyridin-3-yl)methyl)-2-methyl-1-(phenylsulfonyl)-1H-indole-3-carboxamide (9 mg 4.1% yield). LRMS (M+H+) m/z: calcd 449.14. found 450. HPLC Purity (215 nm): 97%. $^1$H NMR (400 MHz, CDCl$_3$): δ 8.25 (d, J=6.8 Hz, 1H), 7.81 (dd, J=8.4 Hz, J=0.8 Hz, 2H), 7.62-7.7.54 (m, 2H), 7.46-7.40 (m, 2H), 7.35-7.28 (m, 2H), 6.80 (t, J=6 Hz, 1H), 6.51 (s, 1H), 4.58 (d, J=4.6 Hz, 2H), 2.80 (s, 3H), 2.64 (s, 3H), 2.45 (s, 3H).

Example 18

Synthesis of compound N-((2-hydroxy-4,6-dimethylpyridin-3-yl)methyl)-2-methyl-1-(1-phenylethyl)-1H-pyrrolo[2,3-b]pyridine-3-carboxamide (Compound 146)

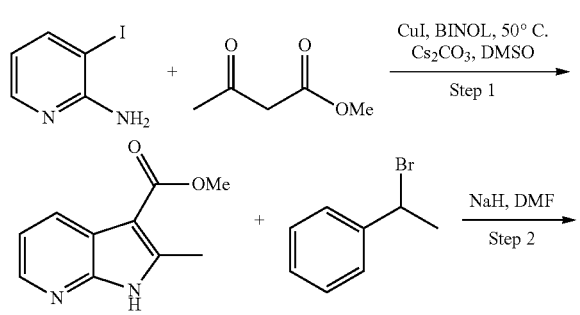

Synthesis of methyl 2-methyl-1H-pyrrolo[2,3-b]pyridine-3-carboxylate

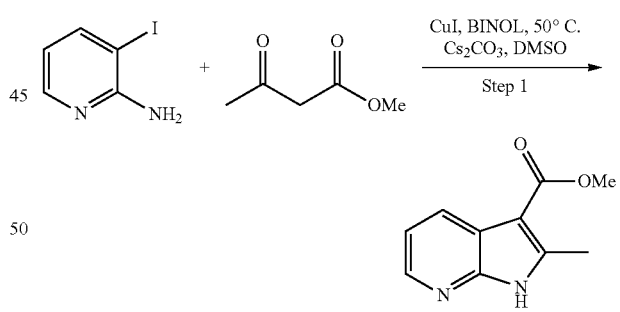

To a solution of 3-iodopyridin-2-amine (5.5 g, 25 mmol) in dimethylsulfoxide (40 mL) were added methyl acetoacetate (3.48 g, 30 mmol), copper iodide (476 mg, 2.5 mmol), 1,1'-binaphthyl-2,2'-diol (1.43 g, 5.0 mmol) and cesium carbonate (8.15 g, 25 mmol). The resultant mixture was stirred at 50° C. for 4 hours. To the reaction mixture was added ethyl acetate (400 mL). The organic phase was washed with brine (80 mL×3), dried over anhydrous magnesium sulfate, filtered and concentrated in vacuo to give crude product which was purified by column chromatography (petroleum ether/ethyl acetate=4:1) to afford methyl 2-methyl-1H-pyrrolo[2,3-b]pyridine-3-carboxylate (1.02 g, 21.4%) as a white solid. $^1$H NMR (300 MHz, CD3OD): δ 8.46-8.43 (m, 1H), 7.61-6.69 (m, 2H), 3.89 (s, 3H), 2.73 (s, 3H).

Synthesis of methyl 2-methyl-1-(1-phenylethyl)-1H-pyrrolo[2-b]pyridine-3-carboxylate

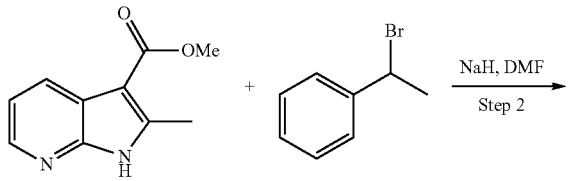

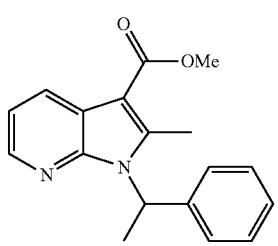

To a cooled (0° C.) solution of methyl 2-methyl-1H-pyrrolo[2,3-b]pyridine-3-carboxylate (1.02 g, 5.36 mmol) in N,N-dimethylformamide (20 mL) was added sodium hydride (60% w/w, 236 mg, 5.90 mmol). The resultant mixture was stirred for 15 minutes. Then (1-bromoethyl)benzene (2.00 g, 10.8 mmol) was added and the reaction was allowed to warm to room temperature. The reaction was maintained at ambient temperature for 12 hours. The reaction mixture was poured into saturated ammonium chloride solution (100 mL) with stirring. The mixture was extracted with ethyl acetate (200 mL×2) and the combined organic phase was washed with brine, dried over magnesium sulfate, filtered, and concentrated to give crude product which was purified by column chromatography (petroleum ether/ethyl acetate=20:1) to afford methyl 2-methyl-1-(1-phenylethyl)-1H-pyrrolo[2,3-b]pyridine-3-carboxylate (500 mg, 31.7%) as a viscous oil. $^1$H NMR (300 MHz, CD$_3$OD): δ 8.38-8.35 (m, 1H), 8.25-8.23 (m, 1H), 7.30-7.14 (m, 6H), 6.55-6.48 (m, 1H), 3.88 (s, 3H), 2.54 (s, 3H), 2.02 (d, J=7.2 Hz, 3H).

Synthesis of 2-methyl-1-(1-phenylethyl)-1H-pyrrolo[2,3-b]pyridine-3-carboxylic acid

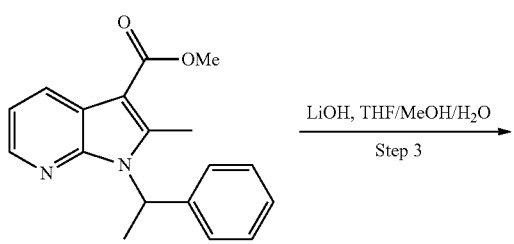

To a solution of methyl 2-methyl-1-(1-phenylethyl)-1H-pyrrolo[2,3-b]pyridine-3-carboxylate (500 mg, 1.70 mmol) in tetrahydrofuran (10 mL), methanol (20 mL) and water (4 mL) was added lithium hydroxide (163 mg, 6.80 mmol). The resultant reaction mixture was stirred at 60° C. for 48 hours. The mixture was concentrated in vacuo. Then the residue was diluted with water (40 mL) and slowly acidified with 1N hydrogen chloride to pH=4-5. The mixture was extracted with ethyl acetate (100 mL×3). The combined organic layers were washed with brine, dried over magnesium sulfate, filtered and concentrated to give 2-methyl-1-(1-phenylethyl)-1H-pyrrolo[2,3-b]pyridine-3-carboxylic acid as a white solid (400 mg, 84.0%).

Synthesis of N-((2-hydroxy-4,6-dimethylpyridin-3-yl)methyl)-2-methyl-1-(1-phenylethyl)-1H-pyrrolo[2,3-b]pyridine-3-carboxamide (Compound 146)

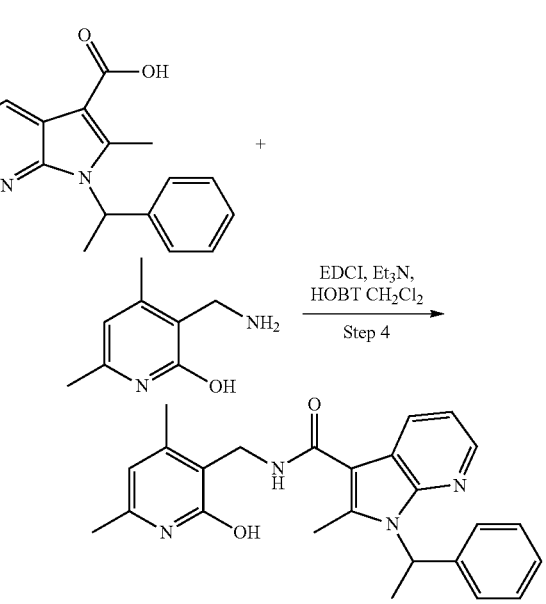

To a solution of 2-methyl-1-(1-phenylethyl)-1H-pyrrolo[2,3-b]pyridine-3-carboxylic acid (400 mg, 1.43 mmol) in dichloromethane (30 mL) were added 1-hydroxybenzotriazole (291 mg, 2.15 mmol), 1-(3-dimethylaminopropyl)-3-ethylcarbodiimide hydrochloride (412 mg, 2.15 mmol) and triethylamine (434 mg, 4.30 mmol). The resultant mixture was stirred at room temperature for 30 minutes. Then 3-(aminomethyl)-4,6-dimethylpyridin-2-ol (262 mg, 1.72 mmol) was added and the resultant mixture was stirred at room temperature for 16 hours. Water (50 mL) was added to the mixture. The mixture was extracted with dichloromethane (100 mL×2). The organic layer was concentrated in vacuo to provide crude product which was purified by column chromatography (silica gel, dichloromethane/methanol=20:1) to afford N-((2-hydroxy-4,6-dimethylpyridin-3-yl)methyl)-2-methyl-1-(1-phenylethyl)-1H-pyrrolo-[2,3-b]pyridine-3-carboxamide (400 mg, 67.6%) as a white solid. LRMS (M+H$^+$) m/z: calcd 414.21. found 414. HPLC purity (214 nm): 94%. $^1$H NMR (300 MHz, CD$_3$OD): δ 8.22-8.13 (m, 2H), 7.28-7.15 (m, 6H), 6.47-6.45 (m, 1H), 6.09 (s, 1H), 4.50 (s, 2H), 2.42 (s, 3H), 2.39 (s, 3H), 2.23 (s, 3H), 2.02 (d, J=7.2 Hz, 3H).

Example 19

Synthesis of compound 1-benzyl-N-((2-hydroxy-4,6-dimethylpyridin-3-yl)methyl)-2-methyl-1H-indole-3-carboxamide (Compound 119)

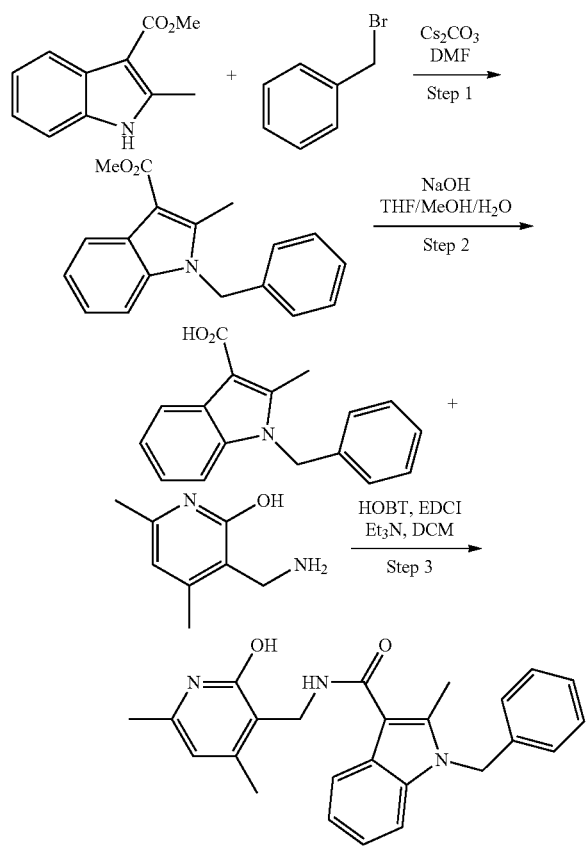

Synthesis of methyl 2-methyl-1H-indole-3-carboxylate

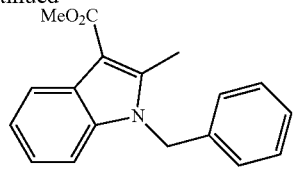

To a solution of methyl 2-methyl-1H-indole-3-carboxylate (378 mg, 2 mmol) in N,N-dimethylformamide (10 mL) was added (bromomethyl)benzene (340 mg, 2 mmol) and cesium carbonate (652 mg, 2 mmol), then stirred at 60° C. for 12 hours. The reaction mixture was concentrated in vacuo. The residue was purified by column chromatography (silica gel, petroleum ether/ethyl acetate=1:1) to give methyl 2-methyl-1H-indole-3-carboxylate (446 mg, 80%). LRMS (M+H$^+$) m/z: calcd 279.13. found 279.

Synthesis of 1-benzyl-2-methyl-1H-indole-3-carboxylic acid

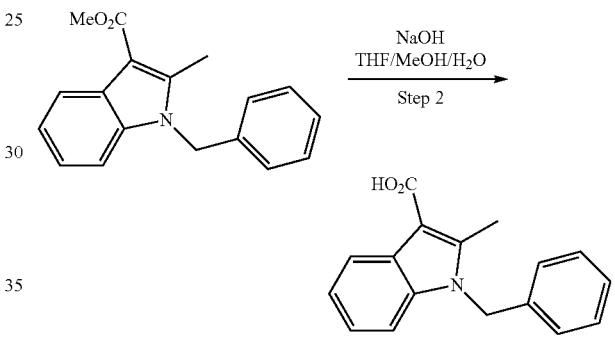

To a solution of methyl 1-benzyl-2-methyl-1H-indole-3-carboxylate (446 mg, 1.6 mmol) in tetrahydrofuran (20 mL) and methanol (7 mL) was added sodium hydroxide (320 mg, 8 mmol) in water (7 mL), then stirred at 60° C. for 12 hours. The reaction mixture was concentrated in vacuo and acidified to PH=4 with 6 N hydrochloric acid, collected and dried to give 1-benzyl-2-methyl-1H-indole-3-carboxylic acid as a white solid (212 mg, 50%). LRMS (M+H$^+$) m/z: calcd 265.11. found 265.

Synthesis of 1-benzyl-N-((2-hydroxy-4,6-dimethylpyridin-3-yl)methyl)-2-methyl-1H-indole-3-carboxamide (Compound 119)

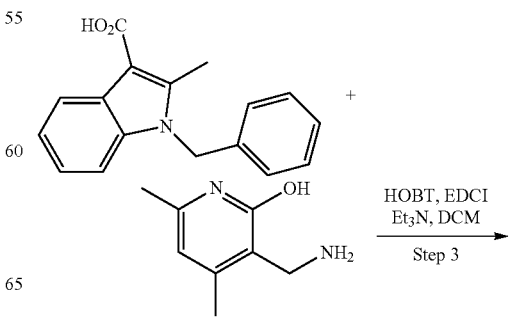

-continued

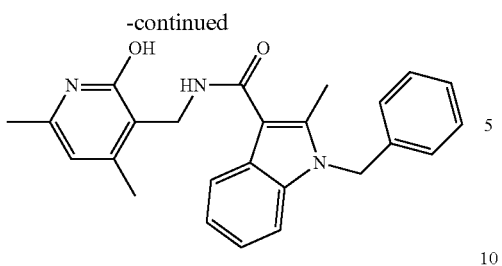

To a solution of 1-benzyl-2-methyl-1H-indole-3-carboxylic acid (212 mg, 0.8 mmol) in dichloromethane (20 mL) was added 1H-benzo[d][1,2,3]triazol-1-ol (135 mg, 1 mmol), 1-(3-Dimethylaminopropyl)-3-ethylcarbodiimide hydrochloride (190 mg, 1 mmol) and triethylamine (252 mg, 2.5 mmol), and stirred at room temperature for 0.5 hour, 3-(aminomethyl)-4,6-dimethylpyridin-2-ol (152 mg, 1 mmol) was added and stirred for 4 hours. To the reaction mixture was added water (20 mL), which was extracted with dichloromethane (2×20 mL), combined and the organic layers were concentrated, the residue was purified by column chromatography (dichloromethane/methanol=20:1) to afford 1-benzyl-N-((2-hydroxy-4,6-dimethylpyridin-3-yl)methyl)-2-methyl-1H-indole-3-carboxamide (200 mg, 63%). LRMS (M+H$^+$) m/z: calcd 399.19. found 399. HPLC purity (214 nm): 100%. $^1$H NMR (300 MHz, d$^6$-DMSO): δ 11.61 (s, 1H), 7.80-7.69 (m, 2H), 7.46-7.42 (m, 1H), 7.30-7.22 (m, 3H), 7.11-7.07 (m, 2H), 6.98 (d, J=7.5 Hz, 2H), 5.89 (s, 1H), 5.46 (s, 2H), 4.33 (d, J=4.5 Hz, 2H), 2.57 (s, 3H), 2.26 (s, 3H), 2.11 (s, 3H).

Example 20

Synthesis of compound N-((2-hydroxy-4,6-dimethylpyridin-3-yl)methyl)-2-methyl-1-(1-phenylethyl)-1H-pyrrolo[3,2-b]pyridine-3-carboxamide (Compound 126)

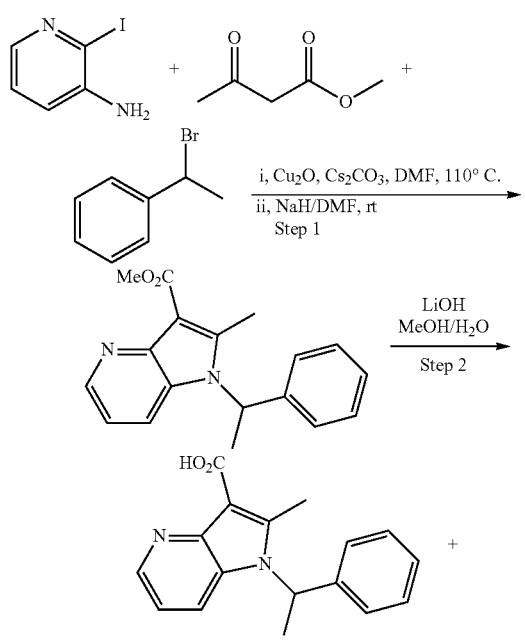

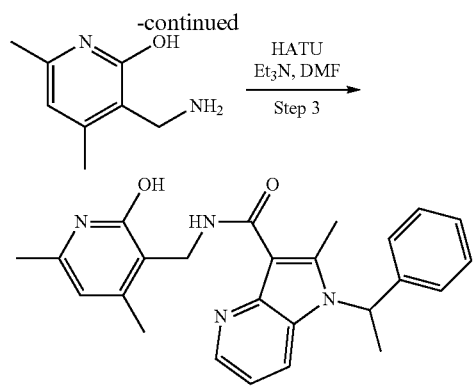

Synthesis of methyl 2-methyl-1-(1-phenylethyl)-1H-pyrrolo[3,2-b]pyridine-3-carboxylate

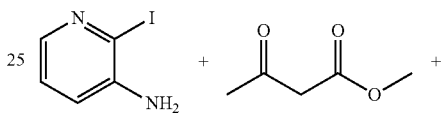

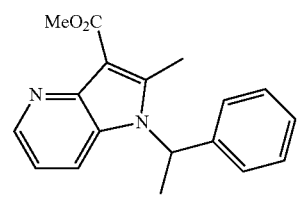

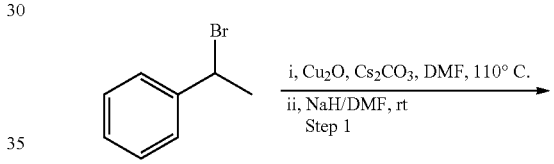

To a solution of 2-iodopyridin-3-amine (500 mg, 2.27 mmol), cuprous oxide (32 mg, 0.23 mmol), cesium carbonate (740 mg, 2.27 mmol) in N,N-dimethylformamide (100 mL) was added methyl methacrylate (290 mg, 2.5 mmol). The reaction solution was stirred at 110° C. for 12 hours. Then the reaction mixture was cooled with an ice bath and sodium hydride (60% in oil, 91 mg, 2.27 mmol) was added under. The resulting mixture was stirred at room temperature for half an hour. Then (1-bromoethyl)benzene (418 mg, 2.27 mmol) was added. Then the mixture was stirred at room temperature for 1 hour. After the reaction was completed, it was quenched with water (100 mL), and extracted with ethyl acetate (50 mL×3). The combined organic phase were washed with water (20 mL×3) and brine (20 mL), dried over anhydrous sodium sulfate, concentrated and purified by column chromatography (silica gel, petroleum ether/ethyl acetate=6:1) to give methyl 2-methyl-1-(1-phenylethyl)-1H-pyrrolo[3,2-b]pyridine-3-carboxylate (80 mg, 12%). LRMS (M+H$^+$) m/z: calcd 295.14. found 295.

Synthesis of 2-methyl-1-(1-phenylethyl)-1H-pyrrolo[3,2-b]pyridine-3-carboxylic acid

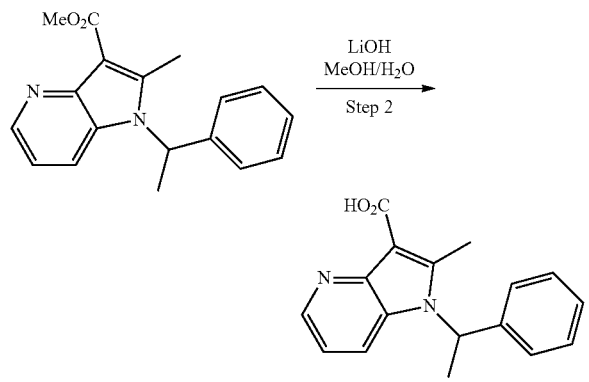

To a solution of methyl 2-methyl-1-(1-phenylethyl)-1H-pyrrolo[3,2-b]pyridine-3-carboxylate (80 mg, 0.27 mmol) in methanol (3 mL) and water (1 mL) was added lithium hydroxide (57 mg, 1.36 mmol). The reaction mixture was stirred with refluxing for 15 hours. The mixture was adjusted pH 3 with 1N aqueous hydrochloric acid. The aqueous phase was extracted with dichloromethane (50 mL×3). The organic layers were washed with brine, dried over anhydrous sodium sulfate, filtered and concentrated to give a residue, which was purified by column chromatography (silica gel, dichloromethane/methanol=20:1) to give 2-methyl-1-(1-phenylethyl)-1H-pyrrolo-[3,2-b]pyridine-3-carboxylic acid (20 mg, 26%). LRMS (M–H$^+$) m/z: calcd 279.12. found 279.

Synthesis of N-((2-hydroxy-4,6-dimethylpyridin-3-yl)methyl)-2-methyl-1-(1-phenylethyl)-1H-pyrrolo[3,2-b]pyridine-3-carboxamide (Compound 126)

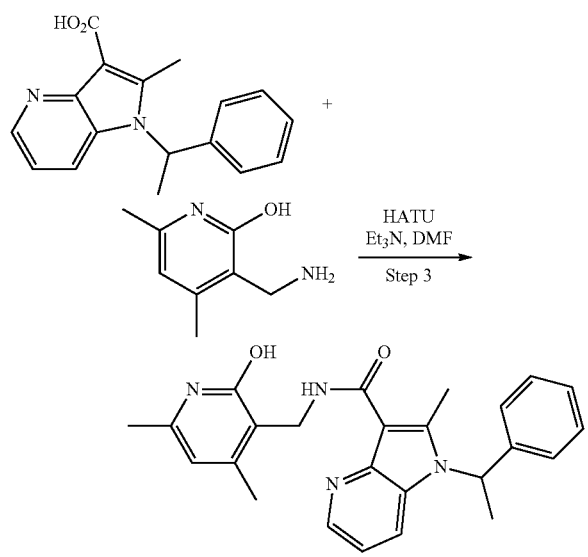

The mixture of 2-methyl-1-(1-phenylethyl)-1H-pyrrolo[3,2-b]pyridine-3-carboxylic acid (20 mg, 0.11 mmol), 2-(1H-7-Azabenzotriazol-1-yl)-1,1,3,3-tetramethyl uronium hexafluorophosphate Methanaminium (50 mg, 0.13 mmol), 3-(aminomethyl)-4,6-dimethylpyridin-2-ol (19 mg, 0.12 mmol) and triethylamine (23 mg, 0.22 mmol) in N,N-dimethylformamide (5 mL) was stirred for 12 hours. After the reaction was completed, the reaction was diluted with ethyl acetate (100 mL), and washed with water (20 mL×3) and brine (20 mL), dried over anhydrous sodium sulfate and concentrated to give the residue, which was purified by column chromatography (silica gel, dichloromethane/methanol=30:1) to give N-((2-hydroxy-4,6-dimethylpyridin-3-yl)methyl)-2-methyl-1-(1-phenylethyl)-1H-pyrrolo[3,2-b]pyridine-3-carboxamide (15 mg, 33%). LRMS (M+H$^+$) m/z: calcd 415.20. found 415. HPLC Purity (214 nm): 99%. $^1$H NMR (300 MHz, d$^6$-DMSO) δ 11.46 (s, 1H), 9.49 (t, $J_1$=4.2 Hz, $J_2$=8.1 Hz, 1H), 8.28 (d, J=3.6 Hz, 1H), 7.50 (d, J=6.3 Hz, 1H), 7.36-7.27 (m, 3H), 7.16 (d, J=5.7 Hz, 1H), 7.03-7.00 (m, 1H), 6.03 (m, 1H), 5.85 (s, 1H), 4.37 (s, 2H), 2.89 (s, 3H), 2.50 (s, 3H), 2.10 (s, 3H), 1.89 (d, J=5.4 Hz, 3H).

Example 21

Synthesis of (R or S)-1-sec-butyl-N-((2-hydroxy-46-dimethylpyridin-3-yl)methyl)-2-methyl-1H-indole-3-carboxamide (Compound 147) and (S or R)-1-sec-butyl-N-((2-hydroxy-4,6-dimethylpyridin-3-yl)methyl)-2-methyl-1H-indole-3-carboxamide (Compound 148)

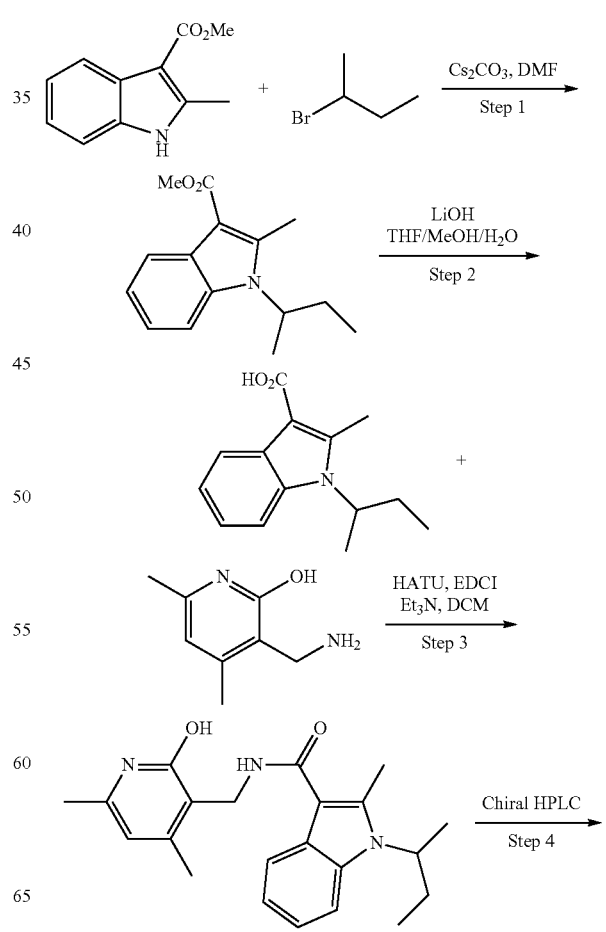

-continued

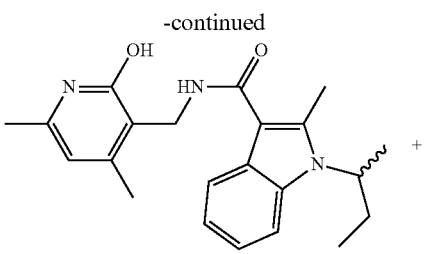

+

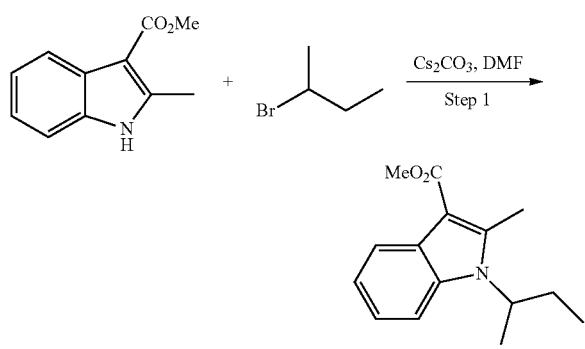

Synthesis of methyl 1-sec-butyl-2-methyl-1H-indole-3-carboxylate

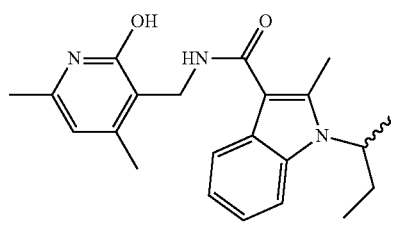

To a solution of methyl 2-methyl-1H-indole-3-carboxylate (0.5 g, 2.6 mmol) in N,N-dimethylformamide (20 mL) was added cesium carbonate (1.7 g, 5.2 mmol) and 2-bromobutane (0.71 g, 5.2 mmol), the mixture was stirred at 100° C. under microwave for 1 hour, the mixture was concentrated and purified by column chromatography (silica gel, ethyl acetate/petroleum ether=1:20) to give methyl 1-sec-butyl-2-methyl-1H-indole-carboxylate (141 mg, 22%).

Synthesis of 1-sec-butyl-2-methyl-1H-indole-3-carboxylic acid

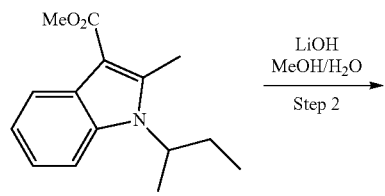

-continued

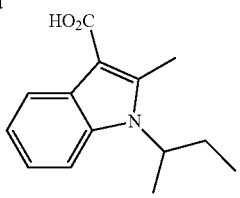

To a mixed solution of methanol (10 mL) and water (2 mL), methyl 1-sec-butyl-2-methyl-1H-indole-3-carboxylate (141 mg, 0.58 mmol) and lithium hydroxide (100 mg, 2.4 mmol) were added. The mixture was stirred at room temperature for 12 hours. Then the reaction mixture was acidified by hydrochloric (1 M) to adjust pH=6 and extracted with dichloromethane (10 mL×3). The organic layers were combined and concentrated to give 1-sec-butyl-2-methyl-1H-indole-3-carboxylic acid (97 mg, 72%).

Synthesis of 1-sec-butyl-N-((2-hydroxy-4,6-dimethylpyridin-3-yl)methyl)-2-methyl-1H-indole-3-carboxamide (Compound 123)

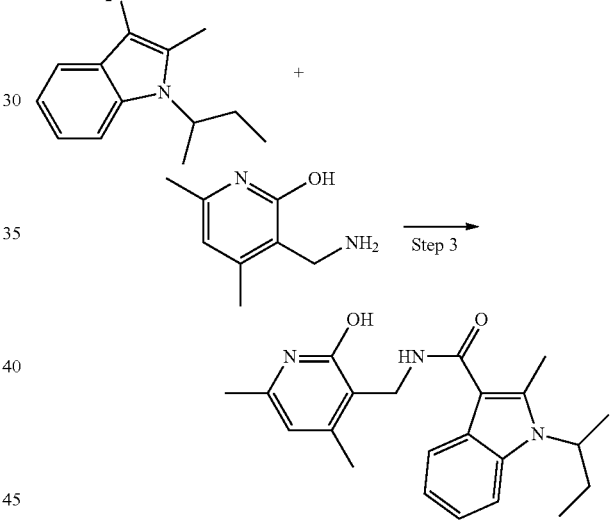

A mixture of 1-sec-butyl-2-methyl-1H-indole-3-carboxylic acid (97 mg, 0.42 mmol), 1-ethyl-3-(3-dimethyllaminopropyl)carbodiimide hydrochloride (121 mg, 0.63 mmol), N-hydroxybenzotrizole (85 mg, 0.63 mmol) and triethylamine (127.26 mg, 1.26 mmol) in dichloromethane (30 mL) was stirred for 30 minutes at room temperature. Then to the mixture, 3-(aminomethyl)-4,6-dimethylpyridin-2-ol (63.8 mg, 0.42 mmol) was added. The resulting mixture was stirred at room temperature for 12 hours. Then the mixture was washed with water (20 mL×3). The organic layer was concentrated to give a residue which was purified by column chromatography (silica gel, dichloromethane/methanol=20:1) to give 1-sec-butyl-N-((2-hydroxy-4,6-dimethylpyridin-3-yl)methyl)-2-methyl-1H-indole-3-carboxamide (57 mg, 30%). LRMS (M+H$^+$) m/z: calcd 365.2. found 365. HPLC purity (214 nm): 99%. $^1$H.NMR (300 MHz, CD$_3$OD): δ 7.72-7.69 (m, 1H), 7.53 (d, J=7.2 Hz, 1H), 7.11-7.06 (m, 2H), 6.10 (s, 1H), 4.53-4.51 (m, 3H), 2.62 (s, 3H), 2.41 (s, 3H), 2.24 (s, 3H), 1.95-1.93 (m, 2H), 1.59 (d, J=6.9 Hz, 3H), 0.72 (t, J=7.5 Hz, 3H).

89

Synthesis of (R or S)-1-sec-butyl-N-((2-hydroxy-4,6-dimethylpyridin-3-yl)methyl)-2-methyl-1H-indole-3-carboxamide and (S or R)-1-sec-butyl-N-((2-hydroxy-4,6-dimethylpyridin-3-yl)methyl)-2-methyl-1H-indole-3-carboxamide

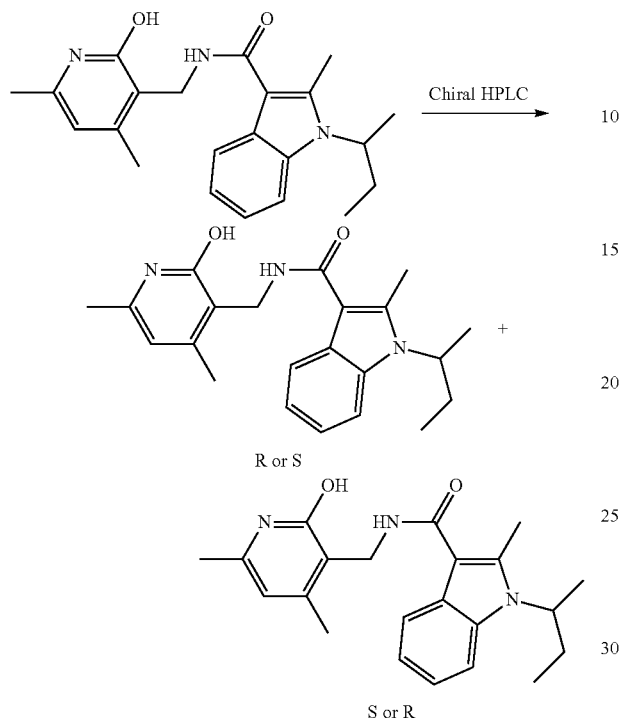

1-sec-butyl-N-((2-hydroxy-4,6-dimethylpyridin-3-yl)methyl)-2-methyl-1H-indole-3-carboxamide (35 mg, 0.1 mmol) was separated by chiral prep-HPLC (Daicel IA (200 mm×20 mm×5 um), hexane:ethanol (0.2% DEA)=70:30, flow rate: 19 mL/min), then (R or S) 1-sec-butyl-N-((2-hydroxy-4,6-dimethylpyridin-3-yl)methyl)-2-methyl-1H-indole-3-carboxamide (11 mg, 30%) and (S or R)-1-sec-butyl-N-((2-hydroxy-4,6-dimethylpyridin-3-yl)methyl)-2-methyl-1H-indole-3-carboxamide (6 mg, 16%) was obtained. The retention times were 8.030 minutes ("Peak 1"; Compound 147) and 14.126 minutes ("Peak 2"; Compound 148) respectively in chiral HPLC chromatography. LRMS (M+H+) m/z: calcd 365.2. found 365. HPLC purity (214 nm): 99%. $^1$H.NMR (300 MHz, CD$_3$OD): δ 7.73-7.70 (m, 1H), 7.56-7.53 (m, 1H), 7.12-7.09 (m, 2H), 6.11 (s, 1H), 4.54 (s, 3H), 2.64 (s, 3H), 2.43 (s, 3H), 2.25 (s, 3H), 1.97-1.90 (m, 2H), 1.61 (d, J=6.9 Hz, 3H), 0.73 (t, J=7.5 Hz, 3H).

Example 22

Synthesis of compound N-((2-hydroxy-4,6-dimethylpyridin-3-yl)methyl-2-methyl-1-phenyl-1H-indole-3-carboxamide (Compound 133)

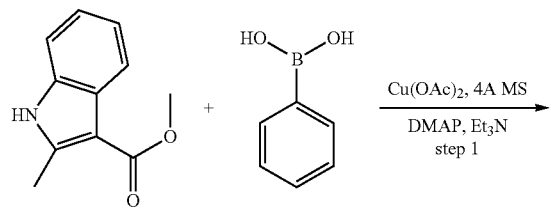

90

-continued

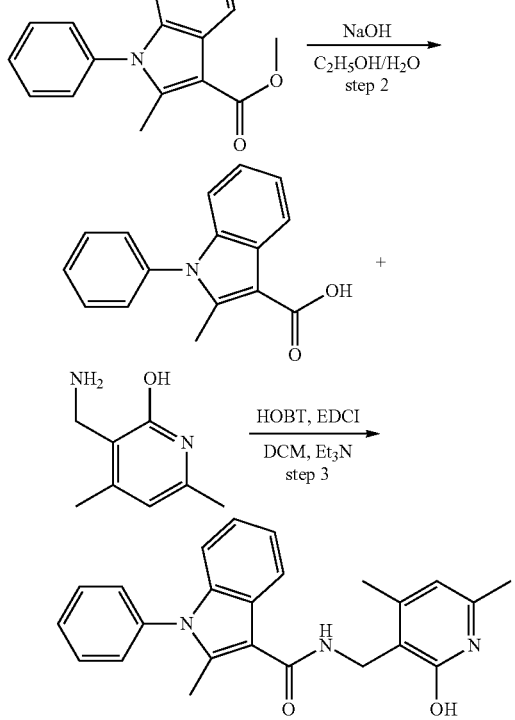

Synthesis of methyl 2-methyl-1-phenyl-1H-indole-3-carboxylate

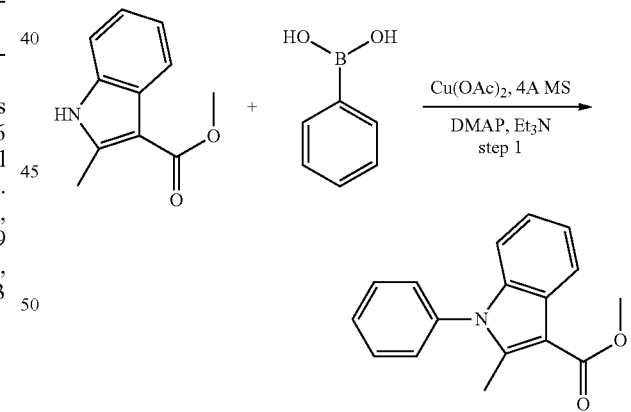

A mixture of methyl 2-methyl-1H-indole-3-carboxylate (500 mg, 2.65 mmol), phenylboronic acid (384 mg, 3.17 mmol), diacetylcopper (453 mg, 3.98 mmol), triethylamine (0.44 ml, 3.98 mmol), N,N-dimethylpyridin-4-amine (486 ml, 3.98 mmol) and 4 A molecular sieve (1.02 g) in dichloromethane (15 mL) was stirred at room temperature for 12 hours. After filtration, the mixture was concentrated and purified by chromatography (silica gel, petroleum:ethyl acetate=10:1) to afford methyl 2-methyl-1-phenyl-1H-indole-3-carboxylate as white solid (272 mg, 39%). $^1$H NMR (400 MHz, CDCl$_3$) δ 8.19 (d, J=8.0 Hz, 1H), 7.66-7.51 (m, 3H), 7.36 (dd, J=5.3, 3.2 Hz, 2H), 7.30 (s, 1H), 7.21-7.14 (m, 1H), 7.04 (d, J=8.2 Hz, 1H), 4.00 (s, 3H), 2.62 (s, 3H).

Synthesis of 2-methyl-1-phenyl-1H-indole-3-carboxylic acid

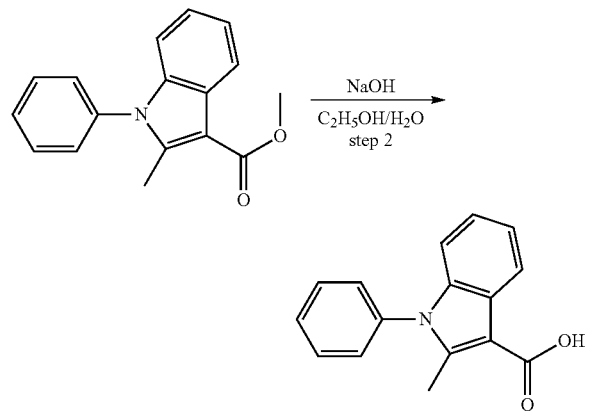

To a solution of methyl 2-oxo-1-phenyl-1,2-dihydropyridine-4-carboxylate (272 mg, 1.03 mmol) in alcohol/water (v/v=1/1, 5 mL) was added lithium hydroxide (62 mg, 1.55 mmol), and the mixture was stirred at room temperature for 8 hours. The reaction mixture was concentrated, acidified by diluted aqueous hydrochloric acid (1 N, 5 mL) and extracted with ethyl acetate (2×10 ml). The combined organic layer was dried over anhydrous sodium sulfate, filtered and concentrated under reduced pressure to afford 2-methyl-1-phenyl-1H-indole-3-carboxylic acid as white solid (115 mg, 44%). LRMS (M–H$^+$) m/z: calcd for 251.09. found 251.

Synthesis of N-((2-hydroxy-4,6-dimethylpyridin-3-yl)methyl)-2-methyl-1-phenyl-1H-indole-3-carboxamide (Compound 133)

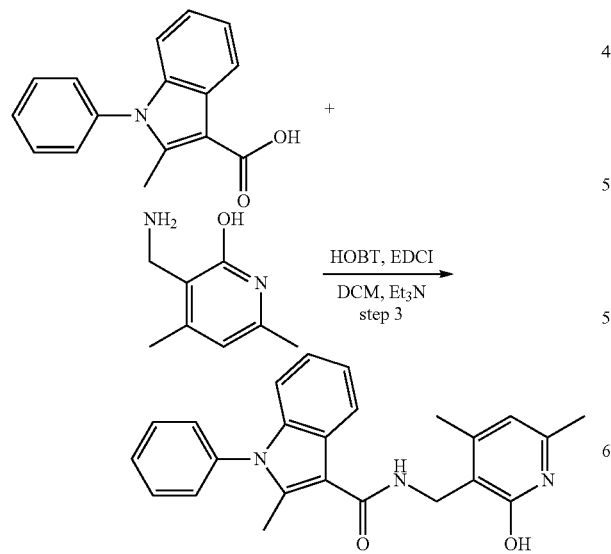

To a solution of 2-methyl-1-phenyl-1H-indole-3-carboxylic acid (115 mg, 0.46 mmol) in anhydrous dichloromethane (3 mL) was added 1H-benzo[d][1,2,3]triazol-1-ol (75 mg, 0.55 mmol), 1-Ethyl-3-(3-dimethyllaminopropyl)carbodiimide hydrochloride (106 mg, 0.55 mmol) and triethylamine (0.16 mL, 1.15 mmol). The mixture was stirred at room temperature for half an hour, 3-(aminomethyl)-4,6-dimethylpyridin-2-ol (70 mg, 0.46 mmol) was added and stirred at room temperature for 3 hours. The reaction mixture was added water (20 mL), extracted with dichloromethane (20 mL×2), combined and concentrated the organic layers to give the residue, which was purified by column chromatography (silica gel, dichloromethane/methanol=25:1) to afford N-((2-hydroxy-4,6-dimethylpyridin-3-yl)methyl)-2-methyl-1-phenyl-1H-indole-3-carboxamide (12 mg, 50% yield. LRMS (M+H$^+$) m/z: calcd for 385.18. found 385. $^1$H NMR (300 MHz, CDCl$_3$) δ 12.62 (s, 1H), 7.89 (d, J=8.0 Hz, 1H), 7.77-7.40 (m, 3H), 7.43-7.18 (m, 3H), 7.22-7.00 (m, 2H), 5.98 (s, 1H), 4.65 (s, 2H), 2.60-2.52 (m, 3H), 2.45 (s, 3H), 2.25 (s, 3H).

Example 23

Synthesis of compound N-((4,6-dimethyl-2-oxo-1,2-dihydropyridin-3-yl)methyl)-2-methyl-1-(pyrimidin-5-ylmethyl)-1H-indole-3-carboxamide (Compound 149)

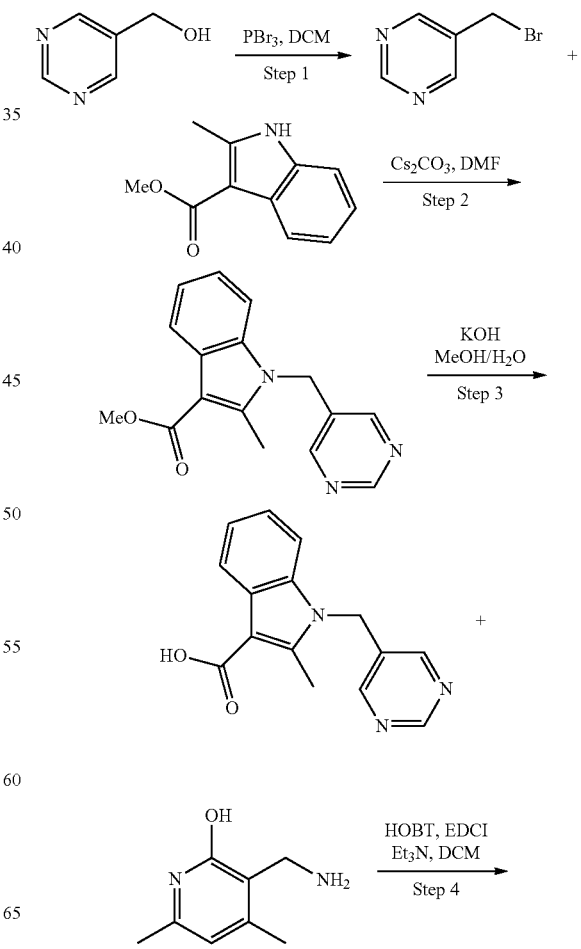

-continued

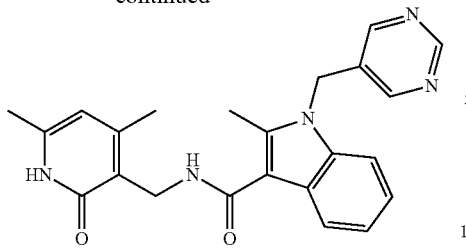

Synthesis of 5-(bromomethyl)pyrimidine

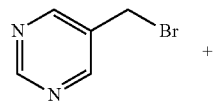

To a solution of pyrimidin-5-ylmethanol (0.5 g, 4.5 mmol) in dichloromethane (50 mL) was added phosphorus tribromide (0.6 g, 2.25 mmol) at 0° C. The solution was stirred at room temperature for 12 hours. The solution was washed with sodium bicarbonate and concentrated to give a residue, which was purified by column chromatography (silica gel, ethyl acetate/petroleum ether=1:10) to give 5-(bromomethyl)pyrimidine (0.3 g, 39%).

Synthesis of methyl 2-methyl-1-(pyrimidin-5-ylmethyl)-1H-indole-3-carboxylate

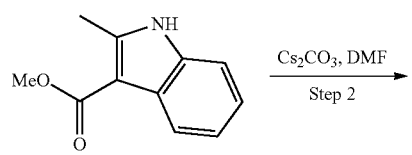

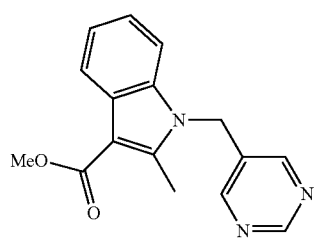

To a solution of methyl 2-methyl-1H-indole-3-carboxylate (0.5 g, 2.6 mmol) in N,N-dimethylformamide (20 mL) was added cesium carbonate (1.7 g, 5.2 mmol) and 5-(bromomethyl)pyrimidine (0.3 g, 1.7 mmol). The mixture was stirred at 100° C. for 1 hour and then concentrated to give a residue. The residue was purified by column chromatography (silica gel, ethyl acetate/petroleum ether=1:20) to give methyl 2-methyl-1-(pyrimidin-5-ylmethyl)-1H-indole-3-carboxylate (110 mg, 14%)

Synthesis of 2-methyl-1-(pyrimidin-5-ylmethyl)-1H-indole-3-carboxylic acid

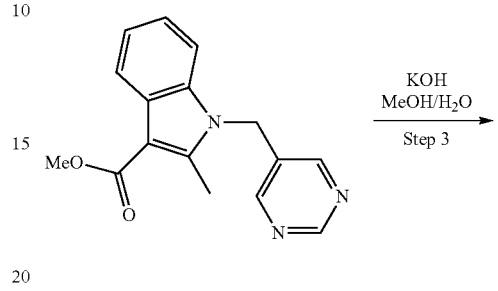

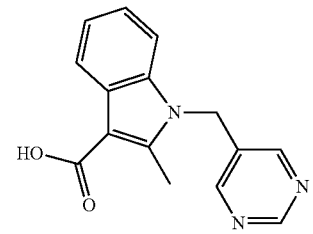

To a mixed solution of methanol (10 mL) and water (2 mL), methyl methyl 2-methyl-1-(pyrimidin-5-ylmethyl)-1H-indole-3-carboxylate (110 mg, 0.39 mmol) and potassium hydroxide (50 mg, 0.98 mmol) was added. The mixture was stirred at reflux for 12 hours. Then the reaction mixture was acidified by hydrochloric acid aqueous solution (1N) to adjust pH=6 and extracted with dichloromethane (10 mL*3). The organic layers were combined and concentrated to give 1-isopropyl-2-methyl-1H-indole-3-carboxylic acid (60 mg, 58%).

Synthesis of N-((4,6-dimethyl-2-oxo-1,2-dihydropyridin-3-yl)methyl)-2-methyl-1-(pyrimidin-5-ylmethyl)-1H-indole-3-carboxamide (Compound 149)

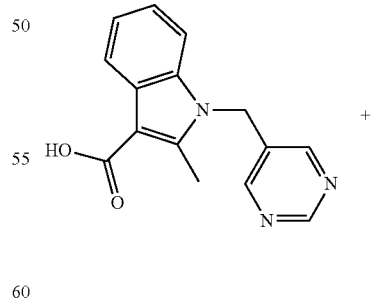

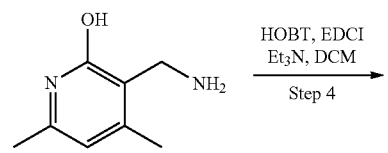

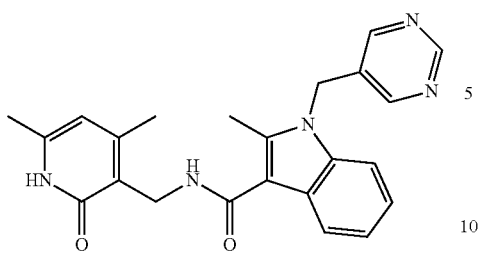

A mixture of 2-methyl-1-(pyrimidin-5-ylmethyl)-1H-indole-3-carboxylic acid (60 mg, 0.22 mmol), 1-ethyl-3-(3-dimethyllaminopropyl)carbodiimide hydrochloride (65 mg, 0.34 mmol), N-hydroxybenzotrizole (180 mg, 1.33 mmol) and triethylamine (46 mg, 0.34 mmol) in dichloromethane (30 mL) was stirred for 30 minutes at room temperature. Then to the mixture, 3-(aminomethyl)-4,6-dimethyl pyridin-2-ol (33.44 mg, 0.22 mmol) was added. The resultant mixture was stirred at room temperature for 12 hours. Then the mixture was washed with water (20 mL×3). The organic layer was concentrated to give a residue which was purified by column chromatography (silica gel, dichloromethane/methanol=20: 1) to give N-((4,6-dimethyl-2-oxo-1,2-dihydropyridin-3-yl) methyl)-2-methyl-1-(pyrimidin-5-ylmethyl)-1H-indole-3-carboxamide (17 mg, 19%). LRMS (M+H$^+$) m/z: calcd 401.19. found 401. HPLC purity (214 nm): 92%. $^1$H.NMR (300 MHz, CD$_3$OD): δ 9.03 (s, 1H), 8.43 (s, 2H), 7.80-7.78 (m, 1H), 7.39-7.36 (m, 1H), 7.19-7.16 (m, 2H), 5.56 (s, 2H), 4.55 (s, 2H), 2.62 (s, 3H), 2.42 (s, 3H), 2.45 (s, 3H).

Example 24

Synthesis of compound 1-benzoyl-N-((2-hydroxy-4,6-dimethylpyridin-3-yl)methyl)-2-methyl-1H-indole-3-carboxamide (Compound 150)

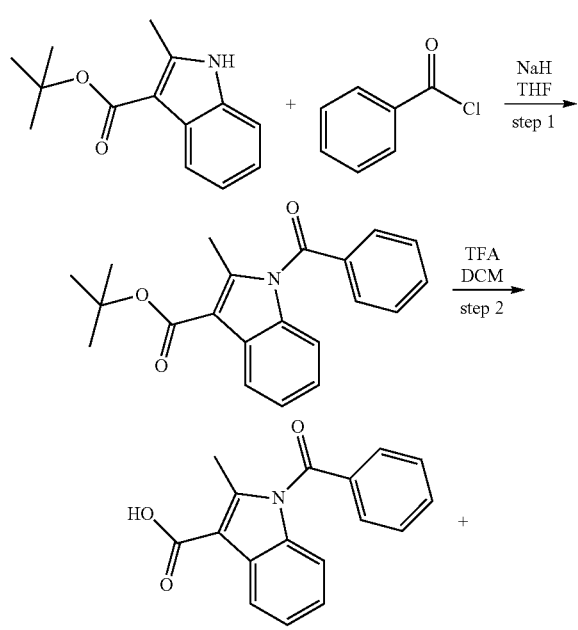

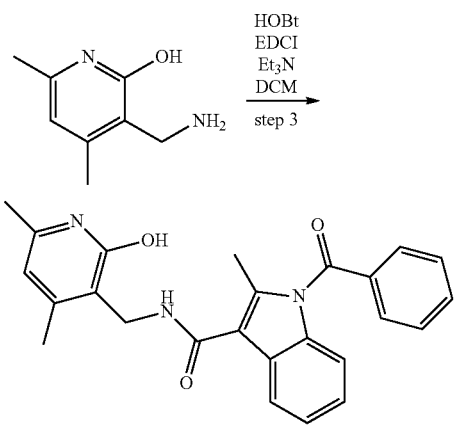

Synthesis of tert-butyl 1-benzoyl-2-methyl-1H-indole-3-carboxylate

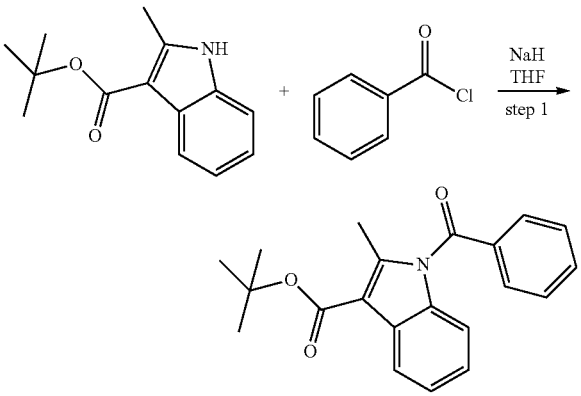

To a suspension of sodium hydride (73 mg, w/w=60%, 1.8 mmol) tert-butyl 2-methyl-1H-indole-3-carboxylate (350 mg, 1.5 mmol) in tetrahydrofuran (30 mL) was added benzoyl chloride (250 mg, 1.8 mmol). The reaction solution was stirred at room temperature for 12 hours. The mixture was concentrated to give a residue, which was purified by column chromatography (silica gel, petroleum ether/ethyl acetate=3: 1) to give tert-butyl 1-benzoyl-2-methyl-1H-indole-3-carboxylate (440 mg, 88%).

Synthesis of 1-benzoyl-2-methyl-1H-indole-3-carboxylic acid

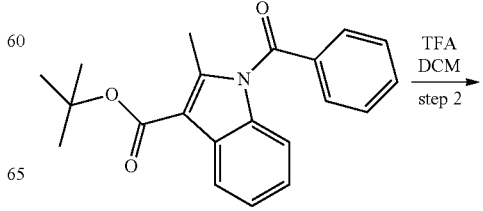

97

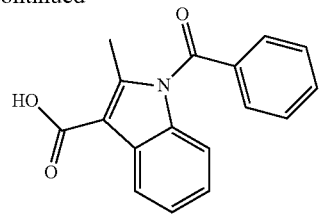

A mixture of tert-butyl 1-benzoyl-2-methyl-1H-indole-3-carboxylate (440 mg, 1.3 mmol), lithium hydroxide monohydrate (276 mg, 6.6 mmol), tetrahydrofuran (12 mL), methanol (4 mL) and water (4 mL) was stirred at room temperature for 4 hours. The mixture was concentrated, acidified to pH=2 with concentrated hydrochloric acid and extracted with ethyl acetate (20 mL×3). The organic phase was dried over anhydrous sodium sulfate, filtered and concentrated to give 1-benzoyl-2-methyl-1H-indole-3-carboxylic acid (260 mg, 72%). LRMS (M+H$^+$) m/z: calcd 279.13. found 279.

Synthesis of 1-benzoyl-N-((2-hydroxy-4,6-dimethylpyridin-3-yl)methyl)-2-methyl-1H-indole-3-carboxamide (Compound 150)

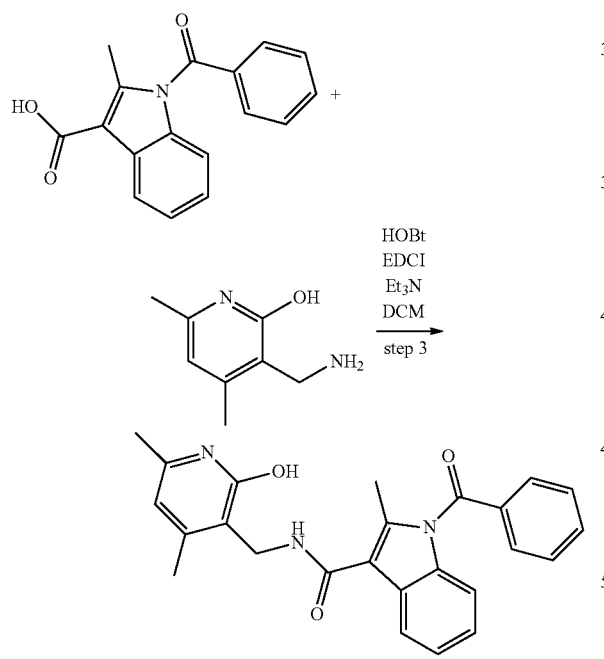

To a solution of 1-benzoyl-2-methyl-1H-indole-3-carboxylic acid (125 mg, 0.45 mmol), 1-hydroxybenzotriazole (122 mg, 0.9 mmol), 1-(3-dimethylaminopropyl)-3-ethylcarbodiimide hydrochloride (173 mg, 0.9 mmol), triethylamine (0.4 mL) in dichloromethane (20 mL) was added 3-(aminomethyl)-4,6-dimethylpyridin-2-ol (137 mg, 0.9 mmol). The reaction mixture was stirred at 20° C. for 13 hours. The mixture was washed with water (20 mL×2). The organic phase was dried over anhydrous sodium sulfate and filtered. The filtrate was concentrated to give the residue, which was purified by column chromatography (silica gel, dichloromethane/methanol=10:1) to give 1-benzoyl-N-((2-hydroxy-4,6-dimethylpyridin-3-yl)methyl)-2-methyl-1H-indole-3-carboxamide as a white solid (50 mg, 53%). LRMS

98

(M+H$^+$) m/z: calcd 413.17. found 413. HPLC Purity (214 nm): 96%. $^1$H NMR (300 MHz, d$^6$-DMSO): δ 11.57 (s, 1H), 8.13 (q, J=5.1 Hz, 1H), 7.74-7.70 (m, 4H), 7.60-7.58 (m, 2H), 7.20-7.00 (m, 3H), 5.88 (s, 1H), 4.32 (d, J=5.1 Hz, 2H), 2.37 (s, 3H), 2.267 (s, 3H), 2.12 (s, 3H).

Example 25

Synthesis of compound N-((4,6-dimethyl-2-oxo-1,2-dihydropyridin-3-yl)methyl)-2-methyl-1-(1-oxo-1-(pyrrolidin-1-yl)propan-2-yl)-1H-indole-3-carboxamide (Compound 151)

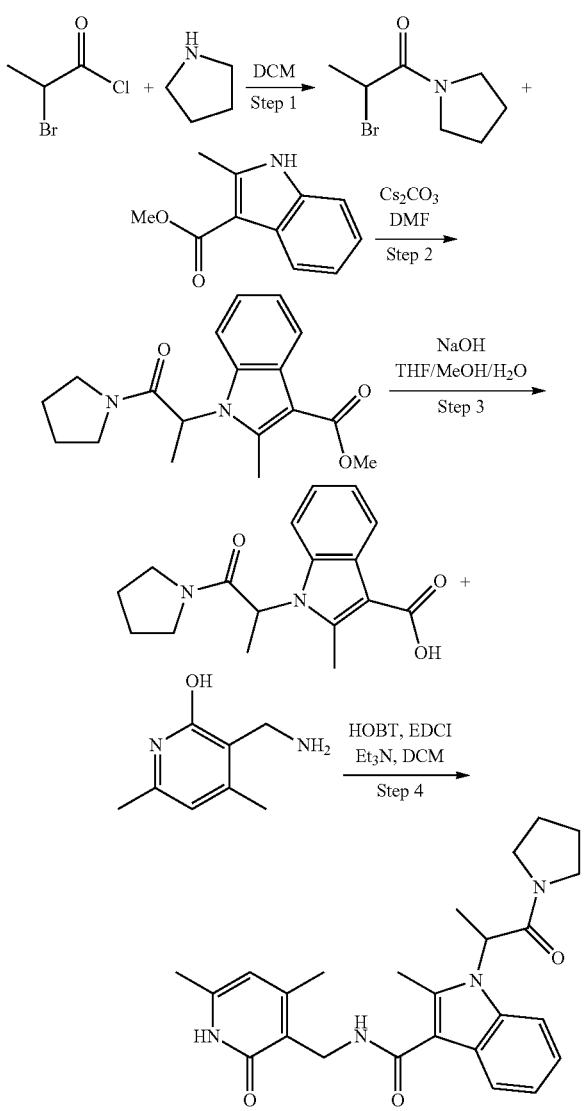

Synthesis of 2-bromo-1-(pyrrolidin-1-yl)propan-1-one

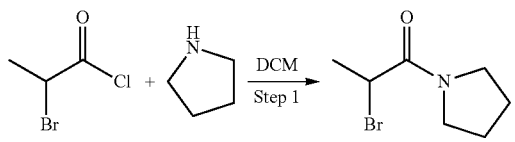

Pyrrolidine (0.12 mol, 8.3 g) was added to stirred solution of 2-bromopropanoyl chloride (0.58 mol, 10 g) in dichloromethane (200 ml) at 0° C. After 0.5 hour, the reaction mixture was warmed to room temperature, stirred for 2 hours, and saturated ammonium chloride solution (20 ml) was added. The solvent was evaporated and the mixture was extracted with ethyl acetate (200 ml). The organic phase was separated, dried over anhydrous sodium sulfate, filtered and concentrated to dryness. The residue was purified by column chromatography (silica gel, dichloromethane/methanol=55: 1) to give 2-bromo-1-(pyrrolidin-1-yl)propan-1-one (9.8 g, 93%). LCMS (M+H$^+$) m/z: calcd 205.01. found 205.

Synthesis of methyl 2-methyl-1-(1-oxo-1-(pyrrolidin-1-yl)propan-2-yl)-1H-indole-3-carboxylate

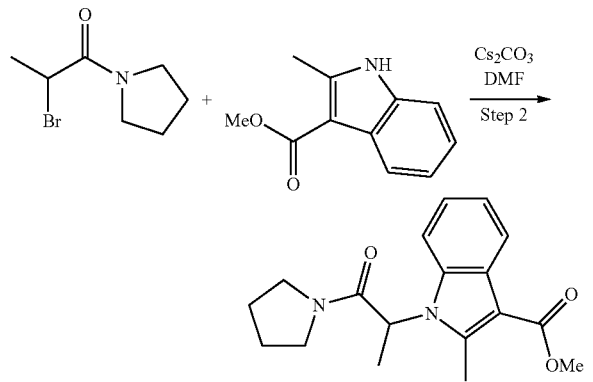

To a solution of methyl 2-methyl-1H-indole-3-carboxylate (0.52 mmol, 0.1 g) in N,N-dimethylformamide (5 mL), 2-bromo-1-(pyrrolidin-1-yl)propan-1-one (0.52 mmol, 0.137 mg) and cesium carbonate (1.05 mmol, 384 mg) was added. The reaction mixture was heated at 100° C. for 12 hours. LC-MS showed the start material was consumed. The solvent was evaporated and the residue was washed with water (10 ml), extracted with dichloromethane (20 ml). The organic layer was separated, concentrated to give a residue. The residue was purified by column chromatography (silica gel, dichloromethane/methanol=45:1) to give methyl 2-methyl-1-(1-oxo-1-(pyrrolidin-1-yl)propan-2-yl)-1H-indole-3-carboxylate (100 mg, 93%). $^1$H NMR (300 MHz, CD3OD): δ 8.07-8.03 (m, 1H), 7.44-7.40 (m, 1H), 7.19-7.14 (m, 2H), 5.53-5.49 (m, 1H), 3.90 (s, 3H), 2.80 (s, 3H), 2.00-1.80 (m, 2H), 1.74 (d, J=5.1 Hz, 3H), 1.67-1.64 (m, 4H), 1.32-1.28 (m, 2H).

Synthesis of 2-methyl-1-(1-oxo-1-(pyrrolidin-1-yl) propan-2-yl)-1H-indole-3-carboxylic acid

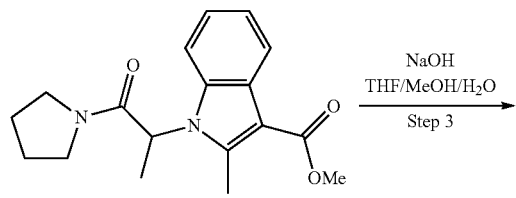

-continued

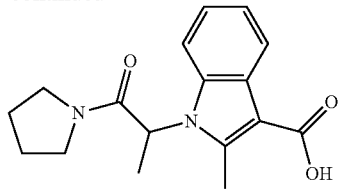

To a solution of sodium hydroxide solution (50 mg, 1.2 mmol) in tetrahydrofuran, menthol and water (20 mL, 3:1:1, V/V) was added methyl 2-methyl-1-(1-oxo-1-(pyrrolidin-1-yl)propan-2-yl)-1 H-indole-3-carboxylate (100 mg, 0.318 mmol). The reaction mixture was stirred at 70° C. for 10 hours. The mixture was quench with 10% hydrochloric acid aqueous (2 mL), extracted with dichloromethane and menthol (60 mL, 10:1). The combine organic layer was dried by anhydrous sodium sulfate, filtered and concentrated to give 2-methyl-1-(1-oxo-1-(pyrrolidin-1-yl)propan-2-yl)-1H-indole-3-carboxylic acid (90 mg, 92%). LCMS (M+H$^+$) m/z: calcd 300.15. found 300.

Synthesis of N-((4,6-dimethyl-2-oxo-1,2-dihydropyridin-3-yl)methyl)-2-methyl-1-(1-oxo-1-(pyrrolidin-1-yl)propan-2-yl)-1H-indole-3-carboxamide (Compound 151)

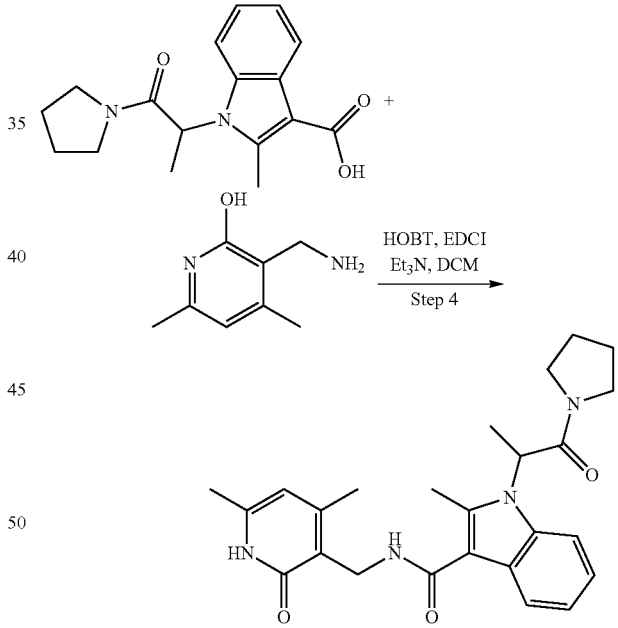

2-Methyl-1-(1-oxo-1-(pyrrolidin-1-yl)propan-2-yl)-1H-indole-3-carboxylic acid (90 mg, 0.30 mmol) was dissolved in dichloromethane (15 mL), and then N-hydroxybenzotrizole (0.45 mmol, 60 mg), 1-(3-dimethylaminopropyl)-3-ethylcarbodiimide hydrochloride (0.45 mmol, 86 mg), and triethylamine (1.69 mmol, 2 ml) was added to the mixture. After the mixture was stirred at room temperature for 10 minutes, 3-(aminomethyl)-4,6-dimethylpyridin-2-ol (0.30 mol, 50 mg) was added. The mixture was stirred at room temperature for 18 hours. Then washed with water (20 mL), extracted with dichloromethane (20 mL). The organic layer was separated, and concentrated to give a residue and the residue was purified by column chromatography (silica gel, dichloromethane/methanol=15:1) to give N-((4,6-dimethyl-2-oxo-1,2-dihydropyridin-3-yl)methyl)-2-methyl-1-(1-oxo-1-(pyrrolidin-1-yl)propan-2-yl)-1H-indole-3-carboxamide (60 mg, 70%). LCMS (M+H$^+$) m/z: calcd 434.23. found 434. HPLC Purity (214 nm): 99%. $^1$H NMR (300 MHz, DMSO-d6) δ 11.62 (s, 1H), 7.75-7.72 (m, 2H), 7.42 (d, J=5.7 Hz, 1H), 7.10-7.06 (m, 2H), 5.89 (s, 1H), 5.49-5.44 (m, 1H), 4.32-4.30 (m, 2H), 3.42-3.32 (m, 3H), 3.28-3.16 (m, 1H), 2.61 (s, 3H), 2.26 (s, 3H), 2.12 (m, 3H), 2.02-1.96 (m, 1H), 1.70-1.57 (m, 3H), 1.42 (d, J=5.1 Hz, 3H).

Example 26

Synthesis of Compounds 326, 327, 346 and Related Compounds and Intermediates

The title compounds of this Example and other related compounds were prepared according to the following general scheme. In addition, where indicated, modifications of this scheme are disclosed for the synthesis of still additional related compounds of the invention and intermediates thereof.

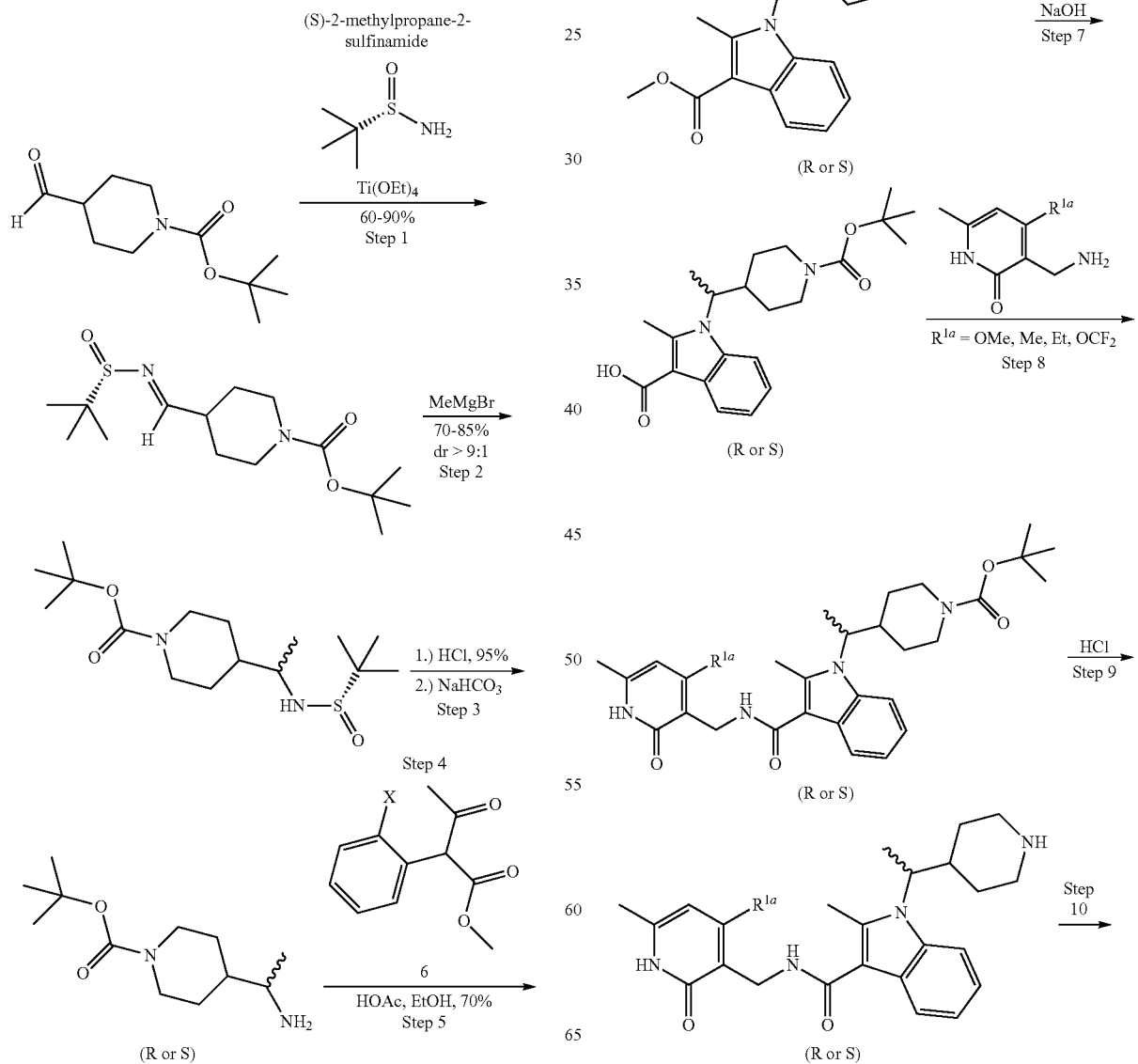

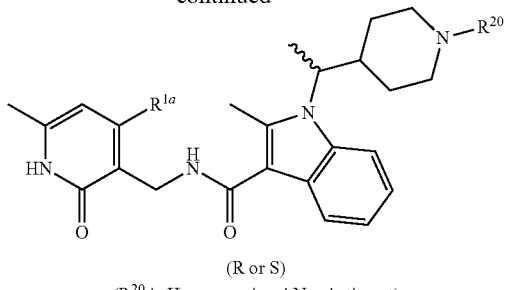

(R or S)
(R[20] is H or an optional N-substituent)

Step 1: (S,E)-tert-butyl 4-(((tert-butylsulfinyl)imino)methyl)piperidine-1-carboxylate

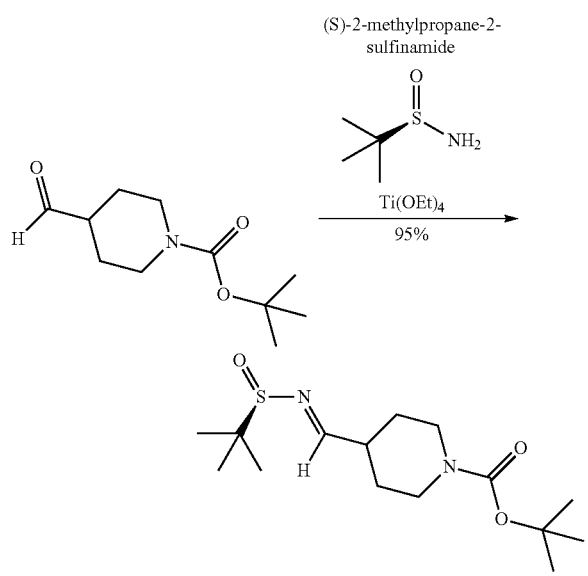

To a round bottomed flask charged with a magnetic stir bar was added (S)-2-methylpropane-2-sulfinamide (20.46 g, 169 mmol), tert-butyl 4-formylpiperidine-1-carboxylate (30 g, 141 mmol), DCM (300 mL), and Ti(OEt)$_4$ (59.0 ml, 281 mmol). The solution was stirred at room temperature for 3 h before it was quenched with brine (80 mL). The solution was stirred for 30 minutes before filtering. The filter cake was washed with DCM and the filtrate was placed in a separatory funnel and washed with water. The organics layer was dried over Na$_2$SO$_4$, filtered, and concentrated in vacuo. The crude residue solidified to the title compound (29 g, 92 mmol, 65.1% yield) m/z 217.

The intermediates shown in the following table were prepared according to the general procedure outlined in Step 1 using the appropriate starting materials and modifications.

| Name | Structure | m/z |
|---|---|---|
| (S,E)-2-methyl-N-((tetrahydro-2H-pyran-4-yl)methylene)propane-2-sulfinamide | | |
| (S,E)-2-methyl-N-((tetrahydro-2H-thiopyran-4-yl)methylene)propane-2-sulfinamide | 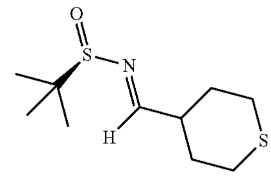 | 234 |
| (±)-(E)-2-methyl-N-((3-methyloxetan-3-yl)methylene)propane-2-sulfinamide | 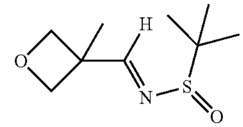 | 204 |

Step 2: Tert-butyl 4-((S)-1-((R or S)-1,1-dimethyl-ethylsulfinamido)ethyl)piperidine-1-carboxylate

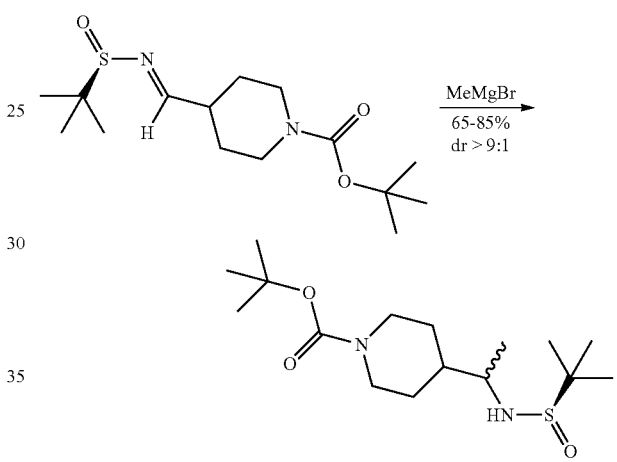

To a round bottomed flask charged with a magnetic stir bar was added (S,E)-tert-butyl 4-((tert-butylsulfinylimino)methyl)piperidine-1-carboxylate (36.4 g, 115 mmol), DCM (400 mL), and the solution was cooled to 0° C. in an ice bath with stirring. To this solution was added MeMgBr (77 ml, 230 mmol) (3M in diethyl ether) and the reaction stirred for 4 h while warming to room temperature. The reaction was carefully quenched via the addition of saturated aqueous NH$_4$Cl. The solid were broken up by the addition of 1N HCl. The layers were separated and the aqueous phase was extracted with DCM. The combined organics phase was dried over Na$_2$SO$_4$, filtered, and concentrated in vacuo to afford the title compound (29 g, >9:1 dr) which is used without further purification in the next step.

The intermediates shown in the following table were prepared according to the general procedure outlined in Step 2 using the appropriate starting materials and modifications.

| Name | Structure | m/z |
|---|---|---|
| (S)-2-methyl-N-((R or S)-1-(tetrahydro-2H-pyran-4-yl)ethyl)propane-2-sulfinamide | 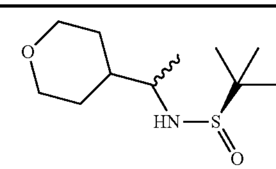 | 234 |

-continued

| Name | Structure | m/z |
|---|---|---|
| (S)-2-methyl-N-((R or S)-1-(tetrahydro-2H-thiopyran-4-yl)ethyl)propane-2-sulfinamide | 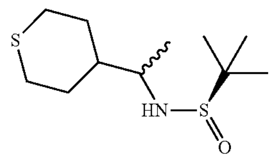 | 250 |
| (±)-2-methyl-N-(1-(3-methyloxetan-3-yl)ethyl)propane-2-sulfinamide | 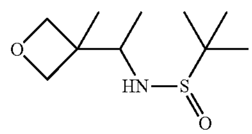 | 220 |

Step 3: (R or S)-tert-butyl 4-(1-aminoethyl)piperidine-1-carboxylate

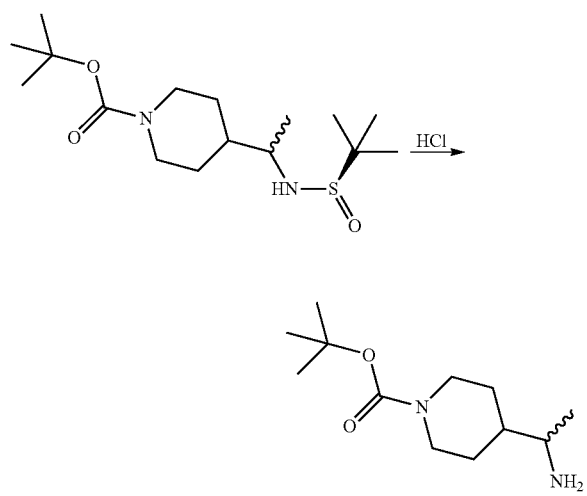

To a 1 L round bottomed flask charged with a magnetic stir bar was added crude tert-butyl 4-((S)-1-((S)-1,1-dimethylethylsulfinamido)ethyl)piperidine-1-carboxylate (29 g) was taken up in MeOH (200 mL) before addition of a 4 N solution of HCl in 1,4-dioxane (24.06 ml, 96 mmol). The resulting solution was then stirred at room temperature for 1 h at rt. The methanol was then removed in vacuo to afford viscous oil which was treated with sat'd aqueous NaHCO₃ (~500 mL) and extracted with ethyl acetate (2×500 mL). This organic phase was combined, dried with MgSO₄, filtered, and solvent was then removed in vacuo affording the title compound (22 g) which was used without further purification.

The intermediates shown in the following table were prepared according to the general procedure outlined in Step 3 using the appropriate starting materials.

| Name | Structure | m/z |
|---|---|---|
| (R or S)-1-(tetrahydro-2H-pyran-4-yl)ethanamine | | 130 |
| (R or S)-1-(tetrahydro-2H-thiopyran-4-yl)ethanamine | 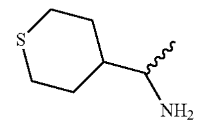 | 146 |
| (±)-1-(3-methyloxetan-3-yl)ethanamine | 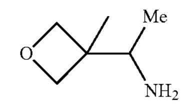 | 116 |

Step 4: Methyl 2-(2-bromophenyl)-3-oxobutanoate

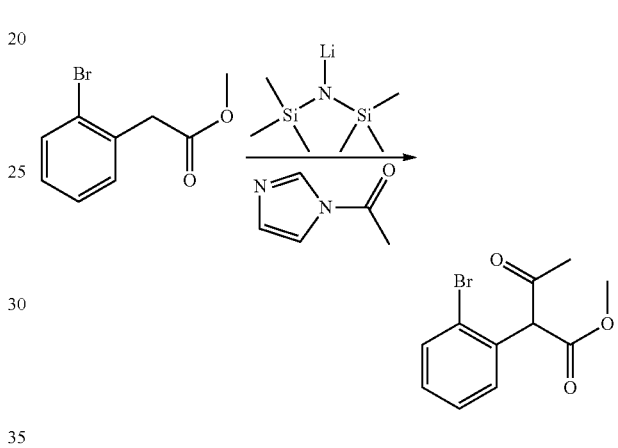

A round bottomed flask was charged with a magnetic stir bar and methyl 2-(2-bromophenyl)acetate (25 g, 109 mmol) and THF (50 mL). This solution was cooled to −78° C. before drop wise addition of a 1M solution of LiHMDS in THF (218 ml, 218 mmol). The reaction was stirred for 30 min at −78° C. before addition of 1-(1H-imidazol-1-yl)ethanone (14.42 g, 131 mmol) dissolved in a mixture of THF:DMF (112 mL THF, 24 mL DMF). The solution was stirred for 1 h before quenching with sat'd aqueous NH₄Cl (~250 mL) and diluting with EtOAc. The layers were separated and the aqueous phase was extracted with EtOAc (~2×250 mL). The combined organic extract was washed with brine, dried over Na₂SO₄, filtered, and concentrated in vacuo. The crude residue was purified via silica gel chromatography using an eluent of ethyl acetate/hexanes (10:1) to afford methyl 2-(2-bromophenyl)-3-oxobutanoate (32.5 g, 102 mmol, 93% yield).

The intermediates shown in the following table were prepared according to the general procedure outlined in Step 4 using the appropriate starting materials.

| Name | Structure | m/z |
|---|---|---|
| methyl 2-(2-bromo-4-chlorophenyl)-3-oxobutanoate | 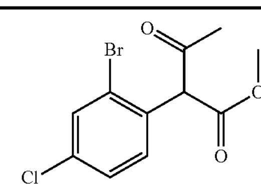 | 304 |

-continued

| Name | Structure | m/z |
|---|---|---|
| methyl 2-(2-bromo-4-methoxyphenyl)-3-oxobutanoate | 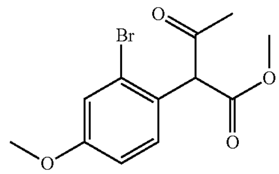 | 302 |
| methyl 2-(2-bromo-4-fluorophenyl)-3-oxobutanoate | 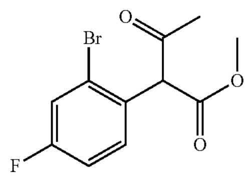 [SMILES: COC(=O)C(C(C)=O)c1ccc(F)cc1Br] | 289 |

Step 5: (R or S, Z)-tert-butyl 4-(1-(3-(2-bromophenyl)-4-methoxy-4-oxobut-2-en-2-ylamino)ethyl)piperidine-1-carboxylate

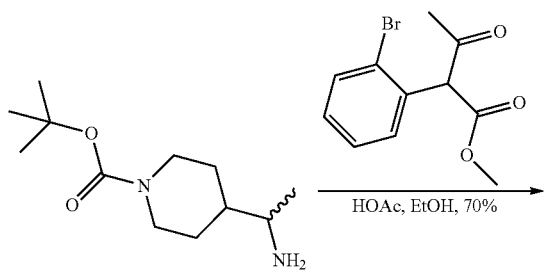

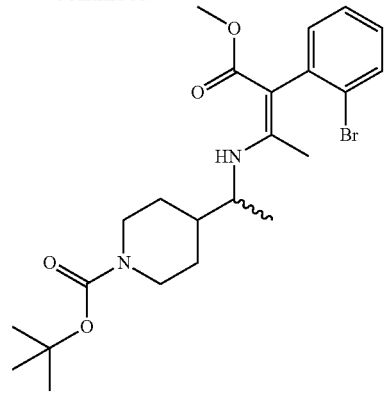

To a round bottomed flask was added (R or S)-tert-butyl 4-(1-aminoethyl)piperidine-1-carboxylate (9.35 g, 40.9 mmol), EtOH (75 mL), and methyl 2-(2-bromophenyl)-3-oxobutanoate (7.40 g, 27.3 mmol) (from Step 4). To this solution was added AcOH (1.563 ml, 27.3 mmol) and the reaction was heated overnight at 85° C. before cooling to room temperature and concentrating. The crude residue was purified via silica gel chromatography (330 g, 100% hexanes to 25% EA in hexanes) to afford the title compound (6.45 g, 13.40 mmol, 49.1% yield).

The intermediates shown in the following table were prepared according to the general procedure outlined in Step 5 using the appropriate starting materials.

| Name | Structure | m/z |
|---|---|---|
| (R or S,Z)-methyl 2-(2-bromophenyl)-3-((1-(tetrahydro-2H-pyran-4-yl)ethyl)amino)but-2-enoate | 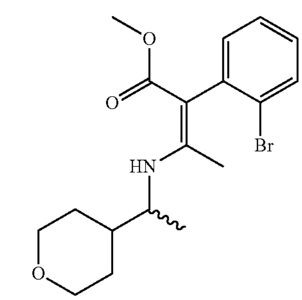 [SMILES: COC(=O)/C(=C(/C)NC(C)C1CCOCC1)c1ccccc1Br] | 383 |
| (R or S,Z)-methyl 2-(2-bromo-4-chlorophenyl)-3-((1-(tetrahydro-2H-pyran-4-yl)ethyl)amino)but-2-enoate | 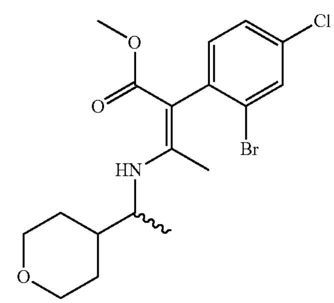 [SMILES: COC(=O)/C(=C(/C)NC(C)C1CCOCC1)c1ccc(Cl)cc1Br] | 417 |

-continued

| Name | Structure | m/z |
|---|---|---|
| (R or S,Z)-methyl 2-(2-bromo-4-chlorophenyl)-3-((1-(tetrahydro-2H-pyran-4-yl)ethyl)amino)but-2-enoate | 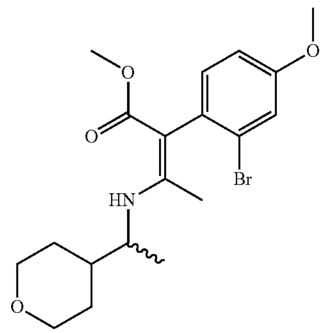 [SMILES: COC(=O)/C(=C(/C)NC(C)C1CCOCC1)c1ccc(OC)cc1Br] | 417 |
| (R or S,Z)-methyl 2-(2-bromo-4-fluorophenyl)-3-((1-(tetrahydro-2H-pyran-4-yl)ethyl)amino)but-2-enoate | 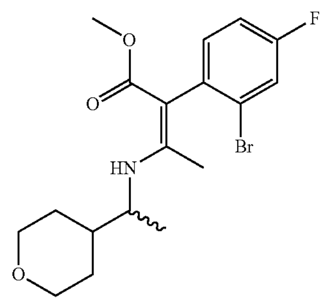 [SMILES: COC(=O)/C(=C(/C)NC(C)C1CCOCC1)c1ccc(F)cc1Br] | 401 |
| (R or S,Z)-methyl 2-(2-bromophenyl)-3-((1-(tetrahydro-2H-thiopyran-4-yl)ethyl)amino)but-2-enoate | 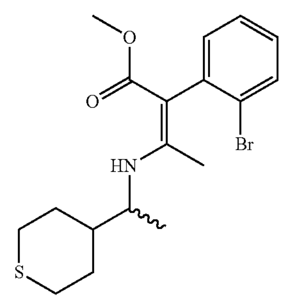 [SMILES: COC(=O)/C(=C(/C)NC(C)C1CCSCC1)c1ccccc1Br] | 399 |
| (±)-(Z)-methyl 2-(2-bromophenyl)-3-((1-(3-methyloxetan-3-yl)ethyl)amino)but-2-enoate | 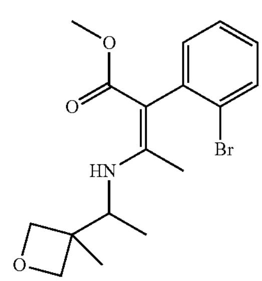 [SMILES: COC(=O)/C(=C(/C)NC(C)C1(C)COC1)c1ccccc1Br] | 368 |

Step 6: (R or S)-methyl 1-(1-(1-(tert-butoxycarbonyl)piperidin-4-yl)ethyl)-2-methyl-1H-indole-3-carboxylate

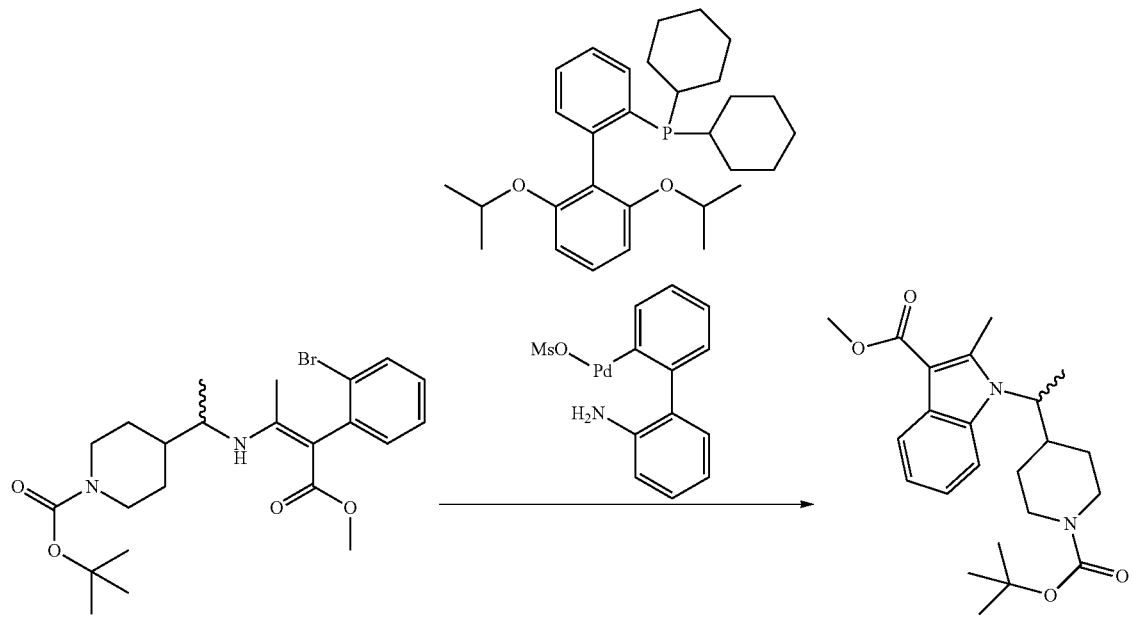

A 250 mL round bottom flask was charged with a magnetic stir bar, (R or S,Z)-tert-butyl 4-(1-(3-(2-bromophenyl)-4-methoxy-4-oxobut-2-en-2-ylamino)ethyl)piperidine-1-carboxylate (3.33 g, 6.92 mmol), RuPhos Pre-catalyst II (Chloro-(2-Dicyclohexylphosphino-2',6'-diisopropoxy-1,1'-biphenyl)[2-(2-aminoethyl)phenyl]palladium(II)-methyl-t-butyl ether adduct) (0.463 g, 0.553 mmol), dicyclohexyl(2',6'-diisopropoxybiphenyl-2-yl)phosphine (0.387 g, 0.830 mmol), anhydrous 1,4-dioxane (27.7 ml, 6.92 mmol), and sodium methoxide (0.561 g, 10.38 mmol). The reaction mixture was purged and back-filled with nitrogen and heated to 100° C. with stirring overnight before being allowed to cool to rt. The reaction was diluted with ethyl acetate (~100 ml) and the mixture was filtered through a bed of diatomaceous earth. The filtrate was pre-absorbed onto silica gel (~30 g) and purified via silica gel chromatography (120 g) using ethyl acetate/hexanes (1:1) as eluent to afford the title compound (2.01 g, 4.77 mmol, 68.9% yield).

The intermediates shown in the following table were prepared according to the general procedure outlined in Step 6 using the appropriate starting materials.

| Name | Structure | m/z |
|---|---|---|
| (R or S)-methyl 2-methyl-1-(1-(tetrahydro-2H-pyran-4-yl)ethyl)-1H-indole-3-carboxylate | 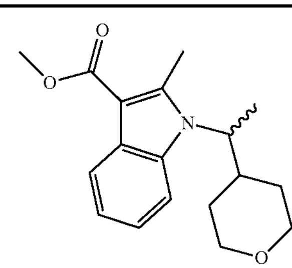 | 302 |
| (R or S)-methyl 6-chloro-2-methyl-1-(1-(tetrahydro-2H-pyran-4-yl)ethyl)-1H-indole-3-carboxylate | 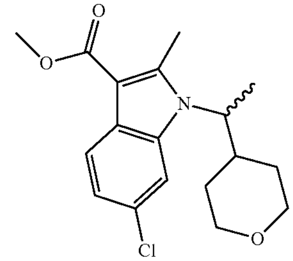 [SMILES: COC(=O)c1c(C)n(C(C)C2CCOCC2)c2cc(Cl)ccc12] | 337 |

| Name | Structure | m/z |
|---|---|---|
| (R or S)-methyl 6-methoxy-2-methyl-1-(1-(tetrahydro-2H-pyran-4-yl)ethyl)-1H-indole-3-carboxylate | | 332 |
| (R or S)-methyl 6-fluoro-2-methyl-1-(1-(tetrahydro-2H-pyran-4-yl)ethyl)-1H-indole-3-carboxylate | 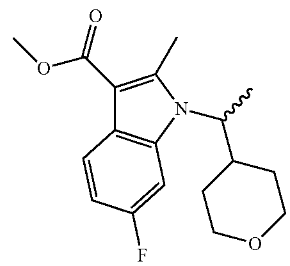 [SMILES: COC(=O)c1c(C)n(C(C)C2CCOCC2)c2cc(F)ccc12] | 320 |
| (R or S)-methyl 2-methyl-1-(1-(tetrahydro-2H-thiopyran-4-yl)ethyl)-1H-indole-3-carboxylate | 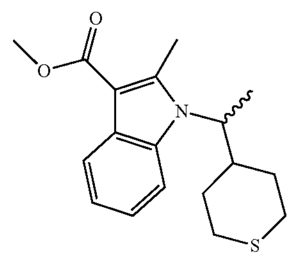 [SMILES: COC(=O)c1c(C)n(C(C)C2CCSCC2)c2ccccc12] | 318 |
| (±)-methyl 2-methyl-1-(1-(oxetan-3-yl)ethyl)-1H-indole-3-carboxylate | 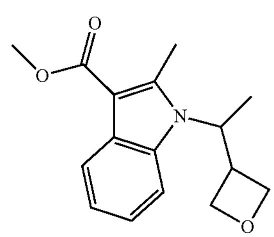 [SMILES: COC(=O)c1c(C)n(C(C)C2COC2)c2ccccc12] | 274 |

Step 7: (R or S)-2-methyl-1-(1-(tetrahydro-2H-pyran-4-yl)ethyl)-1H-indole-3-carboxylic acid

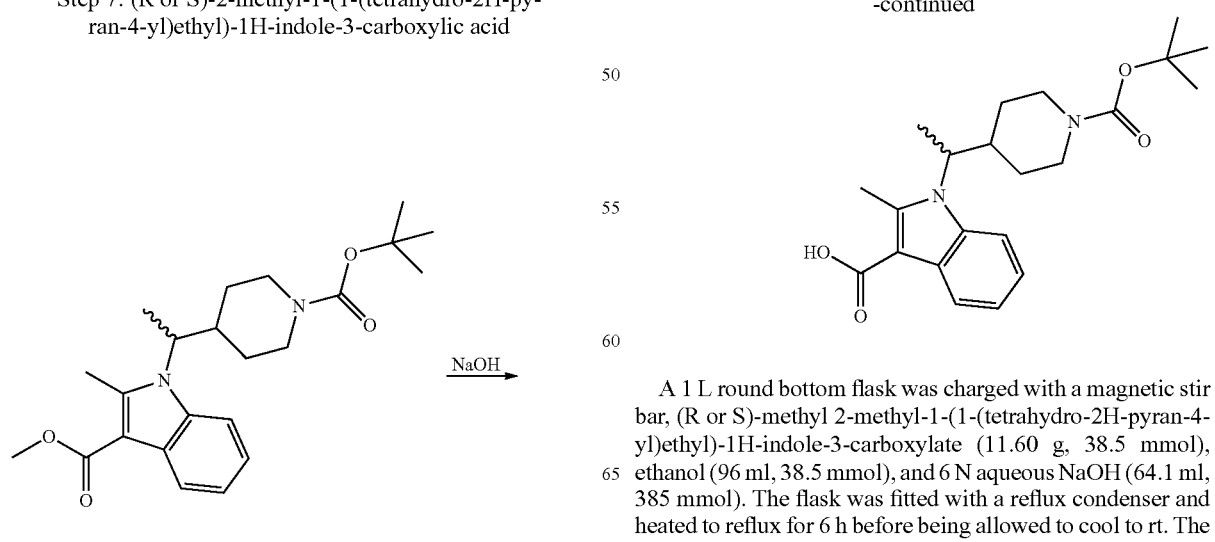

A 1 L round bottom flask was charged with a magnetic stir bar, (R or S)-methyl 2-methyl-1-(1-(tetrahydro-2H-pyran-4-yl)ethyl)-1H-indole-3-carboxylate (11.60 g, 38.5 mmol), ethanol (96 ml, 38.5 mmol), and 6 N aqueous NaOH (64.1 ml, 385 mmol). The flask was fitted with a reflux condenser and heated to reflux for 6 h before being allowed to cool to rt. The volatiles were removed in vacuo and the resulting mixture was poured into 10% HCl (~300 mL). A precipitate formed which was collected via vacuum filtration using a Buchner funnel. The filter cake was rinsed with an additional portion of water (~200 mL), collected, and dried under vacuum to afford the title compound (10.87 g, 35.9 mmol, 93% yield) as an off-white solid.

The intermediates shown in the following table were prepared according to the general procedure outlined in Step 7 using the appropriate starting materials.

| Name | Structure | m/z |
|---|---|---|
| (R or S)-2-methyl-1-(1-(tetrahydro-2H-pyran-4-yl)ethyl)-1H-indole-3-carboxylic acid | 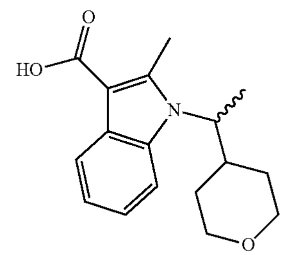 [SMILES: Cc1c(C(=O)O)c2ccccc2n1C(C)C1CCOCC1] | 287 |
| (R or S)-6-chloro-2-methyl-1-(1-(tetrahydro-2H-pyran-4-yl)ethyl)-1H-indole-3-carboxylic acid | 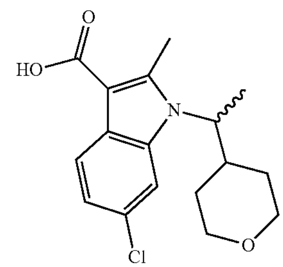 [SMILES: Cc1c(C(=O)O)c2ccc(Cl)cc2n1C(C)C1CCOCC1] | 321 |
| (R or S)-6-methoxy-2-methyl-1-(1-(tetrahydro-2H-pyran-4-yl)ethyl)-1H-indole-3-carboxylic acid | 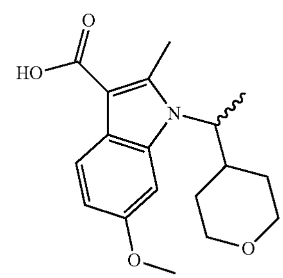 [SMILES: COc1ccc2c(C(=O)O)c(C)n(C(C)C3CCOCC3)c2c1] | 317 |
| (R or S)-6-fluoro-2-methyl-1-(1-(tetrahydro-2H-pyran-4-yl)ethyl)-1H-indole-3-carboxylic acid | 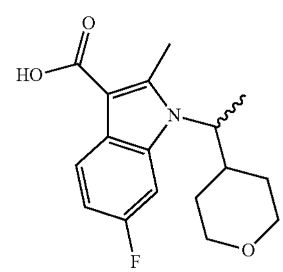 [SMILES: Cc1c(C(=O)O)c2ccc(F)cc2n1C(C)C1CCOCC1] | 306 |
| (R or S)-1-(1-(1,1-dioxidotetrahydro-2H-thiopyran-4-yl)ethyl)-2-methyl-1H-indole-3-carboxylic acid | 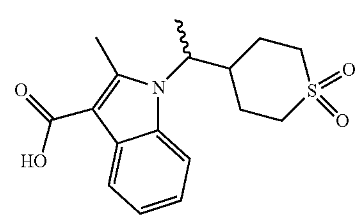 [SMILES: Cc1c(C(=O)O)c2ccccc2n1C(C)C1CCS(=O)(=O)CC1] | 334 |

-continued

| Name | Structure | m/z |
|---|---|---|
| (±)-2-methyl-1-(1-(oxetan-3-yl)ethyl)-1H-indole-3-carboxylic acid | 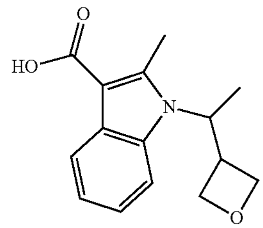 [SMILES: Cc1c(C(=O)O)c2ccccc2n1C(C)C1COC1] | 274 |
| (R or S)-2-methyl-6-(pyridin-3-yl)-1-(1-(tetrahydro-2H-pyran-4-yl)ethyl)-1H-indole-3-carboxylic acid | 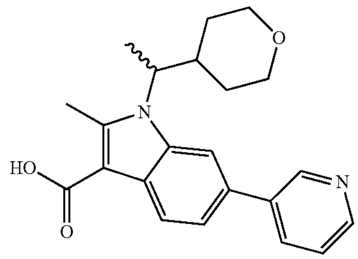 [SMILES: Cc1c(C(=O)O)c2ccc(-c3cccnc3)cc2n1C(C)C1CCOCC1] | 365 |
| (R or S)-2-methyl-6-(pyrazin-2-yl)-1-(1-(tetrahydro-2H-pyran-4-yl)ethyl)-1H-indole-3-carboxylic acid | 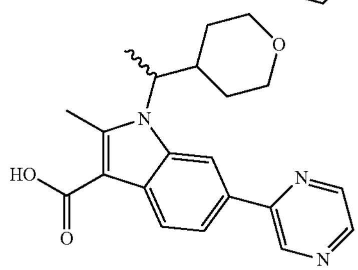 | 366 |
| (R or S)-2-methyl-1-(1-(tetrahydro-2H-pyran-4-yl)ethyl)-6-(thiazol-4-yl)-1H-indole-3-carboxylic acid | 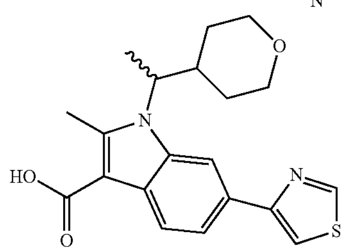 | 371 |

Step 8: (R or S)-tert-butyl 4-(1-(3-((4-methoxy-6-methyl-2-oxo-1,2-dihydropyridin-3-yl)methylcarbamoyl)-2-methyl-1H-indol-1-yl)ethyl)piperidine-1-carboxylate (Compound 327)

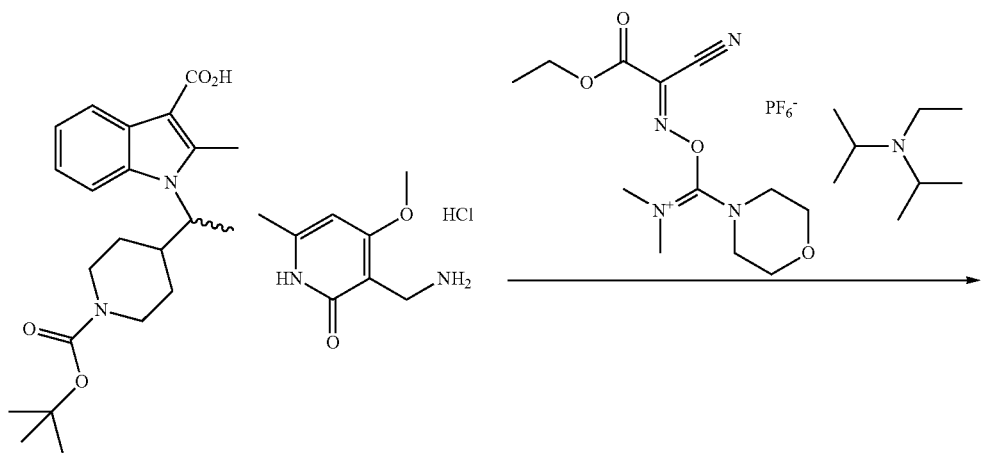

-continued

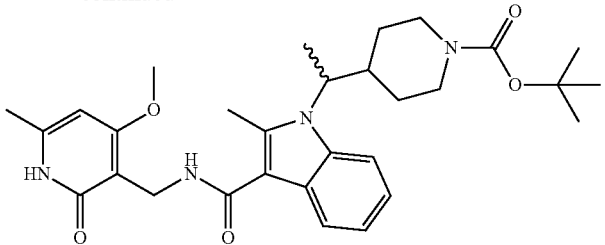

A 250 mL round bottom flask was charged with a magnetic stir bar, (R or S)-1-(1-(1-(tert-butoxycarbonyl)piperidin-4-yl)ethyl)-2-methyl-1H-indole-3-carboxylic acid (1.950 g, 5.05 mmol), 3-(aminomethyl)-4-methoxy-6-methylpyridin-2(1H)-one hydrochloride (2.065 g, 10.09 mmol), DMF (25.2 ml, 5.05 mmol). Hunig's base (3.52 ml, 20.18 mmol). The reaction mixture was cooled to 0° C. and COMU (2.16 g, 5.05 mmol) was added. The reaction was allowed to stir overnight to room temperature. The reaction mixture was diluted with water and extracted with EtOAc. The combined organic extract was washed with brine, dried with MgSO$_4$, filtered and conc. in vacuo to afford the crude material which was purified via silica gel chromatography (120 g) using MeOH/ethyl acetate (1:5) as eluent to afford the title compound (1.86 g, 3.29 mmol, 65.3% yield). LCMS 537 (M+1)$^+$ $^1$H NMR (400 MHz, DMSO-d$_6$) δ=11.83-11.71 (m, 1 H), 7.80 (br. s., 1 H), 7.73 (d, J=7.6 Hz, 1 H), 7.62 (d, J=7.8 Hz, 1 H), 7.06 (td, J=7.1, 14.4 Hz, 2 H), 6.21 (s, 1 H), 4.32 (br. s., 2 H), 4.16 (br. s., 1 H), 4.02 (br. s., 1 H), 3.85 (s, 3 H), 3.75 (br. s., 1 H), 2.70 (br. s., 1 H), 2.58 (s, 3 H), 2.37 (br. s., 1 H), 2.21 (s, 3 H), 1.90 (d, J=12.9 Hz, 1 H), 1.53 (d, J=6.9 Hz, 3 H), 1.35 (s, 10H), 1.21 (br. s., 1 H), 0.89 (d, J=8.7 Hz, 1 H), 0.67 (d, J=11.8 Hz, 1 H).

The compounds shown in the following table were prepared according to the general procedure outlined in Step 8 using the appropriate starting materials. The structures of the compounds are shown in FIG. 1.

| Compound Number | Name | $^1$H NMR | m/z |
|---|---|---|---|
| 305 | (R or S)-1-(1-(1,1-dioxidotetrahydro-2H-thiopyran-4-yl)ethyl)-N-((4-methoxy-6-methyl-2-oxo-1,2-dihydropyridin-3-yl)methyl)-2-methyl-1H-indole-3-carboxamide | (400 MHz, DMSO-d$_6$) δ 11.66-11.52 (m, 1H), 7.80-7.67 (m, 2H), 7.67-7.58 (m, 1H), 7.16-7.02 (m, 2H), 6.15 (s, 1H), 4.32 (d, J = 4.5 Hz, 2H), 3.84 (s, 3H), 3.24-3.06 (m, 2H), 2.91-2.77 (m, 1H), 2.75-2.65 (m, 1H), 2.60 (br. s., 3H), 2.35-2.23 (m, 1H), 2.20 (s, 3H), 1.93-1.76 (m, 2H), 1.56 (d, J = 6.5 Hz, 4H), 1.17-1.03 (m, 2H) | 486 |
| 435 | (R or S)-tert-butyl 4-(1-(3-(((4,6-dimethyl-2-oxo-1,2-dihydropyridin-3-yl)methyl)carbamoyl)-2-methyl-1H-indol-1-yl)ethyl)piperidine-1-carboxylate | | 521 |
| 436 | (R or S)-tert-butyl 4-(1-(3-(((4-(difluoromethoxy)-6-methyl-2-oxo-1,2-dihydropyridin-3-yl)methyl)carbamoyl)-2-methyl-1H-indol-1-yl)ethyl)piperidine-1-carboxylate | | 573 |
| 437 | (R or S)-tert-butyl 4-(1-(3-(((4-ethyl-6-methyl-2-oxo-1,2-dihydropyridin-3-yl)methyl)carbamoyl)-2-methyl-1H-indol-1-yl)ethyl)piperidine-1-carboxylate | | 535 |
| 298 | (R or S)-N-((4-methoxy-6-methyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DMSO-d$_6$) δ 11.60 (s, 1H), 7.73-7.62 (m, 3H), 7.60 (d, 2H) 7.07-7.05 (m, 2H), 6.15 (s 1H) 4.33 (s, 1H), 4.21-4.11 (m, 1H), 3.92 (br. d., 1H), 3.65 (d, 1H), 3.34-3.32 (m, 1H), 3.02 (t, 1H), 2.61 (s, 3H), 2.48-2.44 (m, 1H), 2.20 (s, 3H), 1.84-1.81 (m, 1H), 1.54 (d, 3H), 1.40-1.38 (m, 12H), 1.25-1.22 (m, 1H), 1.08-1.04 (m, 1H), 0.86 (br. s., 1H), 0.58 (br. d., 1H) | 438 |

| Compound Number | Name | ¹H NMR | m/z |
|---|---|---|---|
| 300 | (R or S)-6-fluoro-N-((4-methoxy-6-methyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DMSO-$d_6$) δ = 11.57 (br. s., 1H), 7.75-7.67 (m, 2H), 7.48 (d, J = 10.7 Hz, 1H), 6.90 (t, J = 8.5 Hz, 1H), 6.13 (s, 1H), 4.29 (d, J = 4.5 Hz, 2H), 4.12 (br. s., 1H), 3.94-3.87 (m, 1H), 3.83 (s, 3H), 3.64 (dd, J = 3.6, 10.9 Hz, 1H), 3.35 (br. s., 1H), 3.05 (br. s., 1H), 2.56 (s, 3H), 2.45-2.37 (m, 1H), 2.38 (s, 3H), 1.81 (d, J = 12.7 Hz, 1H), 1.50 (d, J = 6.9 Hz, 3H), 1.40-1.29 (m, 1H), 1.11-0.99 (m, 1H), 0.61 (br. s., 1H) | 456 |
| 314 | (R or S)-6-chloro-N-((4-methoxy-6-methyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DMSO-$d_6$) δ 11.57 (s, 1H), 7.75 (s, 2H), 7.66 (d, J = 8.9 Hz, 1H), 7.08 (d, J = 8.5 Hz, 1H), 6.14 (s, 1H), 4.30 (d, J = 4.5 Hz, 2H), 4.21-4.05 (m, 2H), 3.91 (d, J = 11.4 Hz, 1H), 3.85 (s, 3H), 3.65 (d, J = 10.5 Hz, 1H), 3.02 (t, J = 11.3 Hz, 1H), 2.58 (s, 3H), 2.46-2.31 (m, 1H), 2.19 (s, 3H), 1.82 (d, J = 12.0 Hz, 1H), 1.59-1.45 (m, 4H), 1.44-1.29 (m, 1H), 0.57 (d, J = 12.9 Hz, 1H) | 472 |
| 321 | (R or S)-6-methoxy-N-((4-methoxy-6-methyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DSO-$d_6$) δ = 11.59 (s, 1H), 7.67-7.59 (m, 2H), 7.03 (s, 1H), 6.75-6.68 (m, 1H), 6.14 (s, 1H), 4.30 (d, J = 5.1 Hz, 2H), 4.10 (dd, J = 7.5, 10.4 Hz, 1H), 3.91 (dd, J = 3.0, 11.3 Hz, 1H), 3.83 (s, 3H), 3.80-3.76 (m, 3H), 3.68-3.60 (m, 1H), 3.38-3.32 (m, 1H), 3.10-3.00 (m, 1H), 2.56 (s, 3H), 2.19 (s, 3H), 1.83 (d, J = 12.7 Hz, 1H), 1.55-1.43 (m, 4H), 1.34 (br. s., 1H), 1.10-0.96 (m, 1H), 0.62 (d, J = 13.4 Hz, 1H) | 468 |
| 335 | (R or S)-N-((4-(difluoromethoxy)-6-methyl-2-oxo-1,2-dihydropyridin-3-yl)methyl)-2-methyl-1-(1-(tetrahydro-2H-pyran-4-yl)ethyl)-1H-indole-3-carboxamide | | 474 |
| 394 | (R or S)-N-((4,6-dimethyl-2-oxo-1,2-dihydropyridin-3-yl)methyl)-2-methyl-1-(1-(tetrahydro-2H-pyran-4-yl)ethyl)-1H-indole-3-carboxamide | | 422 |
| 291 | (±)-N-((4-Methoxy-6-methyl-2-oxo-1,2-dihydropyridin-3-yl)methyl)-2-methyl-1-(1-(3-methyloxetan-3-yl)ethyl)-1H-indole-3-carboxamide | (400 MHz, $d^6$-DMSO) δ 11.59 (br. s., 1H), 7.72 (br. s., 2H), 7.05 (d, J = 7.58 Hz, 3H), 6.14 (s, 1H), 5.03-5.16 (m, 1H), 4.64 (d, J = 6.24 Hz, 1H), 4.43-4.54 (m, 1H), 4.32 (d, J = 4.24 Hz, 2H), 4.19 (d, J = 5.80 Hz, 1H), 4.10-4.16 (m, 1H), 3.84 (s, 3H), 2.53-2.71 (m, 3H), 2.20 (s, 3H), 1.72 (d, J = 6.91 Hz, 3H), 1.00 (s, 3H) | 424 |
| 442 | (R or S)-6-chloro-N-((4,6-dimethyl-2-oxo-1,2-dihydropyridin-3-yl)methyl)-2-methyl-1-(1-(tetrahydro-2H-pyran-4-yl)ethyl)-1H-indole-3-carboxamide | | 456 |
| 413 | (R or S)-N-((4,6-dimethyl-2-oxo-1,2-dihydropyridin-3-yl)methyl)-2-methyl-6-(pyridin-3-yl)-1-(1-(tetrahydro-2H-pyran-4-yl)ethyl)-1H-indole-3-carboxamide | (400 MHz, DMSO-$d_6$) δ 11.54 (s, 1H), 8.92 (br. s., 1H), 8.53 (br. s., 1H), 8.10 (d, J = 8.0 Hz, 1H), 8.02 (s, 1H), 7.91-7.82 (m, 1H), 7.75 (d, J = 8.7 Hz, 1H), 7.54-7.40 (m, 2H), 5.89 (s, 1H), 4.39-4.27 (m, 2H), 4.24-4.12 (m, 1H), 3.93 (d, J = 7.6 Hz, 1H), 3.66 (d, J = 7.4 Hz, 1H), 3.04 (t, J = 12.5 Hz, 1H), 2.61 (s, 3H), 2.48-2.37 (m, 1H), 2.26 (s, 3H), 2.12 (s, 3H), 1.86 (d, J = 12.5 Hz, 1H), 1.63-1.48 (m, 4H), 1.46-1.32 (m, 1H), 1.17-0.99 (m, 1H), 0.65 (d, J = 12.7 Hz, 1H) | 499 |

-continued

| Compound Number | Name | ¹H NMR | m/z |
|---|---|---|---|
| 443 | (R or S)-N-((4,6-dimethyl-2-oxo-1,2-dihydropyridin-3-yl)methyl)-2-methyl-6-(pyrazin-2-yl)-1-(1-(tetrahydro-2H-pyran-4-yl)ethyl)-1H-indole-3-carboxamide | | 500 |
| 444 | (R or S)-N-((4,6-dimethyl-2-oxo-1,2-dihydropyridin-3-yl)methyl)-2-methyl-1-(1-(tetrahydro-2H-pyran-4-yl)ethyl)-6-(thiazole-4-yl)-1H-indole-3-carboxamide | | 505 |

Step 9: (R or S)-N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (Compound 326)

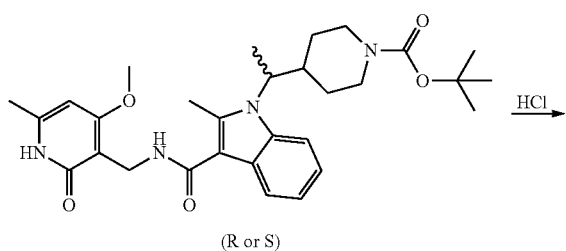

(R or S)

HCl

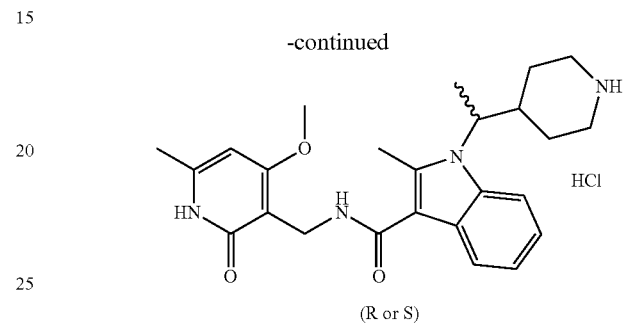

(R or S)

A 250 mL round bottom flask was charged with a magnetic stir bar, (R or S)-tert-butyl 4-(1-(3-((4-methoxy-6-methyl-2-oxo-1,2-dihydropyridin-3-yl)methylcarbamoyl)-2-methyl-1H-indol-1-yl)ethyl)piperidine-1-carboxylate (Compound 327) (1.850 g, 3.45 mmol), MeOH (13.79 ml, 3.45 mmol), and HCl (2.59 ml, 10.34 mmol) (4 N in dioxane). The reaction was allowed to stir at rt for 6 h before being conc, in vacuo to afford the title compound (1.65 g, 3.14 mmol, 91% yield). LCMS 437 (M+1)⁺.

The compounds shown in the following table were prepared according to the general procedure outlined in Step 9 using the appropriate starting materials. The structures of the compounds are shown in FIG. 1.

| Compound Number | Name | ¹H NMR | m/z |
|---|---|---|---|
| 379 | (R or S)-N-((4,6-dimethyl-2-oxo-1,2-dihydropyridin-3-yl)methyl)-2-methyl-1-(1-(piperidin-4-yl)ethyl)-1H-indole-3-carboxamide hydrochloride | (400 MHz, DMSO-d₆) δ 11.61 (br. s., 1H), 8.52 (d, J = 10.3 Hz, 1H), 8.14 (br. s., 1H), 7.75 (d, J = 7.8 Hz, 1H), 7.68-7.58 (m, 2H), 7.15-7.03 (m, 2H), 5.90 (s, 1H), 4.38-4.25 (m, 2H), 4.25-4.14 (m, 1H), 3.37 (d, J = 12.0 Hz, 1H), 3.08 (d, J = 12.7 Hz, 1H), 2.91 (d, J = 12.7 Hz, 1H), 2.73-2.61 (m, 2H), 2.58 (s, 3H), 2.27 (s, 3H), 2.12 (s, 3H), 2.07 (br. s., 1H), 1.56 (d, J = 6.9 Hz, 3H), 1.46 (br. s., 1H), 1.16 (d, J = 11.1 Hz, 1H), 0.86 (d, J = 13.4 Hz, 1H) | 421 |
| 438 | (R or S)-N-((4-(difluoromethoxy)-6-methyl-2-oxo-1,2-dihydropyridin-3-yl)methyl)-2-methyl-1-(1-(piperidin-4-yl)ethyl)-1H-indole-3-carboxamide hydrochloride | | 473 |
| 439 | (R or S)-N-((4-ethyl-6-methyl-2-oxo-1,2-dihydropyridin-3-yl)methyl)-2-methyl-1-(1-(piperidin-4-yl)ethyl)-1H-indole-3-carboxamide hydrochloride | | 435 |

| Compound Number | Name | ¹H NMR | m/z |
|---|---|---|---|
| 376 | (R or S)-1-(1-(1-(azetidin-3-yl)piperidin-4-yl)ethyl)-N-((4,6-dimethyl-2-oxo-1,2-dihydropyridin-3-yl)methyl)-2-methyl-1H-indole-3-carboxamide hydrochloride | (400 MHz, DMSO-$d_6$) δ 12.27-12.10 (m, 1H), 11.96-11.72 (m, 1H), 9.80 (br. s., 1H), 9.19 (br. s., 2H), 7.89-7.67 (m, 2H), 7.62 (d, J = 7.6 Hz, 1H), 7.09 (quin, J = 6.6 Hz, 2H), 5.99 (s, 1H), 4.59-4.36 (m, 3H), 4.24-3.95 (m, 2H), 3.48 (d, J = 13.2 Hz, 1H), 3.17 (d, J = 12.0 Hz, 1H), 2.87 (br. s, 1H), 2.70 (br. s., 2H), 2.58 (s, 3H), 2.34-2.25 (m, 3H), 2.19-2.10 (m, 3H), 1.75 (d, J = 12.3 Hz, 1H), 1.57 (d, J = 6.7 Hz, 3H), 1.47 (d, J = 12.7 Hz, 2H), 1.33-1.21 (m, 2H), 0.85 (d, J = 13.6 Hz, 1H) | 476 |

Step 10: (R or S)-isopropyl 4-(1-(3-((4-methoxy-6-methyl-2-oxo-1,2-dihydropyridin-3-yl)methylcarbamoyl)-2-methyl-1H-indol-1-yl)ethyl)piperidine-1-carboxylate (Compound 346)

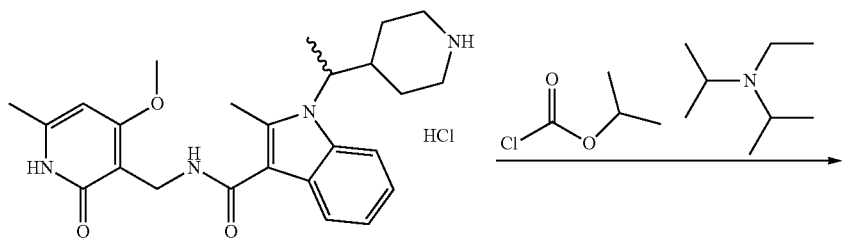

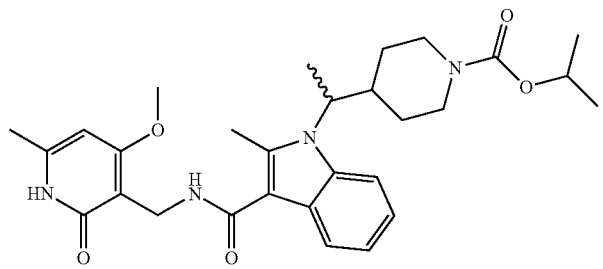

A 250 mL round bottom flask was charged with a magnetic stir bar, (R or S)-N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (0.467 g, 0.987 mmol) (Compound 326), DMF (2.468 ml, 0.987 mmol), THF (2.468 ml, 0.987 mmol), and N-ethyl-N-isopropylpropan-2-amine (0.638 g, 4.94 mmol). The reaction was cooled to 0° C. and isopropyl carbonochloridate (0.160 ml, 1.086 mmol) was added drop wise via syringe. The reaction was allowed to stir for 2 h to rt and was then treated with 5 N LiOH for 1 h to remove any acylated pyridone. This material was extracted with ethyl acetate, washed with brine, dried with MgSO₄ and filtered and conc. in vacuo. The resulting material was purified via silica gel chromatography (50 g) using ethyl acetate/MeOH (5:1) as eluent to afford pure title compound as a pale yellow solid (0.300 g, 0.545 mmol, 55.2% yield). LCMS 523 (M+1)⁺; ¹H NMR (DMSO-d6, 400 MHz) δ 11.59 (br. s., 1 H), 7.74 (d, J=7.8 Hz, 1 H), 7.69 (t, J=4.9 Hz, 1 H), 7.62 (d, J=7.8 Hz, 1 H), 7.13-7.01 (m, 2 H), 6.15 (s, 1 H), 4.78-4.67 (m, 1 H), 4.32 (d, J=4.9 Hz, 2 H), 4.23-4.12 (m, 1 H), 4.12-4.02 (m, 1 H), 3.84 (s, 3 H), 3.82-3.74 (m, 1 H), 2.79-2.66 (m, 1 H), 2.58 (s, 3 H), 2.46-2.34 (m, 2 H), 2.20 (s, 3 H), 1.96-1.88 (m, 1 H), 1.58-1.46 (m, 4 H), 1.15 (d, J=6.0 Hz, 6 H), 0.95-0.89 (m, 1 H), 0.74-0.65 (m, 1 H).

The compounds shown in the following table were prepared according to the general procedure outlined in Step 10 using the appropriate starting materials. The structures of the compounds are shown in FIG. 1.

| Compound Number | Name | ¹H NMR | m/z |
|---|---|---|---|
| 336 | (R or S)-N-((4-methoxy-6-methyl-2-oxo-1,2-dihydropyridin-3-yl)methyl)-2-methyl-1-(1-(1-(methylsulfonyl)piperidin-4-yl)ethyl)-1H-indole-3-carboxamide | (400 MHz, DMSO-$d_6$) δ = 11.59 (s, 1H), 7.78-7.66 (m, 2H), 7.64-7.57 (m, 1H), 7.06 (s, 2H), 6.14 (s, 1H), 4.31 (d, J = 4.9 Hz, 2H), 4.25-4.15 (m, 1H), 3.83 (s, 3H), 3.63 (s, 1H), 3.40-3.33 (m, 1H), 2.79 (s, 3H), 2.75-2.65 (m, 1H), 2.60 (s, 3H), 2.45-2.27 (m, 1H), 2.19 (s, 3H), 2.06-1.98 (m, 1H), 1.55 (d, J = 6.9 Hz, 3H), 1.45-1.36 (m, 1H), 1.28-1.18 (m, 3H), 1.14-1.03 (m, 1H), 0.83-0.74 (m, 1H) | 515 |
| 337 | (R or S)-1-(1-(2-hydroxy-2-methylpropanoyl)piperidin-4-yl)-N-((4-methoxy-6-methyl-2-oxo-1,2-dihydropyridin-3-yl)methyl)-2-methyl-1H-indole-3-carboxamide | (400 MHz, DMSO-$d_6$) δ 11.58 (br. s., 1H), 7.77-7.67 (m, 2H), 7.66-7.60 (m, 1H), 7.06 (s, 2H), 6.14 (s, 1H), 5.32-5.23 (m, 1H), 4.31 (d, J = 4.5 Hz, 2H), 4.19-4.10 (m, 1H), 3.83 (s, 3H), 2.75-2.62 (m, 2H), 2.58 (s, 3H), 2.19 (s, 4H), 2.00-1.90 (m, 2H), 1.54 (d, J = 6.7 Hz, 3H), 1.32-1.18 (m, 8H), 0.87-0.78 (m, 1H), 0.77-0.67 (m, 1H) | 523 |
| 342 | (R or S)-1-(1-(1-isobutyrylpiperidin-4-yl)ethyl)-N-((4-methoxy-6-methyl-2-oxo-1,2-dihydropyridin-3-yl)methyl)-2-methyl-1H-indole-3-carboxamide | (400 MHz, DMSO-$d_6$) δ = 11.59 (s, 1H), 7.75 (d, J = 7.4 Hz, 1H), 7.72-7.67 (m, 1H), 7.64 (d, J = 8.0 Hz, 1H), 7.14-7.01 (m, 2H), 6.15 (s, 1H), 4.58-4.46 (m, 1H), 4.32 (d, J = 4.9 Hz, 2H), 4.09-3.99 (m, 1H), 3.84 (s, 3H), 3.81-3.72 (m, 1H), 3.08-2.97 (m, 1H), 2.92-2.81 (m, 1H), 2.78-2.65 (m, 3H), 2.59 (br. s., 3H), 2.20 (s, 3H), 2.03-1.90 (m, 1H), 1.59-1.47 (m, 4H), 1.02-0.86 (m, 6H), 0.78-0.69 (m, 1H) | 507 |
| 344 | (R or S)-N-((4-(difluoromethoxy)-6-methyl-2-oxo-1,2-dihydropyridin-3-yl)methyl)-2-methyl-1-(1-(1-(methylsulfonyl)piperidin-4-yl)ethyl)-1H-indole-3-carboxamide | (400 MHz, DMSO-$d_6$) δ 12.02-11.95 (m, 1H), 7.74 (d, J = 8.0 Hz, 1H), 7.66-7.57 (m, 2H), 7.11-7.00 (m, 2H), 6.08 (s, 1H), 4.32 (d, J = 4.5 Hz, 2H), 4.18 (d, J = 7.1 Hz, 1H), 3.64 (d, J = 12.3 Hz, 1H), 3.36 (d, J = 12.0 Hz, 1H), 2.79 (s, 3H), 2.75-2.65 (m, 2H), 2.58 (s, 3H), 2.45-2.27 (m, 2H), 2.20 (s, 3H), 2.07-1.98 (m, 1H), 1.55 (d, J = 6.9 Hz, 3H), 1.40 (d, J = 8.2 Hz, 1H), 1.10 (d, J = 8.9 Hz, 1H), 0.79 (d, J = 12.5 Hz, 1H) | 551 |
| 345 | (R or S)-1-(1-(1-(ethylsulfonyl)piperidin-4-yl)ethyl)-N-((4-methoxy-6-methyl-2-oxo-1,2-dihydropyridin-3-yl)methyl)-2-methyl-1H-indole-3-carboxamide | (400 MHz, DMSO-$d_6$) δ 11.57 (s, 1H), 7.75 (d, J = 8.0 Hz, 1H), 7.69 (t, J = 5.0 Hz, 1H), 7.62 (d, J = 7.4 Hz, 1H), 7.06 (d, J = 7.1 Hz, 2H), 6.15 (s, 1H), 4.32 (d, J = 5.1 Hz, 2H), 4.25-4.15 (m, 1H), 3.84 (s, 3H), 3.73-3.65 (m, 1H), 3.45-3.36 (m, 1H), 3.02-2.93 (m, J = 7.8 Hz, 2H), 2.87-2.77 (m, 1H), 2.75-2.66 (m, 1H), 2.60 (s, 3H), 2.42-2.30 (m, 1H), 2.20 (s, 3H), 2.06-1.97 (m, 1H), 1.58-1.48 (m, 4H), 1.42-1.31 (m, 1H), 1.17 (t, J = 7.5 Hz, 3H), 1.13-1.00 (m, 1H), 0.83-0.73 (m, 1H) | 529 |
| 355 | (R or S)-1-(1-(4-(isopropylsulfonyl)cyclohexyl)ethyl)-N-((4-methoxy-6-methyl-2-oxo-1,2-dihydropyridin-3-yl)methyl)-2-methyl-1H-indole-3-carboxamide | (400 MHz, DMSO-$d_6$) δ 11.59 (s, 1H), 7.76-7.69 (m, 2H), 7.62 (d, 1H), 7.10-7.03 (m, 2H), 6.15 (s, 1H), 4.32 (d, 2H), 4.29-4.26 (m, 2H), 3.84 (s, 3H), 3.72 (br. d., 1H), 3.45 (br. d., 1H), 3.26 (tt, 1H), 2.91 (dt, 1H), 2.60 (s, 3H), 2.20 (s, 3H), 1.97 (br. d., 1H), 1.54 (d, 3H), 1.35-1.24 (m, 2H), 1.18 (d, 3H), 1.16 (d, 3H), 1.05-0.78 (m, 2H) | 543 |

-continued

| Compound Number | Name | $^1$H NMR | m/z |
|---|---|---|---|
| 357 | (R or S)-isobutyl 4-(1-(3-(((4-methoxy-6-methyl-2-oxo-1,2-dihydropyridin-3-yl)methyl)carbamoyl)-2-methyl-1H-indol-1-yl)ethyl)piperidine-1-carboxylate | (400 MHz, DMSO-$d_6$) δ 11.60 (br. s., 1H), 7.75-7.60 (m, 3H), 7.10-7.03 (m, 2H), 6.15 (s, 1H) 4.33 (d, 1H), 4.13-4.06 (m, 1H), 3.84 (s, 3H), 3.74 (d, 1H), 2.80-2.60 (m, 3H), 2.58 (s, 1H), 2.50-2.42 (m, 2H), 1.96-1.90 (m, 1H), 1.54 (d, 3H), 1.25-1.22 (m, 1H), 0.98-0.72 (m, 6H) | 537 |
| 368 | (R or S)-N-((4,6-dimethyl-2-oxo-1,2-dihydropyridin-3-yl)methyl)-1-(1-(1-(ethylsulfonyl)piperidin-4-yl)ethyl)-2-methyl-1H-indole-3-carboxamide | (400 MHz, DMSO-$d_6$) δ 11.59 (s, 1H), 7.78-7.71 (m, 1H), 7.66-7.57 (m, 2H), 7.07 (s, 2H), 5.89 (s, 1H), 4.32 (s, 2H), 4.25-4.15 (m, 1H), 3.65-3.59 (m, 1H), 3.19-3.10 (m, 1H), 2.98 (d, J = 7.4 Hz, 2H), 2.87-2.77 (m, 1H), 2.72-2.65 (m, 1H), 2.58 (s, 3H), 2.27 (s, 3H), 2.12 (s, 3H), 1.55 (d, J = 6.9 Hz, 4H), 1.42-1.33 (m, 2H), 1.17 (t, J = 7.4 Hz, 3H), 1.12-1.00 (m, 1H), 0.84-0.74 (m, 1H) | 513 |
| 382 | (R or S)-N-((4,6-dimethyl-2-oxo-1,2-dihydropyridin-3-yl)methyl)-2-methyl-1-(1-(1-(methylsulfonyl)piperidin-4-yl)ethyl)-1H-indole-3-carboxamide | (400 MHz, DMSO-$d_6$) δ 11.60 (s, 1H), 7.75 (d, J = 7.1 Hz, 1H), 7.65-7.58 (m, 2H), 7.12-7.02 (m, 2H), 5.89 (s, 1H), 4.38-4.25 (m, 2H), 4.20 (dd, J = 7.0, 10.6 Hz, 1H), 2.80 (s, 3H), 2.76-2.67 (m, 2H), 2.59 (s, 3H), 2.46-2.31 (m, 2H), 2.27 (s, 3H), 2.12 (s, 3H), 1.55 (d, J = 6.9 Hz, 3H), 1.51 (br. s., 1H), 1.47-1.34 (m, 1H), 1.29-3.21 (m, 1H), 1.17-1.04 (m, 1H), 0.80 (d, J = 12.9 Hz, 1H) | 499 |

Example 27

Synthesis of (R or S)-1-(1-(1-isopropylpiperidin-4-yl)ethyl)-N-((4-methoxy-6-methyl-2-oxo-1,2-dihydropyridin-3-yl)methyl)-2-methyl-1H-indole-3-carboxamide (Compound 358)

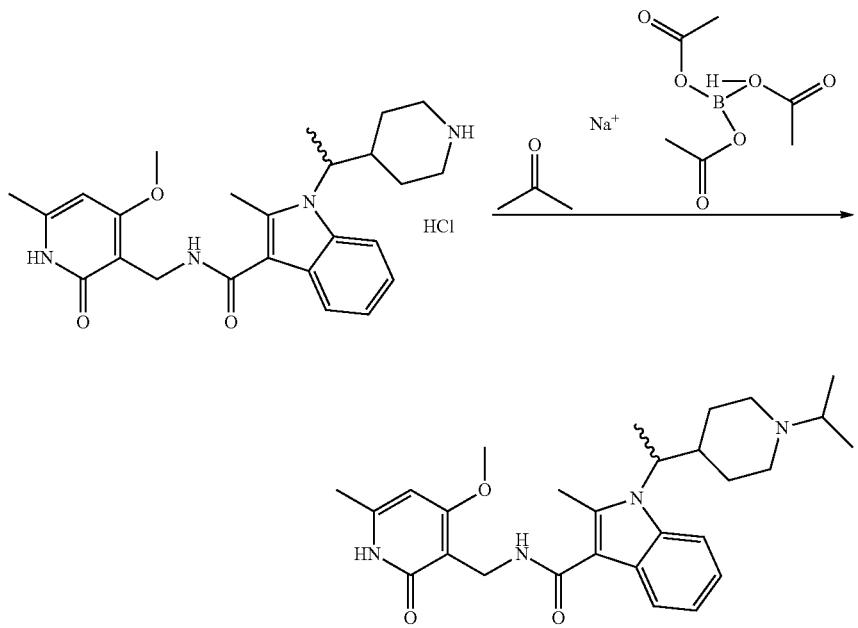

A 25 mL vial was charged with a magnetic stir bar, (R or S)-N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (Compound 326), THF (2.114 ml, 0.211 mmol), propan-2-one (0.061 g, 1.057 mmol), and sodium triacetoxyborohydride (0.224 g, 1.057 mmol). The reaction was allowed to stir at rt for 12 h. The reaction was inverse quenched onto sat'd aqueous NaHCO$_3$, extracted with ethyl acetate and conc. in vacuo. The resulting material was treated with 10 mL 7 N ammonia in MeOH and was conc in vacuo to yield material which was purified via silica gel chromatography (10 g) using DCM/MeOH/NH$_4$OH (90:1: 0.1) as eluent to afford 33 mg, (0.065 mmol, 31.0% yield) of the title compound as a white solid.). LCMS 479 (M+1)$^+$; $^1$H NMR (DMSO-d6, 400 MHz) δ 11.59 (s., 1H), 7.64-7.82 (m, 2H), 7.59 (d, 1H), 6.95-7.17 (m, 2H), 6.15 (s, 1H), 4.32 (d, 2H), 4.04-4.24 (m, 1H), 3.84 (σ, 3H), 2.77-2.93 (μ, 2H), 2.68 (δ, 1H), 2.60 (σ, 3H), 2.20 (σ, 3H), 2.08-2.15 (μ, 1H), 1.92 (δ, 1H), 1.83 (βρ. σ., 1H), 1.54 (δ, 3H), 1.27-1.43 (μ, 2H), 0.91 (τ, 6H), 0.71-0.67 (μ, 2H).

The compounds shown in the following table were prepared according to the general procedure outlined in this Example using the appropriate starting materials. The structures of the compounds are shown in FIG. 1.

| Compound Number | Name | $^1$H NMR | m/z |
| --- | --- | --- | --- |
| 341 | (R or S)-N-((4-methoxy-6-methyl-2-oxo-1,2-dihydropyridin-3-yl)methyl)-2-methyl-1-(1-(1-(oxetan-3-yl)piperidin-4-yl)ethyl)-1H-indole-3-carboxamide | (400 MHz, DMSO-d$_6$) δ 11.58 (s, 1H), 7.76-7.65 (m, 2H), 7.59 (d, J = 7.8 Hz, 1H), 7.10-6.99 (m, 2H), 6.14 (s, 1H), 4.49 (t, J = 6.4 Hz, 1H), 4.43 (t, J = 6.5 Hz, 1H), 4.37 (t, J = 6.1 Hz, 1H), 4.34-4.28 (m, 3H), 4.21-4.10 (m, 1H), 3.83 (s, 3H), 3.30-3.23 (m, 1H), 2.75 (br. s., 1H), 2.71-2.64 (m, 1H), 2.60 (s, 3H), 2.19 (s, 4H), 1.90 (br. s., 1H), 1.75 (br. s., 1H), 1.53 (d, J = 6.9 Hz, 3H), 1.42 (br. s., 2H), 1.11-0.98 (m, 1H), 0.72-0.63 (m, 1H) | 493 |
| 343 | (R or S)-N-((4-methoxy-6-methyl-2-oxo-1,2-dihydropyridin-3-yl)methyl)-2-methyl-1-(1-(1-methylpiperidin-4-yl)ethyl)-1H-indole-3-carboxamide | (400 MHz, DMSO-d$_6$) δ 11.58 (s, 1H), 7.76-7.65 (m, 2H), 7.59 (d, J = 7.6 Hz, 1H), 7.11-6.99 (m, 2H), 6.14 (s, 1H), 4.31 (d, J = 5.1 Hz, 2H), 4.13 (br. s., 1H), 3.83 (s, 3H), 2.83 (d, J = 10.0 Hz, 1H), 2.61-2.52 (m, 5H), 2.19 (s, 3H), 2.09 (s, 4H), 1.88 (d, J = 10.7 Hz, 2H), 1.53 (d, J = 6.7 Hz, 3H), 1.34 (br. s., 1H), 1.02 (d, J = 8.2 Hz, 1H), 0.66 (br. s., 1H) | 451 |
| 359 | (R or S)-N-((4-methoxy-6-methyl-2-oxo-1,2-dihydropyridin-3-yl)methyl)-1-(1-(1-(2-methoxyethyl)piperidin-4-yl)ethyl)-2-methyl-1H-indole-3-carboxamide | (400 MHz, DMSO-d$_6$) δ 11.59 (s, 1H), 7.77-7.66 (m, 2H), 7.60 (d, J = 7.8 Hz, 1H), 7.12-7.01 (m, 2H), 6.15 (s, 1H), 4.32 (d, J = 4.9 Hz, 2H), 4.13 (d, J = 7.1 Hz, 1H), 3.85 (s, 3H), 3.36 (t, J = 5.9 Hz, 2H), 3.19 (s, 3H), 2.94 (d, J = 10.5 Hz, 1H), 2.71-2.56 (m, 5H), 2.43-2.32 (m, 2H), 2.24-2.12 (m, 4H), 1.54 (d, J = 6.9 Hz, 4H), 1.39-1.27 (m, 2H), 1.02 (d, J = 8.7 Hz, 1H), 0.65 (d, J = 12.7 Hz, 1H) | 495 |
| 360 | (R or S)-1-(1-(1-ethylpiperidin-4-yl)ethyl)-N-((4-methoxy-6-methyl-2-oxo-1,2-dihydropyridin-3-yl)methyl)-2-methyl-1H-indole-3-caboxamide | (400 MHz, DMSO-d$_6$) δ 11.79-11.45 (m, 1H), 7.78-7.65 (m, 2H), 7.59 (d, J = 7.8 Hz, 1H), 7.14-6.99 (m, 2H), 6.15 (s, 1H), 4.32 (d, J = 4.9 Hz, 2H), 4.20-4.08 (m, 1H), 3.84 (s, 3H), 2.98-2.89 (m, 1H), 2.71-2.61 (m, 2H), 2.59 (s, 3H), 2.27-2.21 (m, 2H), 2.20 (s, 3H), 1.94-1.80 (m, 2H), 1.54 (s, 4H), 1.38-1.28 (m, 1H), 1.06-0.98 (m, 1H), 0.93 (t, J = 7.1 Hz, 3H), 0.71-0.63 (m, 1H) | 465 |
| 363 | (R or S)-ethyl 2-(4-(1-(3-(((4-methoxy-6-methyl-2-oxo-1,2-dihydropyridin-3-yl)methyl)carbamoyl)-2-methyl-1H-indol-1-yl)ethyl)piperidin-1-yl)acetate | (400 MHz, DMSO-d$_6$) δ 11.59 (br. s., 1H), 7.81-7.65 (m, 2H), 7.60 (d, J = 7.4 Hz, 1H), 7.16-6.98 (m, 2H), 6.15 (s, 1H), 4.32 (d, J = 4.9 Hz, 2H), 4.23-4.11 (m, 1H), 4.04 (q, J = 7.0 Hz, 2H), 3.84 (s, 3H), 2.95-2.86 (m, 1H), 2.60 (s, 5H), 2.20 (s, 4H), 1.94-1.79 (m, 2H), 1.54 (d, J = 6.9 Hz, 4H), 1.41-1.32 (m, 1H), 1.15 (t, J = 7.1 Hz, 3H), 1.04 (d, J = 6.0 Hz, 2H), 0.71-0.61 (m, 1H) | 523 |
| 366 | (R or S)-N-((4-ethyl-6-methyl-2-oxo-1,2-dihydropyridin-3-yl)methyl)-2-methyl-1-(1-(1-methylpiperidin-4-yl)ethyl)-1H-indole-3-carboxamide | (400 MHz, DMSO-d$_6$) δ 11.63 (s, 1H), 7.74 (d, J = 7.6 Hz, 1H), 7.65-7.56 (m, 2H), 7.12-7.01 (m, 2H), 5.94 (s, 1H), 4.34 (t, J = 5.1 Hz, 2H), 4.19-4.09 (m, 1H), 2.88 (br. s., 1H), 2.71-2.56 (m, 6H), 2.14 (s, 7H), 1.91 (d, J = 12.5 Hz, 1H), 1.54 (d, J = 6.9 Hz, 4H), 1.41-1.31 (m, 2H), 1.14 (t, J = 7.6 Hz, 3H), 1.05 (d, J = 9.1 Hz, 1H), 0.68 (d, J = 12.7 Hz, 1H) | 449 |

| Compound Number | Name | ¹H NMR | m/z |
|---|---|---|---|
| 367 | (R or S)-N-((4,6-dimethyl-2-oxo-1,2-dihydropyridin-3-yl)methyl)-2-methyl-1-(1-(1-methylpiperidin-4-yl)ethyl)-1H-indole-3-carboxamide | (400 MHz, DMSO-d₆) δ 11.59 (s, 1H), 7.74 (d, J = 6.9 Hz, 1H), 7.65-7.56 (m, 2H), 7.12-7.01 (m, 2H), 5.89 (s, 1H), 4.38-4.25 (m, 2H), 4.20-4.09 (m, 1H), 2.95 (br. s., 1H), 2.68 (br. s., 2H), 2.58 (s, 3H), 2.27 (s, 3H), 2.21 (br. s., 3H), 2.12 (s, 3H), 1.94 (d, J = 13.8 Hz, 1H), 1.54 (d, J = 6.9 Hz, 4H), 1.44-1.31 (m, 2H), 1.07 (d, J = 12.5 Hz, 1H), 0.71 (d, J = 13.2 Hz, 1H) | 435 |
| 375 | (R or S)-N-((4,6-dimethyl-2-oxo-1,2-dihydropyridin-3-yl)methyl)-2-methyl-1-(1-(1-(oxetan-3-yl)piperidin-4-yl)ethyl)-1H-indole-3-carboxamide | (400 MHz, DMSO-d₆) δ 11.59 (br. s., 1H), 7.73 (d, J = 7.6 Hz, 1H), 7.65-7.55 (m, 2H), 7.12-7.00 (m, 2H), 5.89 (s, 1H), 4.53-4.48 (m, 1H), 4.47-4.42 (m, 1H), 4.38 (s, 1H), 4.31 (t, J = 5.2 Hz, 3H), 4.21-4.10 (m, 1H), 3.31-3.24 (m, 2H), 2.81-2.64 (m, 2H), 2.59 (s, 3H), 2.26 (s, 3H), 2.23-2.16 (m, 1H), 2.12 (s, 3H), 1.98-1.85 (m, 1H), 1.81-1.70 (m, 1H), 1.54 (d, J = 6.9 Hz, 3H), 1.51-1.22 (m, 1H), 1.12-0.96 (m, 2H), 0.73-0.64 (m, 1H) | 477 |
| 380 | (R or S)-N-((4-ethyl-6-methyl-2-oxo-1,2-dihydropyridin-3-yl)methyl)-2-methyl-1-(1-(1-(oxetan-3-yl)piperidin-4-yl)ethyl)-1H-indole-3-carboxamide | (400 MHz, DMSO-d₆) δ 11.63 (br. s., 1H), 7.74 (d, J = 7.36 Hz, 1H), 7.60 (d, J = 8.47 Hz, 2H), 7.06 (quin, J = 7.13 Hz, 3H), 5.94 (s, 1H), 4.51 (t, J = 6.47 Hz, 1H), 4.46 (t, J = 6.35 Hz, 1H), 4.40 (t, J = 6.13 Hz, 1H), 4.37-4.30 (m, 2H), 4.28-4.11 (m, 1H), 3.57 (s, 1H), 3.34 (br. s., 2H), 2.81 (d, J = 10.70 Hz, 1H), 2.67 (d, J = 14.94 Hz, 1H), 2.64-2.57 (m, 4H), 2.21 (d, J = 10.93 Hz, 1H), 2.14 (s, 3H), 1.93 (d, J = 12.49 Hz, 1H), 1.83 (t, J = 11.37 Hz, 1H), 1.54 (d, J = 6.91 Hz, 3H), 1.37 (d, J = 10.48 Hz, 1H), 1.25 (q, J = 6.91 Hz, 1H), 1.14 (t, J = 7.58 Hz, 3H), 1.06 (d, J = 9.81 Hz, 1H), 0.70 (d, J = 12.49 Hz, 1H) | 491 |
| 381 | (R or S)-N-((4,6-dimethyl-2-oxo-1,2-dihydropyridin-3-yl)methyl)-2-methyl-1-(1-(1-(tetrahydro-2H-pyran-4-yl)piperidin-4-yl)ethyl)-1H-indole-3-carboxamide | ¹H NMR (400 MHz, DMSO-d₆) δ 11.60 (br. s., 1H), 7.74 (d, J = 7.13 Hz, 1H), 7.66-7.50 (m, 2H), 7.15-6.99 (m, 2H), 5.89 (s, 1H), 4.40-4.24 (m, 2H), 4.21-4.07 (m, 1H), 3.95-3.78 (m, 2H), 3.57 (s, 1H), 3.32-3.17 (m, 3H), 2.68 (br. s., 1H), 2.58 (s, 3H), 2.33 (br. s., 2H), 2.27 (s, 3H), 2.12 (s, 3H), 2.00-1.88 (m, 2H), 1.75 (d, J = 12.04 Hz, 1H), 1.62 (br. s., 2H), 1.54 (d, J = 6.91 Hz, 3H), 1.46-1.30 (m, 2H), 1.01 (br. s., 1H), 0.72 (br. s., 1H) | 505 |
| 440 | (R or S)-tert-butyl 3-(4-(1-(3-(((4,6-dimethyl-2-oxo-1,2-dihydropyridin-3-yl)methyl)carbamoyl)-2-methyl-1H-indol-1-yl)ethyl)piperidin-1-yl)azetidine-1-carboxylate | | 576 |
| 377 | (R or S)-N-((4,6-dimethyl-2-oxo-1,2-dihydropyridin-3-yl)methyl)-2-methyl-1-(1-(1-(1-methylazetidin-3-yl)piperidin-4-yl)ethyl)-1H-indole-3-carboxamide | (400 MHz, DMSO-d₆) δ 11.63-11.56 (m, 1H), 7.76-7.70 (m, 1H), 7.64-7.55 (m, 2H), 7.05 (s, 2H), 5.89 (s, 1H), 4.56 (s, 4H), 4.31 (s, 2H), 4.19-4.09 (m, 1H), 3.36 (d, J = 4.9 Hz, 1H), 2.77-2.56 (m, 5H), 2.26 (s, 3H), 2.18 (s, 3H), 2.12 (s, 3H), 1.94-1.85 (m, 1H), 1.78-1.67 (m, 1H), 1.53 (d, J = 6.9 Hz, 3H), 1.50-1.45 (m, 1H), 1.44-1.22 (m, 2H), 1.07-0.93 (m, 1H), 0.71-0.61 (m, 1H) | 490 |

Example 28

Synthesis of (R or S)-1-(1-(1-(2-fluoroethyl)piperidin-4-yl)ethyl)-N-((4-methoxy-6-methyl-2-oxo-1,2-dihydropyridin-3-yl)methyl)-2-methyl-1H-indole-3-carboxamide (Compound 356)

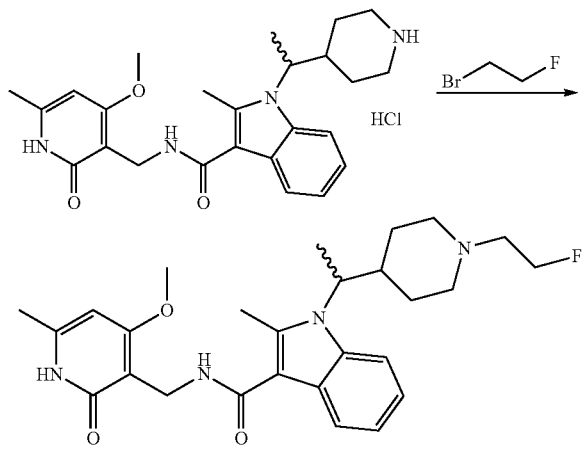

A 25 mL vial was charged with a magnetic stir bar, (R or S)-N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (Compound 326) (0.062 g, 0.131 mmol), K$_2$CO$_3$ (0.072 g, 0.524 mmol), MeCN (0.655 ml, 0.131 mmol), DMF (0.262 ml, 0.131 mmol) and 1-bromo-2-fluoroethane (0.020 ml, 0.262 mmol). The reaction was capped and heated to 82° C. with stirring for 4 h. The reaction was allowed to cool to rt, filtered, and the filtrate was pre-absorbed onto silica gel (12 g). The material was purified via SiO$_2$ chromatography (25 g) using DCM/MeOH/Et$_3$N (85:15:0.5) as eluent to afford the title compound as an off white solid (30 mg, 0.059 mmol, 45.1% yield).). LCMS 483 (M+1)$^+$; $^1$H NMR (DMSO-d6, 400 MHz) δ 11.59 (s, 1H), 7.75-7.68 (m, 2H), 7.60 (d, 1H) 7.09-7.03 (m, 2H), 6.15 (s, 1H) 4.53-4.51 (m, 1H), 4.42-4.39 (m, 1H), 4.32 (d, 2H), 4.24-4.2 (m, 1H), 3.84 (s, 3H), 2.98 (br. d., 1H), 2.70-2.49 (m, 4H), 2.60 (s, 3H), 2.20 (s, 3H), 2.01 (dt, 1H), 1.92-1.90 (m, 1H), 1.75-1.71 (m, 1H), 1.54 (d, 3H), 1.38-1.36 (m, 1H), 1.02-0.98 (m, 1H), 0.7-0.66 (br. d., 1H).

The compounds shown in the following table were prepared according to the general procedure outlined in this Example using the appropriate starting materials. The structures of the compounds are shown in FIG. 1.

| Compound Number | Name | $^1$H NMR | m/z |
|---|---|---|---|
| 362 | (R or S)-1-(1-(1-(2,2-difluoroethyl)piperidin-4-yl)ethyl)-N-((4-methoxy-6-methyl-2-oxo-1,2-dihydropyridin-3-yl)methyl)-2-methyl-1H-indole-3-carboxamide | (400 MHz, DMSO-d$_6$) δ = 11.60 (br. s., 1 H), 7.77-7.66 (m, 2 H), 7.60 (d, J = 7.6 Hz, 1 H), 7.14-7.00 (m, 2 H), 6.15 (s, 1 H), 6.06 (t, J = 55.7 Hz, 1 H), 4.32 (d, J = 4.9 Hz, 2 H), 4.15 (br. s., 1 H), 3.84 (s, 3 H), 3.03-2.93 (m, 2 H), 2.73-2.62 (m, 3 H), 2.60 (s, 3 H), 2.26-2.10 (m, 4 H), 1.93-1.79 (m, 1 H), 1.59-1.46 (m, 4 H), 1.41-1.29 (m, 1 H), 1.11-0.97 (m, 1 H), 0.67 (br. s., 1 H) | 501 |
| 378 | (R or S)-N-((4-methoxy-6-methyl-2-oxo-1,2-dihydropyridin-3-yl)methyl)-2-methyl-1-(1-(1-(3,3,3-trifluoropropyl)piperidin-4-yl)ethyl)-1H-indole-3-carboxamide | (400 MHz, DMSO-d$_6$) δ = 11.60 (br. s., 1 H), 7.78-7.66 (m, 2 H), 7.60 (d, J = 8.2 Hz, 1 H), 7.13-7.00 (m, 2 H), 6.15 (s, 1 H), 4.32 (d, J = 4.9 Hz, 2 H), 4.22-4.09 (m, 1 H), 3.84 (s, 3 H), 3.03-2.91 (m, 1 H), 2.73-2.64 (m, 1 H), 2.60 (s, 3 H), 2.48-2.31 (m, 5 H), 2.20 (s, 3 H), 2.01-1.85 (m, 2 H), 1.58-1.46 (m, 4 H), 1.36-1.29 (m, 1 H), 1.08-0.98 (m, 1 H), 0.73-0.62 (m, 1 H) | 533 |
| 365 | (R or S)-N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide | (500 MHz, DMSO-d$_6$) δ = 11.59 (s, 1 H), 7.74 (d, J = 7.6 Hz, 1 H), 7.71-7.66 (m, 1 H), 7.61 (d, J = 7.8 Hz, 1 H), 7.13-7.01 (m, 2 H), 6.15 (s, 1 H), 4.32 (4, J = 4.9 Hz, 2 H), 4.22-4.12 (m, 1 H), 3.84 (s, 3 H), 3.15-2.95 (m, 3 H), 2.75-2.66 (m, 1 H), 2.60 (s, 3 H), 2.39-2.31 (m, 1 H), 2.20 (s, 3 H), 2.05-1.98 (m, 1 H), 1.92-1.84 (m, 1 H), 1.56-1.46 (m, 4 H), 1.42-1.32 (m, 1 H), 1.11-1.01 (m, 1 H), 0.69-0.62 (m, 1 H) | 519 |
| 441 | (R or S)-1-(1-(1-(2,2-difluoroethyl)piperidin-4-yl)ethyl)-N-((4,6-dimethyl-2-oxo-1,2-dihydropyridin-3-yl)methyl)-2-methyl-1H-indole-3-carboxamide | (400 MHz, DMSO-d$_6$) δ = 11.59 (s, 1 H), 7.73 (d, J = 7.8 Hz, 1 H), 7.65-7.55 (m, 2 H), 7.12-7.00 (m, 2 H), 6.22-5.90 (m, 1 H), 5.89 (s, 1 H), 4.36-4.25 (m, 2 H), 4.20-4.09 (m, 1 H), 3.01-2.93 (m, 1 H), 2.72-2.59 (m, 3 H), 2.58 (s, 3 H), 2.26 (s, 3 H), 2.21-2.13 (m, 2 H), 2.12 (s, 3 H), 1.92-1.79 (m, 2 H), 1.53 (s, 4 H), 1.41-1.29 (m, 1 H), 1.10-0.97 (m, 1 H), 0.70-0.59 (m, 1 H) | 485 |

Example 29

Synthesis of (R or S)-N-((4-methoxy-6-methyl-2-oxo-1,2-dihydropyridin-3-yl)methyl)-2-methyl-1-(1-(1-(pyrimidin-2-yl)piperidin-4-yl)ethyl)-1H-indole-3-carboxamide (Compound 361)

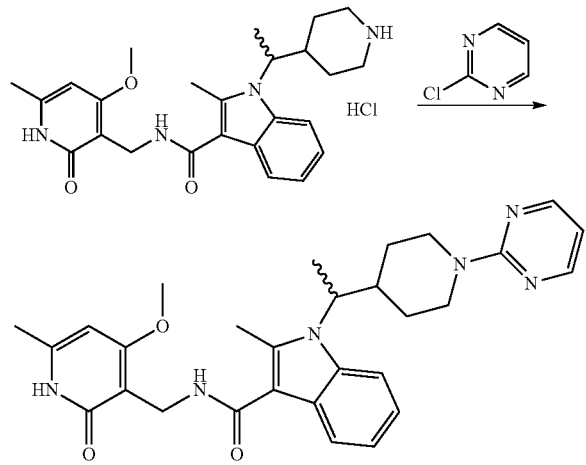

To a re-sealable vial was added 2-chloropyrimidine (185 mg, 1.611 mmol), (R or S)-N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (508 mg, 1.074 mmol) (Compound 326), and EtOH (8 mL). To this solution was added Et$_3$N (449 µl, 3.22 mmol). The vial was sealed and heated to 100° C. overnight. The solution was allowed to cool to room temperature and concentrated in vacuo. The crude residue was purified via silica gel chromatography (hexanes: (3:2 DCM:IPA)) to afford the title compound as a solid (357 mg, 0.694 mmol, 64.6% yield). LCMS 515 (M+1)$^+$; $^1$H NMR (DMSO-d6, 400 MHz) δ 11.60 (s, 1 H), 8.30 (d, J=4.7 Hz, 2 H), 7.76 (d, J=7.6 Hz, 1 H), 7.73-7.64 (m, 2 H), 7.14-7.01 (m, 2 H), 6.55 (t, J=4.7 Hz, 1 H), 6.15 (s, 1 H), 4.84-4.75 (m, 1 H), 4.57-4.47 (m, 1 H), 4.33 (d, J=4.2 Hz, 2 H), 4.22-4.11 (m, 1 H), 3.84 (s, 3 H), 2.92-2.81 (m, 1 H), 2.63-2.52 (m, 4 H), 2.20 (s, 3H), 2.05-1.94 (m, 1 H), 1.61-1.49 (m, 4 H), 1.34-1.21 (m, 1 H), 1.04-0.91 (m, 1 H), 0.83-0.75 (m, 1 H).

The compound shown in the following table was prepared according to the general procedure outlined in this Example using the appropriate starting materials. The structure of the compound is shown in FIG. 1.

Example 30

Synthesis of (R or S)-1-(1-(1-(2-hydroxyethyl)piperidin-4-yl)ethyl-N-((4-methoxy-6-methyl-2-oxo-1,2-dihydropyridin-3-yl)methyl)-2-methyl-1H-indole-3-carboxamide (Compound 347)

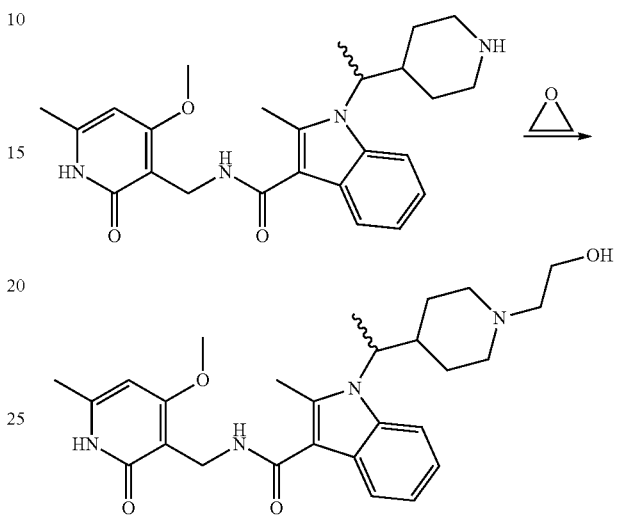

To a sealed tube charged with a magnetic stir bar was added (R or S)-N-((4-methoxy-6-methyl-2-oxo-1,2-dihydropyridin-3-yl)methyl)-2-methyl-1-(1-(piperidin-4-yl)ethyl)-1H-indole-3-carboxamide (Compound 326) (0.1 g, 0.229 mmol) was added DCM (3 mL) and the reaction cooled to 0° C. To the cooled reaction mixture was added oxirane which was condensed into the reaction vial (~1 mL). The reaction was allowed to stir to rt over 4 h and was then conc. in vacuo to afford the crude material which was purified via silica gel chromatography (12 g) using ethyl acetate/MeOH (4:1) as eluent to afford the title compound as a white solid (50 mg). LCMS 481 (M+1)$^+$; $^1$H NMR (DMSO-d6, 400 MHz) δ) δ 11.58 (s, 1 H), 7.77-7.65 (m, 2 H), 7.59 (d, J=7.8 Hz, 1 H), 7.11-6.99 (m, 2 H), 6.14 (s, 1 H), 4.54-4.44 (m, 1 H), 4.31 (d, J=5.1 Hz, 3 H), 4.13 (dd, J=7.1, 10.3 Hz, 1 H), 3.83 (s, 3H), 3.42 (q, J=6.0 Hz, 2 H), 2.93 (br. s., 1 H), 2.71-2.56 (m, 4 H), 2.31 (br. s., 2 H), 2.19 (s, 3 H), 2.03-1.83 (m, 2 H), 1.64 (br. s., 1 H), 1.53 (d, J=6.9 Hz, 3 H), 1.32 (d, J=11.1 Hz, 1 H), 1.02 (d, J=10.3 Hz, 1 H), 0.65 (d, J=11.8 Hz, 1 H).

The compounds shown in the following table were prepared according to the general procedure outlined in this

| Compound Number | Name | $^1$H NMR | m/z |
|---|---|---|---|
| 373 | (R or S)-N-((4-methoxy-6-methyl-2-oxo-1,2-dihydropyridin-3-yl)methyl)-2-methyl-1-(1-(1-(pyridin-2-yl)piperidin-4-yl)ethyl)-1H-indole-3-carboxamide | (400 MHz, DMSO-d$_6$) δ 11.60 (br. s., 1 H), 8.06 (d, J = 3.6 Hz, 1 H), 7.82-7.62 (m, 3 H), 7.51-7.39 (m, 1 H), 7.17-6.98 (m, 2 H), 6.75 (d, J = 8.5 Hz, 1 H), 6.61-6.49 (m, 1 H), 6.15 (s, 1 H), 4.49-4.38 (m, 1 H), 4.33 (d, J = 3.8 Hz, 2 H), 4.24-4.03 (m, 2 H), 3.85 (s, 3 H), 2.90-2.70 (m, 2 H), 2.58 (s, 3 H), 2.20 (s, 3 H), 2.06-1.91 (m, 1 H), 1.63-1.47 (m, 4 H), 1.40-1.27 (m, 1 H), 1.07-0.94 (m, 1 H), 0.82-0.72 (m, 1 H) | 514 |

Example using the appropriate starting materials. The structures of the compounds are shown in FIG. 1.

| Compound Number | Name | 1H NMR | m/z |
|---|---|---|---|
| 352 | (R or S)-1-(1-(2-hydroxy-2-methylpropyl)piperidin-4-yl)ethyl)-N-((4-methoxy-6-methyl-2-oxo-1,2-dihydropyridin-3-yl)methyl)-2-methyl-1H-indole-3-caxboxamide | NMR (400 MHz, DMSO-d6) δ 11.58 (br. s., 1 H), 7.76-7.65 (m, 2 H), 7.58 (d, J = 7.8 Hz, 1 H), 7.10-6.99 (m, 2 H), 6.14 (s, 1 H), 4.31 (d, J = 4.9 Hz, 2 H), 4.14 (br. s., 1 H), 3.94 (s, 1 H), 3.83 (s, 3 H), 3.56 (s, 2 H), 3.01 (d, J = 11.4 Hz, 1 H), 2.73-2.64 (m, 1 H), 2.59 (s, 3 H), 2.19 (s, 3 H), 2.16-2.03 (m, 2 H), 1.52 (d, J = 6.9 Hz, 4 H), 1.34 (br. s., 2 H), 1.02 (d, J = 4.5 Hz, 7 H), 0.66-0.58 (m, 1 H) | 509 |
| 369 | (R or S)-N-((4,6-dimethyl-2-oxo-1,2-dihydropyridin-3-yl)methyl)-1-(1-(2-hydroxy-2-methylpropyl)piperidin-4-yl)ethyl)-2-methyl-1H-indole-3-carboxamide | (400 MHz, DMSO-d6) δ 11.59 (br. s., 1 H), 7.77-7.69 (m, 1 H), 7.60 (br. s., 2 H), 7.06 (br. s., 2 H), 5.89 (s, 1 H), 4.31 (t, J = 5.7 Hz, 2 H), 4.20-4.09 (m, 1 H), 4.00-3.92 (m, 1 H), 3.58-3.55 (m, 2 H), 3.19-3.10 (m, 1 H), 3.07-2.95 (m, 1 H), 2.74-2.63 (m, 1 H), 2.59 (br. s., 3 H), 2.27 (s, 3 H), 2.12 (s, 3 H), 1.89-1.72 (m, 1 H), 1.54 (br. s., 4 H), 1.30-1.14 (m, 2 H), 1.03 (br. s., 6 H), 0.84-0.57 (m, 2 H) | 493 |

Example 31

Synthesis of (R or S)-N-((4-methoxy-6-methyl-2-oxo-1,2-dihydropyridin-3-yl)methyl)-2-methyl-6-phenyl-1-(1-(tetrahydro-2H-pyran-4-yl)ethyl)-1H-indole-3-carboxamide (Compound 374)

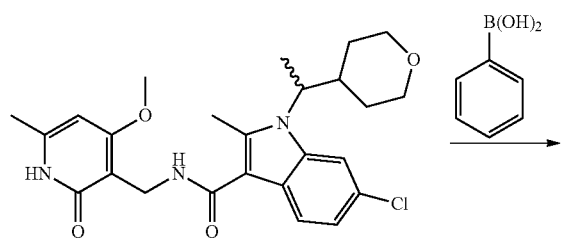

A 25 mL reaction tube was charged with a magnetic stir bar, phenyl boronic acid (72.6 mg, 0.596 mmol), K₃PO₄ (103 mg, 0.447 mmol), X-Phos pre-catalyst (Chloro(2-dicyclohexylphosphino-2',4',6'-triisopropyl-1,1'-biphenyl)[2-(2-aminoethyl)phenyl)]palladium(II)) (4.92 mg, 5.96 μmol), and the vial was sealed. The vial was evacuated/backfilled with nitrogen (3x) before the addition of methyl 6-chloro-2-methyl-1-(1-(tetrahydro-2H-pyran-4-yl)ethyl)-1H-indole-3-carboxylate (Compound 314) (100 mg, 0.298 mmol) as a solution in 1,4-dioxane (1 mL). The vial was then heated to 100° C. overnight with stirring. The vial was then allowed to cool to room temperature and the reaction concentrated in vacuo. The crude residue was purified via SiO₂ chromatography (10 g) using an eluent of ethyl acetate/hexanes (4:1) the title compound as a white solid (106 mg, 0.281 mmol, 94% yield).). LCMS 514 (M+1)⁺; ¹H NMR ¹H NMR (400 MHz, DMSO-d₆) δ=11.59 (s, 1 H), 7.98-7.84 (m, 2 H), 7.75-7.67 (m, 3 H), 7.47 (t, J=7.8 Hz, 2 H), 7.39 (d, J=8.5 Hz, 1 H), 7.35-7.27 (m, 1 H), 6.15 (s, 1 H), 4.35 (d, J=4.9 Hz, 2 H), 4.25-4.12 (m, 1 H), 3.93 (d, J=8.5 Hz, 1 H), 3.86-3.77 (m, 3 H), 3.67 (d, J=8.5 Hz, 1 H), 3.39-3.32 (m, 1 H), 3.10-3.00 (m, 1 H), 2.62 (s, 3 H), 2.21 (s, 3 H), 1.85 (d, J=10.0 Hz, 1 H), 1.63-1.49 (m, 4 H), 1.45-1.33 (m, 1 H), 1.20-0.99 (m, 1 H), 0.66 (d, J=12.0 Hz, 1 H).

Example 32

Synthesis of (R or S)-2-(4-(4-(3-((4-methoxy-6-methyl-2-oxo-1,2-dihydropyridin-3-yl)methylcarbamoyl)-2-methyl-1H-indol-1-yl)ethyl)piperidin-1-yl)acetic acid (Compound 364)

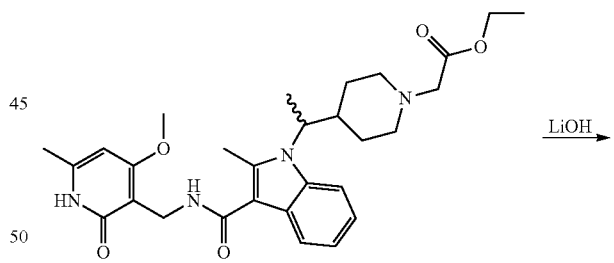

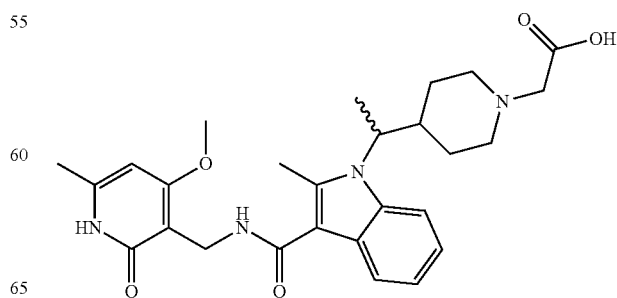

To a round bottomed flask was charged with a magnetic stir bar was added (R or S)-ethyl-2-(4-(1-(3-((4-methoxy-6-methyl-2-oxo-1,2-dihydropyridin-3-yl)methylcarbamoyl)-2-methyl-1H-indol-1-yl)ethyl)piperidin-1-yl)acetate (Compound 363) (69 mg, 0.132 mmol), THF (1.5 mL), MeOH (1.5 mL), and water (0.75 mL). To this solution was added lithium hydroxide monohydrate (5.54 mg, 0.132 mmol) and the reaction stirred at room temperature for 1 h. The organics were removed under reduced pressure and the resulting aqueous solution purified via reverse phase-HPLC (water/MeCN) 0→95% to afford the title compound (66 mg, 0.108 mmol, 82% yield). LCMS 514 (M+1)+ 1H NMR (400 MHz, DMSO-d$_6$) δ=11.67 (s, 1 H), 9.65 (s, 1 H), 7.84-7.68 (m, 2 H), 7.63 (d, J=7.4 Hz, 1 H), 7.14-7.03 (m, 2 H), 6.18 (s, 1 H), 4.33 (d, J=3.6 Hz, 2 H), 4.27-4.15 (m, 1 H), 4.04 (br. s., 2 H), 3.85 (s, 3 H), 3.57 (s, 1 H), 3.35-3.23 (m, 1 H), 3.14-2.99 (m, 1 H), 2.86-2.74 (m, 1 H), 2.62 (s, 3 H), 2.21 (s, 3 H), 2.18-2.08 (m, 1 H), 1.75 (s, 1 H), 1.60-1.49 (m, 4 H), 1.46-1.33 (m, 1 H), 0.92-0.81 (m, 1 H).

Example 33

Synthesis of (R or S)-methyl 2-methyl-1-(1-(tetrahydro-2H-thiopyran-4-yl)ethyl-1H-indole-3-carboxylate

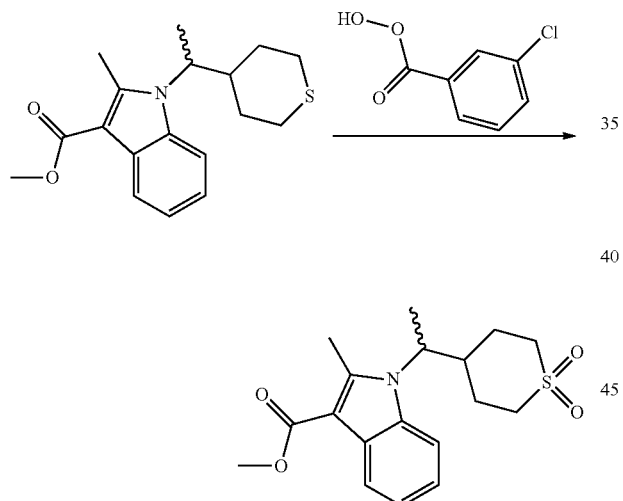

To a round bottomed flask charged with a magnetic stir bar was added (R or S)-methyl 2-methyl-1-(1-(tetrahydro-2H-thiopyran-4-yl)ethyl)-1H-indole-3-carboxylate (Step 6) (109 mg, 0.343 mmol) and DCM (5 mL). This solution was cooled to 0° C. before addition of m-CPBA (154 mg, 0.687 mmol) and the reaction stirred at 0° C. for 30 minutes. The solution was then diluted with water and sat'd aqueous sodium thiosulfate solution and the layers separated. The aqueous was extracted with DCM and the combined organic layers were dried over Na$_2$SO$_4$, filtered, and concentrated in vacuo. The crude residue was purified via silica gel chromatography (12 g) using ethyl acetate/hexanes (1:1) as eluent to afford the title compound (109 mg, 0.343 mmol, 95%). LCMS 350 (M+1)+.

The title compound was used as an alternate starting material in Step 7 of Example 26 for the synthesis of other compounds of the invention.

Example 34

Synthesis of (R or S)-methyl 2-methyl-6-(pyridin-3-yl)-1-(1-(tetrahydro-2H-pyran-4-yl)ethyl)-1H-indole-3-carboxylate This intermediate was used as an alternate starting material in Step 7 set forth in Example 26 for the synthesis of other compounds of the invention.

(R or S)-methyl 2-methyl-1-(1-(tetrahydro-2H-pyran-4-yl)ethyl)-6-(4,4,5,5-tetramethyl-1,3,2-dioxaborolan-2-yl)-1H-indole-3-carboxylate To a round bottomed flask was added Pd(OAc)$_2$ (10.03 mg, 0.045 mmol), potassium acetate (219 mg, 2.233 mmol), 4,4,4',4',5,5,5',5'-octamethyl-2,2'-bi(1,3,2-dioxaborolane) (567 mg, 2.233 mmol), and 2-dicyclohexylphosphino-2',4',6'-triisopropylbiphenyl (XPhos) (85 mg, 0.179 mmol), and the vial was sealed. To this vessel was added (R or S)-methyl 6-chloro-2-methyl-1-(1-(tetrahydro-2H-pyran-4-yl)ethyl)-1H-indole-3-carboxylate (Step 6) (500 mg, 1.489 mmol) dissolved in dioxane (3.4 mL) and the reaction evacuated/backfilled with N$_2$ (3×) before heating to 100° C. overnight. The reaction was then allowed to cool to rt and was diluted with EtOAc. The reaction was filtered through diatomaceous earth and the filtrate concentrated to afford the title compound which was used in subsequent reactions without further purification. LCMS 428 (M+1)⁺.

(R or S)-methyl 2-methyl-6-(pyridin-3-yl)-1-(1-(tetrahydro-2H-pyran-4-yl)ethyl)-1H-indole-3-carboxylate

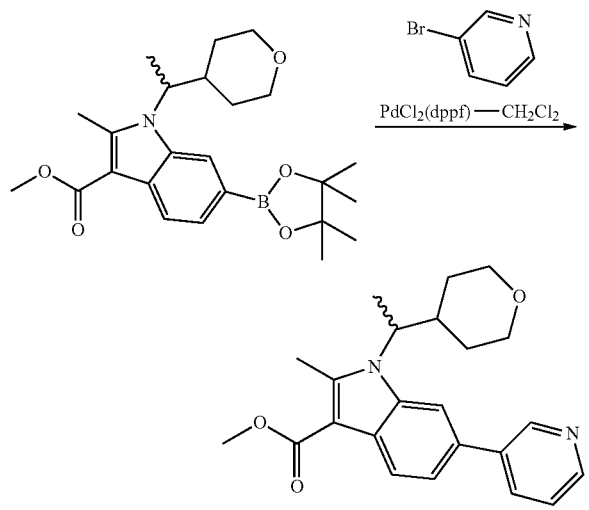

To a re-sealable vial was added K₂CO₃ (206 mg, 1.488 mmol), PdCl₂(dppf)-CH₂Cl₂ adduct (60.8 mg, 0.074 mmol), and the vial was sealed. This vial was evacuated/backfilled with N₂ (3×) before addition of (R or S)-methyl 2-methyl-1-(1-(tetrahydro-2H-pyran-4-yl)ethyl)-6-(4,4,5,5-tetramethyl-1,3,2-dioxaborolan-2-yl)-1H-indole-3-carboxylate (318 mg, 0.744 mmol) dissolved in 1,4-dioxane (4 mL), 3-bromopyridine (71.7 μl, 0.744 mmol), and water (400 μL). The reaction was evacuated/backfilled with N₂ (3×) before heating to 100° C. The solution was cooled to room temperature and diluted with EtOAc. The solution was filtered and concentrated in vacuo. The crude residue was purified via silica gel chromatography (10 g, EtOAc/hex (1:1)) to afford the title compound (101 mg, 0.267 mmol, 35.9% yield). LCMS 379 (M+1)⁺.

The intermediates shown in the following table were prepared according to the general procedure outlined in this Example using the appropriate starting materials.

Example 35

Synthesis of (±)-N-((4,6-dimethyl-2-oxo-1,2-dihydropyridin-3-yl)methyl)-1-(1-(4-fluorophenyl)ethyl)-2-methyl-1H-indole-3-carboxamide (Compound 166)

(±)-1-(1-bromoethyl)-4-fluorobenzene

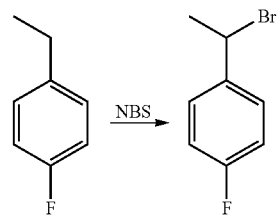

A mixture of 1-ethyl-4-fluorobenzene (0.248 g, 2 mmol), NBS (0.35 g, 2 mmol) and benzoyl peroxide (0.14 g, 0.6 mmol) were dissolved in 20 mL CCl₄. The mixture was stirred at 80° C. for 5 hours and then the reaction was conc. in vacuo and resulting oil was purified via silica gel chromatography (PE-EtOAC 5:1) to give the title compound (330 mg, 80%) as a yellow oil. LCMS 202 (M+H⁺).

The intermediates shown in the following table were prepared according to the general procedure outlined above using the appropriate starting materials and modifications.

| Name | Structure | m/z |
|---|---|---|
| (±)-1-(1-bromoethyl)-4-chlorobenzene | 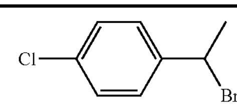 | 218 |
| (±)-1-(1-bromoethyl)-2-methoxybenzene | 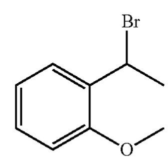 | 206 |

| Name | Structure | m/z |
|---|---|---|
| (R or S)-methyl 2-methyl-6-(pyrazin-2-yl)-1-(1-(tetrahydro-2H-pyran-4-yl)ethyl)-1H-indole-3-carboxylate | 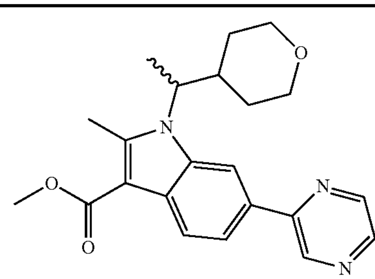 | 379 |
| (R or S)-methyl 2-methyl-1-(1-(tetrahydro-2H-pyran-4-yl)ethyl)-6-(thiazol-4-yl)-1H-indole-3-carboxylate | 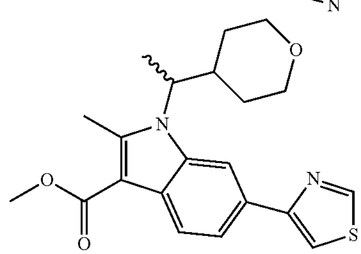 | 385 |

-continued

| Name | Structure | m/z |
|---|---|---|
| (±)-1-bromo-3-(1-bromoethyl)benzene | 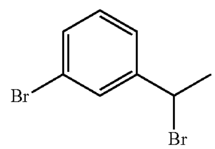 | 264 |
| (±)-2-(1-bromoethyl)-benzonitrile | 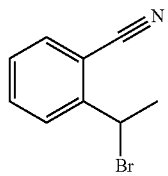 | 210 |
| (±)-1-(1-bromoethyl)-3-methoxybenzene | 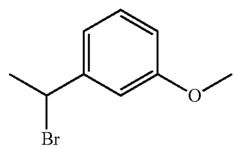 | 216 |

(±)-N-((4,6-dimethyl-2-oxo-1,2-dihydropyridin-3-yl)methyl)-1-(1-(4-fluorophenyl)ethyl)-2-methyl-1H-indole-3-carboxamide (Compound 166)

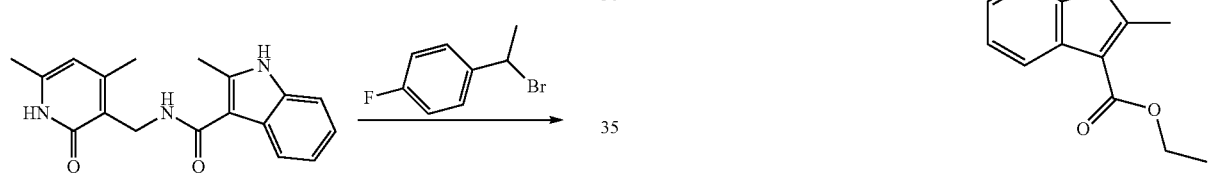

N-((4,6-dimethyl-2-oxo-1,2-dihydropyridin-3-yl)methyl)-2-methyl-1H-indole-3-carboxamide (309 mg, 1.0 mmol) was dissolved in 4 mL DMF, NaH (80 mg, 2.0 mmol) was added, the mixture was stirred at room temperature for 30 min, and then 1-(1-bromoethyl)-4-fluorobenzene (0.404 mg,  2.0 mmol) was added. The mixture was stirred at room temperature overnight and was directly purified by reverse phase HPLC (A:CH$_3$CN, B:water+0.1% HCl. A:B=35:65 ASB C18 150*25 mm) to afford the title compound as a white solid (11 mg, yield 3%). LCMS 432 (M+H$^+$) $^1$H NMR (400 MHz, CDCl$_3$) δ 7.78 (d, J=8 Hz, 1H), 7.33 (m, 1H), 7.14 (s, 1H), 6.96 (m, 2H), 6.92 (m, 1H), 6.85-6.92 (m, 4H), 5.85 (s, 1H), 5.72 (m, 1H), 4.56 (s, 2H), 2.64 (s, 3H), 2.37 (s, 3H), 2.11 (s, 3H), 1.85 (d, J=7.2 Hz, 3H).

Example 36

Synthesis of (±)-1-(1-(4-chlorophenyl)ethyl)-N-((2-hydroxy-4,6-dimethylpyridin-3-yl)methyl)-2-methyl-1H-indole-3-carboxamide (Compound 170)

Step 1: Ethyl 2-methyl-1H-indole-3-carboxylate

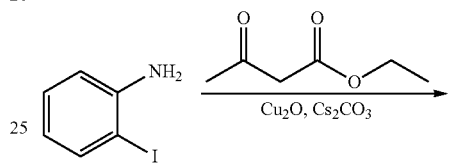

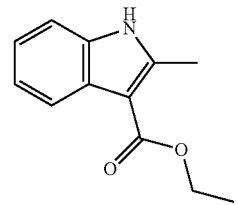

To a mixed solution of dimethyl sulfoxide (100 mL) and water (34 mL), 2-iodobenzenamine (50 g, 228 mmol), ethyl 3-oxobutanoate (35.6 g, 274 mmol), copper(I) oxide (3.3 g, 22.8 mmol) and cesium carbonate (75 g, 228 mmol) was added. The mixture was stirred at 100° C. for 16 hours under nitrogen gas atmosphere. The reaction mixture was filtered through a pad of celite. The filtrate was diluted with water and extracted with ethyl acetate. The organic phase was concentrated in vacuo, and then the residue was purified by column chromatography (silica gel, petroleum ether/ethyl acetate=5:1) to afford the title compound as a light yellow solid (26.6 g, 57.5%). LCMS 204 (M+H)$^+$.

The intermediates shown in the following table were prepared according to the general procedure outlined above for ethyl 2-methyl-1H-indole-3-carboxylate using the appropriate starting materials and modifications.

| Name | Structure | m/z |
|---|---|---|
| ethyl 6-chloro-2-methyl-1H-indole-3-carboxylate | 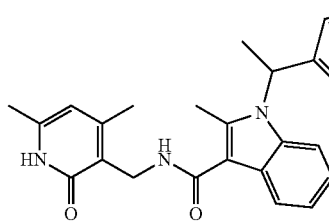 | 239 |

| Name | Structure | m/z |
|------|-----------|-----|
| tert-butyl 2-methyl-1H-indole-3-carboxylate | 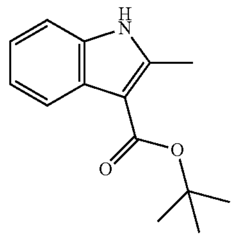 [SMILES: Cc1[nH]c2ccccc2c1C(=O)OC(C)(C)C] | 254 (M + Na$^+$) |
| ethyl 2-methyl-6-(methylsulfonyl)-1H-indole-3-carboxylate | 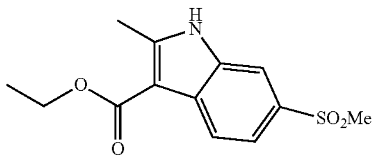 [SMILES: CCOC(=O)c1c(C)[nH]c2cc(S(C)(=O)=O)ccc12] | 282 |

Step 2: (±)-ethyl 1-(1-(4-chlorophenyl)ethyl)-2-methyl-1H-indole-3-carboxylate

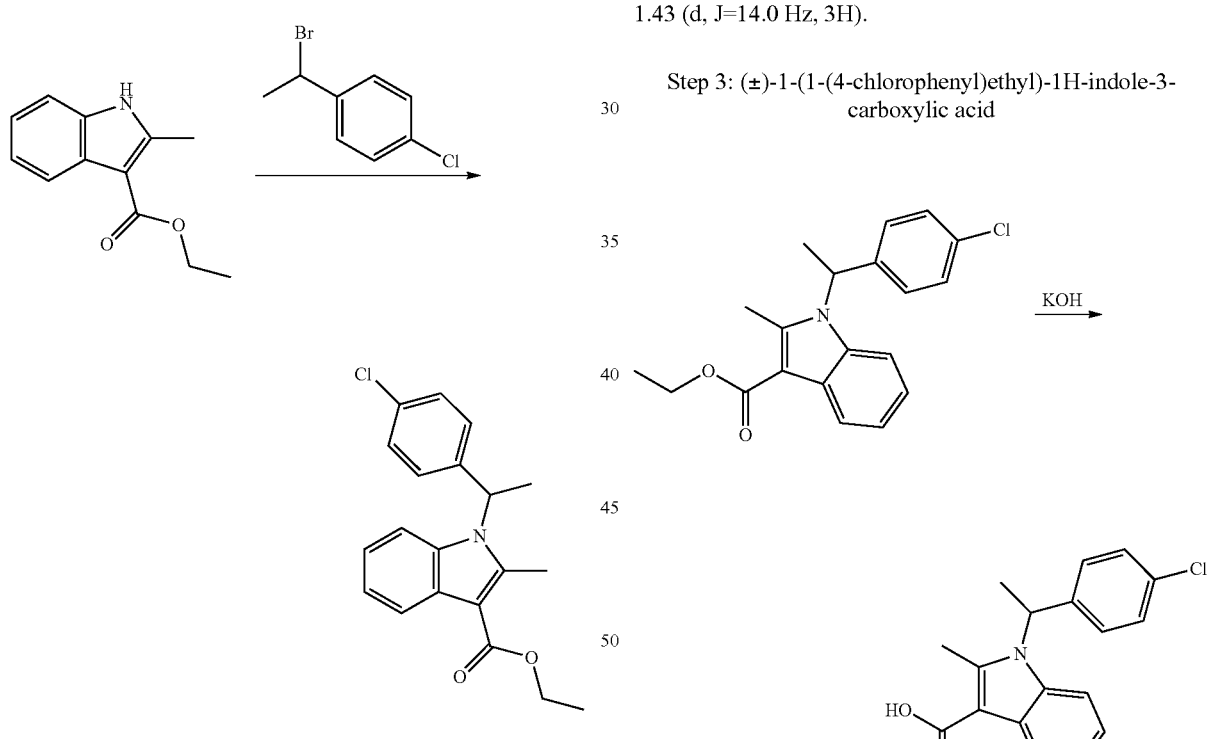

To a solution of ethyl 2-methyl-1H-indole-3-carboxylate (250 mg, 1.23 mmol) in anhydrous DMF (2 mL) was added NaH (60% in mineral oil, 74 mg, 1.85 mmol) at room temperature under N$_2$. The reaction was stirred at 50-60° C. for 30 min. Then the reaction was cooled to 0° C. and a solution of 1-(1-bromoethyl)-4-chlorobenzene (from Example 35; 400 mg, 1.85 mmol) in DMF (1 mL) was added drop-wise. The reaction was stirred at room temperature overnight. Then the mixture was diluted with water and extracted with EtOAc. The organic extract was combined, dried over Na$_2$SO$_4$ and concentrated in vacuo. The residue was purified by silica gel chromatography using an eluent of petroleum ether/EtOAc (60:1) to afford the title compound as a yellow oil. (210 mg, yield 50.1%) $^1$H NMR (Methanol-d4, 400 MHz) δ 8.07-8.04 (m, 1H), 7.33-7.29 (m, 2H), 7.16-7.15 (m, 2H), 7.14-7.08 (m, 1H), 7.07-6.96 (m, 2H), 5.97 (q, J=7.2 Hz, J$_2$=14.4 Hz, 1H), 4.37 (d, J=7.2 Hz, 2H), 2.76 (m, 3H), 1.95 (d, J=6.8 Hz, 3H), 1.43 (d, J=14.0 Hz, 3H).

Step 3: (±)-1-(1-(4-chlorophenyl)ethyl)-1H-indole-3-carboxylic acid

To a mixture of ethyl 1-(1-(4-chlorophenyl)ethyl)-2-methyl-1H-indole-3-carboxylate (210 mg, 0.61 mmol) in MeOH/H$_2$O (6 mL/2 mL) was added KOH (340 mg, 6.1 mmol) at room temperature. The reaction was refluxed overnight. Then the mixture was adjusted to Ph=4 with 1 N HCl and extracted with EtOAc (3×). The combined organic extract were combined and concentrated in vacuo to afford the title compound as a yellow solid (200 mg, yield 105%) which was used without further purification.

Step 4: (±)-1-(1-(4-chlorophenyl)ethyl)-N-((2-hydroxy-4,6-dimethylpyridin-3-yl)methyl)-2-methyl-1H-indole-3-carboxamide (Compound 170)

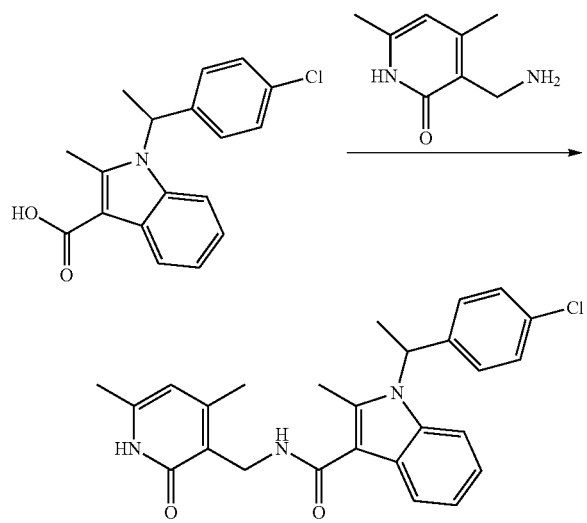

To a solution of 1-(1-(4-chlorophenyl)ethyl)-2-methyl-1H-indole-3-carboxylic acid (200 mg, 0.64 mmol) in anhydrous DCM (5 mL) was added HOBt (130 mg, 0.96 mmol), EDCI (184 mg, 0.96 mmol) and Et$_3$N (194 mg, 1.92 mmol) at room temperature under N$_2$. The reaction was stirred for 30 min and then 3-(aminomethyl)-4,6-dimethylpyridin-2-ol (107 mg, 0.7 mmol) was added. The reaction was stirred at room temperature overnight. The mixture was diluted with water and adjusted to pH 7 and extracted with DCM. The crude product was purified by silica gel chromatography (Eluent: DCM:MeOH=30:1) to afford the title compound a yellow solid. (120 mg, yield 41.9%) $^1$H NMR (DMSO-d6, 400 MHz) δ 11.6 (s, 1H), 7.74-7.68 (m, 2H), 7.39 (dd, J$_1$=2.0 Hz, J$_2$=6.8 Hz, 2H), 7.16 (d, J=8.4 Hz, 2H), 7.06-6.93 (m, 3H), 5.92 (t, J=7.2 Hz, 2H), 4.33 (d, J=5.6 Hz, 2H), 2.59 (s, 3H), 2.26 (s, 3H), 2.11 (s, 3H), 1.87 (d, J=7.2 Hz, 3H); ESI-MS: m/z 447.8 [M+H]$^+$.

Example 37

Synthesis of (±)-1-(1-bromoethyl)-3-methylbenzene

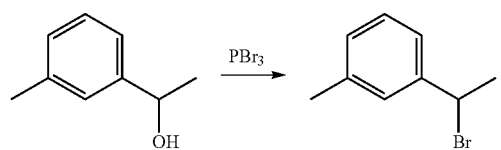

Phosphorus tribromide (4.28 g, 15.9 mmol) was added drop-wise to a stirred neat solution of 1-(m-tolyl)ethanol (0.9 g, 6.6 mmol) at 0° C. After being stirred to room temperature over 12 h, the reaction was carefully quenched with sat'd saturated aqueous NaHCO$_3$ solution and the mixture was extracted with EtOAc. The organic extract was washed with water, dried with MgSO$_4$, and conc. in vacuo to afford the title compound (1.2 g, 91%) as a colorless oil, that was used directly in the next step without further purification. LCMS 200 (M+H$^+$).

The intermediates shown in the following table were prepared according to the general procedure outlined in this example using the appropriate starting materials and modifications.

| Name | Structure | m/z |
|---|---|---|
| (±)-1-(1-bromoethyl)-4-methylbenzene | 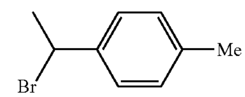 | 200 |
| (±)-1-(1-bromoethyl)-2-methylbenzene | 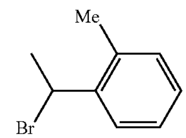 | 200 |
| (±)-1-(1-bromoethyl)-4-(methylsulfonyl)benzene | 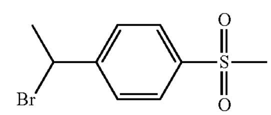 | 264 |
| (±)-1-(1-bromoethyl)-3-chlorobenzene | 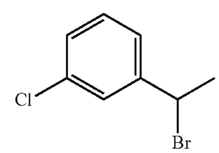 | 220 |
| (±)-1-(1-bromoethyl)-3-(methylsulfonyl)benzene | 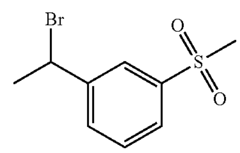 | 264 |
| (±)-3-(1-hydroxyethyl)benzonitrile | 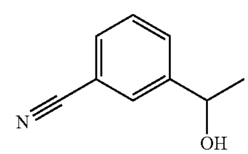 | 211 |

These intermediates were used in place of (±)-1-(1-bromoethyl)-4-fluorobenzene in Example 35 or 1-(1-bromoethyl)-4-chlorobenzene in Example 36, as appropriate, to make other compounds of the invention.

Example 38

Synthesis of (±)-1-(pyridine-4-yl)ethyl 4-methylbenzenesulfonate

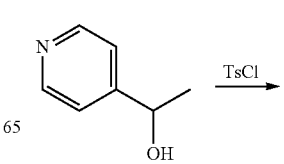

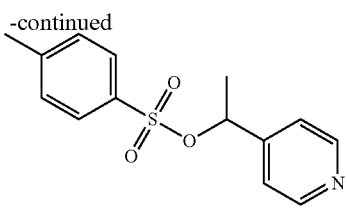

To a solution of 1-(pyridine-4-yl)ethanol (400 mg, 3.25 mmol) in THF (10 mL) was added sodium hydride (301 mg, 12.54 mmol) at 0° C. The mixture was stirred at 0° C. for 30 min. 4-methylbenzene-1-sulfonyl chloride (744 mg, 3.90 mmol) was added and the mixture was stirred at room temperature for 4 hr. Water (10 mL) was added and THF was removed under reduced pressure. The residue was extracted with ethyl acetate (20 mL×3). The organic layer was washed with brine and dried over sodium sulfate. The solvent was removed under vacuum and the residue was purified by column chromatography on silica gel (eluted: petroleum ether/ethyl acetate=2/1) to give 1-(pyridine-4-yl)ethyl 4-methylbenzenesulfonate (0.56 g, 62.2%). LCMS 278 (M+H$^+$).

The intermediates shown in the following table were prepared according to the general procedure outlined in this example using the appropriate starting materials and modifications.

| Name | Structure | m/z |
|---|---|---|
| (±)-1-(pyridine-3-yl)ethyl 4-methylbenzenesulfonate | 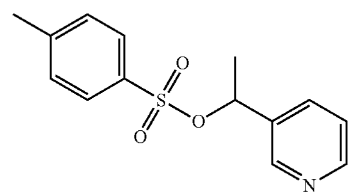 [SMILES: Cc1ccc(S(=O)(=O)OC(C)c2cccnc2)cc1] | 278 |
| (±)-1-(pyridine-2-yl)ethyl 4-methylbenzenesulfonate | 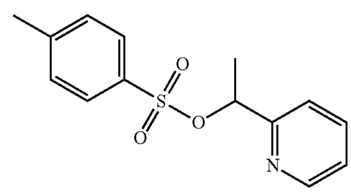 [SMILES: Cc1ccc(S(=O)(=O)OC(C)c2ccccn2)cc1] | 278 |
| (±)-1-(1-methyl-1H-pyrazol-4-yl)ethyl 4-methylbenzenesulfonate | 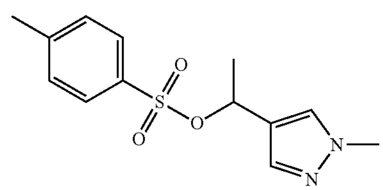 | 281 |
| (±)-1-(2-methoxypyridin-4-yl)ethyl 4-methylbenzenesulfonate | 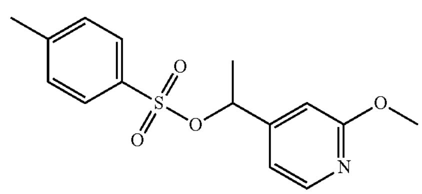 | 308 |
| (±)-1-methoxypropan-2-yl methanesulfonate | 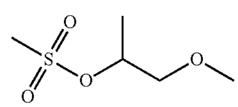 | 169 |
| (±)-1-ethoxypropan-2-yl 4-methylbenzenesulfonate | 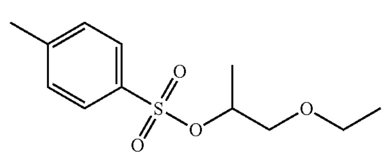 [SMILES: CCOCC(C)OS(=O)(=O)c1ccc(C)cc1] | 259 |
| (±)-1-(5-methoxypyridin-3-yl)ethyl 4-methylbenzenesulfonate | 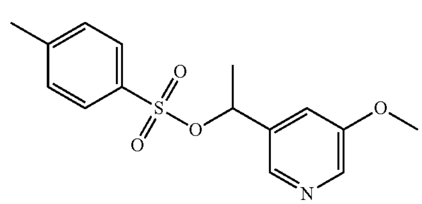 | 308 |

-continued

| Name | Structure | m/z |
|---|---|---|
| 1-(2-methoxypyrimidin-4-yl)ethyl 4-methylbenzenesulfonate | 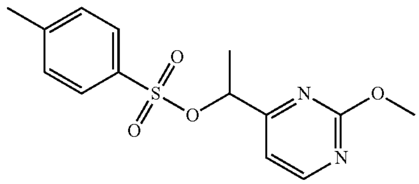 | 309 |
| 3-methoxybutan-2-yl 4-methylbenzenesulfonate | 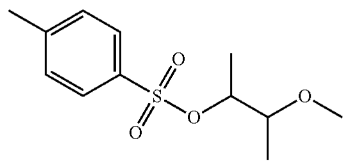 | 259 |
| (±)-4-((tert-butyldimethylsilyl)oxy)butan-2-yl methanesulfonate | 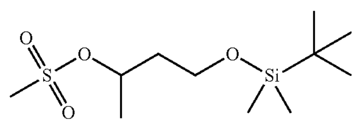 [SMILES: CC(CCO[Si](C)(C)C(C)(C)C)OS(C)(=O)=O] | 283 |

These intermediates were used in place of (±)-1-(1-bromoethyl)-4-fluorobenzene in Example 35 or 1-(1-bromoethyl)-4-chlorobenzene in Example 36, as appropriate, to make other compounds of the invention.

Example 39

Other Alkyl Carboxylate Intermediates

The following alkyl carboxylate intermediates were synthesized in an analogous manner to that set forth in Step 2 of Example 36, using an appropriate starting material and reactant.

| Name | Structure | m/z |
|---|---|---|
| (±)-ethyl 2-methyl-1-(1-(p-tolyl)ethyl)-1H-indole-3-carboxytate | 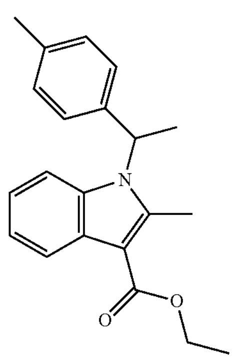 [SMILES: CCOC(=O)c1c(C)n(C(C)c2ccc(C)cc2)c2ccccc12] | 321 |

| Name | Structure | m/z |
|---|---|---|
| (±)-ethyl 2-methyl-1-(1-(o-tolyl)ethyl)-1H-indole-3-carboxylate | 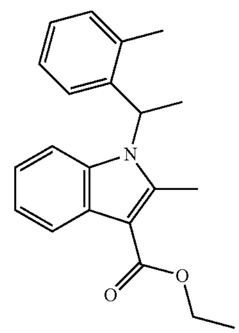 [SMILES: CCOC(=O)c1c(C)n(C(C)c2ccccc2C)c2ccccc12] | 321 |
| (±)-ethyl 2-methyl-1-(1-(m-tolyl)ethyl)-1H-indole-3-carboxylate | 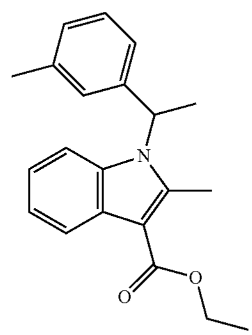 [SMILES: CCOC(=O)c1c(C)n(C(C)c2cccc(C)c2)c2ccccc12] | 321 |
| (±)-ethyl 2-methyl-1-(1-(4-(methylsulfonyl)phenyl)ethyl)-1H-indole-3-carboxylate | 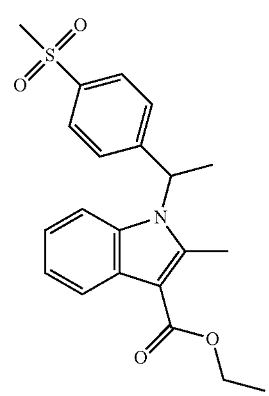 [SMILES: CCOC(=O)c1c(C)n(C(C)c2ccc(S(C)(=O)=O)cc2)c2ccccc12] | 386 |
| (±)-ethyl 1-(1-(3-chlorophenyl)ethyl)-2-methyl-1H-indole-3-carboxylate | 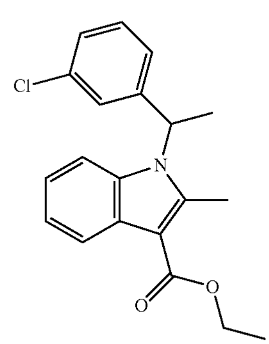 [SMILES: CCOC(=O)c1c(C)n(C(C)c2cccc(Cl)c2)c2ccccc12] | 343 |

-continued

| Name | Structure | m/z |
|---|---|---|
| (±)-ethyl 1-(1-(2-methoxyphenyl)ethyl)-2-methyl-1H-indole-3-carboxylate | 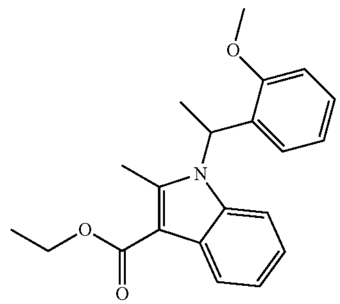 [SMILES: CCOC(=O)c1c(C)n(C(C)c2ccccc2OC)c2ccccc12] | 338 |
| (±)-ethyl 1-(1-(3-bromophenyl)ethyl)-2-methyl-1H-indole-3-carboxylate | 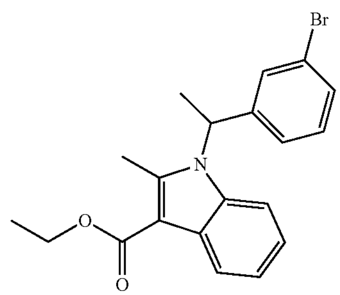 [SMILES: CCOC(=O)c1c(C)n(C(C)c2cccc(Br)c2)c2ccccc12] | 387 |
| (±)-ethyl 2-methyl-1-(1-(3-(methylsulfonyl)phenyl)ethyl)-1H-indole-3-carboxylate | 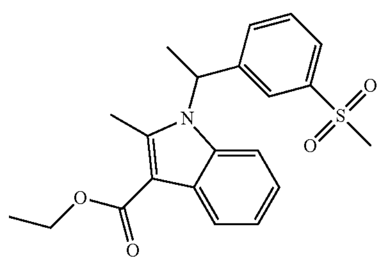 [SMILES: CCOC(=O)c1c(C)n(C(C)c2cccc(S(C)(=O)=O)c2)c2ccccc12] | 386 |
| (±)-ethyl 2-methyl-1-(1-(pyridine-4-yl)ethyl)-1H-indole-3-carboxylate | 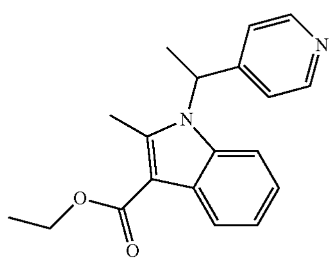 [SMILES: CCOC(=O)c1c(C)n(C(C)c2ccncc2)c2ccccc12] | 309 |
| (±)-ethyl 2-methyl-1-(1-(pyridine-3-yl)ethyl)-1H-indole-3-carboxylate | 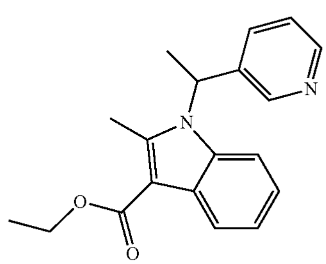 [SMILES: CCOC(=O)c1c(C)n(C(C)c2cccnc2)c2ccccc12] | 309 |

-continued

| Name | Structure | m/z |
|---|---|---|
| (±)-ethyl 2-methyl-1-(1-(pyridine-2-yl)ethyl)-1H-indole-3-carboxylate | 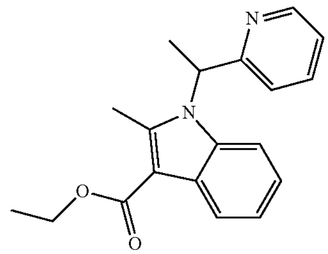 [SMILES: CCOC(=O)c1c(C)n(C(C)c2ccccn2)c2ccccc12] | 309 |
| ethyl 2-methyl-1-((3-methyloxetan-3-yl)methyl)-1H-indole-3-carboxylate | 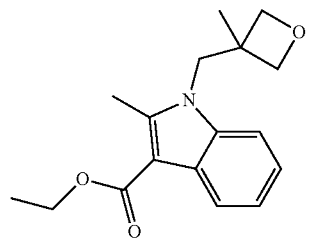 [SMILES: CCOC(=O)c1c(C)n(CC2(C)COC2)c2ccccc12] | 288 |
| (±)-ethyl 2-methyl-1-(1-(1-methyl-1H-pyrazol-4-yl)ethyl-1H-indole-3-carboxylate | 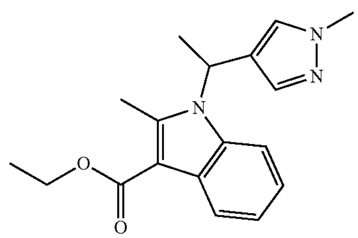 [SMILES: CCOC(=O)c1c(C)n(C(C)c2cnn(C)c2)c2ccccc12] | 312 |
| (±)-ethyl 1-(1-(2-methoxypyridin-4-yl)ethyl)-2-methyl-1H-indole-3-carboxylate | 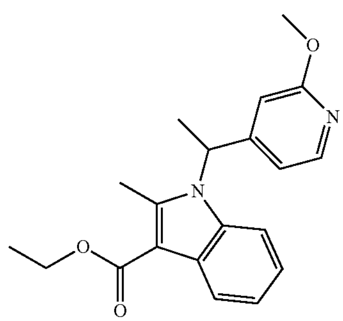 [SMILES: CCOC(=O)c1c(C)n(C(C)c2ccnc(OC)c2)c2ccccc12] | 339 |
| (±)-ethyl 5-fluoro-1-(1-methoxypropan-2-yl)-2-methyl-1H-indole-3-carboxylate | 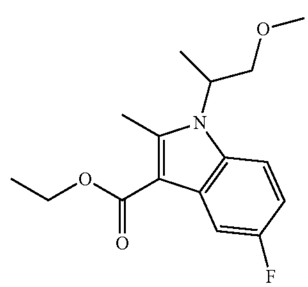 [SMILES: CCOC(=O)c1c(C)n(C(C)COC)c2ccc(F)cc12] | 294 |
| (±)-ethyl 6-fluoro-1-(1-methoxypropan-2-yl)-2-methyl-1H-indole-3-carboxylate | 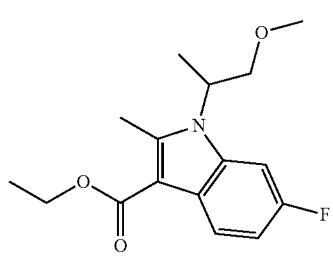 [SMILES: CCOC(=O)c1c(C)n(C(C)COC)c2cc(F)ccc12] | 294 |

-continued

| Name | Structure | m/z |
|---|---|---|
| (±)-ethyl 1-(1-methoxypropan-2-yl)-2-methyl-1H-indole-3-carboxylate | 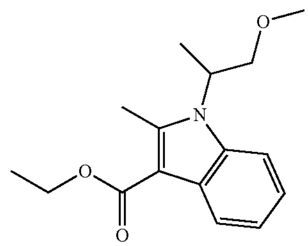 [SMILES: CCOC(=O)c1c(C)n(C(C)COC)c2ccccc12] | 276 |
| (±)-ethyl 1-(1-(3-cyanophenyl)ethyl)-2-methyl-1H-indole-3-carboxylate | 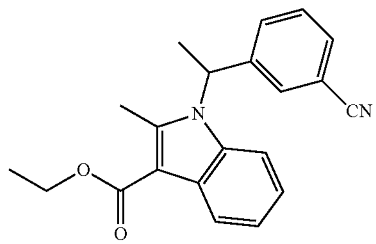 [SMILES: CCOC(=O)c1c(C)n(C(C)c2cccc(C#N)c2)c2ccccc12] | 333 |
| (±)-ethyl 1-(sec-butyl)-6-chloro-2-methyl-1H-indole-3-carboxylate | 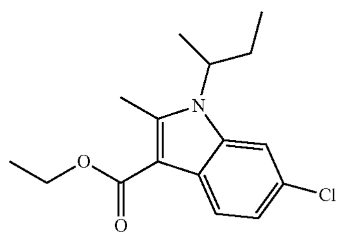 [SMILES: CCOC(=O)c1c(C)n(C(C)CC)c2cc(Cl)ccc12] | 295 |
| (±)-ethyl 1-(1-(2-cyanophenyl)ethyl)-2-methyl-1H-indole-3-carboxylate | 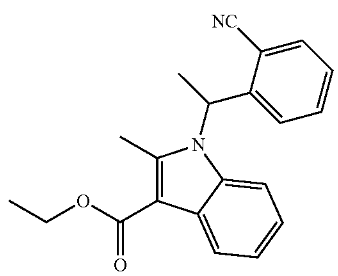 [SMILES: CCOC(=O)c1c(C)n(C(C)c2ccccc2C#N)c2ccccc12] | 333 |
| (±)-1-(sec-butyl)-2-methyl-1H-pyrrolo[2,3-b]pyridine-3-carboxylate | 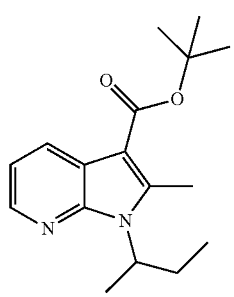 [SMILES: CCC(C)n1c(C)c(C(=O)OC(C)(C)C)c2cccnc21] | 289 |
| (±)-tert-butyl 1-(1-methoxypropan-2-yl)-2-methyl-1H-pyrrolo[2,3-b]pyridine-3-carboxylate | 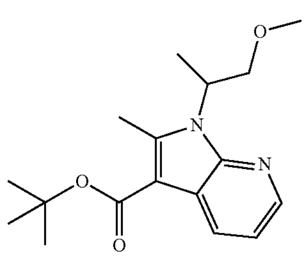 [SMILES: COCC(C)n1c(C)c(C(=O)OC(C)(C)C)c2cccnc21] | 305 |

| Name | Structure | m/z |
|------|-----------|-----|
| (±)-tert-butyl 1-(1-(3-methoxyphenyl)ethyl)-2-methyl-1H-pyrrolo[2,3-b]pyridine-3-carboxylate | 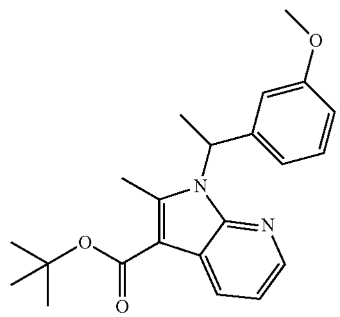 [SMILES: COc1cccc(C(C)n2c(C)c(C(=O)OC(C)(C)C)c3cccnc32)c1] | 367 |
| (±)-tert-butyl 1-(1-(2-methoxypyridin-4-yl)ethyl)-2-methyl-1H-pyrrolo[2,3-b]pyridine-3-carboxylate | 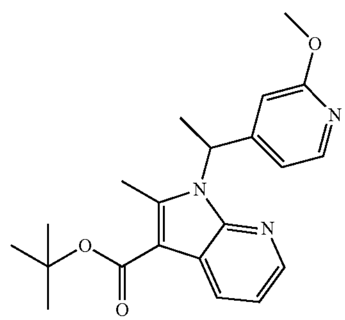 [SMILES: COc1cc(C(C)n2c(C)c(C(=O)OC(C)(C)C)c3cccnc32)ccn1] | 368 |
| (±)-tert-butyl 1-(1-ethoxypropan-2-yl)-2-methyl-1H-pyrrolo[2,3-b]pyridine-3-carboxylate | 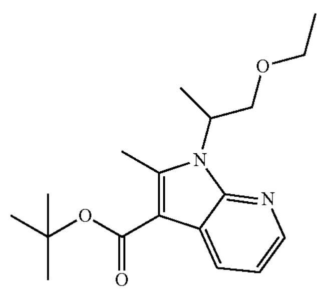 [SMILES: CCOCC(C)n1c(C)c(C(=O)OC(C)(C)C)c2cccnc21] | 319 |
| (±)-tert-butyl 1-(1-cyanoethyl)-2-methyl-1H-pyrrolo[2,3-b]pyridine-3-carboxylate | 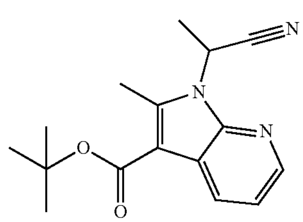 [SMILES: Cc1c(C(=O)OC(C)(C)C)c2cccnc2n1C(C)C#N] | 286 |
| (±)-tert-butyl 1-(1-(5-methoxypyridin-3-yl)ethyl)-2-methyl-1H-pyrrolo[2,3-b]pyridine-3-carboxylate | 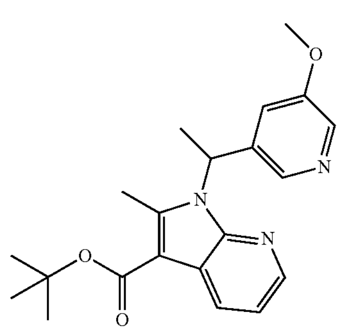 | 368 |

| Name | Structure | m/z |
|---|---|---|
| (±)-tert-butyl 1-(1-(2-methoxypyrimidin-4-yl)ethyl)-2-methyl-1H-pyrrolo[2,3-b]pyridine-3-carboxylate | 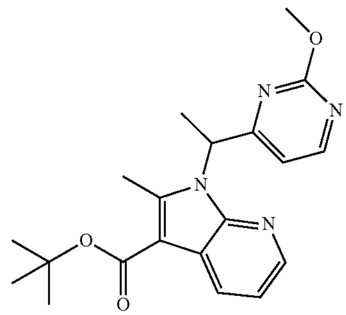 [SMILES: COc1nccc(C(C)n2c(C)c(C(=O)OC(C)(C)C)c3cccnc32)n1] | 369 |
| (±)-tert-butyl 2-methyl-1-(1-morpholinopropan-2-yl)-1H-pyrrolo[2,3-b]pyridine-3-carboxylate | 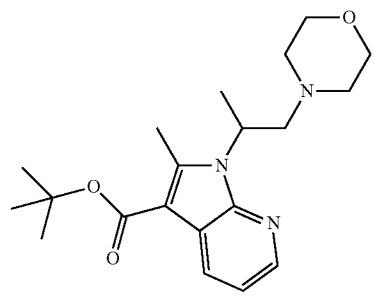 [SMILES: Cc1c(C(=O)OC(C)(C)C)c2cccnc2n1C(C)CN1CCOCC1] | 360 |
| (±)-tert-butyl 1-(1-(1H-benzo[d]imidazol-1-yl)propan-2-yl)-2-methyl-1H-pyrrolo[2,3-b]pyridine-3-carboxylate | 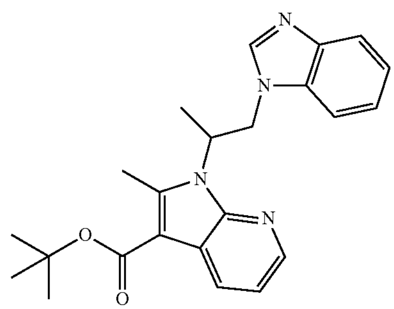 [SMILES: Cc1c(C(=O)OC(C)(C)C)c2cccnc2n1C(C)Cn1cnc2ccccc21] | 391 |
| (±)-tert-butyl 1-(1-(3-cyanophenyl)ethyl)-2-methyl-1H-pyrrolo[2,3-b]pyridine-3-carboxylate | 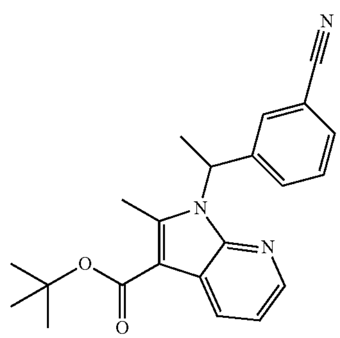 [SMILES: Cc1c(C(=O)OC(C)(C)C)c2cccnc2n1C(C)c1cccc(C#N)c1] | 362 |
| tert-butyl 1-(3-methoxybutan-2-yl)-2-methyl-1H-pyrrolo[2,3-b]pyridine-3-carboxylate | 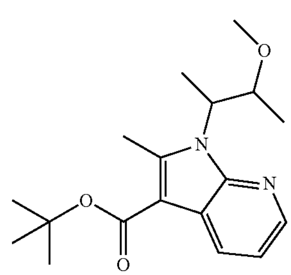 [SMILES: COC(C)C(C)n1c(C)c(C(=O)OC(C)(C)C)c2cccnc21] | 319 |

| Name | Structure | m/z |
|---|---|---|
| (±)-tert-butyl 1-(1-(3-carbamoylphenyl)ethyl)-2-methyl-1H-pyrrolo[2,3-b]pyridine-3-carboxylate | 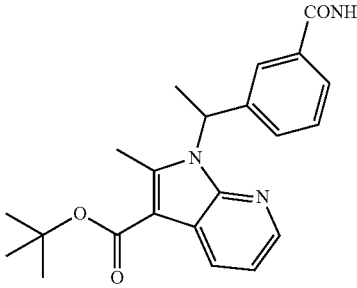 | 380 |
| (±)-tert-butyl 2-methyl-1-(1-(2-oxopyridin-1(2H)-yl)propan-2-yl)-1H-pyrrolo[2,3-b]pyridine-3-carboxylate | 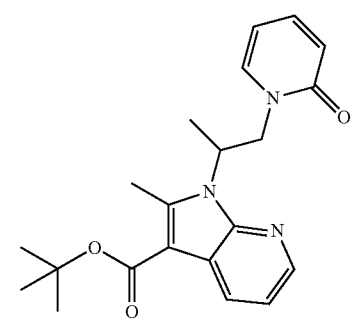 [SMILES: Cc1c(C(=O)OC(C)(C)C)c2cccnc2n1C(C)Cn1ccccc1=O] | 368 |
| (±)-tert-butyl 2-methyl-1-(1-(methylsulfonyl)propan-2-yl)-1H-pyrrolo[2,3-b]pyridine-3-carboxylate | 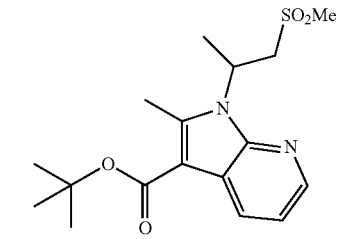 [SMILES: Cc1c(C(=O)OC(C)(C)C)c2cccnc2n1C(C)CS(C)(=O)=O] | 353 |
| (±)-tert-butyl 2-methyl-1-(1-(pyridine-2-yloxy)propan-2-yl)-1H-pyrrolo[2,3-b]pyridine-3-carboxylate | 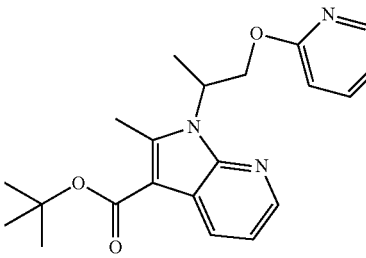 | 368 |
| ethyl 1-(3-methoxybutan-2-yl)-2-methyl-6-(methylsulfonyl)-1H-indole-3-carboxylate | 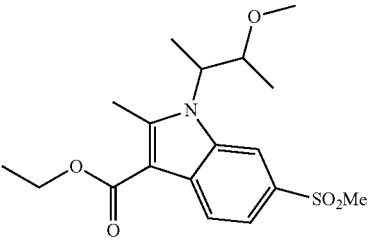 [SMILES: CCOC(=O)c1c(C)n(C(C)C(C)OC)c2cc(S(C)(=O)=O)ccc12] | 368 |

-continued

| Name | Structure | m/z |
|---|---|---|
| (±)-tert-butyl 1-(1-cyanopropan-2-yl)-2-methyl-1H-pyrrolo[2,3-b]pyridine-3-carboxylate | 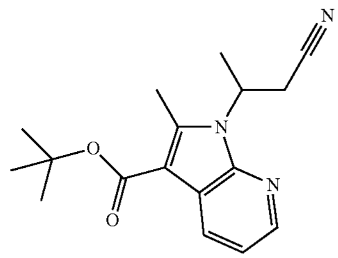 [SMILES: Cc1c(C(=O)OC(C)(C)C)c2cccnc2n1C(C)CC#N] | 300 |
| (±)-tert-butyl 1-(4-((tert-butyldimethylsilyl)oxy)butan-2-yl)-2-methyl-1H-pyrrolo[2,3-b]pyridine-3-carboxylate | 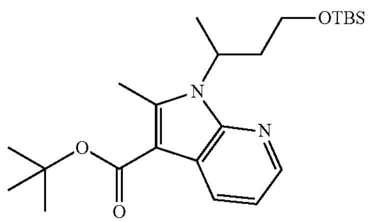 [SMILES: Cc1c(C(=O)OC(C)(C)C)c2cccnc2n1C(C)CCO[Si](C)(C)C(C)(C)C] | 419 |
| tert-butyl 2-methyl-1-(piperidin-1-ylsulfonyl)-1H-pyrrolo[2,3-b]pyridine-3-carboxylate | 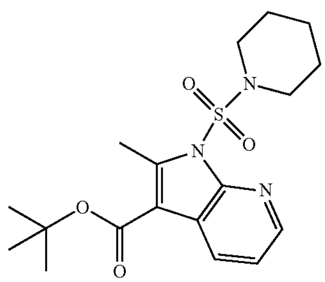 [SMILES: Cc1c(C(=O)OC(C)(C)C)c2cccnc2n1S(=O)(=O)N1CCCCC1] | 380 |
| (±)-tert-butyl 1-(2-((tert-butyldimethylsilyl)oxy)propyl)-2-methyl-1H-pyrrolo[2,3-b]pyridine-3-carboxylate | 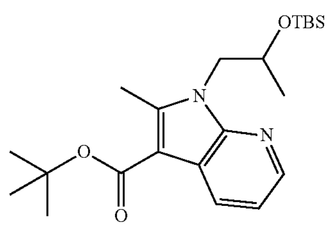 [SMILES: Cc1c(C(=O)OC(C)(C)C)c2cccnc2n1CC(C)O[Si](C)(C)C(C)(C)C] | 405 |
| (±)-ethyl (3-methoxypentan-2-yl)-2-methyl-1H-indole-3-carboxylate | 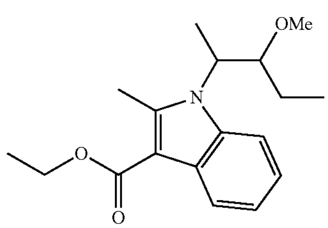 [SMILES: CCOC(=O)c1c(C)n(C(C)C(CC)OC)c2ccccc12] | 304 |
| (±)-tert-butyl 1-(1-methoxypropan-2-yl)-2-methyl-6-(trifluoromethyl)-1H-pyrrolo[2,3-b]pyridine-3-carboxylate | 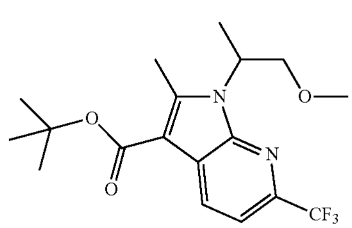 | 373 |

-continued

| Name | Structure | m/z |
|---|---|---|
| (±)-ethyl 6-(4-tert-butoxycarbonyl)piperazin-1-yl)-1-(1-methoxypropan-2-yl)-2-methyl-1H-pyrroro[2,3-b]pyridine-3-carboxylate | 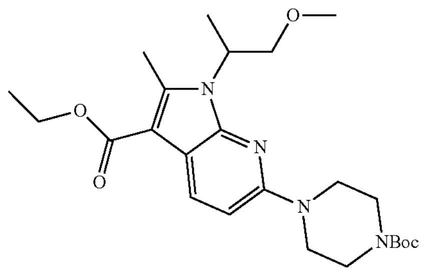 [SMILES: CCOC(=O)c1c(C)n(C(C)COC)c2nc(N3CCN(C(=O)OC(C)(C)C)CC3)ccc12] | 461 |

Example 40

Other Carboxylic Acid Intermediates

The following carboxylic acid intermediates were synthesized in an analogous manner to that set forth in Step 3 of Example 36, using an appropriate starting material (e.g., one of the alkyl carboxylate intermediates set forth in the previous Example).

| Name | Structure | m/z |
|---|---|---|
| (±)-2-methyl-1-(1-(p-tolyl)ethyl)-1H-indole-3-carboxylic acid | 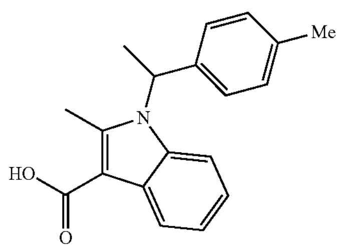 [SMILES: Cc1ccc(C(C)n2c(C)c(C(=O)O)c3ccccc32)cc1] | 293 |
| (±)-2-methyl-1-(1-(o-tolyl)ethyl)-1H-indole-3-carboxylic acid | 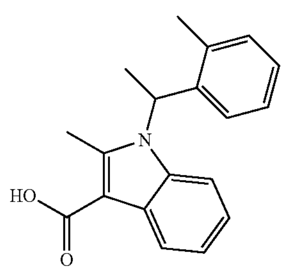 [SMILES: Cc1ccccc1C(C)n1c(C)c(C(=O)O)c2ccccc21] | 293 |
| (±)-2-methyl-1-(1-(m-tolyl)ethyl)-1H-indole-3-carboxylic acid | 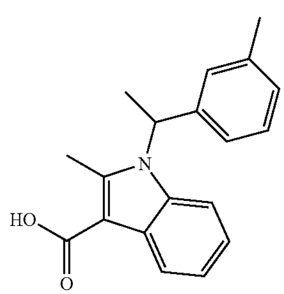 [SMILES: Cc1cccc(C(C)n2c(C)c(C(=O)O)c3ccccc32)c1] | 293 |

-continued

| Name | Structure | m/z |
|---|---|---|
| (±)-2-methyl-1-(1-(4-(methylsulfonyl)phenyl)ethyl)-1H-indole-3-carboxylic acid | 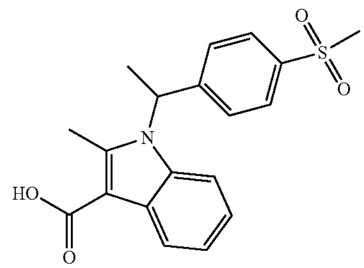 [SMILES: Cc1c(C(=O)O)c2ccccc2n1C(C)c1ccc(S(C)(=O)=O)cc1] | 358 |
| (±)-1-(1-(3-chlorophenyl)ethyl)-2-methyl-1H-indole-3-carboxylic acid | 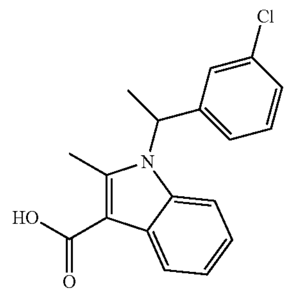 [SMILES: Cc1c(C(=O)O)c2ccccc2n1C(C)c1cccc(Cl)c1] | 315 |
| (±)-1-(1-(2-methoxyphenyl)ethyl)-2-methyl-1H-indole-3-carboxylic acid | 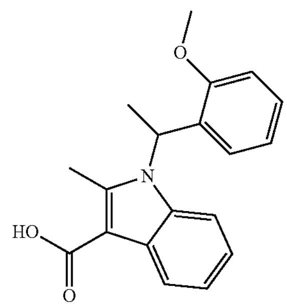 [SMILES: COc1ccccc1C(C)n1c(C)c(C(=O)O)c2ccccc21] | 310 |
| (±)-1-(1-(3-bromophenyl)ethyl)-2-methyl-1H-indole-3-carboxylic acid | 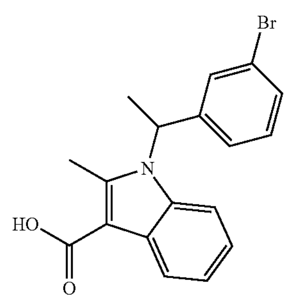 [SMILES: Cc1c(C(=O)O)c2ccccc2n1C(C)c1cccc(Br)c1] | 359 |
| (±)-2-methyl-1-(1-(3-(methylsulfonyl)phenyl)ethyl)-1H-indole-3-carboxylic acid | 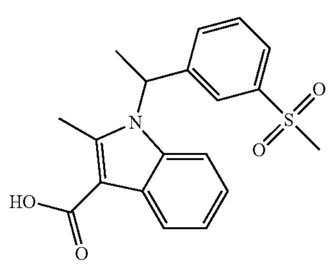 [SMILES: Cc1c(C(=O)O)c2ccccc2n1C(C)c1cccc(S(C)(=O)=O)c1] | 358 |

| Name | Structure | m/z |
|---|---|---|
| (±)-2-methyl-1-(1-(pyridine-4-yl)ethyl)-1H-indole-3-carboxylic acid | 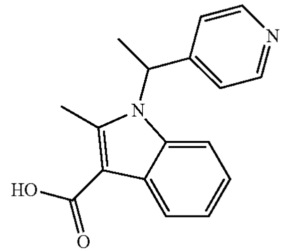 [SMILES: Cc1c(C(=O)O)c2ccccc2n1C(C)c1ccncc1] | 281 |
| (±)-2-methyl-1-(pyridine-3-yl)ethyl)-1H-indole-3-carboxylic acid | 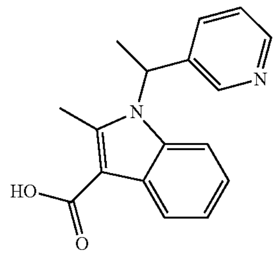 [SMILES: Cc1c(C(=O)O)c2ccccc2n1C(C)c1cccnc1] | 281 |
| (±)-2-methyl-1-(1-(pyridine-2-yl)ethyl)-1H-indole-3-carboxylic acid | 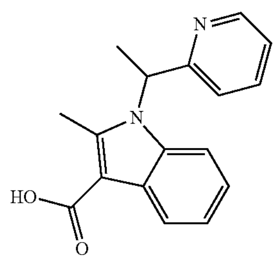 [SMILES: Cc1c(C(=O)O)c2ccccc2n1C(C)c1ccccn1] | 281 |
| 1-(1-(1,4-dioxan-2-yl)ethyl)-2-methyl-1H-indole-3-carboxylic acid | 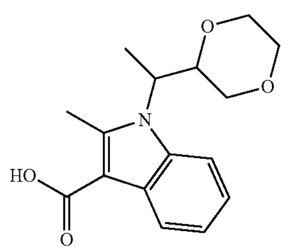 [SMILES: Cc1c(C(=O)O)c2ccccc2n1C(C)C1COCCO1] | 290 |
| 1-(1-(1-(tert-butoxycarbonyl)piperidin-3-yl)ethyl)-2-methyl-1H-indole-3-carboxylic acid | 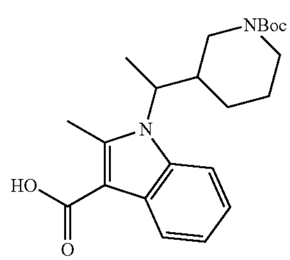 [SMILES: Cc1c(C(=O)O)c2ccccc2n1C(C)C1CCCN(C(=O)OC(C)(C)C)C1] | 387 |
| (±)-1-(1-(4,4-difluorocyclohexyl)133yrid)-2-methyl-1H-indole-3-carboxylic acid | 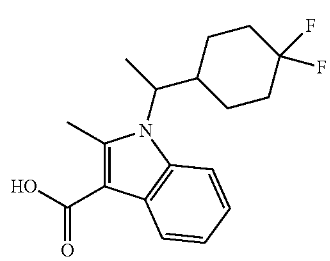 [SMILES: Cc1c(C(=O)O)c2ccccc2n1C(C)C1CCC(F)(F)CC1] | 322 |

-continued

| Name | Structure | m/z |
|---|---|---|
| 2-Methyl-1-((3-methyloxetan-3-yl)methyl)-1H-indole-3-carboxylic acid | 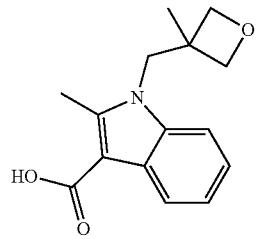 [SMILES: Cc1c(C(=O)O)c2ccccc2n1CC1(C)COC1] | 260 |
| (±)-2-methyl-1-(1-(1-methyl-1H-pyrazol-4-yl)ethyl)-1H-indole-3-carboxylic acid | 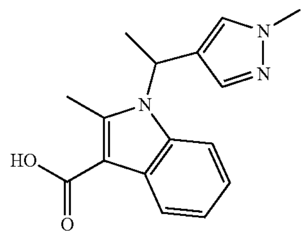 [SMILES: Cc1c(C(=O)O)c2ccccc2n1C(C)c1cnn(C)c1] | 283 |
| (±)-2-methyl-1-(1-(1-methyl-2-oxo-1,2-dihydropyridin-4-yl)ethyl)-1H-indole-3-carboxylic acid | 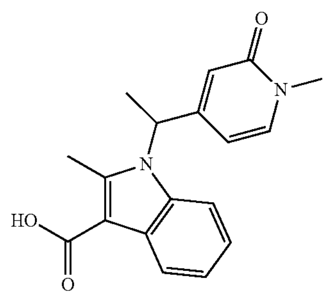 [SMILES: Cc1c(C(=O)O)c2ccccc2n1C(C)c1ccn(C)c(=O)c1] | 310 |
| 1-(1-(tert-butoxycarbonyl)piperidin-4-yl)-2-methyl-1H-indole-3-carboxylic acid | 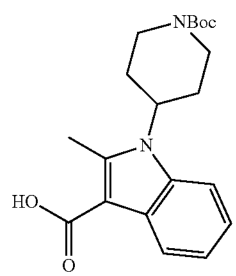 [SMILES: Cc1c(C(=O)O)c2ccccc2n1C1CCN(C(=O)OC(C)(C)C)CC1] | 359 |
| 2-methyl-1-(quinolin-5-yl)-1H-indole-3-carboxylic acid | 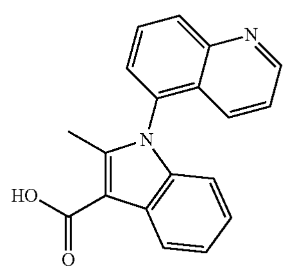 [SMILES: Cc1c(C(=O)O)c2ccccc2n1-c1cccc2ncccc12] | 303 |
| 1-cyclopentyl-2-methyl-1H-indole-3-carboxylic acid | 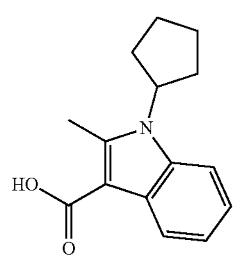 [SMILES: Cc1c(C(=O)O)c2ccccc2n1C1CCCC1] | 244 |

-continued

| Name | Structure | m/z |
|---|---|---|
| (±)-5-fluoro-1-(1-methoxypropan-2-yl)-2-methyl-1H-indole-3-carboxylic acid | 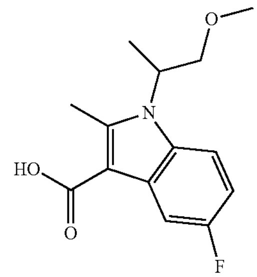 [SMILES: COCC(C)n1c(C)c(C(=O)O)c2cc(F)ccc21] | 266 |
| (±)-6-fluoro-1-(1-methoxypropan-2-yl)-2-methyl-1H-indole-3-carboxylic acid | 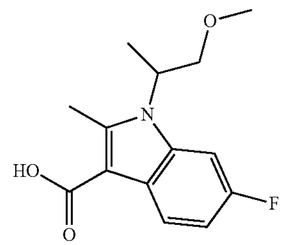 [SMILES: COCC(C)n1c(C)c(C(=O)O)c2ccc(F)cc21] | 266 |
| (±)-1-(1-methoxypropan-2-yl)-2-methyl-1H-indole-3-carboxylic acid | 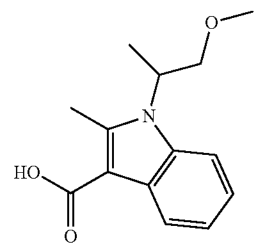 [SMILES: COCC(C)n1c(C)c(C(=O)O)c2ccccc21] | 248 |
| (±)-1-(1-(3-cyanophenyl)ethyl)-2-methyl-1H-indole-3-carboxylic acid | 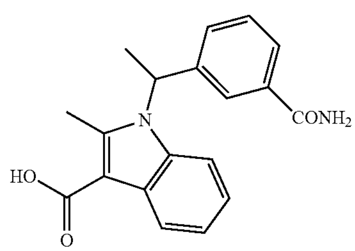 [SMILES: Cc1c(C(=O)O)c2ccccc2n1C(C)c1cccc(C(N)=O)c1] | 323 |
| 2-methyl-1-(6-methylquinolin-5-yl)-1H-indole-3-carboxylic acid | 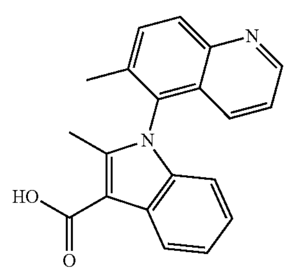 [SMILES: Cc1ccc2ncccc2c1-n1c(C)c(C(=O)O)c2ccccc21] | 317 |
| (±)-1-(sec-butyl)-6-chloro-2-methyl-1H-indole-3-carboxylic acid | 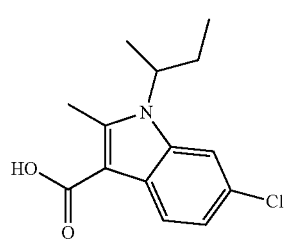 [SMILES: CCC(C)n1c(C)c(C(=O)O)c2ccc(Cl)cc21] | 267 |

-continued

| Name | Structure | m/z |
|---|---|---|
| (±)-2-methyl-1-(1-(1-(methylsulfonyl)azetidin-3-yl)ethyl)-1H-indole-3-carboxylic acid | 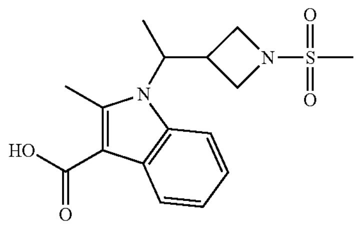 [SMILES: Cc1c(C(=O)O)c2ccccc2n1C(C)C1CN(S(C)(=O)=O)C1] | 337 |
| (±)-1-(1-(2-(4-(tert-butoxycarbonyl)piperazin-1-yl)pyridine-4-yl)ethyl)-2-methyl-1H-indole-3-carboxylic acid | 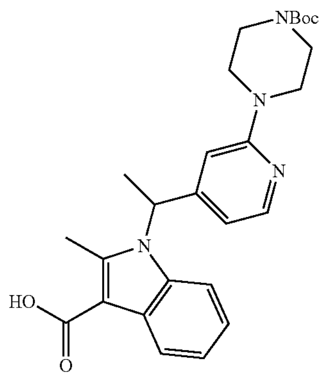 [SMILES: Cc1c(C(=O)O)c2ccccc2n1C(C)c1ccnc(N2CCN(C(=O)OC(C)(C)C)CC2)c1] | 465 |
| (±)-1-(1-(2-cyanophenyl)ethyl)-2-methyl-1H-indole-3-carboxylic acid | 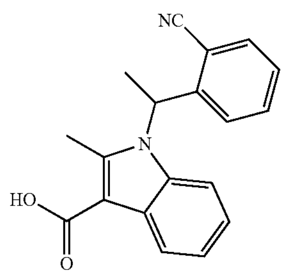 [SMILES: Cc1c(C(=O)O)c2ccccc2n1C(C)c1ccccc1C#N] | 305 |
| 1-(2,5-dimethylphenyl)-2-methyl-1H-indole-3-carboxylic acid | | 280 |
| 1-(2,5-dimethylphenyl)-2-methyl-1H-indole-3-carboxylic acid | | 280 |

-continued

| Name | Structure | m/z |
|---|---|---|
| 2-methyl-1-(quinolin-6-yl)-1H-indole-3-carboxylic acid | 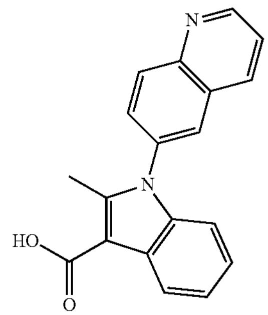 [SMILES: Cc1c(C(=O)O)c2ccccc2n1-c1ccc2ncccc2c1] | 303 |
| 1-(3-methoxybutan-2-yl)-2-methyl-6-(methylsulfonyl)-1H-indole-3-carboxylic acid | 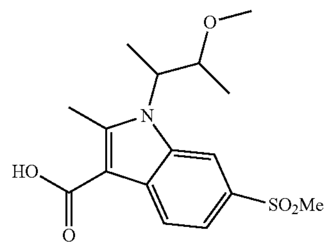 [SMILES: COC(C)C(C)n1c(C)c(C(=O)O)c2ccc(S(C)(=O)=O)cc21] | 340 |
| (R or S)-2-methyl-1-(1-(tetrahydro-2H-pyran-4-yl)ethyl)-1H-pyrrolo[2,3-b]pyridine-3-carboxylic acid | 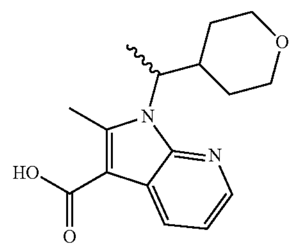 [SMILES: Cc1c(C(=O)O)c2cccnc2n1C(C)C1CCOCC1] | 289 |
| (S)-2-methyl-1-(1-phenylethyl)-1H-pyrrolo[2,3-b]pyridine-3-carboxylic acid | 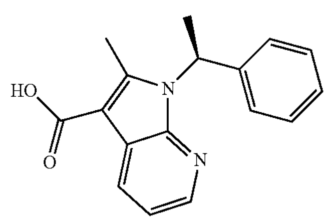 [SMILES: Cc1c(C(=O)O)c2cccnc2n1[C@@H](C)c1ccccc1] | 281 |
| 1-(3-methoxypentan-2-yl)-2-methyl-1H-indole-3-carboxylic acid | 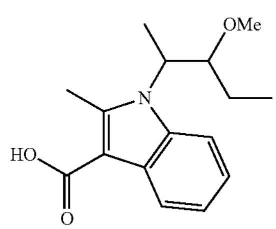 [SMILES: CCC(OC)C(C)n1c(C)c(C(=O)O)c2ccccc21] | 276 |
| (±)-6-(4-(tert-butoxycarbonyl)piperazin-1-yl)-1-(1-methoxypropan-2-yl)-2-methyl-1H-pyrrolo[2,3-b]pyridine-3-carboxylic acid | 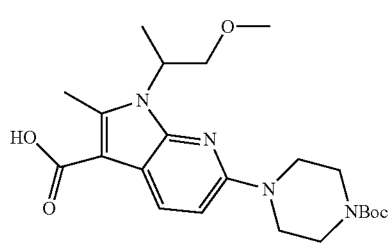 [SMILES: COCC(C)n1c(C)c(C(=O)O)c2ccc(N3CCN(C(=O)OC(C)(C)C)CC3)nc21] | 433 |

Example 41

Other Compounds of the Invention Produced from Carboxylic Acid Intermediates The following compounds were synthesized in an analogous manner to that set forth in Step 4 of Example 36, using an appropriate starting material (e.g., one of the carboxylic acid intermediates set forth in the previous example). Structures of these compounds are set forth in FIG. 1.

| Compound | Name | $^1$H NMR | m/z |
|---|---|---|---|
| 172 | (±)-N-((4,6-dimethyl-2-oxo-1,2-dihydropyridin-3-yl)methyl)-2-methyl-1-(1-(p-tolyl)ethyl)-1H-indole-3-carboxamide | (400 MHz, CDCl$_3$) δ 11.39 (s, 1H), 7.76 (d, J = 8.0 Hz, 1H), 7.30 (t, J = 6.4 Hz, 1H), 7.02-6.87 (m, 7H), 5.83 (s, 1H), 5.72 (q, J = 6.4 Hz, 1H), 4.59-4.50 (m, 2H), 2.63 (s, 3H), 2.37 (s, 3H), 2.23 (s, 3H), 2.10 (s, 3H), 1.83 (d, J = 7.2 Hz, 3H). | 427 |
| 174 | (±)-N-((4,6-dimethyl-2-oxo-1,2-dihydropyridin-3-yl)methyl)-2-methyl-1-(1-(o-tolyl)ethyl)-1H-indole-3-carboxamide | (400 MHz, CDCl$_3$) δ 1.80 (s, 3 H) 1.88 (d, J = 7.03 Hz, 3 H) 2.17 (s, 3 H) 2.44 (s, 3 H) 2.65 (s, 3 H) 4.61 (d, J = 6.02 Hz, 2 H) 5.78 (q, J = 7.11 Hz, 1 H) 5.91 (s, 1 H) 6.91-6.97 (m, 1 H) 6.98-7.05 (m, 2 H) 7.08 (d, J = 7.53 Hz, 1 H) 7.20-7.25 (m, 1 H) 7.28-7.40 (m, 2 H) 7.61 (d, J = 7.78 Hz, 1 H) 7.81 (d, J = 8.78 Hz, 1 H) | 428 |
| 190 | (±)-N-((4,6-dimethyl-2-oxo-1,2-dihydropyridin-3-yl)methyl)-2-methyl-1-(1-(m-tolyl)ethyl)-1H-indole-3-carboxamide | (400 MHz, Methanol-d4) δ 7.83 (d, J = 7.2 Hz, 1H), 7.42 (s, 1H), 7.24 (s, 1H), 7.14-7.18 (m, 2 H), 6.92-6.99 (m, 5 H), 5.92 (s, 1H), 5.78 (m, 1 H), 4.62 (s, 2 H), 2.70 (s, 3 H) 2.43 (s, 3H), 2.16 (s, 3H), 1.99 (s, 3H), 1.89 (s, 1H), 1.88 (d, J = 7.2 Hz, 3H) | 428 |
| 179 | (±)-N-((4,6-dimethyl-2-oxo-1,2-dihydropyridin-3-yl)methyl)-2-methyl-1-(1-(4-(methylsulfonyl)phenyl)ethyl)-1H-indole-3-carboxamide | (400 MHz, CDCl$_3$) δ ppm 2.00 (d, J = 7.06 Hz, 3H) 2.20 (s, 3H) 2.46 (s, 3H) 2.72 (s, 3H) 3.04 (s, 3H) 4.57-4.71 (m, 2H) 5.85 (q, J = 7.20 Hz, 1H) 5.95 (s, 1 H) 6.89 (d, J = 8.16 Hz, 1H) 6.98 (t, J = 7.61 Hz, 1H) 7.02-7.08 (m, 1H) 7.32 (d, J = 8.16 Hz, 2H) 7.47 (t, J = 5.84 Hz, 1H) 7.87 (d, J = 8.38 Hz, 3H) | 492 |
| 181 | (±)-1-(1-(3-chlorophenyl)ethyl)-N-((4,6-dimethyl-2-oxo-1,2-dihydropyridin-3-yl)methyl)-2-methyl-1H-indole-3-carboxamide | (400 MHz, CDCl3) δ 7.71-7.79 (d, 1H), 7.31-7.77 (t, 1H), 7.11-7.16 (m, 3H), 6.94-6.99 (m, 1H), 6.87-6.92 (m, 3H), 5.84 (s, 1H), 5.67-5.72 (m, 1H), 4.53-4.56 (t, 2H), 2.64 (s, 3H), 2.37 (s, 3H), 2.11 (s, 3H), 2.57 (s, 3H), 1.83-1.88 (d, 3H) | 449 |
| 186 | (±)-N-((4,6-dimethyl-2-oxo-1,2-dihydropyridin-3-yl)methyl)-1-(1-(2-methoxyphenyl)ethyl)-2-methyl-1H-indole-3-carboxamide | (400 MHz, CDCl$_3$) δ 7.72 (d, J = 7.2 Hz, 1H), 7.39 (d, J = 7.2 Hz, 1H), 7.28 (s, 1H),, 7.16-7.19 (m, 2H), 6.83-6.92 (m, 3H), 6.72 (d, J = 8.4 Hz, 1H), 5.88 (d, J = 11.2 Hz, 2H), 4.55 (s, 2H), 3.51 (s, 3H), 2.73 (s, 3H), 2.36 (s, 3H), 2.10 (s, 3H), 1.73 (d, J = 6 Hz, 3H) | 444 |
| 171 | (±)-1-(1-(3-bromophenyl)ethyl)-N-((4,6-dimethyl-2-oxo-1,2-dihydropyridin-3-yl)methyl)-2-methyl-1H-indole-3-carboxamide | (400 MHz, CDCl$_3$) δ 7.47-7.38 (m, 3H), 7.14-7.10 (t, 1H), 6.99-6.94 (m, 4H), 5.92 (s, 1 H), 5.76-5.74 (dd, 1H), 4.64-4.61 (dd, 2H), 2.70 (s, 3 H), 2.43 (s, 3 H), 2.14 (s, 3 H), 1.90-1.88 (t, 3H) | 493 |
| 210 | (±)-N-((4,6-dimethyl-2-oxo-1,2-dihydropyridin-3-yl)methyl)-2-methyl-1-(1-(3-(methylsulfonyl)phenyl)ethyl)-1H-indole-3-carboxamide | | 492 |
| 387 | (±)-N-((4-methoxy-6-methyl-2-oxo-1,2-dihydropyridin-3-yl)methyl)-2-methyl-1-(1-(pyridine-4-yl)ethyl)-1H-indole-3-carboxamide | (CDCl$_3$, 400 MHz) δ 8.55 (s, 2H), 7.87-7.85 (d, J = 7.6 Hz, 1 H), 7.61 (s, 1H), 7.05-6.97 (m, 4H), 6.88-6.86 (d, J = 8.0 Hz, 1H, 5.95 (s, 1H), 5.78-5.76 (d, J = 7.2 Hz, 1H), 4.69-4.68 (d, J = 5.2 Hz, 2H), 3.92 (s, 3H), 3.16-3.05 (m, 1H), 2.73 (s, 3H), 2.21 (s, 3H), 1.97-1.95 (d, J = 7.2 Hz, 3H) | 431 |

-continued

| Compound | Name | ¹H NMR | m/z |
|---|---|---|---|
| 392 | (±)-N-((4-methoxy-6-methyl-2-oxo-1,2-dihydropyridin-3-yl)methyl)-2-methyl-1-(1-(pyridine-3-yl)ethyl)-1H-indole-3-carboxamide | (CD₃OD, 400 MHz) δ 8.86-8.84 (d, J = 5.6, 1H), 8.74 (s, 1H), 8.37-8.35 (d, J = 7.2, 1H), 8.09-8.06 (m, J = 14.4, 1H), 7.82-7.80 (d, J = 8.0, 1H), 7.21-7.18 (t, J = 7.2, 1H), 7.11-7.07 (t, J = 7.6, 1H), 7.03-7.01 (m, 2H), 6.29-6.24 (q, J = 7.2, 1H), 4.67 (s, 2H), 4.17 (s, 3H), 2.77 (s, 3H), 2.58 (s, 3H,), 2.13-2.12 (d, J = 7.2, 3H) | 431 |
| 393 | (±)-N-((4-methoxy-6-methyl-2-oxo-1,2-dihydropyridin-3-yl)methyl)-2-methyl-1-(1-(pyridine-2-yl)ethyl)-1H-indole-3-carboxamide | (CD₃OD, 400 MHz) δ 8.56-8.54 (d, J = 4.4 Hz, 1H), 7.79-7.75 (t, J = 7.2 Hz, 1H), 7.72-7.70 (d, J = 8.0 Hz, 1H), 7.36-7.33 (t, J = 7.2 Hz, 1H), 7.19-7.17 (d, J = 8.0 Hz, 1H), 7.05-7.03 (d, J = 8.0 Hz, 1H), 6.97-6.95 (m, 2H), 6.42 (s, 1H), 6.03-5.98 (q, J = 7.2 Hz, 1H), 4.55 (s, 2H), 3.98 (s, 3H), 2.65 (s, 3H), 2.36 (s, 3H), 1.99-1.97 (d, J = 7.2 Hz, 3H) | 431 |
| 264 | (±)-N-((4,6-dimethyl-2-oxo-1,2-dihydropyridin-3-yl)methyl)-2-methyl-1-(1-(pyridine-2-yl)ethyl)-1H-indole-3-carboxamide | (500 MHz, DMSO-d₆) δ = 11.60 (s, 1 H), 8.59 (d, J = 4.1 Hz, 1 H), 7.74-7.65 (m, 3 H), 7.29 (dd, J = 4.9, 7.1 Hz, 1 H), 7.09-7.05 (m, 2 H), 7.00 (t, J = 7.4 Hz, 1 H), 6.95 (t, J = 7.7 Hz, 1 H), 6.00 (q, J = 7.1 Hz, 1 H), 5.89 (s, 1 H), 4.33 (d, J = 5.2 Hz, 2 H), 2.62 (s, 3 H), 2.27 (s, 3 H), 2.12 (s, 3 H), 1.90 (d, J = 7.1 Hz, 3 H) | 415 |
| 348 | 1-(1-(1,4-dioxan-2-yl)ethyl)-N-((4-methoxy-6-methyl-2-oxo-1,2-dihydropyridin-3-yl)methyl)-2-methyl-1H-indole-3-carboxamide | (400 MHz, CDCl₃) δ 1.63 (d, J = 7.2, 3H), 2.14 (s, 3H), 2.70 (s, 3H), 3.18-3.14 (m, 2H), 3.60-3.53 (m, 1H), 3.69-3.67 (m, 1H), 3.81-3.75 (m, 1H), 3.18-3.14 (m, 1H), 3.86 (s, 1H), 3.89 (s, 3H), 4.30-4.25 (m, 1H), 4.43-4.36 (m, 1H), 4.67-4.65 (m, 2H), 5.91 (s, 1H), 7.05-7.01 (m, 1H), 7.12-7.08 (m, 1H), 7.47-7.44 (m, 1H), 7.59-7.56 (m, 1H), 7.84-7.83 (m, 1H), 12.85 (s, 1H) | 440 |
| 315 | N-((4-methoxy-6-methyl-2-oxo-1,2-dihydropyridin-3-yl)methyl)-2-methyl-1-(1-(piperidin-3-yl)ethyl)-1H-indole-3-carboxamide | (400 MHz, METHANOL-d₄) δ = 7.75 (d, J = 8.0 Hz, 1H), 7.57 (d, J = 7.5 Hz, 1H), 7.15 (quin, J = 6.5 Hz, 2H), 6.31 (s, 1H), 4.62 (s, 1H), 4.56 (s, 2H), 4.38-4.28 (m, 1H), 3.97 (s, 3H), 3.57 (d, J = 11.0 Hz, 1H), 3.23 (d, J = 12.5 Hz, 1H), 2.85-2.74 (m, 2H), 2.64 (s, 3H), 2.35 (s, 3H), 1.72 (s, 1H), 1.69-1.62 (m, 3H), 1.47-1.30 (m, 1H), 1.15-1.04 (m, 2H) | 437 |
| 304 | (±)-1-(1-(4,4-difluorocyclohexyl)ethyl)-N-((4-methoxy-6-methyl-2-oxo-1,2-dihydropyridin-3-yl)methyl)-2-methyl-1H-indole-3-carboxamide | (CDCl₃, 400 MHz) δ 12.63-12.64 (d, J = 3.2 Hz, 1H), 7.84 (s, 1H), 7.49 (s, 1H), 7.42-7.40 (d, J = 9.2 Hz, 1H), 7.06-7.00 (m, 2H), 5.90-5.89 (d, J = 3.6 Hz 1H), 4.66-4.62 (t, J = 14 Hz, 2H), 4.11-4.08 (m, 1H), 3.88-3.87 (d, J = 3.6 Hz, 3H), 2.99-2.76 (m, 3H), 2.36 (s, 1H), 2.25 (s, 3H), 2.17-2.16 (d, J = 3.2 Hz, 2H), 2.08-2.05 (m, 2H), 1.84-1.70 (m, 2H), 1.61 (s, 1H), 1.51-1.47 (m, 2H) | 427 |
| 246 | N-((4,6-dimethyl-2-oxo-1,2-dihydropyridin-3-yl)methyl)-2-methyl-1-((3-methyloxetan-3-yl)methyl)-1H-indole-3-carboxamide | (400 MHz, d⁶-DMSO) δ 11.60 (br. S, 1 H), 7.79-7.74 (m, 1 H), 7.73-7.67 (m, 1 H), 7.52-7.47 (m, 1 H), 7.18-7.11 (m, 1 H), 7.10-7.05 (m, 1 H), 5.89 (s, 1 H), 4.51 (d, J = 5.8 Hz, 2 H), 4.33 (d, J = 5.6 Hz, 2 H), 4.30 (s, 2 H), 4.10 (d, J = 6.0 Hz, 2 H), 2.54 (s, 3 H), 2.26 (s, 3 H), 2.12 (s, 3 H), 1.27 (s, 3 H) | 394 |
| 245 | (±)-N-((4,6-dimethyl-2-oxo-1,2-dihydropyridin-3-yl)methyl)-2-methyl-1-(1-(1-methyl-1H-pyrazol-4-yl)ethyl)-1H-indole-3-carboxamide | (400 MHz, DMSO-d₆) δ 11.69 (s, 1 H), 7.74-7.64 (m, 2 H), 7.57 (s, 1 H), 7.28-7.23 (m, 2 H), 7.04-6.96 (m, 2 H), 5.93 (s, 1 H), 5.79 (q, J = 7.3 Hz, 1 H), 4.35-4.31 (m, 2 H), 3.76 (s, 3 H), 2.64 (s, 3 H), 2.28 (s, 3 H), 2.13 (s, 3 H), 1.79 (d, J = 7.1 Hz, 3 H) | 418 |
| 222 | (±)-N-((4,6-dimethyl-2-oxo-1,2-dihydropyridin-3-yl)methyl)-2-methyl-1-(1-(1-methyl-2-oxo-1,2-dihydropyridin-4-yl)ethyl)-1H-indole-3-carboxamide | | 445 |
| 331 | tert-butyl 4-(3-(((4-methoxy-6-methyl-2-oxo-1,2-dihydropyridin-3-yl)methyl)carbamoyl)-2-methyl-1H-indol-1-yl)piperidine-1-carboxylate | (400 MHz, CDCl3) δ 11.9 (s, 1H), 7.85-7.82 (d, 1H), 7.51-7.41 (m, 2H), 7.10-7.01 (m, 2 H), 5.90 (s, 1H), 4.64 (s, 2H), 4.37 (s, 1 H), 3.89 (s, 3 H), 2.84 (s, 2 H), 2.75 (s, 3 H), 2.49 (s, 2 H), 2.17 (s, 3H), 1.79-1.76 (d, 2H), 1.50 (s, 9H) | 509 |

| Compound | Name | ¹H NMR | m/z |
|---|---|---|---|
| 330 | N-((4-methoxy-6-methyl-2-oxo-1,2-dihydropyridin-3-yl)methyl)-2-methyl-1-(quinolin-5-yl)-1H-indole-3-carboxamide | (CDCl₃, 400 MHz) δ 8.97 (dd, J₁ = 1.6 Hz, J₂ = 4.4 Hz, 1H), 8.31 (d, J = 8.4 Hz, 1H), 8.01 (d, J = 8.0 Hz, 1H), 7.88 (t, J = 8.8 Hz, 1H), 7.76 (s, 1H), 7.56 (d, J = 7.2 Hz, 1H), 7.40 (d, J = 8.4 Hz, 1H), 7.31-7.28 (m, 1H), 7.15 (t, J = 7.2 Hz, 1H), 7.03 (t, J = 7.6 Hz, 1H), 6.71 (d, J = 8.0 Hz, 1H), 5.97 (s, 1H), 4.80-4.68 (m, 2H), 3.93 (s, 3H), 2.44 (s, 3H), 2.29 (s, 3H) | 453 |
| 324 | 1-cyclopentyl-N-((4-methoxy-6-methyl-2-oxo-1,2-dihydropyridin-3-yl)methyl)-2-methyl-1H-indole-3-carboxamide | | 394 |
| 230 | (±)-5-fluoro-N-((4-methoxy-6-methyl-2-oxo-1,2-dihydropyridin-3-yl)methyl)-1-(1-methoxypropan-2-yl)-2-methyl-1H-indole-3-carboxamide | (400 MHz, CD₃OD) δ 7.59-7.55 (m, 1H), 7.42-7.39 (m, 1H), 6.95-6.90 (m, 2H), 4.57 (s, 2H), 4.12 (s, 3H), 3.99-3.94 (m, 1H), 3.72-3.65 (m, 1H), 3.19 (s, 3H), 2.64 (s, 3H), 2.54 (s, 3H), 1.59-1.57 (d, 3H) | 416 |
| 231 | (±)-6-fluoro-N-((4-methoxy-6-methyl-2-oxo-1,2-dihydropyridin-3-yl)methyl)-1-(1-methoxypropan-2-yl)-2-methyl-1H-indole-3-carboxamide | (400 MHz, CD₃OD) δ 7.70-7.66 (m, 1H), 7.36-7.33 (m, 1H), 6.94-6.89 (m, 2H), 4.56 (s, 2H), 4.11 (s, 3H), 3.97-3.92 (m, 1H), 3.71-3.67 (m, 1H), 3.20 (s, 3H), 2.62 (s, 3H), 2.53 (s, 3H), 1.58-1.56 (d, 3H) | 416 |
| 218 | (±)-N-((4-methoxy-6-methyl-2-oxo-1,2-dihydropyridin-3-yl)methyl)-1-(1-methoxypropan-2-yl)-2-methyl-1H-indole-3-carboxamide | (400 MHz, CD₃OD) δ 7.69 (d, J = 7.2 Hz, 1H), 7.53 (d, J = 7.6 Hz, 1H), 7.12 (m, 2H), 6.26 (s, 1H), 4.80 (m, 1H), 4.52 (s, 2H), 3.99 (m, 4H), 3.75 (m, 1H), 3.20 (s, 3H), 2.62 (s, 3H), 2.31 (s, 3H), 1.59 (d, J = 7.2 Hz, 3H) | 398 |
| 183 | (±)-N-((4,6-dimethyl-2-oxo-1,2-dihydropyridin-3-yl)methyl)-1-(1-methoxypropan-2-yl)-2-methyl-1H-indole-3-carboxamide | (400 MHz, CD₃OD) δ 7.74 (m, 1H), 7.57 (d, J = 7.6 Hz, 1H), 7.15 (m, 2H), 6.14 (s, 1H), 4.86 (m, 1H), 4.55 (s, 2H), 4.02 (m, 1H), 3.77 (m, 1H), 3.22 (s, 3H), 2.65 (s, 3H), 2.43 (s, 3H), 2.26 (s, 3H), 1.62 (d, J = 7.2 Hz, 3H) | 382 |
| 175 | (±)-1-(1-(3-cyanophenyl)ethyl)-N-(4,6-dimethyl-2-oxo-1,2-dihydropyridin-3-yl)-2-methyl-1H-indole-3-carboxamide | (400 MHz, Methanol-d4) δ 7.84 (d, J = 8 Hz, 1H), 7.66 (d, J = 8.4 Hz, 2H), 7.33-7.37 (m, 2H), 7.04 (m, 1 H), 6.88-6.96 (m, 2H), 5.90 (s, 2H), 5.81-5.82 (m, 1 H), 4.57-4.63 (m, 2 H), 3.54 (s, 1 H), 2.99 (s, 3H), 2.70 (s, 3H), 2.45 (s, 3H), 2.22 (s, 3H), 1.96 (d, J = 7.2 Hz, 3H) | 457 |
| 390 | N-((4-methoxy-6-methyl-2-oxo-1,2-dihydropyridin-3-yl)methyl)-2-methyl-1-(6-methylquinolin-5-yl)-1H-indole-3-carboxamide | (CD₃OD, 400 MHz) δ 9.27 (s, 1H), 8.48 (m, 1H), 8.35 (s, 1H), 8.13 (s, 1H), 8.01 (s, 1H), 7.95 (d, J = 7.06 Hz, 1H), 7.29 (s, 1H), 7.15 (s, 1H), 7.01 (s, 1H), 6.68 (s, 1H), 4.67 (s, 2H), 4.16 (s, 3H), 2.57 (s, 3H), 2.33 (s, 3H), 2.21 (s, 3H) | 467 |
| 385 | (±)-1-(sec-butyl)-6-chloro-N-((4-methoxy-6-methyl-2-oxo-1,2-dihydropyridin-3-yl)methyl)-2-methyl-1H-indole-3-carboxamide | (400 MHz, CD₃OD): δ 7.71 (d, J = 8.8, 1H), 7.63 (s, 1H), 7.15 (d, J = 8.8, 1H), 7.00 (s, 1H), 4.60 (s, 3H), 4.15 (s, 3H), 2.67 (s, 3H), 2.57 (s, 3H), 2.15-2.25 (m, 1H), 1.95-2.01 (m, 1H), 1.62 (d, J = 7.2, 3H), 0.73 (t, J = 7.6, 3H) | 416 |
| 354 | (±)-N-((4-methoxy-6-methyl-2-oxo-1,2-dihydropyridin-3-yl)methyl)-2-methyl-1-(1-(1-(methylsulfonyl)azetidin-3-yl)ethyl)-1H-indole-3-carboxamide | (CDCl₃, 400 MHz) δ 12.52 (s, 1 H), 7.86-7.03 (m, 5H), 5.92 (s, 1 H), 4.71-4.62 (m, 3H), 4.16-4.12 (m, 1H), 3.90 (s, 3 H), 3.79-3.32 (m, 4H), 2.80 (s, 6 H), 2.18 (s, 3 H), 1.28 (d, J = 8 Hz, 3H) | 487 |
| 353 | (±)-N-((4-methoxy-6-methyl-2-oxo-1,2-dihydropyridin-3-yl)methyl)-2-methyl-1-(1-(2-(piperazin-1-yl)pyridine-4-yl)ethyl)-1H-indole-3-carboxamide | NMR (400 MHz, CDCl₃) δ 8.10-8.11 (d, J = 5.6 Hz, 1H), 7.72-7.75 (d, J = 8.0 Hz, 1H), 6.98-7.11 (m, 3H), 6.57-6.61 (m, 2H), 6.30 (s, 1H), 5.87-5.92 (m, 1H), 4.55 (s, 1H), 3.96 (s, 3H), 3.66-3.69 (m, 4H), 3.22-3.24 (d, J = 2.8 Hz, 3H), 2.96-2.99 (d, J = 9.6 Hz, 1H), 2.63 (s, 3H), 2.33 (s, 3H), 1.94-1.96 (d, J = 7.6 Hz, 3H), 1.30-1.34 (m, 3H) | 515 |

| Compound | Name | ¹H NMR | m/z |
|---|---|---|---|
| 339 | N-((4-methoxy-6-methyl-2-oxo-1,2-dihydropyridin-3-yl)methyl)-2-methyl-1-(1,2,3,4-tetrahydroquinolin-5-yl)-1H-indole-3-carboxamide | (CDCl$_3$, 400 MHz) δ 7.91 (d, J = 7.2 Hz, 1H), 7.59 (s, 1H), 7.12-7.04 (m, 3H), 6.89 (d, J = 7.6 Hz, 1H), 6.59 (d, J = 8.0 Hz, 1H), 6.48 (d, J = 7.6 Hz, 1H), 5.95 (s, 1H), 4.75-4.64 (m, 2H), 3.91 (s, 3H), 3.27 (t, J = 6.0 Hz, 2H), 2.50 (s, 3H), 2.27 (s, 3H), 2.10-1.98 (m, 2H), 1.77-1.63 (m, 2H) | 457 |
| 178 | (±)-1-(1-(2-cyanophenyl)ethyl)-N-((4,6-dimethyl-2-oxo-1,2-dihydropyridin-3-yl)methyl)-2-methyl-1H-indole-3-carboxamide | (400 MHz, CDCl$_3$) δ ppm 2.02 (d, J = 6.62 Hz, 3 H) 2.19 (br. S., 3 H) 2.44 (br. S., 3 H) 2.77 (br. S., 3 H) 4.62 (br. S., 2 H) 5.92 (br. S., 1 H) 5.96-6.05 (m, 1 H) 6.92-7.12 (m, 3 H) 7.33-7.50 (m, 3 H) 7.54-7.62 (m, 1 H) 7.66 (d, J = 6.84 Hz, 1 H) 7.86 (d, J = 7.50 Hz, 1 H) | 439 |
| 191 | N-((4,6-dimethyl-2-oxo-1,2-dihydropyridin-3-yl)methyl)-1-(2,5-dimethylphenyl)-2-methyl-1H-indole-3-carboxamide | (400 MHz, CDCl$_3$) δ 10.86 (s, 1H), 7.91 (d, J = 8.0, 1H), 7.46 (s, 1H), 7.29-7.19 (m, 2H), 7.12 (d, J = 7.2, 1H), 7.06 (d, J = 7.2, 1H), 6.96 (s, 1H), 6.78 (d, J = 8.0, 1H), 5.91 (s, 1H), 4.69-4.57 (m, 2H), 2.45 (s, 3H), 2.44 (s, 3H), 2.35 (s, 3H), 2.22 (s, 3H), 1.85 (s, 3H) | 413 |
| 173 | N-((4,6-dimethyl-2-oxo-1,2-dihydropyridin-3-yl)methyl)-1-(2,3-dimethylphenyl)-2-methyl-1H-indole-3-carboxamide | | 414 |
| 391 | N-((4-methoxy-6-methyl-2-oxo-1,2-dihydropyridin-3-yl)methyl)-2-methyl-1-(6-methyl-1,2,3,4-tetrahydroquinolin-5-yl)-1H-indole-3-carboxamide | (MeOD, 400 MHz) δ 7.88 (d, J = 7.94 Hz, 1H), 7.56-7.51 (m, 2H), 7.26 (t, J = 7.5 Hz, 1H), 7.18 (t, J = 7.61 Hz, 1H), 7.16 (s, 1H), 6.76 (d, J = 7.94 Hz, 1H), 4.63 (s, 2H), 4.14 (s, 3H), 3.51 (t, J = 5.29 Hz, 2H), 2.56 (s, 3H), 2.33 (s, 3H), 2.31-2.20 (m, 1H), 2.18-2.14 (m, 1H), 2.02-1.99 (m, 2H), 1.89 (m, 3H) | 471 |
| 386 | N-((4-methoxy-6-methyl-2-oxo-1,2-dihydropyridin-3-yl)methyl)-2-methyl-1-(1,2,3,4-tetrahydroquinolin-6-yl)-1H-indole-3-carboxamide | (400 MHz, METHANOL-d$_4$) δ ppm 7.82 (d, J = 7.94 Hz, 1 H) 7.60 (d, J = 8.38 Hz, 1 H) 7.37-7.48 (m, 2 H) 7.13-7.28 (m, 2 H) 6.97-7.07 (m, 2 H) 4.62 (s, 2 H) 4.15 (s, 3 H) 3.57-3.66 (m, 2 H) 3.06 (t, J = 6.28 Hz, 2 H) 2.56 (s, 3 H) 2.49 (s, 3 H) 2.16-2.29 (m, 2 H) | 457 |
| 329 | N-((4-methoxy-6-methyl-2-oxo-1,2-dihydropyridin-3-yl)methyl)-2-methyl-1-(3-methylbutanoyl)-1H-indole-3-carboxamide | (400 MHz, METHANOL-d$_4$) δ 1.03 (d, J = 6.62 Hz, 6 H) 2.32 (s, 4 H) 2.70 (s, 3 H) 2.96 (d, J = 7.06 Hz, 2 H) 3.95 (s, 3 H) 4.52 (s, 2 H) 6.28 (s, 1 H) 7.20-7.30 (m, 2 H) 7.66 (d, J = 6.84 Hz, 1 H) 7.91 (d, J = 7.72 Hz, 1 H) | 410 |
| 372 | N-((4-methoxy-6-methyl-2-oxo-1,2-dihydropyridin-3-yl)methyl)-2-methyl-1-(tetrahydro-2H-pyran-4-carbonyl)-1H-indole-3-carboxamide | (400 MHz, CD$_3$OD): δ 7.78-7.76 (d, 1H), 7.68-7.66 (d, 1H), 7.33-7.26 (m, 2H), 6.97 (s, 1H), 4.58 (s, 2H), 4.12 (s, 3H), 3.95-3.94 (m, 2H), 3.63-3.57 (m, 1H), 3.54-3.52 (m, 2H), 2.69 (s, 3H), 2.55 (s, 3H), 1.88-1.82 (m, 4H) | 438 |
| 201 | (±)-(4,6-dimethyl-2-oxo-1,2-dihydropyridin-3-yl)methyl 1-(2,3-dihydro-1H-inden-1-yl)-2-methyl-1H-pyrrolo[2,3-b]pyridine-3-carboxylate | (400 MHz, CDCl$_3$) δ 11.14 (s, 1H), 8.16 (s, 1H), 8.12 (d, J = 7.6 Hz, 1H), 7.32 (t, J = 5.6 Hz, 1H), 7.25-7.01 (m, 2H), 7.05-7.01 (m, 2H), 6.76 (d, J = 7.6 Hz, 1H), 5.86 (s, 1H), 4.52-4.50 (m, 2H), 3.13 (bs, 1H), 3.05-2.97 (m, 1H), 2.66 (bs, 1H), 2.73 (s, 3H), 2.29 (bs, 2H), 2.13 (s, 3H) | 428 |
| 185 | (±)-1-(sec-butyl)-N-((4,6-dimethyl-2-oxo-1,2-dihydropyridin-3-yl)methyl)-2-methyl-1H-pyrrolo[2,3-b]pyridine-3-carboxamide | (400 MHz, CDCl$_3$) δ 8.116-8.132 (d, 1H), 8.011-8.035 (d, 1H), 7.037-7.057 (t, 1H), 6.056 (s, 1H), 4.462 (d, 2H), 6.30 (s, 1H), 2.63 (s, 3H), 2.356 (s, 3H), 2.189 (s, 3H), 1.880-1.933 (m, 1H), 1.587-1.605 (d, 2H), 1.226 (s, 2H), 0.658 (t, 3H) | 368 |
| 202 | (±)-(4,6-dimethyl-2-oxo-1,2-dihydropyridin-3-yl)methyl 2-methyl-1-(tetrahydrofuran-3-yl)-1H-pyrrolo[2,3-b]pyridine-3-carboxylate | (400 MHz, CDCl$_3$) δ 11.03 (s, 1H), 8.15 (dd, J$_1$ = 4.8 Hz, J$_2$ = 1.6 Hz, 1H), 8.06 (dd, J$_1$ = 8.0 Hz, J$_2$ = 1.6 Hz, 1H), 7.32 (t, J = 7.0 Hz, 1H), 6.97 (dd, J$_1$ = 8.0 Hz, J$_2$ = 4.8 Hz, 1H), 5.86 (s, 1H), 5.47-5.39 (m, 1H), 4.52 (d, J = 7.0 Hz, 2H), 4.39-4.32 (m, 1H), 4.17 (dd, J$_1$ = 9.2 Hz, J$_2$ = 6.8 Hz, 1H), 3.98 (t, J = 8.8 Hz, 1H), 3.91-3.86 (q, J = 7.6 Hz, 1H), 2.76 (s, 3H), 2.59-2.50 (m, 1H), 2.36 (s, 3H), 2.34-2.28 (m, 1H), 2.25 (s, 3H) | 382 |

-continued

| Compound | Name | ¹H NMR | m/z |
|---|---|---|---|
| 204 | (±)-N-((4-methoxy-6-methyl-2-oxo-1,2-dihydropyridin-3-yl)methyl)-1-(1-methoxypropan-2-yl)-2-methyl-1H-pyrrolo[2,3-b]pyridine-3-carboxamide | (400 MHz, CDCl₃) δ 13.23 (s, 1H), 8.16-8.17 (m, 1H), 8.11-8.13 (m, 1H), 7.57-7.60 (t, J = 5.2 Hz, 1H), 6.93-6.96 (m, 1H), 5.92 (s, 1H), 4.82-4.83 (d, J = 2.4 Hz, 1H), 4.65-4.66 (d, J = 6.4 Hz, 2H), 3.89 (s, 3H), 3.81-3.85 (m, 1H), 3.22 (s, 3H), 2.79 (s, 3H), 2.17 (s, 3H), 1.64-1.66 (d, J = 8.0 Hz, 3H) | 399 |
| 206 | (±)-N-((4,6-dimethyl-2-oxo-1,2-dihydropyridin-3-yl)methyl)-1-(1-(3-methoxyphenyl)ethyl)-2-methyl-1H-pyrrolo[2,3-b]pyridine-3-carboxamide | | 445 |
| 207 | (±)-N-((4,6-dimethyl-2-oxo-1,2-dihydropyridin-3-yl)methyl)-1-(1-(2-methoxypyridin-4-yl)ethyl)-2-methyl-1H-pyrrolo[2,3-b]pyridine-3-carboxamide | | 446 |
| 209 | 1-(chroman-4-yl)-N-((4,6-dimethyl-2-oxo-1,2-dihydropyridin-3-yl)methyl)-2-methyl-1H-pyrrolo[2,3-b]pyridine-3-carboxamide | | 443 |
| 211 | (±)-1-(1-cyclopropylethyl)-N-((4,6-dimethyl-2-oxo-1,2-dihydropyridin-3-yl)methyl)-2-methyl-1H-pyrrolo[2,3-b]pyridine-3-carboxamide | | 379 |
| 212 | (±)-1-(1-ethoxypropan-2-yl)-N-((4-methoxy-6-methyl-2-oxo-1,2-dihydropyridin-3-yl)methyl)-2-methyl-1H-pyrrolo[2,3-b]pyridine-3-carboxamide | (400 MHz, CDCl₃) δ 8.173-8.189 (m, 1H), 8.13-8.153 (m, 1H), 7.563 (s, 1H), 6.977-7.008 (m, 1H), 5.938 (s, 1H), 4.652-4.667 (d, 2H), 4.177 (s, 1H), 3.309-3.454 (m, 2H), 3.94-3.98 (m, 1H), 2.806 (s, 3H), 2.212 (s, 3H), 1.665-1.682 (d, 3H), 1.044 (t, 3H) | 413 |
| 214 | (±)-1-(1-cyanoethyl)-N-((4-methoxy-6-methyl-2-oxo-1,2-dihydropyridin-3-yl)methyl)-2-methyl-1H-pyrrolo[2,3-b]pyridine-3-carboxamide | (400 MHz, Methanol-d4) δ 8.28-8.26 (dd, J₁ = 4.8 Hz, J₂ = 1.2 Hz, 1H), 8.12-8.09 (dd, J₁ = 4.8 Hz, J₂ = 1.2 Hz, 1H), 7.21-7.18 (dd, J₁ = 8.0 Hz, J₂ = 4.8 Hz, 1H), 6.26 (s, 1H), 6.16-6.11 (q, J = 7.2 Hz, 1H), 4.50 (s, 2H), 3.93 (s, 3H), 2.76 (s, 3H), 2.31 (s, 3H), 1.88 (d, J = 7.2 Hz, 3H) | 379 |
| 215 | (±)-N-((4,6-dimethyl-2-oxo-1,2-dihydropyridin-3-yl)methyl)-1-(1-(5-methoxypyridin-3-yl)ethyl)-2-methyl-1H-pyrrolo[2,3-b]pyridine-3-carboxamide | | 446 |
| 216 | (±)-1-(1-methoxypropan-2-yl)-2-methyl-N-((6-methyl-2-oxo-4-propyl-1,2-dihydropyridin-3-yl)methyl)-1H-pyrrolo[2,3-b]pyridine-3-carboxamide | (400 MHz, CDCl₃) δ 12.74-12.79 (m, 1H), 8.16-8.17 (d, J = 4.0 Hz, 1H), 8.08-8.10 (d, J = 4.0 Hz, 1H), 7.45-7.48 (t, J = 5.6 Hz, 1H), 6.93-6.96 (m, 1H), 5.96 (s, 1H), 4.81 (s, 1H), 4.61-4.62 (d, J = 5.6 Hz, 2H), 4.17-4.22 (t, J = 8.4 Hz, 1H), 3.80-3.84 (m, 1H), 3.22 (s, 3H), 2.78 (s, 3H), 2.71-2.75 (t, J = 8.0 Hz, 2H), 2.18 (s, 3H), 1.64-1.65 (d, J = 6.8 Hz, 5H), 0.98-1.02 (t, J = 7.6 Hz, 3H) | 411 |
| 220 | (±)-N-((4,6-dimethyl-2-oxo-1,2-dihydropyridin-3-yl)methyl)-2-methyl-1-(1-phenylpropyl)-1H-pyrrolo[2,3-b]pyridine-3-carboxamide | (CDCl₃, 400 MHz) δ 11.82 (s, 1H), 8.24-8.15 (m, 2H), 7.25-7.18 (m, 5H), 7.04 (dd, J₁ = 4.8 Hz, J₂ = 8.0 Hz, 1H), 6.19 (s, 1H), 5.93 (s, 1H), 4.58 (s, 2H), 2.64-2.50 (m, 5H), 2.42 (s, 3H), 2.17 (s, 3H), 0.81 (t, J = 7.6 Hz, 3H) | 429 |

-continued

| Compound | Name | ¹H NMR | m/z |
|---|---|---|---|
| 221 | (±)-1-(1-(1H-pyrazol-1-yl)propan-2-yl)-N-((4,6-dimethyl-2-oxo-1,2-dihydropyridin-3-yl)methyl)-2-methyl-1H-pyrrolo[2,3-b]pyridine-3-carboxamide | (CDCl$_3$, 400 MHz) δ 12.03 (s, 1H), 8.23 (dd, J$_1$ = 1.2 Hz, J$_2$ = 4.4 Hz, 1H), 8.12 (dd, J$_1$ = 1.2 Hz, J$_2$ = 7.6 Hz, 1H), 7.43 (d, J = 1.6 Hz, 1H), 7.31 (t, J = 6.0 Hz, 1H), 8.12 (q, J$_1$ = 4.8 Hz, J$_2$ = 8.0 Hz, 1H), 6.58 (d, J = 2.0 Hz, 1H), 5.93 (d, J = 10.8 Hz, 1H), 5.91 (d, J = 2.0 Hz, 1H), 5.35 (q, J$_1$ = 10.0 Hz, J$_2$ = 13.2 Hz, 1H), 4.97 (s, 1H), 4.62-4.54 (m, 3H), 2.41 (s, 6H), 2.19 (s, 3H), 1.74 (d, J = 6.8 Hz, 3H) | 419 |
| 232 | (±)-N-((4-methoxy-6-methyl-2-oxo-1,2-dihydropyridin-3-yl)methyl)-1-(1-(2-methoxypyrimidin-4-yl)ethyl)-2-methyl-1H-pyrrolo[2,3-b]pyridine-3-carboxamide | (400 MHz, MeOD-d4) δ 8.56-78.54 (d, 1H), 8.34-8.32 (d, 1H), 8.26-8.25 (d, 1H), 7.37-7.34 (t, 1H), 7.05-7.02 (t, 1H), 6.28-6.26 (d, 1H), 4.63 (s, 2H), 4.16 (s, 3H), 3.9 (s, 3H), 2.71 (s, 3H), 2.59 (s, 3H), 2.15-2.13 (d, 3H) | 463 |
| 233 | (±)-N-((4,6-dimethyl-2-oxo-1,2-dihydropyridin-3-yl)methyl)-1-(1-(2-methoxypyrimidin-4-yl)ethyl)-2-methyl-1H-pyrrolo[2,3-b]pyridine-3-carboxamide | | 447 |
| 235 | (±)-N-((4-ethoxy-6-methyl-2-oxo-1,2-dihydropyridin-3-yl)methyl)-1-(1-methoxypropan-2-yl)-2-methyl-1H-pyrrolo[2,3-b]pyridine-3-carboxamide | (400 MHz, CDCl$_3$) δ 12.5 (s, 1H), 8.11-8.18 (m, 2H), 7.60 (s, 1H), 6.95-6.98 (m, 1H), 5.90 (s, 1H), 5.96 (s, 1H), 4.83 (s, 1H), 4.10-4.21 (m, 3H), 3.82-3.83 (m, 1H), 3.23 (s, 3H), 3.79 (s, 3H), 2.15 (s, 3H), 1.65-1.66 (d, J = 6.8 Hz, 6H), 1.44-1.47 (t, J = 7.2 Hz, 3H). | 413 |
| 237 | (±)-N-((4,6-dimethyl-2-oxo-1,2-dihydropyridin-3-yl)methyl)-2-methyl-1-(1-morpholinopropan-2-yl)-1H-pyrrolo[2,3-b]pyridine-3-carboxamide | | 438 |
| 238 | (±)-1-(1-(1H-benzo[d]imidazol-1-yl)propan-2-yl)-N-((4,6-dimethyl-2-oxo-1,2-dihydropyridin-3-yl)methyl)-2-methyl-1H-pyrrolo[2,3-b]pyridine-3-carboxamide | | 469 |
| 239 | (±)-1-(1-(3-cyanophenyl)ethyl)-N-((4-methoxy-6-methyl-2-oxo-1,2-dihydropyridin-3-yl)methyl)-2-methyl-1H-pyrrolo[2,3-b]pyridine-3-carboxamide | (400 MHz, CD$_3$OD) δ 8.18-8.12 (m, 1H), 8.10 (d, J = 6.4 Hz, 1H), 7.61-7.57 (m, 1H), 7.45-7.44 (m, 2H), 7.16-7.13 (m, 1H), 6.31 (d, J = 8.4 Hz, 1H), 6.25 (s, 1H), 4.50 (s, 2H), 3.91 (s, 3H), 2.50 (s, 3H), 2.30 (m, 3H), 2.05 (d, J = 7.2 Hz, 3H) | 456 |
| 241 | N-((4,6-dimethyl-2-oxo-1,2-dihydropyridin-3-yl)methyl)-1-(3-methoxybutan-2-yl)-2-methyl-1H-pyrrolo[2,3-b]pyridine-3-carboxamide | (400 MHz, CD$_3$OD): δ 8.67-8.65 (d, 1H), 8.45-8.44 (d, 1H), 7.59-7.55 (m, 1H), 6.70 (s, 1H), 4.79 (s, 1H), 4.61 (s, 2H), 4.07 (s, 1H), 3.32 (s, 3H), 2.75 (s, 3H), 2.56 (s, 3H), 2.42 (s, 3H), 1.68-1.66 (d, 3H), 1.16-1.15 (d, 3H). | 397 |
| 242 | (±)-1-(1-(3-carbamoylphenyl)ethyl)-N-((4-methoxy-6-methyl-2-oxo-1,2-dihydropyridin-3-yl)methyl)-2-methyl-1H-pyrrolo[2,3-b]pyridine-3-carboxamide | (400 MHz, CD$_3$OD-d4) δ 8.31 (br, 2H), 7.78-7.79 (br, 1H), 7.77 (s, 1H), 7.46-7.33 (m, 3H), 6.97 (s, 1H), 6.50-6.48 (d, J = 6.8 MHz, 1H), 4.60 (s, 2H), 4.41 (s, 3H), 2.56 (s, 3H), 2.53 (s, 3H), 2.11-2.10 (d, J = 7.2 MHz, 3H) | 474 |
| 244 | N-((4,6-dimethyl-2-oxo-1,2-dihydropyridin-3-yl)methyl)-2-methyl-1-(tetrahydro-2H-pyran-4-yl)-1H-pyrrolo[2,3-b]pyridine-3-carboxamide | (400 MHz, CD$_3$OD) δ 8.30 (m, 1H), 8.25 (m, 1H), 7.29 (m, 1 H), 6.85 (s, 1H), 4.77 (m, 1H), 4.62 (s, 2 H), 4.13 (m, 2H), 3.65 (m, 2 H), 2.99 (m, 2H), 2.78 (s, 3H), 2.60 (s, 3H), 2.46 (s, 3H), 1.77 (m, 2H) | 395 |

-continued

| Compound | Name | ¹H NMR | m/z |
|---|---|---|---|
| 249 | (±)-N-((4,6-dimethyl-2-oxo-1,2-dihydropyridin-3-yl)methyl)-2-methyl-1-(1-(2-oxopyridin-1(2H)-yl)propan-2-yl)-1H-pyrrolo[2,3-b]pyridine-3-carboxamide | (CDCl$_3$, 400 MHz) δ 11.18 (s, 1H), 8.24 (dd, J$_1$ = 1.2 Hz, J$_2$ = 4.8 Hz, 1H), 8.13 (dd, J$_1$ = 1.2 Hz, J$_2$ = 9.2 Hz, 1H), 7.30 (t, J = 6.0 Hz, 1H), 7.20-7.15 (m, 1H), 7.06 (dd, J$_1$ = 4.8 Hz, J$_2$ = 8.0 Hz, 1H), 6.50-6.43 (m, 2H), 5.93 (s, 1H), 5.70-5.66 (m, 1H), 5.11 (s, 1H), 4.80 (t, J = 12.4 Hz, 1H), 4.69 (dd, J$_1$ = 4.4 Hz, J$_2$ = 12.8 Hz, 1H), 4.53 (dd, J$_1$ = 3.2 Hz, J$_2$ = 5.6 Hz, 2H), 2.50 (s, 3H), 2.40 (s, 3H), 2.20 (s, 3H), 1.74 (d, J = 7.2 Hz, 3H) | 446 |
| 250 | (±)-N-((4,6-dimethyl-2-oxo-1,2-dihydropyridin-3-yl)methyl)-2-methyl-1-(1-(methylsulfonyl)propan-2-yl)-1H-pyrrolo[2,3-b]pyridine-3-carboxamide | (400 MHz, CD$_3$OD): δ 8.31-8.32 (d, J = 6.0 Hz, 3H), 8.18-8.20 (d, J = 8.0 Hz, 3H), 7.26-7.29 (t, 1H), 6.99 (s, 1H), 5.20-5.37 (br, 1H), 4.58 (s, 2H), 4.13 (s, 3H), 3.67-3.71 (d, 1H), 3.1-3.22 (br, 1H), 2.78 (s, 3H), 2.55 (s, 3H), 2.54 (s, 3H), 1.77-1.79 (d, J = 6.8 Hz, 3H). | 431 |
| 251 | (±)-N-((4-methoxy-6-methyl-2-oxo-1,2-dihydropyridin-3-yl)methyl)-2-methyl-1-(1-(pyridine-2-yloxy)propan-2-yl)-1H-pyrrolo[2,3-b]pyridine-3-carboxamide | (400 MHz, CDCl$_3$) δ ppm 3.80 (d, J = 6.84 Hz, 3 H) 2.21 (s, 3 H) 2.73 (s, 3 H) 3.90 (s, 3 H) 4.66 (d, J = 5.51 Hz, 2 H) 4.82-4.90 (m, 1 H) 5.11 (d, J = 9.04 Hz, 2 H) 5.93 (s, 1 H) 6.57 (d, J = 8.38 Hz, 1 H) 6.79-6.86 (m, 1 H) 7.01 (dd, J = 7.94, 4.85 Hz, 1 H) 7.45-7.52 (m, 1 H) 7.58 (br. S., 1 H) 8.07-8.17 (m, 2 H) 8.18-8.23 (m, 1 H) 11.63 (br. S., 1 H) | 462 |
| 260 | (±)-N-((6-cyclopropyl-4-methoxy-2-oxo-1,2-dihydropyridin-3-yl)methyl)-1-(1-methoxypropan-2-yl)-2-methyl-1H-pyrrolo[2,3-b]pyridine-3-carboxamide | (CDCl$_3$, 400 MHz) δ 11.04 (s, 1H), 8.18 (d, J = 4.0 Hz, 1H), 8.10 (d, J = 8.0 Hz, 1H), 7.28 (t, J = 6.0 Hz, 1H), 7.02 (dd, J$_1$ = 4.8 Hz, J$_2$ = 7.6 Hz, 1H), 5.77 (s, 1H), 4.82 (s, 1H), 4.57 (d, J = 6.0 Hz, 2H), 4.19 (t, J = 8.8 Hz, 1H), 3.83 (q, J$_1$ = 5.6 Hz, J$_2$ = 9.6 Hz, 1H), 3.22 (s, 3H), 2.77 (s, 3H), 2.41 (s, 3H), 1.74-1.68 (m, 1H), 1.65 (d, J = 7.2 Hz, 3H), 0.90-0.76 (m, 4H) | 425 |
| 322 | N-((4,6-dimethyl-2-oxo-1,2-dihydropyridin-3-yl)methyl)-1-(3-methoxybutan-2-yl)-2-methyl-6-(methylsulfonyl)-1H-indole-3-carboxamide | (400 MHz, CDCl$_3$): δ 0.97-0.99 (d, J = 6.8 Hz, 3H), δ 1.19-1.21 (d, J = 6.0 Hz, 3H), 2.16 (s, 3H), 2.41 (s, 3H), 2.73 (s, 3H), 2.99 (s, 3H), 3.04 (s, 3H), 3.859 (brs, 1H), 4.47 (brs, 1H), 4.59-4.61 (d, J = 6.0 Hz, 2H), 5.95 (s, 1H), 7.41-7.44 (t, J = 5.6 Hz, 1H), 7.52-7.54 (d, J = 4.8 Hz, 1H), 7.97-7.99 (d, J = 8.4 Hz, 1H), 8.117 (s, 1H) | 474 |
| 323 | N-((4-methoxy-6-methyl-2-oxo-1,2-dihydropyridin-3-yl)methyl)-1-(3-methoxybutan-2-yl)-2-methyl-6-(methylsulfonyl)-1H-indole-3-carboxamide | (400 MHz, CDCl$_3$) δ 1.20-1.24 (d, J = 6.4 Hz, 3H), δ 1.59-1.69 (d, J = 6.4 Hz, 3H), 2.13 (s, 3H), 2.79 (s, 3H), 2.99 (s, 3H), 3.04 (s, 3H), 3.25-3.32 (m, 4H), 4.40 (brs, 1H), 4.65-4.67 (d, J = 5.6 Hz, 2H), 5.94 (s, 1H), 7.49-7.51 (d, J = 8.4 Hz, 1H), 7.61-7.63 (t, J = 5.0 Hz, 1H), 7.98-8.00 (d, J = 8.4 Hz, 1H), 8.119 (brs, 1H), 12.71 (brs, 1H) | 490 |
| 350 | N-((4-methoxy-6-methyl-2-oxo-1,2-dihydropyridin-3-yl)methyl)-2-methyl-1-(3-(methylsulfonyl)butan-2-yl)-1H-indole-3-carboxamide | (400 MHz, CDCl$_3$) δ 0.94 (d, J = 7.2 Hz, 3H), 1.92 (m, 3H), 2.19 (s, 3H), 2.75 (s, 3H), 3.01 (s, 3H), 3.90 (s, 4H), 4.65 (m, 2H), 4.87 (m, 1H), 5.92 (s, 1H), 7.10 (m, 2H), 7.38 (s, 1H), 7.56 (d, J = 5.2 Hz, 1H), 7.89 (d, J = 7.6 Hz, 1H) | 460 |
| 383 | 1-cyclopentyl-N-((4-methoxy-6-methyl-2-oxo-1,2-dihydropyridin-3-yl)methyl)-2-methyl-1H-pyrrolo[2,3-b]pyridine-3-carboxamide | (CDCl$_3$ 400 MHz) δ 12.76 (s, 1H), 8.19-8.20 (d, J = 2.0 Hz, 1H), 8.11-8.13 (d, J = 3.6 Hz, 1H), 7.58 (s, 1H), 6.95-6.99 (m, 1H), 5.94 (s, 1H), 5.01-5.10 (m, 1H), 4.65-4.66 (d, J = 5.6 Hz, 2H), 3.90 (s, 3H), 2.82 (s, 3H), 2.39-2.42 (d, J = 11.6 Hz, 2H), 2.19 (s, 3H), 2.02-2.07 (m, 3H), 1.72-1.75 (m, 3H), 1.26-1.51 (m, 1H) | 395 |
| 384 | 1-cyclopentyl-N-((4,6-dimethyl-2-oxo-1,2-dihydropyridin-3-yl)methyl)-2-methyl-1H-pyrrolo[2,3-b]pyridine-3-carboxamide | | 379 |
| 280 | (±)-N-((6-ethyl-4-methoxy-2-oxo-1,2-dihydropyridin-3-yl)methyl)-1-(1-methoxypropan-2-yl)-2-methyl-1H-pyrrolo[2,3-b]pyridine-3-carboxamide | ¹H NMR (400 MHz, CD$_3$OD) δ 8.25-8.29 (m, 2H), δ 7.28-7.31 (m, 1H), 6.89 (s, 1H), 4.93-4.95 (br, 1H), 4.58 (s, 2H), 4.2-4.25 (m, 1H), 4.13 (s, 3H), 3.77-3.81 (m, 1H), 3.24 (s, 3H), 2.79-2.84 (q, 1H), 2.72 (s, 3H), 1.66-1.68 (d, J = 7.2 Hz, 3H) 1.32-1.36 (t, 3H) | 413 |

| Compound | Name | ¹H NMR | m/z |
|---|---|---|---|
| 288 | (R or S)-N-((4-Methoxy-6-methyl-2-oxo-1,2-dihydropyridin-3-yl)methyl)-2-methyl-1-(1-(tetrahydro-2H-pyran-4-yl)ethyl)-1H-pyrrolo[2,3-b]pyridine-3-carboxamide | (400 MHz, d6-DMSO) δ 11.57-11.65 (m, 1H), 8.18-8.23 (m, 1H), 8.07-8.12 (m, 1H), 7.83-7.91 (m, 1H), 7.07-7.15 (m, 1H), 6.15 (s, 1H), 4.31 (d, J = 4.46 Hz, 1H), 4.04-4.20 (m, 1H), 3.88-3.97 (m, 1H), 3.84 (s, 3H), 3.59-3.70 (m, 1H), 2.97-3.10 (m, 1H), 2.79-2.93 (m, 1H), 2.67 (br. S., 3H), 2.20 (s, 3H), 1.78-1.88 (m, 1H), 1.53-1.68 (m, 3H), 1.28-1.41 (m, 2H), 0.97-1.13 (m, 2H), 0.56-0.68 (m, 1H) | 439 |
| 276 | (S)-N-((4-methoxy-6-methyl-2-oxo-1,2-dihydropyridin-3-yl)methyl)-2-methyl-1-(1-phenylethyl)-1H-pyrrolo[2,3-b]pyridine-3-carboxamide | (400 MHz, DMSO-d$_6$) δ = 11.82-11.68 (m, 1 H), 8.20 (dd, J = 1.6, 4.7 Hz, 1 H), 8.13 (dd, J = 1.6, 8.0 Hz, 1 H), 8.02-7.94 (m, 1 H), 7.33-7.26 (m, 2 H), 7.24 (d, J = 7.1 Hz, 1 H), 7.17-7.10 (m, 3 H), 6.29 (s, 1 H), 6.19 (s, 1 H), 4.31 (br. S., 2 H), 3.83 (s, 3 H), 2.48 (br. S., 3 H), 2.22-2.18 (m, 3 H), 2.20 (s, 3 H), 2.02-1.97 (m, 3 H), 2.00 (d, J = 7.4 Hz, 3 H) | 431 |
| 306 | (R or S)-N-((4,6-dimethyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DMSO-d$_6$) δ = 11.73-11.56 (m, 1 H), 8.19 (d, J = 3.1 Hz, 1 H), 8.06 (dd, J = 1.4, 7.9 Hz, 1 H), 7.82 (br. S., 1 H), 7.10 (dd, J = 4.7, 7.8 Hz, 1 H), 5.91 (s, 1 H), 4.30 (br. S., 2 H), 4.19-4.02 (m, 1 H), 3.90 (d, J = 8.5 Hz, 1 H), 3.63 (d, J = 7.8 Hz, 1 H), 3.29 (s, 1 H), 3.06 (s, 1 H), 2.92-2.74 (m, 1 H), 2.64 (br. S., 3 H), 2.25 (s, 3 H), 2.11 (s, 3 H), 1.80 (br. S., 1 H), 1.59 (br. S., 3 H), 1.41-1.24 (m, 1 H), 1.09 (s, 2 H), 0.67-0.52 (m, 1 H) | 423 |
| 296 | 1-(4-amino-4-oxobutan-2-yl)-N-((4-methoxy-6-methyl-2-oxo-1,2-dihydropyridin-3-yl)methyl)-2-methyl-1H-pyrrolo[2,3-b]pyridine-3-carboxamide | (CDCl$_3$, 400 MHz) δ 8.14-8.12 (dd, J = 1.2 Hz, 4.8 Hz, 1H), 8.09-8.07 (dd, J = 1.2 Hz, 8.0 Hz, 1H), 7.51-7.46 (m, 1H), 6.94-6.91 (dd, J = 4.8 Hz, 8.0 Hz, 1H), 6.50 (s, 1H), 5.90 (s, 1H), 5.51 (s, 1H), 4.79-4.74 (dd, J = 6.4 Hz, 14.8 Hz, 1H), 4.44-4.39 (dd, J = 4.8 Hz, 14.8 Hz, 1H), 3.87 (s, 3H), 3.81-3.75 (m, 1H), 2.83-2.78 (dd, J = 5.2 Hz, 14.8 Hz, 1H), 2.75 (s, 3H), 2.23 (s, 3H), 1.63-1.62 (d, J = 6.8 Hz, 3H) | 412 |
| 301 | (±)-1-(1-cyanopropan-2-yl)-N-((4-methoxy-6-methyl-2-oxo-1,2-dihydropyridin-3-yl)methyl)-2-methyl-1H-pyrrolo[2,3-b]pyridine-3-carboxamide | (CDCl$_3$, 400 MHz) δ 12.64 (s, 1H), 8.17-8.12 (m, 2H), 7.56 (s, 1H), 7.03-7.00 (dd, J = 4.4 Hz, 7.6 Hz, 1H), 5.94 (s, 1H), 4.89-4.80 (m, 1H), 4.64-4.62 (d, J = 5.2 Hz, 1H), 3.90 (s, 3H), 3.74-3.68 (dd, J = 8.8 Hz, 17.2 Hz, 1H), 3.27-3.21 (dd, J = 6.4 Hz, 16.8 Hz, 1H), 2.79 (s, 3H), 2.19 (s, 3H), 1.78-1.76 (d, J = 6.8 Hz, 3H). | 394 |
| 262 | (±)-N-((6-(hydroxymethyl)-4-methoxy-2-oxo-1,2-dihydropyridin-3-yl)methyl)-1-(1-methoxypropan-2-yl)-2-methyl-1H-pyrrolo[2,3-b]pyridine-3-carboxamide | (400 MHz, CDCl$_3$): δ 11.16 (br, 1 H), 8.19 (dd, 1 H, J1 = 4.63 Hz, J2 = 1.10 Hz), 8.06 (dd, 1H, J1 = 7.49 Hz, J2 = 1.10 Hz), 7.14 (t, 1 H, J = 5.51 Hz), 7.05 (dd, 1 H, J1 = 7.49 Hz, H, J2 = 4.63 Hz), 6.02 (s, 1H), 4.88-4.73 (br, 1 H), 4.57 (d, 2H, J = 5.95 Hz), 4.47 (s, 2H), 4.22 (t, 1H, J = 8.60 Hz), 3.81 (dd, 1H, J1 = 9.70 Hz, J2 = 3.8 Hz), 3.37~3.15 (br, 1H), 3.21 (s, 3H), 2.76 (s, 3H), 2.44 (s, 3H), 1.64 (d, 3 H, J = 7.06 Hz) | 399 |
| Racemic 268/269 | (±)-N-((4-methoxy-6-methyl-2-oxo-1,2-dihydropyridin-3-yl)methyl)-2-methyl-1-(1-(1-methyl-2-oxo-1,2-dihydropyridin-4-yl)ethyl)-1H-pyrrolo[2,3-b]pyridine-3-carboxamide | | 462 |
| 271 | N-((4,6-dimethyl-2-oxo-1,2-dihydropyridin-3-yl)methyl)-1-(3-hydroxy-3-methylbutan-2-yl)-2-methyl-1H-pyrrolo[2,3-b]pyridine-3-carboxamide | (CDCl$_3$, 400 MHz) δ 12.87 (brs, 1H), 8.18-8.11 (m, 2H), 7.56 (s, 1H), 7.47 (s, 1H), 7.01-7.00 (dd, J = 4.8 Hz, 8 Hz, 1H), 5.96 (s, 1H), 4.64-4.55 (m, 2H), 4.32-4.27 (dd, J = 6.8 Hz, 14 Hz, 1H), 2.73 (s, 3H), 2.42 (s, 3H), 2.16 (s, 3H), 1.52-1.50 (d, J = 7.2 Hz, 3H), 1.39 (s, 3H), 0.91 (s, 3H) | 396 |

-continued

| Compound | Name | ¹H NMR | m/z |
|---|---|---|---|
| 272 | (±)-N-((4,6-dimethyl-2-oxo-1,2-dihydropyridin-3-yl)methyl)-2-methyl-1-(1-(piperidin-1-yl)propan-2-yl)-1H-pyrrolo[2,3-b]pyridine-3-carboxamide | (CDCl₃, 400 M Hz) δ 11.92 (s, 1H), 8.21 (dd, J₁ = 1.6 Hz, J₂ = 4.8 Hz, 1H), 8.13 (dd, J₁ = 1.2 Hz, J₂ = 7.6 Hz, 1H), 7.43 (t, J = 6.0 Hz, 1H), 7.01 (dd, J₁ = 4.8 Hz, J₂ = 8.0 Hz, 1H), 5.94 (s, 1H), 4.60 (d, J = 6.0 Hz, 2H), 4.29 (d, J = 6.0 Hz, 2H), 3.13 (s, 1H), 2.80 (s, 3H), 2.66 (s, 2H), 2.43 (s, 5H), 2.20 (s, 3H), 1.44 (d, J = 44.0 Hz, 6H), 0.90 (d, J = 6.8 Hz, 3H) | 435 |
| 193 | (±)-N-((4,6-dimethyl-2-oxo-1,2-dihydropyridin-3-yl)methyl)-1-(4-hydroxybutan-2-yl)-2-methyl-1H-pyrrolo[2,3-b]pyridine-3-carboxamide | (400 MHz, Methanol-d4) δ: 8.24-8.23 (m, 1H), 8.18-8.16 (m, 1H), 7.21-7.18 (m, 1H), 6.37 (s, 1H), 4.58 (s, 2 H), 3.51-3.45 (m, 1 H), 3.49-3.15 (m, 2H), 2.74 (s, 4 H), 2.50 (s, 3 H), 2.34 (s, 3 H), 2.31-2.26 (m, 1 H), 1.73-1.71 (m, 3 H) | 383 |
| 194 | N-((4,6-dimethyl-2-oxo-1,2-dihydropyridin-3-yl)methyl)-2-methyl-1-(piperidin-1-ylsulfonyl)-1H-pyrrolo[2,3-b]pyridine-3-carboxamide | (400 MHz, CDCl₃): δ 8.31-8.32 (d, 1H), 8.07-8.10 (d, 1H), 7.38-7.40 (t, 1H), 7.10-7.12 (t, 1H), 5.93 (s, 1H), 6.30 (s, 1H), 4.56-4.57 (d, 2H), 3.41-3.43 (t, 4H), 2.66 (s, 3H), 2.40 (s, 3H), 2.15 (s, 3H), 1.47 (m, 6H) | 458 |
| 209 | (±)-N-((4,6-dimethyl-2-oxo-1,2-dihydropyridin-3-yl)methyl)-1-(2-hydroxypropyl)-2-methyl-1H-pyrrolo[2,3-b]pyridine-3-carboxamide | | 369 |
| 254 | (±)-N-((4,6-dimethyl-2-oxo-1,2-dihydropyridin-3-yl)methyl)-4-(1-methoxypropan-2-yl)-5-methyl-4H-pyrrolo[2,3-d]thiazole-6-carboxamide | (400 MHz, Methanol-d4) δ 1.63 (d, J = 6.8 Hz, 3H), 2.47 (s, 3H), 2.60 (s, 3H), 2.71 (s, 3H), 3.23 (s, 3H), 3.73-3.77 (m, 1H), 4.10-4.15 (m, 1H), 4.60 (m, 2H), 4.70-4.79 (m, 1H), 6.81 (s, 1H), 8.68 (s, 1H) | 389 |
| 277 | (±)-1-(3-methoxy-3-methylbutan-2-yl)-N-((4-methoxy-6-methyl-2-oxo-1,2-dihydropyridin-3-yl)methyl)-2-methyl-1H-indole-3-carboxamide | (400 MHz, DMSO-d₆) δ = 12.01-11.82 (m, 1 H), 7.91-7.82 (m, 2 H), 7.71-7.64 (m, 1 H), 7.06-6.96 (m, 2 H), 6.25 (s, 1 H), 4.43 (q, J = 7.1 Hz, 1 H), 4.33 (br. S., 2 H), 3.86 (s, 3 H), 3.14-3.09 (m, 3 H), 2.61 (s, 3 H), 2.23 (s, 3 H), 1.58-1.52 (m, 3 H), 1.27 (s, 3 H), 0.88 (s, 3 H) | 426 |
| 275 | (±)-N-((4,6-dimethyl-2-oxo-1,2-dihydropyridin-3-yl)methyl)-1-(3-methoxypentan-2-yl)-2-methyl-1H-indole-3-carboxamide | | 410 |
| 294 | (±)-N-((4-methoxy-6-methyl-2-oxo-1,2-dihydropyridin-3-yl)methyl)-1-(3-methoxybutan-2-yl)-2-methyl-1H-indole-3-carboxamide | (CDCl₃, 400 MHz) δ 7.85 (t, J = 6.4 Hz, 1H), 7.45 (s, 2H), 7.08-7.03 (m, 2H), 5.93 (s, 1H), 4.71-4.61 (m, 2H), 4.36 (s, 1H), 3.90 (s, 4H), 2.95 (s, 3H), 2.75 (s, 3H), 2.17 (s, 3H), 1.57 (d, J = 7.2 Hz, 3H), 1.23 (d, J = 6.0 Hz, 3H) | 412 |
| 309 | (±)-N-((4-methoxy-6-methyl-2-oxo-1,2-dihydropyridin-3-yl)methyl)-1-(1-methoxypropan-2-yl)-2-methyl-6-(trifluoromethyl)-1H-pyrrolo[2,3-b]pyridine-3-carboxamide | (400 MHz, METHANOL-d₄) δ = 8.24 (d, J = 8.0 Hz, 1H), 7.52 (d, J = 8.5 Hz, 1H), 6.30 (s, 1H), 4.94-4.90 (m, 1H), 4.54 (s, 2H), 4.36 (t, J = 9.5 Hz, 1H), 3.96 (s, 3H), 3.79 (dd, J = 4.8. 9.8 Hz, 1H), 3.22 (s, 3H), 2.73 (s, 3H), 2.34 (s, 3H), 1.70 (d, J = 7.0 Hz, 3H) | 467 |
| 312 | N-((4-methoxy-6-methyl-2-oxo-1,2-dihydropyridin-3-yl) methyl)-2-methyl-1-(4,4,4-trifluoro-3-methoxybutan-2-yl)-1H-pyrrolo [2,3-b] pyridine-3-carboxamide | (400 MHz, CDCl₃): δ 8.18-8.14 (m, 2H), 7.57-7.51 (m, 1H), 7.05-7.02 (m, 1H), 5.92 (s, 1H), 5.01 (s, 2H), 4.63-4.60 (m, 1H), 3.89 (s, 3H), 3.73 (s, 3H), 2.73 (s, 3H), 2.20 (s, 3H), 1.75-1.73 (d, J = 6.8, 3H). | 467 |
| 338 | 1-(1-methoxy-2-methylpropan-2-yl)-N-((4-methoxy-6-methyl-2-oxo-1,2-dihydropyridin-3-yl)methyl)-2-methyl-1H-indole-3-carboxamide | (400 MHz, CDCl₃): δ 1.84 (s, 6H), 2.08 (s, 2H), 2.86 (s, 3H), 3.24 (s, 3H), 3.82 (s, 2H), 3.88 (s, 3H), 4.65 (d, J = 5.6 Hz, 2H), 5.88 (m, 1H), 6.99-6.95 (m, 1H), 7.05-7.02 (m, 1H), 7.43-7.40 (m, 1H), 7.60-7.57 (m, 1H), 7.77-7.75 (m, 1H), 12.98 (s, 1H) | 412 |
| 290 | (±)-1-(3-ethoxybutan-2-yl)-N-((4-methoxy-6-methyl-2-oxo-1,2-dihydropyridin-3- | (400 MHz, DMSO-d₆) δ = 11.60 (br. s., 1H), 7.72 (d, J = 7.6 Hz, 1 H), 7.67 (d, J = 5.1 Hz, 2 H), 7.09-6.98 (m, 2 H), 6.14 (s, 1 H), | 426 |

| Compound | Name | ¹H NMR | m/z |
|---|---|---|---|
|  | yl)methyl)-2-methyl-1H-indole-3-carboxamide | 4.41-4.35 (m, 1 H), 4.32 (d, J = 4.9 Hz, 2 H), 4.03-3.93 (m, 1 H), 3.83 (s, 3 H), 3.25 (d, J = 9.4 Hz, 1 H), 2.82-2.72 (m, 1 H), 2.62 (br. s., 3 H), 2.19 (s, 3 H), 1.52 (d, J = 7.1 Hz, 3 H), 1.15 (d, J = 6.0 Hz, 3 H), 0.68 (t, J = 6.9 Hz, 3 H) |  |
| 293 | N-((4-methoxy-6-methyl-2-oxo-1,2-dihydropyridin-3-yl) methyl)-1-(3-methoxypentan-2-yl)-2-methyl-1H-pyrrolo [2,3-b] pyridine-3-carboxamide | (400 MHz, CDCl₃): δ 8.19-8.13 (m, 2H), 7.57-7.55 (t, 1H), 6.99-6.96 (m, 1H), 5.94 (s, 1H), 4.67-4.65 (m, 2H), 4.40 (m, 1H), 4.16 (m, 1H), 3.16 (s, 3H), 2.80 (s, 3H), 2.77 (s, 3H), 2.20 (s, 3H), 1.87-3.81 (m, 1H), 1.67-1.65 (m, 3H), 1.53-1.45 (m, 3H), 1.02-0.99 (m, 3H) | 427 |
| 299 | N-((4-methoxy-6-methyl-2-oxo-1,2-dihydropyridin-3-yl)methyl)-1-(3-methoxypentan-2-yl)-2-methyl-1H-indole-3-carboxamide | (400 MHz, CDCl₃) δ 7.87-7.86 (d, 1H), 7.52-7.45 (m, 2H), 7.10-7.02 (m, 2H), 4.72-4.64 (dd, 2H), 4.45-4.42 (s 1H), 3.9 (s, 3H), 3.73 (s, 1H), 2.8-2.7 (d, 6H), 2.17 (s, 3H), 1.80-1.75 (m, 1H), 1.58 (s, 3H), 1.25 (m, 1H), 1.03-0.99 (t, 3H) | 425 |
| 265 | 1-(1-methoxy-1-phenylpropan-2-yl)-N-((4-methoxy-6-methyl-2-oxo-1,2-dihydropyridin-3-yl)methyl)-2-methyl-1H-pyrrolo[2,3-b]pyridine-3-carboxamide | (CDCl₃, 400 MHz) δ 13.19 (s, 1H), 8.22-8.21 (d, J = 4.4 Hz, 1H), 8.16-8.14 (d, J = 8.0 Hz, 2H), 7.61-7.26 (m, 6H), 7.00-6.97 (dd, J = 4.8 Hz, 8.0 Hz, 1H), 5.94 (s, 1H), 5.33-5.30 (d, J = 9.2 Hz, 1H), 4.73-4.63 (m, 2H), 4.48 (s, 1H), 3.90 (s, 3H), 2.85 (s, 3H), 2.82 (s, 3H), 2.19 (s, 3H), 1.41-1.39 (d, J = 6.8 Hz, 3H) | 475 |

Example 42

Synthesis of (±)-N-((4,6-dimethyl-2-oxo-1,2-dihydropyridin-3-yl)methyl)-2-methyl-1-(1-(3-(pyrimidin-4-yl)phenyl)ethyl)-1H-indole-3-carboxamide (Compound 205)

Step 1: (±)-N-((4,6-dimethyl-2-oxo-1,2-dihydropyridin-3-yl)methyl)-2-methyl-1-(1-(3-(4,4,5,5-tetramethyl-1,3,2-dioxaborolan-2-yl)phenyl)ethyl)-1H-indole-3-carboxamide A 50 mL round bottomed flask was charged with a magnetic stir bar, 1-(1-(3-bromophenyl)ethyl)-N-((4,6-dimethyl-2-oxo-2,3-dihydropyridin-3-yl)methyl)-2-methyl-1H-indole-3-carboxamide (171) (50 mg, 0.1 mmol), 4,4,4',4',5,5,5',5'-octamethyl-2,2'-bi(1,3,2-dioxaborolane) (38.7 mg, 0.15 mmol), potassium acetate (19.6 mg, 0.2 mmol), 1,1'-Bis(diphenylphosphino)ferrocene palladium dichloride (110 mg, 0.15 mmol) and anhydrous 1,4-dioxane (5 mL) under N₂. The reaction flask was fitted with a reflux condenser and the mixture was then heated to refluxed overnight. The reaction as allowed to cool to rt and the solvent was removed in vacuo and the resulting residue was purified by silica gel chroma-

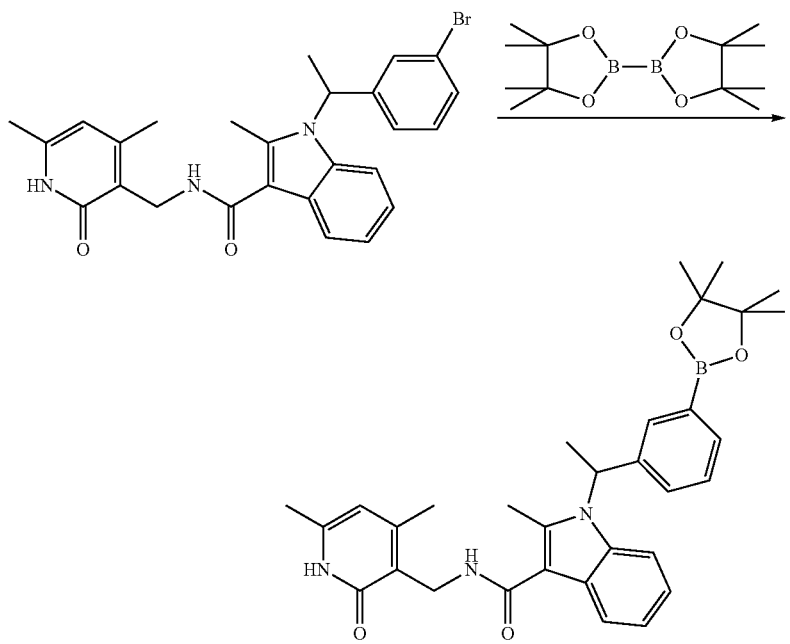

tography (Eluent: PE/EA=10:1) to the title compound as a yellow oil. (20 mg, yield 36%) LCMS (M+H+) m/z: calc'd 491.12. found 492.3.

Step 2: (±)-N-((4,6-dimethyl-2-oxo-1,2-dihydropyridin-3-yl)methyl)-2-methyl-1-(1-(3-pyrimidin-4-yl)phenyl)ethyl)-1H-indole-3-carboxamide (Compound 205)

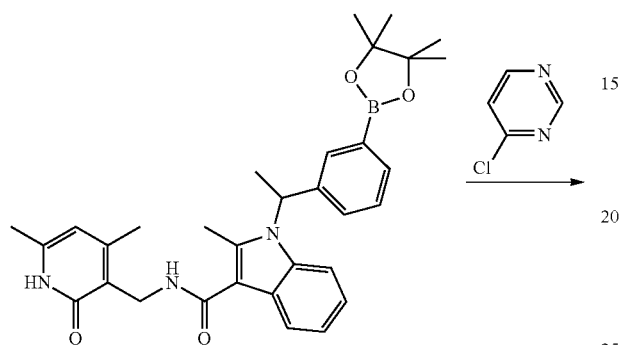

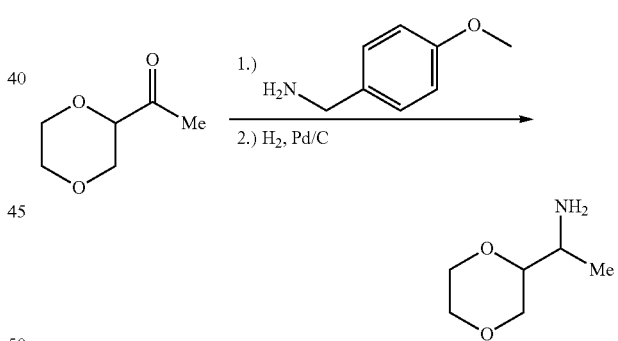

A round bottom flask was charged with a magnetic stir bar, 1-[1-(3-Bromo-phenyl)-ethyl]-2-methyl-1H-indole-3-carboxylic acid (4,6-dimethyl-2-oxo-2,3-dihydro-pyridin-3-yl-methyl)-amide (Step 8) (20 mg, 0.04 mmol), 4-Chloro-pyrimidine (6.95 mg, 0.06 mmol), potassium carbonate (10.9 mg, 0.08 mmol), 1,1'-Bis(diphenylphosphino)ferrocene palladiumdichloride (44 mg, 0.06 mmol) and 1,4-dixoane/H₂O (4:1, 8 mL). The mixture was purged and placed under N₂ and stirred heated to reflux with stirring overnight. The reaction was then allowed to cool to rt and the mixture was concentrated in vacuo. The resulting residue was purified by preparative-HPLC (Column: YMC—Actus Triart C18 150*30 mm*5 um; Mobile phase A: water with 0.1% HCl solution; Mobile phase B: MeCN; column temperature: 30° C.; Gradient: 35-65% B). The collected fractions were combined and lyophilized to afford the title compound (6.3 mg, yield 35%) LCMS (M+H+) m/z: calc'd 491.23. found 492.0; ¹H NMR (400 MHz, MeOD-d4) δ 9.2 (s, 1H), 8.85-8.54 (d, 2H), 8.14-8.06 (m, 2H), 7.78-7.72 (m, 1H), 7.58-7.54 (t, 1H), 7.44-7.42 (d, 1H), 7.15-7.12 (d, 1H), 7.04-7.01 (t, 2H), 7.01-6.79 (t, 1H), 6.8 (s, 1H), 6.14-6.12 (t, 1H), 4.88 (m, 2H), 4.67 (s, 1H), 2.73 (s, 3H), 2.6 (s, 3H), 2.47 (s, 3H), 2.08-2.07 (d, 3H).

Example 43

Synthesis of Methyl 1-(1-(1,4-dioxan-2-yl)ethyl)-2-methyl-1H-indole-3-carboxylate The title compound was used as an alternate alkyl carboxylate starting material in Step 3 of Example 36.

Step 1: 1-(1,4-dioxan-2-yl)ethanone

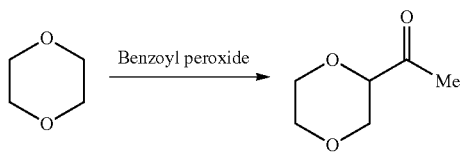 [SMILES: C1COCCO1 ; CC(=O)C1COCCO1]

To a solution of benzoic peroxide (20 g, 141 mmol) in 200 mL 1,4-dioxane at room temperature under nitrogen atmosphere was added biacetyl (24.3 g, 282 mmol). After the addition, the mixture was heated to reflux and stirred for 24 hours. The reaction mixture was cooled to 0° C. The pH was adjusted to around 9 by progressively adding 2N sodium hydroxide below 0° C., extracted with 2-methoxy-2-methylpropane (10 mL×3), and concentrated to give 1-(1,4-dioxan-2-yl)ethanone (13 g, 36%) as a yellow oil which was used directly in the next step without purification.

Step 2: 1-(1,4-dioxan-2-yl)ethanamine

To a solution of 1-(1,4-dioxan-2-yl)ethanone (12 g, 92.2 mmol) in 1,2-dichloroethane (100 mL) was added (4-methoxyphenyl)methanamine (25 g, 184.4 mmol) at room temperature. The mixture was allowed to stir for 3 hours, and then sodium triacetoxyborohydride (39 g, 184.4 mmol) was added. The resulting mixture was allowed to stir for 48 hours at room temperature. The reaction mixture was quenched by adding water, extracted with dichloromethane (100 mL×3). The combined organic phase was dried by anhydrous sodium sulphate, and then filtered. The filtrate was concentrated and purified by column chromatograph on silica gel (elute: dichloromethane/methanol 100:1→50:1→20:1) to give 1-(1,4-dioxan-2-yl)-N-(4-methoxybenzyl)ethanamine (16.4 g, 71%) as a yellow solid. LCMS (M+H⁺) m/z: calcd. 251.15. found 251.9. To a solution of 1-(1,4-dioxan-2-yl)-N-(4-methoxybenzyl)ethanamine (5 g, 19.9 mmol) in anhydrous methanol (100 mL) was added palladium 10% on carbon (240 mg, 2 mmol), then purged with hydrogen (30 psi), the mixture was allowed to stir overnight at room temperature. The reaction mixture was filtered, and the filtrate was concentrated to afford the title compound (2.5 g, 96%) as a brown solid.

The amine intermediates shown in the following table were prepared according to the general procedure outlined above using the appropriate starting materials and modifications.

| Name | Structure | m/z |
|------|-----------|-----|
| tert-butyl 3-(1-aminoethyl)piperidine-1-carboxylate | 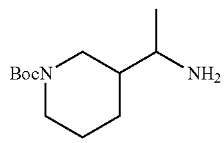 | 228 |
| (±)-1-(4,4-difluorocyclohexyl)ethanamine | 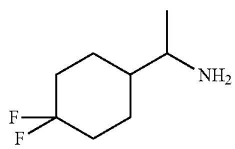 | 164 |
| (±)-1-(1-(methylsulfonyl)azetidin-3-yl)ethanamine | 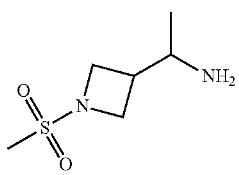 | 179 |
| (±)-tert-butyl 4-(4-(1-aminoethyl)154yridine-2-yl)piperazine-1-carboxylate | 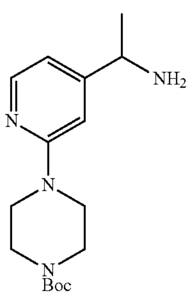 [SMILES: CC(N)c1ccnc(N2CCN(C(=O)OC(C)(C)C)CC2)c1] | 307 |

Step 3: (E)-methyl 3-((1-(1,4-dioxan-2-yl)ethyl)imino)-2-(2-bromophenyl)butanoate

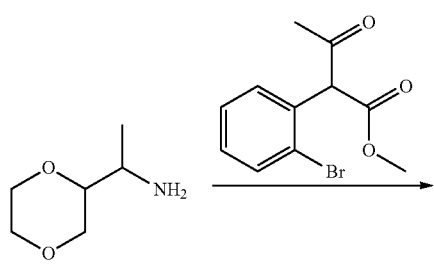

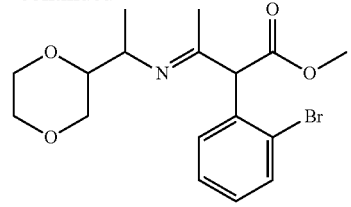

To a solution of 1-(1,4-dioxan-2-yl)ethanamine (2.5 g, 19 mmol) in methanol (100 mL) was added methyl 2-(2-bromophenyl)-3-oxobutanoate (5.4 g, 20 mmol) and acetic acid (1.8 g, 30 mmol). The resulting reaction system was warm to reflux and allowed to stir overnight. The reaction mixture was concentrated and purified by column chromatographed on silica gel (eluted: dichloromethane/methanol 50:1→20:1→5:1) the title compound (1 g, 14%) as a brown solid. LCMS (M+H$^+$) m/z: calcd. 383.07. found 384.9.

The imino-bromo intermediates shown in the following table were prepared according to the general procedure outlined above using the appropriate starting materials (e.g., one of the amines set forth in the table in Step 2 of this example) and modifications.

| Name | Structure | m/z |
|------|-----------|-----|
| (E)-tert-butyl 3-(1-((3-(2-bromophenyl)-4-methoxy-4-oxobutan-2-ylidene)amino)ethyl)piperidine-1-carboxylate | 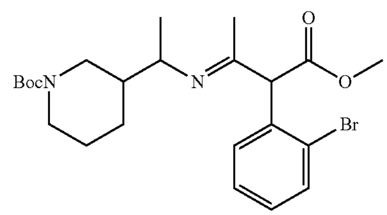 [SMILES: COC(=O)C(/C(C)=N/C(C)C1CCCN(C(=O)OC(C)(C)C)C1)c1ccccc1Br] | 482 |
| (±)-(E)-methyl 2-(2-bromophenyl)-3-((1-(4,4-difluorocyclohexyl)ethyl)imino)butanoate | 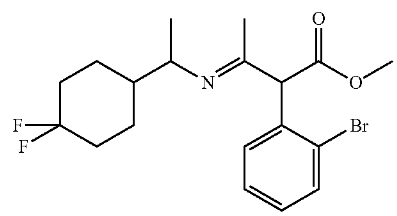 [SMILES: COC(=O)C(/C(C)=N/C(C)C1CCC(F)(F)CC1)c1ccccc1Br] | 417 |
| (E)-tert-butyl 4-((3-(2-bromophenyl)-4-methoxy-4-oxobutan-2-ylidene)amino)piperidine-1-carboxylate | 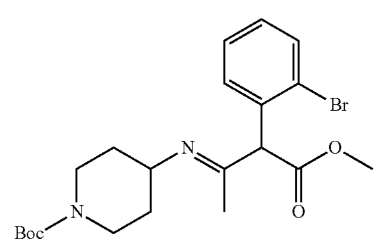 [SMILES: COC(=O)C(/C(C)=N/C1CCN(C(=O)OC(C)(C)C)CC1)c1ccccc1Br] | 454 |
| (Z)-methyl 2-(2-bromophenyl)-3-(quinolin-5-ylamino)but-2-enoate | 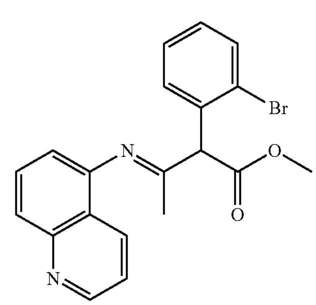 [SMILES: COC(=O)C(/C(C)=N/c1cccc2ncccc12)c1ccccc1Br] | 398 |

| Name | Structure | m/z |
|---|---|---|
| (E)-methyl 2-(2-bromophenyl)-3-(cyclopentylimino)butanoate | 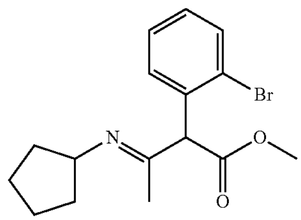 [SMILES: COC(=O)C(/C(C)=N/C1CCCC1)c1ccccc1Br] | 339 |
| (E)-methyl 2-(2-bromophenyl)-3-((6-methylquinolin-5-yl)imino)butanoate | 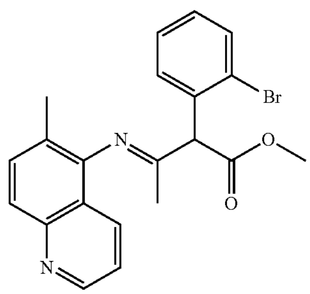 [SMILES: COC(=O)C(/C(C)=N/c1c(C)ccc2ncccc12)c1ccccc1Br] | 412 |
| (±)-(E)-methyl 2-(2-bromophenyl)-3-((1-(1-(methylsulfonyl)azetidin-3-yl)ethyl)imino)butanoate | 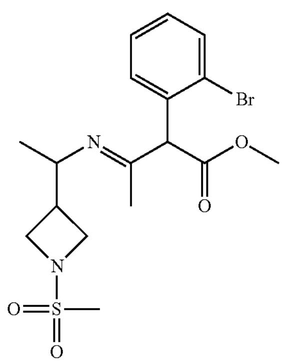 [SMILES: COC(=O)C(/C(C)=N/C(C)C1CN(S(C)(=O)=O)C1)c1ccccc1Br] | 432 |
| (±)-(E)-tert-butyl 4-(4-((3-(2-bromophenyl)-4-methoxy-4-oxobutan-2-ylidene)amino)pyridine-2-yl)piperazine-1-carboxylate | 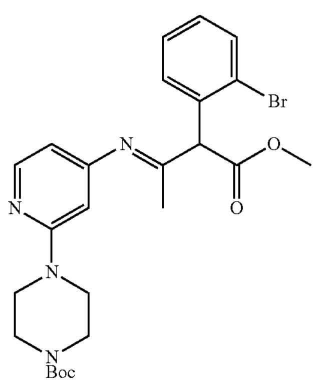 [SMILES: COC(=O)C(/C(C)=N/c1ccnc(N2CCN(C(=O)OC(C)(C)C)CC2)c1)c1ccccc1Br] | 559 |
| (E)-methyl 2-(2-bromophenyl)-3-((2,5-dimethylphenyl)amino)but-2-enoate | 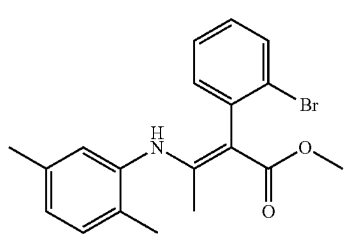 | 375 |
| (E)-methyl 2-(2-bromophenyl)-3-((2,3-dimethylphenyl)amino)but-2-enoate | 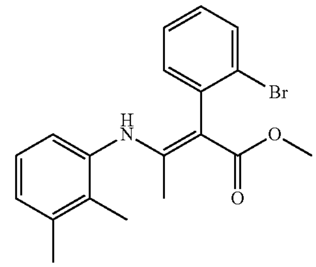 [SMILES: COC(=O)/C(=C(\C)Nc1cccc(C)c1C)c1ccccc1Br] | 375 |
| (E)-methyl 2-(2-bromophenyl)-3-(quinolin-6-ylimino)butanoate | 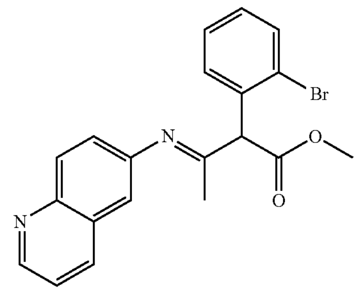 [SMILES: COC(=O)C(/C(C)=N/c1ccc2ncccc2c1)c1ccccc1Br] | 398 |

Step 4: Methyl 1-(1-(1,4-dioxan-2-yl)ethyl)-2-methyl-1H-indole-3-carboxylate

To a solution of (E)-methyl 3-((1-(1,4-dioxan-2-yl)ethyl)imino)-2-(2-bromophenyl)butanoate (400 mg, 1.1 mmol) in dioxane (3 mL) was added Chloro[2-(dicyclohexylphosphino)-3,6-dimethoxy-2',4',6'-triisopropylbiphenyl][2-(2-aminoethyl)phenyl]Pd(II) (160 mg, 0.2 mmol), 2-Dicyclohexyphosphino-2',6'-diisopropoxybiphenyl (93 mg, 0.2 mmol) and sodium tert-butoxide (192 mg, 2 mmol). The resulting reaction mixture was heated to 120° C. with stirring for 30 mins in a microwave. The reaction mixture was quenched by adding water and was extracted with ethyl acetate (25 mL×3). The combined organic phase was dried by anhydrous sodium sulphate, and then filtered. The filtrate was concentrated and purified by column chromatograph on silica gel (eluted: petrol ether lacetic ester 10:1→5:1→2:1) to afford the title compound (282 mg, 89%) as yellow solid. LCMS (M+H⁺) m/z: calcd. 303.15. found 303.9.

The compounds shown in the following table were prepared according to the general procedure outlined above using the appropriate starting materials (e.g., one of the imino-bromo intermediates shown in the table in Step 3 of this example) and modifications.

| Name | Structure | m/z |
|---|---|---|
| methyl 1-(1-(1-(tert-butoxycarbonyl)piperidin-3-yl)ethyl)-2-methyl-1H-indole-3-carboxylate | 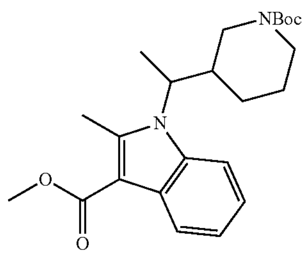 [SMILES: COC(=O)c1c(C)n(C(C)C2CCCN(C(=O)OC(C)(C)C)C2)c2ccccc12] | 401 |
| (±)-methyl 1-(1-(4,4-difluorocyclohexyl)ethyl)-2-methyl-1H-indole-3-carboxylate | 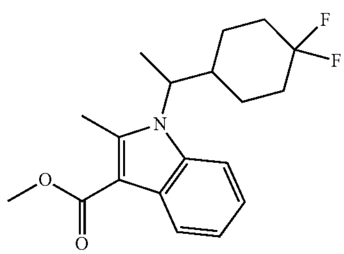 [SMILES: COC(=O)c1c(C)n(C(C)C2CCC(F)(F)CC2)c2ccccc12] | 336 |
| methyl 1-(1-(tert-butoxycarbonyl)piperidin-4-yl)-2-methyl-1H-indole-3-carboxylate | 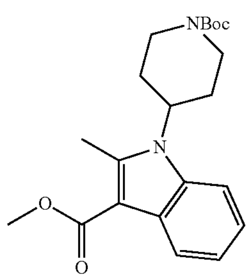 [SMILES: COC(=O)c1c(C)n(C2CCN(C(=O)OC(C)(C)C)CC2)c2ccccc12] | 373 |
| methyl 2-methyl-1-(quinolin-5-yl)-1H-indole-3-carboxylate | 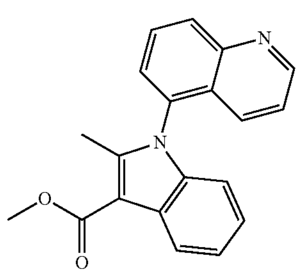 [SMILES: COC(=O)c1c(C)n(-c2cccc3ncccc23)c2ccccc12] | 317 |
| methyl 1-cyclopentyl-2-methyl-1H-indole-3-carboxylate | 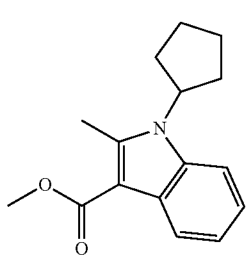 [SMILES: COC(=O)c1c(C)n(C2CCCC2)c2ccccc12] | 258 |
| methyl 2-methyl-1-(6-methylquinolin-5-yl)-1H-indole-3-carboxylate | | 331 |
| (±)-methyl 2-methyl-1-(1-(1-(methylsulfonyl)azetidin-3-yl)ethyl)-1H-indole-3-carboxylate | | 351 |
| (±)-methyl 1-(1-(2-(4-(tert-butoxycarbonyl)piperazin-1-yl)pyridine-4-yl)ethyl)-2-methyl-1H-indole-3-carboxylate | | 479 |
| methyl 1-(2,5-dimethylphenyl)-2-methyl-1H-indole-3-carboxylate | | 294 |
| methyl 1-(2,5-dimethylphenyl)-2-methyl-1H-indole-3-carboxylate | | 294 |

-continued

| Name | Structure | m/z |
|---|---|---|
| methyl 2-methyl-1-(quinolin-6-yl)-1H-indole-3-carboxylate | 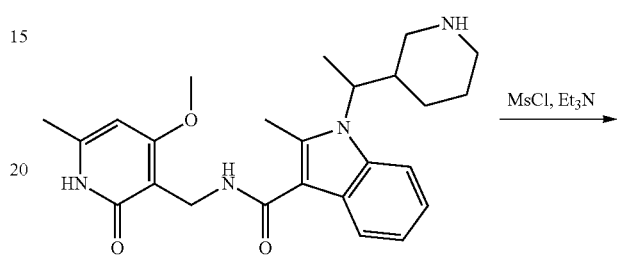 | 317 |

These alkyl carboxylates were also used as starting material in Step 3 of Example 36 in the synthesis of certain compounds of the invention.

Example 44

Synthesis of ethyl 2-methyl-1-(1-(1-methyl-2-oxo-1,2-dihydropyridin-4-yl)ethyl)-1H-indole-3-carboxylate

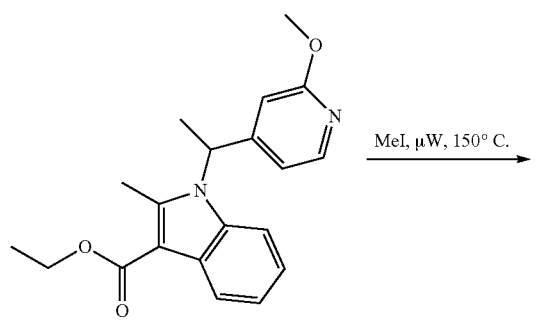

MeI, μW, 150° C.

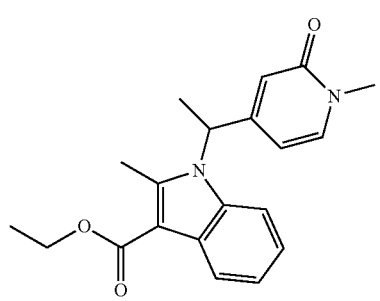

Iodomethane (57.94 mg, 0.408 mmol) was added to (±)-ethyl 1-(1-(2-methoxypyridin-4-yl)ethyl)-2-methyl-1H-indole-3-carboxylate (Example 39; 50 mg, 0.136 mmol). The mixture was stirred in the microwave at 150° C. for 15 minutes. The mixture was evaporated to afford the title compound which was used without further purification (50 mg, yield: 100%) as a starting alkyl carboxylate in Step 3 of Example 36 in the synthesis of certain compounds of the invention.

Example 45

Synthesis of N-((4-methoxy-6-methyl-2-oxo-1,2-dihydropyridin-3-yl)methyl)-2-methyl-1-(1-(1-(methylsulfonyl)piperidin-3-yl)ethyl)-1H-indole-3-carboxamide (Compound 318)

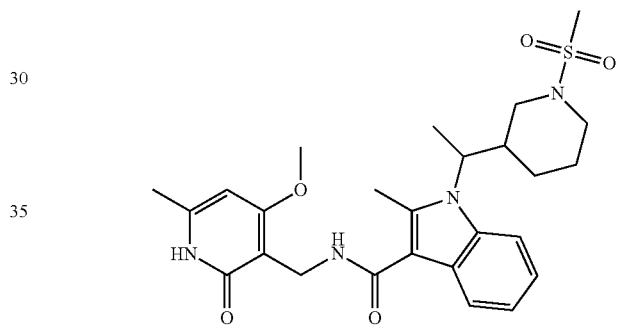

MsCl, Et₃N

To a solution of N-((4-methoxy-6-methyl-2-oxo-1,2-dihydropyridin-3-yl)methyl)-2-methyl-1-(1-(piperidin-3-yl)ethyl)-1H-indole-3-carboxamide (20 mg, 45.81 mol) in dichloromethane (3 mL) was added triethylamine (9.27 mg, 91.63 μmol) and methanesulfonyl chloride (7.87 mg, 68.72 μmol). The mixture was stirred at room temperature for 12 hours. The mixture was evaporated and purified by preparative-HPLC (Instrument: Gilson GX281 Column: Phenomenex Gemini C18 250*21.2 mm Mobile phase A: water with 0.01 mol/1NH₄HCO₃; Mobile phase B: MeCN Column temperature: 30° C. Gradient: 23-53% B 10 min) to afford the title compound (7 mg, yield: 29.69%). LRMS (M+H⁺) m/z: calc'd 515.22. found 515.2. ¹H NMR (400 MHz, METHANOL-d₄) δ 0.94-1.12 (m, 2 H) 1.39 (br. S., 2 H) 1.57-1.70 (m, 4 H) 2.33 (s, 3 H) 2.63 (s, 3 H) 2.83 (d, J=9.54 Hz, 2 H) 2.88 (s, 3 H) 3.48 (br. S., 1 H) 3.79-3.87 (m, 1 H) 3.95 (s, 3 H) 4.38 (br. S., 1 H) 4.54 (s, 2 H) 6.28 (s, 1 H) 7.07-7.17 (m, 2 H) 7.58 (d, J=8.03 Hz, 1 H) 7.72 (d, J=7.53 Hz, 1 H).

The compounds shown in the following table were prepared according to the general procedure outlined in this example using the appropriate starting materials and modifications. The structure of these compounds is shown in FIG. 1.

| Compound | Name | ¹H NMR | m/z |
|---|---|---|---|
| 320 | N-((4-methoxy-6-methyl-2-oxo-1,2-dihydropyridin-3-yl)methyl)-2-methyl-1-(1-(1-(methylsulfonyl)piperidin-3-yl)ethyl)-1H-indole-3-carboxamide | ¹H NMR (400 MHz, METHANOL-d₄) δ 7.74 (d, J = 7.0 Hz, 1H), 7.65-7.54 (m, 1H), 7.17-7.08 (m, 2H), 6.30 (s, 1H), 4.70-4.60 (m, 1H), 4.56 (s, 2H), 4.34-4.24 (m, 1H), 3.97 (s, 3H), 3.80 (d, J = 13.6 Hz, 1H), 3.19-3.01 (m, 1H), 2.77-2.69 (m, 1H), 2.64 (s, 3H), 2.56-2.41 (m, 1H), 2.35 (s, 3H), 2.26-2.12 (m, 3H), 1.73-1.63 (m, 3H), 1.62-1.50 (m, 1H), 1.35-1.23 (m, 1H), 1.09 (s, 2H) | 479 |
| 371 | N-((4-methoxy-6-methyl-2-oxo-1,2-dihydropyridin-3-yl)methyl)-2-methyl-1-(1-(methylsulfonyl)-1,2,3,4-tetrahydroquinolin-5-yl)-1H-indole-3-carboxamide | (CDCl₃, 400 MHz) δ 7.94 (d, J = 7.6 Hz, 1H), 7.88 (d, J = 8.0 Hz, 1H), 7.63 (d, J = 6.0 Hz, 1H), 7.36 (t, J = 8.0 Hz, 1H), 7.16-7.01 (m, 3H), 6.78 (d, J = 7.6 Hz, 1H), 5.97 (s, 1H), 4.70 (t, J = 19.6 Hz, 2H), 3.92 (s, 3H), 3.78 (d, J = 5.6 Hz, 2H), 3.00 (s, 3H), 2.49 (s, 3H), 2.32 (s, 3H), 2.18-2.13 (m, 2H), 1.85-1.81 (m, 2H) | 535 |

Example 46

Chiral Separation of Compound 219 to afford Compounds 223 and 224

N-((4-methoxy-6-methyl-2-oxo-1,2-dihydropyridin-3-yl)methyl)-1-(1-methoxypropan-2-yl)-2-methyl-1H-indole-3-carboxamide (200 mg) (Compound 219) was subjected to chiral chromatography via supercritical fluid chromatography (SFC) (A:C₂H₅OH, B:NH₃.H₂O. A:B=55:45 AD column) to afford the separate enantiomers 223 (peak 1) and 224 (Peak 2) (60 mg each) LCMS 398 (M+1)⁺ ¹H NMR (400 MHz, CD₃OD) δ 7.69 (d, J=7.2 Hz, 1H), 7.53 (d, J=7.6 Hz, 1H), 7.12 (m, 2H), 6.26 (s, 1H), 4.80 (m, 1H), 4.52 (s, 2H), 3.99 (m, 4H), 3.75 (m, 1H), 3.20 (s, 3H), 2.62 (s, 3H), 2.31 (s, 3H), 1.59 (d, J=7.2 Hz, 3H). The optical rotation of each enantiomer was not determined.

The compounds shown in the following table were prepared according to the general chiral chromatography procedure outlined above. The optical rotation of the separated enantiomers was not determined, but the elution peak ("Peak 1" or "Peak 2") is indicated. Structures of each compound are shown in FIG. 1.

| Compound | Name | ¹H NMR | m/z |
|---|---|---|---|
| 217 | (R or S)-N-((4,6-dimethyl-2-oxo-1,2-dihydropyridin-3-yl)methyl)-1-(1-methoxypropan-2-yl)-2-methyl-1H-indole-3-carboxamide-PEAK 1 | (400 MHz, CD₃OD) δ 7.74 (m, 1H), 7.57 (d, J = 7.6 Hz, 1H), 7.15 (m, 2H), 6.14 (s, 1H), 4.86 (m, 1H), 4.55 (s, 2H), 4.02 (m, 1H), 3.77 (m, 1H), 3.22 (s, 3H), 2.65 (s, 3H), 2.43 (s, 3H), 2.26 (s, 3H), 1.62 (d, J = 7.2 Hz, 3H) | 382 |
| 218 | (R or S)-N-((4,6-dimethyl-2-oxo-1,2-dihydropyridin-3-yl)methyl)-1-(1-methoxypropan-2-yl)-2-methyl-1H-indole-3-carboxamide-PEAK 2 | (400 MHz, CD₃OD) δ 7.74 (m, 1H), 7.57 (d, J = 7.6 Hz, 1H), 7.15 (m, 2H), 6.14 (s, 1H), 4.86 (m, 1H), 4.55 (s, 2H), 4.02 (m, 1H), 3.77 (m, 1H), 3.22 (s, 3H), 2.65 (s, 3H), 2.43 (s, 3H), 2.26 (s, 3H), 1.62 (d, J = 7.2 Hz, 3H) | 382 |
| 225 | (R or S)-1-(1-(3-carbamoylphenyl)ethyl)-N-((4,6-dimethyl-2-oxo-1,2-dihydropyridin-3-yl)methyl)-2-methyl-1H-indole-3-carboxamide PEAK 1 | (400 MHz, Methanol-d4) δ 7.84 (d, J = 8 Hz, 1H), 7.66 (d, J = 8.4 Hz, 2H), 7.33-7.37 (m, 2H), 7.04 (m, 1 H), 6.88-6.96 (m, 2H), 5.90 (s, 2H), 5.81-5.82 (m, 1 H), 4.57-4.63 (m, 2 H), 3.54 (s, 1 H), 2.99 (s, 3H), 2.70 (s, 3H), 2.45 (s, 3H), 2.22 (s, 3H), 1.96 (d, J = 7.2 H_z, 3H) | 457 |
| 226 | (R or S)-1-(1-(3-carbamoylphenyl)ethyl)-N-((4,6-dimethyl-2-oxo-1,2-dihydropyridin-3-yl)methyl)-2-methyl-1H-indole-3-carboxamide PEAK 2 | (400 MHz, Methanol-d4) δ7.84 (d, J = 8 H_z, 1H), 7.66 (d, J = 8.4 H_z, 2H), 7.33-7.37 (m, 2H), 7.04 (m, 1 H), 6.88-6.96 (m, 2H), 5.90 (s, 2H), 5.81-5.82 (m, 1 H), 4.57-4.63 (m, 2 H), 3.54 (s, 1 H), 2.99 (s, 3H), 2.70 (s, 3H), 2.45 (s, 3H), 2.22 (s, 3H), 1.96 (d, J = 7.2 H_z, 3H) | 457 |
| 227 | (R or S)-1-(1-(3-cyanophenyl)ethyl)-N-((4,6-dimethyl-2-oxo-1,2-dihydropyridin-3-yl)methyl)-2-methyl-1H-indole-3-carboxamide PEAK 1 | (400 MHz, Methanol-d4) δ 7.78 (d, J = 8 Hz, 1H), 7.67 (d, J = 7.2 Hz, 1H), 7.54 (m, 3H), 7.13 (m, 1H), 7.03 (d, J = 4 Hz, 2 H), 6.45 (s, 1H), 6.04 (m, 1H), 4.61 (s, 2H), 2.66 (s, 3 H), 2.52 (s, 3 H), 2.36 (s, 1H), 2.02 (d J = 7.2 Hz, 3H) | |
| 228 | (R or S)-1-(1-(3-cyanophenyl)ethyl)-N-((4,6-dimethyl-2-oxo-1,2-dihydropyridin-3-yl)methyl)-2-methyl-1H-indole-3-carboxamide PEAK 2 | (400 MHz, Methanol-d4) δ 7.78 (d, J = 8 Hz, 1H), 7.67 (d, J = 7.2 Hz, 1H), 7.54 (m, 3H), 7.13 (m, 1H), 7.03 (d, J = 4 Hz, 2 H), 6.45 (s, 1H), 6.04 (m, 1H), 4.61 (s, 2H), 2.66 (s, 3 H), 2.52 (s, 3 H), 2.36 (s, 1 H), 2.02 (d, J = 7.2 Hz, 3H) | |

| Compound | Name | ¹H NMR | m/z |
|---|---|---|---|
| 213 | (R or S)-(4,6-dimethyl-2-oxo-1,2-dihydropyridin-3-yl)methyl 1-(2,3-dihydro-1H-inden-1-yl)-2-methyl-1H-indole-3-carboxylate PEAK 1 | (400 MHz, CD₃OD) δ 8.10 (brs, 1H), 8.06-8.04 (d, J = 8.0 Hz, 1H), 7.26-7.24 (d, J = 8.0 Hz, 1H), 7.18-7.14 (t, J = 7.6 Hz, 1H), 7.08-7.02 (m, 2H), 6.69-6.67 (d, J = 6.8 Hz, 1H), 6.00 (s, 1H), 4.41 (s, 2H), 2.74-2.64 (m, 2H), 2.46 (s, 3H), 2.30 (s, 3H), 2.17-2.11 (m, 1H), 1.52-1.49 (m, 2H) | 427 |
| 195 | (R or S)-1-(sec-butyl)-N-((4,6-dimethyl-2-oxo-1,2-dihydropyridin-3-yl)methyl)-2-methyl-1H-pyrrolo[2,3-b]pyridine-3-carboxamide PEAK 1 | (400 MHz, CDCl₃) δ 8.116-8.132 (d, 1H), 8.011-8.035 (d, 1H), 7.037-7.057 (t, 1H), 6.056 (s, 1H), 4.462 (d, 2H), 6.30 (s, 1H), 2.63 (s, 3H), 2.356 (s, 3H), 2.189 (s, 3H), 1.880-1.933 (m, 1H), 1.587-1.605 (d, 2H), 1.226 (s, 2H), 0.658 (t, 3H) | 368 |
| 196 | (R or S)-1-(sec-butyl)-N-((4,6-dimethyl-2-oxo-1,2-dihydropyridin-3-yl)methyl)-2-methyl-1H-pyrrolo[2,3-b]pyridine-3-carboxamide PEAK 2 | (400 MHz, CDCl₃) δ 8.116-8.132 (d, 1H), 8.011-8.035 (d, 1H), 7.037-7.057 (t, 1H), 6.056 (s, 1H), 4.462 (d, 2H), 6.30 (s, 1H), 2.63 (s, 3H), 2.356 (s, 3H), 2.189 (s, 3H), 1.880-1.933 (m, 1H), 1.587-1.605 (d, 2H), 1.226 (s, 2H), 0.658 (t, 3H) | 368 |
| 252 | (R or S)-(±)-1-(1-cyclopropylethyl)-N-((4,6-dimethyl-2-oxo-1,2-dihydropyridin-3-yl)methyl)-2-methyl-1H-pyrrolo[2,3-b]pyridine-3-carboxamide PEAK 1 | NMR (400 MHz, CDCl₃): δ 8.32-8.34 (d, 1H), 8.18-8.2 (d, 1H), 7.27-7.30 (m, 1H), 6.70 (s, 1H), 4.47 (s, 2H), 3.94-3.95 (d, 1H), 2.61 (s, 3H), 2.43 (s, 3H), 2.29-2.30 (s, 3H), 1.57-1.59 (d, 3H), 0.63-0.64 (t, 1H), 0.27-0.64 (m, 2H), 0.02-0.04 (t, 1H) | 379 |
| 253 | (R or S)-(±)-1-(1-cyclopropylethyl)-N-((4,6-dimethyl-2-oxo-1,2-dihydropyridin-3-yl)methyl)-2-methyl-1H-pyrrolo[2,3-b]pyridine-3-carboxamide PEAK 2 | NMR (400 MHz, CDCl₃): δ 8.32-8.34 (d, 1H), 8.18-8.2 (d, 1H), 7.27-7.30 (m, 1H), 6.70 (s, 1H), 4.47 (s, 2H), 3.94-3.95 (d, 1H), 2.61 (s, 3H), 2.43 (s, 3H), 2.29-2.30 (s, 3H), 1.57-1.59 (d, 3H), 0.63-0.64 (t, 1H), 0.27-0.64 (m, 2H), 0.02-0.04 (t, 1H) | 379 |
| 256 | (R or S)-N-((4-methoxy-6-methyl-2-oxo-1,2-dihydropyridin-3-yl)methyl)-1-(1-methoxypropan-2-yl)-2-methyl-1H-pyrrolo[2,3-b]pyridine-3-carboxamide PEAK 1 | (400 MHz, CDCl₃) δ 13.23 (s, 1H), 8.16-8.17 (m, 1H), 8.11-8.13 (m, 1H), 7.57-7.60 (t, J = 5.2 Hz, 1H), 6.93-6.96 (m, 1H), 5.92 (s, 1H), 4.82-4.83 (d, J = 2.4 Hz, 1H), 4.65-4.66 (d, J = 6.4 Hz, 2H), 3.89 (s, 3H), 3.81-3.85 (m, 1H), 3.22 (s, 3H), 2.79 (s, 3H), 2.17 (s, 3H), 1.64-1.66 (d, J = 8.0 Hz, 3H) | 399 |
| 257 | (R or S)-N-((4-methoxy-6-methyl-2-oxo-1,2-dihydropyridin-3-yl)methyl)-1-(1-methoxypropan-2-yl)-2-methyl-1H-pyrrolo[2,3-b]pyridine-3-carboxamide PEAK 2 | (400 MHz, CDCl₃) δ 13.23 (s, 1H), 8.16-8.17 (m, 1H), 8.11-8.13 (m, 1H), 7.57-7.60 (t, J = 5.2 Hz, 1H), 6.93-6.96 (m, 1H), 5.92 (s, 1H), 4.82-4.83 (d, J = 2.4 Hz, 1H), 4.65-4.66 (d, J = 6.4 Hz, 2H), 3.89 (s, 3H), 3.81-3.85 (m, 1H), 3.22 (s, 3H), 2.79 (s, 3H), 2.17 (s, 3H), 1.64-1.66 (d, J = 8.0 Hz, 3H) | 399 |
| 278 | (R or S)-N-((4-methoxy-6-methyl-2-oxo-1,2-dihydropyridin-3-yl)methyl)-2-methyl-1-(1-(methylsulfonyl)propan-2-yl)-1H-indole-3-carboxamide PEAK 1 | (400 MHz, METHANOL-d₄) δ ppm 1.77 (d, J = 6.84 Hz, 3 H) 2.34 (s, 3 H) 2.39 (s, 3 H) 2.75 (s, 3 H) 3.64 (dd, J = 14.66, 3.64 Hz, 1 H) 3.96 (s, 3 H) 4.54 (s, 2 H) 5.21 (br. S., 2 H) 6.30 (s, 1 H) 7.16 (dd, J = 7.94, 4.85 Hz, 1 H) 8.10 (dd, J = 7.94, 1.54 Hz, 1 H) 8.27 (dd, J = 4.63, 1.54 Hz, 1 H) | 446 |
| 279 | (R or S)-N-((4-methoxy-6-methyl-2-oxo-1,2-dihydropyridin-3-yl)methyl)-2-methyl-1-(1-(methylsulfonyl)propan-2-yl)-1H-indole-3-carboxamide PEAK 2 | (400 MHz, METHANOL-d₄) δ ppm 1.76 (d, J = 7.06 Hz, 3 H) 2.33 (s, 3 H) 2.37 (s, 3 H) 2.74 (s, 3 H) 3.62 (dd, J = 14.66, 3.64 Hz, 1 H) 3.94 (s, 3 H) 4.52 (s, 2 H) 5.19 (br. S., 2 H) 6.28 (s, 1 H) 7.15 (dd, J = 7.94, 4.85 Hz, 1 H) 8.09 (dd, J = 7.94, 0.77 Hz, 1 H) 8.25 (dd, J = 4.85, 1.54 Hz, 1 H) | 446 |
| 268 | (R or S)-N-((4-methoxy-6-methyl-2-oxo-1,2-dihydropyridin-3-yl)methyl)-2-methyl-1-(1-(1-methyl-2-oxo-1,2-dihydropyridin-4-yl)ethyl)-1H-pyrrolo[2,3-b]pyridine-3-carboxamide PEAK 1 | (400 MHz, CDCl₃) δ ppm 1.90 (d, J = 7.28 Hz, 3 H) 2.26 (s, 3 H) 2.61 (s, 3 H) 3.49 (s, 3 H) 3.91 (s, 3 H) 4.65 (d, J = 5.51 Hz, 2 H) 5.72 (dd, J = 7.06, 1.76 Hz, 1 H) 5.96 (s, 1 H) 6.47 (s, 1 H) 7.06-7.14 (m, 2 H) 7.61 (br. S., 1 H) 8.18-8.28 (m, 2 H) | 462 |

-continued

| Compound | Name | ¹H NMR | m/z |
|---|---|---|---|
| 269 | (R or S)-N-((4-methoxy-6-methyl-2-oxo-1,2-dihydropyridin-3-yl)methyl)-2-methyl-1-(1-(1-methyl-2-oxo-1,2-dihydropyridin-4-yl)ethyl)-1H-pyrrolo[2,3-b]pyridine-3-carboxamide PEAK 2 | (400 MHz, CDCl$_3$) δ ppm 1.90 (d, J = 7.28 Hz, 3 H) 2.26 (s, 3 H) 2.61 (s, 3 H) 3.49 (s, 3 H) 3.91 (s, 3 H) 4.65 (d, J = 5.51 Hz, 2 H) 5.72 (dd, J = 7.06, 1.76 Hz, 1 H) 5.96 (s, 1 H) 6.47 (s, 1 H) 7.06-7.14 (m, 2 H) 7.61 (br. S., 1 H) 8.18-8.28 (m, 2 H) | 462 |
| 307 | Trans-(R or S, R or S)-N-((4-methoxy-6-methyl-2-oxo-1,2-dihydropyridin-3-yl)methyl)-1-(3-methoxybutan-2-yl)-2-methyl-1H-indole-3-carboxamide PEAK 1 | (CDCl$_3$, 400 M Hz) δ 7.85 (t, J = 6.4 Hz, 1H), 7.45 (s, 2H), 7.08-7.03 (m, 2H), 5.93 (s, 1H), 4.71-4.61 (m, 2H), 4.36 (s, 1H), 3.90 (s, 4H), 2.95 (s, 3H), 2.75 (s, 3H), 2.17 (s, 3H), 1.57 (d, J = 7.2 Hz, 3H), 1.23 (d, J = 6.0 Hz, 3H) | 412 |
| 308 | Trans-(R or S, R or S)-N-((4-methoxy-6-methyl-2-oxo-1,2-dihydropyridin-3-yl)methyl)-1-(3-methoxybutan-2-yl)-2-methyl-1H-indole-3-carboxamide PEAK 2 | (CDCl$_3$, 400 MHz) δ 7.85 (t, J = 6.4 Hz, 1H), 7.45 (s, 2H), 7.08-7.03 (m, 2H), 5.93 (s, 1H), 4.71-4.61 (m, 2H), 4.36 (s, 1H), 3.90 (s, 4H), 2.95 (s, 3H), 2.75 (s, 3H), 2.17 (s, 3H), 1.57 (d, J = 7.2 Hz, 3H), 1.23 (d, J = 6.0 Hz, 3H) | 412 |
| 116 | N-((4,6-dimethyl-2-oxo-1,2-dihydropyridin-3-yl)methyl)-2-methyl-1-(1-phenylethyl)-1H-pyrrolo[2,3-b]pyridine-3-carboxamide PEAK 2 | | 415 |
| 117 | N-((4,6-dimethyl-2-oxo-1,2-dihydropyridin-3-yl)methyl)-2-methyl-1-(1-phenylethyl)-1H-pyrrolo[2,3-b]pyridine-3-carboxamide PEAK 1 | | 415 |

Example 47

Synthesis of 1-(1-(3-cyanophenyl)ethyl)-N-((46-dimethyl-2-oxo-1,2-dihydropyridin-3-yl)methyl)-2-methyl-1H-indole-3-carboxamide (Compound 187)

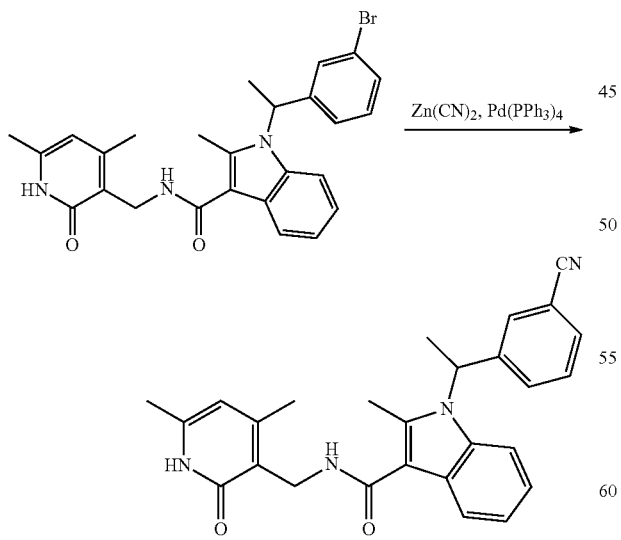

1-(1-(3-bromophenyl)ethyl)-N-((4,6-dimethyl-2-oxo-1,2-dihydropyridin-3-yl)methyl)-2-methyl-1H-indole-3-carboxamide (Compound 171; 100 mg, 0.2 mmol), Zn(CN)$_2$ (36 mg, 0.3 mmol), Pd(PPh$_3$)$_4$ (47 mg, 0.04 mmol) were combined in 2 ml DMF, then stirred at 100° C. for 30 min under N$_2$ in m.w. After the complete of the reaction, purified by pre-HPLC (A:CH$_3$CN, B:water+0.1% HCl. A:B=32:62 ASB C18 150*25 mm) to afford the title compound (35 mg, yield: 40%). 1H NMR (400 MHz, Methanol-d4) 67.78 (d, J=8 Hz, 1H), 7.67 (d, J=7.2 Hz, 1H), 7.54 (m, 3H), 7.13 (m, 1H), 7.03 (d, J=4 Hz, 2H), 6.45 (s, 1H), 6.04 (m, 1H), 4.61 (s, 2H), 2.66 (s, 3 H), 2.52 (s, 3 H), 2.36 (s, 1 H), 2.02 (d, J=7.2 Hz, 3H).

Example 48

Synthesis of (±)-1-(sec-butyl)-N-((4-methoxy-6-methyl-2-oxo-1,2-dihydropyridin-3-yl)methyl)-2-methyl-6-(pyridine-3-yl)-1H-indole-3-carboxamide, (Compound 388)

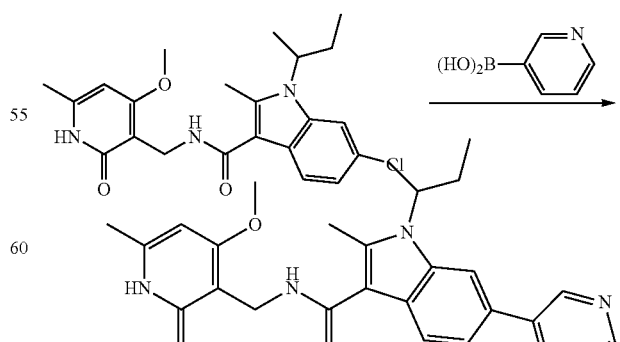

A solution of (±)-1-(sec-butyl)-6-chloro-N-((4-methoxy-6-methyl-2-oxo-1,2-dihydropyridin-3-yl)methyl)-2-methyl- 1H-indole-3-carboxamide (Compound 185) (50 mg, 0.12 mmol), pyridine-3-ylboronic acid (22 mg, 0.18 mmol), tricyclohexylmethane (7 mg, 0.024 umol), K₃PO₄ (120 mg, 0.60 mmol), Tris(dibenzylideneacetone)dipalladium(0)(10 mg), water (1 mL) and 1,4-dioxane (4 mL) was stirred under N₂ at 100° C. for 16 h. The reaction was then allowed to cool to rt and the mixture was diluted with water and dichloromethane, the aqueous layer was extracted with dichloromethane. The organic layers were dried with Na₂SO₄ and evaporated. The residue was purified by preparative-HPLC (Instrument: Gilson 215; Column: Gemini C18 10u 150*25 mm; Mobile phase A: Water (0.0225% HCl v/v); Mobile phase B: Acetonitrile(neutral); Gradient: 42-62(B %); Flowrate: 25 ml/min) The collected fractions were combined and lyophilized to give 1-(sec-butyl)-N-((4-methoxy-6-methyl-2-oxo-1,2-dihydropyridin-3-yl)methyl)-2-methyl-6-(pyridine-3-yl)-1H-indole-3-carboxamide as a yellow solid (3.2 mg, yield 5.7%). LCMS (M+H+) m/z: calcd 458.23. found 459.0. 1H NMR (400 MHz, CD3OD): δ9.25 (s, 1H), 8.98 (d, J=8.4, 1H), 8.80 (d, J=5.6, 1H), 8.18 (t, J=5.6, 1H), 8.05 (s, 1H), 7.97 (d, J=8.0, 1H), 7.60 (d, J=8.4, 1H), 6.86 (s, 1H), 4.64 (m, 1H), 4.62 (s, 2H), 4.13 (s, 3H), 2.73 (s, 3H), 2.53 (s, 3H), 2.30 (m, 1H), 2.03-2.10 (m, 1H), 1.71 (d, J=6.8, 3H), 0.77 (t, J=7.6, 3H).

The compounds shown in the following table were prepared according to the general procedure outlined in this example using the appropriate starting materials and modifications. Structures are shown in FIG. 1.

To a solution of 2-methyl-1-(quinolin-5-yl)-1H-indole-3-carboxylic acid (Example 40) (25 mg) in acetic acid (3 mL) was added PtO₂ (50 mg) at 22° C. The reaction was stirred at 22° C. under H₂ ball for 20 hrs. Then the mixture was filtered and the filtrate was purified by column chromatography on silica gel eluted with dichloromethane:methanol=70:1 to the title compound as a yellow solid (20 mg, 71%).

The compounds shown in the following table were prepared according to the general procedure outlined in this example using the appropriate starting alkyl carboxylate.

| Name | Structure | m/z |
|---|---|---|
| 2-methyl-1-(6-methyl-1,2,3,4-tetrahydroquinolin-5-yl)-1H-indole-3-carboxylic acid | 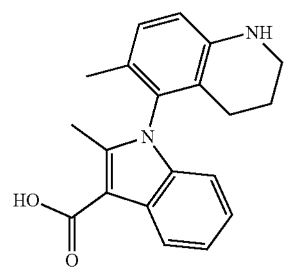 | 321 |

| Compound | Name | ¹H NMR | m/z |
|---|---|---|---|
| 389 | (±)-1-(sec-butyl)-N-((4-methoxy-6-methyl-2-oxo-1,2-dihydropyridin-3-yl)methyl)-2-methyl-6-phenyl-1H-indole-3-carboxamide | (400 MHz, CDCl₃) δ 7.77 (d, J = 8.4, 1H), 7.68 (s, 1H), 7.60 (d, J = 7.6, 2H), 7.43-7.48 (m, 3H), 7.35 (t, J = 7.6, 1H), 7.20 (s, 1H), 6.31 (s, 1H), 4.62 (s, 2H), 4.49 (s, 1H), 3.95 (s, 3H), 2.76 (s, 3H), 2.67 (s, 3H), 2.18-2.24 (m, 1H), 1.94-2.01 (m, 1H), 1.64 (d, J = 7.2, 3H), 0.76 (t, J = 7.6, 3H) | 458 |
| 349 | (±)-1-(sec-butyl)-N-((4-methoxy-6-methyl-2-oxo-1,2-dihydropyridin-3-yl)methyl)-2-methyl-6-(6-(piperazin-1-yl)pyridine-3-yl)-1H-indole-3-carboxamide | (400 MHz, CDCl₃) δ 0.74-0.78 (t, J = 7.2 Hz, 3H), 1.59-1.61 (d, J = 6.8 Hz, 3H), 1.88-1.98 (m, 1H), 2.18 (s, 5H), 2.74 (s, 3H), 3.02-3.04 (t, J = 5.0 Hz, 3H), 3.55-3.58 (t, J = 5.2 Hz, 3H), 3.85-3.86 (d, J = 4.4 Hz, 3H), 4.45 (brs, 1H), 4.66-4.68 (d, J = 5.6 Hz, 2H), 5.89 (s, 1H), 6.62-6.65 (d, J = 8.8 Hz, 1H), 7.15-7.17 (t, J = 7.6 Hz, 1H), 7.54 (s, 1H), 7.64-7.67 (m, 2H), 7.85-7.87 (d, J = 8 Hz, 1H), 8.42-8.43 (d, J = 2.8 Hz, 1H) | 543 |

Example 49

Synthesis of 2-methyl-1-(1,2,3,4-tetrahydroquinolin-5-yl)-1H-indole-3-carboxylic acid

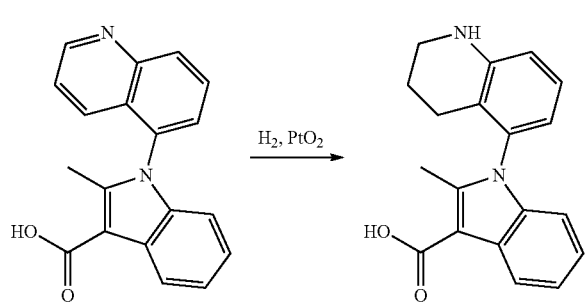 [SMILES: Cc1c(C(=O)O)c2ccccc2n1-c1cccc2ncccc12 ; Cc1c(C(=O)O)c2ccccc2n1-c1cccc2c1CCCN2]

-continued

| Name | Structure | m/z |
|---|---|---|
| 2-methyl-1-(1,2,3,4-tetrahydroquinolin-6-yl)-1H-indole-3-carboxylic acid | 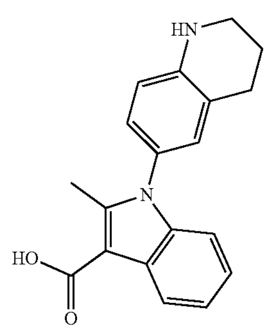 [SMILES: Cc1c(C(=O)O)c2ccccc2n1-c1ccc2c(c1)CCCN2] | 307 |

The carboxylic acids of this example were used as starting material in Step 4 of Example 36 in the synthesis of certain compounds of the invention.

Example 50

Synthesis of 2-methyl-1-(3-methylbutanoyl)-1H-indole-3-carboxylic acid

The title compound was used as starting material in Step 4 of Example 36 in the synthesis of certain compounds of the invention.

Step 1: tert-butyl 2-methyl-1-(3-methylbutanoyl)-1H-indole-3-carboxylate

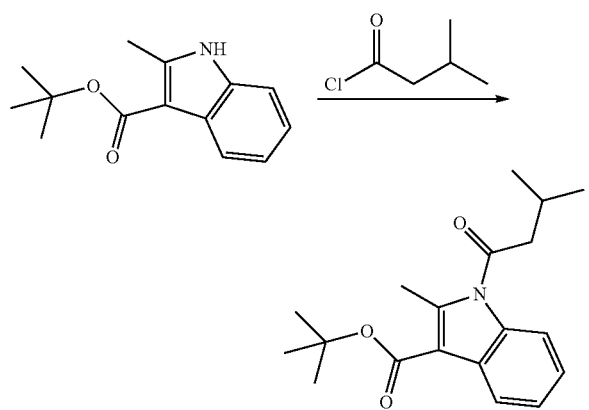

To a solution of tert-butyl 2-methyl-1H-indole-3-carboxylate (300 mg, 1.30 mmol) in N,N-dimethylformamide (10 mL) was added sodium hydride (103.76 mg, 2.59 mmol, 60%). The mixture was stirred at 0° C. for 30 minutes. Then 3-methylbutanoyl chloride (234.60 mg, 1.95 mmol) was added at 0° C. and the mixture was stirred at room temperature (25° C.) for 2 hours. The mixture was cooled with ice, quenched with water (5 mL), diluted with ethyl acetate (20 mL), washed with brine (20 mL), extracted with ethyl acetate three times (20 mL×3), then dried over sodium sulfate. After concentration, the residue was purified by column on silica gel (0%-5% PE/EA) to afford the title compound (200 mg, yield: 48.89%).

The compound shown below was prepared according to the general procedure outlined in above using the appropriate starting materials and modifications.

| Name | Structure | m/z |
|---|---|---|
| tert-butyl 2-methyl-1-(tetrahydro-2H-pyran-4-carbonyl)-1H-indole-3-carboxylate | 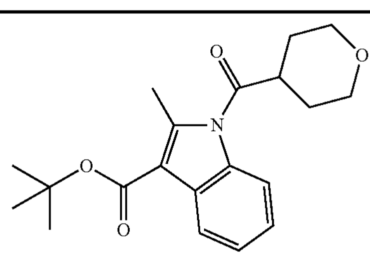 | 344 |

Step 2: 2-methyl-1-(3-methylbutanoyl)-1H-indole-3-carboxylic acid

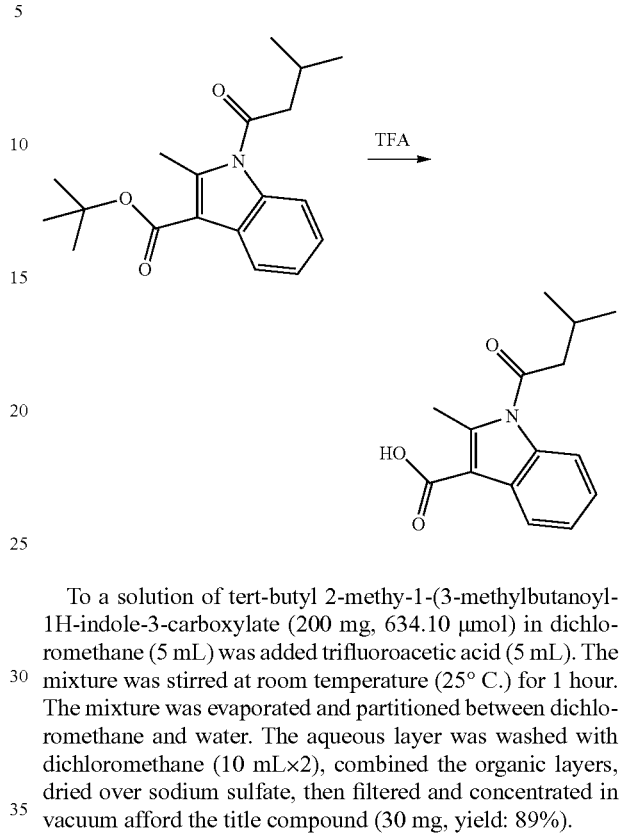

To a solution of tert-butyl 2-methy-1-(3-methylbutanoyl-1H-indole-3-carboxylate (200 mg, 634.10 μmol) in dichloromethane (5 mL) was added trifluoroacetic acid (5 mL). The mixture was stirred at room temperature (25° C.) for 1 hour. The mixture was evaporated and partitioned between dichloromethane and water. The aqueous layer was washed with dichloromethane (10 mL×2), combined the organic layers, dried over sodium sulfate, then filtered and concentrated in vacuum afford the title compound (30 mg, yield: 89%).

The carboxylic acids shown in the following table were prepared according to the general procedure outlined above using the appropriate starting materials and modifications.

| Name | Structure | m/z |
|---|---|---|
| 2-methyl-1-(tetrahydro-2H-pyran-4-carbonyl)-1H-indole-3-carboxylic acid | 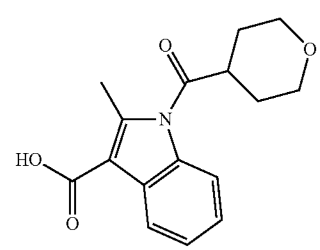 [SMILES: Cc1c(C(=O)O)c2ccccc2n1C(=O)C1CCOCC1] | 288 |
| (±)-1-(2,3-dihydro-1H-inden-1-yl)-2-methyl-1H-pyrrolo[2,3-b]pyridine-3-carboxylic acid | 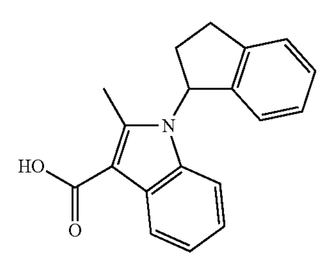 [SMILES: Cc1c(C(=O)O)c2ccccc2n1C1CCc2ccccc21] | 292 |

| Name | Structure | m/z |
|---|---|---|
| (±)-2-methyl-1-(tetrahydrofuran-3-yl)-1H-pyrrolo[2,3-b]pyridine-3-carboxylic acid | 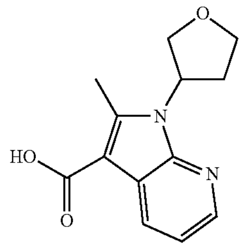 [SMILES: Cc1c(C(=O)O)c2cccnc2n1C1CCOC1] | 247 |
| (±)-1-(1-methoxypropan-2-yl)-2-methyl-1H-pyrrolo[2,3-b]pyridine-3-carboxylic acid | 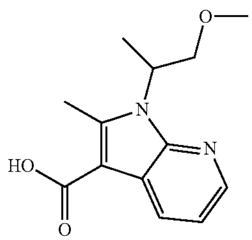 [SMILES: COCC(C)n1c(C)c(C(=O)O)c2cccnc21] | 249 |
| (±)-1-(1-(3-methoxyphenyl)ethyl)-2-methyl-1H-pyrrolo[2,3-b]pyridine-3-carboxylic acid | 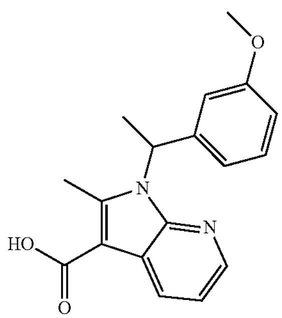 [SMILES: COc1cccc(C(C)n2c(C)c(C(=O)O)c3cccnc32)c1] | 311 |
| (±)-1-(1-(2-methoxypyridin-4-yl)ethyl)-2-methyl-1H-pyrrolo[2,3-b]pyridine-3-carboxylic acid | 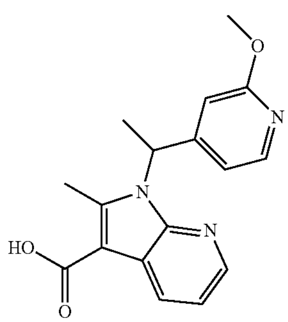 | 312 |
| 1-(chroman-4-yl)-2-methyl-1H-pyrrolo[2,3-b]pyridine-3-carboxylic acid | 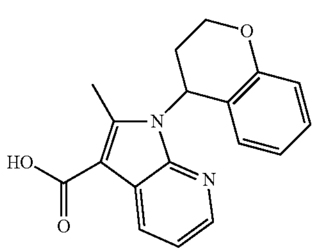 [SMILES: Cc1c(C(=O)O)c2cccnc2n1C1CCOc2ccccc21] | 309 |
| (±)-1-(1-cyclopropylethyl)-2-methyl-1H-pyrrolo[2,3-b]pyridine-3-carboxylic acid | 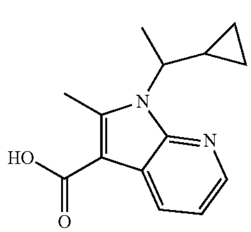 [SMILES: Cc1c(C(=O)O)c2cccnc2n1C(C)C1CC1] | 245 |
| (±)-1-(1-ethoxypropan-2-yl)-2-methyl-1H-pyrrolo[2,3-b]pyridine-3-carboxylic acid | | 263 |
| (±)-1-(1-cyanoethyl)-2-methyl-1H-pyrrolo[2,3-b]pyridine-3-carboxylic acid | | 230 |
| (±)-1-(1-(5-methoxypyridin-3-yl)ethyl)-2-methyl-1H-pyrrolo[2,3-b]pyridine-3-carboxylic acid | | 312 |
| (±)-2-methyl-1-(1-phenylpropyl)-1H-pyrrolo[2,3-b]pyridine-3-carboxylic acid | | 295 |
| (±)-1-(1-(1H-pyrazol-1-yl)propan-2-yl)-2-methyl-1H-pyrrolo[2,3-b]pyridine-3-carboxylic acid | | 285 |

-continued

| Name | Structure | m/z |
|---|---|---|
| (±)-1-(1-(2-methoxypyrimidin-4-yl)ethyl)-2-methyl-1H-pyrrolo[2,3-b]pyridine-3-carboxylic acid | 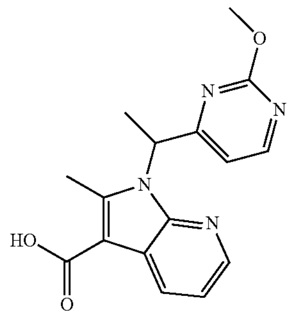 [SMILES: COc1nccc(C(C)n2c(C)c(C(=O)O)c3cccnc32)n1] | 313 |
| (±)-2-methyl-1-(1-morpholinopropan-2-yl)-1H-pyrrolo[2,3-b]pyridine-3-carboxylic acid | 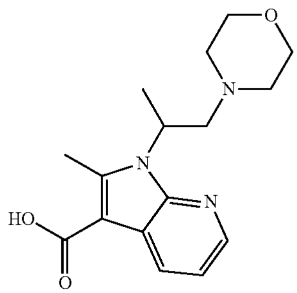 [SMILES: Cc1c(C(=O)O)c2cccnc2n1C(C)CN1CCOCC1] | 304 |
| (±)-1-(1-(1H-benzo[d]imidazol-1-yl)propan-2-yl)-2-methyl-1H-pyrrolo[2,3-b]pyridine-3-carboxylic acid | 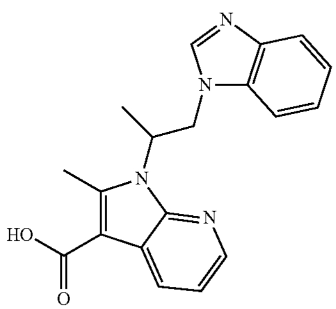 [SMILES: Cc1c(C(=O)O)c2cccnc2n1C(C)Cn1cnc2ccccc21] | 335 |
| (±)-1-(1-(3-cyanophenyl)ethyl)-2-methyl-1H-pyrrolo[2,3-b]pyridine-3-carboxylic acid | 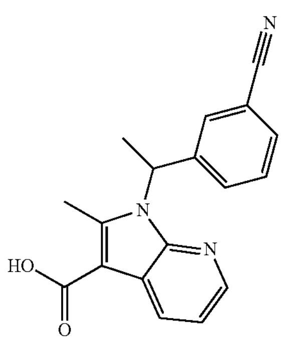 [SMILES: Cc1c(C(=O)O)c2cccnc2n1C(C)c1cccc(C#N)c1] | 306 |
| 1-(3-methoxybutan-2-yl)-2-methyl-1H-pyrrolo[2,3-b]pyridine-3-carboxylic acid | 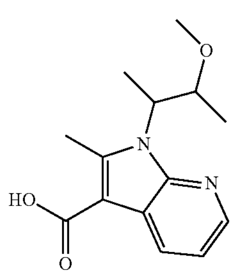 [SMILES: COC(C)C(C)n1c(C)c(C(=O)O)c2cccnc21] | 263 |

-continued

| Name | Structure | m/z |
|---|---|---|
| (±)-1-(1-(3-carbamoylphenyl)ethyl)-2-methyl-1H-pyrrolo[2,3-b]pyridine-3-carboxylic acid | 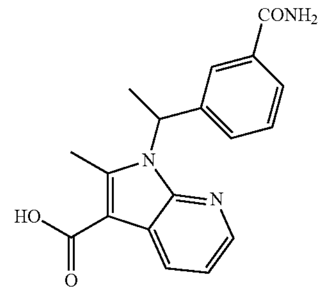 [SMILES: Cc1c(C(=O)O)c2cccnc2n1C(C)c1cccc(C(N)=O)c1] | 324 |
| 2-methyl-1-(tetrahydro-2H-pyran-4-yl)-1H-pyrrolo[2,3-b]pyridine-3-carboxylic acid | 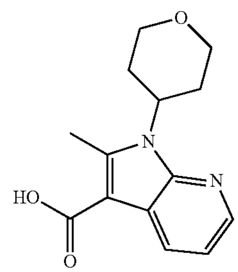 [SMILES: Cc1c(C(=O)O)c2cccnc2n1C1CCOCC1] | 261 |
| (±)-2-methyl-1-(1-(2-oxopyridin-1(2H)-yl)propan-2-yl)-1H-pyrrolo[2,3-b]pyridine-3-carboxylic acid | 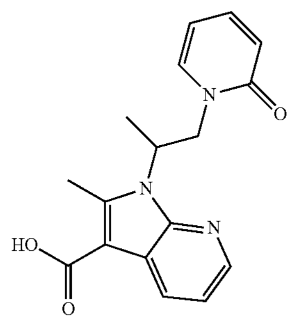 [SMILES: Cc1c(C(=O)O)c2cccnc2n1C(C)Cn1ccccc1=O] | 312 |
| (±)-2-methyl-1-(1-(methylsulfonyl)propan-2-yl)-1H-pyrrolo[2,3-b]pyridine-3-carboxylic acid | 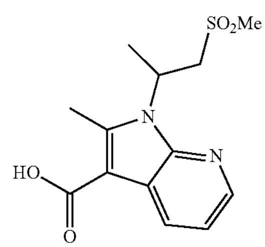 [SMILES: Cc1c(C(=O)O)c2cccnc2n1C(C)CS(C)(=O)=O] | 297 |
| (±)-2-methyl-1-(1-(pyridine-2-yloxy)propan-2-yl)-1H-pyrrolo[2,3-b]pyridine-3-carboxylic acid | 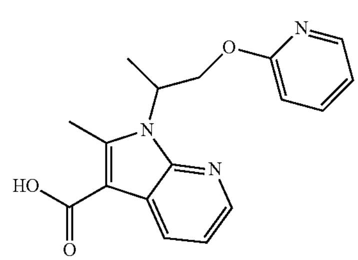 [SMILES: Cc1c(C(=O)O)c2cccnc2n1C(C)COc1ccccn1] | 312 |

| Name | Structure | m/z |
|---|---|---|
| 2-methyl-1-(3-(methylsulfonyl)butan-2-yl)-1H-indole-3-carboxylic acid | 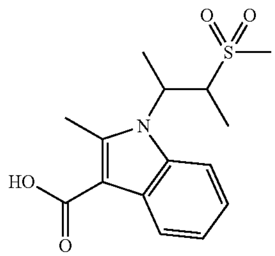 [SMILES: Cc1c(C(=O)O)c2ccccc2n1C(C)C(C)S(C)(=O)=O] | 310 |
| 1-cyclopentyl-2-methyl-1H-pyrrolo[2,3-b]pyridine-3-carboxylic acid | 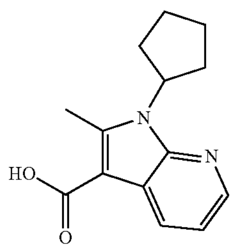 [SMILES: Cc1c(C(=O)O)c2cccnc2n1C1CCCC1] | 245 |
| (±)-1-(1-cyanopropan-2-yl)-2-methyl-1H-pyrrolo[2,3-b]pyridine-3-carboxyiic acid | 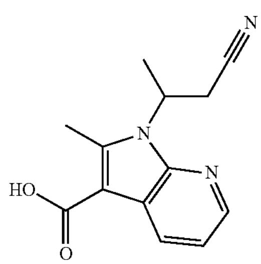 [SMILES: Cc1c(C(=O)O)c2cccnc2n1C(C)CC#N] | 244 |
| (±)-1-(4-amino-4-oxobutan-2-yl)-2-methyl-1H-pyrrolo[2,3-b]pyridine-3-carboxylic acid | 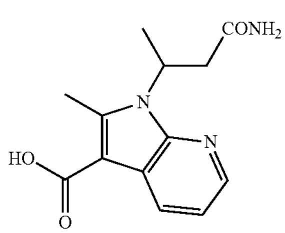 [SMILES: Cc1c(C(=O)O)c2cccnc2n1C(C)CC(N)=O] | 262 |
| (±)-2-methyl-1-(1-(1-methyl-2-oxo-1,2-dihydropyridin-4-yl)ethyl)-1H-pyrrolo[2,3-b]pyridine-3-carboxylic acid | 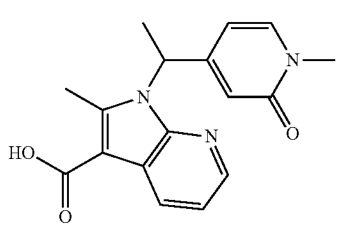 [SMILES: Cc1c(C(=O)O)c2cccnc2n1C(C)c1ccn(C)c(=O)c1] | 312 |

| Name | Structure | m/z |
|---|---|---|
| 1-(3-hydroxy-3-methylbutan-2-yl)-2-methyl-1H-pyrrolo[2,3-b]pyridine-3-carboxylic acid | 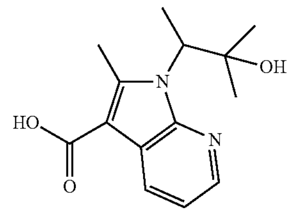 [SMILES: Cc1c(C(=O)O)c2cccnc2n1C(C)C(C)(C)O] | 263 |
| (±)-2-methyl-1-(1-(piperidin-1-yl)propan-2-yl)-1H-pyrrolo[2,3-b]pyridine-3-carboxylic acid | 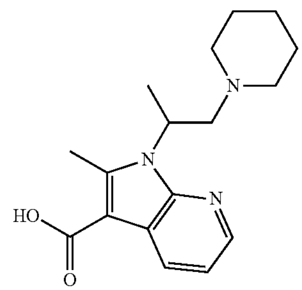 [SMILES: Cc1c(C(=O)O)c2cccnc2n1C(C)CN1CCCCC1] | 302 |
| (±)-1-(4-hydroxybutan-2-yl)-2-methyl-1H-pyrrolo[2,3-b]pyridine-3-carboxylic acid | 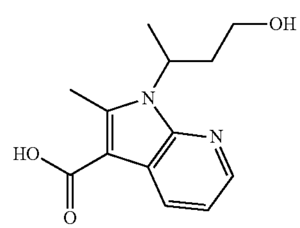 [SMILES: Cc1c(C(=O)O)c2cccnc2n1C(C)CCO] | 249 |
| (±)-2-methyl-1-(piperidin-1-ylsulfonyl)-1H-pyrrolo[2,3-b]pyridine-3-carboxylic acid | 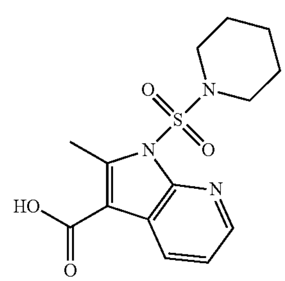 [SMILES: Cc1c(C(=O)O)c2cccnc2n1S(=O)(=O)N1CCCCC1] | 324 |
| (±)-1-(2-hydroxypropyl)-2-methyl-1H-pyrrolo[2,3-b]pyridine-3-carboxylic acid | 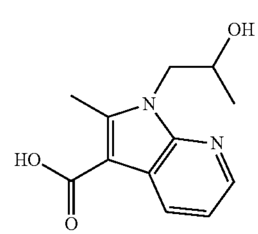 [SMILES: Cc1c(C(=O)O)c2cccnc2n1CC(C)O] | 235 |

-continued

| Name | Structure | m/z |
|---|---|---|
| (±)-1-(3-methoxybutan-2-yl)-2-methyl-1H-indole-3-carboxylic acid | 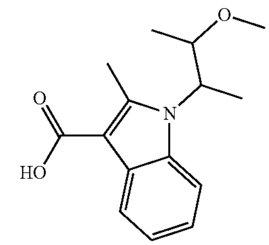 [SMILES: COC(C)C(C)n1c(C)c(C(=O)O)c2ccccc21] | 262 |
| (±)-1-(1-methoxypropan-2-yl)-2-methyl-6-(trifluoromethyl)-1H-pyrrolo[2,3-b]pyridine-3-carboxylic acid | 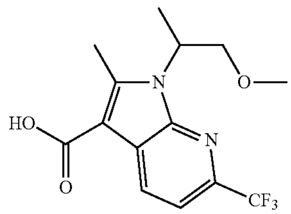 | 317 |
| (±)-2-methyl-1-(4,4,4-trifluoro-3-methoxybutan-2-yl)-1H-indole-3-carboxylic acid | 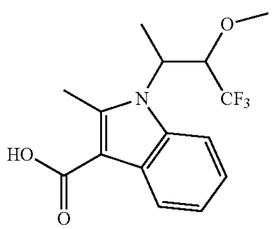 [SMILES: COC(C(C)n1c(C)c(C(=O)O)c2ccccc21)C(F)(F)F] | 316 |
| (±)-1-(3-methoxypentan-2-yl)-2-methyl-1H-pyrrolo[2,3-b]pyridine-3-carboxylic acid | 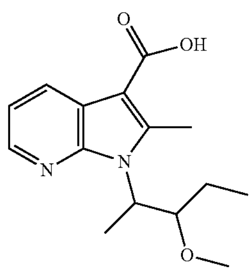 [SMILES: CCC(OC)C(C)n1c(C)c(C(=O)O)c2cccnc21] | 277 |
| 1-(3-methoxypentan-2-yl)-2-methyl-1H-indole-3-carboxylic acid | 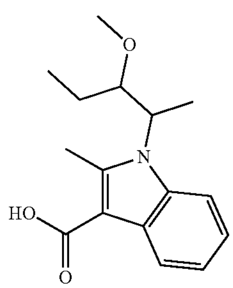 [SMILES: CCC(OC)C(C)n1c(C)c(C(=O)O)c2ccccc21] | 276 |
| 1-(1-methoxy-1-phenylpropan-2-yl)-2-methyl-1H-pyrrolo[2,3-b]pyridine-3-carboxylic acid | 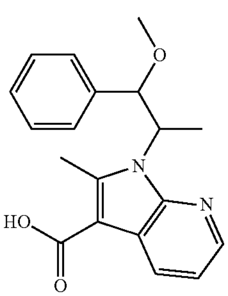 [SMILES: COC(c1ccccc1)C(C)n1c(C)c(C(=O)O)c2cccnc21] | 325 |

Each of the above carboxylic acids was used as starting material in Step 4 of Example 36 in the synthesis of certain compounds of the invention.

Example 51

Synthesis of tert-butyl 1-(2,3-dihydro-1H-inden-1-yl)-2-methyl-1H-pyrrolo[2,3-b]pyridine-3-carboxylate The title compound as starting material in Step 3 of Example 36 in the synthesis of certain compounds of the invention.

Tert-butyl 2-methyl-1H-pyrrolo[2,3-b]pyridine-3-carboxylate

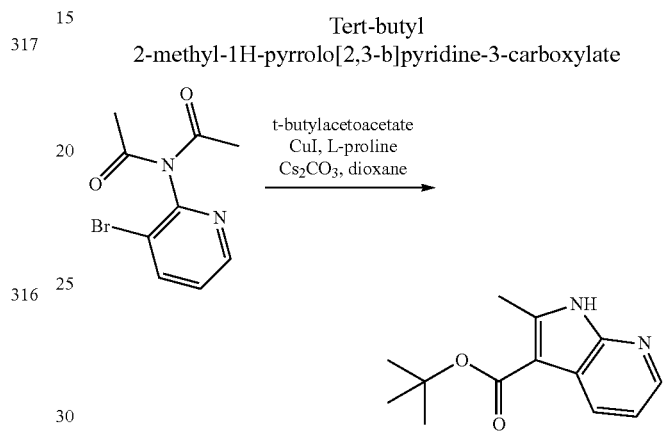

To a 500 mL round-bottom flask that contains N-acetyl-N-(3-bromopyridin-2-yl)acetamide (14.815 g, 57.6 mmol), was added copper(I) iodide (1.098 g, 5.76 mmol), L-proline (1.327 g, 11.53 mmol), cesium carbonate (28.2 g, 86 mmol), then t-butyl acetoacetate (11.47 ml, 69.2 mmol) and dioxane (100 mL). The reaction was vac/purged with $N_2$ 3× then fitted with a septum and a $N_2$ inlet and heated overnight at 70° C. The inorganic solids were removed by filtration over celite and the cake was washed with 100 mL EtOAc. This solution was concentrated and the residue was partitioned between 250 mL brine and 250 mL EtOAc. The aq. Layer was further extracted with EtOAc (2×250 mL) and the combined organic layer was dried over $Na_2SO_4$, filtered, concentrated and purified by CC using 1:1 EtOAc:Hex as eluent to provide (2.7 g, 20.2%) of tert-butyl 2-methyl-1H-pyrrolo[2,3-b]pyridine-3-carboxylate. LRMS (M+H$^+$) m/z: calc'd 233.28. found 233.1.

The compounds shown in the following table were prepared according to the general procedure outlined above using the appropriate starting materials and modifications.

| Name | Structure | m/z |
|---|---|---|
| tert-butyl 2-methyl-6-(trifluoromethyl)-1H-pyrrolo[2,3-b]pyridine-3-carboxylate | 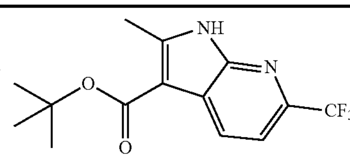 | 301 |
| ethyl 6-(4-(tert-butoxycarbonyl)piperazin-1-yl)-2-methyl-1H-pyrrolo[2,3-b]pyridine-3-carboxylate | 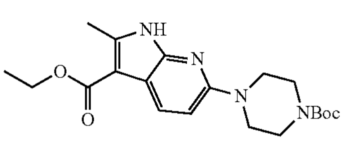 [SMILES: CCOC(=O)c1c(C)[nH]c2nc(N3CCN(C(=O)OC(C)(C)C)CC3)ccc12] | 389 |

Tert-butyl 1-(2,3-dihydro-1H-inden-1-yl)-2-methyl-1H-pyrrolo[2,3-b]pyridine-3-carboxylate

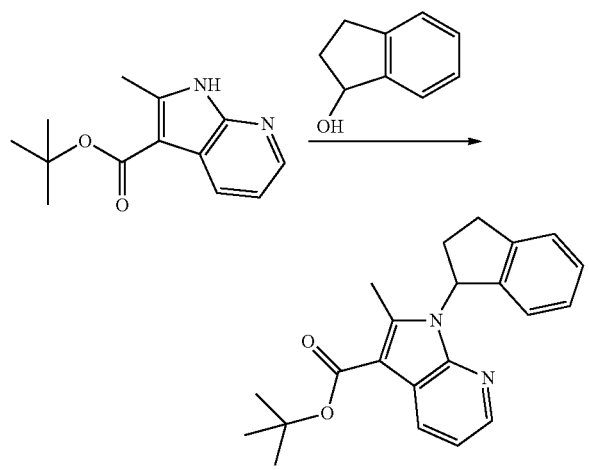

A solution of ethyl tert-butyl 2-methyl-1H-pyrrolo[2,3-b]pyridine-3-carboxylate (100 mg, 0.74 mmol), 2,3-dihydro-1H-inden-1-ol (176 mg, 0.74 mmol), PPh₃ (195 mg, 1.49 mmol) was stirred in dry THF (10 mL) at 0° C. under a nitrogen atmosphere. To this mixture was added drop-wise DIAD (150 mg, 1.48 mmol) over a period of 5 min, and the reaction was stirred at room temperature for 16 hours. The mixture was washed with brine, dried and concentrated to afford the crude product. The crude product was purified by silca gel chromatography (petroleum ether/ethyl acetate=5:1) to afford the tert-butyl-1-(2,3-dihydro-1H-inden-1-yl)-2-methyl-1H-pyrrolo[2,3-b]pyridine-3-carboxylate (150 mg, 60%).

The compounds shown in the following table were prepared according to the general procedure outlined above using the appropriate starting materials and modifications.

| Name | Structure | m/z |
|---|---|---|
| (±)-tert-butyl 1-(sec-butyl)-2-methyl-1H-pyrrolo[2,3-b]pyridine-3-carboxylate | | 289 |
| (±)-tert-butyl 2-methyl-1-(tetrahydrofuran-3-yl)-1H-pyrrolo[2,3-b]pyridine-3-carboxylate | | 303 |
| tert-butyl 1-(chroman-4-yl)-2-methyl-1H-pyrrolo[2,3-b]pyridine-3-carboxylate | 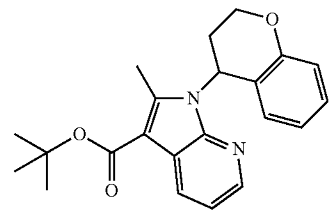 [SMILES: Cc1c(C(=O)OC(C)(C)C)c2cccnc2n1C1CCOc2ccccc21] | 364 |
| (±)-tert-butyl 1-(1-cyclopropylethyl)-2-methyl-1H-pyrrolo[2,3-b]pyridine-3-carboxylate | 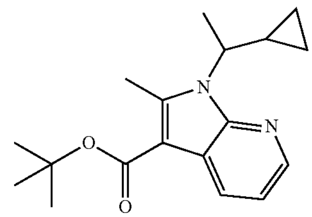 [SMILES: Cc1c(C(=O)OC(C)(C)C)c2cccnc2n1C(C)C1CC1] | 301 |
| (±)-tert-butyl 2-methyl-1-(1-phenylpropyl)-1H-pyrrolo[2,3-b]pyridine-3-carboxylate | 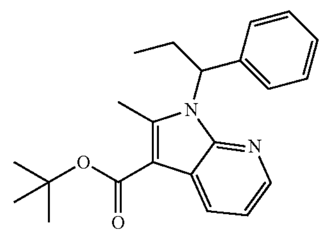 [SMILES: CCC(c1ccccc1)n1c(C)c(C(=O)OC(C)(C)C)c2cccnc21] | 351 |
| (±)-tert-butyl 1-(1-(1H-pyrazol-1-yl)propan-2-yl)-2-methyl-1H-pyrrolo[2,3-b]pyridine-3-carboxylate | 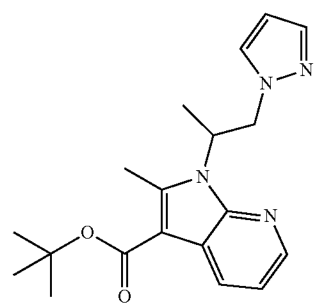 [SMILES: Cc1c(C(=O)OC(C)(C)C)c2cccnc2n1C(C)Cn1cccn1] | 341 |
| tert-butyl 2-methyl-1-(tetrahydro-2H-pyran-4-yl)-1H-pyrrolo[2,3-b]pyridine-3-carboxylate | 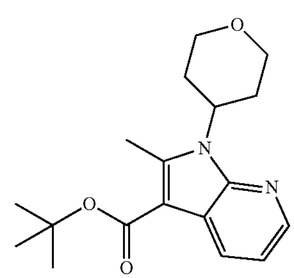 [SMILES: Cc1c(C(=O)OC(C)(C)C)c2cccnc2n1C1CCOCC1] | 317 |
| tert-butyl 1-cyclopentyl-2-methyl-1H-pyrrolo[2,3-b]pyridine-3-carboxylate | 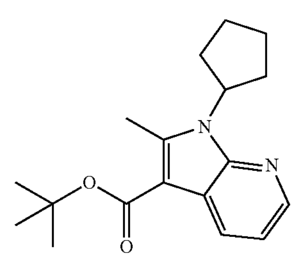 [SMILES: Cc1c(C(=O)OC(C)(C)C)c2cccnc2n1C1CCCC1] | 301 |

| Name | Structure | m/z |
|---|---|---|
| (±)-tert-butyl 2-methyl-1-(1-(piperidin-1-yl)propan-2-yl)-1H-pyrrolo[2,3-b]pyridine-3-carboxylate | 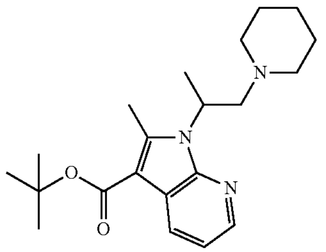 [SMILES: Cc1c(C(=O)OC(C)(C)C)c2cccnc2n1C(C)CN1CCCCC1] | 358 |

Each of the above alkyl carboxylates was used as starting material in Step 3 of Example 36 in the synthesis of certain compounds of the invention.

Example 52

Synthesis of tert-butyl 2-methyl-1-(3-(methylthio)butan-2-yl)-1H-indole-3-carboxylate The title compound was used as starting material in Step 3 of Example 36 in the synthesis of certain compounds of the invention.

Step 1: tert-butyl 2-methyl-1-(3-oxobutan-2-yl)-1H-indole-3-carboxylate

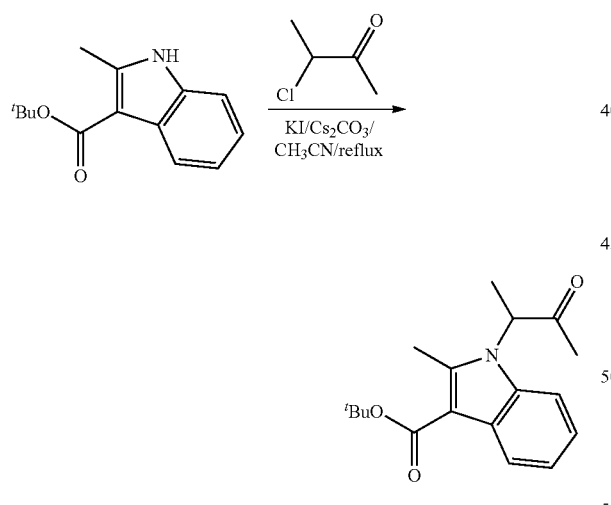

To a solution of tert-butyl 2-methyl-1H-indole-3-carboxylate (2 g, 8.65 mmol) and 3-chlorobutan-2-one (1.1 g, 10.38 mmol) in acetonitrile (18 mL) were added potassium carbonate (3.2 g, 25.8 mmol) and potassium iodide (1.4 g, 8.65 mmol). The reaction mixture was stirred at 90° C. overnight. To the reaction mixture was added water (20 mL). The aqueous layer was extracted with ethyl acetate (50 mL×4). The combined organic layers were dried over sodium sulfate and concentrated. The crude product was purified by silica gel column (petroleum ether/ethyl acetate 100:1 to 80:1) to give tert-butyl 2-methyl-1-(3-oxobutan-2-yl)-1H-indole-3-carboxylate (600 mg, yield: 23%) as a yellow oil. LRMS (M+H+) m/z: calcd 301.17. found 302.

Step 2: tert-butyl 1-(3-hydroxybutan-2-yl)-2-methyl-1H-indole-3-carboxylate

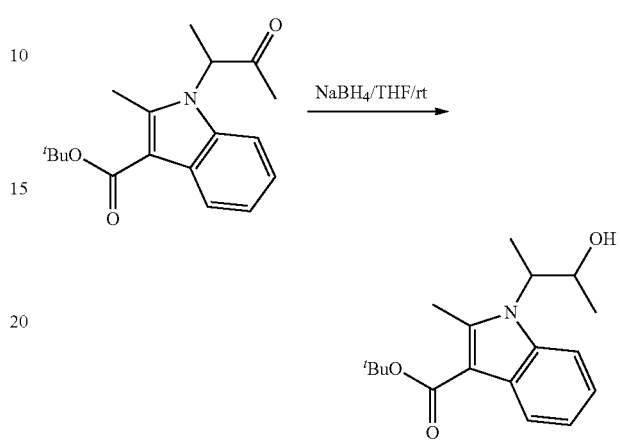

To a mixture of tert-butyl 2-methyl-1-(3-oxobutan-2-yl)-1H-indole-3-carboxylate (120 mg, 0.39 mmol) in tetrahydrofuran (3 mL) was added sodium borohydride (79 mg, 2.08 mmol). The reaction mixture was stirred at room temperature for 3 hours. The reaction mixture was quenched by adding water (3 ml) and extracted with ethyl acetate (20 mL×4). The combined organic layers was dried over sodium sulfate and concentrate to afford tert-butyl 1-(3-hydroxybutan-2-yl)-2-methyl-1H-indole-3-carboxylate (110 mg, yield: 93%) as a yellow oil. LRMS (M+H+) m/z: calcd 303.17. found 304.

Step 3: tert-butyl 2-methyl-1-(3-(tosyloxy)butan-2-yl)-1H-indole-3-carboxylate

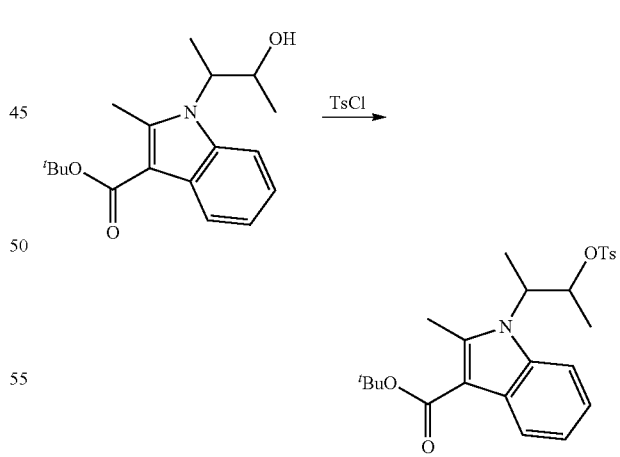

To a mixture of tert-butyl 2-methyl-1-(3-oxobutan-2-yl)-1H-indole-3-carboxylate (1.1 g, 3.6 mmol) in dichloromethane (4 mL) were added 4-methylbenzene-1-sulfonyl chloride (1.3 g, 7.2 mmol), and 1,4-diazabicyclo[2.2.2]octane (1.2 g, 10.8 mmol) at 0° C. The reaction mixture was stirred at 0° C. for 3 hours. The reaction mixture was added to water (30 mL). The aqueous layers was extracted with dichloromethane (10 mL×3), The combined organic layers was

Step 4: tert-butyl 2-methyl-1-(3-(methylthio)butan-2-yl)-1H-indole-3-carboxylate

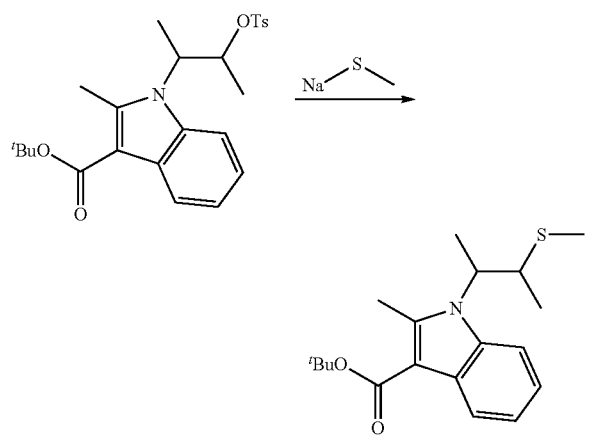

A mixture of compound tert-butyl 2-methyl-1-(3-(tosyloxy)butan-2-yl)-1H-indole-3-carboxylate (200 mg, 0.43 mmol) in N,N-dimethyl formamide (2 mL) was added sodium methanethiolate (994 mg, 1.44 mmol). The reaction mixture was stirred at 110° C. for 4 hours. The reaction was quenched by adding water (6 mL). The aqueous layer was extracted with ethyl acetate (30 mL×3), and the organic layer was concentrated. The crude product was purified by preparative TLC (elute: petroleum/ethyl acetate: 5:1) to give product tert-butyl 2-methyl-1-(3-(methylthio)butan-2-yl)-1H-indole-3-carboxylate (100 mg, yield: 68%). LRMS (M+H$^+$) m/z: calc'd 333.18. found 334.

Step 5: tert-butyl 2-methyl-1-(3-(methylthio)butan-2-yl)-1H-indole-3-carboxylate

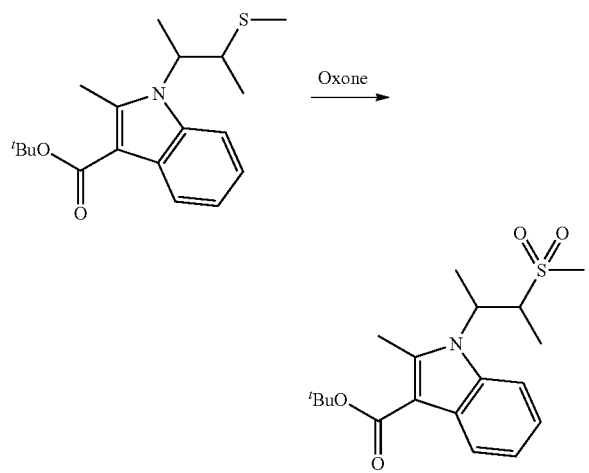

To a solution of compound (4-methoxy-6-methylpyridin-3-yl)methanamine (100 mg, 0.3 mmol) in dichloromethane (3 mL) and water (3 mL) was added oxone (3.7 g, 6 mmol). The reaction mixture was stirred at room temperature for 48 hours. The reaction was quenched by adding water (20 mL). The aqueous layer was extracted with dichloromethane (50 mL×3) and organic layer was concentrated. The crude product was purified by preparative TLC (elute: petroleum ether: ethyl acetate 3:1) to give compound tert-butyl 2-methyl-1-(3-(methylsulfonyl)butan-2-yl)-1H-indole-3-carboxylate (30 mg, yield: 27.5%) as a yellow solid. LRMS (M+H$^+$) m/z: calc'd 365.17. found 366.

Example 53

Synthesis of (R or S)-Ethyl 2-methyl-1-(1-(tetrahydro-2H-pyran-4-yl)ethyl)-1H-pyrrolo[2,3-b]pyridine-3-carboxylate The title compound was used as starting material in Step 3 of Example 36 in the synthesis of certain compounds of the invention.

Step 1: (R or S)-N-((4-Methoxy-6-methyl-2-oxo-1,2-dihydropyridin-3-yl)methyl)-2-methyl-1-(1-(tetrahydro-2H-pyran-4-yl)ethyl)-1H-pyrrolo[2,3-b]pyridine-3-carboxamide

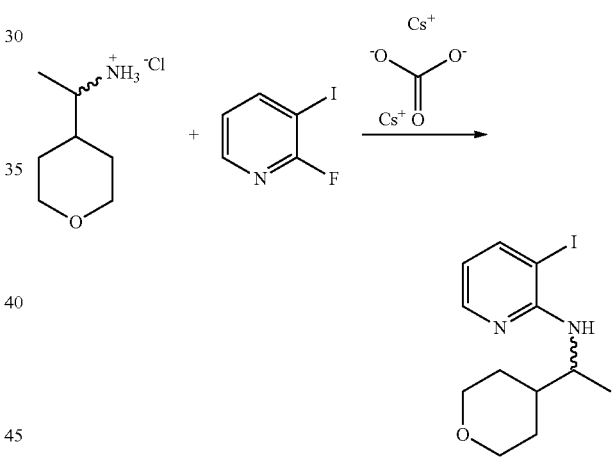

To a re-sealable vial containing 2-fluoro-3-iodopyridine (2.14 g, 9.60 mmol), (S)- or (R)-1-(tetrahydro-2H-pyran-4-yl)ethanaminium chloride (1.2175 g, 7.35 mmol) and cesium carbonate (7.54 g, 23.14 mmol) was added DMAc (10 mL). The vial was subsequently sealed and placed in a 125° C. bath. After stirring at 125° C. for 48 h, the reaction mixture was cooled to room temperature and partitioned between EtOAc with water. The aqueous layer was extracted with EtOAc (3×). The combined organic layers were washed with a minimal amount of water (2×), dried over Na$_2$SO$_4$, and concentrated to give a heterogeneous brown oil. The oil was diluted with EtOAc/Hexanes (1:3) and filtered. The solids were washed with EtOAc:Hexanes (1:3) and the filtrate was concentrated to give a brown oil. The resultant oil was purified on a Biotage system (40 g, gradient elution 2% EtOAc: 98% Hexanes to 10% EtOAc: 90% Hexanes, then isocratic 10% EtOAc: 90% Hexanes). The product (S)- or (R)-3-iodo-N-(1-(tetrahydro-2H-pyran-4-yl)ethyl)pyridin-2-amine (0.84 g, 2.53 mmol, 34.4% yield) was isolated as a clear colorless oil. LRMS (M+H$^+$) m/z: calcd 333.0. found 333.

The compounds shown in the following table were prepared according to the general procedure outlined above using the appropriate starting materials and modifications.

| Name | Structure | m/z |
|---|---|---|
| (S)-3-iodo-N-(1-phenylethyl)pyridin-2-amine | 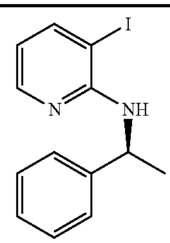 | 325 |

Step 2: (R or S)-Ethyl 2-methyl-1-(1-(tetrahydro-2H-pyran-4-yl)ethyl)-1H-pyrrolo[2,3-b]pyridine-3-carboxylate

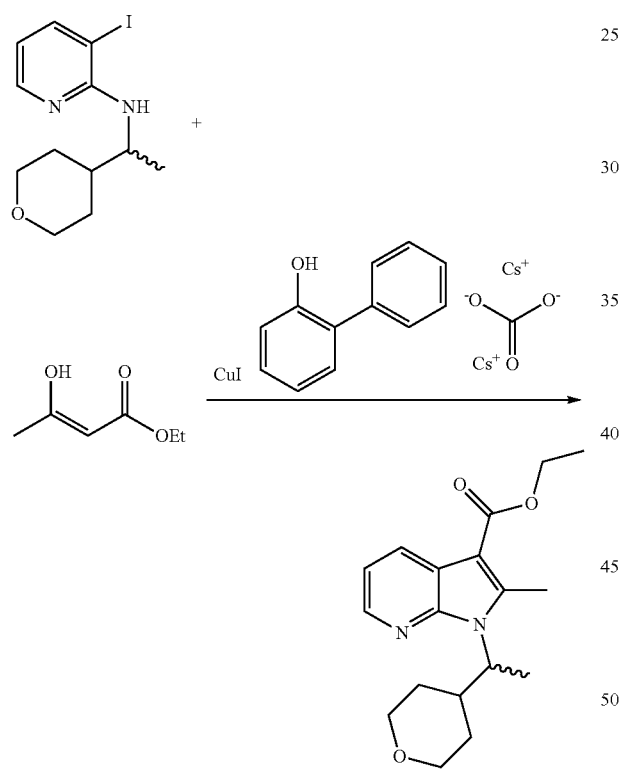

A re-sealable vial containing (S)- or (R)-3-iodo-N-(1-(tetrahydro-2H-pyran-4-yl)ethyl)pyridin-2-amine (0.333 g, 1.002 mmol), copper(I) iodide (0.0084 g, 0.044 mmol), biphenyl-2-ol (0.018 g, 0.106 mmol), and cesium carbonate (0.672 g, 2.062 mmol) was diluted with THF (3.5 mL). To the orange mixture was added ethyl 3-hydroxybut-2-enoate (0.25 mL, 1.977 mmol). The resultant blue-green contents were evacuated and purged with $N_2$ (g) (3×). The vial was subsequently sealed and heated to 100° C. After 24 h, the reaction mixture was cooled to room temperature and filtered over a pad of Celite. The filter pad was washed with EtOAc (3×) and the filtrate was concentrated to give a thick brown oil. The resultant oil was purified on a Biotage system (50 g, gradient elution 2% EtOAc: 98% Hexanes to 15% EtOAc: 85% Hexanes, then 15% EtOAc: 85% Hexanes). The product (S)- or (R)-ethyl 2-methyl-1-(1-(tetrahydro-2H-pyran-4-yl)ethyl)-1H-pyrrolo[2,3-b]pyridine-3-carboxylate (0.257 g, 0.812 mmol, 81.0% yield) was isolated as a white foam. LRMS (M+H⁺) m/z: calcd 317.2. found 317.

The compound shown in the following table was prepared according to the general procedure outlined above using the appropriate starting materials and modifications.

| Name | Structure | m/z |
|---|---|---|
| (S)-ethyl 2-methyl-1-(1-phenylethyl)-1H-pyrrolo[2,3-b]pyridine-3-carboxylate | 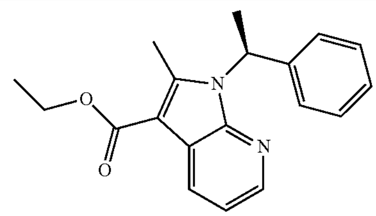 [SMILES: CCOC(=O)c1c(C)n([C@@H](C)c2ccccc2)c2ncccc12] | 309 |

This compound was also used as starting material in Step 3 of Example 36 in the synthesis of certain compounds of the invention.

Example 54

Synthesis of N-((4-methoxy-6-methyl-2-oxo-1,2-dihydropyridin-3-yl)methyl)-2-methyl-1-(1-(3-(methylcarbamoyl)phenyl)ethyl)-1H-pyrrolo[2,3-b]pyridine-3-carboxamide (Compound 263)

Step 1: 3-(1-(3-(((4-methoxy-6-methyl-2-oxo-1,2-dihydropyridin-3-yl)methyl)carbamoyl)-2-methyl-1H-pyrrolo[2,3-b]pyridin-1-yl)ethyl)benzoic acid

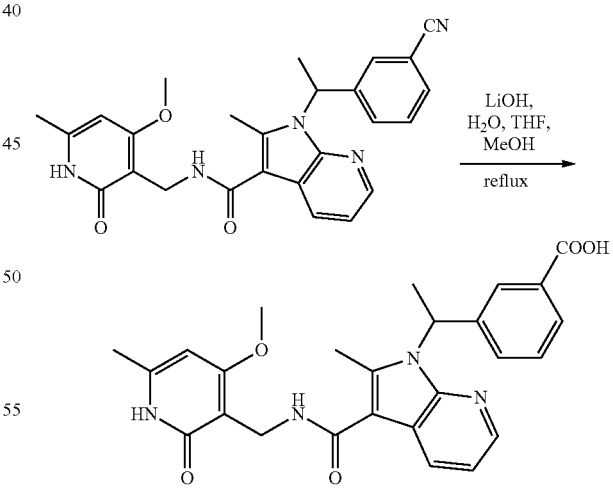

Lithium hydroxide anhydrate (10.51 mg, 0.439 mmol) in water (5 mL) was added to 1-(1-(3-cyanophenyl)ethyl)-N-((4-methoxy-6-methyl-2-oxo-1,2-dihydropyridin-3-yl)methyl)-2-methyl-1H-pyrrolo[2,3-b]pyridine-3-carboxamide (20 mg, 0.044 mmol) in tetrahydrofuran (2 mL) and methanol (3 mL) and the resultant mixture was stirred at 100° C. for 12 hours. The mixture was evaporated, added with water (1 mL), acidified with aqueous hydrochloric acid (1M) to pH=2. The precipitate solid was filtered and dried to obtain the title compound (20 mg, yield: 96%).

Step 2: Methyl 3-(1-(3-(((4-methoxy-6-methyl-2-oxo-1,2-dihydropyridin-3-yl)methyl)carbamoyl)-2-methyl-1H-pyrrolo[2,3-b]pyridin-1-yl)ethyl)benzoate

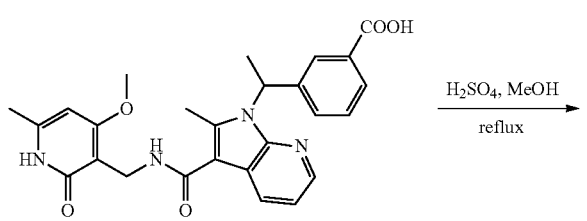

To a solution of 3-(1-(3-(((4-methoxy-6-methyl-2-oxo-1,2-dihydropyridin-3-yl)methyl)carbamoyl)-2-methyl-1H-pyrrolo[2,3-b]pyridin-1-yl)ethyl)benzoic acid (20 mg, 0.042 mmol) in MeOH (6 mL) was added 2-3 drops of sulfuric acid. The mixture was stirred at 70° C. for 1 hour. The solvent was evaporated. The residue was dissolved in water (3 mL), quenched by saturated NaHCO, solution, extracted with EA (10×3). The combined organic phase was dried by sodium sulfate, and then filtered. The filtrate was concentrated to give the title compound (20 mg, yield: 97%).

Step 3: N-((4-methoxy-6-methyl-2-oxo-1,2-dihydropyridin-3-yl)methyl)-2-methyl-1-(1-(3-(methylcarbamoyl)phenyl)ethyl)-1H-pyrrolo[2,3-b]pyridine-3-carboxamide (Compound 263)

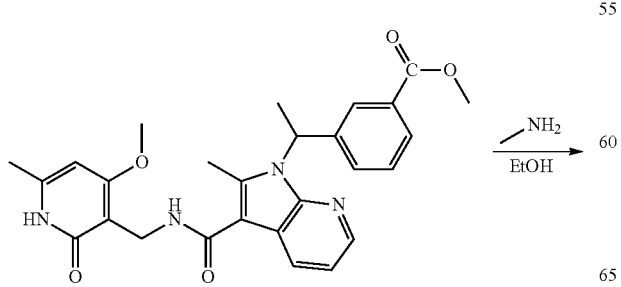

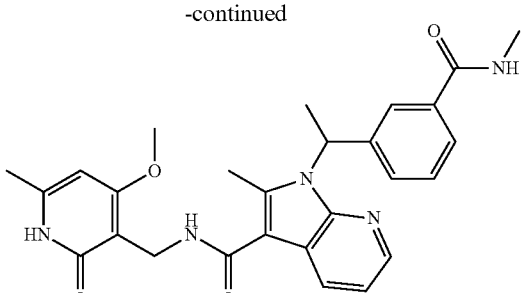

Methyl 3-(1-(3-(((4-methoxy-6-methyl-2-oxo-1,2-dihydropyridin-3-yl)methyl)carbamoyl)-2-methyl-1H-pyrrolo[2,3-b]pyridin-1-yl)ethyl)benzoate (20 mg, 0.041 mmol) was added to 30% methylamine ethanol solution (10 mL). The mixture was stirred under 50 Psi at 100° C. for 12 hours in a 100 mL of sealed tube. The solvent was evaporated and the residue was purified by preparative-HPLC (Instrument: Gilson GX281 Column: ASB C18 150*25 mm*5 um Mobile phase A: water with 0.05% ammonia solution Mobile phase B: MeCN Column temperature: 30° C. Gradient: 17-47% B 15 min) to afford the title compound (17.4 mg, yield: 30%). LRMS (M+H$^+$) m/z: calcd 488.22. found 488.0. $^1$H NMR (400 MHz, chloroform-d) δ ppm 2.01 (d, J=7.28 Hz, 3 H) 2.26 (s, 3 H) 2.50 (s, 3 H) 2.96 (d, J=4.63 Hz, 3 H) 3.91 (s, 3 H) 4.64 (d, J=5.51 Hz, 2 H) 5.95 (s, 1 H) 6.14 (br. S., 1 H) 6.55 (d, J=8.16 Hz, 1 H) 7.05-7.13 (m, 1 H) 7.33 (t, J=8.05 Hz, 1 H) 7.51-7.59 (m, 1 H) 7.60-7.64 (m, 1 H) 8.24 (d, J=5.51 Hz, 2 H).

Example 55

Synthesis of tert-butyl 1-(3-hydroxy-3-methylbutan-2yl)-2-methyl-1H-pyrrolo[2,3-b]pyridine-3-carboxylate The title compound was used as starting material in Step 3 of Example 36 in the synthesis of certain compounds of the invention.

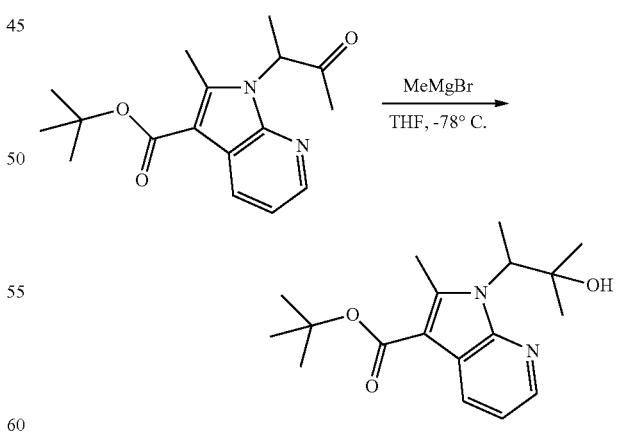

To a solution of tert-butyl 2-methyl-1-(3-oxobutan-2-yl)-1H pyrrolo[2,3-b]pyridine-3-carboxylate (0.6 g, 2 mmol) in THF (10 mL) were added CH$_3$MgBr (2 mL, 6 mmol) at −78° C. The mixture was stirred at −78° C. for 3 hr. Water (4 mL) was added and the mixture was extracted by ethyl acetate (30 mL*3). The organic layer was washed with brine and dried

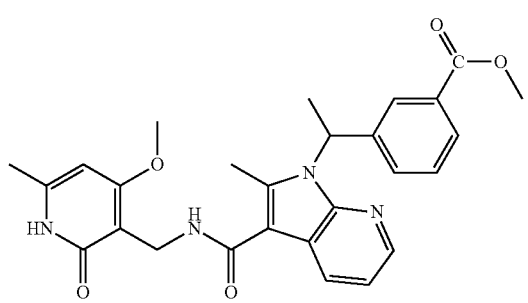

over sodium sulfate. The crude product was concentrated and purified by pre-TLC (eluted: petroleum ether/ethyl acetate=4/1) to give tert-butyl 1-(3-hydroxy-3-methylbutan-2-yl)-2-methyl-1H-pyrrolo[2,3-b]pyridine-3-carboxylate (300 mg, 49%).

Example 56

Synthesis of (±)-tert-butyl 1-(1-methoxy(methyl)amino)-1-oxopropan-2-yl)-2-methyl-1H-pyrrolo[2,3-b]pyridine-3-carboxylate The title compound was used as starting material in Step 3 of Example 36 in the synthesis of certain compounds of the invention.

Step 1: (±)-tert-butyl 1-(1-methoxy-1-oxopropan-2-yl)-2-methyl-1H-pyrrolo[2,3-b]pyridine-3-carboxylate

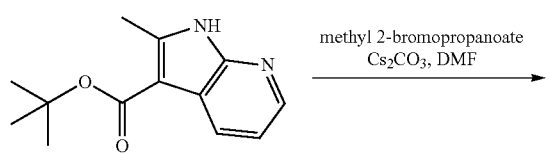

Step 2: (±)-tert-butyl 1-(1-(methoxy(methyl)amino)-1-oxopropan-2-yl)-2-methyl-1H-pyrrolo[2,3-b]pyridine-3-carboxylate

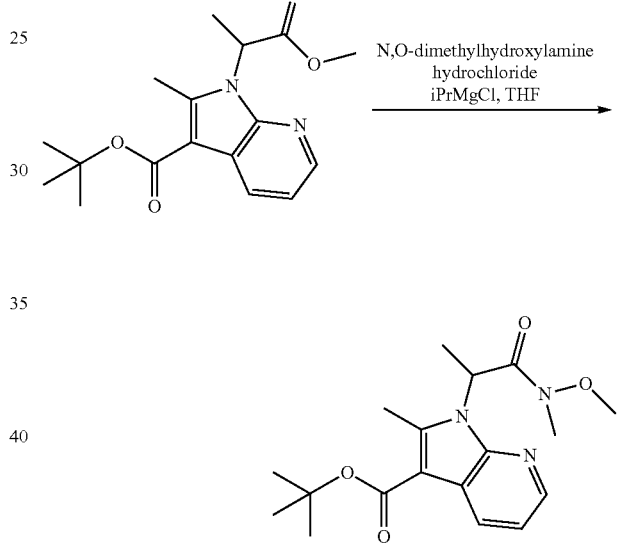

To a pyrex vial was added tert-butyl 2-methyl-1H-pyrrolo[2,3-b]pyridine-3-carboxylate (2.491 g, 10.72 mmol) and cesium carbonate (4.54 g, 13.94 mmol). The atmosphere in the vial was vac/purged 3× with $N_2$ then DMF (24 mL) and methyl 2-bromopropanoate (2.393 ml, 21.45 mmol) were added. The reaction was mixed at ambient temperature overnight. The reaction was poured into half-saturated brine and extracted with EtOAc. The combined organic layer was washed 1× each with water then brine, dried over $Na_2SO_4$, filtered, deposited onto silica gel and purified by CC (Biotage, 100 g column) using 25% EtOAc in Hex (6 CV) then 50% (6 CV) as eluent to provide (±)-tert-butyl 1-(1-methoxy-1-oxopropan-2-yl)-2-methyl-1H-pyrrolo[2,3-b]pyridine-3-carboxylate (2.132 g, 64%). LRMS (M+H$^+$) m/z: calcd 319.37. found 319.2.

The compound shown in the following table was prepared according to the general procedure outlined in Step 1 of this example using the appropriate starting materials and modifications.

| Name | Structure | m/z |
|---|---|---|
| tert-butyl 2-methyl-1-(1-oxo-1-phenylpropan-2-yl)-1H-pyrrolo[2,3-b]pyridine-3-carboxylate | 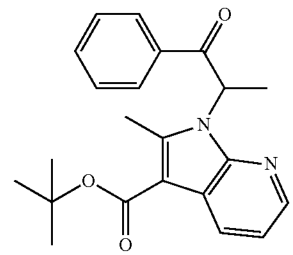 [SMILES: Cc1c(C(=O)OC(C)(C)C)c2cccnc2n1C(C)C(=O)c1ccccc1] | 365 |

To a 100 mL round-bottom flask was added (±)-tert-butyl 1-(1-methoxy-1-oxopropan-2-yl)-2-methyl-1H-pyrrolo[2,3-b]pyridine-3-carboxylate (0.958 g, 3.01 mmol) and N,O-dimethylhydroxylamine hydrochloride (0.440 g, 4.51 mmol). The flask was vac/purged 3× with $N_2$ then THF (17 mL) were added and the reaction was cooled to −40° C. isopropylmagnesium chloride (4.51 ml, 9.03 mmol) was added dropwise and the reaction was mixed at that temperature for 1 h then warmed to 0° C. for 1 h then quenched with 1N HCl, extracted with EtOAc. The org layer was washed with water then brine, dried over $Na_2SO_4$, filtered, concentrated, deposited onto silica gel with aid of DCM, and purified by CC using 25% EtOAc in Hex as eluent to provide (±)-tert-butyl 1-(1-(methoxy(methyl)amino)-1-oxopropan-2-yl)-2-methyl-1H-pyrrolo[2,3-b]pyridine-3-carboxylate (0.630 g, 60.3%). LRMS (M+H$^+$) m/z: calcd 348.41. found 348.2.

Step 3: (±)-tert-butyl 2-methyl-1-(3-oxobutan-2-yl)-1H-pyrrolo[2,3-b]pyridine-3-carboxylate

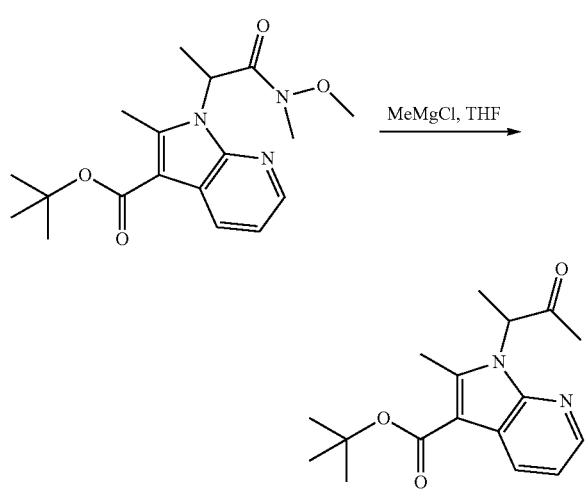

In a 50 mL round-bottom flask, under an atmosphere of N₂, was added (±)-tert-butyl 1-(1-(methoxy(methyl)amino)-1-oxopropan-2-yl)-2-methyl-1H-pyrrolo[2,3-b]pyridine-3-carboxylate (0.630 g, 1.813 mmol) and THF (30 mL). The solution was cooled to 0° C. then methylmagnesium bromide (2.59 ml, 3.63 mmol) was added and the reaction was slowly warmed to ambient temperature while being monitored by LCMS. The reaction was done in 3 h at ambient temperature. Quenched with 50 mL 1N HCl, 50 mL brine, extracted with EtOAc, dried over Na₂SO₄, filtered, concentrated to provide (±)-tert-butyl 2-methyl-1-(3-oxobutan-2-yl)-1H-pyrrolo[2,3-b]pyridine-3-carboxylate, which was used directly in the following reaction. LRMS (M+H⁺) m/z: calcd 303.37. found 303.1.

Example 57

Synthesis of (±)-N-((4-methoxy-6-methyl-2-oxo-1,2-dihydropyridin-3-yl)methyl)-1-(3-(2-methoxyethoxy)butan-2-yl)-2-methyl-1H-pyrrolo[2,3-b]pyridine-3-carboxamide 2,2,2-trifluoroacetate
(Compound 297)

Step 1: (±)-tert-butyl-1-(3-(2-methoxyethoxy)butan-2-yl)-2-methyl-1H-pyrrolo[2,3-b]pyridine-3-carboxylate

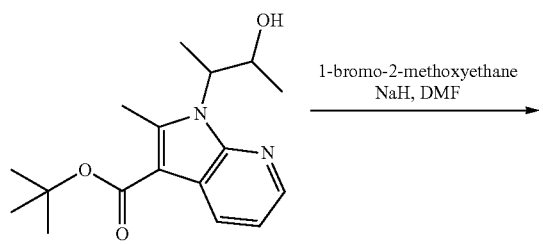

-continued

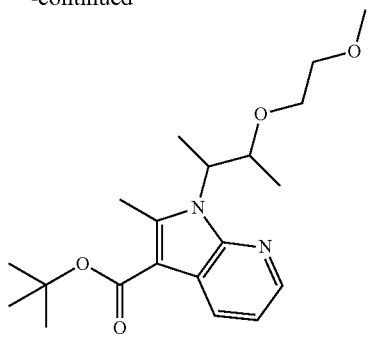

Sodium hydride (0.026 g, 0.657 mmol) and (±)-tert-butyl 1-(3-hydroxybutan-2-yl)-2-methyl-1H-pyrrolo[2,3-b]pyridine-3-carboxylate (0.1 g, 0.329 mmol) were added to a 25 mL rbf and the atmosphere was purged with N2. DMF (5 mL) was added and the reaction was heated at 40° C. for 1 h. The reaction was cooled to ambient temperature and 1-bromo-2-methoxyethane (0.062 ml, 0.657 mmol) was added. The reaction was heated at 90° C. for 3 d. LCMS showed ~60% conversion. The reaction was poured into half-saturated brine, extracted with EtOAc, the org layer was washed with half-saturated brine, brine, filtered, concentrated and loaded onto a column with aid of DCM. 2×12 g column, the column was then treated with 2 CV of Hex then 20% EtAOc in Hex to elute (±)-tert-butyl 1-(3-(2-methoxyethoxy)butan-2-yl)-2-methyl-1H-pyrrolo[2,3-b]pyridine-3-carboxylate (44.4 mg, 37.3%). LRMS (M+H⁺) m/z: calcd 363.46. found 363.1.

The carboxylate shown in the following table was prepared according to the general procedure outlined in Step 1 of this example using the appropriate starting materials and modifications.

| Name | Structure | m/z |
|---|---|---|
| (±)-tert-butyl 1-(3-ethoxybutan-2-yl)-2-methyl-1H-indole-3-carboxylate | 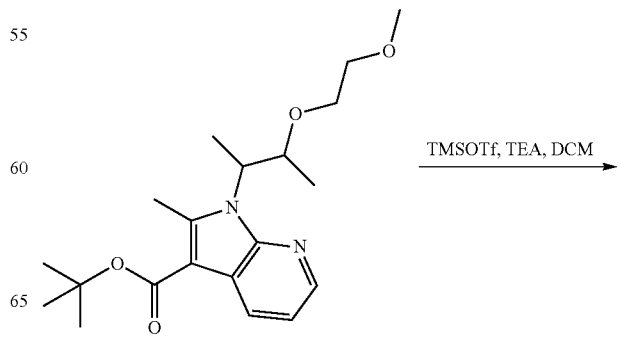 | 332 |

Step 2: (±)-1-(3-(2-methoxyethoxy)butan-2-yl)-2-methyl-1H-pyrrolo[2,3-b]pyridine-3-carboxylic acid

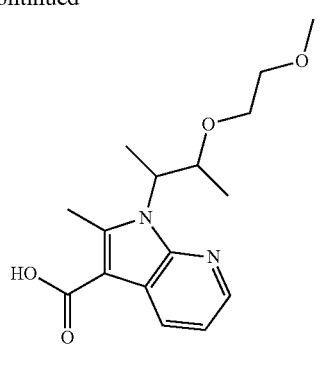

In a 50 mL round-bottom flask, (±)-tert-butyl 1-(3-(2-methoxyethoxy)butan-2-yl)-2-methyl-1H-pyrrolo[2,3-b]pyridine-3-carboxylate (0.0444 g, 0.122 mmol) was added and the atmosphere was vac/purged 3× with N$_2$, then diluted with DCM (10 mL). TEA (0.026 ml, 0.184 mmol) added and the reaction was cooled to 0° C. followed by the addition of TMS-Otf (0.033 ml, 0.184 mmol). The cold bath was removed and the reaction was mixed at ambient temperature for 1 h. LCMS showed complete conversion to the carboxylic acid and the reaction was quenched with 50 mL of 1:1 1N HCl and brine. The aq. Layer was extracted 3× with EtOAc. The combined org layer was dried over Na$_2$SO$_4$, filtered, concentrated to provide crude (±)-1-(3-(2-methoxyethoxy)butan-2-yl)-2-methyl-1H-pyrrolo[2,3-b]pyridine-3-carboxylic acid (38 mg, 100%), which was used directly in the following reaction. LRMS (M+H$^+$) m/z: calcd 307.36. found 307.1.

The carboxylic acids shown in the following table were prepared according to the general procedure outlined in Step 2 of this example using the appropriate starting materials and modifications.

| Name | Structure | m/z |
|---|---|---|
| (±)-1-(3-methoxy-3-methylbutan-2-yl)-2-methyl-1H-indole-3-carboxylic acid | 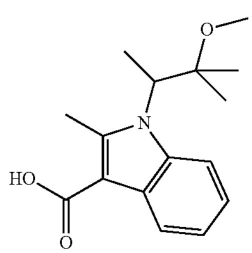 [SMILES: COC(C)(C)C(C)n1c(C)c(C(=O)O)c2ccccc21] | 276 |
| (±)-1-(3-ethoxybutan-2-yl)-2-methyl-1H-indole-3-carboxylic acid | 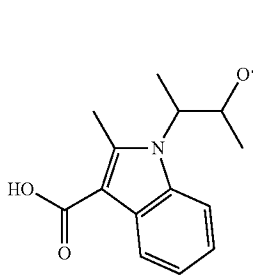 | 276 |

Step 3: (±)-1-(3-(2-methoxyethoxy)butan-2-yl)-2-methyl-1H-pyrrolo[2,3-b]pyridine-3-carbonyl chloride

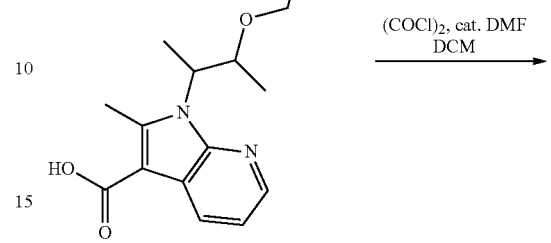

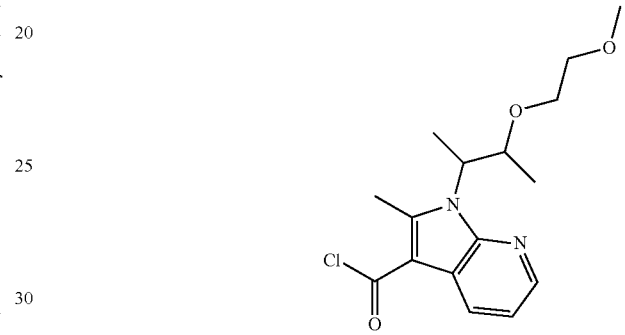

To a solution of (t)-1-(3-(2-methoxyethoxy)butan-2-yl)-2-methyl-1H-pyrrolo[2,3-b]pyridine-3-carboxylic acid (38 mg, 0.124 mmol) in DCM (5 mL, dry at 0° C.) was added 1 drop of DMF and oxalyl chloride (109 μl, 1.240 mmol). The reaction was monitored by LCMS and upon completion (conversion to methyl ester by quenching an aliquot with MeOH), the volatiles removed, concentrated 1× with toluene to provide (±)-1-(3-(2-methoxyethoxy)butan-2-yl)-2-methyl-1H-pyrrolo[2,3-b]pyridine-3-carbonyl chloride (40 mg, 100%), which was used directly in the following reaction. Methyl ester expected in LRMS (M+H$^+$) m/z: calcd 321.17. found 321.2.

Step 4: (±)-N-((4-methoxy-6-methyl-2-oxo-1,2-dihydropyridin-3-yl)methyl)-1-(3-(2-methoxyethoxy)butan-2-yl)-2-methyl-1H-pyrrolo[2,3-b]pyridine-3-carboxamide 2,2-trifluoroacetate (Compound 297)

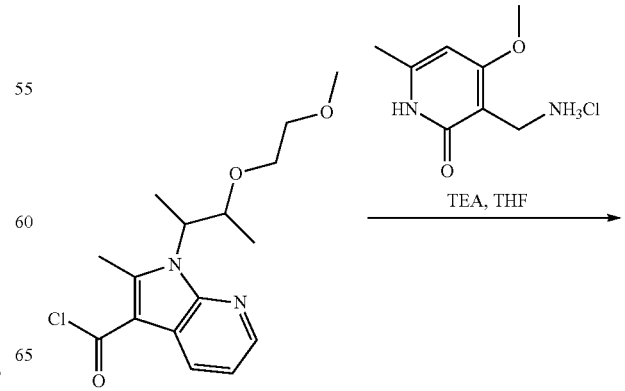

-continued

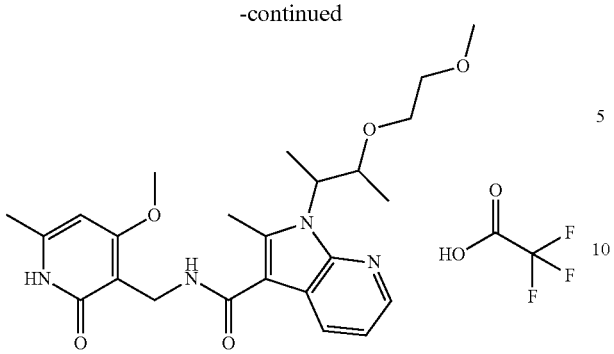

To a solution of (±)-1-(3-(2-methoxyethoxy)butan-2-yl)-2-methyl-1H-pyrrolo[2,3-b]pyridine-3-carbonyl chloride (40.3 mg, 0.124 mmol) and 3-(aminomethyl)-4-methoxy-6-methylpyridin-2(1H)-one hydrochloride (35.5 mg, 0.174 mmol) in THF (5 mL) at 0° C. was added TEA (41.5 µl, 0.298 mmol). The cold bath was removed; the reaction was allowed to stir at ambient temperature and was monitored by LCMS. The reaction was judged to be complete in 3 h.

The crude reaction was concentrated then dissolved in 1 mL DMF, 1.5 mL MeOH, 1 mL H$_2$O, sonicated, filtered through a PTFE screen and purified by reverse-phase HPLC using a H$_2$O:MeCN:TFA 5-95% 7 min. gradient. The pure product fractions were lyophilized to provide the title compound (16 mg, 22.6%) white solid. LRMS (M+H$^+$) m/z: calcd 457.54. found 457.2. $^1$H NMR (400 MHz, DMSO-d$_6$) δ=11.94-11.74 (m, 1 H), 8.19 (dd, J=1.6, 4.7 Hz, 1 H), 8.10 (dd, J=1.4, 7.9 Hz, 1 H), 7.97 (br. S., 1 H), 7.10 (dd, J=4.7, 7.8 Hz, 1 H), 6.23 (s, 1 H), 4.33 (br. S., 4 H), 3.89-3.80 (m, 3 H), 3.27-3.16 (m, 1 H), 2.91-2.86 (m, 3H), 2.84 (s, 4 H), 2.67 (s, 3 H), 2.22 (s, 3 H), 1.60 (d, J=6.7 Hz, 3 H), 1.23-1.16 (m, 3 H).

Example 58

Synthesis of 4-(1-methoxypropan-2-yl)-5-methyl-4H-pyrrolo[2,3-d]thiazole-6-carboxylic acid The title compound was used as starting material in Step 4 of Example 36 in the synthesis of certain compounds of the invention.

Step 1: (Z)-ethyl 2-azido-3-(thiazol-5-yl)acrylate

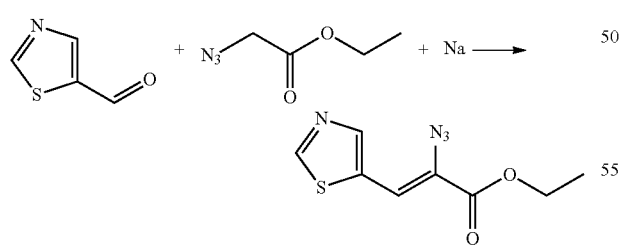

To a solution of thiazole-5-carbaldehyde (20 g, 176.77 mmol) and ethyl 2-azidoacetate (91.2 g, 707.1 mmol) in anhydrous ethanol (100 mL) was added sodium (16.26 g, 707.1 mmol) dissolved in anhydrous ethanol (1000 mL) dropwise between –10° C. and 0° C. After the addition, the mixture was stirred below 0° C. for 4 hours, and then warm to the ambient temperature and allowed to stir overnight. The reaction mixture was washed with saturated ammonium chloride, extracted with acetic ester (500 mL×3), the combined organic phase was dried by anhydrous sodium sulphate, and then filtered. The filtrate was concentrated and purified by column chromatograph on silica gel eluted with (petrol ether/acetic ester 20:1-10:1) to afford the title compound (9 g, 23%) as an yellow solid. LCMS (M+H$^+$) m/z: calcd. 224.04. found 224.9.

Step 2: Ethyl 4H-pyrrolo[2,3-d]thiazole-5-carboxylate

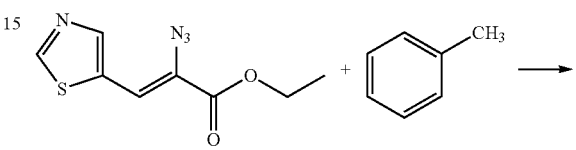

(Z)-ethyl 2-azido-3-(thiazol-5-yl)acrylate (9 g, 40.18 mmol) was dissolved in anhydrous toluene (100 mL), and the resulting reaction was allowed to stir for 2 hours at 120° C. The reaction mixture was concentrated and purified by column chromatograph on silica gel eluted with (petrol ether/acetic ester 15:1→10:1→8:1) to give the title compound (5 g, 63.5%) as an yellow solid. LCMS (M+H$^+$) m/z: calcd. 196.03. found 196.9.

Step 3: (4H-pyrrolo[2,3-d]thiazol-5-yl)methanol

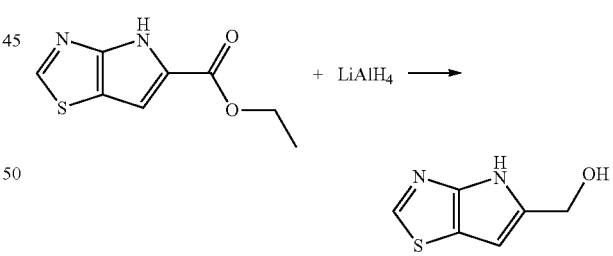

To a solution of ethyl 4H-pyrrolo[2,3-d]thiazole-5-carboxylate (5 g, 25.48 mmol) and in anhydrous tetrahydrofuran (100 mL) was added lithium aluminum hydride (4.34 g, 127.5 mmol) dissolved in anhydrous tetrahydrofuran (50 mL) dropwise between –10° C. and 0° C. After the addition, the mixture was stirred below 0° C. for 1 hours, and then warm to the ambient temperature and allowed to stir for 3 hours at room temperature. The reaction mixture was cooled down to 0° C., quenched by 10 mL water, and then 10 mL 4N sodium hydroxide. The resulting white precipitate was filtered off, washed with acetic ester. The filtrate was dried by anhydrous sodium sulphate. The solvent was removed to afford the crude product (3.5 g, 89%). The crude product was used directly in the next step. LCMS (M+H⁺) m/z: calcd. 154.02. found 154.9.

Step 4: 5-methyl-4H-pyrrolo[2,3-d]thiazole

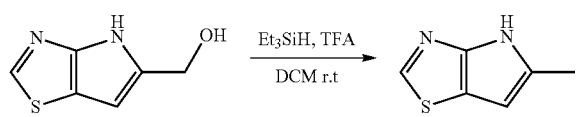

To a solution of (4H-pyrrolo[2,3-d]thiazol-5-yl)methanol (3.5 g, 22.7 mmol) in anhydrous dichloromethane (50 mL) was added triethylsilane (5.23 g, 45.4 mmol) dropwise below 0° C., trifluoroacetic acid (5.18 g, 45.4 mmol) was added dropwise followed below 0° C. The resulting reaction system was warm to the ambient temperature and allowed to stir for 2 hours at room temperature. The reaction mixture was poured into saturated sodium bicarbonate, extracted with dichloromethane (50 mL×3), the combined organic phase was dried by anhydrous sodium sulphate, and then filtered. The filtrate was concentrated and purified by column chromatograph on silica gel eluted with (petrol ether/acetic ester 15:1→8:1) to give the title compound (2.5 g, 80%) as a yellow solid. LCMS (M+H⁺) m/z: calc'd. 138.03. found 138.9.

Step 5: 6-bromo-5-methyl-4H-pyrrolo[2,3-d]thiazole

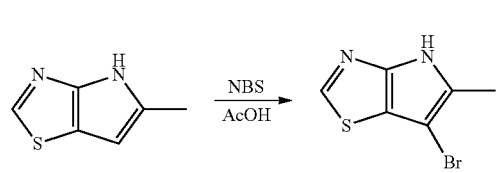

To a solution of 5-methyl-4H-pyrrolo[2,3-d]thiazole (2.5 g, 18.09 mmol) in acetic acid (50 mL) was added 1-bromopyrrolidine-2,5-dione (3 g, 18.10 mmol) slowly below 0° C., and then warm to the ambient temperature and allowed to stir for 2 hours at room temperature. The reaction mixture was concentrated, and acetic acid was removed under reduced pressure. The pH was adjusted to around 7 by progressively adding saturated sodium bicarbonate below 0° C., extracted with acetic ester (50 mL×3). The combined organic phase was dried by anhydrous sodium sulphate, and then filtered. The filtrate was concentrated and purified by column chromatograph on silica gel eluted with (petrol ether/acetic ester 25:1→15:1→10:1) to give the title compound (2.5 g, 64%) as an yellow solid. LCMS (M+H⁺) m/z: calc'd. 215.94. found 219.2.

Step 6: 6-bromo-4-(1-methoxypropan-2-yl)-5-methyl-4H-pyrrolo[2,3-d]thiazole

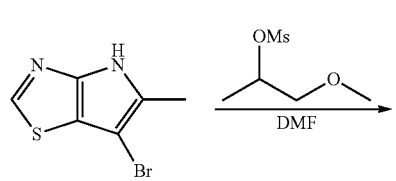

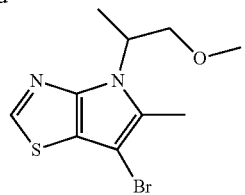

To a solution of 6-bromo-5-methyl-4H-pyrrolo[2,3-d]thiazole (2.5 g, 11.52 mmol) in anhydrous N,N-dimethylformamide (20 mL) was added 1-methoxypropan-2-yl methanesulfonate (3.87 g, 23.03 mmol), and potassium carbonate (3.18 g, 23.03 mmol) followed. The resulting reaction mixture was heated to 70° C. and allowed to stir over night at 70° C. The reaction mixture was washed with water and brine, extracted with acetic ester (30 mL×3). The combined organic phase was dried by anhydrous sodium sulphate, and then filtered. The filtrate was concentrated and purified by column chromatograph on silica gel eluted with (petrol ether/acetic ester 30:1→20:1→10:1) to the title compound (2.0 g, 60%) as orange oil. LCMS (M+H⁺) m/z: calc'd. 287.99. found 290.9.

Step 7: 4-(1-methoxypropan-2-yl)-5-methyl-4H-pyrrolo[2,3-d]thiazole-6-carbonitrile

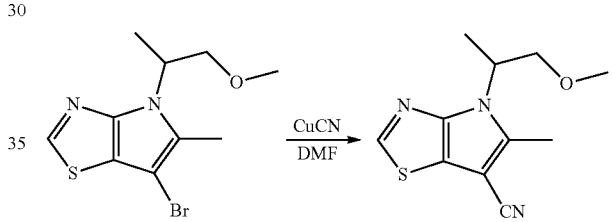

To a solution of 6-bromo-4-(1-methoxypropan-2-yl)-5-methyl-4H-pyrrolo[2,3-d]thiazole (2.0 g, 6.92 mmol) in anhydrous N,N-dimethylformamide (15 mL) was added cyano copper (1.24 g, 13.84 mmol). The resulting reaction mixture was heated to 150° C. and allowed to stir for 2 hours at 150° C. The reaction mixture was washed with water and brine, and extracted with acetic ester (30 mL×3). The combined organic phase was dried by anhydrous sodium sulphate, and then filtered. The filtrate was concentrated and purified by column chromatograph on silica gel eluted with (petrol ether/acetic ester 30:1→20:1→10:1) to give the title compound (1.0 g, 62%) as yellow oil. LCMS (M+H⁺) m/z: calc'd. 235.08. found 236.0.

Step 8: 4-(1-methoxypropan-2-yl)-5-methyl-4H-pyrrolo[2,3-d]thiazole-6-carboxylic acid

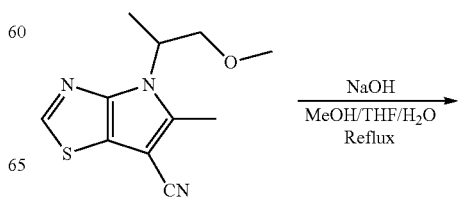

-continued

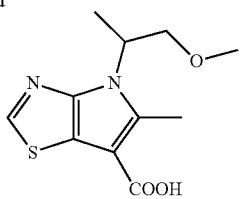

To a solution of 4-(1-methoxypropan-2-yl)-5-methyl-4H-pyrrolo[2,3-d]thiazole-6-carbonitrile (1.0 g, 4.25 mmol) in tetrahydrofuran/methanol=1:1 (30 mL) was added sodium hydroxide (680 mg, 17 mmol) resolved in 15 mL water. The resulting reaction system was heated to 80° C. and allowed to stir for 24 hours at 80° C. The pH was adjusted to around 7 by progressively adding 4N hydrogen chloride below 0° C., solvent and water was removed in reduced pressure to give the title compound (500 mg, 46%) as an yellow solid. LCMS (M+H$^+$) m/z: calc'd. 254.07. found 254.7.

Example 59

Synthesis of (±)-tert-butyl 1-(3-methoxy-3-methylbutan-2-yl)-2-methyl-1H-indole-3-carboxylate The title compound was used as the starting material in Step 3 of Example 36 in the synthesis of certain compounds of the invention.

Step 1: (±)-tert-butyl 1-(3-hydroxy-3-methylbutan-2-yl)-2-methyl-1H-indole-3-carboxylate

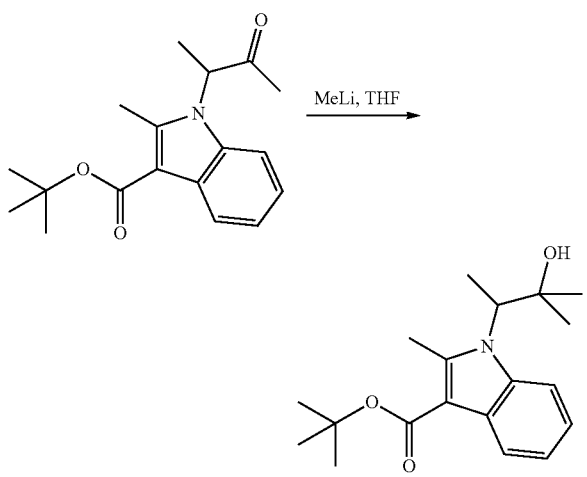

A 50 mL round bottom flask was charged with (±)-tert-butyl 2-methyl-1-(3-oxobutan-2-yl)-1H-indole-3-carboxylate (0.2441 g, 0.810 mmol), vac/purged with N$_2$, diluted with THF (5 mL) and cooled to −78° C. Methyllithium (0.648 ml, 0.972 mmol) was then added slowly, drop-wise, and the solution was allowed to slowly warm to ambient temperature. The reaction was then quenched with 1N HCl, extracted with EtOAc. The org layer was washed with water then brine, dried over Na$_2$SO$_4$, filtered, concentrated, purified by column chromatography using 10% EtOAc in Hex (10 CV), 15% (10 CV) to elute (±)-tert-butyl 1-(3-hydroxy-3-methylbutan-2-yl)-2-methyl-1H-indole-3-carboxylate (157.2 mg, 61.1%). LRMS (M+H$^+$) m/z: calcd 318.42. found 318.2.

Step 2: (±)-tert-butyl 1-(3-methoxy-3-methylbutan-2-yl)-2-methyl-1H-indole-3-carboxylate

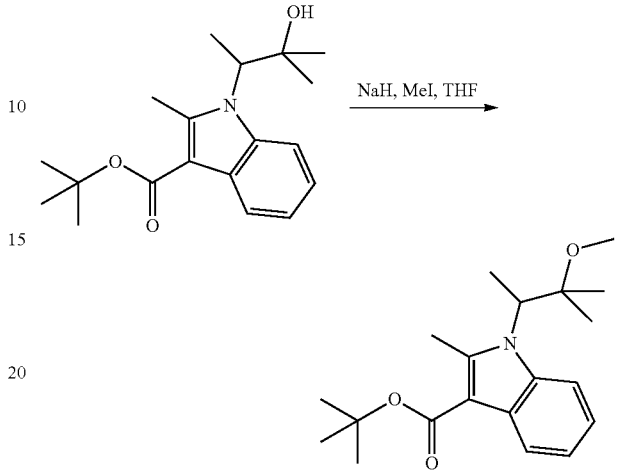

To a solution of (±)-tert-butyl 1-(3-hydroxy-3-methylbutan-2-yl)-2-methyl-1H-indole-3-carboxylate (0.2594 g, 0.817 mmol) and THF (8 mL), in a 50 mL round bottom flask, cooled to 0° C. was added sodium hydride (0.065 g, 1.634 mmol). The reaction was then heated at 45° C. for 2 h then iodomethane (0.102 ml, 1.634 mmol) was added and the reaction was heated at that temperature overnight. The reaction was quenched with 1N HCl and brine, extracted with EtOAc, dried over Na$_2$SO$_4$, filtered, concentrated, deposited onto silica gel with aid of DCM, and purified by column chromatography using 5% EtOAc in Hex as eluent to provide (±)-tert-butyl 1-(3-methoxy-3-methylbutan-2-yl)-2-methyl-1H-indole-3-carboxylate (257.8 mg, 95%). LRMS (M+H$^+$) m/z: calcd 332.45. found 332.2.

Example 60

Synthesis of (tert-butyl 1-(3-methoxybutan-2-yl)-2-methyl-1H-indole-3-carboxylate)

The title compound was used as the starting material in Step 3 of Example 36 in the synthesis of certain compounds of the invention.

Step 1: (tert-butyl 1-(3-hydroxybutan-2-yl)-2-methyl-1H-indole-3-carboxylate)

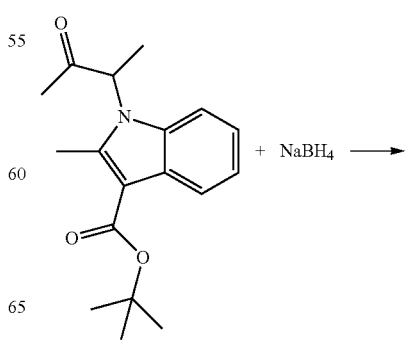

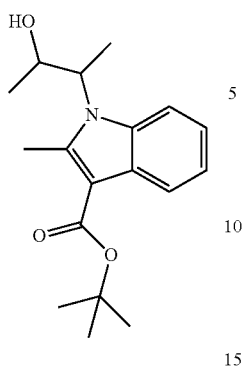

To a solution of tert-butyl 2-methyl-1-(3-oxobutan-2-yl)-1H-indole-3-carboxylate (550 mg, 1.83 mmol) in THF (8 mL) was added NaBH$_4$ (139 mg, 3.66 mmol) at 0° C. under N$_2$. The reaction was stirred at 31° C. for 20 hrs. The mixture was diluted with ethyl acetate, washed with water and saturated aqueous NaHCO$_3$. The organic layer was concentrated in vacuo to afford the title compound (520 mg) as a yellow oil which was used directly without purification.

The compound shown in the following table was prepared according to the general procedure outlined in Step 1 of this example using the appropriate starting materials and modifications.

| Name | Structure | m/z |
|---|---|---|
| tert-butyl 1-(1-hydroxy-1-phenylpropan-2-yl)-2-methyl-1H-pyrrolo[2,3-b]pyridine-3-carboxylate | 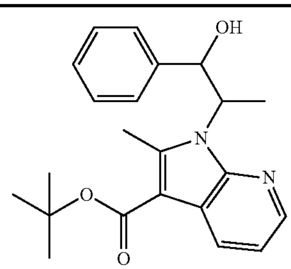 | 367 |

Step 2: (tert-butyl 1-(3-methoxybutan-2-yl)-2-methyl-1H-indole-3-carboxylate)

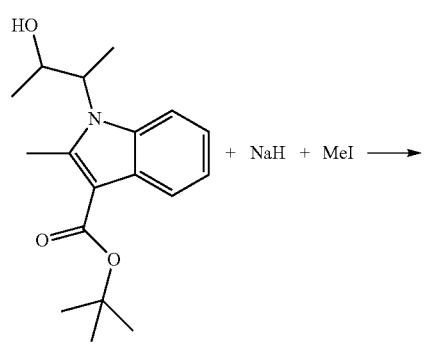

To a suspension of tert-butyl 1-(3-hydroxybutan-2-yl)-2-methyl-1H-indole-3-carboxylate (500 mg, 1.65 mmol) in THF (8 mL) was added sodium hydride (330 mg, 8.25 mmol) at 30° C. under N$_2$. The reaction was stirred for 20 min. Then iodomethane (0.4 mL) was added and the reaction was stirred at 60° C. for 3 hrs. Then the mixture was diluted with ethyl acetate, washed with water and saturated aqueous NaHCO$_3$. The crude product was purified by column chromatography on silica gel eluted with petroleum ether:ethyl acetate=80:1 to afford the title compound as a yellow solid which was used directly (400 mg, 76.8%).

The compounds shown in the following table were prepared according to the general procedure outlined in Step 2 of this example using the appropriate starting materials and modifications.

| Name | Structure | m/z |
|---|---|---|
| (±)-tert-butyl 2-methyl-1-(4,4,4-trifluoro-3-methoxybutan-2-yl)-1H-indole-3-carboxylate | 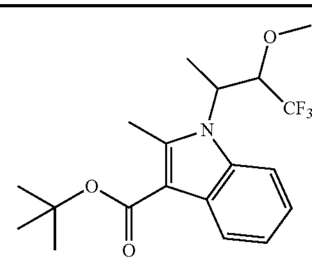 | 372 |
| (±)-tert-butyl 1-(3-methoxypentan-2-yl)-2-methyl-1H-pyrrolo[2,3-b]pyridine-3-carboxylate | 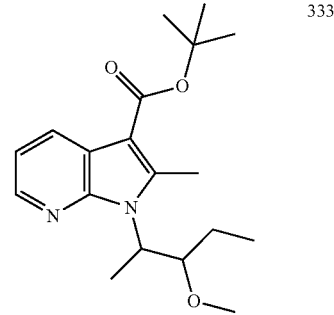 | 333 |

-continued

| Name | Structure | m/z |
|------|-----------|-----|
| (±)-tert-butyl 1-(3-methoxypentan-2-yl)-2-methyl-1H-indole-3-carboxylate | 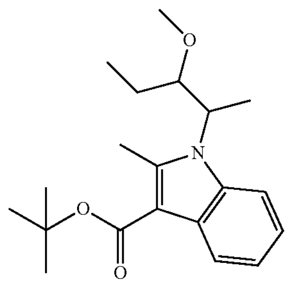 [SMILES: CCC(OC)C(C)n1c(C)c(C(=O)OC(C)(C)C)c2ccccc21] | 332 |
| tert-butyl 1-(1-methoxy-1-phenylpropan-2-yl)-2-methyl-1H-pyrrolo[2,3-b]pyridine-3-carboxylate | 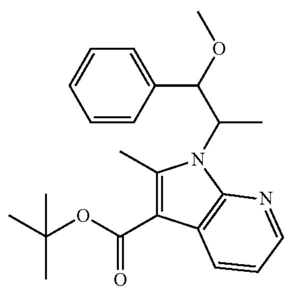 [SMILES: COC(c1ccccc1)C(C)n1c(C)c(C(=O)OC(C)(C)C)c2cccnc21] | 381 |

These t-butyl carboxylates were also used as starting material in Step 3 of Example 36 in the synthesis of certain compounds of the invention.

Example 61

Synthesis of tert-butyl 2-methyl-1-(4,4,4-trifluoro-3-hydroxybutan-2-yl)-1H-pyrrolo[2,3-b]pyridine-3-carboxylate The title compound was used as the starting material in Step 3 of Example 36 in the synthesis of certain compounds of the invention.

Step 1: 2-(3-(tert-butoxycarbonyl)-2-methyl-1H-pyrrolo[2,3-b]pyridin-1-yl)propanoic acid

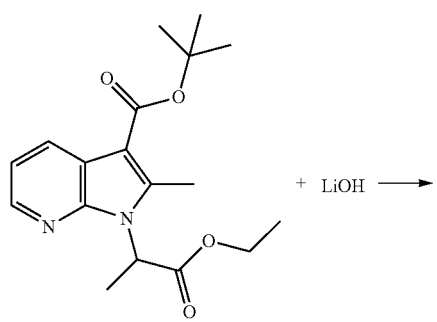
+ LiOH →

To tert-butyl 1-(1-ethoxy-1-oxopropan-2-yl)-2-methyl-1H-pyrrolo[2,3-b]pyridine-3-carboxylate (760 mg, 2.29 mmol) in CH₃OH (5 ml) and H₂O (5 ml) were added LiOH (548 mg, 22.86 mmol) at 25° C., the solution was stirred for 3 h. After the reaction completed. The solution was concentrated under vacuum and acidified to PH 3 with HCl (1 M), solid was precipitate out after adjusted. The mixture was extracted with EtOAc. The organic layer was separated and washed H₂O and dried over Na₂SO₄, and evaporated under reduced pressure to give 6-methyl-7-(1-phenylethyl) pyrrolo [1,2-b]pyridazine-5-carboxylic acid as a white oil (760 mg, yield 100%).

Step 2: Synthesis of tert-butyl 1-(1-hydroxypropan-2-yl)-2-methyl-1H-pyrrolo[2,3-b]pyridine-3-carboxylate

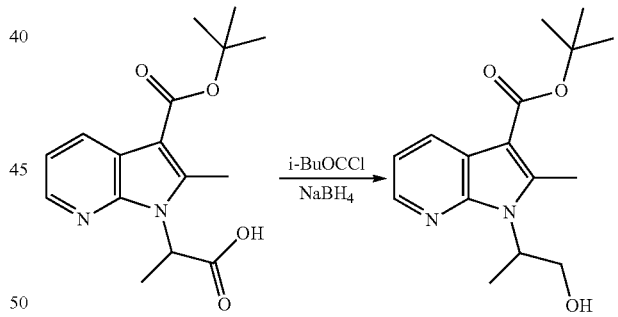

To a solution of 6-methyl-7-(1-phenylethyl) pyrrolo[1,2-b]pyridazine-5-carboxylic acid (760 mg, 2.5 mmol), NMM (505 mg, 4.99 mmol) in THF (10 ml) was added i-BuOCCl (512 mg, 3.75 mmol) dropwise at −15° C. for 15 min. and added NaBH₄ (283 mg, 7.49 mmol) in portions. The solution was allowed to warm 25° C. and stirred for 1 h. The reaction mixture was added H₂O (0.18 ml) dropwise at 0° C. for 5 min. The mixture was allowed to warm 25° C. and stirred for 1 h. After the reaction completed, the solution was concentrated under vacuum. The solid was partitioned between DCM and H₂O. The organic layer was separated and washed TCA (1%) and dried over Na₂SO₄, and evaporated under reduced pressure to give tert-butyl 1-(1-hydroxypropan-2-yl)-2-methyl-1H-pyrrolo[2,3-b]pyridine-3-carboxylate as white oil (700 mg, yield 97%).

Step 3: Tert-butyl 2-methyl-1-(1-oxopropan-2-yl)-1H-pyrrolo[2,3-b]pyridine-3-carboxylate

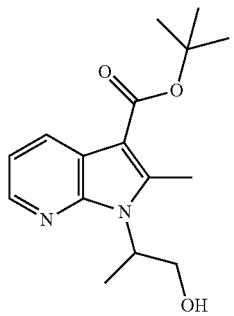

+ DMP ⟶

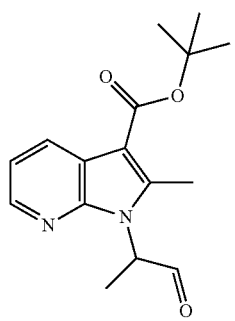

To tert-butyl 1-(1-hydroxypropan-2-yl)-2-methyl-1H-pyrrolo[2,3-b]pyridine-3-carboxylate (380 mg, 1.31 mmol) in CH$_2$Cl$_2$ (5 ml) were added DMP (610.6 mg, 1.44 mmol) at 25° C. for 18 h. After the reaction completed, the solution was purified by silica gel and concentrated under reduced pressure to give tert-butyl 2-methyl-1-(1-oxopropan-2-yl)-1H-pyrrolo[2,3-b]pyridine-3-carboxylate as a white oil (200 mg, yield 53%).

Step 4: Tert-butyl 2-methyl-1-(4,4,4-trifluoro-3-hydroxybutan-2-yl)-1H-pyrrolo[2,3-b]pyridine-3-carboxylate

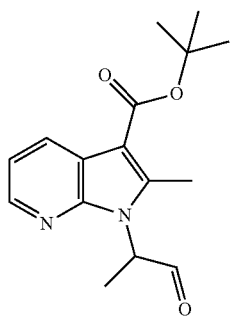

+ TMS-CF$_3$ + TBAF ⟶

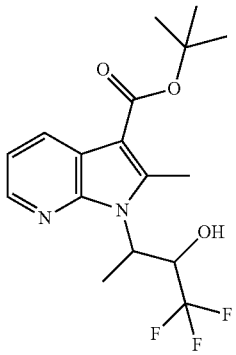

To a solution of tert-butyl 2-methyl-1-(1-oxopropan-2-yl)-1H-pyrrolo[2,3-b]pyridine-3-carboxylate (100 mg, 0.35 mmol) in dry THF (2 ml) was added a solution of TMS-CF$_3$ (0.02 ml, 1M in THF) and the reaction mixture was cooled to 0° C. under Ar, Added TBAF (73.97 mg, 0.52 mmol), via drop-wise addition and stirred for 30 min at 0° C. A solution of saturated NH$_4$Cl was added and most of the solvent was stripped on the ratary evaporator. The reminder was taken up EtOAc and H$_2$O and transferred to a separatory funnel. The mixture was shaken and the organic layer was separated, dried over Na$_2$SO$_4$, and evaporated under reduced pressure to give tert-butyl 2-methyl-1-(4,4,4-trifluoro-3-hydroxybutan-2-yl)-1H-pyrrolo[2,3-b]pyridine-3-carboxylate as a white crystal (40 mg, yield 32%).

Example 62

Synthesis of 1-(1-methoxy-2-methylpropan-2-yl)-2-methyl-1H-indole-3-carboxylic acid The title compound was used as the starting material in Step 4 of Example 36 in the synthesis of certain compounds of the invention.

Step 1: Ethyl 2-(2-methyl-1H-indol-1-yl)acetate

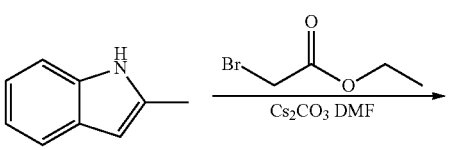

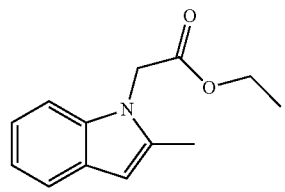

To a solution of 2-methyl-1H-indole[2,3-d]thiazole (1.0 g, 7.6 mmol) in anhydrous N,N-dimethylformamide (10 mL) was added ethyl 2-bromoacetate (1.9 g, 11.4 mmol), and cesium carbonate (3.7 g, 11.4 mmol) followed. The resulting reaction mixture was heated to 70° C. and allowed to stir for 4 hours at 70° C. The reaction mixture was washed with water and brine, extracted with acetic ester (30 mL×3). The combined organic phase was dried by anhydrous sodium sulphate, and then filtered. The filtrate was concentrated and purified by column chromatograph on silica gel (eluted with petroleum ether/acetic ester 30:1→20:1→10:1) to give ethyl 2-(2-methyl-1H-indol-1-yl)acetate (1.5 g, 90%) as a yellow oil. LCMS (M+H⁺) m/z: calcd. 217.11. found 217.9.

Step 2: Ethyl 2-methyl-2-(2-methyl-1H-indol-1-yl)propanoate

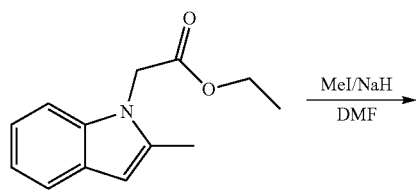

To a solution of ethyl 2-(2-methyl-1H-indol-1-yl)acetate (1.4 g, 6.4 mmol) in anhydrous N,N-dimethylformamide (10 mL) was added sodium hydride (1.6 g, 64.4 mmol) at 0° C., then it was allowed to stirred at 0° C. After 1 hour, iodomethane (9.1 g, 64.4 mmol) was added dropwise at 0° C. The resulting reaction mixture was allowed to stir for 4 hours at room temperature. The reaction mixture was quenched by adding water (10 ml). The pH was adjusted to around 6 by progressively adding 2N hydrogen chloride below 0° C., extracted with acetic ester (50 mL×3). The combined organic phase was dried by anhydrous sodium sulphate, and then filtered. The filtrate was concentrated and purified by column chromatograph on silica gel eluted with (petroleum ether/acetic ester 50:1→30:1→10:1) to give ethyl 2-methyl-2-(2-methyl-1H-indol-1-yl)propanoate (1.2 g, 76%) as a light yellow oil. LCMS (M+H⁺) m/z: calcd. 245.14. found 245.9.

Step 3: 2-methyl-2-(2-methyl-1H-indol-1-yl)propan-1-ol

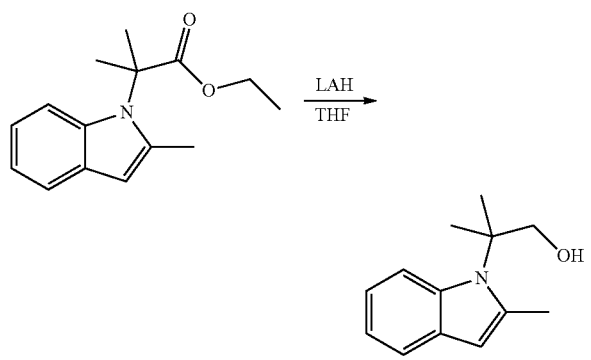

To a solution of ethyl 2-methyl-2-(2-methyl-1H-indol-1-yl)propanoate (1.2 g, 4.9 mmol) in anhydrous tetrahydrofuran (10 mL) was added lithium aluminum hydride (1 g, 24.5 mmol) dissolved in anhydrous tetrahydrofuran (5 mL) dropwise between −10° C. and 0° C. After the addition, the mixture was stirred below 0° C. for 1 hour, and then allowed to stir for 3 hours at room temperature. The reaction mixture was cooled down to 0° C., quenched by 10 mL water, and then 10 mL 4N sodium hydroxide. The resulting white precipitate was filtered off, washed with acetic ester. The filtrate was dried by anhydrous sodium sulphate. The solvent was removed to afford the crude product an purified by column chromatograph on silica gel eluted with (petrol ether/acetic ester 20:1→10:1→5:1) to give 2-methyl-2-(2-methyl-1H-indol-1-yl)propan-1-ol (780 mg, 79%) as a light green oil. LCMS (M+H⁺) m/z: calcd. 202.14. found 202.9.

Step 4: 1-(1-methoxy-2-methylpropan-2-yl)-2-methyl-1H-indole

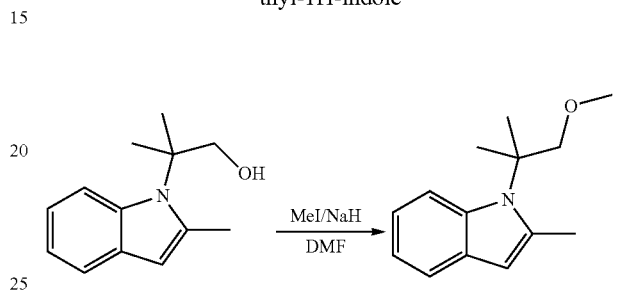

To a solution of 2-methyl-2-(2-methyl-1H-indol-1-yl)propan-1-ol (780 mg, 3.8 mmol) in anhydrous N,N-dimethylformamide (10 mL) was added sodium hydride (919 mg, 38.3 mmol) at 0° C. The resultant reaction mixture was allowed to stirred at 0° C. for 1 h. Iodomethane (5.4 g, 38.3 mmol) was added dropwise at 0° C., And then the resulting reaction mixture was allowed to stir for 3 hours at room temperature. The reaction mixture was quenched with water. The pH was adjusted to around 6 by progressively adding 2N hydro chloride below 0° C., extracted with acetic ester (50 mL×3). The combined organic phase was dried by anhydrous sodium sulphate, and then filtered. The filtrate was concentrated and purified by column chromatograph on silica gel eluted with (petrol ether/acetic ester 10:1→5:1) to give 1-(1-methoxy-2-methylpropan-2-yl)-2-methyl-1H-indole (800 mg, 96%) as a light yellow oil. LCMS (M+H⁺) m/z: calcd. 217.15. found 217.9.

Step 5: 1-(1-methoxy-2-methylpropan-2-yl)-2-methyl-1H-indole-3-carbaldehyde

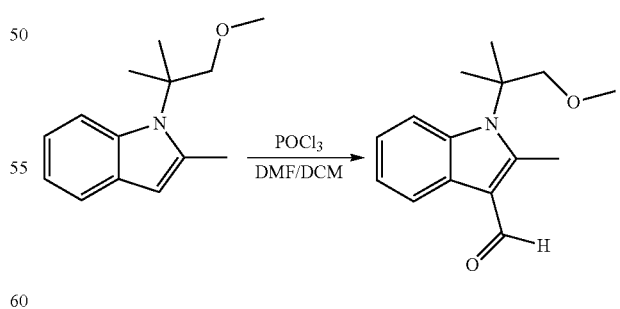

To a solution of 2 ml anhydrous N,N-dimethylformamide dissolved in 80 ml anhydrous dichloromethane was added phosphoryl trichloride (5 g, 32.6 mmol) at 0° C. The resultant reaction mixture was allowed to stirred at 0° C. for 3 hours. 1-(1-methoxy-2-methylpropan-2-yl)-2-methyl-1H-indole (800 mg, 3.7 mmol) was added dropwise at 0° C. Then the resulting reaction mixture was allowed to stir for 1 hour at 0°

C., and then warmed to the ambient temperature. The reaction mixture was allowed to stir for 24 hours at room temperature. The reaction mixture was quenched with saturated sodium acetate. The pH was adjusted to around 8 by progressively adding 2N sodium hydroxide below 0° C., extracted with dichloromethane (100 mL×3). The combined organic phase was dried by anhydrous sodium sulphate, and then filtered. The filtrate was concentrated and purified by column chromatograph on silica gel eluted with (petrol ether/acetic ester 10:1→5:1→2:1) to give 1-(1-methoxy-2-methylpropan-2-yl)-2-methyl-1H-indole-3-carbaldehyde (510 mg, 57%) as a light yellow oil. LCMS (M+H$^+$) m/z: calcd. 245.14. found 245.9.

Step 6: 1-(1-methoxy-2-methylpropan-2-yl)-2-methyl-1H-indole-3-carboxylic acid

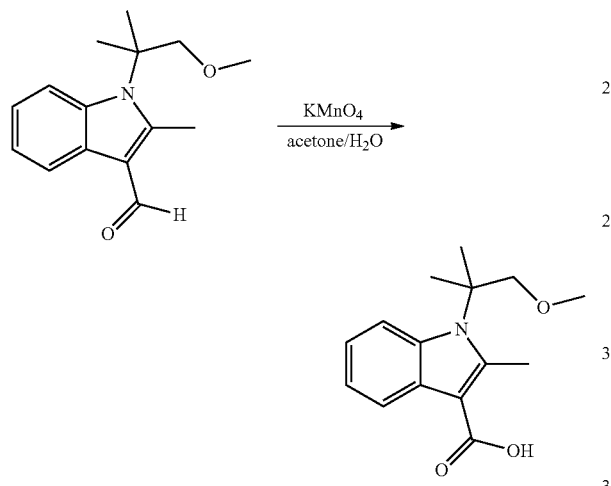

To a solution of 1-(1-methoxy-2-methylpropan-2-yl)-2-methyl-1H-indole-3-carbaldehyde (50 mg, 0.2 mmol) in acetone (2 mL) and water (2 mL) was added potassium permanganate (95 mg, 0.6 mmol). The resulting reaction mixture was allowed to stir for 3 hours at room temperature. The reaction mixture was lyophilized directly to give 1-(1-methoxy-2-methylpropan-2-yl)-2-methyl-1H-indole-3-carboxylic acid (50 mg, 94%) as a brown solid. LCMS (M+H$^+$) m/z: calcd. 261.14. found 261.9.

Example 63

Synthesis of tert-butyl 1-(3-hydroxypentan-2-yl)-2-methyl-1H-pyrrolo[2,3-b]pyridine-3-carboxylate The title compound was used as starting material in Step 3 of Example 36 in the synthesis of certain compounds of the invention.

Step 1: 2-bromopentan-3-one

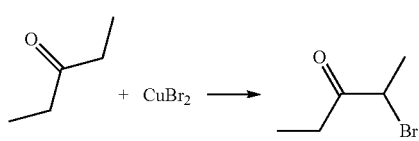

To pentan-3-one (5.0 g, 58.05 mmol) in CHCl$_3$ (25 mL) and EtOAc (25 mL) were added CuBr$_2$ (13.0 g, 58.05 mmol) at 70° C. The solution was stirred at 70° C. for 18 h. After the reaction completed, the reaction mixture was cooled to r.t. and filtered through a Celite pad. The filtration was evaporated under vacuum to give 2-bromopentan-3-one as green oil. (8.0 g, yield 84%)

Step 2: Tert-butyl 2-methyl-1-(3-oxopentan-2-yl)-1H-pyrrolo[2,3-b]pyridine-3-carboxylate

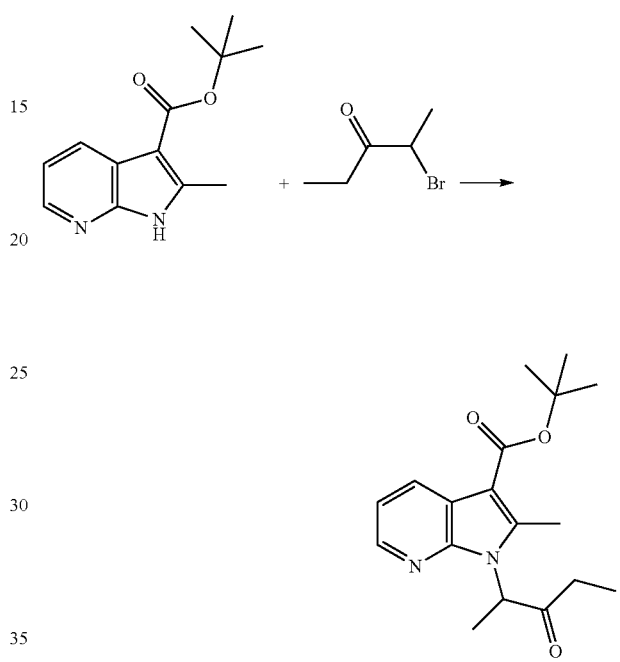

The solution of tert-butyl 2-methyl-1H-pyrrolo[2,3-b]pyridine-3-carboxylate (1.0 g, 4.31 mmol), 2-bromopentan-3-one (1.1 g, 6.46 mmol), Cs$_2$CO$_3$ (2.8 g, 8.61 mmol), KI (142.9 mg, 0.86 mmol) in CH$_3$CN (4 ml) were stirred at 70° C. for 2 h. After the reaction completed, the solution was cooled to r.t. and filtered off. The filtration was evaporated under vacuum. The residue was purified by flash column (Eluent: PE:EtOAc=5:1) to get tert-butyl 2-methyl-1-(3-oxopentan-2-yl)-1H-pyrrolo[2,3-b]pyridine-3-carboxylate as a white oil. (100 mg yield 7%)

Step 3: Tert-butyl 1-(3-hydroxypentan-2-yl)-2-methyl-1H-pyrrolo[2,3-b]pyridine-3-carboxylate

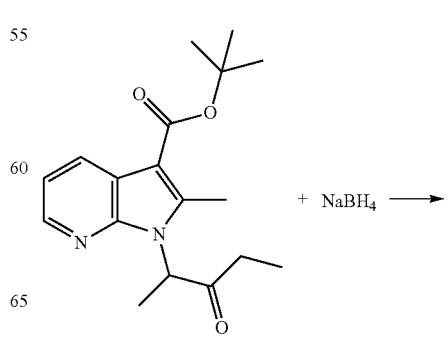

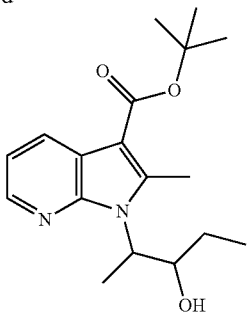

To tert-butyl 2-methyl-1-(3-oxopentan-2-yl)-1H-pyrrolo[2,3-b]pyridine-3-carboxylate (100 mg, 0.32 mmol) in CH$_3$OH (2 ml) were added NaBH$_4$ (35.9 mg, 0.95 mmol) at 0° C. The mixture was allowed to warm 25° C. with stir for 2 h. After the reaction completed, the solution was concentrated under vacuum and the solid was partitioned between EtOAc and H$_2$O. The organic was separated, dried over Na$_2$SO$_4$ and evaporated under reduced pressure to give tert-butyl 1-(3-hydroxypentan-2-yl)-2-methyl-1H-pyrrolo[2,3-b]pyridine-3-carboxylate as a white oil. (50 mg yield 50%).

Example 64

Synthesis of (±)-N-((4-methoxy-6-methyl-2-oxo-1,2-dihydropyridin-3-ylmethyl)-1-(1-methoxypropan-2-yl)-2-methyl-6-(piperazin-1-yl)-1H-pyrrolo[2,3-b]pyridine-3-carboxamide (Compound 295)

Step 1: Tert-butyl 4-(6-aminopyridin-2-yl)piperazine-1-carboxylate

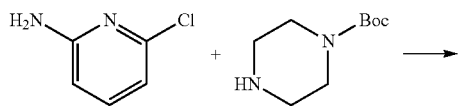

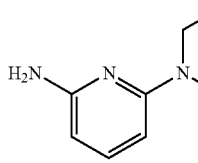

A mixture of 6-chloropyridin-2-amine (10 g, 78 mmol) and tert-butyl piperazine-1-carboxylate (29 g, 156 mmol) was refluxed at 140° C. for 3 days. The reaction mixture was purified by silica gel column chromatography (elute: petroleum ether/ethyl acetate=2:1) to give tert-butyl 4-(6-aminopyridin-2-yl)piperazine-1-carboxylate (6 g, 28%). LCMS (M+H) m/z: calcd 278.17. found 279.

Step 2: Tert-butyl 4-(6-amino-5-bromopyridin-2-yl)piperazine-1-carboxylate

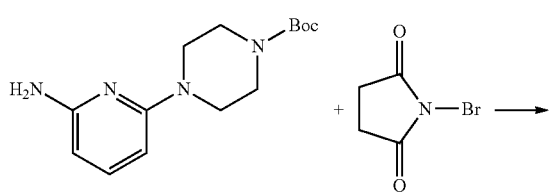

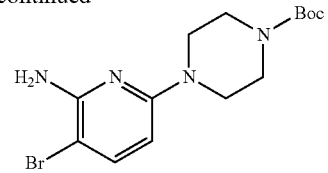

To a solution of tert-butyl 4-(6-aminopyridin-2-yl)piperazine-1-carboxylate (1.9 g, 8 mmol) in N,N-dimethylformamide (20 ml) was added dropwise 1-bromopyrrolidine-2,5-dione (1.4 g, 8 mmol) at 0° C. The reaction was allowed to stirred for 4 h at rt. The reaction mixture was quenched with water (30 mL), and extracted with acetic ester (30 mL×3). The combined organic phase was dried by anhydrous sodium sulphate, and then filtered. The filtrate was concentrated and purified by column chromatograph silica gel (elute: petroleum ether/ethyl acetate=1:1) to give tert-butyl 4-(6-amino-5-bromopyridin-2-yl)piperazine-1-carboxylate (0.2 g, 8.2%) as a yellow solid. LCMS (M+H) m/z: calcd. 356.08. found 357.

Step 3: Tert-butyl 4-(3-(((4-methoxy-6-methyl-2-oxo-1,2-dihydropyridin-3-yl)methyl)carbamoyl)-1-(1-methoxypropan-2-yl)-2-methyl-1H-pyrrolo[2,3-b]pyridin-6-yl)piperazine-1-carboxylate

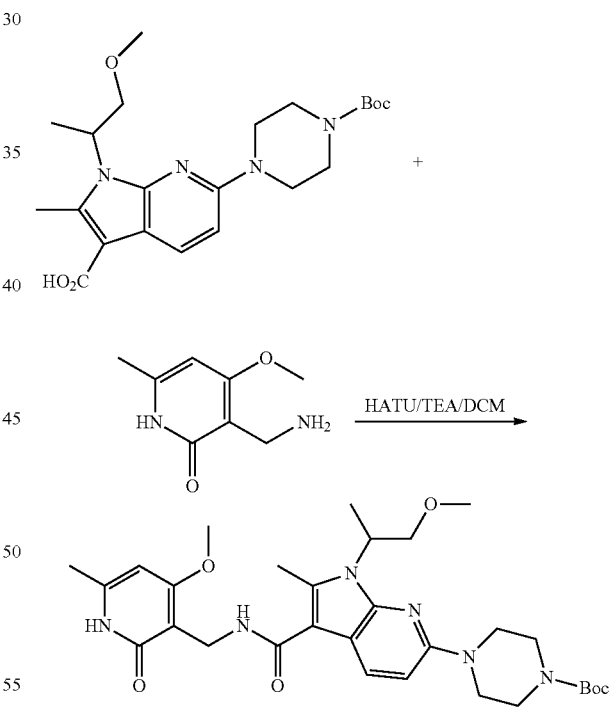

To a solution of 1-(1-methoxypropan-2-yl)-2-methyl-6-(piperazin-1-yl)-1H-pyrrolo[2,3-b]pyridine-3-carboxylic acid (80 mg, 0.19 mmol) in anhydrous dichloromethane (10 mL) was added 3-(aminomethyl)-4-methoxy-6-methylpyridin-2(1H)-one (65 mg, 0.38 mmol), 2-(7-Aza-1H-benzotriazole-1-yl)-1,1,3,3-tetramethyluronium hexafluorophosphate (145 mg, 0.38 mmol) and triethylamine (96 mg, 0.95 mmol). The mixture was stirred at room temperature for 24 hour. The reaction mixture was concentrated and used directly in the next step. LRMS (M+H) m/z: calcd 582.69. found 584.

Step 4: (±)-N-((4-methoxy-6-methyl-2-oxo-1,2-dihydropyridin-3-yl)methyl)-1-(1-methoxypropan-2-yl)-2-methyl-6-(piperazin-1-yl)-1H-pyrrolo[2,3-b]pyridine-3-carboxamide (Compound 295)

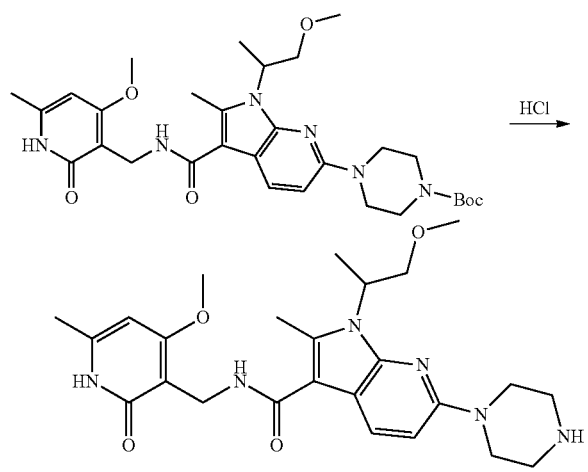

To tert-butyl 4-(3-(((4-methoxy-6-methyl-2-oxo-1,2-dihydropyridin-3-yl)methyl)carbamoyl)-1-(1-methoxypropan-2-yl)-2-methyl-1H-pyrrolo[2,3-b]pyridin-6-yl)piperazine-1-carboxylate (crude, used directly from last step), was added saturated hydrochloride solution in methanol (5 ml) at 0° C. The reaction mixture was allowed to room temperature and stirred for 2 hours. The reaction mixture was concentrated and purified by preparative HPLC (Mobile phase A: water with 0.05% ammonia solution; Mobile phase B: MeCN; column temperature: 30° C. Gradient: 30-60% B 10 min) to give a N-((4-methoxy-6-methyl-2-oxo-1,2-dihydropyridin-3-yl)methyl)-1-(1-methoxypropan-2-yl)-2-methyl-6-(piperazin-1-yl)-1H-pyrrolo[2,3-b]pyridine-3-carboxamide (23 mg, 24.7%, two steps.). LRMS (M+H) m/z: calcd 482.26. found 483. $^1$H NMR (400 MHz, CDCl$_3$) δ: 1.59-1.62 (d, J=7.2 Hz, 3H), 2.21 (s, 3H), 2.71 (s, 3H), 2.96-3.01 (m, 4H), 3.23 (s, 3H), 3.40-3.43 (m, 4H), 3.81-3.88 (m, 4H), 4.10-4.14 (m, 1H), 4.61-4.63 (d, J=5.6 Hz, 2H), 5.91 (s, 1H), 6.41-6.44 (d, J=8.8 Hz, 1H), 7.41-7.45 (m, 1H), 7.90-7.93 (d, J=8.8 Hz, 1H).

Example 65

Synthesis of isolated N-((4-methoxy-6-methyl-2-oxo-1,2-dihydropyridin-3-yl)methyl)-1-((2R or 2S,3R or 3S)-3-methoxybutan-2-yl)-2-methyl-1H-pyrrolo[2,3-b]pyridine-3-carboxamide diastereomers (Compounds 261, 266, 267 and 302)

Step 1: Tert-butyl 2-methyl-1-(3-oxobutan-2-yl)-1H-pyrrolo[2,3-b]pyridine-3-carboxylate

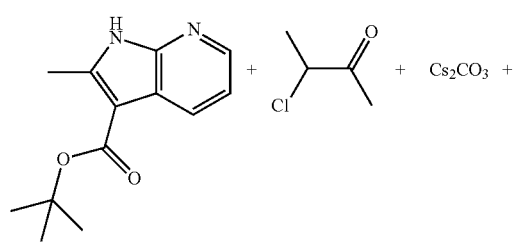

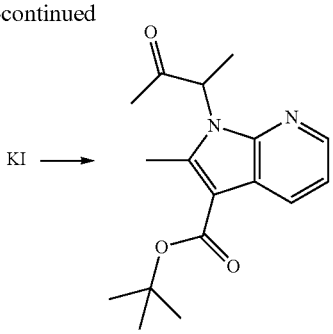

To a solution of tert-butyl 2-methyl-1H-pyrrolo[2,3-b]pyridine-3-carboxylate (5.0 g, 21.53 mmol) in CH$_3$CN (50 mL) was added Cs$_2$CO$_3$ (21.0 g, 64.58 mmol), potassium iodide (3.57 g, 21.53 mmol). The mixture was stirred at 27° C. for 30 minutes. Then 3-chlorobutan-2-one (2.75 g, 25.83 mmol) was added and the mixture was stirred at 70° C. for 12 hours. The mixture was filtered and the filtrate was concentrated. The residue was purified by column (Elute: Petroleum ether:Ethyl acetate=50:1) to give tert-butyl 2-methyl-1-(3-oxobutan-2-yl)-1H-pyrrolo[2,3-b]pyridine-3-carboxylate as a yellow-green oil. (3.23 g, yield 50%) LCMS (M+H$^+$) m/z: calcd 303.37. found 302.9. 1H NMR (400 MHz, CDCl$_3$): ä 8.32-8.30 (m, 1H), 8.25-8.23 (m, 1H), 7.17-7.14 (m, 1H), 5.50-5.44 (m, 1H), 2.71 (s, 3H), 1.96 (s, 3H), 1.65-1.67 (d, 3H), 1.64 (s, 9H).

Step 2: Tert-butyl 1-(3-hydroxybutan-2-yl)-2-methyl-1H-pyrrolo[2,3-b]pyridine-3-carboxylate

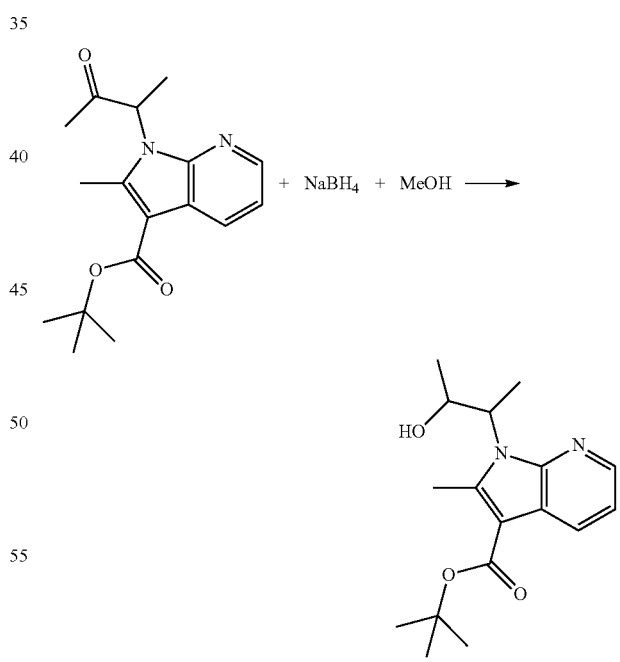

To the solution of tert-butyl 2-methyl-1-(3-oxobutan-2-yl)-1H-pyrrolo[2,3-b]pyridine-3-carboxylate (3.1 g, 10.25 mmol) in methanol (30 mL) was added sodium borohydride (0.30 g, 8.2 mmol) at 0° C. After 30 minutes, another batch of sodium borohydride (0.30 g, 8.2 mmol) was added at 0° C. After the reaction completed about 2 h later, water (30 ml) was added dropwise very carefully to quench the reaction.

The mixture was extracted with CH$_2$Cl$_2$. The extraction was dried over Na$_2$SO$_4$, filtered and concentrated under vacuum to give tert-butyl 1-(3-hydroxybutan-2-yl)-2-methyl-1H-pyrrolo[2,3-b]pyridine-3-carboxylate as a yellow solid. (3.0 g, yield 96%) LCMS (M+H$^+$) m/z: calcd 305.38. found 304.9. 1H NMR (400 MHz, CDCl$_3$): ä 8.31-8.29 (m, 1H), 8.13-8.12 (m, 1H), 7.11-7.07 (m, 1H), 4.46-4.43 (m, 1H), 4.12 (m, 1H), 2.73 (s, 3H), 1.58 (s, 9H), 1.51-1.49 (d, 3H), 0.92-0.91 (d, 3H).

Step 3: Tert-butyl-1-(3-methoxybutan-2-yl)-2-methyl-1H-pyrrolo[2,3-b]pyridine-3-carboxylate

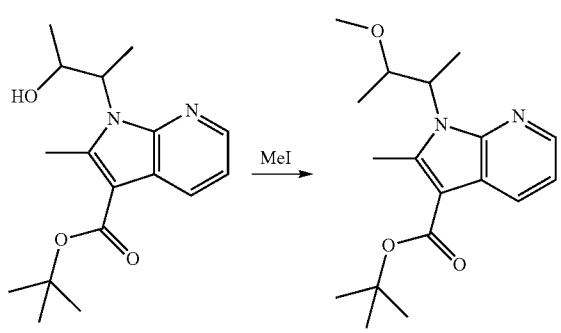 [SMILES: "MeI" ; Cc1c(C(=O)OC(C)(C)C)c2cccnc2n1C(C)C(C)O ; COC(C)C(C)n1c(C)c(C(=O)OC(C)(C)C)c2cccnc21]

To dry THF (20 mL) was added NaH (60% in mineral oil, 2.37 g, 59.14 mmol). Then the mixture was stirred at 27° C. for 20 minutes, then tert-butyl 1-(3-hydroxybutan-2-yl)-2-methyl-1H-pyrrolo[2,3-b]pyridine-3-carboxylate (3.0 g, 9.86 mmol) was added. The mixture was stirred at 27° C. for 1 hour, then added by CH$_3$I (13.99 g, 98.6 mmol). The mixture was stirred for 12 hours at 27° C. and then cooled to 0° C. Sat. NH$_4$Cl was added and extracted with CH$_2$Cl$_2$. The extraction was dried over sodium sulfate, filtered and concentrated to give tert-butyl-1-(3-methoxybutan-2-yl)-2-methyl-1H-pyrrolo[2,3-b]pyridine-3-carboxylate as a yellow oil. (3.2 g, yield 100%) LCMS (M+H$^+$) m/z: calcd. 319.41. found 318.9.

Step 4: 1-(3-methoxybutan-2-yl)-2-methyl-1H-pyrrolo[2,3-b]pyridine-3-carboxylic acid

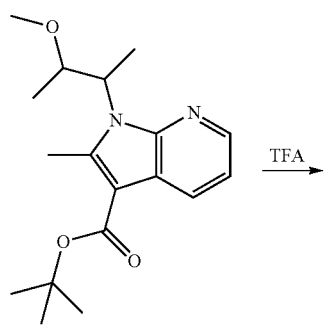

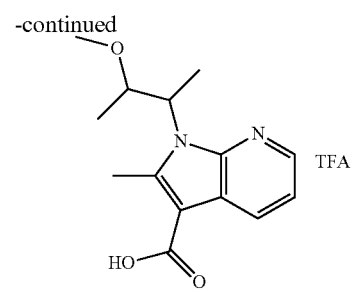

To the pre-cooled solution of tert-butyl 1-(3-methoxybutan-2-yl)-2-methyl-1H-pyrrolo[2,3-b]pyridine-3-carboxylate (3.0 g, 9.42 mmol) in CH$_2$Cl$_2$ (20 mL) was added trifluoroacetic acid (20 mL) dropwise. The solution was stirred at 27° C. for 1.5 hours. The solvent was removed under vacuum at 27° C. The residue was used for next step without purified. LCMS (M+H+) m/z: calcd 263.30. found 262.9.

Step 5: N-((4-methoxy-6-methyl-2-oxo-1,2-dihydropyridin-3-yl)methyl)-1-(3-methoxybutan-2-yl)-2-methyl-1H-pyrrolo[2,3-b]pyridine-3-carboxamide

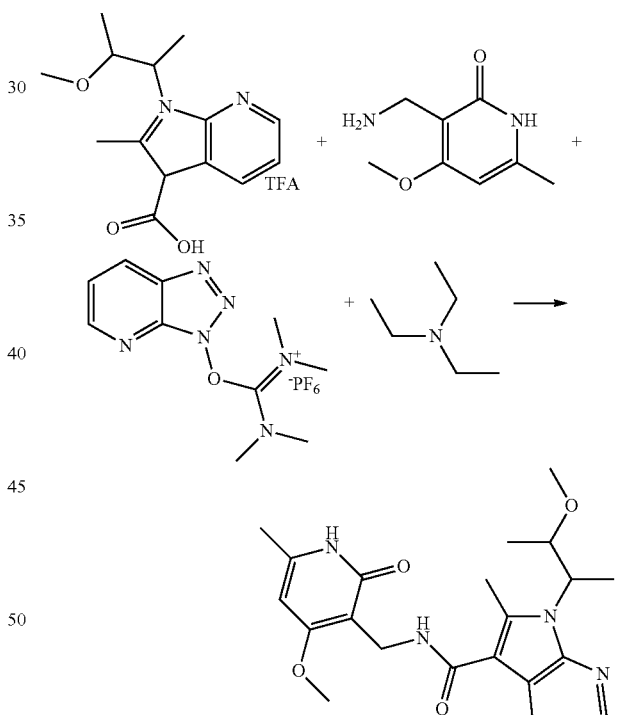

To a solution of 1-(3-methoxybutan-2-yl)-2-methyl-1H-pyrrolo[2,3-b]pyridine-3-carboxylic acid (2.4 g, 9.15 mmol) in DMF (30 mL) was added TEA (4.2 g, 41.50 mmol), 3-(aminomethyl)-4-methoxy-6-methylpyridin-2(1H)-one hydrochloride (2.1 g, 12.81 mmol) After stirred for 10 minutes at 27° C., the mixture was cooled and added HATU (5.56 g, 14.64 mmol). The mixture was stirred at 27° C. for 72 hours and 30% of S.M. remained. Then the mixture was heated at 80° C. for 5 hours. The solution was diluted with brine (100 mL) and extracted with CH$_2$Cl$_2$ (100 mL*3). The extractions were combined and dried over Na$_2$SO$_4$. The solvent was evaporated under vacuum and the residue was purified by flash column (Eluent: dichloromethane:methanol=95:5) to give N-((4-methoxy-6-methyl-2-oxo-1,2-dihydropyridin-3-yl)methyl)-1-(3-methoxybutan-2-yl)-2-methyl-1H-pyrrolo[2,3-b]pyridine-3-carboxamide. (3.6 g, yield 95%)

Step 6: Separation of N-((4-methoxy-6-methyl-2-oxo-1,2-dihydropyridin-3-yl)methyl)-1-(3-methoxybutan-2-yl)-2-methyl-1H-pyrrolo[2,3-b]pyridine-3-carboxamide: Isomers (Compounds 261, 266, 267, and 302)

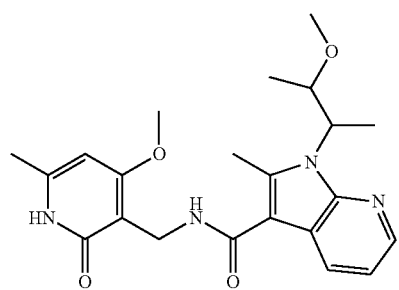

Method 94
Major isomer

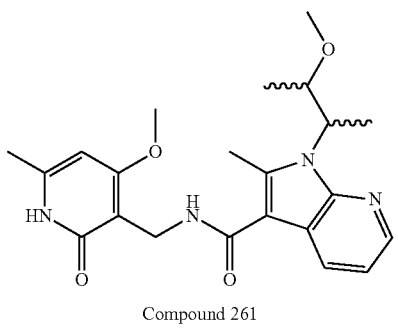

Compound 261
Peak 1

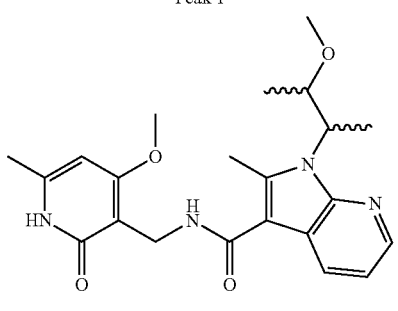

Compound 266
Peak 2

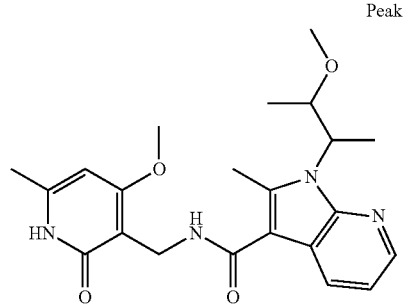

Method 94
Minor isomer

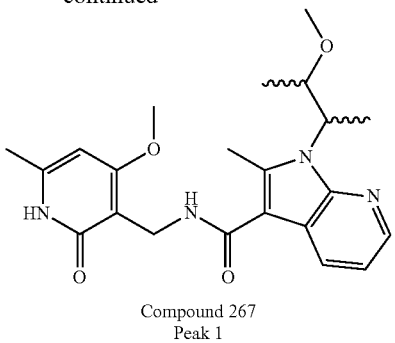

Compound 267
Peak 1

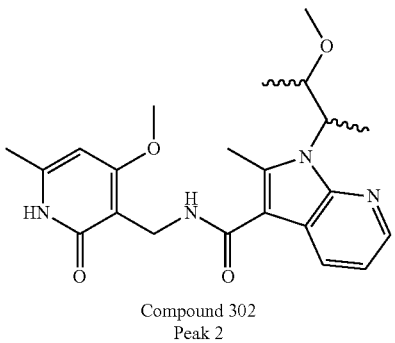

Compound 302
Peak 2

The mixture of isomers from Step 5, N-((4-methoxy-6-methyl-2-oxo-1,2-dihydropyridin-3-yl)methyl)-1-(3-methoxybutan-2-yl)-2-methyl-1H-pyrrolo[2,3-b]pyridine-3-carboxamide was purified by prep-HPLC (Condition: Column: SHIMADZU LC-8A, 250*50 mm*10 um; Mobile phase A: water with 0.2% formic acid; Mobile phase B: MeCN; column temperature: 30° C.; Gradient: B in A 10-50%) to give a major isomer pair (Compound 261 and Compound 266 combined) (1.0 g, purity 98.8%) and a minor isomer pair (Compound 267 and Compound 302 combined) (180 mg, purity 63%). The resulting isomer pairs were individually separated by SFC (Condition: Column: Chiralpak AD 250*30 mm*5 um; Mobile phase A: Supercritical $CO_2$; Mobile phase B: IPA+$NH_3$.$H_2O$; Gradient: B/A: 75:25) to give the following individual single compounds:

Compound 261, N-((4-methoxy-6-methyl-2-oxo-1,2-dihydropyridin-3-yl)methyl)-1-((2R or 2S,3R or 3S)-3-methoxybutan-2-yl)-2-methyl-1H-pyrrolo[2,3-b]pyridine-3-carboxamide (Major Isomer Pair; Peak 1): $^1$H NMR (400 MHz, $CDCl_3$): δ 8.173-8.157 (m, 1H), 8.140-8.116 (m, 1H), 7.582-7.555 (m, 1H), 6.968-6.936 (m, 1H), 5.927 (s, 1H), 4.707-4.609 (m, 2H), 4.348 (s, 1H), 3.892 (s, 3H), 2.869 (s, 3H), 2.788 (s, 3H), 2.173 (s, 3H), 1.644-1.627 (d, 3H), 1.263-1.249 (d, 3H).

Compound 266, N-((4-methoxy-6-methyl-2-oxo-1,2-dihydropyridin-3-yl)methyl)-1-((2R or 2S,3R or 3S)-3-methoxybutan-2-yl)-2-methyl-1H-pyrrolo[2,3-b]pyridine-3-carboxamide (Major Isomer Pair; Peak 2): $^1$H NMR (400 MHz, $CDCl_3$): δ 8.179-8.163 (m, 1H), 8.143-8.120 (m, 1H), 7.558-7.531 (m, 1H), 6.986-6.954 (m, 1H), 5.931 (s, 1H), 4.702-4.605 (m, 2H), 3.897 (s, 3H), 2.892 (s, 3H), 2.789 (s, 3H), 2.189 (s, 3H), 1.647-1.629 (d, 3H), 1.267-1.252 (d, 3H).

Compound 267, N-((4-methoxy-6-methyl-2-oxo-1,2-dihydropyridin-3-yl)methyl)-1-((2R or 2S,3R or 3S)-3-methoxybutan-2-yl)-2-methyl-1H-pyrrolo[2,3-b]pyridine-3-carboxamide (Minor Isomer Pair; Peak 1): $^1$H NMR (400 MHz, $CDCl_3$): δ 8.174-8.162 (d, 1H), 8.111-8.094 (d, 1H), 7.551-7.526 (m, 1H), 6.993-6.961 (m, 1H), 5.935 (s, 1H), 4.683-

4.579 (m, 2H), 3.887 (s, 3H), 3.442 (s, 3H), 2.753 (s, 3H), 2.194 (s, 3H), 1.695-1.678 (d, 3H), 0.781-0.768 (d, 3H).

Compound 302, N-((4-methoxy-6-methyl-2-oxo-1,2-dihydropyridin-3-yl)methyl)-1-((2R or 2S,3R or 3S)-3-methoxybutan-2-yl)-2-methyl-1H-pyrrolo[2,3-b]pyridine-3-carboxamide (Minor Isomer Pair; Peak 2): $^1$H NMR (400 MHz, CDCl$_3$): δ 8.177-8.166 (d, 1H), 8.122-8.104 (d, 1H), 7.587-7.562 (m, 1H), 6.984-6.952 (m, 1H), 5.933 (s, 1H), 4.698-4.591 (m, 2H), 4.426 (s, 2H), 3.983 (s, 3H), 3.448 (s, 3H), 2.764 (s, 3H), 2.180 (s, 3H), 1.701-1.684 (d, 3H), 0.786-0.772 (d, 3H).

Example 66

Synthesis of 1-(1-cyclopropyl-1-methoxypropan-2-yl)-N-((4-methoxy-6-methyl-2-oxo-1,2-dihydropyridin-3-yl)methyl)-2-methyl-1H-pyrrolo[2,3-b]pyridine-3-carboxamide (Compound 283) and its Individual Diastereomers (Compounds 285, 286 and 292)

Step 1: N-methoxy-N-methylcyclopropanecarboxamide

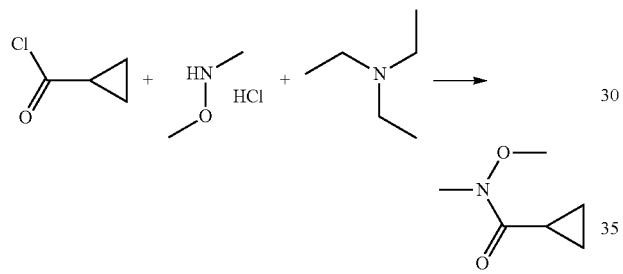

N,O-dimethylhydroxylamine hydrochloride (11.2 g, 114.79 mmol) and TEA (19.36 g, 191.32 mmol) were dissolved in CH$_2$Cl$_2$ (60 ml). Cyclopropanecarbonyl chloride (10 g, 95.66 mmol) was added dropwise at 0° C. After addition, the mixture was allowed to warm to 25° C. and stirred for 18 h. After the reaction completed, the solution was washed with H$_2$O, saturated NaHCO$_3$, 1 N HCl and brine. The organic layer was dried over Na$_2$SO$_4$ and evaporated under reduced pressure to get N-methoxy-N-methylcyclopropanecarboxamide as a yellow oil. (8.6 g, yield 70%).

Step 2: 1-cyclopropylpropan-1-one

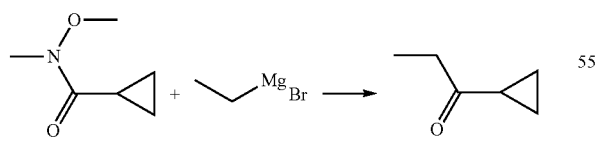

To N-methoxy-N-methylcyclopropanecarboxamide (2.0 g, 15.49 mmol) in THF (20 mL) was added C$_2$H$_5$MgBr (1.2 M in THF, 15.4 ml, 18.58 mmol) dropwise below −70° C. After addition, the solution was allowed to warm to 25° C. and stirred for 18 h. After the reaction completed, the solution was quenched by addition of 1 mL of saturated NH$_4$Cl. Then the mixture was diluted with water and then extracted by EtOAc. The organic layer was separated, combined, dried over Na$_2$SO$_4$ and evaporated under reduced pressure to get 1-cyclopropylpropan-1-one as a white oil. (800 mg, yield 53%).

Step 3: 2-bromo-1-cyclopropylpropan-1-one

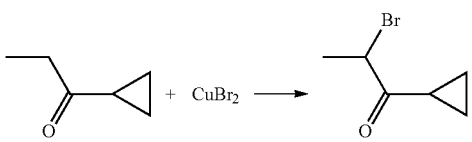

To 1-cyclopropylpropan-1-one (800 mg, 8.15 mmol) in CHCl$_3$ (5 mL) and EtOAc (5 mL) were added CuBr$_2$ (3.64 g, 16.30 mmol) at 70° C. The solution was stirred at 70° C. for 18 h. After the reaction completed, the solution was filtered off. The filtration was evaporated under vacuum to obtain 2-bromo-1-cyclopropylpropan-1-one as green oil. (1.0 g, yield 69%).

Step 4: Tert-butyl 1-(1-cyclopropyl-1-oxopropan-2-yl)-2-methyl-1H-pyrrolo[2,3-b]pyridine-3-carboxylate

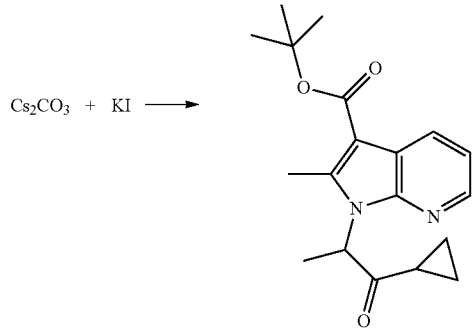

The solution of tert-butyl 2-methyl-1H-pyrrolo[2,3-b]pyridine-3-carboxylate (300.00 mg, 1.29 mmol), 2-bromo-1-cyclopropylpropan-1-one (342.98 mg, 1.94 mmol), Cs$_2$CO$_3$ (841.63 mg, 2.58 mmol), KI (42.88 mg, 0.26 mmol) in DMF (4 ml) were stirred at 25° C. for 18 h. After the reaction completed, the solution was partitioned between EtOAc and H$_2$O. The organic layer was separated, dried over Na$_2$SO$_4$ and evaporated under reduced pressure. The residue was purified by flash column (Eluent: PE:EtOAc=10:1) to get tert-butyl 1-(1-cyclopropyl-1-oxopropan-2-yl)-2-methyl-1H-pyrrolo[2,3-b]pyridine-3-carboxylate as a white oil. (230 mg, yield 54%).

Step 5: Tert-butyl 1-(1-cyclopropyl-1-hydroxypropan-2-yl)-2-methyl-1H-pyrrolo[2,3-b]pyridine-3-carboxylate

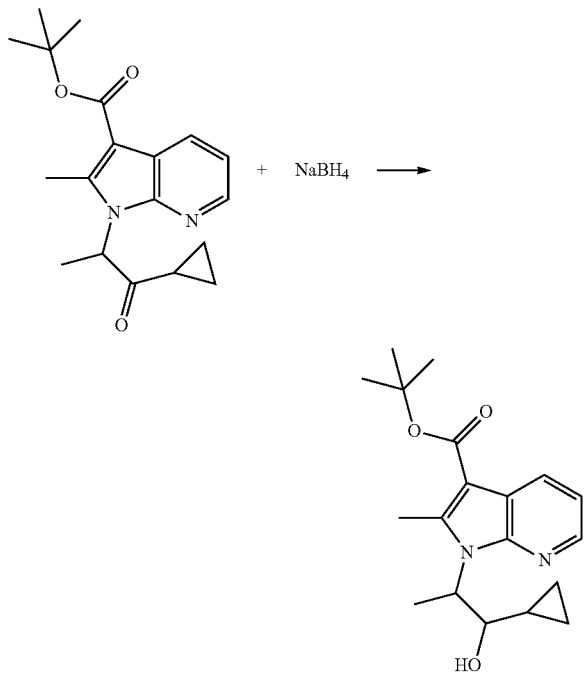

To tert-butyl 1-(1-cyclopropyl-1-oxopropan-2-yl)-2-methyl-1H-pyrrolo[2,3-b]pyridine-3-carboxylate (170 mg, 0.52 mmol) in CH$_3$OH (3 ml) were added NaBH$_4$ (58.75 mg, 1.55 mmol) at 0° C. The mixture was allowed to warm 25° C. with stirred for 2 h. After the reaction mixture completed, the solution was concentrated under vacuum and the solid was partition between EtOAc and H$_2$O. The organic was separated, dried over Na$_2$SO$_4$ and evaporated under reduced pressure to give tert-butyl 1-(1-cyclopropyl-1-hydroxypropan-2-yl)-2-methyl-1H-pyrrolo[2,3-b]pyridine-3-carboxyla as a white oil. (140 mg, yield 84%).

Step 6: Tert-butyl 1-(1-cyclopropyl-1-methoxypropan-2-yl)-2-methyl-1H-pyrrolo[2,3-b]pyridine-3-carboxylate

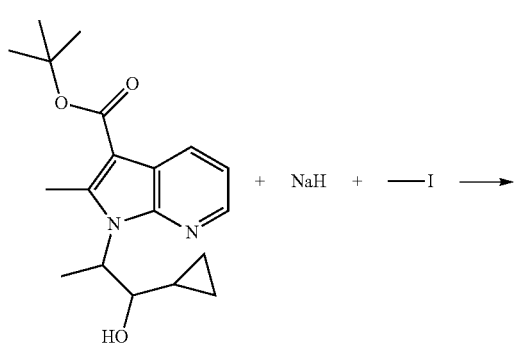

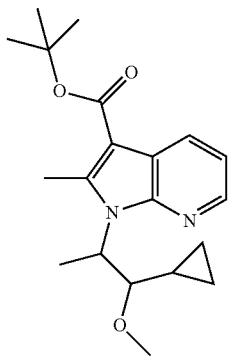

To NaH (72.63 mg, 1.82 mmol) in THF (2 mL) was added tert-butyl 1-(1-cyclopropyl-1-hydroxypropan-2-yl)-2-methyl-1H-pyrrolo[2,3-b]pyridine-3-carboxyla (100 mg, 0.30 mmol) at 25° C. for 30 min. To the reaction mixture was added CH$_3$I (429.57 mg, 3.03 mmol) dropwise with stirring for 3 h. After the reaction completed, the mixture was quenched by addition of 10 mL of saturated NH$_4$Cl, and a clear white solution was obtained which was poured into water and extracted by EtOAc. The extraction was dried over Na$_2$SO$_4$ and evaporated under reduced pressure to give tert-butyl 1-(1-cyclopropyl-1-methoxypropan-2-yl)-2-methyl-11H-pyrrolo[2,3-b]pyridine-3-carboxylate as white oil. (100 mg, yield 95%).

Step 7: 1-(1-cyclopropyl-1-methoxypropan-2-yl)-2-methyl-1H-pyrrolo[2,3-b]pyridine-3-carboxylic acid

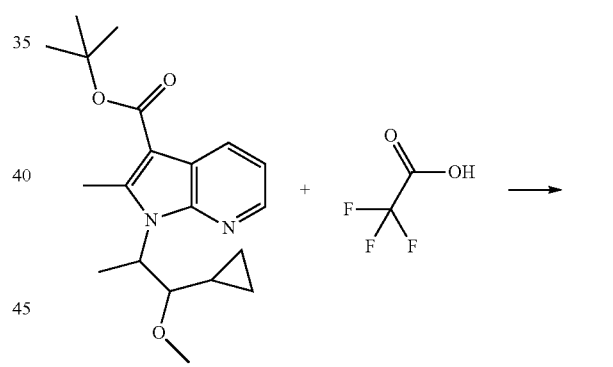

To a solution of tert-butyl 1-(1-cyclopropyl-1-methoxypropan-2-yl)-2-methyl-1H-pyrrolo[2,3-b]pyridine-3-carboxylate (100 mg, 0.29 mmol) in CH$_2$Cl$_2$ (2 mL) were added CF$_3$CO$_2$H (2 mL). The solution was stirred at 25° C. for 2 h. After the reaction completed, the solution was concentrated under reduced pressure to obtain 1-(1-cyclopropyl-1-methoxypropan-2-yl)-2-methyl-1H-pyrrolo[2,3-b]pyridine-3-carboxylic acid as red oil. (87 mg, yield 99%).

Step 8: 1-(1-cyclopropyl-1-methoxypropan-2-yl)-N-((4-methoxy-6-methyl-2-oxo-1,2-dihydropyridin-3-yl)methyl)-2-methyl-1H-pyrrolo[2,3-b]pyridine-3-carboxamide (Compound 283)

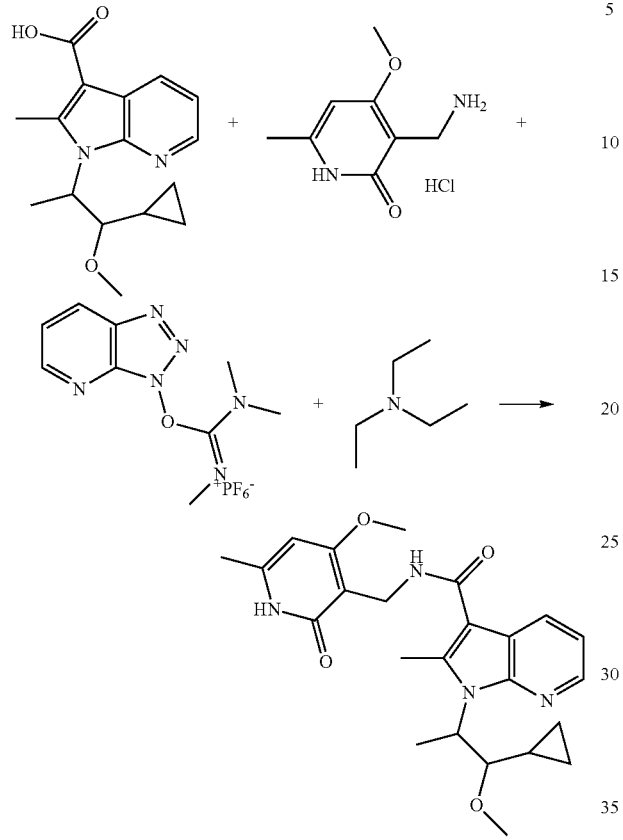

To a solution of 1-(1-cyclopropyl-1-methoxypropan-2-yl)-2-methyl-1H-pyrrolo[2,3-b]pyridine-3-carboxylic acid (100 mg, 0.35 mmol) in dichloromethane (2 mL) was added HATU (192 mg, 0.52 mmol), TEA (105.28 mg, 1.04 mmol). After stirred for 50 min at room temperature, 3-(aminomethyl)-4-methoxy-6-methylpyridin-2(1H)-one hydrochloride (87.5 mg, 0.52 mmol) was added. The mixture was stirred at room temperature for 3 hours. After the reaction completed, the solution was partitioned between EtOAc and H₂O. The organic was separated, dried over Na₂SO₄ and evaporated under vacuum.

Step 9: Separation of Isomers of 1-(1-cyclopropyl-1-methoxypropan-2-yl)-N-((4-methoxy-6-methyl-2-oxo-1,2-dihydropyridin-3-yl)methyl)-2-methyl-1H-pyrrolo[2,3-b]pyridine-3-carboxamide (Compounds 285, 286 and 292)

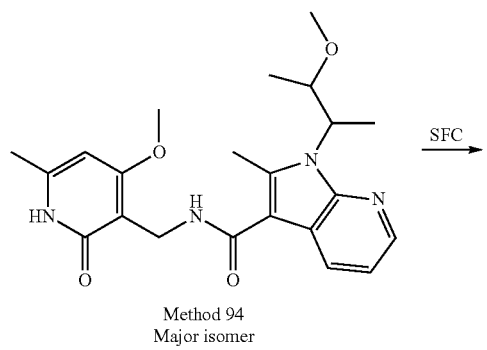

Method 94
Major isomer

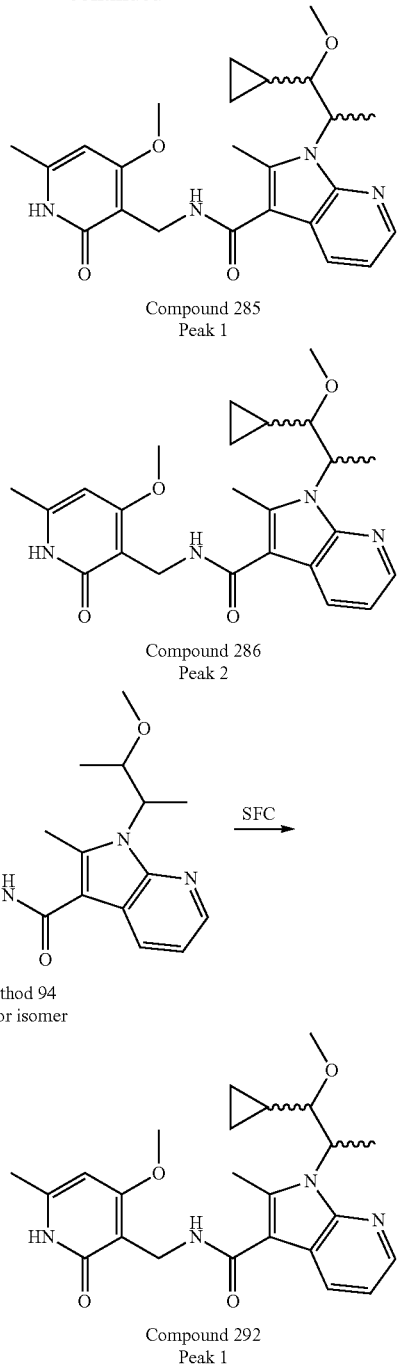

The residue from the previous step was solidified by MTBE to give major isomer 1 (Compounds 285 and 286) (4 mg, purity 90%). The filtrate was purified by preparative-HPLC (Instrument: Gilson 281; Column: Grace C18 5u 150*25 mm; Mobile phase A: Water (0.0225% HCOOH v/v); Mobile phase B: Acetonitrile (neutral); Gradient: 30-60(B %); Flowrate: 22 ml/min) to give major isomer 1 (285 and 286) (0.30 mg, purity 100%) and minor isomer 2 (Compound 292) (2.3 mg 100%). Isomer 1 was separated by SFC (Column: AD (250*30 mm, 5 um); Flow rate: 60 mL/min: Mobile A, phase: 30% IPA+NH₃.H₂O, B, 70% CO₂; Wavelength: 220 nm) to give Compound 285 (15.1 mg, purity 94%) and Compound 286 (14.5 mg, purity 97%).

Compound 285, 1-((1R or S,2R or S)-1-cyclopropyl-1-methoxypropan-2-yl)-N-((4-methoxy-6-methyl-2-oxo-1,2-dihydropyridin-3-yl)methyl)-2-methyl-1H-pyrrolo[2,3-b]pyridine-3-carboxamide: LCMS (M+H+) m/z: calcd 438.23. found 439.1. 1H NMR (400 MHz, CDCl₃): δ 8.112-8.162 (m, 2H), 7.550 (t, 1H), 6.933-6.964 (m, 1H), 5.931 (s, 1H), 4.609-4.708 (m, 2H), 3.761 (s, 3H), 3.755-3.728 (m, 1H), 3.482 (s, 1H), 2.879 (s, 1H), 2.798 (s, 3H), 2.184 (s, 3H), 1.868-1.835 (m, 1H), 1.868-1.835 (m, 1H), 1.764 (s, 3H), 0.837 (m, 1H), 0.603-0.585 (d, 2H, J=7.2 Hz), 0.482-0.473 (d, 2H, J=3.6 Hz).

Compound 286, 1-((1R or S,2R or S)-1-cyclopropyl-1-methoxypropan-2-yl)-N-((4-methoxy-6-methyl-2-oxo-1,2-dihydropyridin-3-yl)methyl)-2-methyl-1H-pyrrolo[2,3-b]pyridine-3-carboxamide: LCMS (M+H+) m/z: calcd 438.23. found 439.2. 1H NMR (400 MHz, CDCl₃): δ8.123-8.175 (m, 2H), 7.500 (t, 1H), 6.976-7.008 (m, 1H), 5.939 (s, 1H), 4.627-4.657 (t, 2H), 4.284-4.459 (m, 1H), 3.906 (s, 3H), 3.795-3.814 (m, 1H), 2.86 (s, 3H), 2.801 (s, 3H), 2.236 (s, 3H), 1.754-1.770 (d, 3H, J=6.4), 0.844 (m, 1H), 0.589-0.606 (d, 2H, J=6.8), 0.487 (m, 2H).

Compound 292, 1-((1R or S,2R or S)-1-cyclopropyl-1-methoxypropan-2-yl)-N-((4-methoxy-6-methyl-2-oxo-1,2-dihydropyridin-3-yl)methyl)-2-methyl-1H-pyrrolo[2,3-b]pyridine-3-carboxamide: LCMS (M+H+) m/z: calcd 438.23. found 439.2. 1H NMR (400 MHz, CDCl₃): δ 8.124-8.175 (m, 2H), 7.500 (t, 1H), 6.976-7.008 (m, 1H), 5.939 (s, 1H), 5.625-4.655 (t, 2H), 4.355-4.490 (m, 1H), 3.907 (s, 3H), 3.787-3.813 (m, 1H), 2.879 (s, 3H), 2.801 (s, 3H) 2.232 (s, 3H), 1.754-1.771 (d, 3H, J=6.8), 0.840-0.866 (m, 2H) 0.589-0.608 (d, 2H, J=7.6), 0.487 (m, 2H).

Example 67

Synthesis of (±)-N-((4,6-dimethyl-2-oxo-1,2-dihydropyridin-3-yl)methyl)-2-methyl-1-(1-phenylethyl)-1H-pyrrolo[2,3-c]pyridine-3-carboxamide (Compound 203)

Step 1: 1-(3-methoxyphenyl)ethanol

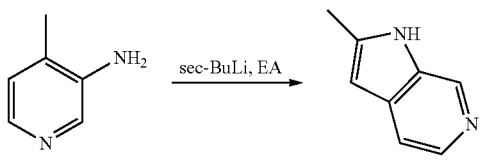

To a stirred solution of 3-Amino-4-picoline (7 g, 64.8 mmol) in anhydrous THF (200 mL), sec-BuLi (150 mL, 1.3M in cyclohexane, 194 mmol) was added dropwise over 20 minutes at −78° C. The solution was warmed to room temperature and stirred at 3 hours. Ethyl acetate (2.3 g, 25.9 mmol) was added dropwise into the reaction at −78° C. and the mixture was stirred at the same temperature for 2 hours. Methanol (50 mL) was added dropwise into the reaction over 10 minutes. The mixture was warmed to room temperature and stirred for 1 hour. A half-saturated NH4Cl (250 mL) was added. The mixture was extracted with EA. The combined organic layers were washed with brine, dried and concentrated to afford the crude product. The crude product was purified by silica gel chromatography (petroleum ether/ethyl acetate=10:1) to afford 2-methyl-1H-pyrrolo[2,3-c]pyridine (2.5 g, 73.5%).

Step 2: 2,2,2-trichloro-1-(2-methyl-1H-pyrrolo[2,3-c]pyridin-3-yl)ethanone

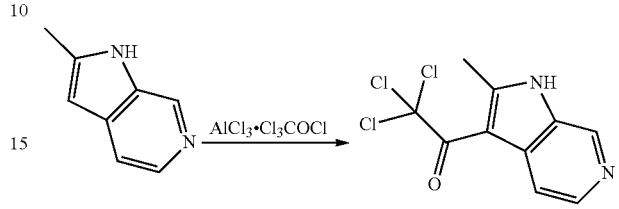

To a stirred solution of 2-methyl-1H-pyrrolo[2,3-c]pyridine (2.5 g, 18.9 mmol) and aluminum chloride (5 g, 37.8 mmol) in DCM (100 mL), trichloroacetylchloride (4.1 g, 22.7 mmol) was added dropwise into the reaction over 0.5 hours at room temperature. After stirring 2 hours, the reaction was cooled to 0° C. and was quenched with water (100 mL). The resulting precipitate was isolated by filtration to afford 2,2,2-trichloro-1-(2-methyl-1H-pyrrolo[2,3-c]pyridin-3-yl)ethanone which was used for next step without further purification. Assumed 100% yield. (5.24 g).

Step 3: Methyl 2-methyl-1H-pyrrolo[2,3-c]pyridine-3-carboxylate

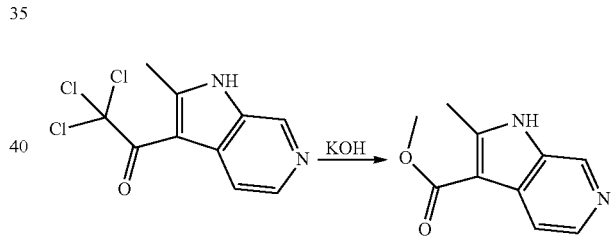

A mixture of 2,2,2-trichloro-1-(2-methyl-1H-pyrrolo[2,3-c]pyridin-3-yl)ethanone (5.24 g, 18.9 mmol) and KOH (1.2 g, 20.9 mmol) in MeOH (100 mL) was stirred at room temperature for 16 hour. The reaction mixture was concentrated to remove MeOH, the residue was partitioned between EA and Water. The organic layer was washed with brine, dried and concentrated to afford methyl 2-methyl-1H-pyrrolo[2,3-c]pyridine-3-carboxylate (3 g, 83%).

Step 4: Methyl methyl 2-methyl-1-(1-phenylethyl)-1H-pyrrolo[2,3-c]pyridine-3-carboxylate

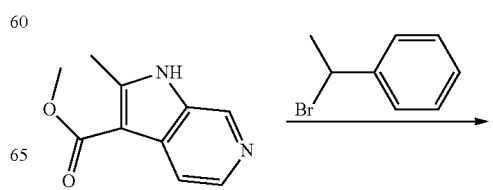

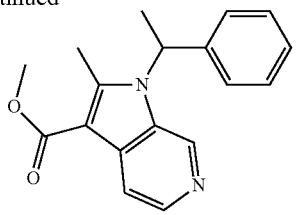

A mixture of methyl 2-methyl-1H-pyrrolo[2,3-c]pyridine-3-carboxylate (550 mg, 2.89 mmol) and sodium hydride (200 mg, 4.34 mmol) in N,N-dimethylformamide (3.0 mL) was stirred at room temperature for 0.5 hour, and then (1-bromoethyl)benzene (589 mg, 3.18 mmol) was added. The mixture was stirred at room temperature for 3 hours. The reaction mixture was poured into saturated NH$_4$Cl and extracted with ethyl acetate. Organic layers were combined and concentrated to give a residue. The residue was purified by chromatography (petroleum ether/ethyl acetate=5:1) to give methyl 2-methyl-1-(1-phenylethyl)-1H-pyrrolo[2,3-c]pyridine-3-carboxylate (800 mg, 94%).

Step 5: 2-methyl-1-(1-phenylethyl)-1H-pyrrolo[2,3-c]pyridine-3-carboxylic acid

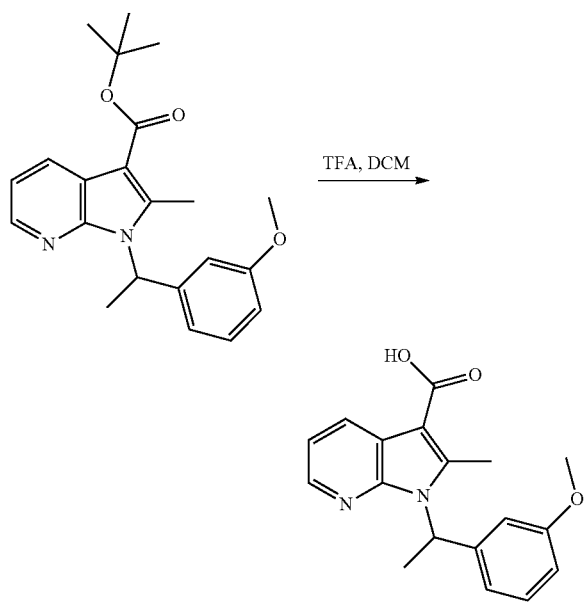

To a mixture of methyl 2-methyl-1-(1-phenylethyl)-1H-pyrrolo[2,3-c]pyridine-3-carboxylate (800 mg, 2.72 mmol) and KOH (1.5 g, 27.2 mmol) in (15 mL) and water (5 mL) was refluxed for 2 hours. The mixture was adjust PH to 2 by 10% HCl and extracted with EA. The combined organic layers were washed with brine, dried and concentrated to afford the crude product. The crude product was used into the next step without more purification. 100% yield. (760 mg).

Step 6: (±)-N-((4,6-dimethyl-2-oxo-1,2-dihydropyridin-3-yl)methyl)-2-methyl-1-(1-phenylethyl)-1H-pyrrolo[2,3-c]pyridine-3-carboxamide (Compound 203)

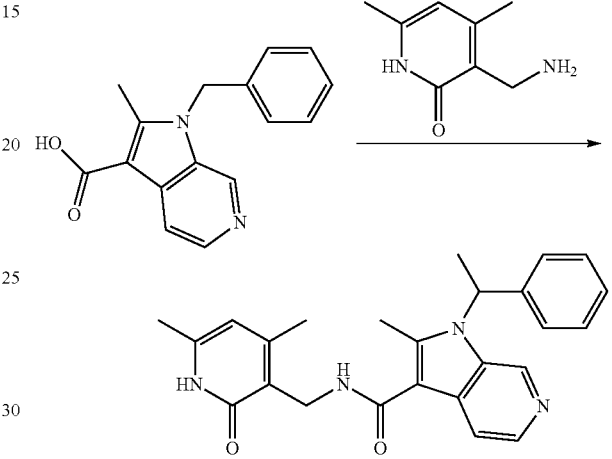

A mixture of 2-methyl-1-(1-phenylethyl)-1H-pyrrolo[2,3-c]pyridine-3-carboxylic acid (280 mg, 1.0 mmol) was added HATU (456 mg, 1.2 mmol), TEA (1 g, 10 mmol) and 3-(aminomethyl)-4,6-dimethylpyridin-2(1H)-one (182 mg, 1.2 mmol) in anhydrous dichloromethane (30 mL) was stirred at room temperature for 16 hours. To the reaction mixture was added water (10 mL), extracted with dichloromethane (30 mL×2). The organic layers were combined and concentrated to give a residue. The residue was recrystallized from MeCN to afford compound N-((4,6-dimethyl-2-oxo-1,2-dihydropyridin-3-yl)methyl)-2-methyl-1-(1-phenylethyl)-1H-pyrrolo[2,3-c]pyridine-3-carboxamide as an off-white solid (80 mg, 21.6%). LRMS (M+H$^+$) m/z: calcd 414.21. found 414. $^1$H NMR (400 MHz, Methanol-d4) δ: 8.84 (s, 1H), 8.16 (d, J=7.6 Hz, 1H), 8.03 (d, J=6.8 Hz, 1H), 7.44-7.37 (m, 5H), 6.09 (s, 1H), 6.01-5.99 (m, 1H), 4.49 (s, 2H), 2.73 (s, 3H), 2.38 (s, 3H), 2.22 (s, 3H), 2.06 (d, J=7.2 Hz, 3H).

The compounds shown in the following table were prepared according to the general procedure outlined in this example using the appropriate starting materials and modifications. Structures are shown in FIG. 1.

| Compound | Name | NMR | m/z |
|---|---|---|---|
| 255 | (±)-N-((4-ethoxy-6-methyl-2-oxo-1,2-dihydropyridin-3-yl)methyl)-2-methyl-1-(1-phenylethyl)-1H-pyrrolo[2,3-c]pyridine-3-carboxamide | NMR (400 MHz, CDCl$_3$) δ: 8.34 (s, 1H), 8.11-8.34 (d, J = 5.6 Hz, 1H), 7.75-7.82 (m, 2H), 7.26-7.32 (m, 2H), 7.13-7.16 (d, J = 7.2 Hz, 2H), 5.85-5.90 (m, 2H), 4.68-4.70 (m, 2H), 4.10-4.16 (m, 2H), 2.80 (s, 3H), 2.14 (s, 3H), 1.96-1.99 (d, J = 7.2 Hz, 3H), 1.44-1.48 (m, 3H). | 445 |

| Compound | Name | NMR | m/z |
|---|---|---|---|
| 240 | (±)-N-((4,6-dimethyl-2-oxo-1,2-dihydropyridin-3-yl)methyl)-1-(1-methoxypropan-2-yl)-2-methyl-1H-pyrrolo[2,3-c]pyridine-3-carboxamide | (400 MHz, CHLOROFORM-d) δ ppm 1.63 (br. s., 3 H) 2.21 (s, 3 H) 2.41 (s, 3 H) 2.73 (s, 3 H) 3.24 (s, 3 H) 3.72 (dd, J = 9.81, 5.40 Hz, 1 H) 3.80-3.88 (m, 1 H) 4.60 (d, J = 5.95 Hz, 2 H) 4.71 (dd, J = 13.23, 7.06 Hz, 1 H) 5.92 (s, 1 H) 7.31 (d, J = 5.73 Hz, 1 H) 7.38 (br. s., 1 H) 8.26 (d, J = 5.29 Hz, 1 H) 9.09 (br. s., 1 H) 11.07 (br. s., 1 H) | 383 |
| 243 | (±)-N-((4-methoxy-6-methyl-2-oxo-1,2-dihydropyridin-3-yl)methyl)-2-methyl-1-(1-phenylethyl)-1H-pyrrolo[2,3-c]pyridine-3-carboxamide | (400 MHz, CHLOROFORM-d) δ ppm 1.62 (br. s., 3 H) 2.26 (s, 3 H) 2.75 (s, 3 H) 3.25 (s, 3 H) 3.72 (dd, J = 9.81, 5.40 Hz, 1 H) 3.80-3.87 (m, 1 H) 3.90 (s, 3 H) 4.65 (d, J = 5.29 Hz, 2 H) 4.71 (dd, J = 13.78, 6.95 Hz, 1 H) 5.93 (s, 1 H) 7.32 (br. s., 1 H) 7.50 (br. s., 1 H) 8.25 (br. s., 1 H) 9.11 (br. s., 1 H) | 431 |

Step 7: Chiral separation of N-((4,6-dimethyl-2-oxo-1,2-dihydropyridin-3-yl)methyl)-2-methyl-1-(1-phenylethyl)-1H-pyrrolo[2,3-c]pyridine-3-carboxamide Isomers (Compounds 247 and 248)

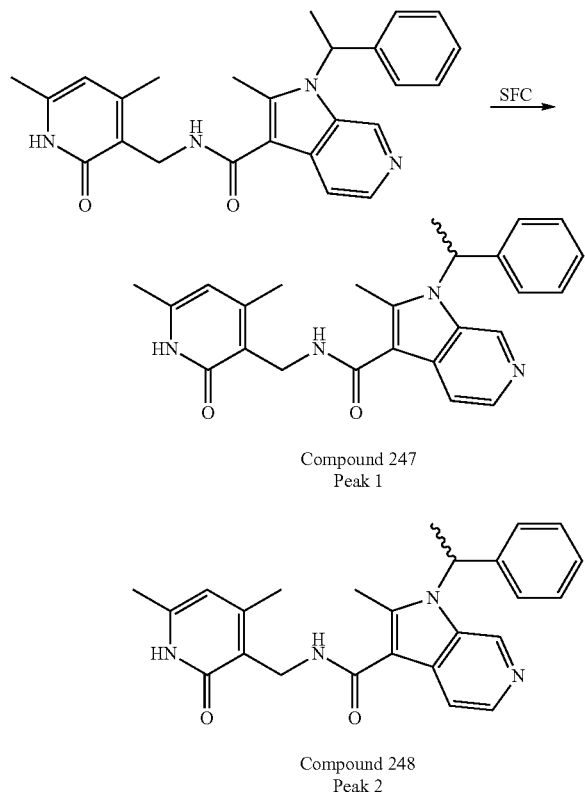

Compound 247
Peak 1

Compound 248
Peak 2

Compound 203, 45 mg was separated by SFC (Column: Chiralpak AD (250*30 mm, 5 um); Flow rate: 50 mL/min: Mobile: A, phase: 35% IPA+NH$_3$.H$_2$O, B, 65% CO$_2$; Wavelength: 220 nm) to give (R or S)-N-((4,6-dimethyl-2-oxo-1,2-dihydropyridin-3-yl)methyl)-2-methyl-N-(1-phenylethyl)-1H-pyrrolo[2,3-c]pyridine-3-carboxamide (Peak 1; Compound 247; 12 mg, purity 98%) and (R or S)-N-((4,6-dimethyl-2-oxo-1,2-dihydropyridin-3-yl)methyl)-2-methyl-1-(1-phenylethyl)-1H-pyrrolo[2,3-c]pyridine-3-carboxamide (Peak 2; Compound 248; 11 mg, purity 98%).

Compound 247, (R or S)-N-((4,6-dimethyl-2-oxo-1,2-dihydropyridin-3-yl)methyl)-2-methyl-1-(1-phenylethyl)-1H-pyrrolo[2,3-c]pyridine-3-carboxamide: LRMS (M+H+) m/z: calcd 414.21. found 414. 1H NMR (400 MHz, CD3OD): δ 8.61 (s, 1H), 8.25-8.21 (q, J=6.8 Hz, 2H), 7.41-7.36 (m, 3H), 7.35-7.27 (m, 2H), 6.60 (s, 1H), 6.28-6.23 (q, J=6.8 Hz, 1H), 4.61 (s, 2H), 2.81 (s, 3H), 2.53 (s, 3H), 2.38 (s, 3H), 2.05-2.03 (d, J=7.2 Hz, 3H).

Compound 248, (R or S)-N-((4,6-dimethyl-2-oxo-1,2-dihydropyridin-3-yl)methyl)-2-methyl-1-(1-phenylethyl)-1H-pyrrolo[2,3-c]pyridine-3-carboxamide: LRMS (M+H$^+$) m/z: calcd 414.21. found 414. 1H NMR (400 MHz, CD3OD): δ 8.63 (bs, 1H), 8.27-8.22 (q, J=6.4 Hz, 2H), 7.42-7.37 (m, 3H), 7.36-7.28 (m, 2H), 6.80 (s, 1H), 6.29-6.24 (q, =6.8 Hz, 1H), 4.65 (s, 2H), 2.82 (s, 3H), 2.59 (s, 3H), 2.45 (s, 3H), 2.06-2.04 (d, J=7.2 Hz, 3H).

The compounds shown in the following table were prepared according to the general procedure outlined in this example using the appropriate starting materials and modifications. Structures are shown in FIG. 1.

| Compound | Name | NMR | m/z |
|---|---|---|---|
| 258 | (R or S)-N-((4-methoxy-6-methyl-2-oxo-1,2-dihydropyridin-3-yl)methyl)-2-methyl-1-(1-phenylethyl)-1H-pyrrolo[2,3-c]pyridine-3-carboxamide PEAK 1 | (400 MHz, CDCl$_3$) δ 12.2-12.1 (br, 1H), 8.29-8.27 (d, J = 5.2 Hz, 1H), 8.07-8.06 (d, J = 5.2 Hz, 1H), 7.70-7.62 (m, 2H), 7.26-7.21 (m, 3H), 7.08-7.06 (d, J = 7.2 Hz, 2H), 5.86 (s, 1H), 5.82-5.76 (q, J = 7.2 Hz, 1H), 4.61-4.60 (d, J = 4.0 Hz, 2H), 3.83 (s, 3H), 2.73 (s, 3H), 2.14 (s, 3H), 1.91-1.89 (d, J = 7.2 Hz, 3H) | 431 |

| Compound | Name | NMR | m/z |
|---|---|---|---|
| 259 | (R or S)-N-((4-methoxy-6-methyl-2-oxo-1,2-dihydropyridin-3-yl)methyl)-2-methyl-1-(1-phenylethyl)-1H-pyrrolo[2,3-c]pyridine-3-carboxamide PEAK 2 | (400 MHz, CDCl$_3$) δ 8.28-8.27 (d, J = 5.2 Hz, 1H), 8.07-8.06 (d, J = 5.2 Hz, 1H), 7.70-7.62 (m, 2H), 7.26-7.21 (m, 3H), 7.08-7.06 (d, J = 7.2 Hz, 2H), 5.86 (s, 1H), 5.82-5.76 (q, J = 7.2 Hz, 1H), 4.61-4.60 (dd, J$_1$ = 1.6 Hz J$_2$ = 4.0 Hz, 2H), 3.83 (s, 3H), 2.73 (s, 3H), 2.14-2.13 (d, J = 4.0 Hz, 3H), 1.91-1.89 (d, J = 6.8 Hz, 3H) | 431 |

Example 68

Synthesis of 3-(aminomethyl)-4-methoxy-6-methylpyridin-2-ol

The title intermediate was synthesized according to the following Scheme:

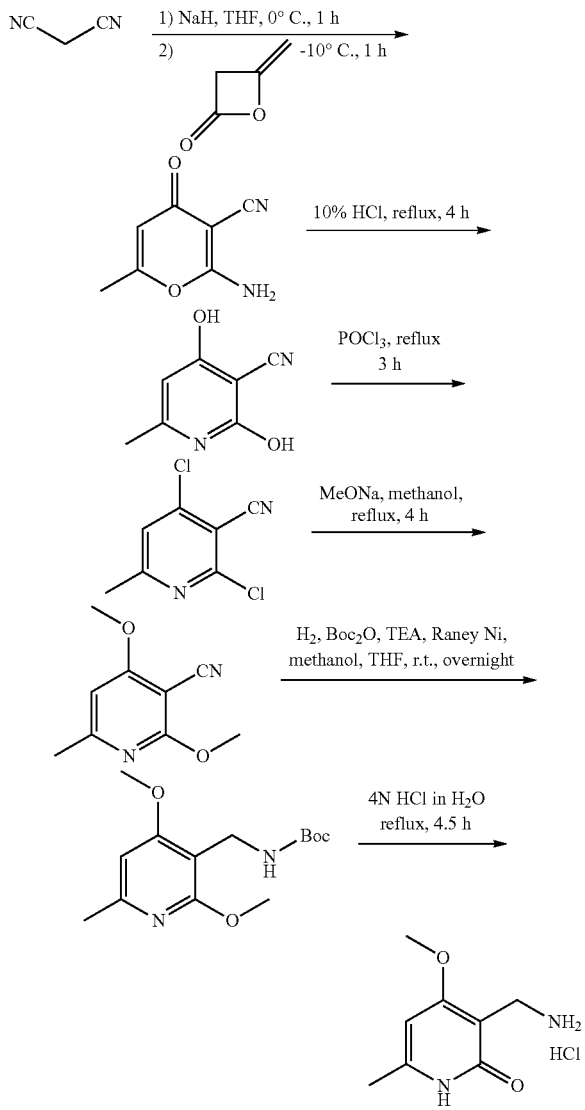

Step 1: 2-amino-6-methyl-4-oxo-4H-pyran-3-carbonitrile: Malononitrile (110 g, 1.67 mol) was dissolved in dry THF (1000 ml) and cooled in ice-water bath. NaH (60% in mineral oil, 67 g, 1.67 mol) was added portionwise below 10° C. very carefully while the reaction flash was evacuted with N$_2$ flow. After addition completed, the mixture was stirred at 0° C. for 30 min. Then 4-methylencoxetan-2-one (140 g, 1.67 mol) was added dropwise below 0° C. After addition completed, the mixture was stirred at −10° C. for 1 h. The reaction mixture was neutralized by 4 N HCl and concentrated under vacuum to give compound 2-amino-6-methyl-4-oxo-4H-pyran-3-carbonitrile as an orange oil. The crude product was used to next step without further purification.

Step 2: 2,4-dihydroxy-6-methylnicotinonitrile: 2-amino-6-methyl-4-oxo-4H-pyran-3-carbonitrile from above was dissolved in 4 N HCl/H$_2$O (2500 ml) and refluxed for 5 h with stirring strongly. After cooled to r.t., the precipitate was filtered, washed with H$_2$O (500 ml), ethanol (500 ml) and MTBE (200 ml) and dried under high vacuum. 2,4-dihydroxy-6-methylnicotinonitrile was obtained as a yellow powder. (165 g, yield 66%).

Step 3; 2,4-dichloro-6-methylnicotinonitrile: 2,4-dihydroxy-6-methylnicotinonitrile (40 g, 266.4 mmol) was dissolved in POCl$_3$ (120 ml) and added by DMF (4 drops). The mixture was heated for 3 h. Then the mixture was concentrated under vacuum. The residue was dissolved in EtOAc (2 L) and neutralized by saturated NaHCO$_3$. Then the mixture was filtered through a Celite pad to remove the dark flocculating. The organic layer was separated, dried over Na$_2$SO$_4$ and concentrated under vacuum to give 2,4-dichloro-6-methylnicotinonitrile as an off-white solid. (45 g, yield 90%).

Step 4: 2,4-dimethoxy-6-methylnicotinonitrile: 2,4-dichloro-6-methylnicotinonitrile (45 g, 240 mmol) was dissolved in CH$_3$OH (300 ml). NaOMe (30% in MeOH, 100 ml, 1680 mmol) was added. The mixture was refluxed for 4 h. After cooled to r.t., the reaction mixture was neutralized by HOAc. The solvent was removed under vacuum and the residue was washed with H$_2$O (300 ml) and MTBE (100 ml). The resulting solid was coevaporated with dry THF (300 ml) to give 2,4-dimethoxy-6-methylnicotinonitrile as a dark-yellow solid. (40 g, yield 95%).

Step 5: tert-butyl((2,4-dimethoxy-6-methylpyridin-3-yl)methyl)carbamate: 2,4-dimethoxy-6-methylnicotinonitrile (10.0 g, 56 mmol) was dissolved in the mixture of THF (260 ml) and methanol (260 ml). Raney Ni (wet, 10.0 g), TEA (29.0 g, 280 mmol) and Boc$_2$O (36.8 g, 168 mmol) were added. Then the mixture was hydrogenated (1 atom) at r.t. overnight. After reaction completed, the reaction mixture was filtered through a Celite pad. 6 parallel reactions were combined and concentrated under vacuum to give tert-butyl((2,4-dimethoxy-6-methylpyridin-3-yl)methyl)carbamate as a yellow solid. (84 g, yield 88%).

Step 6: 3-(aminomethyl)-4-methoxy-6-methylpyridin-2-ol: tert-butyl((2,4-dimethoxy-6-methylpyridin-3-yl)methyl)carbamate (83 g, 294 mmol) was dissolved in 4 N HCl/H$_2$O (830 ml). Then the mixture was refluxed for 4.5 h. (The reaction mixture was monitored by MS spectrum to make sure the methyl group at 2-position de-protect completely.) After the reaction completed, the mixture was concentrated under vacuum to give a brown oil. The oil was suspended in EtOH (300 ml) for 15 min to give a yellow precipitate. The precipitate was filtered, washed with ethanol (100 ml) and MTBE (100 ml) and dried under high vacuum to give 38 g of fraction 1 3-(aminomethyl)-4-methoxy-6-methylpyridin-2-ol (Purity 98% by LCMS, yield 63%) as a yellow powder. In the meantime, the filtration from fraction 1 was concentrated under vacuum and the residue was solidified by ethanol (100 ml). The precipitate was filtered, washed with ethanol (100 ml) and MTBE (100 ml) and dried under high vacuum to give 20 g of fraction 2 3-(aminomethyl)-4-methoxy-6-methylpyridin-2-ol (Purity 94% by LCMS, yield 33%) as a yellow powder.

Example 69

Synthesis of 3-(aminomethyl)-4-ethyl-6-methylpyridin-2(1H)-one

The title intermediate was synthesized according to the following Scheme:

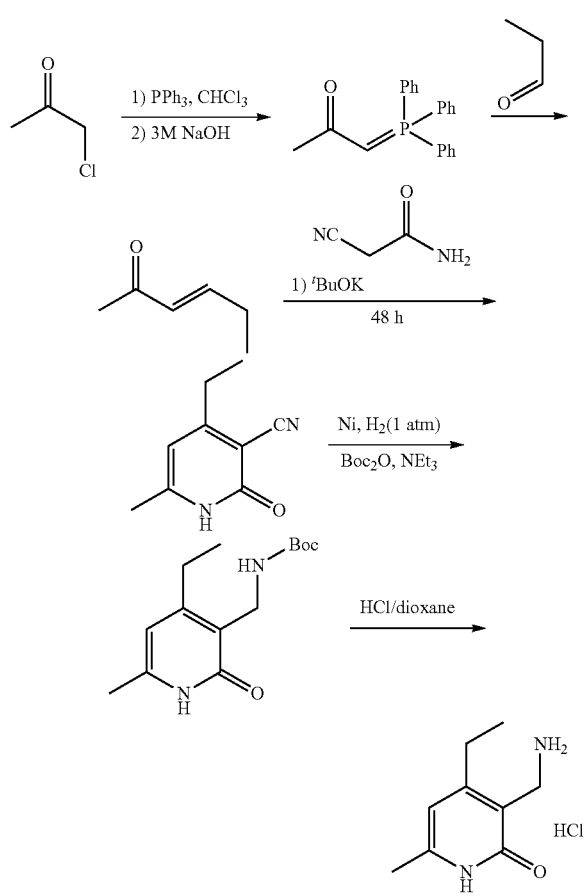

Step 1: 1-(triphenylphosphoranylidene)propan-2-one: A solution of 1-chloropropan-2-one (50 g, 540.4 mmol) in chloroform (150 mL) was added dropwise to a solution of triphenylphosphine (141.72 g, 540.4 mmol) in chloroform (150 mL) under nitrogen. The mixture was stirred at 70° C. for 12 hr, and the resulting phosphonium salt was filtered. The precipitate was washed with ethyl acetate and dried under vacuum. The dried phosphonium salt was suspended in a mixture of water (250 mL) and methanol (250 mL), and the mixture was stirred for 1 hr. Aqueous sodium hydroxide (2.00 M) was added to the mixture until a pH between 7 and 8 was reached. The mixture was then stirred vigorously for 1 hr. The phosphorane precipitate was filtered and washed with water. After drying in vacuum, the phosphorane was recrystallized from ethyl acetate and dried under vacuum to afford 1-(triphenylphosphoranylidene)propan-2-one (40.00 g, 23.3%) as a white solid.

Step 2: hex-3-en-2-one: To a solution of 1-(triphenylphosphoranylidene)propan-2-one (40 g, 125.65 mmol) in dichloromethane (150 mL) was added propionaldehyde (45.83 g, 789.07 mmol) at 24° C. The reaction mixture was then stirred at 24° C. for 12 hr. After concentration, the residue was then distilled under vacuum (73° C./−0.09 MPa) to give hex-3-en-2-one (5.36 g, 43.5%).

Step 3: 4-ethyl-6-methyl-2-oxo-1,2-dihydropyridine-3-carbonitrile: To a stirred solution of potassium 2-methylpropan-2-olate (4.92 g, 43.81 mmol) and 2-cyanoacetamide (4.05 g, 48.19 mmol) in (methylsulfinyl)methane (60 mL) was added hex-3-en-2-one (4.30 g, 43.81 mmol) under nitrogen atmosphere at 25° C. The reaction mixture was then stirred at 25° C. for 30 min, and then additional potassium 2-methylpropan-2-olate (14.75 g, 131.44 mmol) was added. Nitrogen gas was displaced by oxygen gas and the mixture was stirred at 25° C. for 48 hr. The mixture was diluted with 4 volumes water (240 mL), and then 5 volumes of 4 N HCl (300 mL), which were added slowly. The reaction mixture was filtered, washed with water, and dried to give 4-ethyl-6-methyl-2-oxo-1,2-dihydropyridine-3-carbonitrile (1.30 g, 18.3%) as a gray solid.

Step 4: tert-butyl((4-ethyl-6-methyl-2-oxo-1,2-dihydropyridin-3-yl)methyl)carbamate: To a solution of Raney Ni (0.8 g) in methanol/tetrahydrofuran (72 mL, 1/1) was added 4-ethyl-6-methyl-2-oxo-1,2-dihydropyridine-3-carbonitrile (1.20 g, 7.40 mmol), triethylamine (1.50 g, 14.80 mmol) and di-tert-butyl dicarbonate (1.94 g, 8.88 mmol). The reaction mixture was stirred at 23° C. under hydrogen pressure (1 atm) for 20 hr. The reaction mixture was filtered through Celite. The filtrate was diluted with ethyl acetate, washed with brine and dried over anhydrous sodium sulfate. The solvent was then removed under vacuum to afford crude tert-butyl((4-ethyl-6-methyl-2-oxo-1,2-dihydropyridin-3-yl)methyl)carbamate (1.46 g, 71.2%) as a white solid for the next step.

Step 5: 3-(aminomethyl)-4-ethyl-6-methylpyridin-2(1H)-one: Tert-butyl((4-ethyl-6-methyl-2-oxo-1,2-dihydropyridin-3-yl)methyl)carbamate (1.00 g, 3.75 mmol) was dissolved in a solution of hydrogen chloride in 1,4-dioxane (20 mL). The mixture was stirred for 2 hr. The reaction mixture was filtered. The residue was washed with dichloromethane, dried to afford 3-(aminomethyl)-4-ethyl-6-methylpyridin-2 (1H)-one hydrochloride (593 mg, 77.9%) as a light yellow solid. LRMS (M+H+) m/z: calcd 166.11. found 167.1. $^1$H NMR (400 MHz, D$_2$O): δ ppm 6.31 (s, 1 H), 4.06 (s, 2 H), 2.57 (q, J=7.86 Hz, 2 H), 2.25 (s, 3 H), 1.10 (t, J=7.53 Hz, 3 H).

Example 70

Synthesis of 3-(aminomethyl)-4-(difluoromethoxy)-6-methylpyridin-2(1H)-one: The title intermediate was synthesized according to the following Scheme:

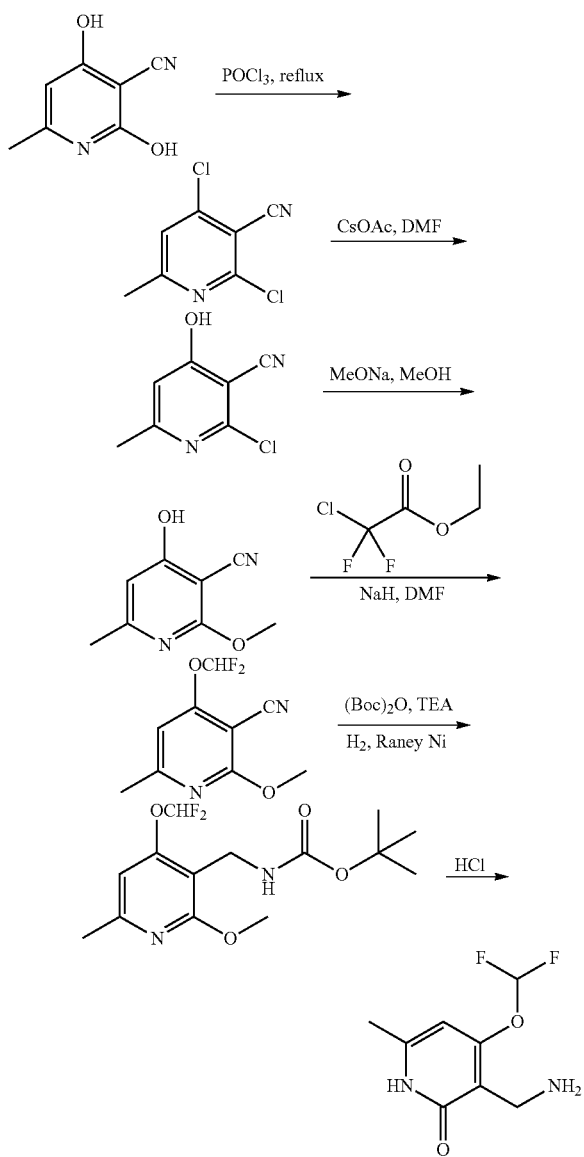

Step 1: 2,4-dichloro-6-methylnicotinonitrile: To a solution of 2,4-dihydroxy-6-methylnicotinonitrile (20.0 g, 133.0 mmol) in POCl$_3$ (150 mL) was stirred at 120° C. for 2 hours under N$_2$. It was partitioned between water (500 mL) and ethyl acetate (500 mL), the organic layer was dried and concentrated to afford 2,4-dichloro-6-methylnicotinonitrile (15.3 g brown solid, 61.4% yield).

Step 2: 2-chloro-4-hydroxy-6-methylnicotinonitrile: A mixture of 2,4-dichloro-6-methylnicotinonitrile (12.0 g, 64.2 mmol), CsOAc (37.0 g, 193.0 mmol) in N,N-dimethylformamide (50 mL) was stirred at 80° C. overnight under N$_2$. The mixture was partitioned between water (800 mL) and ethyl acetate (800 mL), the organic layer was dried and concentrated to afford 2-chloro-4-hydroxy-6-methylnicotinonitrile (9.0 g brown solid, 84.1% yield).

Step 3: 4-hydroxy-2-methoxy-6-methylnicotinonitrile: A mixture of 2-chloro-4-hydroxy-6-methylnicotinonitrile (2.0 g, 11.9 mmol), sodium methanolate (3.2 g, 59.5 mmol) in methanol (20 mL) was stirred at 60° C. overnight under N$_2$. The mixture was quenched with HCl (1M) to pH=2. It was partitioned between water (500 mL) and ethyl acetate (500 mL), the organic layer was dried and concentrated to afford 4-hydroxy-2-methoxy-6-methylnicotinonitrile (2.0 g brown solid, 100% yield).

Step 4: 4-(difluoromethoxy)-2-methoxy-6-methylnicotinonitrile: To a solution of 4-hydroxy-2-methoxy-6-methylnicotinonitrile (2.0 g, 12.2 mmol) in N,N-dimethylformamide (10 mL) was added sodium hydride (880 mg, 36.6 mmol) at 0° C. and the mixture was stirred for 0.5 hour, Ethyl 2-chloro-2,2-difluoroacetate (5.4 g, 39.0 mmol) was added with vigorous stirring, over the course of 20 min. The suspension was warmed to 80° C. overnight under N$_2$. The mixture was quenched into Na$_2$CO$_3$ (200 mL). It was partitioned between water (500 mL) and ethyl acetate (500 mL), the organic layer was dried and concentrated to afford the crude, which was purified by flash column (PE:EA=20:1) to afford 4-(difluoromethoxy)-2-methoxy-6-methylnicotinonitrile (550 mg yellow solid, 22.0% yield).

Step 5: tert-butyl((4-(difluoromethoxy)-2-methoxy-6-methylpyridin-3-yl)methyl)carbamate: To a solution of 4-(difluoromethoxy)-2-methoxy-6-methylnicotinonitrile (550 mg, 2.58 mmol), di-tert-butyl dicarbonate (844 mg, 3.87 mmol), Triethylamine (391 mg, 3.87 mmol) and Raney Ni (2 g) in Tetrahydrofuran (10 mL) was stirred at room temperature overnight under H$_2$. It was filtered and the filtrate was concentrated to afford tert-butyl((4-(difluoromethoxy)-2-methoxy-6-methylpyridin-3-yl)methyl)carbamate. (830 mg yellow solid, 100% yield).

Step 6: 3-(aminomethyl)-4-(difluoromethoxy)-6-methylpyridin-2(1H)-one: To a solution of tert-butyl((4-(difluoromethoxy)-2-methoxy-6-methylpyridin-3-yl)methyl)carbamate (830 mg, 2.61 mmol) in HCl (10 mL) was stirred at 100° C. for 1.5 hours under N$_2$. The mixture was concentrated to afford 3-(aminomethyl)-4-(difluoromethoxy)-6-methylpyridin-2(1H)-one (430 mg, yellow solid, 80.8% yield). LCMS (M+H+) m/z: calcd 204.07. found 205.0. $^1$H NMR (400 MHz, DMSO): δ 7.621-7.258 (t, 1H), 6.26 (s, 1H), 3.837-3.822 (d, J=6.0 Hz,2H)

Example 71

Synthesis of 3-(aminomethyl)-4,6-dimethylpyridin-2(1H)-one: The title intermediate was synthesized according to the following Scheme:

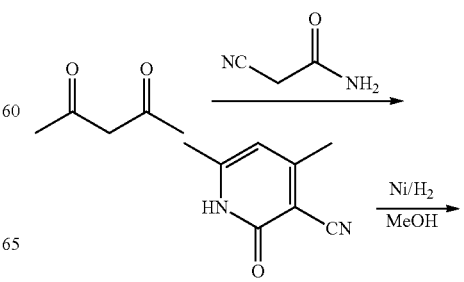

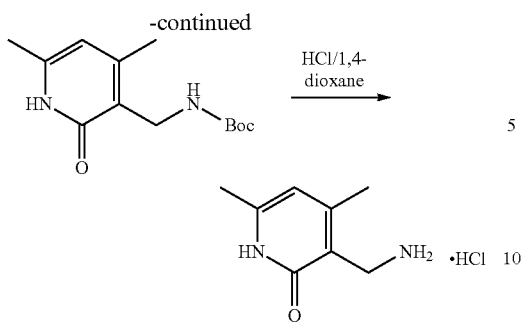

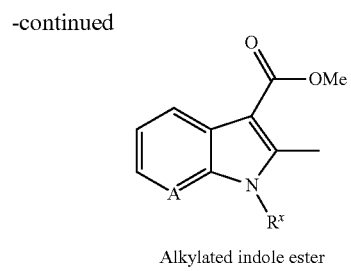

Alkylated indole ester

To a cooled (0° C.) solution of NH indole ester (1 equivalent) in N,N-dimethylformamide (volume to make concentration 0.4M) was added sodium hydride (60% w/w, 1.1 equivalents relative to indole). The resultant mixture was stirred for 15 minutes. Then RX (2 equivalents) was added and the reaction was allowed to warm to room temperature. The reaction was maintained at ambient temperature for 12 hours. The reaction mixture was poured into saturated ammonium chloride solution (100 mL) with stirring. The mixture was extracted with ethyl acetate (200 mL×2) and the combined organic phase was washed with brine, dried over magnesium sulfate, filtered, and concentrated to give crude product which was purified by column chromatography (silica gel, petroleum ether/ethyl acetate=20:1) to afford the desired alkylated Indole ester product.

General Procedure B: Saponification of Alkylated Indole Ester

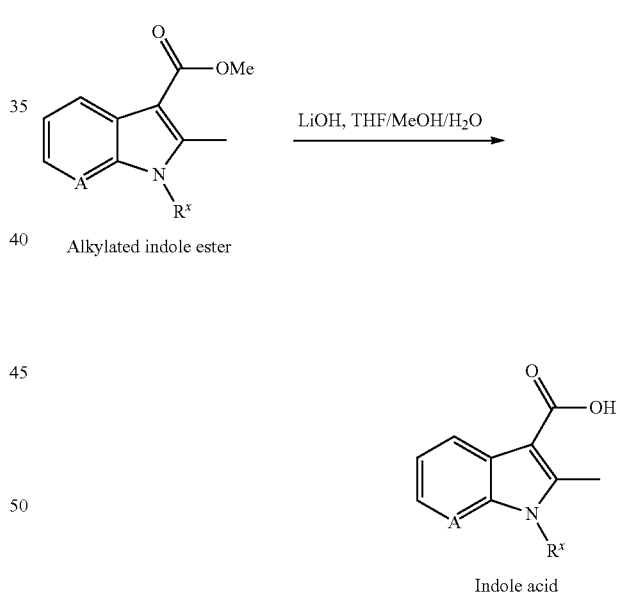

Step 1: 4,6-dimethyl-2-oxo-1,2-dihydropyridine-3-carbonitrile: To a solution of pentane-2,4-dione (100 g, 1.0 mol) in H$_2$O (2 L) were added 2-cyanoacetamide (84 g, 1.0 mol) and K$_2$CO$_3$ (13.8 g, 0.1 mol). Then the mixture was stirred at room temperature for 16 hr. The reaction solution was filtrated to give crude product. The crude was washed with water and concentrated to give 4,6-dimethyl-2-oxo-1,2-dihydropyridine-3-carbonitrile (138 g, 93%).

Step 2: tert-butyl((4,6-dimethyl-2-oxo-1,2-dihydropyridin-3-yl)methyl)carbamate: To a solution of 4,6-dimethyl-2-oxo-1,2-dihydropyridine-3-carbonitrile (40 g, 0.27 mol) in THF/CH$_3$OH (1:1, 2 L) were added Ni (40 g), Boc$_2$O (110 g, 0.5 mol) and Et$_3$N (50 g, 0.5 mol). Then the mixture was stirred in H$_2$ atmosphere at room temperature for 48 hr. The reaction solution was filtrated and concentrated to give crude product. The crude was added H$_2$O (200 mL) and extracted by DCM (600 mL*3). The organic layer was concentrated to give tert-butyl((4,6-dimethyl-2-oxo-1,2-dihydropyridin-3-yl)methyl)carbamate (40 g, 56%) for next step.

Step 3: 3-(aminomethyl)-4,6-dimethylpyridin-2(1H)-one: tert-butyl((4,6-dimethyl-2-oxo-1,2-dihydropyridin-3-yl)methyl)carbamate (40 g, 0.27 mol) was added into dioxane/HCl (1 L) and the mixture was stirred at room temperature for 4 hr. The reaction solution was filtrated and concentrated to give crude product. The crude was washed with ethyl acetate (100 mL*2) and EtOH (50 mL*1) and concentrated to give 3-(aminomethyl)-4,6-dimethylpyridin-2(1H)-one hydrochloride (15 g, 40%). LCMS (M+H+) m/z: calcd. 152.19. found 153.1. $^1$H NMR (DMSO, 400 MHz) δ 11.84 (s, 1H), 8.07 (s, 3H), 5.96 (s, 1H), 3.76-7.75 (d, J=5.6 Hz, 2H), 2.21 (s, 3H), 2.15 (s, 3H).

Example 72

General Procedures for Synthesizing Other Compounds of the Invention

General Procedure A: Indole Alkyation

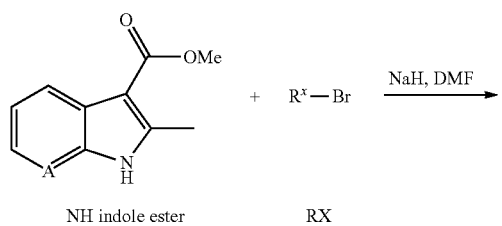

NH indole ester      RX

To a solution of alkylated Indole ester (1 equivalent) in tetrahydrofuran:methanol:water (2.5:5:1, volume to make concentration 0.05M) was added lithium hydroxide (4 equivalents). The resultant reaction mixture was stirred at 60° C. for 48 hours. The mixture was concentrated in vacuo. Then the residue was diluted with water (40 mL) and slowly acidified with 1N hydrogen chloride to pH=4-5. The mixture was extracted with ethyl acetate (100 mL×3). The combined organic layers were washed with brine, dried over magnesium sulfate, filtered and concentrated to give crude indole acid, which was used in the subsequent step without additional purification.

General Procedure C: Amide Bond Formation

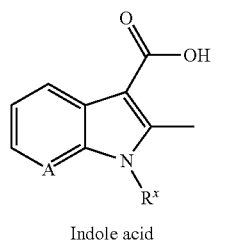

Indole acid

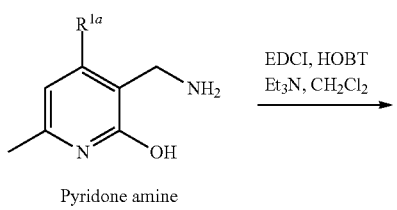

Pyridone amine

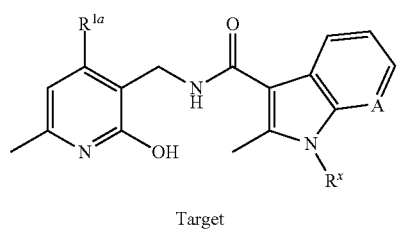

Target

To a solution of Indole acid (1 equivalent) in dichloromethane (volume to make concentration 0.05M) were added 1-hydroxybenzotriazole (1.5 equivalents), 1-(3-dimethylaminopropyl)-3-ethylcarbodiimide hydrochloride (1.5 equiv.) and triethylamine (3 equiv.). The resultant mixture was stirred at room temperature for 30 minutes. Then Pyridone amine (1.2 equiv.) was added and the resultant mixture was stirred at room temperature for 16 hours. Water (50 mL) was added to the mixture. The mixture was extracted with dichloromethane (100 mL×2). The organic layer was concentrated in vacuo to provide crude product which was purified by column chromatography (silica gel, dichloromethane/methanol=20:1) to afford the target compound.

General Procedure D: Chiral Chromatography

Separation of chiral compounds was accomplished via normal phase HPLC or SFC (supercritical carbon dioxide fluid chromatography). Separated compounds were typically >95% ee. The absolute configuration of chiral centers was not determined.

General Procedure E: Amination of Pyrrolopyrimidines

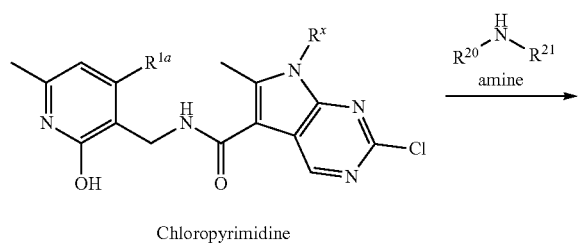

Chloropyrimidine

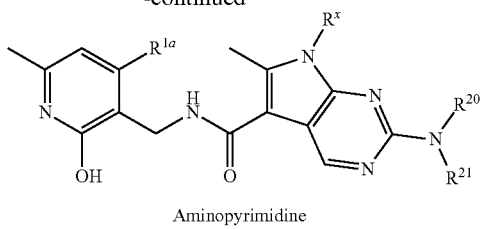

Aminopyrimidine $R^{20}$ and $R^{21}$ are independently any appropriate nitrogen substituent or $R^{20}$ and $R^{21}$ are taken together with the nitrogen atom to which they are bound to form a heterocyclic ring A solution of Chloropyrimidine (1 equiv.) in amine (volume to make concentration 0.1M) was stirred at 150° C. for 30 minutes under microwave (pressure: 12.2 bar, equipment power: 150 W). The mixture was concentrated in vacuo and purified by column chromatography (silica gel, dichloromethane/methanol=10:1) to afford the target aminopyrimidine.

General Procedure F: Suzuki Coupling of Chloropyrimidine

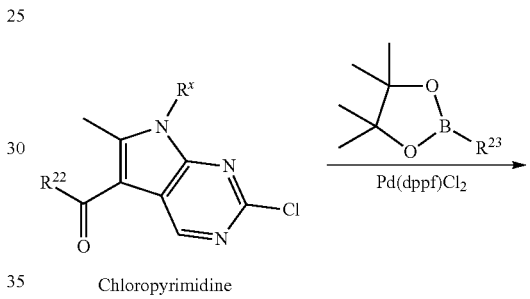

Chloropyrimidine

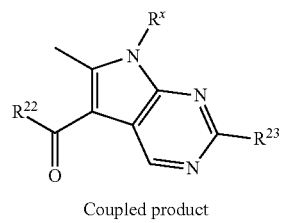

Coupled product

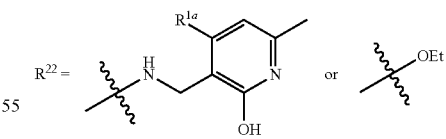

$R^{23}$ = aryl, heteroaryl, partially saturated carbocyclyl, partially satruated heterocycly, alkenyl or any moiety containing a vinyl group Chloropyrimidine (1 equiv.), boronic ester or acid (1.4 equiv.), Pd(dppf)Cl$_2$ (0.1 equiv.), K$_2$CO$_3$ (2 equiv.) were combined in 3:1 dioxane:water (volume to make concentration 0.2M), then stirred at 140° C. under microwave irradiation for 30 mins. The mixture was filtered through celite, concentrated in vacuo and purified by column chromatography to afford the target coupled product.

General Procedure G: Hydrogenation of Coupled Product

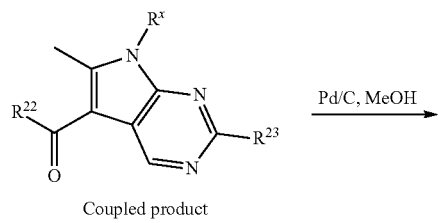

Coupled product $R^{23a}$ = hydrogenated version of $R^{23}$

Pd/C (catalytic) was added to a solution of Coupled product (1 equiv) in MeOH (volume to make concentration 0.1 M) and stirred at r.t for 4 h. The mixture was concentrated in vacuo and purified by preparative-HPLC to afford the desired product.

General Procedure H: Pd-Catalyzed Methylation of Chloropyrimidine Ethyl Ester

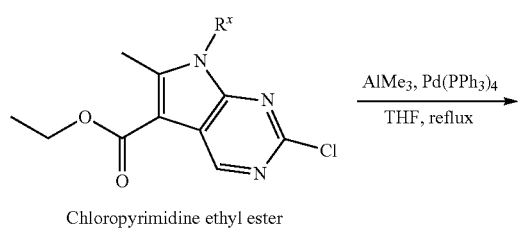

Chloropyrimidine ethyl ester

Methyl pyrimidine ethyl ester

Al(CH$_3$)$_3$ (2 equiv.) was added dropwise under N$_2$ at 20° C. through a septum to a stirred solution of (R)-ethyl 2-chloro-6-methyl-7-(1-phenylethyl)-7H-pyrrolo[2,3-d]pyrimidine-5-carboxylate (400 mg, 1.2 mmol) in 20 ml THF and Pd(PPh$_3$)$_4$ (63 mg, 0.06 mmol). The mixture was then stirred at 70-80° C. for 8 h, then cooled to RT and poured into saturated aqueous NH$_4$Cl/ice and filtered. The filtrate was washed with dichloromethane (3×), then the combined organic phases were dried (Na$_2$SO$_4$), filtered and concentrated. The material was purified by silica gel column chromatography.

General Procedure I: Hydrolysis of Nitrile to Acid

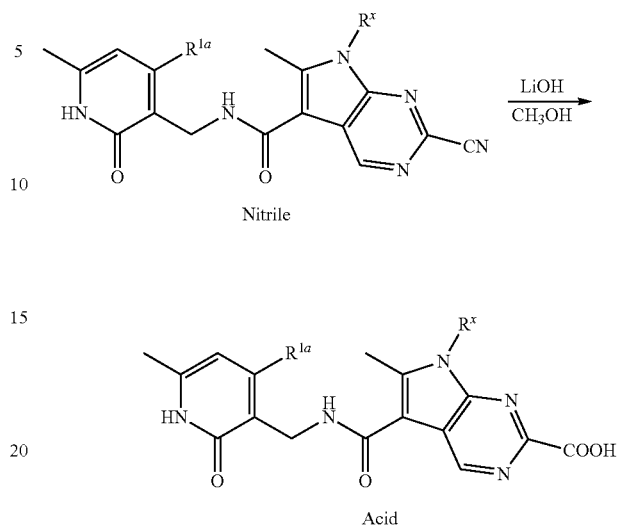

Nitrile

Acid

Lithium hydroxide anhydrate (10 equiv.) in water (2 mL) was added to Nitrile (1 equiv.) in methanol (10 mL) and the resultant mixture was stirred at room temperature for 12 hours. The mixture was evaporated, added with water (5 mL), acidified with aqueous hydrochloric acid (1M) to pH=2. The solid precipitate was filtered and dried to obtain Acid.

General Procedure J: Methyl Ester Formation

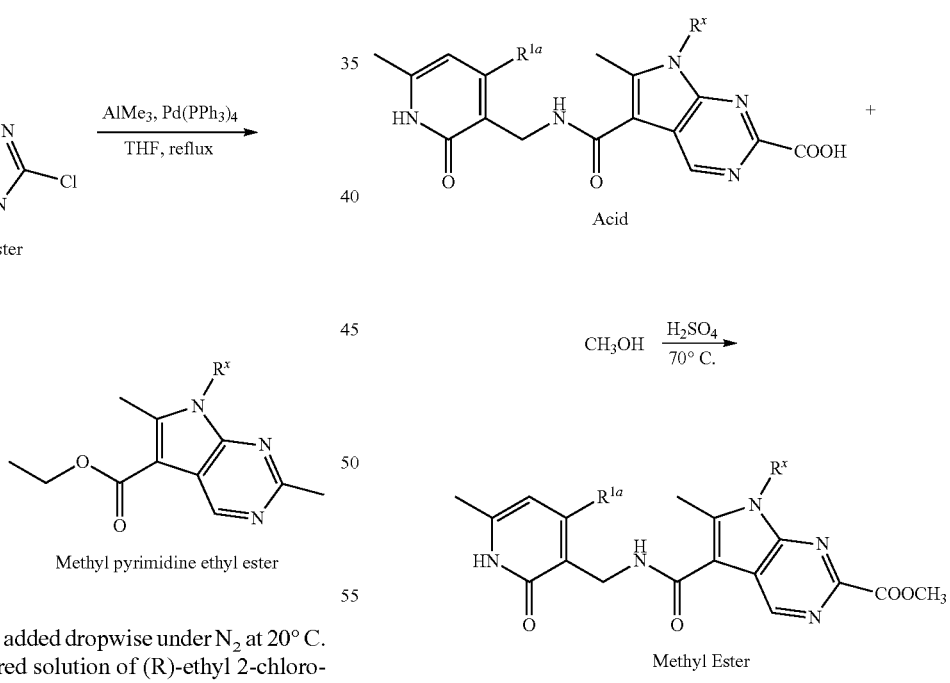

Acid

Methyl Ester

To a solution of Acid (1 equiv.) in CH$_3$OH (Volume to make concentration 0.1 M) was added with H$_2$SO$_4$ (2 equiv.) and the reaction mixture was stirred at 70° C. for 2 hours. The solution was concentrated, diluted with water (20 mL), extracted with ethyl acetate (20 mL). The organic layers were separated, combined, dried over anhydrous sodium sulfate, filtered and concentrated to give a residue Ester, which was used directly in the next reaction.

General Procedure K: Reduction of Methyl Ester to Alcohol

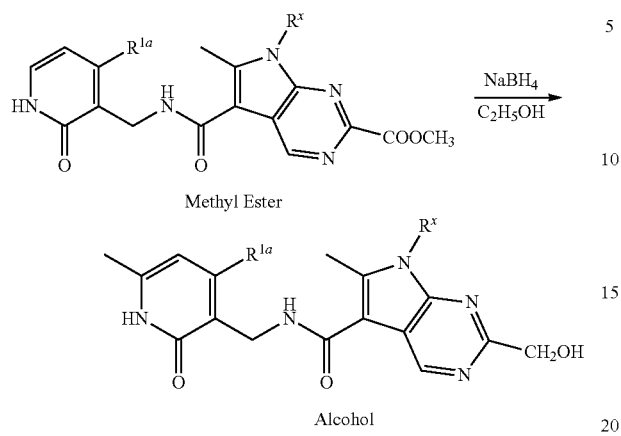

To a solution of Methyl ester (1 equiv.) in EtOH (volume to make concentration 0.1M) was added with NaBH$_4$ (10 equiv.), and the reaction mixture was stirred at 80° C. for 12 hours. After the completion of the reaction, the reaction was quenched by addition of 5 mL of saturated aqueous NH$_4$Cl solution, and extracted with EtOAc (3×). The combined organic washes were washed with H$_2$O, then dried (Na$_2$SO$_4$), filtered and concentrated. Purification by RPHPLC provided the target compound.

General Procedure L: Sulphonylation

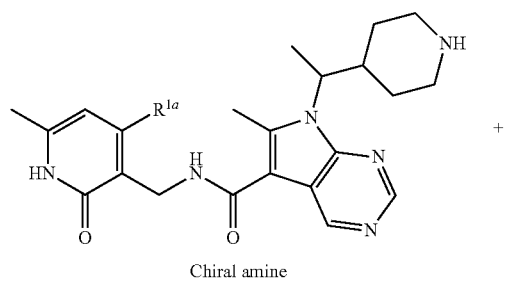

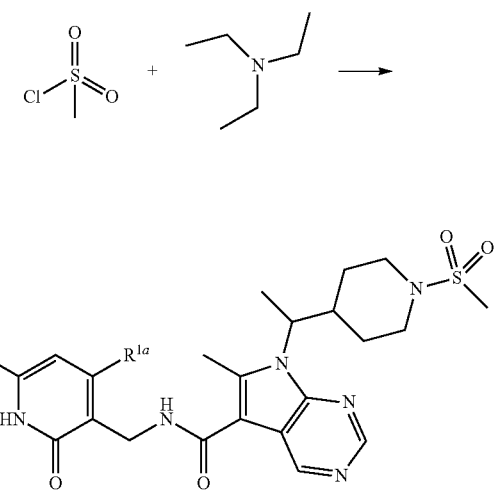

To a solution of Chiral amine (1 equiv.) in dichloromethane (volume to make concentration 0.1M) was added triethylamine (4 equiv.) at 18° C. under N$_2$. The reaction was cooled to 0° C. and methanesulfonyl chloride (1.5 equiv.) was added. The reaction was stirred at 0° C. for 1 h. Then the mixture was concentrated in vacuo and methanol and potassium carbonate were added and the reaction was stirred for another 1 h. The mixture was filtered and the crude product was purified by preparative-HPLC.

The table below lists compounds of the invention and which of the above general methods was used in their synthesis. Structures of these compounds are set forth in FIG. 1.

| Compound | General Methods Used and Notes | Name | NMR data | m/z |
|---|---|---|---|---|
| 146 | A, B, C | (±)-N-((2-hydroxy-4,6-dimethylpyridin-3-yl)methyl)-2-methyl-1-(1-phenylethyl)-1H-pyrrolo[2,3-b]pyridine-3-carboxamide | $^1$H NMR (300 MHz, CD$_3$OD): δ 8.22-8.13 (m, 2H), 7.28-7.15 (m, 6H), 6.47-6.45 (m, 1H), 6.09 (s, 1H), 4.50 (s, 2H), 2.42 (s, 3H), 2.39 (s, 3H), 2.23 (s, 3H), 2.02 (d, J = 7.2 Hz, 3H). | 414 |
| 150 | A, B, C | 1-benzoyl-N-((2-hydroxy-4,6-dimethylpyridin-3-yl)methyl)-2-methyl-1H-indole-3-carboxamide | $^1$H NMR (300 MHz, d$^6$-DMSO): δ 11.57 (s, 1H), 8.13 (q, J = 5.1 Hz, 1H), 7.74-7.70 (m, 4H), 7.60-7.58 (m, 2H), 7.20-7.00 (m, 3H), 5.88 (S, 1H), 4.32 (d, J = 5.1 Hz, 2H), 2.37 (S, 3H), 2.267 (S, 3H), 2.12 (S, 3H). | 413 |
| 149 | A, B, C | N-((4,6-dimethyl-2-oxo-1,2-dihydropyridin-3-yl)methyl)-2-methyl-1-(pyrimidin-5-ylmethyl)-1H-indole-3-carboxamide | $^1$H.NMR (300 MHz, CD$_3$OD): δ 9.03 (s, 1H), 8.53 (s, 2H), 7.80-7.78 (m, 1H), 7.39-7.36 (m, 1H), 7.19-7.16 (m, 2H), 5.56 (s, 2H), 4.55 (s, 2H), 2.62 (s, 3H), 2.42 (s, 3H), 2.45 (s, 3H). | 401 |

| Compound | General Methods Used and Notes | Name | NMR data | m/z |
|---|---|---|---|---|
| 147 | A, B, C, D | (R or S)-1-(sec-butyl)-N-((2-hydroxy-4,6-dimethylpyridin-3-yl)methyl)-2-methyl-1H-indole-3-carboxamide | $^1$H NMR (300 MHz, CD$_3$OD): δ 7.73-7.70 (m, 1H), 7.56-7.53 (m, 1H), 7.12-7.09 (m, 2H), 6.11 (s, 1H), 4.54 (s, 3H), 2.64 (s, 3H), 2.43 (s, 3H), 2.25 (s, 3H), 1.97-1.90 (m, 2H), 1.61 (d, J = 6.9 Hz, 3H), 0.73 (t, J = 7.5 Hz, 3H). | 365 |
| 148 | A, B, C, D | (R or S)-1-(sec-butyl)-N-((2-hydroxy-4,6-dimethylpyridin-3-yl)methyl)-2-methyl-1H-indole-3-carboxamide | Identical to Compound 147 | 365 |
| 167 | Starting material for other pyrrolo[2,3-d]pyrimidines | (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide | | |
| 168 | F, G | (R)-N-((2-hydroxy-4,6-dimethylpyridin-3-yl)methyl)-6-methyl-7-(1-phenylethyl)-2-(tetrahydro-2H-pyran-4-yl)-7H-pyrrolo[2,3-d]pyrimidine-5-carboxamide | $^1$H NMR (400 MHz, CD$_3$OD) δ 8.95 (s, 1H), 7.29-7.23 (m, 5H), 6.20-6.18 (m, 1H), 6.09 (s, 1 H), 4.49 (s, 2 H), 4.02-3.99 (m, 2H), 3.59-3.53 (m, 2 H), 3.17-3.01 (m, 1 H), 2.55 (s, 3H), 2.38 (s, 3H), 2.22 (s, 3H), 2.09 (d, J = 7.2 Hz, 3H), 1.96-1.88 (m, 4H). | |
| 169 | E | (R)-N-((2-hydroxy-4,6-dimethylpyridin-3-yl)methyl)-6-methyl-7-(1-phenylethyl)-2-(piperazin-1-yl)-7H-pyrrolo[2,3-d]pyrimidine-5-carboxamide | $^1$H NMR (400 MHz, CD$_3$OD) δ 8.64 (s, 1H), 7.30-7.21 (m, 5H), 6.09-6.04 (m, 2H), 4.47 (s, 2 H), 3.72-3.67 (m, 4H), 2.84-2.81 (m, 4 H), 2.44 (s, 3H), 2.37 (s, 3H), 2.23 (s, 3H), 2.01 (d, J = 7.2 Hz, 3H). | |
| 176 | H, B, C | (R)-N-((2-hydroxy-4,6-dimethylpyridin-3-yl)methyl)-2,6-dimethyl-7-(1-phenylethyl)-7H-pyrrolo[2,3-d]pyrimidine-5-carboxamide | $^1$H NMR (400 MHz, CD$_3$OD) δ 8.93 (s, 1H), 7.30-7.18 (m, 5H), 6.42-6.35 (m, 1H), 6.09 (s, 1 H), 4.48 (s, 2 H), 2.69 (s, 3H), 2.42 (s, 3 H), 2.37 (s, 3 H), 2.22 (s, 3H), 2.04 (d, J = 7.2 Hz 3H). | |
| 177 | F, G, B, C | (R)-N-((2-hydroxy-4,6-dimethylpyridin-3-yl)methyl)-2-isopropyl-6-methyl-7-(1-phenylethyl)-7H-pyrrolo[2,3-d]pyrimidine-5-carboxamide | $^1$H NMR (400 MHz, Methanol-d4) δ 8.92 (s, 1H), 7.29-7.22 (m, 5H), 6.21-6.09 (m, 2H), 4.49 (s, 2 H), 3.25-3.22 (m, 1 H), 2.53 (s, 3H), 2.38 (s, 3 H), 2.23 (d, J = 0.4, 3 H), 2.09 (d, J = 8.0, 3 H), 1.33-1.26 (m, 6H). | |
| 184 | See Intermediate 1 synthesis below | (R)-7-(sec-butyl)-2-chloro-N-((4,6-dimethyl-2-oxo-1,2-dihydropyridin-3-yl)methyl)-6-methyl-7H-pyrroto[2,3-d]pyrimidine-5-carboxamide | $^1$H NMR (400 MHz, CDCl$_3$): δ 8.94 (s, 1H), 6.85 (s, 1H), 4.62 (s, 2H) 2.72 (s, 3H), 2.59 (s, 3H), 2.43 (s, 3H), 2.35-2.41 (m, 1H), 1.94-2.04 (m, 1H), 1.65-1.67 (d, J = 7.2 Hz, 3H), 0.72-0.76 (t, 3H). | 402 |
| 188 | F | (R)-7-(sec-butyl)-N-((2-hydroxy-4,6-dimethylpyridin-3-yl)methyl)-6-methyl-2-phenyl-7H-pyrrolo[2,3-d]pyrimidine-5-carboxamide | $^1$H NMR (400 MHz, Methanol-d4) δ 9.57 (s, 1H), 9.40 (s, 1H), 8.50 (s, 2H), 7.53 (s, 3 H), 6.48 (s, 1H), 4.56-4.65 (m, 3H), 2.86 (s, 3H), 2.63 (s, 3 H) 2.55 (s, 3 H), 2.41 (s, 1 H) 2.10 (s, 1 H), 1.78 (s, 3 H), 0.83 (s, 3 H). | |
| 189 | G | (R)-7-(sec-butyl)-N-((2-hydroxy-4,6-dimethylpyridin-3-yl)methyl)-6-methyl-7H-pyrrolo[2,3-d]pyrimidine-5-carboxamide | $^1$H NMR (400 MHz, CD$_3$OD): δ 9.4 (s, 1H), 9.14 (s, 1H), 6.86 (s, 1H), 4.79-4.83 (m, 1H), 4.65 (s, 2H), 2.82 (s, 3H), 2.62 (s, 3H), 2.48 (s, 3H), 2.39-2.44 (m, 1H), 2.05-2.12 (m, 1H), 1.72-1.74 (d, J = 6.8 Hz, 3H), 0.77-0.81 (t, 3H). | 368 |

| Compound | General Methods Used and Notes | Name | NMR data | m/z |
|---|---|---|---|---|
| 197 | F, G | (R)-7-(sec-butyl)-N-((4,6-dimethyl-2-oxo-1,2-dihydropyridin-3-yl)methyl)-2-isopropyl-6-methyl-7H-pyrrolo[2,3-d]pyrimidine-5-carboxamide | $^1$H NMR (400 MHz, Methanol-d4) δ 9.20 (s, 1H), 6.64 (s, 1H), 4.73 (s, 2H), 4.59 (s, 2H), 3.44 (m, 1H), 2.77 (s, 3H), 2.55 (s, 3 H), 2.44 (s, 3H), 2.10 (m, 1H), 1.73 (d, J = 6.8 Hz, 3 H), 1.48 (d, J = 7.2 Hz, 6H), 0.81 (m, 3H). | |
| 198 | F (Zn(CN)$_2$ instead of the indicated boronic ester or acid), I, C | (R)-7-(sec-butyl)-N5-((4,6-dimethyl-2-oxo-1,2-dihydropyridin-3-yl)methyl)-N2,6-dimethyl-7H-pyrrolo[2,3-d]pyrimidine-2,5-dicarboxamide | $^1$H NMR (400 MHz, Methanol-d4) δ 9.34 (s, 1H), 6.4 (s, 1H), 4.92 (s, 2H), 4.58 (s, 2H), 3.1 (s, 3H), 2.86 (s, 3H), 2.50 (s, 3H), 2.34 (s, 3H), 1.80 (d, J = 6.8 H$_Z$, 3 H), 0.86 (m, 3H). | 425 |
| 199 | F (Zn(CN)$_2$), I, J, K | (R)-7-(sec-butyl)-N-((4,6-dimethyl-2-oxo-1,2-dihydropyridin-3-yl)methyl)-2-(hydroxymethyl)-6-methyl-7H-pyrrolo[2,3-d]pyrimidine-5-carboxamide | $^1$H NMR (400 MHz, Methanol-d4) δ 8.97 (s, 1H), 6.1 (s, 1H), 4.76 (s, 2H), 4.50 (s, 2H), 2.67 (s, 3H), 2.51 (s, 1H), 2.44 (s, 3H), 2.42 (s, 3H), 2.01 (m, 2 H), 1.95 (d, J = 6.8 Hz, 3H), 0.74 (m, 3H). | 398 |
| 200 | F | (R)-7-(sec-butyl)-N-((4,6-dimethyl-2-oxo-1,2-dihydropyridin-3-yl)methyl)-2,6-dimethyl-7H-pyrrolo[2,3-d]pyrimidine-5-carboxamide | $^1$H NMR (400 MHz, Methanol-d4) δ 8.87 (s, 1H), 6.09 (s, 1H), 4.71 (s, 1H), 4.62 (s, 2H), 2.67 (d, J = 6.4 Hz, 6H), 2.51 (m, 4H), 2.23 (s, 3 H), 2.00 (m, 1H), 1.65 (d, J = 6.8 Hz, 3 H), 0.73 (m, 3H). | |
| 144 | E | (R)-2-amino-N-((2-hydroxy-4,6-dimethylpyridin-3-yl)methyl)-6-methyl-7-(1-phenylethyl)-7H-pyrrolo[2,3-d]pyrimidine-5-carboxamide | $^1$H NMR (300 MHz, CD$_3$OD): δ 8.57 (s, 1H), 7.34-7.19 (m, 5H), 6.19-6.17 (m, 1H), 6.10 (s, 1H), 4.47 (s, 2H), 2.33 (s, 3H), 2.30 (s, 3H), 2.23 (s, 3H), 1.99 (d, J = 7.2 Hz, 3H). | 430 |
| 142 | E | (R)-N-((2-hydroxy-4,6-dimethylpyridin-3-yl)methyl)-6-methyl-7-(1-phenylethyl)-2-(pyrrolidin-1-yl)-7H-pyrrolo[2,3-d]pyrimidine-5-carboxamide | $^1$H NMR (400 MHz, CD$_3$OD) δ 8.56 (s, 1H), 7.27-7.20 (m, 5H), 6.06-6.02 (m, 2H), 4.45 (s, 2H), 3.52-3.45 (m, 4H), 2.40 (s, 3H), 2.35 (s, 3H), 2.21 (s, 3H), 2.01-1.94 (m, 7H). | 484 |
| 143 | E | (R)-N-((2-hydroxy-4,6-dimethylpyridin-3-yl)methyl)-6-methyl-2-morpholino-7-(1-phenylethyl)-7H-pyrrolo[2,3-d]pyrimidine-5-carboxamide | $^1$H NMR (400 MHz, CD$_3$OD) δ 8.65 (s, 1H), 7.28 (dt, J = 11.9, 7.7 Hz, 5H), 6.10 (dd, J = 13.7, 6.5 Hz, 2H), 4.51 (s, 2H), 3.78-3.65 (m, 8H), 2.47 (s, 3H), 2.41 (s, 3H), 2.26 (s, 3H), 2.03 (d, J = 7.2 Hz, 3H). | 500 |
| 141 | E (NaOMe/MeOH instead of amine) | (R)-N-((2-hydroxy-4,6-dimethylpyridin-3-yl)methyl)-2-methoxy-6-methyl-7-(1-phenylethyl)-7H-pyrrolo[2,3-d]pyrimidine-5-carboxamide | 1H NMR (400 MHz, CD3OD) δ 8.75 (s, 1H), 7.29-7.22 (m, 5H), 6.11-6.07 (m, 2H), 4.46 (s, 2H), 3.90 (s, 3H), 2.48 (s, 3H), 2.36 (s, 3H), 2.21 (s, 3H), 2.05 (d, J = 7.2 Hz, 3H). | 445 |
| 139 | A, B, C | (±)-N-((4,6-dimethyl-2-oxo-1,2-dihydropyridin-3-yl)methyl)-2,6-dimethyl-7-oxo-1-(1-phenylethyl)-6,7-dihydro-1H-pyrrolo[2,3-c]pyridine-3-carboxamide | $^1$H NMR (400 MHz, CD$_3$OD): δ 7.22-7.13 (m, 4H), 7.01 (d, J = 7.2 Hz, 2H), 6.69 (d, J = 7.2 Hz, 1H), 5.99 (s, 1H), 4.35 (s, 2H), 3.50-3.21 (m, 4H), 2.26 (s, 3H), 2.13 (s, 3H), 2.06 (s, 3H), 1.82 (d, J = 7.2 Hz, 3H). | 444 |
| 140 | E | (R)-N-((2-hydroxy-4,6-dimethylpyridin-3-yl)methyl)-6-methyl-2-(methylamino)-7-(1-phenylethyl)-7H-pyrrolo[2,3-d]pyrimidine-5-carboxamide | $^1$H NMR (300 MHz, CD$_3$OD): δ 8.55 (s, 1H), 7.30-7.23 (m, 5H), 6.15-6.10 (m, 2H), 4.47 (s, 2H), 3.25 (s, 3H), 2.40 (s, 3H), 2.38 (s, 3H), 2.24 (s, 3H), 2.03 (d, J = 7.2 Hz, 3H). | 444 |

-continued

| Compound | General Methods Used and Notes | Name | NMR data | m/z |
|---|---|---|---|---|
| 133 | B, C | N-((2-hydroxy-4,6-dimethylpyridin-3-yl)methyl)-2-methyl-1-phenyl-1H-indole-3-carboxamide | $^1$H NMR (300 MHz, CDCl$_3$) δ 12.62 (s, 1H), 7.89 (d, J = 8.0 Hz, 1H), 7.77-7.40 (m, 3H), 7.43-7.18 (m, 3H), 7.22-6.94 (m, 2H), 5.98 (s, 1H), 4.65 (s, 2H), 2.60-2.52 (m, 3H), 2.51-2.44 (m, 3H), 2.28-2.22 (m, 3H). | 385 |
| 119 | A, B, C | 1-benzyl-N-((2-hydroxy-4,6-dimethylpyridin-3-yl)methyl)-2-methyl-1H-indole-3-carboxamide | $^1$H NMR (300 MHz, d$^6$-DMSO): δ 11.61 (s, 1H), 7.80-7.69 (m, 2H), 7.46-7.42 (m, 1H), 7.30-7.22 (m, 3H), 7.11-7.07 (m, 2H), 6.98 (d, J = 7.5 Hz, 2H), 5.89 (s, 1H), 5.46 (s, 2H), 4.33 (d, J = 4.5 Hz, 2H), 2.57 (s, 3H), 2.26 (s, 3H), 2.11 (s, 3H). | 399 |
| 126 | B, C | (±)-N-((2-hydroxy-4,6-dimethylpyridin-3-yl)methyl)-2-methyl-1-(1-phenylethyl)-1H-pyrrolo[3,2-b]pyridine-3-carboxamide | $^1$H NMR (300 MHz, d$^6$-DMSO) δ11.46 (s, 1H), 9.49 (t, J$_1$ = 4.2 Hz, J$_2$ = 8.1 Hz, 1H), 8.28 (d, J = 3.6 Hz, 1H), 7.50 (d, J = 6.3 Hz, 1H), 7.36-7.27 (m, 3H), 7.16 (d, J = 5.7 Hz, 1H), 7.03-7.00 (m, 1H), 6.03 (m, 1H), 5.85 (s, 1H), 4.37 (s, 2H), 2.89 (s, 3H), 2.10 (s, 3H), 1.89 (d, J = 5.4 Hz, 1H). | 415 |
| 114 | A, B, C, D | (R or S)-N-((6-hydroxy-2-methoxy-4-methylpyridin-3-yl)methyl)-2-methyl-1-(1-phenylethyl)-1H-indole-3-carboxamide | $^1$H NMR (300 MHz, d$^6$-DMSO): δ 11.59 (s, 1H), 7.75-7.72 (m, 2H), 7.35-7.25 (m, 3H), 7.15 (d, J = 7.5 Hz, 2H), 7.10-7.07 (m, 1H), 7.02-6.93 (m, 2H), 6.15 (s, 1H), 5.96 (q, J = 6.9 Hz, 1H), 4.33 (d, J = 5.1 Hz, 2H), 3.85 (s, 3H), 2.62 (s, 3H), 2.20 (s, 3H), 1.89 (d, J = 7.5 Hz, 3H). | 429 |
| 115 | A, B, C, D | (R or S)-N-((6-hydroxy-2-methoxy-4-methylpyridin-3-yl)methyl)-2-methyl-1-(1-phenylethyl)-1H-indole-3-carboxamide | Identical to Compound 114 | |
| 118 | A, B, C | (±)-N-((2-hydroxy-4,6-dimethylpyridin-3-yl)methyl)-1-(1-phenylethyl)-1H-indole-3-carboxamide | $^1$H NMR (300 MHz, d$^6$-DMSO): δ. 11.50 (s, 1H), 8.46 (s, 1H), 8.16-8.13 (m, 1H), 7.81 (s, 1H), 7.42-7.39 (m, 1H), 7.31-7.20 (m, 5H), 7.10-7.07 (m, 2H), 5.88-5.75 (m, 2H), 4.32 (d, J = 5.1 Hz, 2H), 2.22 (s, 3H), 2.12 (s, 3H), 1.86 (d, J = 6.9 Hz, 3H). | 399 |
| 137 | A, B, C, D | (R or S)-N-((2-hydroxy-4,6-dimethylpyridin-3-yl)methyl)-2-methyl-1-(1-phenylethyl)-1H-indole-3-carboxamide | $^1$H NMR (DMSO-d$_6$, 300 MHz) δ 11.59 (s, 1H), 7.73-7.66 (m, 2H), 7.34-7.29 (m, 3H), 7.24 (d, J = 7.2 Hz, 1H), 7.16-6.89 (m, 4H), 5.94 (q, 1H), 5.88 (s, 1H), 4.32 (d, J = 5.4 Hz, 2H), 2.60 (s, 3H), 2.50 (s, 3H), 2.11 (s, 3H), 1.87 (d, J = 7.2 Hz, 3H). | 413 |
| 136 | A, B, C, D | (R or S)-N-((2-hydroxy-4,6-dimethylpyridin-3-yl)methyl)-2-methyl-1-(1-phenylethyl)-1H-indole-3-carboxamide | Identical to Compound 137 | |

-continued

| Compound | General Methods Used and Notes | Name | NMR data | m/z |
|---|---|---|---|---|
| 445 | B, C, D | (R or S)-N-((2-hydroxy-4,6-dimethylpyridin-3-yl)methyl)-2-phenyl-1-(1-phenylethyl)-1H-indole-3-carboxamide | $^1$H NMR (400 MHz, d$^6$-DMSO): δ 11.58 (s, 1H), 8.50 (s, 1H), 8.21 (d, J = 8.4 Hz, 1H), 7.89 (s, 1H), 7.73 (s, 1H), 7.64 (d, J = 7.2 Hz, 2H), 7.46-7.42 (m, 3H), 7.33-7.27 (m, 5H), 7.25-7.21 (m, 1H), 6.05-6.02 (m, 1H), 5.91 (s, 1H), 4.34-4.33 (d, J = 3.2 Hz, 2H), 2.42 (s, 3H), 2.13 (s, 3H), 1.89-1.88 (d, J = 7.2 Hz, 3H). | 475 |
| 446 | B, C, D | (R or S)-N-((2-hydroxy-4,6-dimethylpyridin-3-yl)methyl)-2-phenyl-1-(1-phenylethyl)-1H-indole-3-carboxamide | $^1$H NMR (400 MHz, d$^6$-DMSO): δ 11.54 (s, 1H), 8.51 (s, 1H), 8.42 (s, 1H), 7.91 (s, 1H), 7.63 (d, J = 7.2 Hz, 2H), 7.51-7.40 (m, 4H), 7.33-7.24 (m, 6H), 5.90 (m, 2H), 4.35-4.34 (d, J = 3.6 Hz, 2H), 2.34 (s, 3H), 2.13 (s, 3H), 1.89-1.87 (d, J = 6.8 Hz, 3H). | 475 |
| 131 | B, C | (±)-2-cyclopropyl-N-((2-hydroxy-4,6-dimethylpyridin-3-yl)methyl)-1-(1-phenylethyl)-1H-indole-3-carboxamide | $^1$H NMR (300 MHz, CD3OD,): δ 8.06 (s, 1H), 7.92 (d, J = 8.4 Hz, 1H), 7.28-7.15 (m, 5H), 7.00 (s, 1H), 6.87 (d, J = 8.1 Hz, 1H), 6.13 (s, 1H), 5.74 (q, J = 7.2 Hz, 1H), 4.52 (s, 2H), 2.41 (s, 3H), 2.25 (s, 3H), 1.91 (d, J = 7.2 Hz, 3H), 1.93-1.89 (m, 1H), 0.92-0.88 (m, 2H), 0.61-0.59 (m, 2H). | 439 |
| 447 | B, C | (±)-2-ethyl-N-((2-hydroxy-4,6-dimethylpyridin-3-yl)methyl)-1-(1-phenylethyl)-1H-indole-3-carboxamide | $^1$H NMR (400 MHz, d$^6$-DMSO): δ 11.58 (s, 1H), 8.37 (s, 1H), 8.03 (d, J = 8.4 Hz, 1H), 7.80 (s, 1H), 7.32-7.20 (m, 6H), 6.98-6.96 (m, 1H), 5.91 (s, 1H), 5.85-5.80 (m, 1H), 4.31 (s, 2H), 2.66-2.60 (m, 2H), 2.23 (s, 3H), 2.13 (s, 3H), 1.85-1.83 (d, J = 7.2 Hz, 3H), 1.21-1.14 (m, 3H). | 427 |
| 287 | See intermeidate 1 below, G | (S)-N-((4-methoxy-6-methyl-2-oxo-1,2-dihydropyridin-3-yl)methyl)-7-(1-methoxypropan-2-yl)-6-methyl-7H-pyrrolo[2,3-d]pyrimidine-5-carboxamide | $^1$H NMR (400 MHz, MeOD): δ 9.311 (S, 1H), 9.122 (S, 1H), 6.826 (S, 1H), 5.063-5.027 (m, 1H), 4.578 (s, 2H), 4.279-4.254 (t, J = 10 Hz, 1H), 4.086 (s, 3H), 3.781-3.744 (m, 1H), 3.203 (s, 3H), 2.805 (s, 3H), 2.500 (s, 3H), 1.739-1.722 (d, J = 6.8 Hz, 3H). | 400 |
| 303 | See intermediate 1 below, G | (R)-N-4-methoxy-6-methyl-2-oxo-1,2-dihydropyridin-3-yl)methyl)-7-(1-methoxypropan-2-yl)-6-methyl-7H-pyrrolo[2,3-d]pyrimidine-5-carboxamide | $^1$H NMR (400 MHz, MeOD): δ 9.352 (S, 1H), 9.152 (S, 1H), 7.018 (S, 1H), 5.075-4.994 (m, 1H), 4.610 (s, 2H), 4.280-4.230 (t, J = 20 Hz, 1H), 4.139 (s, 3H), 3.784-3.747 (m, 1H), 3.204 (s, 3H), 2.806 (s, 3H), 2.567 (s, 3H), 1.748-1.730 (d, J = 7.2 Hz, 3H). | 400 |
| 319 | See intermediate 8 below, G, B, C | (R or S)-N-((4-methoxy-6-methyl-2-oxo-1,2-dihydropyridin-3-yl)methyl)-6-methyl-7-(1-(tetrahydro-2H-pyran-4-yl)ethyl)-7H-pyrrolo[2,3-d]pyrimidine-5-carboxamide | $^1$H NMR (CDCl3, 400 MHz) δ 11.99 (s, 1H), 9.17 (s, 1H), 8.77 (s, 1H), 7.61 (s, 1H), 5.96 (s, 1H), 4.61 (d, J = 4.0 Hz, 2H), 4.04 (dd, J$_1$ = 3.6 Hz, J$_2$ = 11.2 Hz, 1H), 3.91 (s, 3H), 3.76 (dd, J$_1$ = 3.6 Hz, J$_2$ = 11.2 Hz, 1H), 3.43 (t, J = 11.2 Hz, 1H), 3.18 (dd, J$_1$ = 10.4 Hz, J$_2$ = 12.0 Hz, 1H), 2.85 (s, 1H), 2.77 (s, 3H), 2.30 (s, 3H), 1.89 (d, J = 12.0 Hz, 1H), 1.64 (d, J = 6.4 Hz, 4H), 1.40 (d, J = 8.4 Hz, 1H), 1.13 (dd, J$_1$ = 4.8 Hz, J$_2$ = 12.8 Hz, 1H), 1.10-0.79 (m, 1H). | 440 |

-continued

| Compound | General Methods Used and Notes | Name | NMR data | m/z |
|---|---|---|---|---|
| 332 | Intermediate 9, B, C | tert-butyl 4-(1-(5-(((4-methoxy-6-methyl-2-oxo-1,2-dihydropyridin-3-yl)methyl)carbamoyl)-6-methyl-7H-pyrrolo[2,3-d]pyrimidin-7-yl)ethyl)piperidine-1-carboxylate | $^1$H NMR (400 MHz, CD$_3$Cl$_3$): δ 0.93 (m, 2H), 1.24 (m, 1H), 1.42 (s, 9H), 1.67 (m, 6H), 1.96-1.99 (d, J = 12.4 Hz, 1H), 2.30 (s, 3H), 2.48 (m, 1H), 2.78 (s, 4H), 3.9 (s, 4H), 4.20 (brs, 1H), 4.65-4.66 (d, J = 4.0 Hz, 2H), 5.96 (s, 1H), 7.71 (brs, 1H), 8.78 (s, 1H), 9.19 (s, 1H), 12.67 (brs, 1H). | |
| 333 | TFA treatment of Compound 332 | (±)-N-((4-methoxy-6-methyl-2-oxo-1,2-dihydropyridin-3-yl)methyl)-6-methyl-7-(1-(piperidin-4-yl)ethyl)-7H-pyrrolo[2,3-d]pyrimidine-5-carboxamide | $^1$H NMR (400 MHz, CDCl3): δ 1.58 (d, J = 6.4 Hz, 6H), 2.54 (s, 3H), 3.94 (s, 3H), 4.66 (d, J = 5.6 Hz, 2H), 4.78 (m, 1H), 6.56 (brs, 1H), 6.71 (s, 1H), 7.54 (s, 1H), 7.73 (s, 1H), 8.27 (s, 1H), 8.37 (s, 1H). | |
| 334 | Synthesis for intermediate 9, using intermediate 10, B, C. | (±)-7-(1-(4,4-difluorocyclohexyl)ethyl)-N-((4-methoxy-6-methyl-2-oxo-1,2-dihydropyridin-3-yl)methyl)-6-methyl-7H-pyrrolo[2,3-d]pyrimidine-5-carboxamide | $^1$H NMR (CDCl$_3$, 400 MHz) δ 9.19 (s, 1 H), 8.79 (s, 1H), 7.69 (s, 1H), 5.96 (s, 1H), 4.65-4.64 (d, J = 7.2 Hz, 2H), 3.91 (s, 3H), 3.02 (s, 4H), 2.78 (s, 3H), 2.31 (s, 3H), 2.22-2.07 (m, 3H), 1.89 (s, 2H), 1.69 (s, 3H), 1.48-1.42 (m, 2H), 1.14 (s, 3H), 1.11-1.01 (m, 2H). | 474 |
| 351 | Synthesis for intermediate 9 using intermediate 11, G, BOC-on, B, C, TFA | N-((4-methoxy-6-methyl-2-oxo-1,2-dihydropyridin-3-yl)methyl)-6-methyl-7-(1-((R)-morpholin-2-yl)ethyl)-7H-pyrrolo[2,3-d]pyrimidine-5-carboxamide | $^1$H NMR (CDCl$_3$, 400 MHz) δ 9.23-9.22 (d, J = 0.8 Hz, 1H), 9.17-9.16 (d, J = 1.2 Hz, 1H), 6.56 (s, 1H), 4.98-4.94 (m, 1H), 4.76-4.72 (m, 1H), 4.55 (s, 2H), 4.27-4.23 (dd, J = 3.6 Hz, 7.2 Hz, 1H), 4.03 (s, 3H), 4.00-3.96 (m, 1H), 3.40-3.37 (d, J = 13.2 Hz, 1H), 3.26-3.16 (m, 2H), 3.10-3.04 (m, 1H), 2.78 (s, 3H), 2.44 (s, 3H), 1.83-1.85 (d, J = 7.2 Hz, 3H). | 441 |
| 370 | General procedure L on Compound 333 | | $^1$H NMR (CDCl$_3$, 400 MHz) δ 12.12 (s, 1H), 9.20 (s, 1H), 8.78 (s, 1H), 7.68 (s, 1H), 5.97 (s, 1H), 4.70-4.58 (m, 2H), 3.91 (s, 4H), 3.62 (d, J = 12.0 Hz, 1H), 2.76-2.67 (m, 7H), 2.45 (dd, J$_1$ = 2.0 Hz, J$_2$ = 11.6 Hz, 1H), 2.32 (s, 3H), 2.10 (t, J = 12.0 Hz, 1H), 1.67 (d, J = 6.8 Hz, 4H), 1.48-1.40 (m, 1H), 1.37-1.29 (m, 1H), 1.27-1.19 (m, 1H), 0.9-0.78 (m, 1H). | 517 |

Example 73

Synthesis of (R)-N-((2-hydroxy-4,6-dimethylpyridin-3-yl)methyl)-6-methyl-7-(1-phenylethyl)-7H-pyrrolo[2,3-d]pyrimidine-5-carboxamide (Compound 395)

To a solution of (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide (140 mg, 0.30 mmol) in MeOH (10 mL). Palladium-carbon catalyst (10%, 20 mg) was added, the mixture solution was stirred at 25° C. for 12 hours under hydrogen atmosphere (4 bar). The mixture was filtered and concentrated in vacuo and purified by column chromatography (silica gel, dichloromethane/methanol=10: 1) to afford (R)-N-((2-hydroxy-4,6-dimethylpyridin-3-yl) methyl)-6-methyl-7-(1-phenylethyl)-7H-pyrrolo[2,3-d]pyrimidine-5-carboxamide (93 mg, 72%).

Example 74

Synthesis of Novel Indole Cores and Intermediates

Intermediate 1: Intermediate 1 was synthesized according to the scheme below:

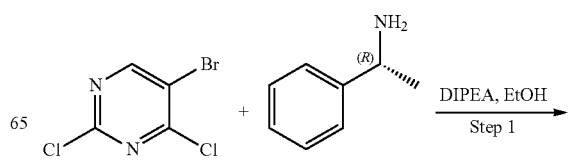

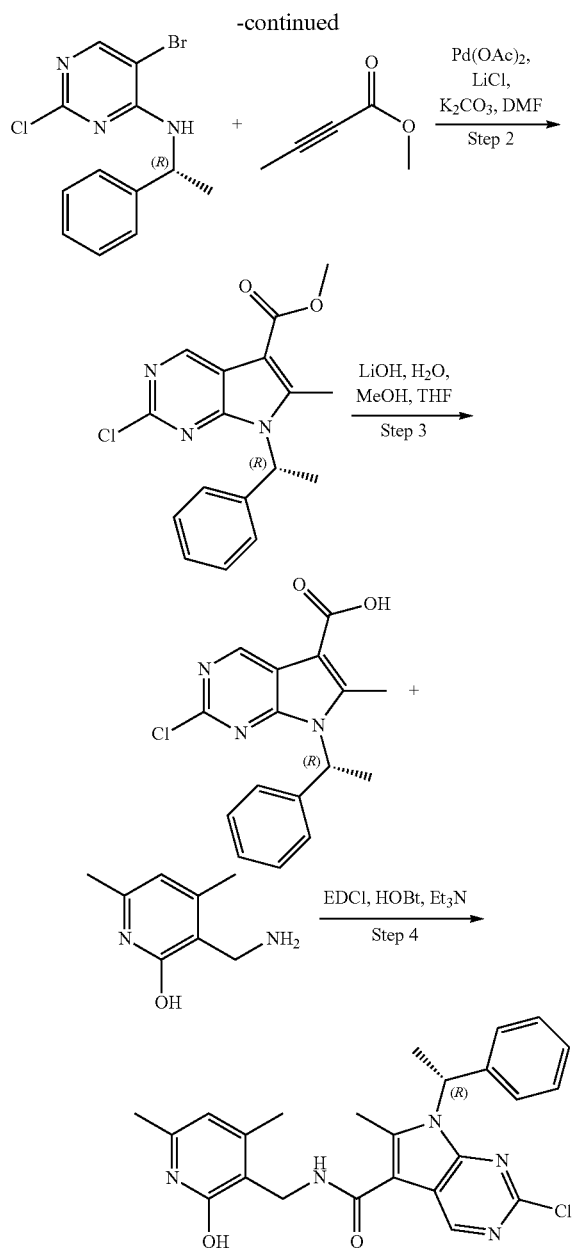

mmol) and palladium acetate (360 mg, 1.6 mmol) in N,N-dimethylformamide (50 mL) was degassed and back-filled with nitrogen for three times, then heated at 120° C. for 4 hours. The reaction mixture was filtered and the filtrate was concentrated in vacuo, extracted with ethyl acetate (50 mL), washed with water (50 mL), dried over anhydrous magnesium sulfate and purified by column chromatography (silica gel, petroleum ether/ethyl acetate=5:1) to give (R)-methyl 2-chloro-6-methyl-7-(1-phenylethyl)-7H-pyrrolo[2,3-d]pyrimidine-5-carboxylate as a yellow oil (800 mg, 15%). LRMS (M+H$^+$) m/z: calcd 329.09. found 329. $^1$H NMR (300 MHz, CDCl$_3$): δ 9.16 (s, 1H), 7.39-7.18 (m, 5H), 6.45-6.42 (m, 1H), 3.96 (s, 3H), 2.57 (s, 3H), 2.05 (d, J=7.2 Hz, 3H).

Step 3: (R)-2-chloro-6-methyl-7-(1-phenylethyl)-7H-pyrrolo[2,3-d]pyrimidine-5-carboxylic acid. Lithium hydroxide anhydrate (882 mg, 21 mmol) in water (3 mL) was added to (R)-methyl 2-chloro-6-methyl-7-(1-phenylethyl)-7H-pyrrolo[2,3-d]pyrimidine-5-carboxylate (700 mg, 2.1 mmol) in tetrahydrofuran (5 mL) and methanol (10 mL) and the resultant mixture was stirred at room temperature for 12 hours. The mixture was evaporated, added with water (5 mL), acidified with aqueous hydrochloric acid (1M) to pH=2. The precipitate solid was filtered and dried to obtain (R)-2-chloro-6-methyl-7-(1-phenylethyl)-7H-pyrrolo[2,3-d]pyrimidine-5-carboxylic acid as a white solid (500 mg, 75%). LRMS (M+H$^+$) m/z: calcd 315.08. found 315.

Step 4: (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide. To a solution of (R)-2-chloro-6-methyl-7-(1-phenylethyl)-7H-pyrrolo[2,3-d]pyrimidine-5-carboxylic acid (100 mg 0.32 mmol) in dichloromethane (10 mL) was added with 1-hydroxybenzotriazole (65 mg, 0.48 mmol), (3-dimethylaminopropyl)ethyl-carbodiimid hydrochloride (92 mg, 0.48 mmol) and triethylamine (97 mg, 0.96 mmol). After stirred for 30 minutes, 3-(aminomethyl)-4,6-dimethylpyridin-2-ol (49 mg, 0.32 mmol) was added and the reaction mixture was stirred at room temperature for 12 hours. The solution was concentrated, diluted with water (20 mL), extracted with ethyl acetate (20 mL). The organic layers were separated, combined, dried over anhydrous sodium sulfate, filtered and concentrated to give a residue. The residue was purified by column chromatography (silica gel, dichloromethane/methanol=20:1) to afford (R)-2-chloro-N-((2-hydroxy-4,6-dimethylpyridin-3-yl)methyl)-6-methyl-7-(1-phenylethyl)-7H-pyrrolo[2,3-d]pyrimidine-5-carboxamide (100 mg, 70%). LRMS (M+H$^+$) m/z: calcd 449.16; found 449.

Intermediate 2: Intermediate 2 was synthesized according to the scheme below:

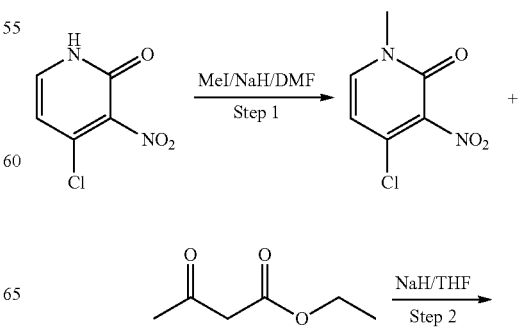

Step 1: (R)-5-bromo-2-chloro-N-(1-phenylethyl)pyrimidin-4-amine. To a solution of 5-bromo-2,4-dichloropyrimidine (5 g, 22 mmol) and (R)-1-phenylethanamine (2.7 g, 22 mmol) in ethanol (50 mL) was added N,N-diisopropylethylamine (4.3 g, 33 mmol). The reaction solution was stirred at room temperature for 12 hours. The resultant mixture was concentrated in vacuo. The residue was purified by column chromatography (silica gel, petroleum ether/ethyl acetate=6:1) to give (R)-5-bromo-2-chloro-N-(1-phenylethyl)pyrimidin-4-amine as a white solid (5 g, 74%). LRMS (M+H$^+$) m/z: calcd 310.98. found 310. $^1$H NMR (300 MHz, CDCl$_3$): δ 8.10 (s, 1H), 7.41-7.25 (m, 5H), 5.73 (d, J=6.9 Hz, 1H), 5.39-5.34 (m, 1H), 1.61 (d, J=6.6 Hz, 3H).

Step 2: (R)-methyl 2-chloro-6-methyl-7-(1-phenylethyl)-7H-pyrrolo[2,3-d]pyrimidine-5-carboxylate. A solution of (R)-5-bromo-2-chloro-N-(1-phenylethyl)pyrimidin-4-amine (5 g, 16 mmol), methyl but-2-ynoate (3.1 g, 32 mmol), lithium chloride (690 mg, 16 mmol), potassium carbonate (5.5 g, 40

-continued

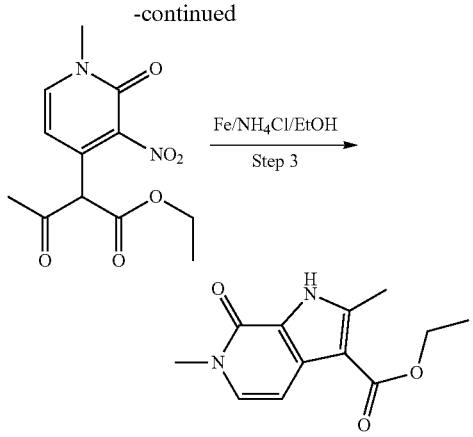

Step 1: 4-chloro-1-methyl-3-nitropyridin-2(1H)-one. To a stirred solution of 4-chloro-3-nitropyridin-2(1H)-one (3.0 g, 17 mmol) in N,N-dimethylformamide (50 mL) was added sodium hydride (60% w/w, 1.0 g, 25.5 mmol) in batches at 0° C. The mixture was stirred at room temperature for 30 minutes. Then iodomethane (2.9 g, 20.4 mmol) was added dropwise to the above solution at room temperature. The resultant solution was stirred at room temperature for 12 hours. Once starting material was consumed, the reaction mixture was quenched with ice water (100 mL) at 0~10° C., and extracted with ethyl acetate (100 mL*3). The organic phase was washed with brine (100 mL*2), dried over anhydrous sodium sulfate, filtered and concentrated to give a residue. The residue was purified by column chromatography (silica gel, dichloromethane/methanol=10:1) to give 4-chloro-1-methyl-3-nitropyridin-2(1H)-one (3 g, 94%) as a yellow solid. LRMS (M+H$^+$) m/z: calcd 188.0. found 188.

Step 2: ethyl 2-(1-methyl-3-nitro-2-oxo-1,2-dihydropyridin-4-yl)-3-oxobutanoate. To a stirred solution of ethyl 3-oxobutanoate (2.5 g, 19 mmol) in tetrahydrofuran (50 mL) was added sodium hydride (60% w/w, 0.96 g, 23.9 mmol) in batches at 0° C. The mixture was stirred at room temperature for 30 minutes. Then the solution of 4-chloro-1-methyl-3-nitropyridin-2(1H)-one (3.0 g, 16 mmol) in tetrahydrofuran (50 mL) was added in one portion. The resultant solution was stirred and heated to 50° C. for 12 hours. Once starting material was consumed, the reaction solution was quenched with water (100 mL) at 0° C., and extracted with ethyl acetate (100 mL*3). The combined organic layers were washed with brine (100 mL*2), dried over anhydrous sodium sulfate, filtered and concentrated to give a residue. The residue was purified by column chromatography (silica gel, dichloromethane/methanol=10:1) to give ethyl 2-(1-methyl-3-nitro-2-oxo-1,2-dihydropyridin-4-yl)-3-oxobutanoate (2.5 g, 56%) as a yellow solid. LRMS (M+H$^+$) m/z: calcd 282.09. found 282.

Step 3: ethyl 2,6-dimethyl-7-oxo-6,7-dihydro-1H-pyrrolo[2,3-c]pyridine-3-carboxylate. To a solution of ethyl 2-(1-methyl-3-nitro-2-oxo-1,2-dihydropyridin-4-yl)-3-oxobutanoate (2.5 g, 8.8 mmol) in ethanol (50 mL) was added ammonium chloride (0.5 g, 9 mmol) in water (5 mL) at room temperature. The mixture was stirred and heated to reflux. Then iron powder (0.5 g, 8.9 mmol) was added in one portion. The mixture was stirred at reflux for 2 hours. Once starting material was consumed, the resultant mixture was filtered when it was hot, and the filtrate was concentrated to give a residue. The residue was purified by column chromatography (silica gel, dichloromethane/methanol=10:1) to give ethyl 2,6-dimethyl-7-oxo-6,7-dihydro-1H-pyrrolo[2,3-c]pyridine-3-carboxylate (1.5 g, 75%) as a brown solid. LRMS (M+H$^+$) m/z: calcd 234.1. found 234. $^1$H NMR (400 MHz, d$^6$-DMSO): δ 12.54 (s, 1H), 7.30 (d, J=5.1 Hz, 1H), 6.78 (d, J=5.1 Hz, 1H), 4.24 (q, J=5.1 Hz, 2H), 3.51 (s, 3H), 2.56 (s, 3H), 1.32 (t, J=5.1 Hz, 3H).

Intermediate 3: Intermediate 3 was synthesized according to the scheme below:

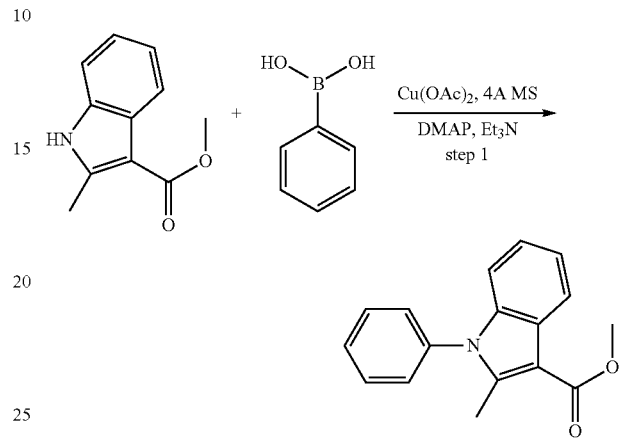

A mixture of methyl 2-methyl-1H-indole-3-carboxylate (500 mg, 2.65 mmol), phenylboronic acid (384 mg, 3.17 mmol), diacetylcopper (453 mg, 3.98 mmol), triethylamine (0.44 ml, 3.98 mmol), N,N-dimethylpyridin-4-amine (486 ml, 3.98 mmol) and 4 A molecular sieve (1.02 g) in dichloromethane (15 mL) was stirred at room temperature for 12 hours. After filtration, the mixture was concentrated and purified by chromatography (silica gel, petroleum:ethyl acetate=10:1) to afford methyl 2-methyl-1-phenyl-1H-indole-3-carboxylate as white solid (272 mg, 39%). $^1$H NMR (400 MHz, CDCl$_3$) δ 8.19 (d, J=8.0 Hz, 1H), 7.66-7.51 (m, 3H), 7.36 (dd, J=5.3, 3.2 Hz, 2H), 7.30 (s, 1H), 7.21-7.14 (m, 1H), 7.04 (d, J=8.2 Hz, 1H), 4.00 (s, 3H), 2.62 (s, 3H).

Intermediate 4: Intermediate 4 was synthesized according to the scheme below:

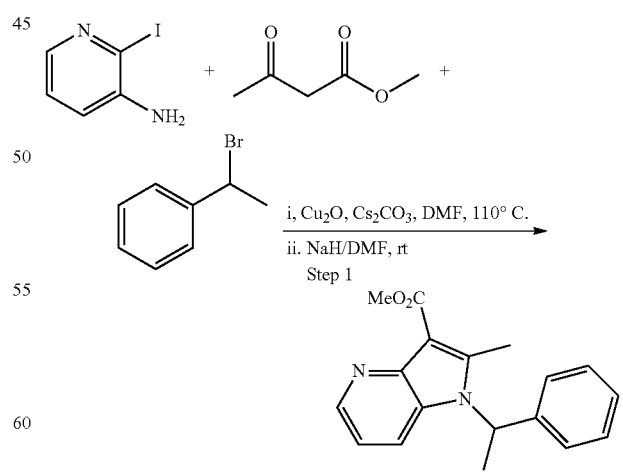

To a solution of 2-iodopyridin-3-amine (500 mg, 2.27 mmol), cuprous oxide (32 mg, 0.23 mmol), cesium carbonate (740 mg, 2.27 mmol) in N,N-dimethylformamide (100 mL) was added methyl methacrylate (290 mg, 2.5 mmol). The reaction solution was stirred at 110° C. for 12 hours. Then the reaction mixture was cooled to room temperature and added sodium hydride (60% in oil, 91 mg, 2.27 mmol) under ice bath. The resulting mixture was stirred at room temperature for half an hour. Then (1-bromoethyl)benzene (418 mg, 2.27 mmol) was added. Then the mixture was stirred at room temperature for 1 hour. After the reaction was completed, it was quenched with water (100 mL), and extracted with ethyl acetate (50 mL×3). The combined organic phase were washed with water (20 mL×3) and brine (20 mL), dried over anhydrous sodium sulfate, concentrated and purified by column chromatography (silica gel, petroleum ether/ethyl acetate=6:1) to give methyl 2-methyl-1-(1-phenylethyl)-1H-pyrrolo[3,2-b]pyridine-3-carboxylate (80 mg, 12%). LRMS (M+H$^+$) m/z: calcd 295.14. found 295.

Intermediate 5: Intermediate 5 was synthesized according to the scheme below:

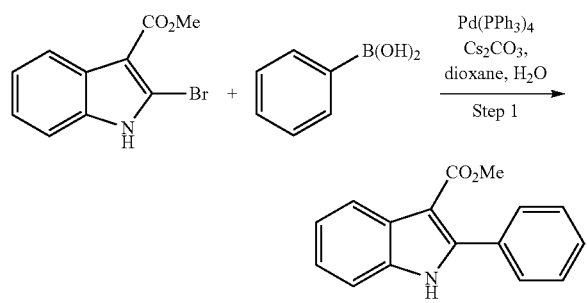

Methyl 2-bromo-1H-indole-3-carboxylate (200 mg, 0.79 mmol), phenylboronic acid (122 mg, 1 mmol), tetrakis(triphenylphosphine)palladium (231 mg, 0.2 mmol) and cesiumcarbonate (652 mg, 2 mmol) in dioxane/water (20 mL/5 mL) were stirred at room temperature 15 hours. Filterated the solid and the solvent was concentrated in vacuum. The resulted residue was purified by silica gel column (ethyl acetate:petroleum ether=1:2) to obtain methyl 2-phenyl-1H-indole-3-carboxylate as a pale yellow solid (160 mg, 80%) LRMS (M+H$^+$) m/z: calcd 251.1 found 251.

Intermediate 6: Intermediate 6 was synthesized according to the scheme below:

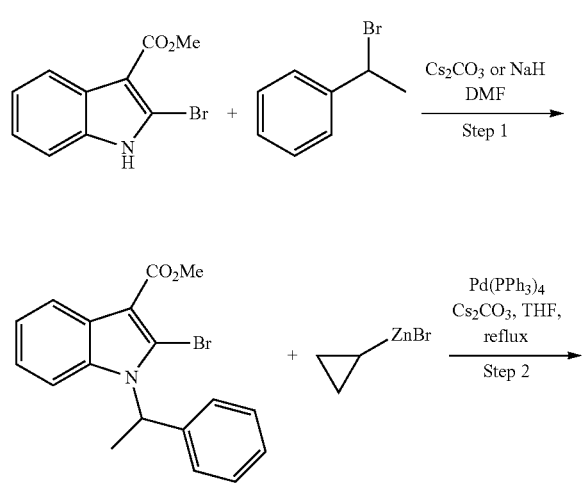

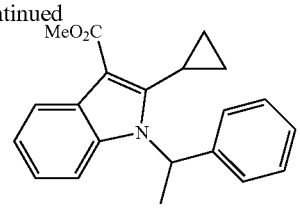

Step 1: methyl 2-bromo-1-(1-phenylethyl)-1H-indole-3-carboxylate. To a solution of methyl 2-bromo-1H-indole-3-carboxylate (1.0 g, 4.0 mmol) in dimethylformamide was added sodium hydride (0.32 g, 8.0 mmol, 60% in oil) under ice bath. The resulting mixture was stirred at room temperature for 0.5 hour. Then (1-bromoethyl)benzene (1.1 g, 6.0 mmol) was added in portion slowly. Then the mixture was stirred at room temperature for 1 hour. After the reaction, it was diluted with water (100 mL), and the product was extracted with ethyl acetate (100 mL), dried over anhydrous sodium sulfate, concentrated and purified by column Chromatography (silica gel: ethyl acetate:petroleum ether=1:8) to give the pure product methyl 2-bromo-1-(1-phenylethyl)-1H-indole-3-carboxylate (1.1 g, 75%) as a yellow oil.

Step 2: methyl 2-cyclopropyl-1-(1-phenylethyl)-1H-indole-3-carboxylate. To a solution of methyl 2-bromo-1-(1-phenylethyl)-1H-indole-3-carboxylate (0.30 g, 0.84 mmol) and tetrakis(triphenylphosphine) palladium(0) (0.09 g, 0.08 mmol) in tetrahydrofuran (20 mL) was added cyclopropylzinc(II) bromide (6.0 mL, 0.5 mol/L in tetrahydrofuran). The reaction mixture was stirred at reflux for 12 hours. After the reaction, it was cooled to room temperature and diluted with water (100 mL). The product was extracted with ethyl acetate (100 mL), dried over anhydrous sodium sulfate, concentrated and purified by column chromatography (silica gel: ethyl acetate:petroleum ether=1:10) to give the crude product methyl 2-cyclopropyl-1-(1-phenylethyl)-1H-indole-3-carboxylate (0.22 g, 82%) as a yellow oil.

Intermediate 7: Intermediate 7 was synthesized according to the scheme below:

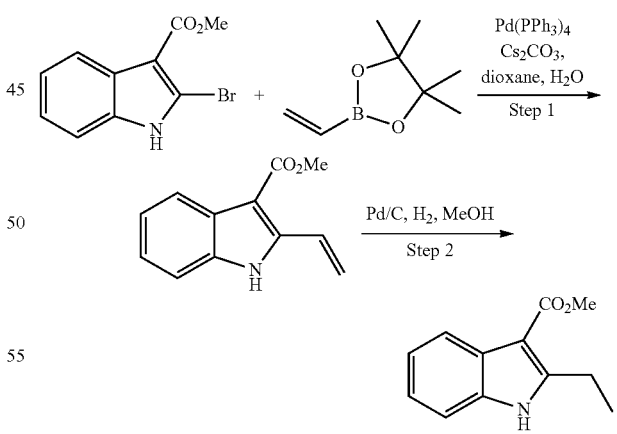

Step 1: methyl 2-vinyl-1H-indole-3-carboxylate. Methyl 2-bromo-1H-indole-3-carboxylate (100 mg, 0.19 mmol), 4,4,5,5-tetramethyl-2-vinyl-1,3,2-dioxaborolane (154 mg, 1 mmol), tetrakis(triphenylphosphine)palladium (116 mg, 0.1 mmol) and cesiumcarbonate (326 mg, 1 mmol) in dioxane/water (20 mL, 5 mL) were stirred at room temperature for 15 hours. Filterated the solid and the solvent was concentrated in vacuum. The resulted residue was purified by silica gel column (ethyl acetate/petroleum ether=1/2) to give methyl 2-vinyl-1H-indole-3-carboxylate as a pale yellow solid (60 mg, 76%) LRMS (M+H⁺) m/z: calcd 201.1 found 201.

Step 2: methyl 2-ethyl-1H-indole-3-carboxylate. Methyl 2-vinyl-1H-indole-3-carboxylate (80 mg, 0.4 mmol) and 10% palladium on charcoal (100 mg) in methanol (30 mL) were stirred under hydrogen 0.2 MPa at room temperature for 15 hours. The mixture was filterated the solid and concentrated in vacuum to obtain methyl 2-ethyl-1H-indole-3-carboxylate as a white solid (79 mg, 99%) LRMS (M+H⁺) m/z: calcd 203.1 found 203.

Intermediate 8. Intermediate 8 was synthesized according to the scheme below:

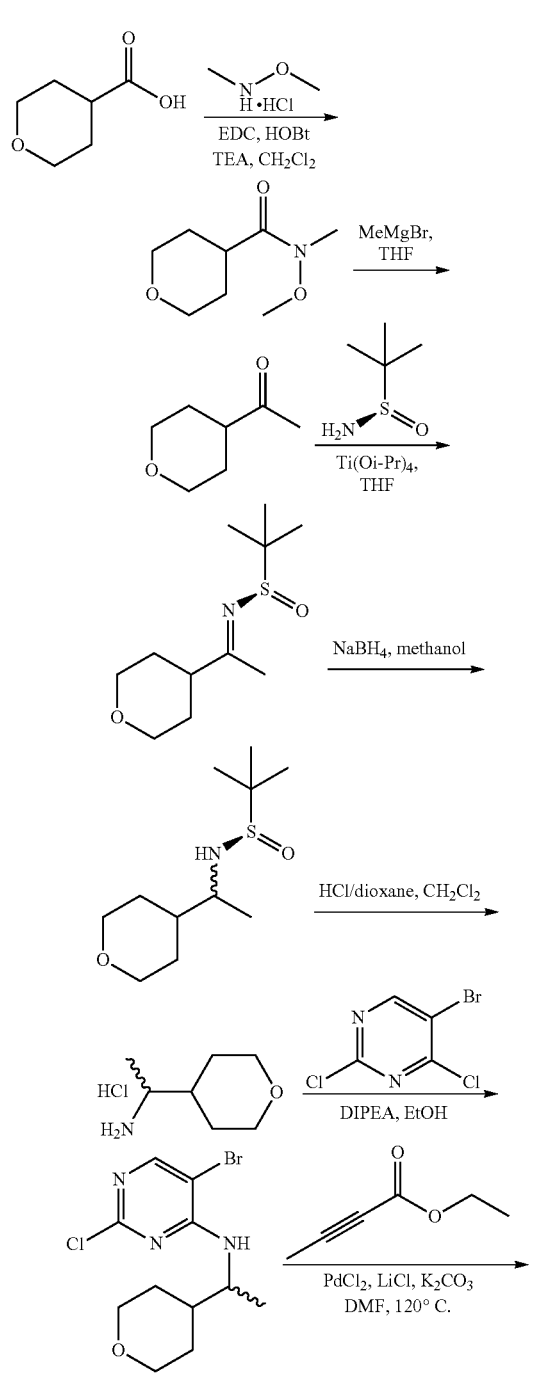

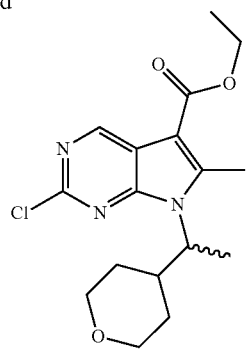

Intermediate 8

Step 1: N-methoxy-N-methyltetrahydro-2H-pyran-4-carboxamide. To a suspension of tetrahydro-2H-pyran-4-carboxylic acid (9.0 g, 69.2 mmol) in CH₂Cl₂ (300 mL) was added N,O-dimethylhydroxylamine hydrochloride (8.05 g, 83.0 mmol), 1-(3-dimethylaminopropyl)-3-ethyl carbodiimide (20.0 g, 103.8 mmol) and triethylamine (17.5 g, 173.0 mmol) at 29° C. under N₂. The reaction was stirred at 29° C. for 24 hrs. Then the mixture was filtered and the filtrate was washed with 1M HCl and saturated aqueous NaHCO₃. The organic layer was concentrated in vacuo to give N-methoxy-N-methyltetrahydro-2H-pyran-4-carboxamide (7.1 g, 59.7%) as a yellow oil. ¹H NMR (CDCl3, 400 MHz) δ 4.02-3.98 (m, 2H), 3.69 (s, 3H), 3.47-3.41 (m, 2H), 3.17 (s, 3H), 2.90 (t, J=11.6 Hz, 3H), 1.90-1.82 (m, 2H), 1.81-1.62 (m, 2H).

Step 2: (1-(tetrahydro-2H-pyran-4-yl)ethanone. To a solution of N-methoxy-N-methyltetrahydro-2H-pyran-4-carboxamide (3.5 g, 20.2 mmol) in tetrahydrofuran (30 mL) was added methylmagnesium bromide (12 mL, 36.4 mmol) at −65° C. under N₂. The reaction was stirred at −65-15° C. for 3 hrs. Then the mixture was quenched by water, extracted with ethyl acetate. The organic layer was washed with 1M HCl, saturated aqueous NaHCO₃ and concentrated in vacuo to give 1-(tetrahydro-2H-pyran-4-yl)ethanone (1.9 g, 73.6%) as a yellow oil. ¹H NMR (CDCl3, 400 MHz) δ 4.01-3.97 (m, 2H), 3.45-3.39 (m, 3H), 2.57-2.49 (m, 1H), 1.80-1.71 (m, 2H), 1.70-1.62 (m, 2H).

Step 3: ((R,E)-2-methyl-N-(1-(tetrahydro-2H-pyran-4-yl)ethylidene)propane-2-sulfinamide): To a solution of 1-(tetrahydro-2H-pyran-4-yl)ethanone (1.9 g, 14.8 mmol) in tetrahydrofuran (30 mL) was added (R)-2-methylpropane-2-sulfinamide (2.15 g, 17.8 mmol) and tetraethoxytitanium (5.06 g, 22.2 mmol) at 25° C. under N₂. The reaction was refluxed for 7 hrs. Then the mixture was quenched by water, extracted with ethyl acetate and filtered. The crude product was purified by column chromatography on silica gel eluted with dichloromethane:methanol=200:1 to give (R,E)-2-methyl-N-(1-(tetrahydro-2H-pyran-4-yl)ethylidene)propane-2-sulfinamide (1.5 g, 44.1%) as a yellow oil.

Step 4: ((R)-2-methyl-N-(1-(tetrahydro-2H-pyran-4-yl)ethyl)Propane-2-sulfinamide). To a solution of (R,E)-2-methyl-N-(1-(tetrahydro-2H-pyran-4-yl)ethylidene)propane-2-sulfinamide (1.25 g, 5.4 mmol) in tetrahydrofuran (6 mL) was added methanol (692 mg, 21.6 mmol) and NaBH₄ (821 mg, 21.6 mmol) at −65° C. under N₂. The reaction was stirred at −65-0° C. for 2 h. Then the reaction was quenched by water and extracted with ethyl acetate. The organic layer was washed with saturated aqueous NaHCO₃ and concentrated in vacuo to give crude (R)-2-methyl-N-(1-(tetrahydro-2H-pyran-4-yl)ethyl)Propane-2-sulfinamide (1.2 g, 52.1%) as a yellow oil.

Step 5: ((S)-1-(tetrahydro-2H-pyran-4-yl)ethanamine). To a solution of (R)-2-methyl-N-(1-(tetrahydro-2H-pyran-4-yl)ethyl)Propane-2-sulfinamide (1.2 g) in CH₂Cl₂ (4 mL) was added HCl-dioxane (4 mL) at 25° C. The reaction was stirred for 2 hrs. Then the mixture was concentrated in vacuo, diluted with water and washed with ethyl acetate to give crude (S)-1-(tetrahydro-2H-pyran-4-yl)ethanamine (1.0 g) as a yellow oil.

Step 5: ((S)-5-bromo-2-chloro-N-(1-(tetrahydro-2H-pyran-4-yl)ethyl)Pyrimidin-4-amine). To a solution of (S)-1-(tetrahydro-2H-pyran-4-yl)ethanamine (1.0 g, 7.75 mmol) in ethanol (15 mL) was added N,N-diisopropylethylamine (3.0 g, 23.3 mmol) and 5-bromo-2,4-ichloropyrimidine (2.0 g, 8.53 mmol) at 25° C. under N₂. The reaction was stirred at 25° C. for 18 hrs. The mixture was diluted with ethyl acetate and washed with water. The crude product was purified by column chromatography on silica gel eluted with petroleum ether:ethyl acetate=20:1 to give (S)-5-bromo-2-chloro-N-(1-(tetrahydro-2H-pyran-4-yl)ethyl)Pyrimidin-4-amine (1.5 g, 60.7%) as a yellow oil.

Step 6: ((S)-ethyl 2-chloro-6-methyl-7-(1-(tetrahydro-2H-pyran-4-yl)ethyl)-7H-pyrrolo[2,3-d]pyrimidine-5-carboxylate), Intermediate 8. To a solution of (S)-5-bromo-2-chloro-N-(1-(tetrahydro-2H-pyran-4-yl)ethyl)Pyrimidin-4-amine (1.5 g, 4.7 mmol) in DMF (20 mL) was added ethyl but-2-ynoate (1.05 g, 9.4 mmol), lithium chloride (296 mg, 7.05 mmol), palladium(II)acetate (105 mg, 0.47 mmol) and potassium carbonate (1.95 g, 14.1 mmol) at 25° C. under N₂. The reaction was stirred at 120° C. for 3 hrs. The mixture was filtered and the crude product was purified by column chromatography on silica gel eluted with petroleum ether:ethyl acetate=30:1 to give (S)-ethyl 2-chloro-6-methyl-7-(1-(tetrahydro-2H-pyran-4-yl)ethyl)-7H-pyrrolo[2,3-d]pyrimidine-5-carboxylate (270 mg, 16.4%) as a yellow oil.

Intermediate 9: Intermediate 9 was synthesized according to the scheme below:

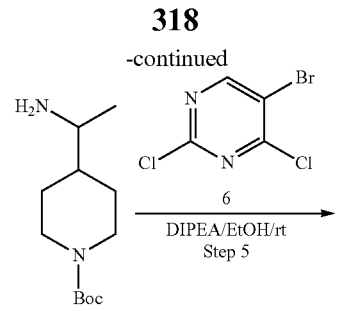

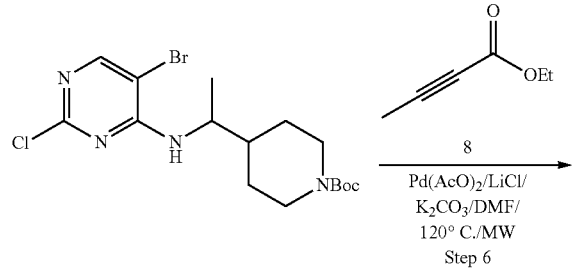

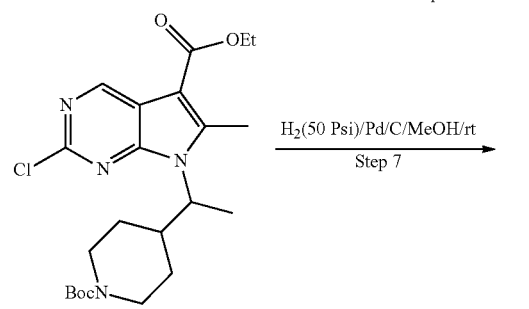

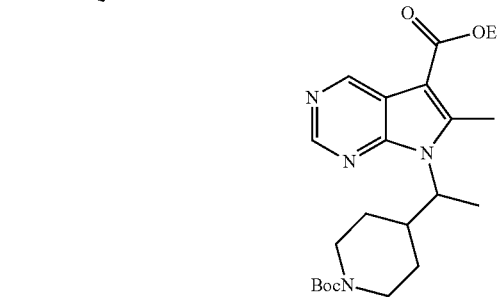

Intermediate 9

Step 1: tert-butyl 4-(methoxy(methyl)carbamoyl)piperidine-1-carboxylate. To a solution of 1-(tert-butoxycarbonyl)piperidine-4-carboxylic acid (5.0 g, 21.8 mmol) in dichloromethane (80 mL) were added N,O-dimethylhydroxylamine hydrochloride (2.55 g, 26.1 mmol), 2-(3H-[1,2,3]triazolo[4,5-b]pyridin-3-yl)-1,1,3,3-tetramethylisouronium hexafluorophosphate(V) (9.95 g, 26.1 mmol), N-ethyl-N-isopropylpropan-2-amine (8.46 g, 65.42 mmol) and stirred at 30° C. for 16 hours. The reaction was quenched by adding water (100 ml) and extracted with ethyl acetate (200 ml*3). The combined organic layers was washed with brine, dried over sodium sulfate and concentrated under vacuum to give tert-butyl 4-(methoxy(methyl)carbamoyl)piperidine-1-carboxylate. (5.7 g, yield 97.6%). LRMS (M+H⁺) m/z: calcd 272.17. found 273.17.

Step 2: tert-butyl 4-acetylpiperidine-1-carboxylate. To a solution of tert-butyl 4-(methoxy(methyl)carbamoyl)piperidine-1-carboxylate (4.0 g, 14.69 mmol) in tetrahydrofuran (50 mL) was added methylmagnesium bromide solution (5.25 g, 44.06 mmol, 3M) at −70° C. over 0.5 hour. The resultant mixture was stirred at room temperature for 16

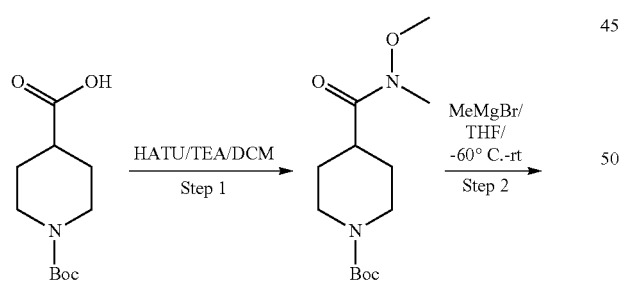

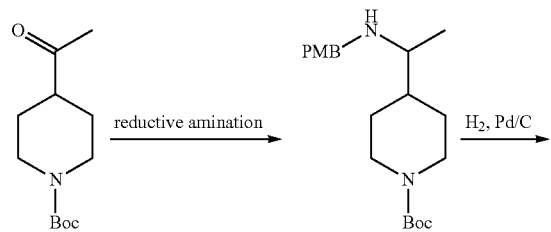

hours. The reaction solution was adjusted pH to 6.0 by 1.0M hydrochloride solution. The aqueous phase was extracted with ethyl acetate (100 ml*3). The combined organic layers was washed with brine, dried over sodium sulfate and concentrated under vacuum to give tert-butyl 4-acetylpiperidine-1-carboxylate as a yellow liquid (2.6 g, yield 77.8%). LRMS (M+H$^+$) m/z: calcd 227.15. found 228.

Step 3: tert-butyl 4-(1-aminoethyl)piperidine-1-carboxylate. To a solution of tert-butyl 4-acetylpiperidine-1-carboxylate (10 g, 44.05 mmol) in tetrahydrofuran (100 ml) and methanol (100 ml) were added ammonium acetate (20 g, 264.3 mmol) and sodium cyanotrihydroborate (20 g, 264.3 mmol). The reaction mixture was stirred at room temperature overnight. The reaction mixture was concentrated in vacuum. The crude product was added water (100 ml), and extracted with ethyl acetate (50 mL×3). The organic layer was dried over sodium sulfate and concentrated to give tert-butyl 4-(1-aminoethyl)piperidine-1-carboxylate (6 g, yield: 60%) as a colorless liquid. LRMS (M+H$^+$) m/z: calcd 228.15. found 229.

Step 4: tert-butyl 4-(1-((5-bromo-2-chloropyrimidin-4-yl) amino)ethyl)piperidine-1-carboxylate. To the solution of tert-butyl 4-(1-aminoethyl)piperidine-1-carboxylate (5 g, 21.9 mmol) in ethanol (50 ml) were added 5-bromo-2,4-dichloropyrimidine (5.97 g, 26.3 mmol), and N-ethyl-N-isopropylpropan-2-amine (8.48 g, 65.7 mmol). The resulting mixture was stirred at room temperature overnight. The reaction mixture was concentrated in vacuum, and the crude product was added to water (100 ml). The aqueous layer was extracted with ethyl acetate (50 mL×4) and organic layer was dried over sodium sulfate and concentrated to give crude product tert-butyl 4-(1-((5-bromo-2-chloropyrimidin-4-yl)amino)ethyl) piperidine-1-carboxylate (7 g, yield: 97.2%) as a yellow oil. LRMS (M+H$^+$) m/z: calcd 418. found 419.

Step 5: ethyl 7-(1-(1-(tert-butoxycarbonyl)piperidin-4-yl) ethyl)-2-chloro-6-methyl-7H-pyrrolo[2,3-d]pyrimidine-5-carboxylate. Into the vial were added tert-butyl 4-(1-((5-bromo-2-chloropyrimidin-4-yl)amino)ethyl)piperidine-1-carboxylate (400 mg, 0.95 mmol) and ethyl but-2-ynoate (128 mg, 1.14 mmol), palladium(II) diacetate (42 mg, 0.19 mmol), lithium chloride (51.8 mg, 1.23 mmol), carbonic acid (393 mg, 2.85 mmol) in N, N-dimethyl formamide. The mixture was degassed for 10 min and refilled with nitrogen, and irradiated in the microwave on a Biotage smith synthesizer at 120° C. for 40 min. The reaction mixture was cooled down and added to water (30 ml), and extracted with ethyl acetate (10 ml×3). The organic layer was dried over sodium sulfate and concentrated. The crude product was purified by column chromatography on silica gel (petroleum/ethyl acetate: 20:1 to 10:1) to give compound ethyl 7-(1-(1-(tert-butoxycarbonyl)piperidin-4-yl)ethyl)-2-chloro-6-methyl-7H-pyrrolo[2,3-d]pyrimidine-5-carboxylate (75 mg, yield: 17.4%) as a yellow oil. LRMS (M+H$^+$) m/z: calcd 450.2. found 451.

Step 6: tethyl 7-(1-(1-(tert-butoxycarbonyl)piperidin-4-yl) ethyl)-6-methyl-7H-pyrrolo[2,3-d]pyrimidine-5-carboxylate, Intermediate 9. A mixture of compound ethyl 7-(1-(1-(tert-butoxycarbonyl)piperidin-4-yl)ethyl)-2-chloro-6-methyl-7H-pyrrolo[2,3-d]pyrimidine-5-carboxylate (75 mg, 0.16 mmol) and Pd/C(10 mg) in methanol (10 mL) was stirred under 50 psi of hydrogen at room temperature overnight. The reaction mixture was filtered and the filtrate was concentrated to give product ethyl 7-(1-(1-(tert-butoxycarbonyl)piperidin-4-yl)ethyl)-6-methyl-7H-pyrrolo[2,3-d]pyrimidine-5-carboxylate (50 mg, yield: 72%). LRMS (M+H$^+$) m/z: calcd 450.2. found 451.

Intermediate 10: Intermediate 10 was synthesized according to the scheme below:

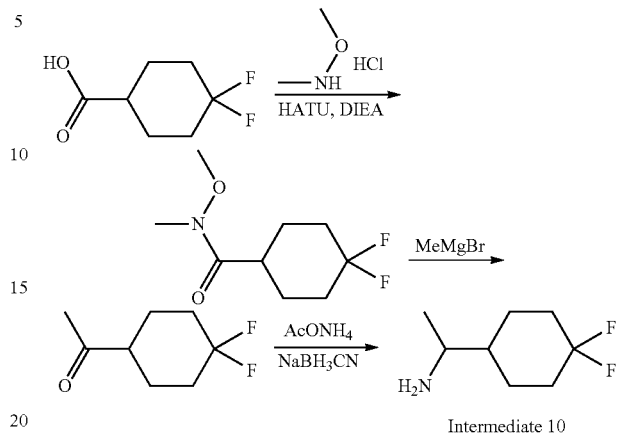

Intermediate 10

Step 1: 4,4-difluoro-N-methyl cyclohexanecarboxamide. To a solution of 4,4-difluorocyclohexanecarboxylic acid (5 g, 30.49 mmol) in DCM (40 mL) were added DIPEA (11.8 g, 91.46 mmol) and HATU (17.38 g, 45.73 mmol). The mixture was stirred for 0.5 hr. The N,O-dimethylhydroxylamine hydrochloride (3.56 g, 36.58 mmol) was added to the mixture. The mixture was stirred at 28° C. for 12 hr. Water (20 mL) was added and the mixture was extracted by CH$_2$Cl$_2$ (30 mL*3). The organic layer was washed with brine and dried over sodium sulfate. The organic layer was concentrated to give the crude product, the crude product was purified by column chromatography on silica gel eluted with (petroleum ether/ ethyl acetate 10:1→2:1) to gave 4,4-difluoro-N-methyl cyclohexanecarboxamide (4.6 g, 73.36%) for next step.

Step 2: 1-(4,4-difluorocyclohexyl)ethanone. To a solution of 4,4-difluoro-N-methyl cyclohexanecarboxamide (3 g, 14.5 mmol) in THF (20 mL) were added CH$_3$MgBr (5.19 g, 43.5 mmol) in −78° C. The mixture was stirred at −78° C. for 5 hr. Water (10 mL) was added and the mixture was concentrated and extracted by CH$_2$Cl$_2$ (40 mL*3). The organic layer was washed with brine and dried over sodium sulfate. The organic layer was concentrated to give 1-(4,4-difluorocyclohexyl) ethanone (1.5 g, crude) for next step.

Step 3: 1-(4,4-difluorocyclohexyl)ethanamine, Intermediate 10. To a solution of 1-(4,4-difluorocyclohexyl)ethanone (1 g, 6.17 mmol) in THF (5 mL) was added a solution of ammonium acetate (9.51 g, 123.4 mmol) and NaBH$_3$CN (3.82 g, 61.7 mmol) in MeOH. The mixture was stirred for 48 hr. The reaction mixture was quenched with aqueous NaHCO$_3$ and extracted with tert-Butyl-methyl ether (20 mL*3). The combined organic layers were washed with 1N HCl, and the organic and aqueous layer were separated. The aqueous layer was brought to above pH 8 with 2N NaOH and extracted with ethyl acetate (20 mL*3). The organic layer was washed with brine, dried over sodium sulfate. The organic layer was concentrated to give 1-(4,4-difluorocyclohexyl) ethanamine (545 mg, crude) for next step.

Intermediate 11: Intermediate 11 was synthesized according to the scheme below:

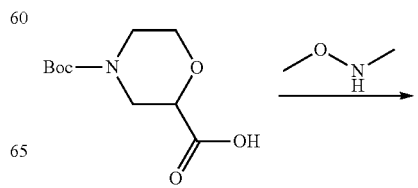

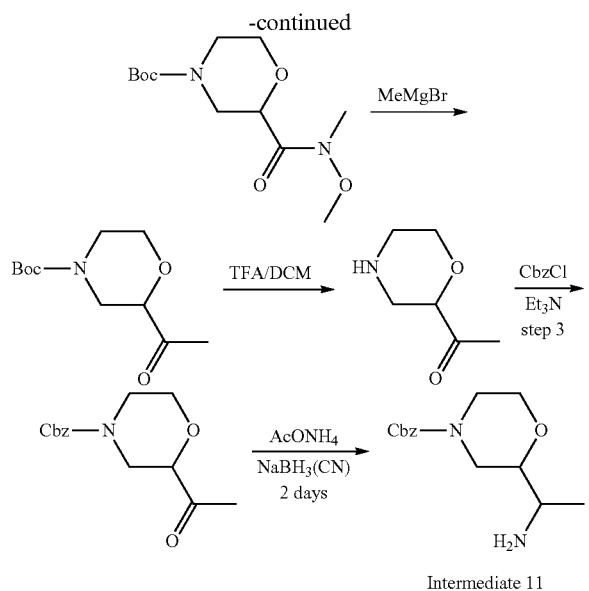

Intermediate 11

Step 1: tert-butyl 2-(methoxy(methyl)carbamoyl)morpholine-4-carboxylate. To a solution of 4-(tert-butoxycarbonyl)morpholine-2-carboxylic acid (10 g, 43 mmol) in DCM (60 mL) was added HATU (19 g, 50 mmol) in portions, The mixture was stirred at room temperature for 0.5 h. Then DIPEA (12.9 g, 100 mmol) and N, O-dimethylhydroxylamine hydrochloride (5.0 g, 51.5 mmol) were added in the mixture. The mixture was stirred at room temperature overnight. Water (40 mL) was added and the mixture was extracted by DCM (100 mL*3). The organic layer was washed with brine (5 mL) and dried over sodium sulfate. Concentration and purification by column chromatography on silica gel (eluted: petroleum ether/ethyl acetate=20/1-10/1) to give tert-butyl 2-(methoxy(methyl)carbamoyl)morpholine-4-carboxylate (10 g, 84%).

Step 2: tert-butyl 2-acetylmorpholine-4-carboxylate. To a solution of tert-butyl 2-(methoxy(methyl)carbamoyl)morpholine-4-carboxylate (11 g, 4.0 mmol) in THF (40 mL) was added $CH_3MgBr$ (4 mL, 12 mmol) at −78° C. The mixture was stirred at −78° C. for 3 hr. Water (20 mL) was added and the mixture was extracted by ethyl acetate (80 mL*3). The organic layer was washed with brine and dried over sodium sulfate. The crude product was concentrated and purified by column chromatography on silica gel (eluted: petroleum ether/ethyl acetate=10/1) to give tert-butyl 2-acetylmorpholine-4-carboxylate (8 g, 86%).

Step 3: 1-(morpholin-2-yl)ethanone. To a solution of tert-butyl 2-acetylmorpholine-4-carboxylate (6.9 g, 30.0 mmol) in DCM (80 mL) was added TFA (20 mL). The mixture was stirred at room temperature for 4 hr. The reaction mixture was concentrated to give 1-(morpholin-2-yl)ethanone (3.9 g, crude) for next step.

Step 4: benzyl 2-acetylmorpholine-4-carboxylate. To a solution of 1-(morpholin-2-yl)ethanone (3.9 g, 30.0 mmol) in DCM (60 mL) was added triethylamine (1.0 g, 10 mmol) to adjust pH 9. Then benzyl carbonochloridate (5.6 g, 33.0 mmol) and triethylamine (3.0 g, 30.0 mmol) were added and the mixture was stirred at room temperature for 16 hr. The reaction solution was added $H_2O$ (20 mL) and extracted by DCM (100 mL*3). The organic layer was concentrated and purified by column chromatography on silica gel (eluted: petroleum ether/ethyl acetate=20/1-15/1-10/1) to give benzyl 2-acetylmorpholine-4-carboxylate (5.0 g, 63%).

Step 5: benzyl 2-(1-aminoethyl)morpholine-4-carboxylate, Intermediate 11. To a solution of benzyl 2-acetylmorpholine-4-carboxylate (5.0 g, 19 mmol) in THF/MeOH (1/5, 100 mL) were added $AcONH_4$ (14.6 g, 190 mmol) and $NaBH_3CN$ (11.8 g, 190 mmol). The mixture was stirred at room temperature for 50 hr. The mixture was concentrated to give the crude. Water (20 mL) was added and the mixture was extracted by ethyl acetate (60 mL*3). 1N HCl was added into the combined organic layers. The aqueous layer was concentrated, brought to above pH >8 with 2N NaOH and extracted by ethyl acetate (60 mL*3). The organic layer was washed with brine, dried over sodium sulfate. The mixture was concentrated to give benzyl 2-(1-aminoethyl)morpholine-4-carboxylate (2.0 g, 40%).

Example 75

$IC_5$ Measurements for Inhibitors Using EZH2

EZH2 Assay: Assays were carried out by mixing rPRC2 together with biotinylated oligonucleosome substrates in the presence of the radio-labeled enzyme co-factor, S-adenosyl-L-methionine ($^3H$ SAM) (Perkin Elmer) and monitoring the enzymatically mediated transfer of tritiated methyl groups from $^3H$ SAM to histone lysine residues. The amount of resulting tritiated methyl histone product was measured by first capturing the biotinylated oligonucleosomes in streptavidin (SAV) coated FlashPlates (Perkin Elmer), followed by a wash step to remove un-reacted $^3H$ SAM, and then counting on a TopCount NXT 384 well plate scintillation counter (Perkin Elmer). The final assay conditions for EZH2 were as follows: 50 mM Tris Buffer pH 8.5, 1 mM DTT, 69 μM Brij-35 detergent, 5.0 mM $MgCl_2$, 0.1 mg/mL BSA, 0.2 μM $^3H$ SAM, 0.2 μM biotinylated oligonucleosomes, 3.6 μM H3K27me3 peptide and 2 nM EZH2.

Compound $IC_{50}$ measurements were obtained as follows: Compounds were first dissolved in 100% DMSO as 10 mM stock solutions. Ten point dose response curves were generated by dispensing varying amounts of the 10 mM compound solution in 10 wells of the 384 well plate (Echo; Labcyte), pure DMSO was then used to backfill the wells to insure all wells have the same amount of DMSO. A 12.5 μL volume of the HMT enzyme, H3K27me3 peptide and oligonucleosome substrate in assay buffer was added to each well of the assay plate using a Multidrop Combi (ThermoFisher). Compounds were pre-incubated with the enzyme for 20 min, followed by initiation of the methyltransferase reaction by addition of 12.5 μL of $^3H$ SAM in assay buffer (final volume=25 μL). The final concentrations of compounds ranged from a top default concentration of 80 LM down to 0.16 μM in ten 2-fold dilution steps. Reactions were carried out for 60 minutes and quenched with 20 μL per well of 1.96 mM SAH, 50 mM Tris pH 8.5, 200 mM EDTA. Stopped reactions were transferred to SAV coated Flashplates (Perkin Elmer), incubated for 120 min, washed with a plate washer, and then read on the TopCount NXT (1.0 min/well) to measure the amount of methyl histone product formed during the reaction. The amount of methyl histone product was compared with the amount of product formed in the 0% and 100% inhibition control wells allowing the calculation of % Inhibition in the presence of the individual compounds at various concentrations. $IC_{50}$'s were computed using a 4 parameter fit non-linear curve fitting software package (XLFIT, part of the database package, ActivityBase (IDBS)) where the four parameters were $IC_{50}$, Hill slope, pre-transitional baseline (0% INH), and post-transitional baseline (100% INH); with the latter two parameters being fixed to zero and 100%, respectively, by default.

Assay for Y641N EZH2 was performed as above using reconstituted H3K27Me2 oligonucleosomes as substrate.

Table 2 shows the activity of selected compounds of this invention in the EZH2 and Y641N EZH2 activity inhibition assay. $IC_{50}$ values are reported as follows: "A" indicates an $IC_{50}$ value of less than 100 nM; "B" indicates an $IC_{50}$ value of 100 nM to 1 µM; "C" indicates an $IC_{50}$ value of greater than 1 LM and less than 10 µM for each enzyme; "D" indicates an $IC_{50}$ value of greater than 10 µM for each enzyme; and "*(X µM)" indicates that no inhibition was observed at the highest concentration (i.e., X µM) of compound tested.

TABLE 2

IC50 Values for Compounds of Formula I against EZH2 and Y641N EZH2 Mutant Enzymes.

| Compound No. | EZH2 $IC_{50}$ | Y641N EZH2 $IC_{50}$ |
|---|---|---|
| 100 | C | D |
| 101 | D | D |
| 102 | D | D |
| 103 | D | D |
| 104 | D | D |
| 105 | B | C |
| 106 | B | C |
| 107 | D | D |
| 108 | D | D |
| 109 | *(10 µM) | *(10 µM) |
| 110 | *(10 µM) | *(10 µM) |
| 111 | A | A |
| 112 | *(10 µM) | *(10 µM) |
| 113 | B | C |
| 114 | A | A |
| 115 | A | A |
| 116 | A | B |
| 117 | A | B |
| 118 | C | *(10 µM) |
| 119 | A | B |
| 121 | *(0.5 µM) | *(10 µM) |
| 122 | | |
| 123 | A | B |
| 124 | | |
| 126 | B | C |
| 128 | | |
| 129 | | |
| 130 | | |
| 131 | *(1.0 µM) | *(1.0 µM) |
| 132 | A | B |
| 133 | A | B |
| 134 | A | B |
| 135 | C | D |
| 136 | A | A |
| 137 | A | A |
| 138 | B | C |
| 139 | B | C |
| 140 | | |
| 141 | B | C |
| 142 | B | C |
| 143 | A | C |
| 144 | A | B |
| 145 | A | B |
| 146 | A | B |
| 147 | A | B |
| 148 | A | B |
| 149 | B | C |
| 150 | B | B |
| 164 | A | B |
| 165 | A | B |
| 166 | A | B |
| 167 | B | B |
| 168 | B | C |
| 169 | A | B |
| 170 | A | B |
| 171 | A | A |
| 172 | A | B |
| 173 | A | B |
| 174 | B | C |
| 175 | A | A |
| 176 | A | B |
| 177 | A | B |
| 178 | B | C |
| 179 | A | B |
| 180 | A | A |
| 181 | A | A |
| 182 | *(10 µM) | *(0.5 µM) |
| 183 | A | A |
| 184 | B | C |
| 185 | B | C |
| 186 | B | B |
| 187 | A | B |
| 188 | B | C |
| 189 | B | C |
| 191 | A | A |
| 192 | A | B |
| 193 | B | C |
| 194 | B | C |
| 195 | B | *(0.5 µM) |
| 196 | B | B |
| 197 | B | B |
| 198 | C | C |
| 199 | B | C |
| 200 | B | C |
| 201 | A | B |
| 202 | B | C |
| 203 | A | B |
| 204 | A | B |
| 205 | B | B |
| 206 | B | C |
| 207 | A | B |
| 208 | B | B |
| 209 | C | *(10 µM) |
| 210 | A | B |
| 211 | A | B |
| 212 | A | B |
| 213 | A | B |
| 214 | B | C |
| 215 | B | C |
| 216 | B | C |
| 217 | B | B |
| 218 | A | A |
| 219 | A | A |
| 220 | A | B |
| 221 | B | C |
| 222 | B | B |
| 223 | A | B |
| 224 | A | A |
| 225 | A | A |
| 226 | B | C |
| 227 | A | A |
| 228 | B | B |
| 229 | C | D |
| 230 | A | B |
| 231 | A | B |
| 232 | B | C |
| 233 | B | C |
| 234 | C | D |
| 235 | B | C |
| 236 | *(0.5 µM) | *(10 µM) |
| 237 | B | C |
| 238 | B | C |
| 239 | A | A |
| 240 | A | B |
| 241 | A | B |
| 242 | A | B |
| 243 | A | B |
| 244 | B | C |
| 245 | A | B |
| 246 | B | B |
| 247 | A | A |
| 248 | A | B |
| 249 | B | C |

TABLE 2-continued

IC50 Values for Compounds of Formula I against EZH2 and Y641N EZH2 Mutant Enzymes.

| Compound No. | EZH2 IC$_{50}$ | Y641N EZH2 IC$_{50}$ |
|---|---|---|
| 250 | A | B |
| 251 | B | B |
| 252 | A | B |
| 253 | A | B |
| 254 | B | B |
| 255 | A | C |
| 256 | A | B |
| 257 | B | C |
| 258 | A | A |
| 259 | A | A |
| 260 | B | C |
| 261 | A | A |
| 262 | B | C |
| 263 | A | B |
| 264 | A | B |
| 265 | A | B |
| 266 | B | B |
| 267 | A | B |
| 268 | A | B |
| 269 | B | C |
| 271 | C | C |
| 272 | C | *(10 μM) |
| 273 | A | A |
| 274 | A | A |
| 275 | A | A |
| 276 | A | A |
| 277 | A | A |
| 278 | B | C |
| 279 | A | B |
| 280 | B | C |
| 281 | A | A |
| 282 | A | A |
| 283 | A | B |
| 284 | A | B |
| 285 | B | C |
| 286 | A | B |
| 287 | B | C |
| 288 | A | A |
| 290 | A | B |
| 291 | A | B |
| 292 | A | B |
| 293 | A | B |
| 294 | A | A |
| 295 | B | C |
| 296 | B | C |
| 297 | A | B |
| 298 | A | A |
| 299 | A | A |
| 300 | A | A |
| 301 | A | B |
| 302 | B | C |
| 303 | A | B |
| 304 | A | A |
| 305 | A | B |
| 306 | A | A |
| 307 | A | A |
| 308 | B | B |
| 309 | B | C |
| 310 | A | A |
| 311 | A | A |
| 312 | B | B |
| 313 | A | A |
| 314 | A | A |
| 315 | A | B |
| 316 | A | A |
| 317 | A | A |
| 318 | A | A |
| 319 | A | A |
| 320 | A | A |
| 321 | A | A |
| 322 | B | B |
| 323 | A | B |
| 324 | A | B |
| 326 | A | A |
| 327 | A | A |
| 329 | B | B |
| 330 | A | A |
| 331 | A | B |
| 332 | A | A |
| 333 | A | B |
| 334 | A | B |
| 335 | A | A |
| 336 | A | A |
| 337 | A | A |
| 338 | A | B |
| 339 | A | A |
| 340 | B | C |
| 341 | A | A |
| 342 | A | A |
| 343 | A | A |
| 344 | A | A |
| 345 | A | A |
| 346 | A | A |
| 347 | A | A |
| 348 | A | A |
| 349 | A | A |
| 350 | A | A |
| 351 | A | B |
| 352 | A | A |
| 353 | A | A |
| 354 | A | A |
| 355 | A | A |
| 356 | A | A |
| 357 | A | A |
| 358 | A | A |
| 359 | A | A |
| 360 | A | A |
| 361 | A | A |
| 362 | A | A |
| 363 | A | A |
| 364 | A | B |
| 365 | A | A |
| 366 | A | A |
| 367 | A | A |
| 368 | A | A |
| 369 | A | A |
| 370 | A | A |
| 371 | A | A |
| 372 | B | *(0.5 uM) |
| 373 | A | A |
| 374 | A | A |
| 375 | A | A |
| 376 | A | A |
| 377 | A | A |
| 395 | A | B |
| 445 | *(10 uM) | *(10 uM) |
| 446 | *(10 uM) | *(10 uM) |

Example 76

EC$_{50}$ Measurements for Inhibitors in Hela Cell Assays

H3K27me3 MSD Hela Assay. Trypsinized HeLa cells were counted and diluted in 10% DMEM (Life Technologies, Cat. #10569) to 5000 cells/75 μL. Seventy-five μL of cells were place in each well of a 96-well flat-bottomed plate and incubated at 37° C. for 4 hours. Twenty-five μL of test compound (at various concentrations) was added to the cells and incubation continued at 37° C. for 96 hours. Media was then removed and the cells rinsed once with ice cold PBS. Forty μL of ice-cold MSD Buffer AT (10 mM HEPES, pH 7.9, 5 mM MgCl$_2$, 0.25M sucrose, Benzonase (1:10000), 1% Triton X-100 supplemented with fresh lx Protease Inhibitor cocktail and 1 mM 4-(2-Aminoethyl)benzenesulfonyl fluoride hydrochloride (AEBSF)) was added to each well and the plates placed on ice for 30 minutes. Ten μL of 5M NaCl was then added to each well and incubation on ice continued for another 15 minutes. The material in each well was suspended pipetting up and down and then transferred to a new 96 well plate. The emptied wells were rinsed with 150 uL ice-cold 20 mM Tris pH 7.5, 1 mM EDTA, 1 mM EGTA, supplemented with fresh 1× Protease Inhibitor cocktail and 1 mM AEBSF ("NO salt NO detergent buffer) and transferred to the respective wells in the new plate. Three hundred μL of NO Salt NO detergent buffer was then added to each well of lysates and the plates frozen at −80° C.

On the same day, an appropriate number of MSD standard bind 96-well plates were coated with 30 μL/well of total H3 capture antibody (Millipore, Cat #MAB3422) at 1 μg/mL concentration in PBS. The antibody solution was evenly distributed first by tapping gently on the sides of the plates and then by shaking the plates for a few minutes at 1000 rpm. Antibody coated plates were stored at 4° C. overnight.

The next day the lysates are thawed to RT. The antibody coated MSD plates are washed 3× with TBS-T (Tris-buffered saline (Fisher Scientific, Cat #BP2471-1)+0.2% Tween-20). One-hundred fifty μL of 5% Blocker A in TBS-T is added to each well. The wells are covered and shaken on a shaker at RT for one hour. The Blocker A step is repeated a second time. After removing the blocker, 25 μL of cell lysate is transferred into each antibody coated well. The plates are shaken for 2 hours at RT, the lysate removed and the plates again washed with Blocker A in TBS-T. Twenty-five μL of appropriate freshly prepared antibody mix (including both primary and secondary antibodies) is added to each well and the plates shaken for 1 hour at RT. The antibody mix used was one (or both) of those indicated in the table below:

| Ab | Concentration (μg/mL) | Primary Ab (μL) | Anti-rabbit detection Ab (μL) | 1% blocker A (μL) |
|---|---|---|---|---|
| H3K27me3 | 33 | 37.88 | 5.00 | 5000 |
| H3 | 12 | 52.08 | 5.00 | 5000 |

Both H3 antibodies were obtained from Cell Signalling (Cat #s 4499 and 9733). The goat anti-rabbit antibody was obtained from Meso-Scale Discovery (Cat #R32AB-1).

The antibody mix was then removed and the wells washed with Blocker A. One hundred-fifty μL of freshly prepared 1×MSD Read Buffer (Meso-Scale Discovery; Cat #R927C-2) was then added to each well and the plates read on a MSD Sector 2400 Plate Reader.

Data was analyzed using Assay Assistant (Constellation Pharmaceuticals In-house product) and Activity Base (IDBS Ltd, Surrey, UK) template. Data files were imported to Assay Assistant and assay conditions were specified. A unique Analysis ID was created and the data files exported to Activity Base. An analysis template was created on Activity Base to measure dose-dependent inhibition of H3K27me3 mark and cell viability respectively. Readout of DMSO wells were used to normalize the data. Resulting curves were fitted using Activity base software Model 205 (IDBS Ltd, Surrey, UK). The data was checked for quality, validated and integrated in excel format using SARview (IDBS Ltd, Surrey, UK).

H3K27Me3 Alpha Hela Assay (AlphaLISA). Ten different doses of each test compound (in a series of 3-fold dilutions) were plated in duplicate 384-well tissue culture treated plates (Catalog #781080; Greiner Bio One; Monroe, N.C.). Hela cells grown in culture were trypsinized and counted using a Countess' cell counter (Catalog #C10281; Life Technologies, Grand Island, N.Y.). Cell were diluted to 67,000 cells per mL in 10% DMEM (Catalog #10569-010 Life Technologies, Grand Island, N.Y.) and 15 μL (1,000 cells) were plated into each well using the Biotek MicroFlo™ Select Dispenser (BioTek Instruments. Inc. Vermont, USA).) of the 384-well plate. Plates were incubated at 37° C./5% $CO_2$ for 72 hrs. One of the duplicate plates was processed for HeLa assay and the other for viability.

To the plate processed for AlphaLISA was added 5 μL per well Cell-Histone Lysis buffer (1×) (Catalog #AL009F1 Perkin Elmer; Waltham, Mass.) and the plate was incubated at RT for 30 minutes on a plate shaker with low speed (Model#4625-Q Thermo Scientific; Waltham, Mass.). Then, 10 μL per well Histone Extraction buffer (catalog #AL009F2; Perkin Elmer; Waltham, Mass.) was added and the plate further incubated at RT for 20 min on plate shaker with low speed. To each well was then added 10 μL per well of a 5× mix of anti-K27me3 acceptor beads plus Biotinylated anti-Histone H3 (C-ter) Antibody (diluted to 3 nM final) (Catalog #AL118 Perkin Elmer; Waltham, Mass.). Dilution of the acceptor beads and then anti-Histone H3 was with 1× Histone Detection buffer (Catalog #AL009F3 Perkin Elmer; Waltham, Mass.) which was produced diluted from the 10× stock provided. The plate was sealed with an aluminum plate sealer and incubated at 23° C. for 60 min. We then added 10 μL 5× solution of Streptavidin Donor beads (Catalog #6760002 Perkin Elmer; Waltham, Mass.) (20 μg/mL final in 1× Histone Detection Buffer), sealed the plate with Aluminum plate sealer and incubated at 23° C. for 30 min. The plates were then read using an EnVision—Alpha Reader (model #2104 Perkin Elmer; Waltham, Mass.).

Cell viability was assayed by adding 15 μL of Cell Titer Glo ((Catalog #G7571 Promega Madison, Wis.) to each well with cells with media. The plates were incubated foat RT for 15-20 minutes on a plate shaker at low speed. The plates were then read using an EnVision-Alpha Reader (model #2104 Perkin Elmer; Waltham, Mass.).

Data from both assays was analyzed using Assay Assistant (Constellation Pharmaceuticals In-house product) and Activity Base (IDBS Ltd. Surrey, UK) template. Data files were imported to Assay Assistant and assay conditions were specified. A unique Analysis ID was created and the data files exported to Activity Base. An analysis template was created on Activity Base to measure dose-dependent inhibition of H3K27me3 mark and cell viability respectively. Readout of DMSO wells were used to normalize the data. Resulting curves were fitted using Activity base software Model 205 (IDBS Ltd, Surrey, UK). The data was checked for quality, validated and integrated in excel format using SARview (IDBS Ltd, Surrey, UK).

Table 3 shows the activity of selected compounds of this invention in the two different HeLa cell assays described above. $EC_{50}$ values are reported as follows: "A" indicates an $EC_{50}$ value of less than 400 nM; "B" indicates an $EC_{50}$ value of 400 nM to 2 μM; "C" indicates an $EC_{50}$ value of greater than 2 μM and less than 10 μM for each enzyme; "D" indicates an $EC_{50}$ value of greater than 10 μM for each enzyme; and "*(X μM)" indicates that no inhibition was observed at the highest concentration (i.e., X μM) of compound tested.

TABLE 3

Ec50 Values for Selected Compounds of the Invention In Hela Cells Expressing H3k27 Mutant EZH2.

| Compound No. | H3K27me3_Alpha_HeLa (EC50) | H3K27me3_MSD_HeLa_(EC50) |
|---|---|---|
| 114 | B | A |
| 116 |   | B |
| 123 |   | B |
| 134 |   | C |
| 137 |   | B |
| 143 |   | C |
| 144 |   | C |
| 145 |   | C |
| 146 |   | B |
| 147 |   | B |
| 165 |   | C |
| 166 |   | C |
| 169 |   | D |
| 170 |   | C |
| 171 |   | C |
| 172 |   | C |
| 175 |   | B |
| 181 |   | B |
| 187 | B | B |
| 191 |   | C |
| 192 |   | C |
| 201 |   | B |
| 203 |   | C |
| 204 |   | B |
| 207 |   | C |
| 210 |   | C |
| 211 |   | B |
| 212 | B | B |
| 215 |   | C |
| 218 |   | A |
| 219 |   | B |
| 222 |   | D |
| 224 | A | A |
| 227 |   | B |
| 230 |   | B |
| 231 |   | B |
| 238 |   | C |
| 239 |   | B |
| 240 |   | C |
| 241 |   | B |
| 242 |   | C |
| 243 |   | C |
| 250 |   | C |
| 253 | A |   |
| 254 |   | C |
| 256 |   | B |
| 258 |   | B |
| 259 |   | B |
| 261 | A | A |
| 273 |   | A |
| 279 |   | C |
| 281 | A | A |
| 283 |   | B |
| 284 |   | B |
| 286 |   | B |
| 288 | A | B |
| 291 |   | B |
| 294 | A | A |
| 298 | A | A |
| 300 | A | A |
| 303 |   | B |
| 304 | A | A |
| 310 | A | A |
| 311 |   | B |
| 313 | A | A |
| 314 | A |   |
| 315 |   | D |
| 316 |   | B |
| 317 |   | A |
| 318 |   | D |
| 319 |   | A |
| 320 |   | B |
| 321 |   | A |
| 324 |   | C |
| 326 | B | B |
| 327 |   | A |
| 330 | B |   |
| 332 | B |   |
| 333 | B |   |
| 335 | A |   |
| 336 | A |   |
| 337 | A |   |
| 338 | B |   |
| 339 | A |   |
| 341 | A |   |
| 342 | A |   |
| 343 | B |   |
| 344 | A |   |
| 345 | A |   |
| 346 | A |   |
| 347 | B |   |
| 349 | C |   |
| 351 | NaN |   |
| 352 | B |   |
| 353 | *(3.33 μM) |   |
| 354 | B |   |
| 355 | A |   |
| 356 | A |   |
| 357 | A |   |
| 358 | B |   |
| 359 | B |   |
| 360 | C |   |
| 361 | A |   |
| 362 | A |   |
| 363 | A |   |
| 364 | *(3.33 μM) |   |
| 365 | A |   |
| 366 | B |   |
| 367 | A |   |
| 368 | A |   |
| 369 | A |   |
| 370 | *(3.33 μM) |   |
| 371 | *(3.33 μM) |   |
| 373 | A |   |
| 374 | A |   |
| 375 | A |   |
| 376 | NaN |   |
| 377 | B |   |
| 395 |   | C |

We claim:

1. A compound having structural formula I:

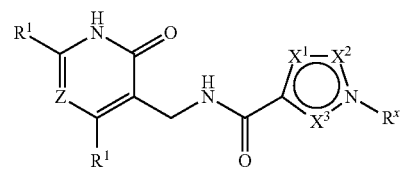

or a pharmaceutically acceptable salt thereof, wherein:

Z is $=C(R^2)-$ or $=N-$;

each of $X^1$ and $X^2$ is independently selected from $=N-$ and $=C(R^3)-$;

$X^3$ is selected from $=N-$ and $=C(R^6)-$;

no more than one of $X^1$, $X^2$, and $X^3$ is $=N-$;

each $R^1$ and $R^2$ is independently selected from hydrogen, halo, —OH, —CN, $C_1$-$C_4$ alkyl, —O—($C_1$-$C_4$ alkyl), —N($R^7$)$_2$, —($C_0$-$C_4$ alkylene)-aryl, —($C_0$-$C_4$ alkylene)-heteroaryl, —($C_0$-$C_4$ alkylene)-heterocyclyl, and —($C_0$-$C_4$ alkylene)-carbocyclyl; or
one $R^1$ and $R^2$ are taken together with atoms to which they are bound to form an aryl, heteroaryl, heterocyclyl, or carbocyclyl ring;
each $R^3$ and $R^6$ is independently selected from hydrogen, halo, —CN, —($C_0$-$C_4$ alkylene)-$R^8$, —($C_2$-$C_6$ alkenyl or alkynyl)-$R^9$, —($C_1$-$C_4$ alkylene)-O—$R^9$, —($C_1$-$C_4$ alkylene)-O—($C_1$-$C_4$ alkylene)-$R^8$, —O—($C_0$-$C_4$ alkylene)-$R^9$, —O—($C_2$-$C_4$ alkylene)-O—$R^8$, —O—($C_1$-$C_4$ alkylene)-$R^9$, —($C_0$-$C_4$ alkylene)-N($R^7$)$_2$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^7$)$_2$, —($C_0$-$C_4$ alkylene)-N($R^9$)—C(O)—$R^9$, —O—($C_1$-$C_4$ alkylene)-C(O)—N($R^7$)$_2$, —O—($C_2$-$C_4$ alkylene)-N($R^9$)—C(O)—($R^7$), —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—N($R^7$)$_2$; or
two $R^3$ are taken together with the carbon atoms to which they are bound to form an aryl, heteroaryl, heterocyclyl, or carbocyclyl fused to the ring comprising $X^1$, $X^2$ and $X^3$;
$R^x$ is Q, —S(O)$_2$-Q, —C(O)-Q, or —CH($R^4$)($R^5$);
Q is selected from aryl, heteroaryl, heterocyclyl, and carbocyclyl;
$R^4$ is selected from $C_2$-$C_6$ alkyl, —CH$_2$—O—($C_1$-$C_4$ alkyl) and —($C_0$-$C_6$ alkylene)-Q, wherein one or two methylene units in the alkyl or alkylene portion of $R^4$ are optionally and independently replaced by —O—, —S—, —S(=O)—, —S(=O)$_2$—, or —N($R^{10}$)—; or
one methylene unit of $R^4$ is taken together with $X^2$ or $X^3$, when the $X^2$ or $X^3$ is =C($R^3$)—, and the intervening atoms to form a heteroaryl or heterocyclyl fused to the ring comprising $X^1$, $X^2$, and $X^3$;
$R^5$ is selected from hydrogen, —($C_0$-$C_6$ alkylene)-Q, and $C_1$-$C_6$ alkyl, wherein one or two methylene units in $R^5$ are optionally and independently replaced by —O—, —S—, —S(=O)—, —S(=O)$_2$—, or —N$R^{10}$—;
each $R^7$ is independently selected from —($C_0$-$C_4$ alkylene)-$R^9$, —($C_0$-$C_4$ alkylene)-O—$R^9$, —S(O)$_2$—$R^8$, —C(=O)—$R^8$, —C(=O)—N($R^9$)$_2$, —($C_1$-$C_4$ alkylene)-O—C(=O)—$R^8$ and —($C_0$-$C_4$ alkylene)-C(=O)—O—$R^9$; or
two $R^7$ are taken together with the nitrogen atom to which they are commonly bound to form an optionally substituted heterocyclyl or heteroaryl ring;
$R^8$ is selected from $C_1$-$C_4$ alkyl, aryl, heteroaryl, carbocyclyl and heterocyclyl;
$R^9$ is selected from hydrogen and $R^8$;
$R^{10}$ is selected from hydrogen, $C_1$-$C_4$ alkyl, —S(=O)$_2$—$R^9$, —C(=O)—$R^8$, —C(=O)—N($R^9$)($R^{12}$), and —C(=O)—O—$R^{11}$;
$R^{11}$ is selected from unsubstituted $C_1$-$C_4$ alkyl and $C_1$-$C_4$ haloalkyl;
$R^{12}$ is selected from hydrogen, unsubstituted $C_1$-$C_4$ alkyl and $C_1$-$C_4$ haloalkyl;
wherein unless otherwise designated any alkyl, alkylene, alkenyl, alkynyl, aryl, heteroaryl, heterocyclyl or carbocyclyl portion of the compound is optionally substituted; and
wherein:
when $X^3$ is =N—, $X^2$ is =C(CH$_3$)—, $X^1$ is =C(H)—, and $R^x$ is 2-fluorophenyl; then $R^1$ and $R^2$ are not taken together with atoms to which they are bound to form

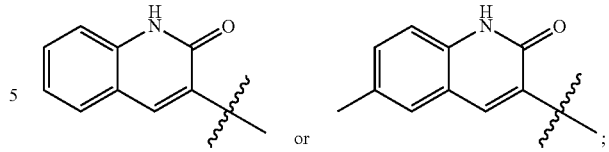

when each $R^1$ is methyl, Z is =C(H)—, each of $X^2$ and $X^3$ is =C(CH$_3$)—, and $X^1$ is =C(H)—; then $R^x$ is other than unsubstituted cyclohexyl, benzyl, pyridin-3-yl, or pyridin-2-yl;
when each $R^1$ is methyl, Z is =C(H)—, $X^3$ is =N—, and $R^x$ is phenyl or 4-fluorophenyl; then the $R^3$ of $X^1$ and the $R^3$ of $X^2$ are not taken together to form unsubstituted $C_5$-$C_7$ cycloalkyl fused to the ring comprising $X^1$, $X^2$ and $X^3$;
when $X^1$ is =N—, $R^5$ is hydrogen, and $R^4$ is taken together with $X^3$ to form

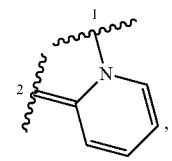

wherein "1" represents the portion of the ring bound to $X^2$, and "2" represents the portion of the ring bound to the ring carbon adjacent to $X^3$; then $X^2$ is other than =C(cyclopropyl)-, =C(C(CH$_3$)$_3$)—, or =C(CH$_2$CH(CH$_3$)$_2$)—, wherein the cyclopropyl is unsubstituted;
when $X^2$ is =N—, $X^3$ is =C(H)—, each $R^1$ is methyl, Z is =C(H)—, and $R^x$ is 4-methylphenyl, unsubstituted phenyl, or unsubstituted benzyl; then $X^1$ is other than =C(3-methylphenyl)-, =C(3-methoxyphenyl)-, =C(phenyl)-, =C(4-chlorophenyl), =C(thien-2-yl)-, or =C(pyridin-3-yl); and
when $X^2$ is =N—, $X^1$ is =C(H)—, each $R^1$ is methyl, Z is =C(H)—, and $R^x$ is pyridin-2-yl, 2,4-dichlorophenyl or 3-methylphenyl; then $X^3$ is other than =C(CH$_3$)—, =C(CH$_2$CH$_3$)—, or =C(cyclopropyl)-;
when $X^2$ is =N—, $X^1$ is =C(CH$_3$)—, and $X^3$ is =C(CH$_3$)—, the $R^x$ is other than 2,4-difluorophenyl or 3-chloro-4-cyanophenyl; and
the compound is other than:

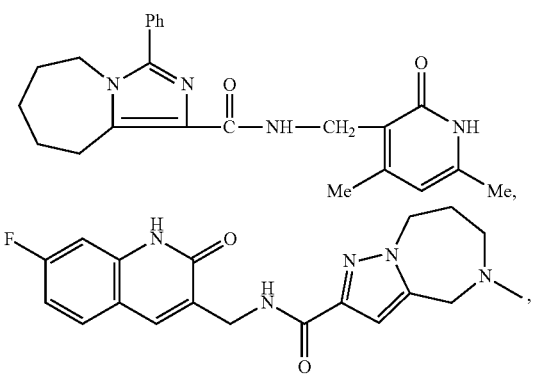

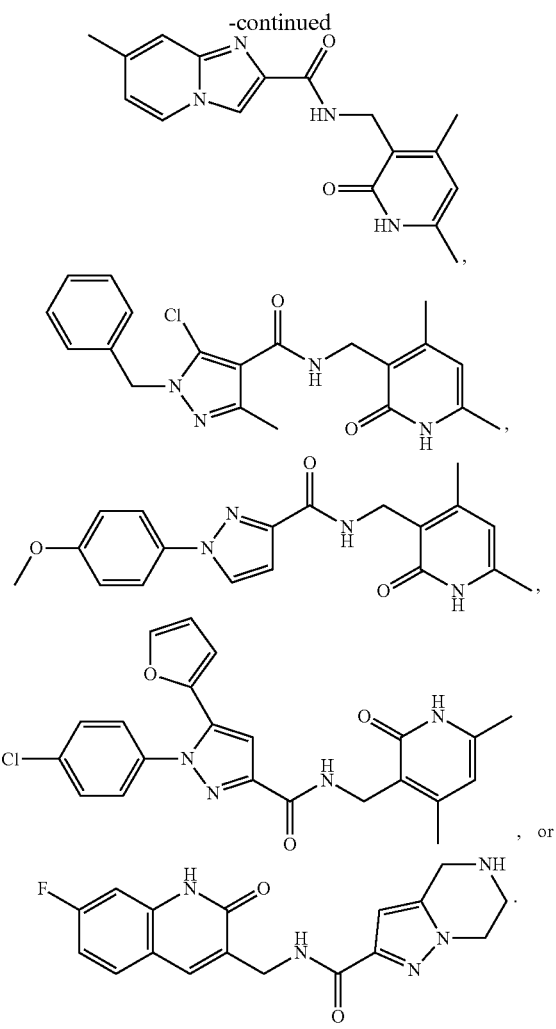

2. The compound of claim 1, wherein one $R^1$ is —CH$_3$; the other $R^1$ is selected from —C$_1$-C$_2$ alkyl optionally substituted with one or more fluoro and —O—(C$_1$-C$_2$ alkyl) optionally substituted with one or more fluoro.

3. The compound of claim 2 represented by the formula:

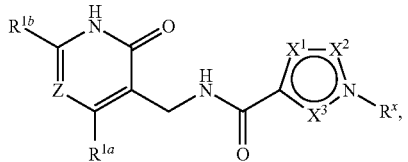

wherein:
$R^{1a}$ is selected from —OCH$_3$, —CH$_3$, —OCHF$_2$, and —CH$_2$CH$_3$;
$R^{1b}$ is —CH$_3$; and
Z is =CH—.

4. The compound of claim 1, wherein each of $X^1$ and $X^2$ is independently =C($R^3$)—, wherein two $R^3$ are taken together with the carbon atoms to which they are bound to form an aryl, heteroaryl, or carbocyclyl fused to the ring comprising $X^1$, $X^2$ and $X^3$.

5. The compound of claim 4, wherein two $R^3$ are taken together with the carbon atoms to which they are bound to form an optionally substituted aryl or a pyridyl ring fused to the ring comprising $X^1$, $X^2$ and $X^3$.

6. The compound of claim 5, wherein the fused ring has the structure:

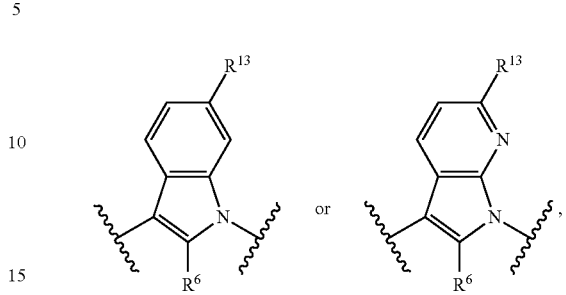

wherein
$R^6$ is as defined in claim 1; and
$R^{13}$ is selected from hydrogen, halo, phenyl, pyridinyl, and —O—(C$_1$-C$_4$ alkyl).

7. The compound of claim 1, wherein:
$R^x$ is —CH($R^4$)($R^5$);
$R^4$ is selected from C$_2$-C$_6$ alkyl, —(C$_0$-C$_2$ alkylene)-aryl, —(C$_0$-C$_2$ alkylene)-heterocyclyl, and —(C$_0$-C$_2$ alkylene)-heteroaryl; and
$R^5$ is selected from hydrogen and methyl.

8. The compound of claim 1, wherein:
$R^x$ is —CH($R^4$)($R^5$);
$R^4$ is selected from —(C$_1$-C$_3$ alkylene)-O—(C$_1$-C$_2$ alkyl), 1-substituted-pipieridin-4-yl, C$_3$-C$_6$ cycloalkyl optionally substituted with one or more fluoro, and tetrahydropyranyl; and
$R^5$ is selected from hydrogen and —CH$_3$.

9. The compound of claim 8, wherein $R^4$ is selected from
—CH$_2$OCH$_3$,
—CH(CH$_3$)OCH$_3$,
4,4-difluorocyclohexyl,
cyclopropyl,
tetrayhyrdopyran-4-yl,
1-(t-butoxycarbonyl)-piperidin-4-yl,
1-(isobutoxycarbonyl)-piperidin-4-yl,
1-(isopropoxycarbonyl)-piperidin-4-yl,
1-(2-fluoroethyl)-piperidin-4-yl,
1-(2,2-difluoroethyl)-piperidin-4-yl,
1-(2,2,2-trifluoroethyl)-piperidin-4-yl,
1-(2-hydroxyisobutyl)-piperidin-4-yl,
1-(hydroxyisopropylcarbonyl)-piperidin-4-yl,
1-(ethoxycarbonylmethyl)-piperidin-4-yl,
1-(isopropylcarbonyl)-piperidin-4-yl,
1-methylpiperidin-4-yl,
1-(methylsulfonyl-piperidin-4-yl,
1-(ethylsulfonyl)-piperidin-4-yl,
1-(isopropylsulfonyl)-piperidin-4-yl,
1-(phenyl)-piperidin-4-yl,
1-(oxetan-3-yl)piperidin-4-yl,
1-(pyridin-2-yl)-piperidin-4-yl, and
1-(pyrimidin-2-yl)-piperidin-4-yl.

10. A composition comprising:
a. a compound having structural formula I:

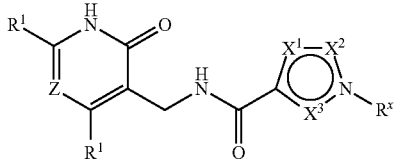

or a pharmaceutically acceptable salt thereof, wherein:
Z is =C($R^2$)— or =N—;
each of $X^1$ and $X^2$ is independently selected from =N— and =C($R^3$)—;
$X^3$ is selected from =N— and =C($R^6$)—;
no more than one of $X^1$, $X^2$, and $X^3$ is =N—;
each $R^1$ and $R^2$ is independently selected from hydrogen, halo, —OH, —CN, $C_1$-$C_4$ alkyl, —O—($C_1$-$C_4$ alkyl), —N($R^7$)$_2$, —($C_0$-$C_4$ alkylene)-aryl, —($C_0$-$C_4$ alkylene)-heteroaryl, —($C_0$-$C_4$ alkylene)-heterocyclyl, and —($C_0$-$C_4$ alkylene)-carbocyclyl; or
one $R^1$ and $R^2$ are taken together with atoms to which they are bound to form an aryl, heteroaryl, heterocyclyl, or carbocyclyl ring;
each $R^3$ and $R^6$ is independently selected from hydrogen, halo, —CN, —($C_0$-$C_4$ alkylene)-$R^8$, —($C_2$-$C_6$ alkenyl or alkynyl)-$R^9$, —($C_1$-$C_4$ alkylene)-O—$R^9$, —($C_1$-$C_4$ alkylene)-O—($C_1$-$C_4$ alkylene)-$R^8$, —O—($C_0$-$C_4$ alkylene)-$R^9$, —O—($C_2$-$C_4$ alkylene)-O—$R^8$, —O—($C_1$-$C_4$ alkylene)-$R^9$, —($C_0$-$C_4$ alkylene)-N($R^7$)$_2$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^7$)$_2$, —($C_0$-$C_4$ alkylene)-N($R^9$)—C(O)—$R^9$, —O—($C_1$-$C_4$ alkylene)-C(O)—N($R^7$)$_2$, —O—($C_2$-$C_4$ alkylene)-N($R^9$)—C(O)—($R^7$), —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—N($R^7$)$_2$; or
two $R^3$ are taken together with the carbon atoms to which they are bound to form an aryl, heteroaryl, heterocyclyl, or carbocyclyl fused to the ring comprising $X^1$, $X^2$ and $X^3$;
$R^x$ is Q, —S(O)$_2$-Q, —C(O)-Q, or —CH($R^4$)($R^5$);
Q is selected from aryl, heteroaryl, heterocyclyl, and carbocyclyl;
$R^4$ is selected from $C_2$-$C_6$ alkyl, —CH$_2$—O—($C_1$-$C_4$ alkyl) and —($C_0$-$C_6$ alkylene)-Q, wherein one or two methylene units in the alkyl or alkylene portion of $R^4$ are optionally and independently replaced by —O—, —S—, —S(=O)—, —S(=O)$_2$—, or —N($R^{10}$)—; or
one methylene unit of $R^4$ is taken together with $X^2$ or $X^3$, when the $X^2$ or $X^3$ is =C($R^3$)—, and the intervening atoms to form a heteroaryl or heterocyclyl fused to the ring comprising $X^1$, $X^2$, and $X^3$;
$R^5$ is selected from hydrogen, —($C_0$-$C_6$ alkylene)-Q, and $C_1$-$C_6$ alkyl, wherein one or two methylene units in $R^5$ are optionally and independently replaced by —O—, —S—, —S(=O)—, —S(=O)$_2$—, or —NR$^{10}$—;

each $R^7$ is independently selected from —($C_0$-$C_4$ alkylene)-$R^9$, —($C_0$-$C_4$ alkylene)-O—$R^9$, —S(O)$_2$—$R^8$, —C(=O)—$R^8$, —C(=O)—N($R^9$)$_2$, —($C_1$-$C_4$ alkylene)-O—C(=O)—$R^8$ and —($C_0$-$C_4$ alkylene)-C(=O)—O—$R^9$; or
two $R^7$ are taken together with the nitrogen atom to which they are commonly bound to form an optionally substituted heterocyclyl or heteroaryl ring;
$R^8$ is selected from $C_1$-$C_4$ alkyl, aryl, heteroaryl, carbocyclyl and heterocyclyl;
$R^9$ is selected from hydrogen and $R^8$;
$R^{10}$ is selected from hydrogen, $C_1$-$C_4$ alkyl, —S(=O)$_2$—$R^9$, —C(=O)—$R^8$, —C(=O)—N($R^9$)($R^{12}$), and —C(=O)—O—$R^{11}$;
$R^{11}$ is selected from unsubstituted $C_1$-$C_4$ alkyl and $C_1$-$C_4$ haloalkyl;
$R^{12}$ is selected from hydrogen, unsubstituted $C_1$-$C_4$ alkyl and $C_1$-$C_4$ haloalkyl;
wherein unless otherwise designated any alkyl, alkylene, alkenyl, alkynyl, aryl, heteroaryl, heterocyclyl or carbocyclyl portion of the compound is optionally substituted; and
wherein the compound is other than

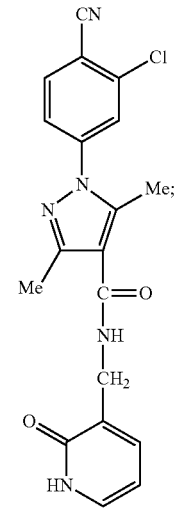 [SMILES: Cc1nn(-c2ccc(C#N)c(Cl)c2)c(C)c1C(=O)NCc1ccc[nH]c1=O]

and
b. a pharmaceutically acceptable carrier.

11. A method of treating a subject with cancer, comprising administering to the subject an effective amount of a compound according to claim 1, or a pharmaceutically acceptable salt thereof.

12. The method of claim 11, wherein the cancer is characterized by the presence of a mutant EZH2 protein.

13. The method of claim 12, wherein the mutant EZH2 protein comprises a Y641N mutation.

14. The method of claim 11, wherein the cancer is characterized by trimethylation of histone H3 at lysine 27.

* * * * *